US012735431B2

(12) United States Patent
Candito et al.

(10) Patent No.: US 12,735,431 B2
(45) Date of Patent: Sep. 15, 2026

(54) 7-PHENYL SUBSTITUTED 2-AMINOQUINAZOLINE INHIBITORS OF HPK1

(71) Applicant: MERCK SHARP & DOHME LLC, Rahway, NJ (US)

(72) Inventors: David A. Candito, Wrentham, MA (US); Joanna L. Chen, Braintree, MA (US); Anthony Donofrio, Cambridge, MA (US); Xavier Fradera, Boston, MA (US); Peter H. Fuller, Ashland, MA (US); Shuhei Kawamura, Cambridge, MA (US); Bing Li, Towaco, NJ (US); Jongwon Lim, Lexington, MA (US); Ping Liu, Westfield, NJ (US); Joey L. Methot, Westwood, NJ (US); Anilkumar G. Nair, Morganville, NJ (US); Alexander Pasternak, Jamaica Plain, MA (US); Brandon A. Vara, Boston, MA (US); Elsie C. Yu, Brighton, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 555 days.

(21) Appl. No.: 18/250,419

(22) PCT Filed: Nov. 4, 2021

(86) PCT No.: PCT/US2021/057968

§ 371 (c)(1),
(2) Date: Apr. 25, 2023

(87) PCT Pub. No.: WO2022/098806

PCT Pub. Date: May 12, 2022

(65) Prior Publication Data

US 2023/0399341 A1 Dec. 14, 2023

Related U.S. Application Data

(60) Provisional application No. 63/111,378, filed on Nov. 9, 2020.

(51) Int. Cl.

| | |
|---|---|
| ***C07D 498/04*** | (2006.01) |
| ***C07D 401/12*** | (2006.01) |
| ***C07D 401/14*** | (2006.01) |
| ***C07D 405/14*** | (2006.01) |
| ***C07D 413/04*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |

(Continued)

(52) U.S. Cl.
CPC ......... *C07D 498/04* (2013.01); *C07D 401/12* (2013.01); *C07D 401/14* (2013.01); *C07D 405/14* (2013.01); *C07D 413/04* (2013.01); *C07D 413/14* (2013.01); *C07D 417/14* (2013.01); *C07D 471/04* (2013.01); *C07D 487/04* (2013.01); *C07D 495/04* (2013.01); *C07D 519/00* (2013.01)

(58) Field of Classification Search
CPC .................................................... C07D 498/04
See application file for complete search history.

(56) References Cited

U.S. PATENT DOCUMENTS

| | | | | |
|---|---|---|---|---|
| 7,906,522 B2 * | 3/2011 | Kishikawa | ............. | A61P 31/00 514/266.4 |
| 2018/0282282 A1 | 10/2018 | Chan et al. | | |

FOREIGN PATENT DOCUMENTS

| | | |
|---|---|---|
| WO | 2007117607 A2 | 10/2007 |
| WO | 2017005137 | 1/2017 |
| WO | 2017005137 A1 | 1/2017 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

(Continued)

*Primary Examiner* — Nizal S Chandrakumar
(74) *Attorney, Agent, or Firm* — Patricia A. Shatynski; John C. Todaro

(57) ABSTRACT

Compounds of the following formula (I); or the pharmaceutically acceptable salts thereof, are inhibitors of haematopoietic progenitor kinase 1 (HPK1) useful in the treatment of diseases or disorders associated with HPK1. Also disclosed herein are uses of these compounds in the potential treatment or prevention of an HPK1-associated disease or disorder. Also disclosed herein are compositions comprising one or more of the compounds. Further disclosed herein are uses of these compositions in the potential prevention or treatment of an HPK1-associated disease or disorder.

(I)

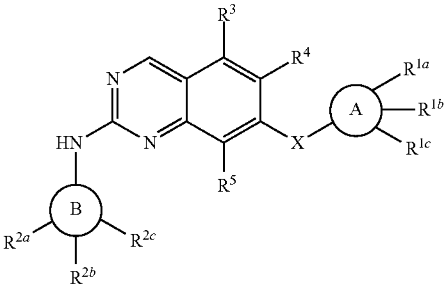

2 Claims, No Drawings

(51) Int. Cl.
*C07D 495/04* (2006.01)
*C07D 519/00* (2006.01)

(56) References Cited

OTHER PUBLICATIONS

"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Dorwald F. A. Side Reactions in Organic Synthesis, 2005, Wiley: VCH, Weinheim p. IX of Preface p. 1.*
Duan, An updated review of small-molecule HPK1 kinase inhibitors (2016-present), Future Med Chem. 2024;16(22):2431-2450.*
Pubchem, SID 412946565, Modify Date: Aug. 19, 2020 [retrieved on Dec. 13, 2021].,Retrieved from the Internet URL: https://pubchem.ncbi.nlm.nih.gov/substance/412946565 entire document (6 pages).
Pubchem, SID 433922013, Available.Date: Sep. 9, 2020 [retrieved on Jan. 29, 2022].,Retrieved from the Internet URL:https://pubchem.ncbi.nlm.nih.gov/substance/433922013 entire document (6 pages).

* cited by examiner

7-PHENYL SUBSTITUTED 2-AMINOQUINAZOLINE INHIBITORS OF HPK1

CROSS-REFERENCE TO RELATED APPLICATIONS

This application is a U.S. National Stage application of International Patent Application No. PCT/US21/057968, filed Nov. 4, 2021, which claims priority to U.S. Provisional Patent Application No. 63/111,378, filed Nov. 9, 2020.

BACKGROUND OF THE INVENTION

Cancer immunotherapy is treatment that uses the human body's own immune system to help fight cancer. This unique approach has witnessed significant clinical successes in the treatment of a variety of tumor types in recent years, particularly with the application of immune checkpoint inhibitors and chimeric antigen T cell therapy. Two of the most investigated checkpoint blockades (i.e., CTLA4 and PD-1 inhibitors) have demonstrated remarkable antitumor activity by overcoming immunosuppressive mechanisms at the tumor site. CTLA4 blockade predominantly enhances T cell activation during the priming phase of the immune response, whereas PD-1 inhibitors appear to release exhausted but otherwise activated effector T cell populations and reduce regulatory T cell function. While these monoclonal antibody-based T cell interventions have proven to be effective, utility of this approach is limited as they can only target receptors on the cell surface. To the contrary, small-molecule T cell activators offer the opportunity to target both extracellular and intracellular immune targets including kinases. Furthermore, inhibiting immune suppressive kinases has the potential to directly activate T cells, thus bypassing checkpoint inhibitory pathways and overcoming intrinsic and acquired resistance to checkpoint receptor blockade.

Haematopoietic progenitor kinase 1 (HPK1; also known as MAP4K1) is a member of the germinal center kinase family of serine/threonine kinases and is mainly expressed by haematopoietic cells. In T cells, it is believed that HPK1 phosphorylates serine 376 of SLP76 after T cell receptor (TCR) triggers and induces the association of SLP76 with 14-3-3 proteins. Knockdown of HPK1 expression in Jurkat T cells has been shown to increase TCR-induced activation of the IL2 gene. Further, antigen-stimulated T cells from HPK1-deficient mice proliferated more vigorously and produced higher amounts of cytokines as compared to antigen-stimulated T-cells from wild-type mice. Importantly, HPK1-deficient mice developed a more severe form of experimental autoimmune encephalomyelitis (EAE), a model of multiple sclerosis. Both in vitro and in vivo, HPK1 knockout dendritic cells (DC) have demonstrated enhanced antigen presentation function. Particularly, both HPK1 knockout T cells and HPK1 knockout DCs have been implicated in tumor rejection in a murine model of lung cancer. These findings have validated HPK1 as a novel target for anti-cancer immunotherapy. Inhibition of HPK1 with small molecule inhibitors therefore has the potential to be a treatment for cancers and other disorders. Compounds disclosed herein are useful in the potential treatment or prevention of HPK1-related diseases.

SUMMARY OF THE INVENTION

Compounds of the formula I:

I

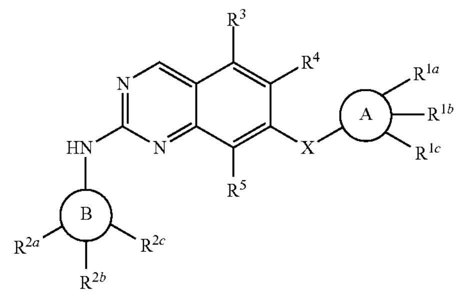

or pharmaceutically acceptable salts thereof, are inhibitors of haematopoietic progenitor kinase 1 (HPK1) useful in the treatment of diseases or disorders associated with HPK1. Also disclosed herein are uses of these compounds in the potential treatment or prevention of an HPK1-associated disease or disorder. Also disclosed herein are compositions comprising one or more of the compounds. Further disclosed herein are uses of these compositions in the potential prevention or treatment of an HPK1-associated disease or disorder.

DETAILED DESCRIPTION OF THE INVENTION

The present invention is directed to compounds of the formula I:

I

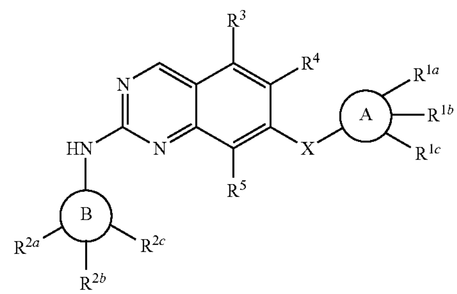

wherein:

A is a phenyl, cycloalkyl, or heterocyclyl ring;

B is a phenyl, pyridyl, pyrimidinyl, benzofuranyl, benzothiophenyl, 2,3-dihydro-indenyl, 2,3-dihydro-isoindolyl, tetrahydro-benzazepinyl, or tetrahydroisoquinolinyl ring;

X is a bond, —O—, —O($C_{1-3}$alkyl)-, —NH—, —NH($C_{1-3}$alkyl)- or —N($CH_3$)($C_{1-3}$alkyl)-:

$R^{1a}$, $R^{1b}$ and $R^{1c}$ as are present are independently selected from:

(1) hydrogen, (2) halogen, (3) hydroxyl, (4) $C_{1-6}$alkyl, which is unsubstituted or substituted with substituents selected from: hydroxy, —$NH_2$, —(CO)NH($C_{1-6}$alkyl), —CN, and fluoro, (5) —O—$C_{1-6}$alkyl, which is unsubstituted or substituted with fluoro, (6) —$C_{3-6}$cycloalkyl, which is unsubstituted or substituted with substituents selected from: hydroxy, methoxy, —$C_{1-6}$alkyl, —(CO)NH($C_{1-6}$alkyl), —(CO)O($C_{1-6}$alkyl), —CN, and fluoro, (7) $C_{2-6}$alkynyl, (8) —$NH_2$, (9) —NH($C_{1-6}$alkyl),

(10) —N($C_{1-6}$alkyl)$_2$,

(11) —(CO)($C_{1-6}$alkyl),

(12) —(CO)$NH_2$,

(13) —(CO)NH($C_{1-6}$alkyl),

(14) —(CO)N($C_{1-6}$alkyl)$_2$,

(15) —(CO)NH($C_{3-6}$cycloalkyl),

(16) —NH(CO)($C_{1-6}$alkyl),

(17) —$SO_2$—$C_{1-6}$alkyl,

(18) —NH—$SO_2$—$C_{1-6}$alkyl,

(19) —NH—$SO_2$—$C_{1-6}$alkyl,

(20) —$SO_2$—$NH_2$,

(21) —$SO_2$—NH($C_{1-6}$alkyl),

(22) —$SO_2$—N($C_{1-6}$alkyl)$_2$,

(23) —$SO_2$—NH($C_{3-6}$cycloalkyl),

(24) —CN,

(25) keto,

(26) -phenyl,

(27) -pyridyl,

(28) -diazolyl,

(29) -morpholinyl,

(30) -oxazolyl,

(31) -oxadiazolyl,

(32) -piperazinyl,

(33) -piperidinyl, and

(34) -thiazolyl, or $R^{1a}$ and $R^{1b}$ may be joined to form a 1,4-dioxanyl, 1,3-dioxolanyl, morpholinyl, oxazolyl, piperidinyl, pyrazolyl, pyrrolidinyl, tetrahydropyranyl, tetrahydroquinolinyl, or thiazolyl ring;

$R^{2a}$, $R^{2b}$ and $R^{2c}$ as are present are independently selected from:

(1) hydrogen, (2) halogen, (3) hydroxyl, (4) $C_{1-6}$alkyl, which is unsubstituted or substituted with substituents selected from: hydroxy, —(CO)NH ($C_{1-6}$ alkyl), —(CO)O($C_{1-6}$alkyl), —$SO_2$—$C_{1-6}$alkyl, —$SO_2$—$C_{3-6}$cycloalkyl, —CN, and fluoro, (5) —O—$C_{1-6}$alkyl, which is unsubstituted or substituted with fluoro, (6) —$C_{3-6}$cycloalkyl, which is unsubstituted or substituted with substituents selected from: hydroxy, methoxy, —(CO)NH($C_{1-6}$alkyl), —(CO)O($C_{1-6}$alkyl), —CN, and fluoro, (7) —$NH_2$, (8) —NH($C_{1-6}$alkyl), (9) —N($C_{1-6}$alkyl)$_2$,

(10) —(CO)($C_{1-6}$alkyl),

(11) —(CO)$NH_2$,

(12) —(CO)NH($C_{1-6}$alkyl),

(13) —NH(CO)($C_{1-6}$alkyl),

(14) —$SO_2$—$C_{1-6}$alkyl,

(15) —$SO_2$—NH($C_{1-6}$alkyl),

(16) —$SO_2$—N($C_{1-6}$alkyl)$_2$,

(17) -oxazolyl,

(18) -oxadiazolyl,

(19) -pyrrolidinyl, and

(20) -thiazolyl;

$R^3$ is selected from:

(1) hydrogen, (2) —$NH_2$, (3) chloro, and (4) fluoro;

$R^4$ is selected from:

(1) hydrogen, (2) cyano, (3) chloro, and (4) fluoro;

$R^5$ is selected from:

(1) hydrogen, (2) methyl, (3) cyano, (4) chloro, (5) fluoro, and (6) bromo;

or a pharmaceutically acceptable salt thereof.

An embodiment of the present invention includes compounds of the formula II:

II

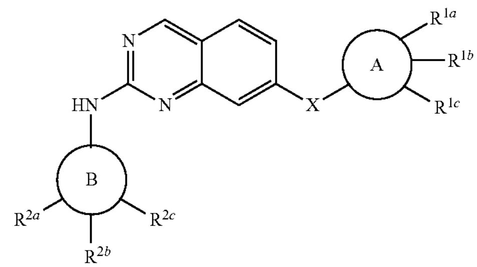

wherein A, B, X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIa:

IIa

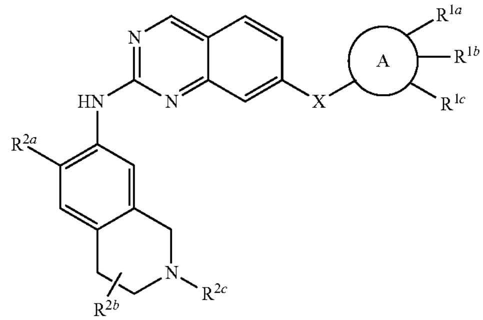

wherein A, X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIb:

IIb

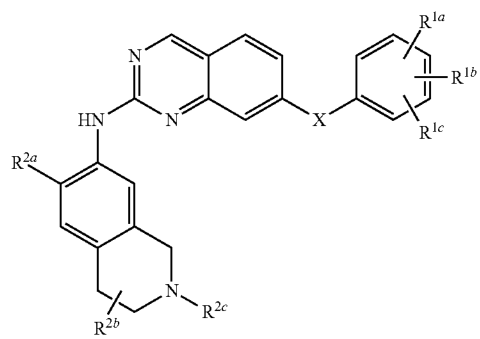

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIc:

IIc

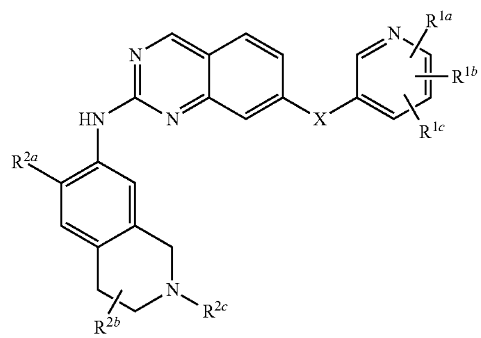

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IId:

IId

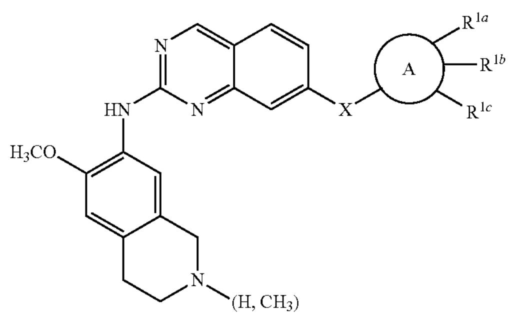

wherein A, X, $R^{1a}$, $R^{1b}$ and $R^{1c}$ are defined herein; or a pharmaceutically acceptable salt thereof.

An embodiment of the resent invention includes compounds of the formula III:

III

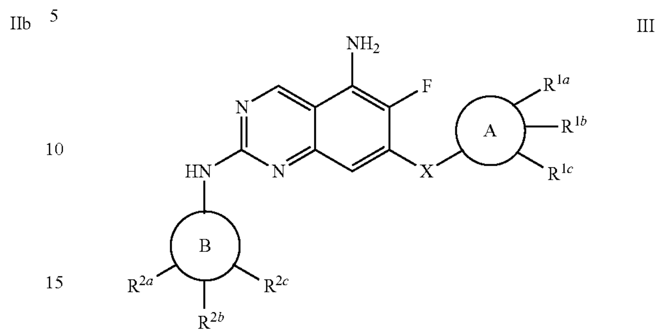

wherein A, B, X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIIa:

IIIa

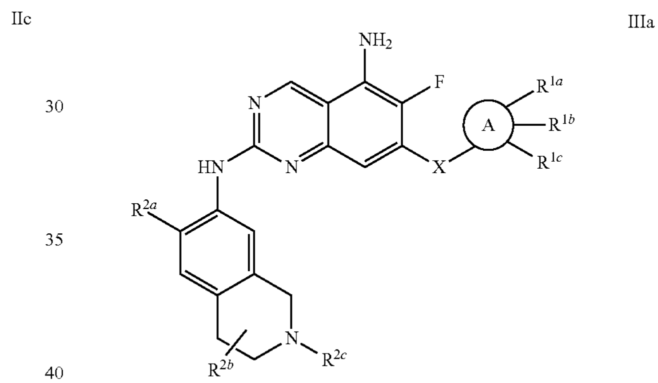

wherein A, X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIIb:

IIIb

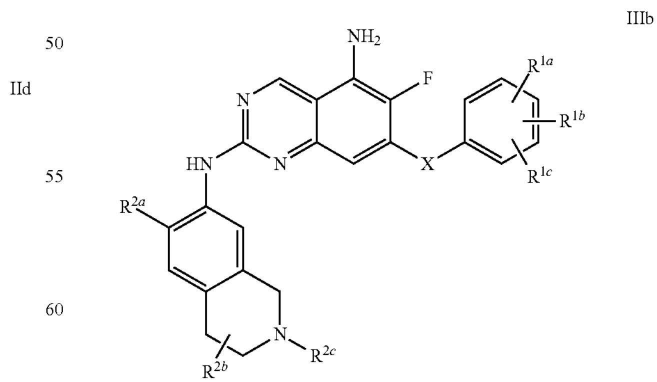

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIIc:

IIIc

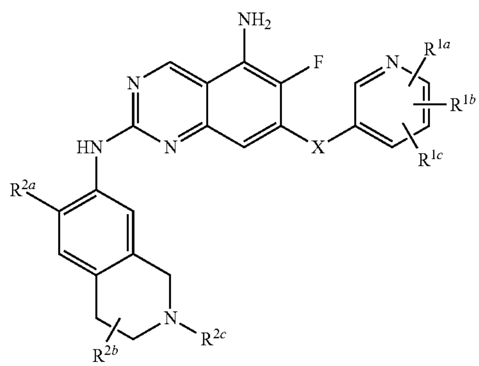

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IIId:

IIId

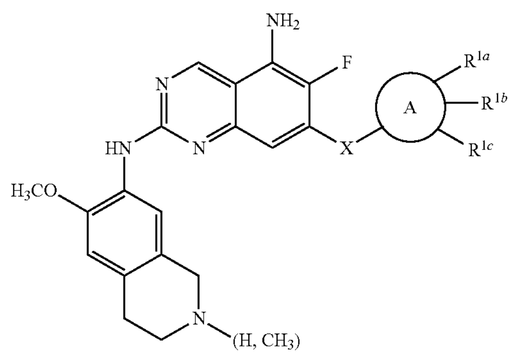

wherein A, X, $R^{1a}$, $R^{1b}$ and $R^{1c}$ are defined herein; or a pharmaceutically acceptable salt thereof.

An embodiment of the present invention includes compounds of the formula IV:

IV

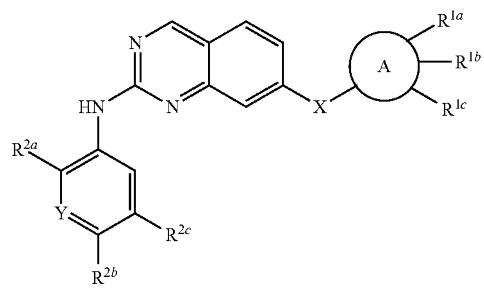

wherein Y is N or CH, and X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IVa:

IVa

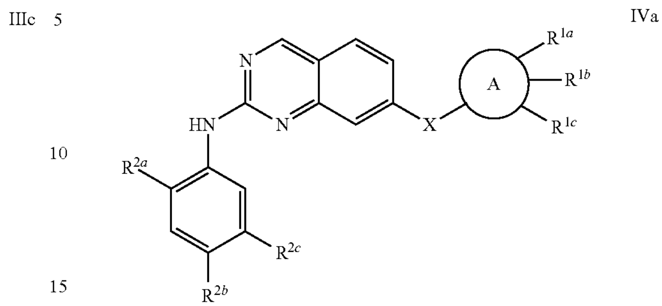

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds of the formula IVb:

IVb

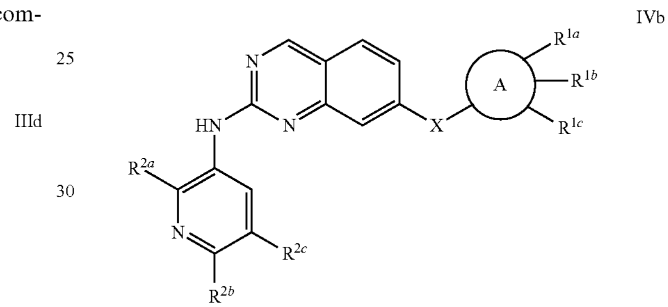

wherein X, $R^{1a}$, $R^{1b}$, $R^{1c}$, $R^{2a}$, $R^{2b}$ and $R^{2c}$ are defined herein; or a pharmaceutically acceptable salt thereof.

An embodiment of the present invention includes compounds wherein A is a phenyl or a pyridyl ring. An embodiment of the present invention includes compounds wherein A is a phenyl ring. An embodiment of the present invention includes compounds wherein A is a pyridyl ring. An embodiment of the present invention includes compounds wherein A is a 2,3-dihydro-1H-pyrido[2,3-b][1,4]oxazin-7-yl ring.

An embodiment of the present invention includes compounds wherein B is a tetrahydroisoquinolinyl, phenyl or pyridyl ring. An embodiment of the present invention includes compounds wherein B is a tetrahydroisoquinolinyl ring. An embodiment of the present invention includes compounds wherein B is a phenyl ring. An embodiment of the present invention includes compounds wherein B is a pyridyl ring.

An embodiment of the present invention includes compounds wherein X is a bond, —O—, or —O($CH_2$)—. An embodiment of the present invention includes compounds wherein X is a bond. An embodiment of the present invention includes compounds wherein X is —O—. An embodiment of the present invention includes compounds wherein X is —O($CH_2$)—.

An embodiment of the present invention includes compounds wherein $R^{1a}$, $R^{1b}$ and $R^{1c}$ as are present are independently selected from:

(1) hydrogen, (2) fluoro, (3) chloro, (4) hydroxyl, (5) $C_{1-3}$alkyl, which is unsubstituted or substituted with hydroxy or one or more fluoro, (6) —O—$C_{1-3}$alkyl, which is unsubstituted or substituted with one or more fluoro,
(7) $C_{3-6}$cycloalkyl,
(8) —$NH_2$,
(9) —NH($C_{1-3}$alkyl),
(10) —N($C_{1-3}$alkyl)$_2$,
(11) keto, and
(12) -phenyl.

An embodiment of the present invention includes compounds wherein $R^{1a}$, $R^{1b}$ and $R^{1c}$ as are present are independently selected from:
(1) hydrogen,
(2) fluoro,
(3) hydroxyl,
(4) —$CH_3$,
(5) —$CHF_2$,
(6) —$CF_3$,
(7) —$CH_2OH$,
(8) —$CH_2CH_3$,
(9) —$C(CH_3)OH$,
(10) —$OCH_3$,
(11) —$OCHF_2$,
(12) —$OCH_2CH_2F$,
(13) —$N(CH_3)_2$,
(14) cyclopropyl, and
(15) phenyl.

An embodiment of the present invention includes compounds wherein $R^{1c}$ is hydrogen and $R^{1a}$ and $R^{1b}$, as are present, are independently selected from:
(1) hydrogen,
(2) fluoro,
(3) hydroxyl,
(4) —$CH_3$,
(5) —$CHF_2$,
(6) —$CF_3$,
(7) —$CH_2OH$,
(8) —$CH_2CH_3$,
(9) —$C(CH_3)OH$,
(10) —$OCH_3$,
(11) —$OCHF_2$,
(12) —$OCH_2CH_2F$,
(13) —$N(CH_3)_2$,
(14) cyclopropyl, and
(15) phenyl.

An embodiment of the present invention includes compounds wherein $R^{1c}$ is hydrogen, and $R^{1a}$ and $R^{1b}$ may be joined to form a morpholinyl ring.

An embodiment of the present invention includes compounds wherein $R^{2a}$, $R^{2b}$ and $R^{2c}$ as are present are independently selected from:
(1) hydrogen,
(2) halogen,
(3) hydroxyl,
(4) $C_{1-6}$alkyl, and
(5) —O—$C_{1-6}$alkyl.

An embodiment of the present invention includes compounds wherein $R^3$ is hydrogen or —$NH_2$. An embodiment of the present invention includes compounds wherein $R^3$ is hydrogen. An embodiment of the present invention includes compounds wherein $R^3$ is —$NH_2$.

An embodiment of the present invention includes compounds wherein $R^4$ is hydrogen or chloro. An embodiment of the present invention includes compounds wherein $R^4$ is hydrogen. An embodiment of the present invention includes compounds wherein $R^4$ is chloro. An embodiment of the present invention includes compounds wherein $R^4$ is fluoro. An embodiment of the present invention includes compounds wherein $R^4$ is cyano.

An embodiment of the present invention includes compounds wherein $R^5$ is hydrogen or chloro. An embodiment of the present invention includes compounds wherein $R^5$ is hydrogen. An embodiment of the present invention includes compounds wherein $R^5$ is chloro.

Certain embodiments of the present invention include a compound which is selected from the group consisting of the subject compounds of the Examples herein or a pharmaceutically acceptable salt thereof.

Certain embodiments of the present invention include a compound which is selected from the group consisting of:
N-(6-methoxy-2-methyl-1,2,3,4-tetrahydroisoquinolin-7-yl)-7-phenylquinazolin-2-amine;
N-(6-methoxy-2-methyl-1,2,3,4-tetrahydroisoquinolin-7-yl)-7-(4-methylpyridin-3-yl)quinazolin-2-amine;
7-(5-amino-4-methylpyridin-3-yl)-N-(6-methoxy-2-methyl-1,2,3,4-tetrahydroisoquinolin-7-yl)quinazolin-2-amine;
N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine;
7-(2-fluoro-6-methylphenyl)-N-(6-methoxy-2-methyl-1,2,3,4-tetrahydroisoquinolin-7-yl)quinazolin-2-amine;
N-(6-methoxy-2-methyl-1,2,3,4-tetrahydroisoquinolin-7-yl)-7-(1,2,3,4-tetrahydroisoquinolin-5-yl)quinazolin-2-amine;
7-[2-(aminomethyl)-5-fluorophenyl]-N-(6-methoxy-2-methyl-1,2,3,4-tetrahydroisoquinolin-7-yl)quinazolin-2-amine;
7-[2-(aminomethyl)-4-fluorophenyl]-N-(6-methoxy-2-methyl-1,2,3,4-tetrahydroisoquinolin-7-yl)quinazolin-2-amine;
N-(6-methoxy-2-methyl-1,2,3,4-tetrahydroisoquinolin-7-yl)-7-(1,2,3,4-tetrahydroisoquinolin-8-yl)quinazolin-2-amine;
3-(2-{2-[(6-methoxy-2-methyl-1,2,3,4-tetrahydroisoquinolin-7-yl)amino]quinazolin-7-yl}phenyl)-1,3-oxazolidin-2-one;
3-(2-{2-[(6-methoxy-2-methyl-1,2,3,4-tetrahydroisoquinolin-7-yl)amino]quinazolin-7-yl}-4-methylphenyl)-1,3-oxazolidin-2-one;
2,2-difluoro-2-(5-{2-[(6-methoxy-2-methyl-1,2,3,4-tetrahydroisoquinolin-7-yl)amino]quinazolin-7-yl}pyridin-2-yl)acetamide
2-(4-{2-[(6-methoxy-2-methyl-1,2,3,4-tetrahydroisoquinolin-7-yl)amino]quinazolin-7-yl}-1H-pyrazol-1-yl)ethan-1-ol;
2-(5-{2-[(6-methoxy-2-methyl-1,2,3,4-tetrahydroisoquinolin-7-yl)amino]quinazolin-7-yl}pyridin-3-yl)propan-2-ol;
2-(5-{2-[(6-methoxy-2-methyl-1,2,3,4-tetrahydroisoquinolin-7-yl)amino]quinazolin-7-yl}-1,3-thiazol-2-yl)propan-2-ol;
N-(6-methoxy-2-methyl-1,2,3,4-tetrahydroisoquinolin-7-yl)-7-([1,2,4]triazolo[1,5-a]pyridin-7-yl)quinazolin-2-amine;
N-(6-methoxy-2-methyl-1,2,3,4-tetrahydroisoquinolin-7-yl)-7-(5-methoxypyridin-3-yl)quinazolin-2-amine;
N-(5-{2-[(6-methoxy-2-methyl-1,2,3,4-tetrahydroisoquinolin-7-yl)amino]quinazolin-7-yl}pyridin-2-yl)acetamide;
7-(2-amino-4-methylpyrimidin-5-yl)-N-(6-methoxy-2-methyl-1,2,3,4-tetrahydroisoquinolin-7-yl)quinazolin-2-amine;
7-(1-ethyl-1H-pyrazol-4-yl)-N-(6-methoxy-2-methyl-1,2,3,4-tetrahydroisoquinolin-7-yl)quinazolin-2-amine;

5-{2-[(6-methoxy-2-methyl-1,2,3,4-tetrahydroisoquinolin-7-yl)amino]quinazolin-7-yl}-N-methylpyridine-2-carboxamide;

6-{2-[(6-methoxy-2-methyl-1,2,3,4-tetrahydroisoquinolin-7-yl)amino]quinazolin-7-yl}pyrazolo[1,5-a]pyrimidine-3-carbonitrile;

N-ethyl-5-{2-[(6-methoxy-2-methyl-1,2,3,4-tetrahydroisoquinolin-7-yl)amino]quinazolin-7-yl}pyridine-2-carboxamide;

N-(6-methoxy-2-methyl-1,2,3,4-tetrahydroisoquinolin-7-yl)-7-(1,6-naphthyridin-8-yl)quinazolin-2-amine;

N-(6-methoxy-2-methyl-1,2,3,4-tetrahydroisoquinolin-7-yl)-7-(1,5-naphthyridin-3-yl)quinazolin-2-amine;

7-[1-(difluoromethyl)-1H-pyrazol-4-yl]-N-(6-methoxy-2-methyl-1,2,3,4-tetrahydroisoquinolin-7-yl)quinazolin-2-amine;

7-(6-aminopyridin-3-yl)-N-(6-methoxy-1,2,3,4-tetrahydroisoquinolin-7-yl)quinazolin-2-amine;

5-{2-[(6-methoxy-1,2,3,4-tetrahydroisoquinolin-7-yl)amino]quinazolin-7-yl}-N-methylpyridine-2-carboxamide;

N-(6-methoxy-1,2,3,4-tetrahydroisoquinolin-7-yl)-7-(4-methyl-3,4-dihydro-2H-pyrido[3,2-b][1,4]oxazin-7-yl)quinazolin-2-amine;

N-(5-{2-[(6-methoxy-1,2,3,4-tetrahydroisoquinolin-7-yl)amino]quinazolin-7-yl}pyridin-2-yl)acetamide;

7-(3-amino-2-methylphenyl)-N-(6-methoxy-1,2,3,4-tetrahydroisoquinolin-7-yl)quinazolin-2-amine;

4-{2-[(6-methoxy-1,2,3,4-tetrahydroisoquinolin-7-yl)amino]quinazolin-7-yl}-3-methylbenzene-1-sulfonamide;

4-{2-[(6-methoxy-1,2,3,4-tetrahydroisoquinolin-7-yl)amino]quinazolin-7-yl}-3-methylbenzonitrile;

N-(6-methoxy-1,2,3,4-tetrahydroisoquinolin-7-yl)-7-(1-methyl-1H-pyrazol-4-yl)quinazolin-2-amine;

7-(5,6-dihydro-4H-pyrrolo[1,2-b]pyrazol-3-yl)-N-(6-methoxy-1,2,3,4-tetrahydroisoquinolin-7-yl)quinazolin-2-amine;

5-{2-[(6-methoxy-1,2,3,4-tetrahydroisoquinolin-7-yl)amino]quinazolin-7-yl}pyridine-3-carbonitrile;

N-(5-{2-[(6-methoxy-1,2,3,4-tetrahydroisoquinolin-7-yl)amino]quinazolin-7-yl}pyridin-3-yl)methanesulfonamide;

7-(4-chloropyridin-3-yl)-N-(6-methoxy-1,2,3,4-tetrahydroisoquinolin-7-yl)quinazolin-2-amine;

7-(6-methoxypyridin-3-yl)-N-(6-methoxy-1,2,3,4-tetrahydroisoquinolin-7-yl)quinazolin-2-amine;

N-(6-methoxy-1,2,3,4-tetrahydroisoquinolin-7-yl)-7-(pyridin-3-yl)quinazolin-2-amine;

N-(6-methoxy-1,2,3,4-tetrahydroisoquinolin-7-yl)-7-(5-methylpyridin-3-yl)quinazolin-2-amine;

N-(6-methoxy-1,2,3,4-tetrahydroisoquinolin-7-yl)-7-[5-(morpholin-4-yl)pyridin-3-yl]quinazolin-2-amine;

N-(6-methoxy-1,2,3,4-tetrahydroisoquinolin-7-yl)-7-[5-(methylsulfonyl)pyridin-3-yl]quinazolin-2-amine;

7-(5-methoxypyridin-3-yl)-N-(6-methoxy-1,2,3,4-tetrahydroisoquinolin-7-yl)quinazolin-2-amine;

N-(6-methoxy-1,2,3,4-tetrahydroisoquinolin-7-yl)-7-(1H-pyrrolo[2,3-c]pyridin-4-yl)quinazolin-2-amine;

N-(6-methoxy-1,2,3,4-tetrahydroisoquinolin-7-yl)-7-(pyridin-4-yl)quinazolin-2-amine;

(5-{2-[(6-methoxy-1,2,3,4-tetrahydroisoquinolin-7-yl)amino]quinazolin-7-yl}pyridin-3-yl)(morpholin-4-yl)methanone;

N-(6-methoxy-1,2,3,4-tetrahydroisoquinolin-7-yl)-7-(6-{[2-(morpholin-4-yl)ethyl]amino}pyridin-3-yl)quinazolin-2-amine;

7-[5-(aminomethyl)pyridin-3-yl]-N-(6-methoxy-1,2,3,4-tetrahydroisoquinolin-7-yl)quinazolin-2-amine;

N-(6-methoxy-1,2,3,4-tetrahydroisoquinolin-7-yl)-7-[5-(piperazin-1-yl)pyridin-3-yl]quinazolin-2-amine;

N-(5-{2-[(6-methoxy-1,2,3,4-tetrahydroisoquinolin-7-yl)amino]quinazolin-7-yl}pyridin-3-yl)propane-2-sulfonamide;

N-(5-{2-[(6-methoxy-1,2,3,4-tetrahydroisoquinolin-7-yl)amino]quinazolin-7-yl}pyridin-3-yl)propenamide;

(5-{2-[(6-methoxy-1,2,3,4-tetrahydroisoquinolin-7-yl)amino]quinazolin-7-yl}pyridin-3-yl)methanol;

N-(6-methoxy-1,2,3,4-tetrahydroisoquinolin-7-yl)-7-[5-(4-methylpiperazin-1-yl)pyridin-3-yl]quinazolin-2-amine;

(3-{2-[(6-methoxy-1,2,3,4-tetrahydroisoquinolin-7-yl)amino]quinazolin-7-yl}phenyl)acetonitrile;

N-(6-methoxy-1,2,3,4-tetrahydroisoquinolin-7-yl)-7-[3-(1H-pyrazol-4-yl)phenyl]quinazolin-2-amine;

7-{4-[(dimethylamino)methyl]phenyl}-N-(6-methoxy-1,2,3,4-tetrahydroisoquinolin-7-yl)quinazolin-2-amine;

7-(3-aminophenyl)-N-(6-methoxy-1,2,3,4-tetrahydroisoquinolin-7-yl)quinazolin-2-amine;

3-{2-[(6-methoxy-1,2,3,4-tetrahydroisoquinolin-7-yl)amino]quinazolin-7-yl}phenol;

(3-{2-[(6-methoxy-1,2,3,4-tetrahydroisoquinolin-7-yl)amino]quinazolin-7-yl}phenyl)-methanol;

7-[3-(aminomethyl)phenyl]-N-(6-methoxy-1,2,3,4-tetrahydroisoquinolin-7-yl)quinazolin-2-amine;

3-amino-5-{2-[(6-methoxy-1,2,3,4-tetrahydroisoquinolin-7-yl)amino]quinazolin-7-yl}benzonitrile;

4-methoxy-3-{2-[(6-methoxy-1,2,3,4-tetrahydroisoquinolin-7-yl)amino]quinazolin-7-yl}benzonitrile;

(4-{2-[(6-methoxy-1,2,3,4-tetrahydroisoquinolin-7-yl)amino]quinazolin-7-yl}phenyl)acetonitrile;

3-{2-[(6-methoxy-1,2,3,4-tetrahydroisoquinolin-7-yl)amino]quinazolin-7-yl}benzonitrile;

1-(3-{2-[(6-methoxy-1,2,3,4-tetrahydroisoquinolin-7-yl)amino]quinazolin-7-yl}phenyl)ethan-1-one;

N-cyclopropyl-3-{2-[(6-methoxy-1,2,3,4-tetrahydroisoquinolin-7-yl)amino]quinazolin-7-yl}benzamide;

2-(cyclopropylmethyl)-6-{2-[(6-methoxy-1,2,3,4-tetrahydroisoquinolin-7-yl)amino]quinazolin-7-yl}-2,3-dihydro-1H-isoindol-1-one;

N-(6-methoxy-1,2,3,4-tetrahydroisoquinolin-7-yl)-7-{3-[(piperidin-1-yl)methyl]phenyl}quinazolin-2-amine;

7-(2,3-dihydro-1,4-benzodioxin-6-yl)-N-(6-methoxy-1,2,3,4-tetrahydroisoquinolin-7-yl)quinazolin-2-amine;

7-(2H-1,3-benzodioxol-5-yl)-N-(6-methoxy-1,2,3,4-tetrahydroisoquinolin-7-yl)quinazolin-2-amine;

7-(2,3-dihydro-1-benzofuran-5-yl)-N-(6-methoxy-1,2,3,4-tetrahydroisoquinolin-7-yl)quinazolin-2-amine;

7-(2-amino-1H-benzimidazol-7-yl)-N-(6-methoxy-1,2,3,4-tetrahydroisoquinolin-7-yl)quinazolin-2-amine;

[1-(4-methoxy-3-{2-[(6-methoxy-1,2,3,4-tetrahydroisoquinolin-7-yl)amino]quinazolin-7-yl}phenyl)cyclopropyl]methanol;

7-(3,4-dihydro-2H-1-benzopyran-6-yl)-N-(6-methoxy-1,2,3,4-tetrahydroisoquinolin-7-yl)quinazolin-2-amine;

7-(3,4-dihydro-1H-2-benzopyran-7-yl)-N-(6-methoxy-1,2,3,4-tetrahydroisoquinolin-7-yl)quinazolin-2-amine;

N-(6-methoxy-1,2,3,4-tetrahydroisoquinolin-7-yl)-7-{3-[(morpholin-4-yl)sulfonyl]phenyl}quinazolin-2-amine;

N-(6-methoxy-1,2,3,4-tetrahydroisoquinolin-7-yl)-7-{2-methyl-5-[(pyrrolidin-1-yl)sulfonyl]phenyl}quinazolin-2-amine;

3-{2-[(6-methoxy-1,2,3,4-tetrahydroisoquinolin-7-yl)amino]quinazolin-7-yl}-N,N,4-trimethylbenzene-1-sulfonamide;

N,N-diethyl-3-{2-[(6-methoxy-1,2,3,4-tetrahydroisoquinolin-7-yl)amino]quinazolin-7-yl}benzene-1-sulfonamide;
N-(6-methoxy-1,2,3,4-tetrahydroisoquinolin-7-yl)-7-{4-[(pyrrolidin-1-yl)sulfonyl]phenyl}quinazolin-2-amine;
N-(6-methoxy-1,2,3,4-tetrahydroisoquinolin-7-yl)-7-{3-[(piperidin-1-yl)sulfonyl]phenyl}quinazolin-2-amine;
3-{2-[(6-methoxy-1,2,3,4-tetrahydroisoquinolin-7-yl)amino]quinazolin-7-yl}-N-[2-(pyrrolidin-1-yl)ethyl]benzamide;
N-ethyl-3-{2-[(6-methoxy-1,2,3,4-tetrahydroisoquinolin-7-yl)amino]quinazolin-7-yl}benzene-1-sulfonamide;
N-(3-{2-[(6-methoxy-1,2,3,4-tetrahydroisoquinolin-7-yl)amino]quinazolin-7-yl}-4-methylphenyl)acetamide;
(3-{2-[(6-methoxy-1,2,3,4-tetrahydroisoquinolin-7-yl)amino]quinazolin-7-yl}phenyl)(pyrrolidin-1-yl)methanone;
7-(2,3-dihydro-1H-indol-5-yl)-N-(6-methoxy-1,2,3,4-tetrahydroisoquinolin-7-yl)quinazolin-2-amine;
6-{2-[(6-methoxy-1,2,3,4-tetrahydroisoquinolin-7-yl)amino]quinazolin-7-yl}-3,4-dihydroquinolin-2(1H)-one;
7-[3-(2-aminopropan-2-yl)phenyl]-N-(6-methoxy-1,2,3,4-tetrahydroisoquinolin-7-yl)quinazolin-2-amine;
4-fluoro-3-{2-[(6-methoxy-1,2,3,4-tetrahydroisoquinolin-7-yl)amino]quinazolin-7-yl}benzonitrile;
N-(6-methoxy-1,2,3,4-tetrahydroisoquinolin-7-yl)-7-[3-(morpholin-4-yl)phenyl]quinazolin-2-amine;
7-(2-cyclopropylphenyl)-N-(6-methoxy-1,2,3,4-tetrahydroisoquinolin-7-yl)quinazolin-2-amine;
7-(5-amino-2-methylphenyl)-N-(6-methoxy-1,2,3,4-tetrahydroisoquinolin-7-yl)quinazolin-2-amine;
7-(2-fluoro-6-methylphenyl)-N-(6-methoxy-1,2,3,4-tetrahydroisoquinolin-7-yl)quinazolin-2-amine;
6-fluoro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine;
6-chloro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine;
2-[(6-methoxy-2-methyl-1,2,3,4-tetrahydroisoquinolin-7-yl)amino]-7-(8-methyl-2,3-dihydro-1H-pyrido[2,3-b][1,4]oxazin-7-yl)quinazoline-6-carbonitrile;
N-[(3-{2-[(6-methoxy-2-methyl-1,2,3,4-tetrahydroisoquinolin-7-yl)amino]quinazolin-7-yl}phenyl)methyl]acetamide;
(R and S)-5-(3-{2-[(6-methoxy-2-methyl-1,2,3,4-tetrahydroisoquinolin-7-yl)amino]quinazolin-7-yl}phenyl)pyrrolidin-2-one;
N-[2-(3-{2-[(6-methoxy-2-methyl-1,2,3,4-tetrahydroisoquinolin-7-yl)amino]quinazolin-7-yl}phenyl)propan-2-yl]acetamide;
3-{2-[(6-methoxy-2-methyl-1,2,3,4-tetrahydroisoquinolin-7-yl)amino]quinazolin-7-yl}benzamide;
(R and S)-1-(4-{2-[(6-methoxy-2-methyl-1,2,3,4-tetrahydroisoquinolin-7-yl)amino]quinazolin-7-yl}-1H-pyrazol-1-yl)propan-2-ol;
5-{2-[(6-methoxy-2-methyl-1,2,3,4-tetrahydroisoquinolin-7-yl)amino]quinazolin-7-yl}pyridine-2-carbonitrile;
5-{2-[(6-methoxy-2-methyl-1,2,3,4-tetrahydroisoquinolin-7-yl)amino]quinazolin-7-yl}-3-methylpyridine-2-carbonitrile;
N-(6-methoxy-2-methyl-1,2,3,4-tetrahydroisoquinolin-7-yl)-7-(3-methyl-1H-pyrazol-4-yl)quinazolin-2-amine;
6-{2-[(6-methoxy-2-methyl-1,2,3,4-tetrahydroisoquinolin-7-yl)amino]quinazolin-7-yl}-1,3-dihydro-2H-imidazo[4,5-b]pyridin-2-one;
N-(6-methoxy-2-methyl-1,2,3,4-tetrahydroisoquinolin-7-yl)-7-[6-(1H-pyrazol-1-yl)pyridin-3-yl]quinazolin-2-amine;
(5-{2-[(6-methoxy-2-methyl-1,2,3,4-tetrahydroisoquinolin-7-yl)amino]quinazolin-7-yl}pyridin-2-yl)acetonitrile;
N-(6-methoxy-2-methyl-1,2,3,4-tetrahydroisoquinolin-7-yl)-7-[2-(1-methyl-1H-pyrazol-5-yl)phenyl]quinazolin-2-amine;
N-(6-methoxy-2-methyl-1,2,3,4-tetrahydroisoquinolin-7-yl)-7-[2-(5-methyl-1,3,4-oxadiazol-2-yl)phenyl]quinazolin-2-amine;
5-{[6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one;
5-{[6-fluoro-7-(8-methyl-2,3-dihydro-1H-pyrido[2,3-b][1,4]oxazin-7-yl)quinazolin-2-yl]amino}-3,3-dimethyl-2-benzofuran-1(3H)-one;
6-fluoro-7-(8-methyl-2,3-dihydro-1H-pyrido[2,3-b][1,4]oxazin-7-yl)-N-(6-((methylsulfonyl)methyl)pyridin-3-yl)quinazolin-2-amine;
6-fluoro-7-(8-methyl-2,3-dihydro-1H-pyrido[2,3-b][1,4]oxazin-7-yl)-N-(2-methyl-1,2,3,4-tetrahydroisoquinolin-7-yl)quinazolin-2-amine;
6-fluoro-7-(8-methyl-2,3-dihydro-1H-pyrido[2,3-b][1,4]oxazin-7-yl)-N-{4-[(methylsulfonyl)methyl]phenyl}quinazolin-2-amine;
(R or S)-2-(4-{[6-fluoro-7-(8-methyl-2,3-dihydro-1H-pyrido[2,3-b][1,4]oxazin-7-yl)quinazolin-2-yl]amino}phenyl)-N-methylpropanamide;
(R or S)-2-(4-{[6-fluoro-7-(8-methyl-2,3-dihydro-1H-pyrido[2,3-b][1,4]oxazin-7-yl)quinazolin-2-yl]amino}phenyl)-N-methylpropanamide;
(R or S)-5-{[6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide;
(R or S)-5-{[6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide;
1-(4-{[6-fluoro-7-(8-methyl-2,3-dihydro-1H-pyrido[2,3-b][1,4]oxazin-7-yl)quinazolin-2-yl]amino}phenyl)-N-methylcyclopentane-1-carboxamide;
1-(4-{[6-fluoro-7-(8-methyl-2,3-dihydro-1H-pyrido[2,3-b][1,4]oxazin-7-yl)quinazolin-2-yl]amino}phenyl)-N-methylcyclobutane-1-carboxamide;
2,2-difluoro-2-(4-{[6-fluoro-7-(8-methyl-2,3-dihydro-1H-pyrido[2,3-b][1,4]oxazin-7-yl)quinazolin-2-yl]amino}phenyl)-N-methylacetamide;
7-(8-methyl-2,3-dihydro-1H-pyrido[2,3-b][1,4]oxazin-7-yl)-N-{4-[(methylsulfonyl)methyl]phenyl}quinazolin-2-amine;
(R or S)-6-fluoro-7-(8-methyl-2,3-dihydro-1H-pyrido[2,3-b][1,4]oxazin-7-yl)-N-{4-[1-(methylsulfonyl)ethyl]phenyl}quinazolin-2-amine;
(R or S)-3-(4-{[6-fluoro-7-(8-methyl-2,3-dihydro-1H-pyrido[2,3-b][1,4]oxazin-7-yl)quinazolin-2-yl]amino}phenyl)-1-methylpyrrolidin-2-one;
(R or S)-6-fluoro-7-(8-methyl-2,3-dihydro-1H-pyrido[2,3-b][1,4]oxazin-7-yl)-N-{4-[1-(methylsulfonyl)ethyl]phenyl}quinazolin-2-amine;
(R or S)-3-(4-{[6-fluoro-7-(8-methyl-2,3-dihydro-1H-pyrido[2,3-b][1,4]oxazin-7-yl)quinazolin-2-yl]amino}phenyl)-1-methylpyrrolidin-2-one;
6-fluoro-N-(4-((isopropylsulfonyl)methyl)phenyl)-7-(8-methyl-2,3-dihydro-1H-pyrido[2,3-b][1,4]oxazin-7-yl)quinazolin-2-amine;

N-(4-((isopropylsulfonyl)methyl)phenyl)-7-(8-methyl-2,3-dihydro-1H-pyrido[2,3-b][1,4]oxazin-7-yl)quinazolin-2-amine;

2-(4-{[6-fluoro-7-(8-methyl-2,3-dihydro-1H-pyrido[2,3-b][1,4]oxazin-7-yl)quinazolin-2-yl]amino}phenyl)-N-methylacetamide;

2-(4-{[6-fluoro-7-(8-methyl-2,3-dihydro-1H-pyrido[2,3-b][1,4]oxazin-7-yl)quinazolin-2-yl]amino}phenyl)acetamide;

2-(4-{[6-fluoro-7-(8-methyl-2,3-dihydro-1H-pyrido[2,3-b][1,4]oxazin-7-yl)quinazolin-2-yl]amino}phenyl)-N,N-dimethylacetamide;

2-(4-{[6-fluoro-7-(8-methyl-2,3-dihydro-1H-pyrido[2,3-b][1,4]oxazin-7-yl)quinazolin-2-yl]amino}phenyl)-1-(morpholin-4-yl)ethan-1-one;

N-{4-[(ethylsulfonyl)methyl]phenyl}-6-fluoro-7-(8-methyl-2,3-dihydro-1H-pyrido[2,3-b][1,4]oxazin-7-yl)quinazolin-2-amine;

6-fluoro-7-(8-methyl-2,3-dihydro-1H-pyrido[2,3-b][1,4]oxazin-7-yl)-N-(6-methyl-5,6,7,8-tetrahydro-1,6-naphthyridin-3-yl)quinazolin-2-amine;

7-(5-amino-4-methylpyridin-3-yl)-6-fluoro-N~2~-(6-methoxy-2-methyl-1,2,3,4-tetrahydroisoquinolin-7-yl)quinazoline-2,5-diamine;

6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

methyl (3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetate;

6-fluoro-N~2~-(6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetonitrile;

4-{[5-amino-6-fluoro-7-(8-methyl-2,3-dihydro-1H-pyrido[2,3-b][1,4]oxazin-7-yl)quinazolin-2-yl]amino}-3-methoxybenzene-1-sulfonamide;

1-[6-{[5-amino-6-fluoro-7-(8-methyl-2,3-dihydro-1H-pyrido[2,3-b][1,4]oxazin-7-yl)quinazolin-2-yl]amino}-3,4-dihydroquinolin-1(2H)-yl]ethan-1-one;

6-fluoro-7-(8-methyl-2,3-dihydro-1H-pyrido[2,3-b][1,4]oxazin-7-yl)-N~2~-[2-(trifluoromethoxy)phenyl]quinazoline-2,5-diamine;

6-fluoro-7-(8-methyl-2,3-dihydro-1H-pyrido[2,3-b][1,4]oxazin-7-yl)-N~2~-(pyridin-3-yl)quinazoline-2,5-diamine;

(R or S)—N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide;

(R or S)—N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide;

1-[7-{[5-amino-6-fluoro-7-(8-methyl-2,3-dihydro-1H-pyrido[2,3-b][1,4]oxazin-7-yl)quinazolin-2-yl]amino}-6-methoxy-3,4-dihydroisoquinolin-2(1H)-yl]ethan-1-one;

2-(4-{[5-amino-6-fluoro-7-(8-methyl-2,3-dihydro-1H-pyrido[2,3-b][1,4]oxazin-7-yl)quinazolin-2-yl]amino}phenyl)-N-methylacetamide;

6-fluoro-7-(8-methyl-2,3-dihydro-1H-pyrido[2,3-b][1,4]oxazin-7-yl)-N~2~-[3-(methylsulfonyl)phenyl]quinazoline-2,5-diamine;

N-(4-{[5-amino-6-fluoro-7-(8-methyl-2,3-dihydro-1H-pyrido[2,3-b][1,4]oxazin-7-yl)quinazolin-2-yl]amino}phenyl)acetamide;

N-(4-{[5-amino-6-fluoro-7-(8-methyl-2,3-dihydro-1H-pyrido[2,3-b][1,4]oxazin-7-yl)quinazolin-2-yl]amino}phenyl)methanesulfonamide;

6-fluoro-7-(8-methyl-2,3-dihydro-1H-pyrido[2,3-b][1,4]oxazin-7-yl)-N~2~-[4-(methylsulfonyl)phenyl]quinazoline-2,5-diamine;

1-(4-{[5-amino-6-fluoro-7-(8-methyl-2,3-dihydro-1H-pyrido[2,3-b][1,4]oxazin-7-yl)quinazolin-2-yl]amino}phenyl)cyclopropane-1-carbonitrile;

6-fluoro-7-(8-methyl-2,3-dihydro-1H-pyrido[2,3-b][1,4]oxazin-7-yl)-N~2~-(pyrimidin-5-yl)quinazoline-2,5-diamine;

6-fluoro-N~2~-(4-methoxypyridin-3-yl)-7-(8-methyl-2,3-dihydro-1H-pyrido[2,3-b][1,4]oxazin-7-yl)quinazoline-2,5-diamine;

7-{[5-amino-6-fluoro-7-(8-methyl-2,3-dihydro-1H-pyrido[2,3-b][1,4]oxazin-7-yl)quinazolin-2-yl]amino}-6-methoxy-1,3,4,5-tetrahydro-2H-3-benzazepin-2-one;

6-fluoro-N~2~-(2-fluorophenyl)-7-(8-methyl-2,3-dihydro-1H-pyrido[2,3-b][1,4]oxazin-7-yl)quinazoline-2,5-diamine;

4-{[5-amino-6-fluoro-7-(8-methyl-2,3-dihydro-1H-pyrido[2,3-b][1,4]oxazin-7-yl)quinazolin-2-yl]amino}-N-methylbenzamide;

6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

6-fluoro-7-(8-methyl-2,3-dihydro-1H-pyrido[2,3-b][1,4]oxazin-7-yl)-N~2~-phenylquinazoline-2,5-diamine;

N~2~-(2-cyclopropylphenyl)-6-fluoro-7-(8-methyl-2,3-dihydro-1H-pyrido[2,3-b][1,4]oxazin-7-yl)quinazoline-2,5-diamine;

6-fluoro-N~2~-(2-methoxypyridin-3-yl)-7-(8-methyl-2,3-dihydro-1H-pyrido[2,3-b][1,4]oxazin-7-yl)quinazoline-2,5-diamine;

(R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one;

(R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one;

N-[(4-{[5-amino-6-fluoro-7-(8-methyl-2,3-dihydro-1H-pyrido[2,3-b][1,4]oxazin-7-yl)quinazolin-2-yl]amino}phenyl)methyl]acetamide;

N~2~-(2-chlorophenyl)-6-fluoro-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2-methylpyridin-3-yl)quinazoline-2,5-diamine;

3-{[5-amino-6-fluoro-7-(8-methyl-2,3-dihydro-1H-pyrido[2,3-b][1,4]oxazin-7-yl)quinazolin-2-yl]amino}-N-tert-butylbenzene-1-sulfonamide;

3-{[5-amino-6-fluoro-7-(8-methyl-2,3-dihydro-1H-pyrido[2,3-b][1,4]oxazin-7-yl)quinazolin-2-yl]amino}-N-methylbenzene-1-sulfonamide;

(R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

N~2~-(6-methoxy-1,2,3,4-tetrahydroisoquinolin-7-yl)-7-(4-methylpyridin-3-yl)quinazoline-2,5-diamine;

7-(2-fluoro-6-methylphenyl)-N~2~-(6-methoxy-2-methyl-1,2,3,4-tetrahydroisoquinolin-7-yl)quinazoline-2,5-diamine;

7-(5-amino-4-methylpyridin-3-yl)-N~2~-(6-methoxy-2-methyl-1,2,3,4-tetrahydroisoquinolin-7-yl)quinazoline-2,5-diamine;

N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

5-{[5-amino-6-fluoro-7-(8-methyl-2,3-dihydro-1H-pyrido[2,3-b][1,4]oxazin-7-yl)quinazolin-2-yl]amino}-3,3-dimethyl-2-benzofuran-1(3H)-one;

5-{[5-amino-6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one;

5-{[5-amino-6-fluoro-7-(8-methyl-2,3-dihydro-1H-pyrido[2,3-b][1,4]oxazin-7-yl)quinazolin-2-yl]amino}-2,3-dihydro-1H-1-benzothiophene-1,1-dione;

6-fluoro-7-(4-methylpyridin-3-yl)-N~2~-{4-[(methylsulfonyl)methyl]phenyl}quinazoline-2,5-diamine;

6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(R and S)-(7-{[5-amino-6-fluoro-7-(8-methyl-2,3-dihydro-1H-pyrido[2,3-b][1,4]oxazin-7-yl)quinazolin-2-yl]amino}-6-methoxy-2-methyl-1,2,3,4-tetrahydroisoquinolin-1-yl)methanol;

6-fluoro-N~2~-(6-methoxy-2-methyl-1,2,3,4-tetrahydroisoquinolin-7-yl)-7-([1,3]thiazolo[4,5-b]pyridin-6-yl)quinazoline-2,5-diamine;

(R,R and S,S)-6-fluoro-N~2~-(6-methoxy-1,2,3-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-(5-amino-6-fluoro-2-((6-methoxy-2-methyl-1,2,3,4-tetrahydroisoquinolin-7-yl)amino)quinazolin-7-yl)-5-methylbenzo[d]oxazol-2(3H)-one;

6-fluoro-N2-(2-methoxy-4-((methylsulfonyl)methyl)phenyl)-7-(8-methyl-2,3-dihydro-1H-pyrido[2,3-b][1,4]oxazin-7-yl)quinazoline-2,5-diamine;

3-(5-amino-6-fluoro-2-((6-methoxy-2-methyl-1,2,3,4-tetrahydroisoquinolin-7-yl)amino)quinazolin-7-yl)-4-methylbenzonitrile;

3-(5-amino-6-fluoro-2-{[4-(methylsulfonyl)phenyl]amino}quinazolin-7-yl)-4-methylbenzonitrile;

3-[5-amino-6-fluoro-2-({4-[(methylsulfonyl)methyl]phenyl}amino)quinazolin-7-yl]-4-methylbenzonitrile;

(R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one;

(R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine;

(R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine;

(R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one;

4-{[5-amino-6-fluoro-7-(8-methyl-2,3-dihydro-1H-pyrido[2,3-b][1,4]oxazin-7-yl)quinazolin-2-yl]amino}-N-(3-methoxycyclobutyl)benzamide;

6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-fluoro-N~2~-(6-methoxy-2-methyl-1,2,3,4-tetrahydroisoquinolin-7-yl)-7-[2-methyl-4-(1,3-oxazol-2-yl)phenyl]quinazoline-2,5-diamine;

6-fluoro-N~2~-(6-methoxy-2-methyl-1,2,3,4-tetrahydroisoquinolin-7-yl)-7-[4-methyl-6-(1,3-oxazol-2-yl)pyridin-3-yl]quinazoline-2,5-diamine;

(R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine;

(R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine;

N~2~-(6-chloro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

6-fluoro-N~2~-(6-methoxy-2-methyl-1,2,3,4-tetrahydroisoquinolin-7-yl)-7-[2-(1-methyl-1H-pyrazol-5-yl)phenyl]quinazoline-2,5-diamine;

6-fluoro-N~2~-(2-methoxy-6-methylpyridin-3-yl)-7-(8-methyl-2,3-dihydro-1H-pyrido[2,3-b][1,4]oxazin-7-yl)quinazoline-2,5-diamine;

3-(4-{[5-amino-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

1-(5-{[5-amino-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

6-fluoro-N~2~-(4-fluoro-2-methoxyphenyl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

6-fluoro-N~2~-(2-methoxyphenyl)-7-(8-methyl-2,3-dihydro-1H-pyrido[2,3-b][1,4]oxazin-7-yl)quinazoline-2,5-diamine;

6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine;

4-{[5-amino-6-fluoro-7-(8-methyl-2,3-dihydro-1H-pyrido[2,3-b][1,4]oxazin-7-yl)quinazolin-2-yl]amino}-3-methoxy-N-methylbenzamide;

6-fluoro-N~2~-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

6-fluoro-N~2~-(6-methoxy-2-methylpyridin-3-yl)-7-(8-methyl-2,3-dihydro-1H-pyrido[2,3-b][1,4]oxazin-7-yl)quinazoline-2,5-diamine;

5-{[5-amino-6-fluoro-7-(8-methyl-2,3-dihydro-1H-pyrido[2,3-b][1,4]oxazin-7-yl)quinazolin-2-yl]amino}-2-methyl-2,3-dihydro-1H-isoindol-1-one;

(R,S and S,R)-6-fluoro-N2-(2-methyl-1,2,3,4-tetrahydro-1,4-methanoisoquinolin-7-yl)-7-(8-methyl-2,3-dihydro-1H-pyrido[2,3-b][1,4]oxazin-7-yl)quinazoline-2,5-diamine;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclohexane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopropane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclobutane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopentane-1-carboxamide;

6-fluoro-7-(8-methyl-2,3-dihydro-1H-pyrido[2,3-b][1,4]oxazin-7-yl)-N2-(6-((methylsulfonyl)methyl)pyridin-3-yl)quinazoline-2,5-diamine;

(R or S)—N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

(R or S)—N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

7-((5-amino-6-fluoro-7-(8-methyl-2,3-dihydro-1H-pyrido[2,3-b][1,4]oxazin-7-yl)quinazolin-2-yl)amino)-2-methyl-1,2,3,4-tetrahydroisoquinoline-6-carboxamide;

6-fluoro-N2-(7-methoxy-2-methyl-1,2,3,4-tetrahydroisoquinolin-6-yl)-7-(8-methyl-2,3-dihydro-1H-pyrido[2,3-b][1,4]oxazin-7-yl)quinazoline-2,5-diamine;

N2-(4-((ethylsulfonyl)methyl)phenyl)-6-fluoro-7-(8-methyl-2,3-dihydro-1H-pyrido[2,3-b][1,4]oxazin-7-yl)quinazoline-2,5-diamine;

(+ and −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

(+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

(+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

(+ and −)-4-{[5-amino-8-chloro-6-fluoro-7-(8-methyl-2,3-dihydro-1H-pyrido[2,3-b][1,4]oxazin-7-yl)quinazolin-2-yl]amino}-3-methoxy-N-methylbenzamide;

(+ and −)-4-{[5-amino-8-chloro-7-(6-chloro-8-methyl-2,3-dihydro-1H-pyrido[2,3-b][1,4]oxazin-7-yl)-6-fluoroquinazolin-2-yl]amino}-3-methoxy-N-methylbenzamide;

(+ or −)-8-chloro-6-fluoro-N~2~-{2-methoxy-4-[(methylsulfonyl)methyl]phenyl}-7-(8-methyl-2,3-dihydro-1H-pyrido[2,3-b][1,4]oxazin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine;

(+ or −)-8-chloro-6-fluoro-N~2~-{2-methoxy-4-[(methylsulfonyl)methyl]phenyl}-7-(8-methyl-2,3-dihydro-1H-pyrido[2,3-b][1,4]oxazin-7-yl)quinazoline-2,5-diamine;

(+ and −)-8-chloro-6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-[4-(methylsulfonyl)phenyl]quinazoline-2,5-diamine;

8-chloro-6-fluoro-N2-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-N2-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(+ and −)-5-amino-6-fluoro-2-((2'-methyl-2',3'-dihydro-1'H-spiro[cyclopropane-1,4'-isoquinolin]-7'-yl)amino)-7-(8-methyl-2,3-dihydro-1H-pyrido[2,3-b][1,4]oxazin-7-yl)quinazoline-8-carbonitrile;

(+ and −)-6-fluoro-8-methyl-N2-(2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(+ and −)-8-bromo-6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

(+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

6-fluoro-N~2~-{3-fluoro-4-[(methanesulfonyl)methyl]phenyl}-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-{4-[(pyrrolidine-1-sulfonyl)methyl]phenyl}quinazoline-2,5-diamine;

3-(4-{[5-amino-6-fluoro-7-(8-methyl-2,3-dihydro-1H-pyrido[2,3-b][1,4]oxazin-7-yl)quinazolin-2-yl]amino}phenyl)propanenitrile;

6-fluoro-7-(8-methyl-2,3-dihydro-1H-pyrido[2,3-b][1,4]oxazin-7-yl)-N~2~-(2-methyl-2,3,4,5-tetrahydro-1H-2-benzazepin-8-yl)quinazoline-2,5-diamine;

N~2~-(3,4-dihydro-1H-2-benzopyran-7-yl)-6-fluoro-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(3-methyl-2,3,4,5-tetrahydro-1H-3-benzazepin-7-yl)quinazoline-2,5-diamine;

6-fluoro-7-(8-methyl-2,3-dihydro-1H-pyrido[2,3-b][1,4]oxazin-7-yl)-N~2~-(2,3,4,5-tetrahydro-1H-2-benzazepin-8-yl)quinazoline-2,5-diamine;

6-fluoro-7-(8-methyl-2,3-dihydro-1H-pyrido[2,3-b][1,4]oxazin-7-yl)-N~2~-(9-methyl-1,2,3,4-tetrahydro-1,4-epiminonaphthalen-6-yl)quinazoline-2,5-diamine;

6-fluoro-7-(4-methylpyridin-3-yl)-N~2~-(2-methyl-1,2,3,4-tetrahydroisoquinolin-7-yl)quinazoline-2,5-diamine;

7-(8-chloro-2,3-dihydro-1H-pyrido[2,3-b][1,4]oxazin-7-yl)-6-fluoro-N~2~-{4-[(methylsulfonyl)methyl]phenyl}quinazoline-2,5-diamine;

7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine;

(R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-6-yl)quinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-5-yl)quinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-7-yl)quinazoline-2,5-diamine;

(R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine;

6-fluoro-7-(7-methyl-1H-pyrrolo[3,2-b]pyridin-6-yl)-N~2~-(2-methyl-1,2,3,4-tetrahydroisoquinolin-7-yl)quinazoline-2,5-diamine;

(+ or −)-8-chloro-6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

(+ or −)-8-chloro-N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine;

8-chloro-N~-2~-{4-[(ethylsulfonyl)methyl]phenyl}-6-fluoro-7-(8-methyl-2,3-dihydro-1H-pyrido[2,3-b][1,4]oxazin-7-yl)quinazoline-2,5-diamine;

8-chloro-6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

(+ or −)-8-chloro-N~-2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

6-{[5-amino-6-fluoro-7-(8-methyl-2,3-dihydro-1H-pyrido[2,3-b][1,4]oxazin-7-yl)quinazolin-2-yl]amino}-3,4-dihydro-2-benzothiopyran-2,2(1H)-dione;

6-fluoro-N~2~-(2-methyl-1,2,3,4-tetrahydroisoquinolin-7-yl)-7-(1H-pyrrolo[2,3-c]pyridin-4-yl)quinazoline-2,5-diamine;

8-chloro-N~-2~-{4-[(ethylsulfonyl)methyl]phenyl}-6-fluoro-7-(8-methyl-2,3-dihydro-1H-pyrido[2,3-b][1,4]oxazin-7-yl)quinazoline-2,5-diamine;

(R or S)-7-(3,8-dimethyl-2,3-dihydro-1H-pyrido[2,3-b][1,4]oxazin-7-yl)-6-fluoro-N2-(2-methyl-1,2,3,4-tetrahydroisoquinolin-7-yl)quinazoline-2,5-diamine;

6-fluoro-7-(8-methyl-2,3-dihydro-1H-pyrido[2,3-b][1,4]oxazin-7-yl)-N~2~-(6-methyl-5,6,7,8-tetrahydro-2,6-naphthyridin-3-yl)quinazoline-2,5-diamine;

N~2~-{4-[(ethylsulfonyl)methyl]-2-fluorophenyl}-6-fluoro-7-(8-methyl-2,3-dihydro-1H-pyrido[2,3-b][1,4]oxazin-7-yl)quinazoline-2,5-diamine;

N~2~-{4-[(ethylsulfonyl)methyl]-2-fluorophenyl}-6-fluoro-7-(3,3,8-trimethyl-2,3-dihydro-1H-pyrido[2,3-b][1,4]oxazin-7-yl)quinazoline-2,5-diamine;

7-(3,8-dimethyl-2,3-dihydro-1H-pyrido[2,3-b][1,4]oxazin-7-yl)-6-fluoro-N2-(2-isopropyl-1,2,3,4-tetrahydroisoquinolin-7-yl)quinazoline-2,5-diamine;

(R or S)-3-(4-{[5-amino-6-fluoro-7-(8-methyl-2,3-dihydro-1H-pyrido[2,3-b][1,4]oxazin-7-yl)quinazolin-2-yl]amino}phenyl)-1-methylpyrrolidin-2-one;

(R or S)-3-(4-{[5-amino-6-fluoro-7-(8-methyl-2,3-dihydro-1H-pyrido[2,3-b][1,4]oxazin-7-yl)quinazolin-2-yl]amino}phenyl)-1-methylpyrrolidin-2-one;

6-fluoro-N~-2~-{4-[1-(methanesulfonyl)cyclopropyl]phenyl}-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~-2~-{4-[(2,2,2-trifluoroethanesulfonyl)methyl]phenyl}quinazoline-2,5-diamine;

6-fluoro-7-(8-methyl-2,3-dihydro-1H-pyrido[2,3-b][1,4]oxazin-7-yl)-N~2~-(2,4,4-trimethyl-1,2,3,4-tetrahydroisoquinolin-7-yl)quinazoline-2,5-diamine;

7-(2,3-dihydro-1H-pyrido[2,3-b][1,4]oxazin-7-yl)-6-fluoro-N~2~-(2'-methyl-2',3'-dihydro-1'H-spiro[cyclopropane-1,4'-isoquinolin]-7'-yl)quinazoline-2,5-diamine;

7-(8-chloro-2,3-dihydro-1H-pyrido[2,3-b][1,4]oxazin-7-yl)-6-fluoro-N~2~-(2'-methyl-2',3'-dihydro-1'H-spiro[cyclopropane-1,4'-isoquinolin]-7'-yl)quinazoline-2,5-diamine;

7-(5-amino-4-methylpyridin-3-yl)-6-fluoro-N~2~-(2'-methyl-2',3'-dihydro-1'H-spiro[cyclopropane-1,4'-isoquinolin]-7'-yl)quinazoline-2,5-diamine;

N~2~-(4,4-difluoro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

3-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine;

6-fluoro-7-(8-methyl-2,3-dihydro-1H-pyrido[2,3-b][1,4]oxazin-7-yl)-N~2~-(2-methyl-1,2,3,4-tetrahydroisoquinolin-6-yl)quinazoline-2,5-diamine;

3-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine;

(+ and −)-8-chloro-6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine;

6-fluoro-7-(7-methyl-1H-imidazo[4,5-b]pyridin-6-yl)-N~2~-(2-methyl-1,2,3,4-tetrahydroisoquinolin-7-yl)quinazoline-2,5-diamine;

8-chloro-6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol;

6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine;

6-fluoro-N~2~-(2-methyl-1,2,3,4-tetrahydroisoquinolin-7-yl)-7-(3,3,8-trimethyl-2,3-dihydro-1H-pyrido[2,3-b][1,4]oxazin-7-yl)quinazoline-2,5-diamine;

1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol;

6-fluoro-N~2~-(2-methoxy-4-{[(propan-2-yl)sulfonyl]methyl}phenyl)-7-(8-methyl-2,3-dihydro-1H-pyrido[2,3-b][1,4]oxazin-7-yl)quinazoline-2,5-diamine;

8-chloro-6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-[4-(methylsulfinyl)phenyl]quinazoline-2,5-diamine;

6-fluoro-N~2~-[6-fluoro-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

6-fluoro-7-(5-fluoro-2-methylphenyl)-N~2~-{4-[(methylsulfonyl)methyl]phenyl}quinazoline-2,5-diamine;

N~2~-(6-ethylpyridin-3-yl)-6-fluoro-7-(8-methyl-2,3-dihydro-1H-pyrido[2,3-b][1,4]oxazin-7-yl)quinazoline-2,5-diamine;

6-fluoro-7-(5-fluoro-2-methylphenyl)-N~2~-(2-methyl-1,2,3,4-tetrahydroisoquinolin-7-yl)quinazoline-2,5-diamine;

6-fluoro-7-(8-methyl-2,3-dihydro-1H-pyrido[2,3-b][1,4]oxazin-7-yl)-N~2~-[6-(propan-2-yl)-5,6,7,8-tetrahydro-1,6-naphthyridin-3-yl]quinazoline-2,5-diamine;

N~2~-(4-cyclopropyl-2-methoxyphenyl)-6-fluoro-7-(8-methyl-2,3-dihydro-1H-pyrido[2,3-b][1,4]oxazin-7-yl)quinazoline-2,5-diamine;

6-fluoro-N~2~-(2-methoxy-4-methylphenyl)-7-(8-methyl-2,3-dihydro-1H-pyrido[2,3-b][1,4]oxazin-7-yl)quinazoline-2,5-diamine;

1-(4-{[5-amino-6-fluoro-7-(8-methyl-2,3-dihydro-1H-pyrido[2,3-b][1,4]oxazin-7-yl)quinazolin-2-yl]amino}phenyl)-2-methylpropan-2-ol;

(+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ or −)-1-(5-{[5-amino-8-chloro-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

(+ or −)-1-(5-{[5-amino-8-chloro-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

6-fluoro-7-(8-methyl-2,3-dihydro-1H-pyrido[2,3-b][1,4]oxazin-7-yl)-N~2~-(6-methyl-5,6,7,8-tetrahydro-1,6-naphthyridin-3-yl)quinazoline-2,5-diamine;

(+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

2-(4-{[5-amino-6-fluoro-7-(8-methyl-2,3-dihydro-1H-pyrido[2,3-b][1,4]oxazin-7-yl)quinazolin-2-yl]amino}phenyl)-2,2-difluoro-N-methylacetamide;

2-(4-{[5-amino-6-fluoro-7-(8-methyl-2,3-dihydro-1H-pyrido[2,3-b][1,4]oxazin-7-yl)quinazolin-2-yl]amino}phenyl)-N,2-dimethylpropanamide;

5-{[5-amino-6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide;

1-{2-[(6-methoxy-2-methyl-1,2,3,4-tetrahydroisoquinolin-7-yl)amino]quinazolin-7-yl}pyrrolidin-2-one;

(S)-3-{2-[(6-methoxy-2-methyl-1,2,3,4-tetrahydroisoquinolin-7-yl)amino]quinazolin-7-yl}-4-methyl-1,3-oxazolidin-2-one;

(S and R)-3-{2-[(6-methoxy-2-methyl-1,2,3,4-tetrahydroisoquinolin-7-yl)amino]quinazolin-7-yl}-1,7-dioxa-3-azaspiro[4,4]nonan-2-one;

(S and R)-5-(hydroxymethyl)-3-{2-[(6-methoxy-2-methyl-1,2,3,4-tetrahydroisoquinolin-7-yl)amino]quinazolin-7-yl}-1,3-oxazolidin-2-one;

3-{2-[(6-methoxy-2-methyl-1,2,3,4-tetrahydroisoquinolin-7-yl)amino]quinazolin-7-yl}-1-oxa-3,8-diazaspiro[4.5]decan-2-one;

3-{2-[(6-methoxy-2-methyl-1,2,3,4-tetrahydroisoquinolin-7-yl)amino]quinazolin-7-yl}-4,4-dimethyl-1,3-oxazolidin-2-one;

(S and R)-5-(hydroxymethyl)-3-{2-[(6-methoxy-2-methyl-1,2,3,4-tetrahydroisoquinolin-7-yl)amino]quinazolin-7-yl}-5-methyl-1,3-oxazolidin-2-one;

(S and R)-3-{2-[(6-methoxy-2-methyl-1,2,3,4-tetrahydroisoquinolin-7-yl)amino]quinazolin-7-yl}-1-oxa-3,8-diazaspiro[4.6]undecan-2-one;

(S and R)-5-(2-hydroxypropan-2-yl)-3-{2-[(6-methoxy-2-methyl-1,2,3,4-tetrahydroisoquinolin-7-yl)amino]quinazolin-7-yl}-1,3-oxazolidin-2-one;

(4R)-3-{2-[(6-methoxy-2-methyl-1,2,3,4-tetrahydroisoquinolin-7-yl)amino]quinazolin-7-yl}-4-(propan-2-yl)-1,3-oxazolidin-2-one;

(S and R)-5-(aminomethyl)-3-{2-[(6-methoxy-2-methyl-1,2,3,4-tetrahydroisoquinolin-7-yl)amino]quinazolin-7-yl}-1,3-oxazolidin-2-one;

(S and R)-3-{2-[(6-methoxy-2-methyl-1,2,3,4-tetrahydroisoquinolin-7-yl)amino]quinazolin-7-yl}-5-[(methylamino)methyl]-1,3-oxazolidin-2-one;

(S or R)-4-ethyl-3-{2-[(6-methoxy-2-methyl-1,2,3,4-tetrahydroisoquinolin-7-yl)amino]quinazolin-7-yl}-1,3-oxazolidin-2-one;

(S or R)-4-ethyl-3-{2-[(6-methoxy-2-methyl-1,2,3,4-tetrahydroisoquinolin-7-yl)amino]quinazolin-7-yl}-1,3-oxazolidin-2-one;

(S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one;

(S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one;

(S)-3-{5-amino-2-[(6-methoxy-2-methyl-1,2,3,4-tetrahydroisoquinolin-7-yl)amino]quinazolin-7-yl}-4-methyl-1,3-oxazolidin-2-one;

3-[({2-[(6-methoxy-2-methyl-1,2,3,4-tetrahydroisoquinolin-7-yl)amino]quinazolin-7-yl}amino)methyl]-7-methyl-1lambda~6~,2,4-benzothiadiazine-1,1(4H)-dione;

(S and R)—N-(6-methoxy-2-methyl-1,2,3,4-tetrahydroisoquinolin-7-yl)-7-[3-methyl-5-(pyrrolidin-2-yl)-1H-1,2,4-triazol-1-yl]quinazolin-2-amine;

(S and R)-1-[(1-{2-[(6-methoxy-2-methyl-1,2,3,4-tetrahydroisoquinolin-7-yl)amino]quinazolin-7-yl}piperidin-3-yl)methyl]pyrrolidin-2-one;

7-({2-[(6-methoxy-2-methyl-1,2,3,4-tetrahydroisoquinolin-7-yl)amino]quinazolin-7-yl}amino)-3,4-dihydroisoquinolin-1(2H)-one;

cyclopropyl[(3S)-3-({2-[(6-methoxy-2-methyl-1,2,3,4-tetrahydroisoquinolin-7-yl)amino]quinazolin-7-yl}amino)pyrrolidin-1-yl]methanone;

6-({2-[(6-methoxy-2-methyl-1,2,3,4-tetrahydroisoquinolin-7-yl)amino]quinazolin-7-yl}amino)-2-methyl-2,3-dihydro-1H-isoindol-1-one;

N~2~-(6-methoxy-2-methyl-1,2,3,4-tetrahydroisoquinolin-7-yl)-N~7~-[2-methyl-5-(methylsulfonyl)phenyl]quinazoline-2,7-diamine;

7-[({2-[(6-methoxy-2-methyl-1,2,3,4-tetrahydroisoquinolin-7-yl)amino]quinazolin-7-yl}amino)methyl]-3-methyl-1lambda~6~,2,4-benzothiadiazine-1,1(4H)-dione;

(S and R)-5-[({2-[(6-methoxy-2-methyl-1,2,3,4-tetrahydroisoquinolin-7-yl)amino]quinazolin-7-yl}amino)methyl]-1,3-oxazolidin-2-one;

6-({2-[(6-methoxy-2-methyl-1,2,3,4-tetrahydroisoquinolin-7-yl)amino]quinazolin-7-yl}amino)pyridine-2-carbonitrile;

6-[({2-[(6-methoxy-2-methyl-1,2,3,4-tetrahydroisoquinolin-7-yl)amino]quinazolin-7-yl}amino)methyl]-2,3-dihydro-1H-isoindol-1-one;

[6-({2-[(6-methoxy-2-methyl-1,2,3,4-tetrahydroisoquinolin-7-yl)amino]quinazolin-7-yl}amino)pyridin-2-yl]methanol;

(S and R)-5-{[{2-[(6-methoxy-2-methyl-1,2,3,4-tetrahydroisoquinolin-7-yl)amino]quinazolin-7-yl}(methyl)amino]methyl}-1,3-oxazolidin-2-one;

[3-({2-[(6-methoxy-2-methyl-1,2,3,4-tetrahydroisoquinolin-7-yl)amino]quinazolin-7-yl}amino)phenyl]methanol;

1-[6-({2-[(6-methoxy-2-methyl-1,2,3,4-tetrahydroisoquinolin-7-yl)amino]quinazolin-7-yl}amino)-2,3-dihydro-1H-indol-1-yl]ethan-1-one;

N~2~-(6-methoxy-2-methyl-1,2,3,4-tetrahydroisoquinolin-7-yl)-N~7~-[3-(methylsulfonyl)phenyl]quinazoline-2,7-diamine;

3-({2-[(6-methoxy-2-methyl-1,2,3,4-tetrahydroisoquinolin-7-yl)amino]quinazolin-7-yl}amino)-N,N-dimethylbenzamide;

[2-({2-[(6-methoxy-2-methyl-1,2,3,4-tetrahydroisoquinolin-7-yl)amino]quinazolin-7-yl}amino)pyrimidin-4-yl]methanol;

N~7~-[2-fluoro-5-(methylsulfonyl)phenyl]-N~2~-(6-methoxy-2-methyl-1,2,3,4-tetrahydroisoquinolin-7-yl)quinazoline-2,7-diamine;

(S and R)-3-[({2-[(6-methoxy-2-methyl-1,2,3,4-tetrahydroisoquinolin-7-yl)amino]quinazolin-7-yl}amino)methyl]-1lambda~6~-thiolane-1,1-dione;

1-[4-({2-[(6-methoxy-2-methyl-1,2,3,4-tetrahydroisoquinolin-7-yl)amino]quinazolin-7-yl}amino)piperidin-1-yl]ethan-1-one;

(±)-3-({2-[(6-methoxy-2-methyl-1,2,3,4-tetrahydroisoquinolin-7-yl)amino]quinazolin-7-yl}amino)cyclohexan-1-ol;

[2-({2-[(6-methoxy-2-methyl-1,2,3,4-tetrahydroisoquinolin-7-yl)amino]quinazolin-7-yl}amino)pyridin-4-yl]methanol;

2-({2-[(6-methoxy-2-methyl-1,2,3,4-tetrahydroisoquinolin-7-yl)amino]quinazolin-7-yl}amino)pyridine-4-carboxamide;

N~7~-[2,4-dimethyl-5-(methylsulfonyl)phenyl]-N~2~-(6-methoxy-2-methyl-1,2,3,4-tetrahydroisoquinolin-7-yl)quinazoline-2,7-diamine;

1-[3-({2-[(6-methoxy-2-methyl-1,2,3,4-tetrahydroisoquinolin-7-yl)amino]quinazolin-7-yl}amino)phenyl]-3-methylimidazolidin-2-one;

5-({2-[(6-methoxy-2-methyl-1,2,3,4-tetrahydroisoquinolin-7-yl)amino]quinazolin-7-yl}amino)-2-methylbenzene-1-sulfonamide;

(5S)-5-[({2-[(6-methoxy-2-methyl-1,2,3,4-tetrahydroisoquinolin-7-yl)amino]quinazolin-7-yl}amino)methyl]pyrrolidin-2-one;

(1s,4s)-4-((2-((6-methoxy-2-methyl-1,2,3,4-tetrahydroisoquinolin-7-yl)amino)quinazolin-7-yl)amino)cyclohexan-1-ol;

(S)—N2-(6-methoxy-2-methyl-1,2,3,4-tetrahydroisoquinolin-7-yl)-N7-(oxepan-4-yl)quinazoline-2,7-diamine;

(4S)-4-[({2-[(6-methoxy-2-methyl-1,2,3,4-tetrahydroisoquinolin-7-yl)amino]quinazolin-7-yl}amino)methyl]-1-methylpyrrolidin-2-one;

(3S)-3-({2-[(6-methoxy-2-methyl-1,2,3,4-tetrahydroisoquinolin-7-yl)amino]quinazolin-7-yl}amino)-1-methylpyrrolidin-2-one;

3-[(3S)-1-{2-[(6-methoxy-2-methyl-1,2,3,4-tetrahydroisoquinolin-7-yl)amino]quinazolin-7-yl}piperidin-3-yl]-1,3-oxazolidin-2-one;

N~7~-(3-methoxycyclobutyl)-N~2~-(6-methoxy-2-methyl-1,2,3,4-tetrahydroisoquinolin-7-yl)quinazoline-2,7-diamine;

N~2~-(6-methoxy-2-methyl-1,2,3,4-tetrahydroisoquinolin-7-yl)-N~7~-[(5-methyl-1,2,4-oxadiazol-3-yl)methyl]quinazoline-2,7-diamine;

1-{2-[(6-methoxy-2-methyl-1,2,3,4-tetrahydroisoquinolin-7-yl)amino]quinazolin-7-yl}azetidine-3-carboxamide;

(S and R)-1-{2-[(6-methoxy-2-methyl-1,2,3,4-tetrahydroisoquinolin-7-yl)amino]quinazolin-7-yl}-3-(trifluoromethyl)azetidin-3-ol N~2~-(6-methoxy-2-methyl-1,2,3,4-tetrahydroisoquinolin-7-yl)-N~7~-(3-methyloxetan-3-yl)quinazoline-2,7-diamine;

(S and R)-3-({2-[(6-methoxy-2-methyl-1,2,3,4-tetrahydroisoquinolin-7-yl)amino]quinazolin-7-yl}amino)-1-methylpyrrolidin-2-one;

N-(6-methoxy-2-methyl-1,2,3,4-tetrahydroisoquinolin-7-yl)-7-(3-methyl-5,6-dihydro[1,2,4]triazolo[4,3-a]pyrazin-7(8H)-yl)quinazolin-2-amine;

(1S,2S)-2-({2-[(6-methoxy-2-methyl-1,2,3,4-tetrahydroisoquinolin-7-yl)amino]quinazolin-7-yl}amino)cyclopentan-1-ol;

(S and R)-4-[({2-[(6-methoxy-2-methyl-1,2,3,4-tetrahydroisoquinolin-7-yl)amino]quinazolin-7-yl}amino)methyl]-1-methylpyrrolidin-2-one;

(±)-5-{2-[(6-methoxy-2-methyl-1,2,3,4-tetrahydroisoquinolin-7-yl)amino]quinazolin-7-yl}hexahydro-1lambda~6~-thieno[2,3-c]pyrrole-1,1(2H)-dione;

1-({2-[(6-methoxy-2-methyl-1,2,3,4-tetrahydroisoquinolin-7-yl)amino]quinazolin-7-yl}amino)-N,N-dimethylcyclobutane-1-carboxamide;

N~2~-(6-methoxy-2-methyl-1,2,3,4-tetrahydroisoquinolin-7-yl)-N~7~-[(3-methyloxetan-3-yl)methyl]quinazoline-2,7-diamine;

N~2~-(6-methoxy-2-methyl-1,2,3,4-tetrahydroisoquinolin-7-yl)-N~7~-[(1,2,5-thiadiazol-3-yl)methyl]quinazoline-2,7-diamine;

2-({2-[(6-methoxy-2-methyl-1,2,3,4-tetrahydroisoquinolin-7-yl)amino]quinazolin-7-yl}amino)-1-(morpholin-4-yl)ethan-1-one;

2-({2-[(6-methoxy-2-methyl-1,2,3,4-tetrahydroisoquinolin-7-yl)amino]quinazolin-7-yl}amino)-1-(pyrrolidin-1-yl)ethan-1-one;

1-({2-[(6-methoxy-2-methyl-1,2,3,4-tetrahydroisoquinolin-7-yl)amino]quinazolin-7-yl}amino)-N,N-dimethylcyclopropane-1-carboxamide;

N~7~-[(3R,4R)-4-fluorooxolan-3-yl]-N~2~-(6-methoxy-2-methyl-1,2,3,4-tetrahydroisoquinolin-7-yl)quinazoline-2,7-diamine;

7-[3-(methoxymethyl)azetidin-1-yl]-N-(6-methoxy-2-methyl-1,2,3,4-tetrahydroisoquinolin-7-yl)quinazolin-2-amine;

(S and R)—N~2~-(6-methoxy-2-methyl-1,2,3,4-tetrahydroisoquinolin-7-yl)-N~7~-(oxan-3-yl)quinazoline-2,7-diamine;

N~2~-{2-[(6-methoxy-2-methyl-1,2,3,4-tetrahydroisoquinolin-7-yl)amino]quinazolin-7-yl}-N-methylglycinamide N~2~-{2-[(6-methoxy-2-methyl-1,2,3,4-tetrahydroisoquinolin-7-yl)amino]quinazolin-7-yl}-N,N-dimethylglycinamide N~7~-[(1,5-dimethyl-1H-pyrazol-3-yl)methyl]-N~2~-(6-methoxy-2-methyl-1,2,3,4-tetrahydroisoquinolin-7-yl)quinazoline-2,7-diamine;

1-cyclopropyl-4-{2-[(6-methoxy-2-methyl-1,2,3,4-tetrahydroisoquinolin-7-yl)amino]quinazolin-7-yl}piperazin-2-one;

N~2~-(6-methoxy-2-methyl-1,2,3,4-tetrahydroisoquinolin-7-yl)-N~7~-(3-oxabicyclo[3.1.0]hexan-6-yl)quinazoline-2,7-diamine;

(S and R)—N~2~-(6-methoxy-2-methyl-1,2,3,4-tetrahydroisoquinolin-7-yl)-N~7~-[(3-methyloxolan-3-yl)methyl]quinazoline-2,7-diamine;

(S)-3-(5-amino-2-((4-(methylsulfonyl)phenyl)amino)quinazolin-7-yl)-4-methyloxazolidin-2-one;

(R)-3-(5-amino-2-((4-(methylsulfonyl)phenyl)amino)quinazolin-7-yl)-4-methyloxazolidin-2-one;

(S)-3-(5-amino-2-((4-((methylsulfonyl)methyl)phenyl)amino)quinazolin-7-yl)-4-methyloxazolidin-2-one;

4-({5-amino-7-[(4S)-4-methyl-2-oxo-1,3-oxazolidin-3-yl]quinazolin-2-yl}amino)-N-methylbenzamide;

[2-({5-amino-6-fluoro-2-[(6-methoxy-2-methyl-1,2,3,4-tetrahydroisoquinolin-7-yl)amino]quinazolin-7-yl}amino)pyridin-4-yl]methanol;

N-(6-methoxy-2-methyl-1,2,3,4-tetrahydroisoquinolin-7-yl)-7-{[6-(piperazin-1-yl)pyridin-3-yl]methoxy}quinazolin-2-amine;

7-[(2,3-dihydro-1H-isoindol-5-yl)methoxy]-N-(6-methoxy-2-methyl-1,2,3,4-tetrahydroisoquinolin-7-yl)quinazolin-2-amine;

N-(6-methoxy-2-methyl-1,2,3,4-tetrahydroisoquinolin-7-yl)-7-[(piperidin-4-yl)methoxy]quinazolin-2-amine;

N-(6-methoxy-2-methyl-1,2,3,4-tetrahydroisoquinolin-7-yl)-7-{[1-(6-methylpyrazin-2-yl)piperidin-4-yl]methoxy}quinazolin-2-amine;

N-(6-methoxy-2-methyl-1,2,3,4-tetrahydroisoquinolin-7-yl)-7-[(1H-pyrazol-4-yl)oxy]quinazolin-2-amine;

[4-({2-[(6-methoxy-2-methyl-1,2,3,4-tetrahydroisoquinolin-7-yl)amino]quinazolin-7-yl}oxy)phenyl](4-methylpiperazin-1-yl)methanone;

1-{4-[4-({2-[(6-methoxy-2-methyl-1,2,3,4-tetrahydroisoquinolin-7-yl)amino]quinazolin-7-yl}oxy)phenyl]piperazin-1-yl}ethan-1-one;

7-{4-[(1S)-1-aminoethyl]phenoxy}-N-(6-methoxy-2-methyl-1,2,3,4-tetrahydroisoquinolin-7-yl)quinazolin-2-amine;

N~2~-(6-methoxy-2-methyl-1,2,3,4-tetrahydroisoquinolin-7-yl)-7-[(1,2,3,4-tetrahydroisoquinolin-6-yl)oxy]quinazoline-2,5-diamine;

7-((1r,4r)-4-aminocyclohexyl)-N-(6-methoxy-2-methyl-1,2,3,4-tetrahydroisoquinolin-7-yl)quinazolin-2-amine; and 7-((1r,4r)-4-(aminomethyl)cyclohexyl)-N-(6-methoxy-2-methyl-1,2,3,4-tetrahydroisoquinolin-7-yl)quinazolin-2-amine;

or a pharmaceutically acceptable salt thereof.

In one embodiment, the present invention is a composition comprising a compound of formula I, II, IIa, IIb, IIc, IId, III, IIIa, IIIb, IIIc, IIId, IV, IVa, IVb, or a pharmaceutically acceptable salt thereof, and at least one pharmaceutically acceptable carrier.

In another embodiment, the present invention is a method of treating cancer, metastasis, inflammation and auto-immune pathogenesis comprising administering to a patient in need thereof a composition of formula I, II, IIa, IIb, IIc, IId, III, IIIa, IIIb, IIIc, IIId, IV, IVa, IVb, or a pharmaceutically acceptable salt thereof.

In another embodiment, the present invention is the use of a compound of formula I, II, IIa, IIb, IIc, IId, III, IIIa, IIIb, IIIc, IIId, IV, IVa, IVb, or a pharmaceutically acceptable salt thereof, in the manufacture of a medicament for treating cancer, metastasis, inflammation and auto-immune pathogenesis.

In another embodiment, the present invention includes compounds of formula I, II, IIa, IIb, IIc, IId, III, IIIa, IIIb, IIIc, IId, IV, IVa, IVb, or a pharmaceutically acceptable salt thereof, for use in the treatment of cancer, metastasis, inflammation and auto-immune pathogenesis.

Also disclosed herein is a method of inhibiting activity of haematopoietic progenitor kinase 1 (HPK1) comprising contacting HPK1 with a compound disclosed herein, or a pharmaceutically acceptable salt thereof.

Also disclosed herein is a method of treating cancer, metastasis, inflammation and auto-immune pathogenesis, comprising administering to a patient suffering from at least one of said diseases or disorder an effective amount of a compound disclosed herein, or a pharmaceutically acceptable salt thereof.

Also disclosed herein is a method of treating melanoma in a patient comprising administering to said patient an effective amount of a compound disclosed herein, or a pharmaceutically acceptable salt thereof.

The present invention relates to compounds and compositions that are capable of inhibiting the activity of HPK1. The invention features methods of treating, preventing or ameliorating a disease or disorder in which HPK1 plays a role by administering to a patient in need thereof a therapeutically effective amount of a compound of Formula (I), or a pharmaceutically acceptable salt thereof. The invention also features methods of treating, preventing or ameliorating a disease or disorder in which HPK1 plays a role by administering to a patient in need thereof a therapeutically effective amount of a compound of Formula (II), or a pharmaceutically acceptable thereof. The methods of the present invention can be used in the treatment of a variety of HPK1 dependent diseases and disorders by inhibiting the activity of HPK1 enzymes. Inhibition of HPK1 provides a novel approach to the treatment, prevention, or amelioration of diseases including, but not limited to, cancer and metastasis Further disclosed herein is a compound disclosed herein, or a pharmaceutically acceptable salt thereof, for use in therapy. In one embodiment, disclosed herein is the use of a compound disclosed herein, or a pharmaceutically acceptable salt thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Cycloalkyl" refers to a non-aromatic ring system comprising from 3 to 6 ring carbon atoms. Non-limiting examples of monocyclic cycloalkyl include cyclopropyl, cyclobutyl, cyclopentyl. Non-limiting examples of cycloalkyl additionally include bicyclic spiro-cycloalkyl including spirohexane ( 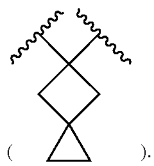 ).

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

'H' refers to hydrogen.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein, "Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

"Celite®" (Fluka) diatomite is diatomaceous earth and can be referred to as "celite".

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers-Diastereomers-Geometric Isomers-Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

Regarding stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated based on the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. A basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^{2}H$ (i.e., Deuterium or "D"), $^{3}H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Substitution with positron emitting isotopes, such as $^{11}C$, $^{18}F$, $^{15}O$ and $^{13}N$, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of haematopoietic progenitor kinase 1 (HPK1). For example, the compounds disclosed herein can potentially be used to inhibit activity of HPK1 in cell or in an individual in need of modulation of the enzyme by administering an effective amount of a compound.

Also disclosed herein are methods of treating diseases associated with activity or expression, including abnormal activity and/or overexpression, of HPK1 in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the HPK1 enzyme, such as over expression or abnormal activity. An HPK1-associated disease can also include any disease, disorder or condition that may be prevented, ameliorated, or cured by modulating enzyme activity.

Examples of HPK1-associated diseases include cancer, metastasis, inflammation and auto-immune pathogenesis. Example cancers potentially treatable by the methods herein include cancer of the colon, pancreas, breast, prostate, lung, brain, ovary, cervix, testes, renal, head and neck, lymphoma, leukemia, melanoma, and the like. In some embodiments, the cancer is selected from liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer. Hodgkin lymphoma and diffuse large B-cell lymphoma. Another aspect of the invention relates to a method of inducing cell cycle arrest, apoptosis in tumor cells, and/or enhanced tumor-specific T cell immunity. The method comprises contacting the cells with an effective amount of a compound of Formula (I). In another embodiment, the present invention relates to a compound of Formula (I) or a pharmaceutical composition comprising a compound of the present invention and a pharmaceutically acceptable carrier used for the treatment of cancers including, but not limited to, liposarcoma, neuroblastoma, glioblastoma, bladder cancer, adrenocortical cancer, multiple myeloma, colorectal cancer, non-small cell lung cancer, oropharyngeal cancer, penis cancer, anal cancer, thyroid cancer, vaginal cancer, gastric cancer, rectal cancer, thyroid cancer, Hodgkin lymphoma and diffuse large B-cell lymphoma. In some embodiments, administration of a compound of Formula (I) or a pharmaceutical composition comprising a compound of the present invention and a pharmaceutically acceptable carrier induces a change in the cell cycle or cell viability As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the HPK1 enzyme with a compound disclosed herein includes the administration of a compound of the present invention to an individual or patient, such as a human, as well as, for example, introducing a compound of the invention into a sample containing a cellular or purified preparation containing the HPK1 enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with HPK1 enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit HPK1 enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an HPK1 enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy: the desired therapeutic effect, and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with HPK1 enzyme activity comprising administration of an effective amount of a compound disclosed herein to a subject in need of treatment thereof. In one embodiment, the disease or disorder associated with an HPK1 enzyme is a cell proliferation disorder.

In one embodiment, disclosed herein is the use of a compound disclosed herein in a therapy. The compound may be useful in a method of inhibiting HPK1 enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to HPK1 enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared using a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein, and other active agents will generally also be within the aforementioned range, but in each case, an effective dose of each active agent should be used. In such combinations, the compound disclosed herein, and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with HPK1 enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with HPK1 enzyme activity, wherein the medicament is prepared for administration with another active agent. The invention also provides the use of another active agent for treating a disease or disorder associated with an HPK1 enzyme, wherein the medicament is administered with a compound disclosed herein.

The invention also provides the use of a compound disclosed herein for treating a disease or disorder associated with HPK1 enzyme activity, wherein the patient has previously (e.g. within 24 hours) been treated with another active agent. The invention also provides the use of another therapeutic agent for treating a disease or disorder associated with HPK1 enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinyimethyj)amino]-3-pyfidinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinonmcin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as daunorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, $F(ab')_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL PROCEDURES

The following examples are intended to be illustrative only and not limiting in any way. Abbreviations not indicated below have their meanings as conventionally used in the art unless specifically stated otherwise.

| | |
|---|---|
| ACN or MeCN | acetonitrile |
| AcOH | acetic acid |
| t-AmOH or tert-AmOH | tert-Amyl alcohol |
| BrettPhos-Pd-G3 | [(2-di-cyclohexylphosphino-3,6-dimethoxy-2',4',6'-triisopropyl-1,1'-biphenyl)-2-(2'-amino-1,1'-biphenyl)]palladium(II) methanesulfonate methanesulfonate |
| t-BuBrettPhos | 2-(di-tert-butylphosphino)-2',4',6'-triisopropyl-3,6-dimethoxy-1,1'-biphenyl |
| t-BuBrettPhos-Pd-G3 | [(2-di-tert-butylphosphino-3,6-dimethoxy-2',4',6'-triisopropyl-1,1'-biphenyl)-2-(2'-amino-1,1'-biphenyl)]palladium(II) methanesulfonate |
| BisPin | bis(pinacolato)diboron |
| Boc | tert-butoxycarbamate |
| $Boc_2O$ | di-tert-butyl dicarbonate |
| DCM | dichloromethane |
| DIEA | diisopropylethylamine |
| DMA | dimethylacetamide |
| DMF | dimethylformamide |
| DMSO | dimethylsulfoxide |
| EI | electron ionization |
| EtOAc | ethyl acetate |
| EtOH | ethanol |
| $^1H$ NMR | proton nuclear magnetic resonance (data) |
| HPLC | high performance liquid chromatography |
| KOAc | potassium acetate |
| $K_3PO_4$ | potassium phosphate |
| LC/MS | liquid chromatography coupled to mass spectrometer |
| LiHMDS | lithium hexamethyldisilazide or lithium bis(trimethylsilyl)amide |
| MeCN | acetonitrile |
| MeOH | methanol |
| MHz | megahertz |
| MS | mass spectrum (data) |
| NBS | N-bromosuccinimide |
| NCS | N-chlorosuccinimide |
| MTBE | methyl tert-butyl ether |
| $N(Et)_3$ | triethylamine |
| NMR | nuclear magnetic resonance (data) |
| $Na_2SO_4$ | sodium sulfate |
| $NaBH(OAc)_3$ | sodium triacetoxyborohydride |
| NaOAc | sodium acetate |
| $PdCl_2$(dppf) | 1,1'-bis(diphenylphosphino)ferrocene-palladium(II)dichloride |
| $PdCl_2$(dtbpf) | [1,1'-bis(di-tert-butylphosphino)ferrocene]dichloropalladium(II) |
| $Pd(PPh_3)_4$ | tetrakis(triphenylphosphine)palladium(0) |
| $Pd[(t-Bu)_3P]_2$ | bis(tri-tert-butylphosphine)palladium(0) |
| $Pd_2(dba)_3$ | tris(dibenzylideneacetone)dipalladium(0) |
| $Pd(PPb_3)_2Cl_2$ | bis(triphenylphosphine)palladium(II) dichloride |
| PMB | para-methoxybenzyl |
| PPA | polyphosphoric acid |
| $i-Pr_2Net$ | N,N-diisopropylethylamine |
| RT | room temperature |
| TFA | trifluoroacetic acid |
| THF | tetrahydrofuran |
| TMSCl | trimethylsilyl chloride |
| TLC | thin layer chromatography |
| Xphos | 2-dicyclohexylphosphino-2',4',6'-triisopropylbiphenyl |
| G2-XPhos Precatalyst | chloro(2-dicyclohexylphosphino-2',4',6'-triisopropyl-1,1'-biphenyl)[2-(2'-amino-1,1'-biphenyl)]palladium(II) |

General Synthetic Schemes

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

While the present invention has been described in conjunction with the specific examples set forth below, many alternatives, modifications, and variations thereof will be apparent to those of ordinary skill in the art. All such alternatives, modifications, and variations are intended to fall within the spirit and scope of the present invention.

Methods of Synthesis

The compounds in the present invention can be prepared according to the following general schemes using appropriate materials and are further exemplified by the subsequent specific examples. The compounds illustrated in the examples are not to be construed as forming the only genus that is considered as the invention. The illustrative examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated, all reactions were stirred (mechanically, stir bar/stir plate, or shaken) and conducted under an inert atmosphere of nitrogen or argon unless specifically stated otherwise. All temperatures are degrees Celsius (° C.) unless otherwise noted. Ambient temperature is 15-25° C. Most compounds were purified by reverse-phase preparative HPLC, MPLC on silica gel, recrystallization and/or trituration (suspension in a solvent followed by filtration of the solid). The course of the reactions was followed by thin layer chromatography (TLC) and/or LC/MS and/or NMR and reaction times are given for illustration only. All end products were analyzed by NMR and LC/MS. Intermediates were analyzed by NMR and/or TLC and/or LC/MS.

General Synthetic Schemes

Several synthetic methods were employed to access the compounds described herein. Final compounds were evaluated for biological activity in the kinase activity assay in either the neutral form, as a TFA salt, or as a HCl salt, and were screened in the kinase activity assay as either the racemate or as resolved enantiomers and diastereomers. The chiral separations were conducted on either the final compounds or on a synthetic intermediate. Chiral separation conditions are noted where appropriate.

Scheme G-1

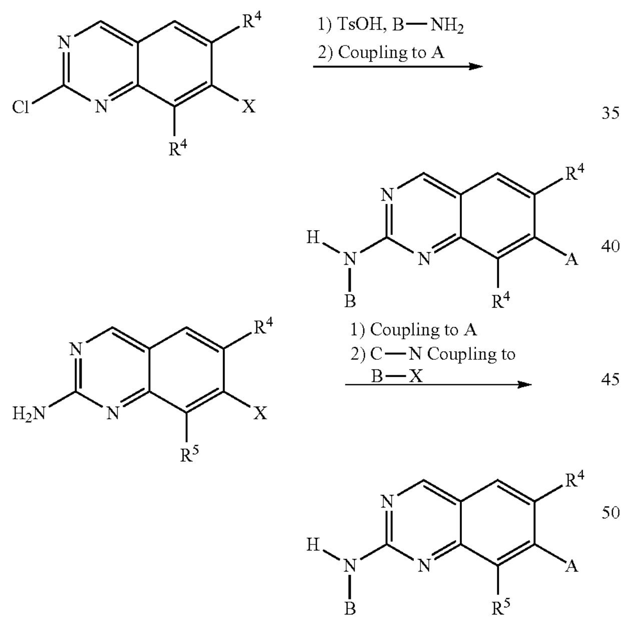

Two general synthetic approaches are outline in Scheme G-1. One in which a substituted 7-bromo-2-chloroquinazoline is first reacted with functionalized aniline or aminoheteroaryl under acid-mediated conditions to give an advanced intermediate with the B group in place. Next, the A group is introduced at the quinazoline C(7) position by Pd-catalyzed C—C, C—N, or C—O coupling, or Ni-catalyzed C—C coupling in the case of $sp^3C$-containing groups.

Conversely, an appropriately substituted 2-amino-7-bromo-quinazoline is used as a precursor, in which the A group is introduced at C(7) position of the quinazoline first. Next, the corresponding advanced intermediate is treated with an aryl halide or heteroaryl halide in the presence of Pd catalyst to install the B group.

Scheme G-2

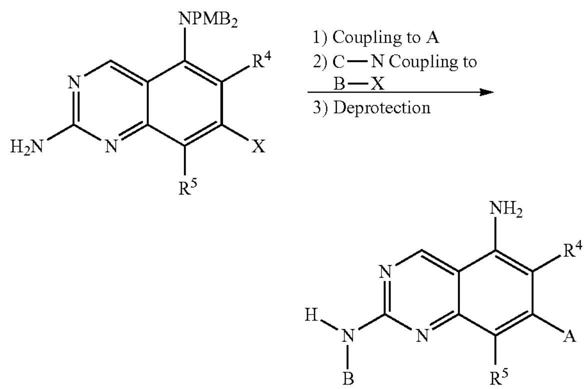

Compounds bearing an amine functional group at the 5-position of the quinazoline ring ($R^3$=$NH_2$) are prepared as shown in Schemes G-2 and G-3. For these compounds, the synthetic sequence is modified in several ways, one shown in Scheme G-2. One modification is to prepare a substituted 2-amino-7-bromoquinazoline bearing an $N(PMB)_2$ group at the 5-position of the quinazoline. Similar to the methods described in Scheme G-1, introduction of the A group at the quinazoline 7-position by Pd-catalyzed C—C, C—N, or C—O coupling, or Ni-catalyzed C—C coupling in the case of $sp^3C$-containing groups is then followed by C—N coupling with aryl halides or heteroaryl halides to introduce the B group. This provides an advanced intermediate bearing the $N(PMB)_2$ group at the 5-position of the quinazoline; acid-mediated deprotection finally provides the final amine-bearing compounds with $R^3$=$NH_2$.

Scheme G-3

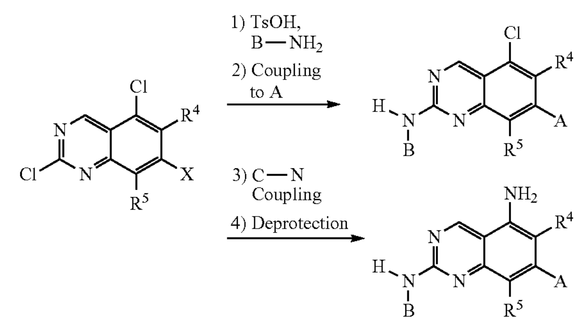

Another modification used to introduce an amine at the 5-position of the quinazoline ($R^3$=$NH_2$) is outlined in Scheme G-3. Here, a chlorine substituent is employed as a handle to later introduce the amine at the 5-position. In this case, a substituted 7-bromo-2,5-dichloroquinazoline is reacted with an aniline or aminoheteroaryl in the presence of acid to install the B group. Next the A group is installed at the 7-position by Pd-catalyzed C—C, C—N, or C—O coupling, or Ni-catalyzed C—C coupling in the case of $sp^3C$-containing groups. This leaves an advanced intermediate functionalized with the A and B group in place. Finally, the C(5)-Cl substituent is converted to a protected amine by Pd-mediated coupling to $NH_2$-Boc reagent, followed by acid-mediated deprotection to provide compounds bearing an amine at C(5) of the quinazoline.

SYNTHESIS OF COMMON INTERMEDIATES

Preparation of Intermediate I-1 (tert-butyl 7-Amino-6-methoxy-1,2,3,4-tetrahydroisoquinoline-2-carboxylate)

Intermediate I-1 was prepared from 2-(3-methoxyphenyl) ethan-1-amine as outlined below.

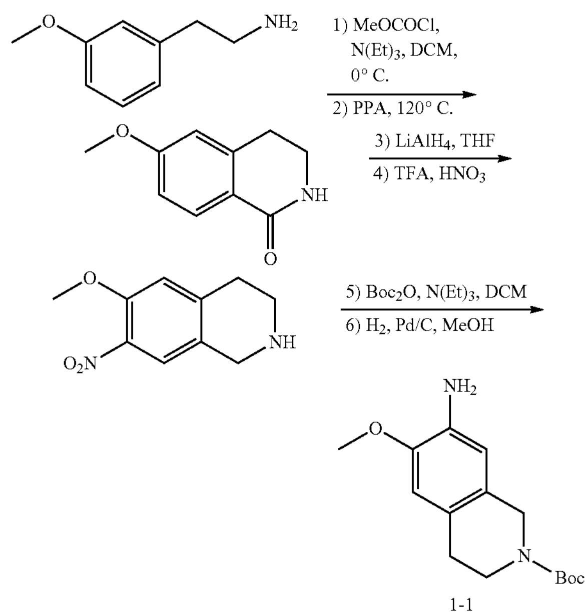

1-1

Step 1. Synthesis of methyl N-[2-(3-methoxyphenyl)ethyl]carbamate

To a stirred solution of 2-(3-methoxyphenyl)ethan-1-amine (300 g, 1.98 mol) and N(Et)3 (602 g, 5.95 mol) in DCM (4 L) was added dropwise at 0° C. methyl carbonochloridate (206 g, 2.18 mol) under nitrogen atmosphere. The resulting mixture was stirred for 4 h at 0° C., then quenched by the addition of water (2 L). The resulting mixture was extracted with DCM (2×3 L). The combined organic layers were washed with 1 N HCl (3 L), water (3 L) and brine (3 L), dried over anhydrous Na2SO4, and concentrated under reduced pressure, giving methyl N-[2-(3-methoxyphenyl) ethyl]carbamate (250 g) as an oil.

Step 2. Synthesis of 6-methoxy-1,2,3,4-tetrahydroisoquinolin-1-one

A 5 L 3-necked round-bottom flask was charged with methyl N-[2-(3-methoxyphenyl)ethyl]-carbamate (250 g, 1.19 mol) and polyphosphoric acid (2 L). The resulting mixture was stirred for 4 h at 120° C. under a nitrogen atmosphere. The mixture was cooled to RT and poured into 500 mL of ice/water. The resulting mixture was extracted with EtOAc (5 L). The organic layers were washed with water (3 L) and brine (3 L), dried over anhydrous $Na_2SO_4$, and concentrated under reduced pressure. The residue was purified by silica gel column chromatography (3:1 hexane/EtOAc) to afford 6-methoxy-1,2,3,4-tetrahydroisoquinolin-1-one (180 g) as an oil.

Step 3. Synthesis of 6-methoxy-1,2,3,4-tetrahydroisoquinoline

To a stirred solution of 6-methoxy-1,2,3,4-tetrahydroisoquinolin-1-one (180 g, 1.02 mol) in THF (3 L) was added $LiAlH_4$ (62.8 g, 1.66 mol) portionwise. The resulting mixture was stirred for 2 h. The reaction was quenched with 500 mL of water and the aqueous layer was extracted with EtOAc (3 L). The organic phase was washed with 1 N NaOH (500 mL), brine (1 L), dried over anhydrous $Na_2SO_4$, and concentrated under reduced pressure. The residue was purified by silica gel column chromatography (20:1 $CH_2Cl_2$/MeOH) to afford 6-methoxy-1,2,3,4-tetrahydroisoquinoline (150 g) as a solid.

Step 4. Synthesis of 6-methoxy-7-nitro-1,2,3,4-tetrahydroisoquinoline

To a stirred solution of 6-methoxy-1,2,3,4-tetrahydroisoquinoline (150 g, 919 mmol) in TFA (3 L) was added $HNO_3$ (100 mL) dropwise under a nitrogen atmosphere. The resulting mixture was stirred for 3 h at room temperature. The reaction was diluted with DCM (4 L), washed with saturated aqueous $NaHCO_3$ (4 L), water (4 L), brine (4 L), dried over anhydrous $Na_2SO_4$, and concentrated under reduced pressure. This resulted in 6-methoxy-7-nitro-1,2,3,4-tetrahydroisoquinoline (170 g) as an oil.

Step 5. Synthesis of tert-butyl 6-methoxy-7-nitro-1,2,3,4-tetrahydroisoquinoline-2-carboxylate To a stirred mixture of 6-methoxy-7-nitro-1,2,3,4-tetrahydroisoquinoline (170 g, 816 mmol) and $N(Et)_3$ (163 g, 1.61 mol) in DCM (3 L) was added $Boc_2O$ (176 g, 815 mmol) portionwise. The resulting mixture was stirred for 2 h. The mixture was diluted with DCM (2 L), washed with 1 N HCl (500 mL), water (500 mL), brine (500 mL), dried over anhydrous $Na_2SO_4$, and concentrated under reduced pressure. The residue was purified by silica gel column chromatography (8:1 petroleum ether/EtOAc) to afford tert-butyl 6-methoxy-7-nitro-1,2,3,4-tetrahydroisoquinoline-2-carboxylate (70 g) as a solid.

Step 6. Synthesis of tert-butyl 7-amino-6-methoxy-3,4-dihydroisoquinoline-2(1H)-carboxylate A 3 L 3-necked round-bottom flask was charged with tert-butyl 6-methoxy-7-nitro-1,2,3,4-tetrahydroisoquinoline-2-carboxylate (70.0 g, 227 mmol), MeOH (1 L) and Pd/C (10.0 g, 93.9 mmol). To this mixture $H_2$ (gas) was introduced and the resulting mixture was stirred for 5 h. The mixture was filtered, and the filtrate concentrated under reduced pressure. The crude product was re-crystallized from petroleum/EtOAc (8:1) to afford tert-butyl 7-amino-6-methoxy-3,4-dihydroisoquinoline-2(1H)-carboxylate (50.7 g) as a solid. $^1H$ NMR (400 MHz, DMSO-$d_6$) δ 6.56 (s, 1H), 6.37 (s, 1H), 4.56 (s, 2H), 4.29 (s, 2H), 3.73 (s, 3H), 3.49 (t, J=5.8 Hz, 2H), 2.61 (t, J=5.9 Hz, 2H), 1.42 (s, 9H). MS (EI) calc'd for $C_{15}H_{23}N_2O_3$ $[M+H]^+$, 279; found 279.

Preparation of Intermediate I-2 (6-methoxy-2-methyl-1,2,3,4-tetrahydroisoquinolin-7-anine)

Intermediate I-2 was prepared from 2-(3-methoxyphenyl) acetonitrile as outlined below.

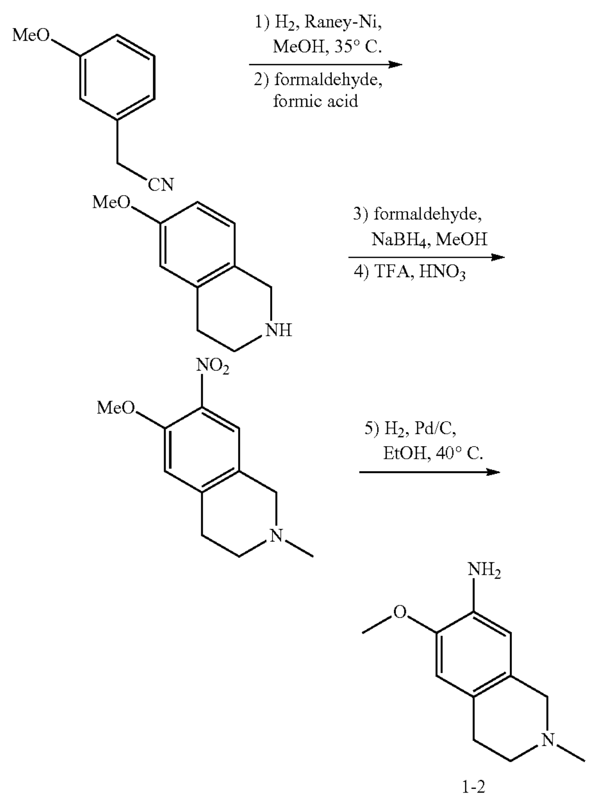

1-2

Step 1. Synthesis of 2-(3-methoxyphenyl)ethanamine

A 20-L pressure reactor was charged with Raney-Ni (200 g), MeOH (10 L) and 2-(3-methoxyphenyl)acetonitrile (1000 g). The resulting solution was stirred overnight at 35° C. under an atmosphere of $H_2$ (30 atm). The resulting mixture was filtered and concentrated in vacuo, giving 740 g of 2-(3-methoxyphenyl)ethanamine as an oil.

Step 2. Synthesis of 6-methoxy-1,2,3,4-tetrahydroisoquinoline

A 20-L 4-necked round-bottom flask was charged with 2-(3-methoxyphenyl)ethanamine (740 g, 4.89 mol), formic acid (7.4 L), $H_2O$ (740 mL), formaldehyde (151 g, 5.04 mol). The resulting solution was stirred overnight, concentrated in vacuo. To this, acetyl chloride (370 mL) in MeOH (6 L) was added and the mixture stirred for 30 minutes. The mixture was concentrated and then triturated with EtOAc (1 L) to provide the desired product, 6-methoxy-1,2,3,4-tetrahydroisoquinoline (370 g) as a semi-solid.

Step 3. Synthesis of 6-methoxy-2-methyl-1,2,3,4-tetrahydroisoquinoline

A 5-L 4-necked round-bottom flask was charged with 6-methoxy-1,2,3,4-tetrahydroisoquinoline (370 g, 2.27 mol), MeOH (4.0 L) and formaldehyde (1.1 L) was added slowly at 0° C. The resulting solution was stirred for 15 min, then $NaBH_4$ (300 g, 7.93 mol) was added in portions at 0° C. The resulting solution was stirred for 3 h, and quenched with water (1 L). The resulting mixture was stirred for 30 min, then concentrated under reduced pressure. The resulting mixture was diluted with water (5 L) and extracted with DCM (3×3 L). The combined organic layers were concentrated in vacuo, giving 6-methoxy-2-methyl-1,2,3,4-tetrahydroisoquinoline (260 g) as an oil.

Step 4. Synthesis of 6-methoxy-2-methyl-7-nitro-1,2,3,4-tetrahydroisoquinoline

A 5-L 4-necked round-bottom flask was charged with TFA (2.0 L), 6-methoxy-2-methyl-1,2,3,4-tetrahydroisoquinoline (260 g, 1.47 mol), and $HNO_3$ (150 g, 2.38 mmol). The resulting solution was stirred for 1 h and concentrated in vacuo. The residue was diluted with water (3 L), adding 4 N NaOH to adjust the pH to 10. The resulting solution was extracted with DCM (3×3 L) and concentrated. The residue was purified by chromatography on $SiO_2$ (5% MeOH/DCM) to provide 6-methoxy-2-methyl-7-nitro-1,2,3,4-tetrahydroisoquinoline (130 g) as an orange oil.

Step 5. Synthesis of 6-methoxy-2-methyl-1,2,3,4-tetrahydroisoquinolin-7-amine

A 3-L 4-necked round-bottom flask was charged with 6-methoxy-2-methyl-7-nitro-1,2,3,4-tetrahydroisoquinoline (130 g, 593 mmol), Pd/C (20 g, 188 mmol), MeOH (1.5 L). The flask was evacuated and flushed three times with nitrogen, followed by flushing with hydrogen gas. The mixture was stirred 3 h at 40° C. under an atmosphere of hydrogen (balloon). The mixture was filtered and the filtrate concentrated in vacuo, providing 6-methoxy-2-methyl-1,2,3,4-tetrahydroisoquinolin-7-amine (97 g) as a solid. $^1H$ NMR (300 MHz, $CDCl_3$) δ 6.53 (s, 1H), 6.39 (s, 1H), 3.83 (s, 3H), 3.62 (s, 2H), 3.46 (d, J=1.2 Hz, 2H), 2.83 (t, J=5.9 Hz, 2H), 2.67 (t, J=5.9 Hz, 2H), 2.45 (s, 3H). MS (EI) calc'd for $C_{11}H_{17}N_2O$ $[M+H]^+$, 193; found 193.

Preparation of Intermediate I-3 (7-chloro-6-methoxy-2-methyl-1,2,3,4-tetrahydroisoquinoline)

Intermediate I-3 was prepared from readily available 7-chloro-6-methoxy-1,2,3,4-tetrahydroisoquinoline using the reaction described below.

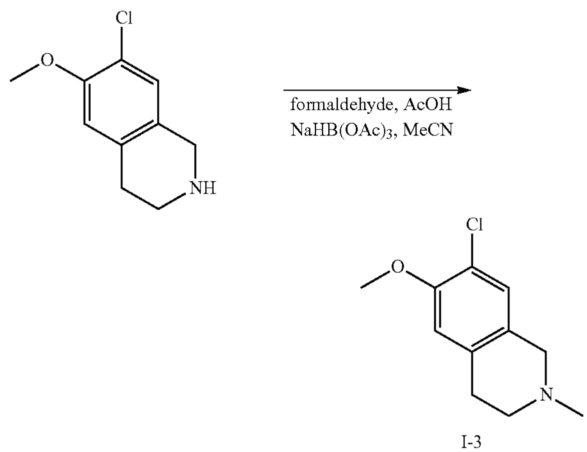

I-3

A mixture containing 7-chloro-6-methoxy-1,2,3,4-tetrahydroisoquinoline (1.0 g, 5.1 mmol), sodium triacetoxyborohydride (3.22 g, 15.2 mmol), AcOH (0.10 mL, 1.7 mmol), formaldehyde (1.9 mL, 26 mmol) in ACN (10 mL)

was stirred overnight. The mixture was filtered and concentrated to an oil. Chromatography on $SiO_2$ (gradient of 0-30% MeOH/DCM with 80 g silica gel) gave the desired product 7-chloro-6-methoxy-2-methyl-1,2,3,4-tetrahydroisoquinoline (883 mg) as an oil. $^1H$ NMR (500 MHz, DMSO-$d_6$) δ 7.11 (s, 1H), 6.87 (s, 1H), 3.80 (s, 3H), 3.38 (m, 2H), 2.79 (m, 2H), 2.56 (m, 2H), 2.31 (s, 3H). MS calc'd for $C_{11}H_{15}ClNO$ $[M+H]^+$, 212; found, 212.

Preparation of Intermediate I-4 (tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate)

Intermediate I-4 was prepared from 4-methyl-3-nitropyridin-2-amine via the sequence outlined below.

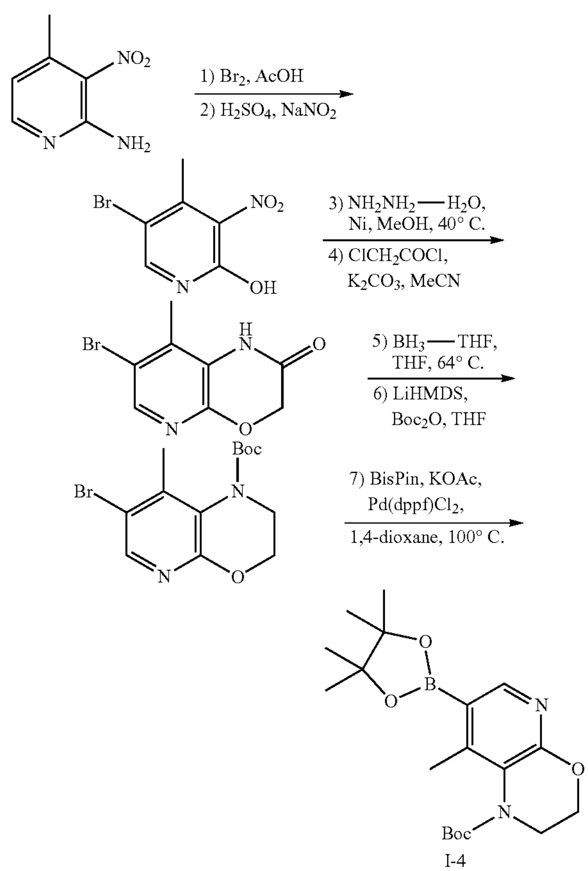

I-4

Step 1. Synthesis of 5-bromo-4-methyl-3-nitropyridin-2-amine

Two mixtures containing 4-methyl-3-nitropyridin-2-amine (400 g, 2.61 mol) in AcOH (2.8 L) were treated with NaOAc (82.0 g, 5.22 mol). Next, a solution of bromine (417 g, 2.61 mol) in AcOH (800 mL) was added dropwise at RT to each, and then the mixtures stirred for 2 h. The crude reaction mixtures were quenched with ice water (2 L), stirred for 30 min and finally combined into one. The combined mixture was filtered, and the filter cake washed with ice water (3×1 L) and dried under reduced pressure obtaining 5-bromo-4-methyl-3-nitropyridin-2-amine (1.0 kg) as a solid.

Step 2. Synthesis of 5-bromo-4-methyl-3-nitropyridin-2-ol

Five equal mixtures containing 5-bromo-4-methyl-3-nitropyridin-2-amine (200 g, 0.862 mol) in water (3.5 L) were treated each with $H_2SO_4$ (200 g, 2.04 mol) followed by $NaNO_2$ at 0° C. (137 g, 1.98 mol in 500 mL of water). The reactions were stirred at RT for 2 h, then at 100° C. for 4 h. The crude reaction mixtures were then combined and filtered. The filter cake was dried under reduced pressure obtaining 5-bromo-4-methyl-3-nitropyridin-2-ol (920 g) as a solid.

Step 3. Synthesis of 3-amino-5-bromo-4-methylpyridin-2-ol

Four equal mixtures containing 5-bromo-4-methyl-3-nitropyridin-2-ol (230 g, 0.987 mol) in MeOH (4.6 L) were treated with Raney-Ni (101 g, 1.18 mol). The mixtures were heated to 40° C., and treated with hydrazine hydrate (74.1 g, 1.48 mol) and the reaction mixtures stirred for 2 h at 40° C. The four mixtures were filtered and the filtrates combined into one. The combined filtrates were concentrated to remove MeOH, obtaining 3-amino-5-bromo-4-methylpyridin-2-ol (680 g) as a solid.

Step 4. Synthesis of 7-bromo-8-methyl-1H-pyrido[2,3-b][1,4]oxazin-2(3H)-one

Three equal mixtures containing 3-amino-5-bromo-4-methylpyridin-2-ol (227 g, 1.12 mol), $K_2CO_3$ (617 g, 4.47 mol) in ACN (3.4 L) were cooled to 15° C., and each treated dropwise with chloroacetyl chloride (189 g, 1.67 mol). The mixtures were stirred at RT for 2 h, then at 40° C. for 6 h, and finally at 60° C. for 10 h. Each was then quenched with MeOH (100 mL), combined into one and filtered. The filtered cake was washed with 2:1 THF/MeOH (3×1 L), and the filtrate concentrated in vacuo to obtain 7-bromo-8-methyl-1H-pyrido[2,3-b][1,4]oxazin-2(3H)-one (600 g) as a solid. $^1H$ NMR (400 MHz, $CD_3OD$) δ 7.78 (s, 1H), 4.68 (s, 2H), 3.35 (s, 1H), 2.38 (s, 3H).

Step 5. Synthesis of 7-bromo-8-methyl-2,3-dihydro-1H-pyrido[2,3-b][1,4]oxazine

Six equal mixtures of 7-bromo-8-methyl-1H-pyrido[2,3-b][1,4]oxazin-2(3H)-one (100 g, 411 mol) in THF (2 L) were treated dropwise at 0° C. with a 10 M solution of $BH_3$-$Me_2S$ in THF (165 mL). The mixtures were stirred at 80° C. for 2 h, cooled to 0° C., and quenched with 500 mL of MeOH each. The six mixtures were stirred at 80° C. for 2 h, then combined into one and concentrated in vacuo, obtaining 7-bromo-8-methyl-2,3-dihydro-1H-pyrido[2,3-b][1,4]oxazine (400 g). $^1H$ NMR (400 MHz, $CD_3OD$) δ 7.50 (s, 1H), 4.31 (s, 2H), 3.43 (m, 2H), 2.23 (s, 3H).

Step 6. Synthesis of tert-butyl 7-bromo-8-methyl-2,3-dihydro-1H-pyrido[2,3-b][1,4]oxazine-1-carboxylate Two equal mixtures of 7-bromo-8-methyl-2,3-dihydro-1H-pyrido[2,3-b][1,4]oxazine (200 g, 873 mol) in THF (3 L) were treated with $Boc_2O$ (229 g, 1.05 mol) and cooled to 0° C. To each were added a 1 M solution of LiHMDS in THF (1.05 L) and the reactions stirred at RT for 15 h. Each were quenched with MeOH (50 mL) and combined into one mixture which was concentrated in vacuo. The residue was then purified by chromatography (gradient of 40:1 to 3:1 petroleum ether/EtOAc) to give crude solid product. The material was then triturated with petroleum ether to obtain tert-butyl 7-bromo-8-methyl-2,3-dihydro-1H-pyrido[2,3-b][1,4]oxazine-1-carboxylate (186 g) as a solid. $^1$H NMR (400 MHz, $CD_3OD$) δ 8.14 (s, 1H), 4.55 (m, 1H), 4.46 (m, 1H), 4.39 (m, 1H), 3.08 (m, 1H), 2.29 (s, 3H), 1.48 (s, 9H).

Step 7. Synthesis of tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate A mixture of tert-butyl 7-bromo-8-methyl-2,3-dihydro-1H-pyrido[2,3-b][1,4]oxazine-1-carboxylate (186 g, 565 mol) in 1,4-dioxane (1.86 L) was treated with bis(pinacolato)diboron (287 g, 1.13 mol), KOAc (166 g, 1.70 mol), and $Pd(dppf)Cl_2$ (41.3 g, 56.5 mmol). The mixture was purged and degassed with nitrogen three times, then stirred at 100° C. for 1 h. The reaction mixture was concentrated in vacuo, EtOAc (1 L) added and the mixture filtered. The EtOAc filtrate was treated with water (200 mL) and extracted with EtOAc (3×200 mL). The combined organic layers was washed with 100 mL of brine, dried ($Na_2SO_4$) and concentrated under reduced pressure. The residue was purified by chromatography on $SiO_2$ (gradient of 50:1 to 1:1 petroleum ether/EtOAc) to give crude product. The material was washed with petroleum ether to obtain tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate (100 g) as a solid. $^1$H NMR (400 MHz, $CD_3OD$) δ 8.37 (s, 1H), 4.53 (m, 1H), 4.46 (m, 1H), 4.34 (m, 1H), 3.08 (m, 1H), 2.40 (s, 3H), 1.47 (s, 9H), 1.33 (s, 12H). MS (EI) calc'd for $C_{19}H_{30}BN_2O_5$ $[M+H]^+$, 377; found 377.

Preparation of Intermediate I-5 (N,N-bis(tert-butylcarbonate)-4-methyl-5-(4,4,5,5-tetramethyl-1,3,2-dioxaborolan-2-yl)pyridin-3-amine)

Intermediate I-5 was prepared from 3-bromo-4-methyl-5-nitropyridine as shown below

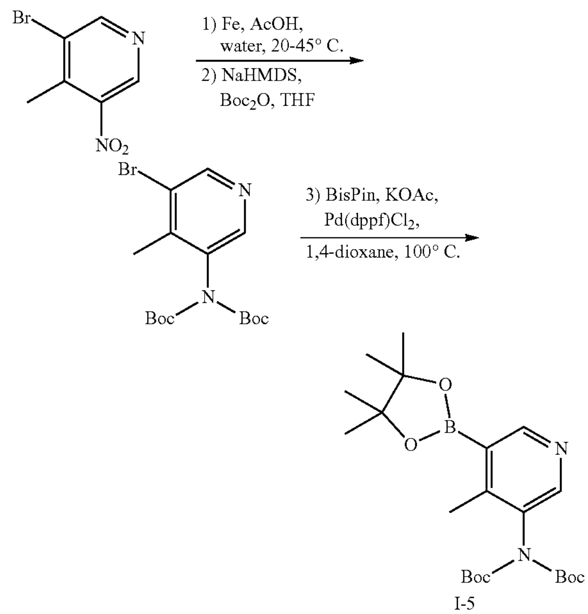

I-5

Step 1. Synthesis of 5-bromo-4-methylpyridin-3-amine

A mixture of 3-bromo-4-methyl-5-nitropyridine (45 g, 197 mmol) in AcOH (405 mL) and water (101 mL) was treated with Fe (33 g, 590 mmol) and the mixture stirred for 45 min at 45° C. The mixture was diluted with EtOAc (500 mL) and 5 M NaOH (1.1 L) and then filtered. The filter cake was washed with EtOAc (3×200 mL) and water (2 L). The organic layer was collected. The aqueous layer was extracted with EtOAc (2×200 mL) and the combined organic layers dried over $Na_2SO_4$ and concentrated. The residue was purified by chromatography on $SiO_2$ (10% MeOH/DCM) to provide 5-bromo-4-methylpyridin-3-amine (38 g) as a solid.

Step 2. Synthesis of N,N-bis(tert-butylcarbonate)-4-methyl-5-bromopyridin-3-amine A solution of 5-bromo-4-methylpyridin-3-amine (19.5 g, 104 mmol) in THF (293 mL) was treated at 0° C. with a 1 M THF solution of NaHMDS (229 mL, 229 mmol) over a 15 min period. The mixture was stirred for 20 min, then treated with a solution of $Boc_2O$ (45.5 g, 209 mmol) in THF (39 mL). The mixture was stirred for 12 h, and quenched by the addition of water (150 mL) at 0° C. The mixture was extracted with EtOAc (3×300 mL), washed with brine, dried over $Na_2SO_4$, filtered and concentrated under reduced pressure. The residue was purified by column chromatography on $SiO_2$ (20:1 to 1:1 petroleum ether/EtOAc) to provide the title compound (19 g) as a solid.

Step 3. Synthesis of (N,N-bis(tert-butylcarbonate)-4-methyl-5-(4,4,5,5-tetramethyl-1,3,2-dioxaborolan-2-yl)pyridin-3-amine)

A solution of N,N-bis(tert-butylcarbonate)-4-methyl-5-bromopyridin-3-amine (24 g, 62 mmol), $Pd(dppf)Cl_2$ (6.80 g, 9.30 mmol), BisPin (20.4 g, 80.6 mmol) and KOAc (18.2 g, 186 mmol) in 1,4-dioxane (360 mL) was stirred at 100° C. for 20 h. The mixture was filtered and concentrated. The residue was purified by chromatography on $SiO_2$ (100 g, 0-20% EtOAc/petroleum ether) to give a solid. The solid was taken-up in 50 mL of petroleum ether, cooled to −30° C. for 30 min, and filtered. The filter cake was collected and dried under reduced pressure to give N,N-bis(tert-butylcarbonate)-4-methyl-5-(4,4,5,5-tetramethyl-1,3,2-dioxaborolan-2-yl)pyridin-3-amine (14.7 g) as a solid. $^1$H NMR (400 MHz, $CDCl_3$) δ 8.79 (s, 1H), 8.24-8.42 (m, 1H), 2.40 (s, 3H), 1.40 (s, 18H), 1.37 (s, 12H).

Preparation of Intermediate I-6 (7-bromoquinazoline-2-amine)

Intermediate I-6 was prepared from 4-bromo-2-fluorobenzaldehyde as shown below.

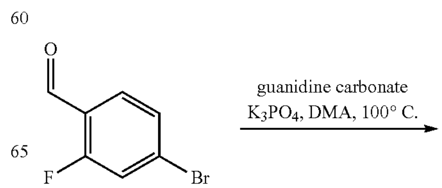

-continued

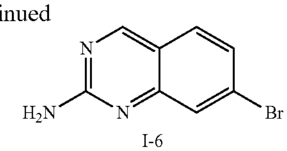

I-6

A 30-mL microwave vial was charged with guanidine carbonate (486 mg, 2.70 mmol), 4-bromo-2-fluorobenzaldehyde (548 mg, 2.70 mmol) and DMA (13 mL). The vial was capped and heated to 100° C. for 4 h. After 4 h, the reaction was cooled, poured into 50 mL of ice water, stirred for 15 min then filtered to give a 7-bromoquinazoline-2-amine (553 mg) as a powdery orange-red solid. MS (EI) calc'd for $C_8H_7BrN_3$ [M+H]$^+$, 224, 226; found 224, 226.

Preparation of Intermediate I-7 (7-bromo-2,5-dichloroquinazoline)

Intermediate I-7 was prepared from 2-chloro-6-fluoroaniline via the route outlined below.

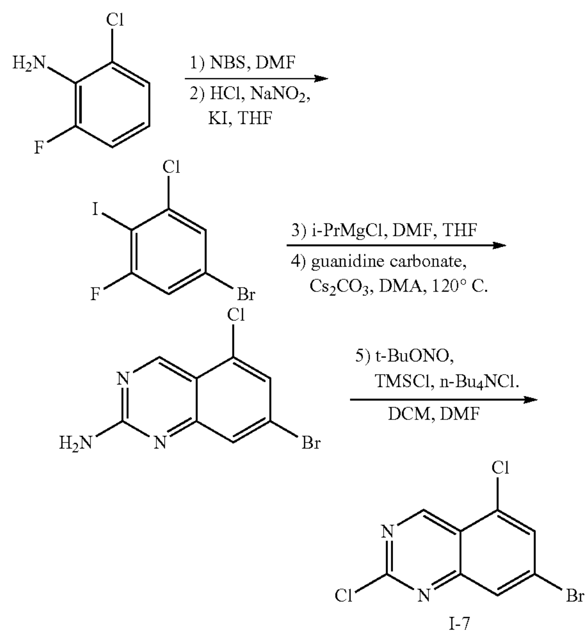

I-7

Step 1. Synthesis of 4-bromo-2-chloro-6-fluoroaniline

A 5-L 4-necked round-bottom flask purged and maintained with an inert atmosphere of nitrogen was charged with 2-chloro-6-fluoroaniline (260 g, 1.78 mol) and DMF (2.6 L). This was followed by the portionwise addition of NBS (317 g, 1.78 mol). The resulting solution was stirred for 1 h, then quenched by the addition of 5 L of ice water. The precipitate was collected by filtration, resulting 4-bromo-2-chloro-6-fluoroaniline (330 g) as a solid.

Step 2. Synthesis of 5-bromo-1-chloro-3-fluoro-2-iodobenzene

A 10-L 4-necked round-bottom flask purged and maintained with an inert atmosphere of nitrogen was charged with a solution 4-bromo-2-chloro-6-fluoroaniline (326 g, 970 mmol) in ACN (3 L). This was followed by the addition of a 6 N aqueous solution of HCl (650 mL). The mixture was cooled to −20° C., then sodium nitrite (73.6 g, 1.07 mol) in 210 mL of water was added. The mixture was stirred for 1 h at −20° C., then treated with KI (469 g, 2.91 mol) in 900 mL of water dropwise. The resulting solution was warmed to RT and stirred for 2 h. The reaction was then quenched by the addition of aqueous $Na_2S_2O_3$ (1 L). The resulting solution was extracted with petroleum ether (3×2 L) and the organic phase was concentrated giving 5-bromo-1-chloro-3-fluoro-2-iodobenzene (390 g) as a solid.

Step 3. Synthesis of 4-bromo-2-chloro-6-fluorobenzaldehyde

A 10-L 4-necked round-bottom flask purged and maintained with an inert atmosphere of nitrogen was charged with a solution of 5-bromo-1-chloro-3-fluoro-2-iodobenzene (386 g, 1.15 mol) in THF (3.5 L). This was followed by the dropwise addition of a 2 M THF solution of i-PrMgCl (0.64 L, 1.26 mol) with stirring at −78° C. The resulting solution was stirred for 1 h at −78° C., then treated dropwise with DMF (168 g, 2.30 mol). The resulting solution was stirred for 1 h at 0° C., then quenched by the addition of 1 N HCl (5 L). The solution was extracted with EtOAc (3×500 mL), the organic phase was washed with brine (1 L) and concentrated. This resulted in 4-bromo-2-chloro-6-fluorobenzaldehyde (205 g) as a solid.

Step 4. Synthesis of 7-bromo-5-chloroquinazolin-2-amine

A 5 L 4-necked round-bottom flask was charged with 4-bromo-2-chloro-6-fluorobenzaldehyde (196 g, 0.83 mol) in DMA (2.0 L), guanidine carbonate (150 g, 0.83 mol) and $Cs_2CO_3$ (160 g, 0.83 mol). The reaction was heated to 120° C., and stirred for 1 h. Once cooled to RT, the reaction was quenched with water (20 L) and a precipitate collected by filtration. This gave 7-bromo-5-chloroquinazolin-2-amine (160 g) as a solid.

Step 5. Synthesis of 7-bromo-2,5-dichloroquinazoline

A 2-L 4-necked round-bottom flask purged and maintained with an inert atmosphere of nitrogen was charged with 7-bromo-5-chloroquinazolin-2-amine (157 g, 600 mmol), $n\text{-}Bu_4NCl$ (200 g, 720 mmol), TMSCl (260 g, 2.40 mol) in DCM (1.57 L), and DMF (157 mL) was treated dropwise with tert-butyl nitrite (62 g, 1.8 mol). The mixture was stirred at RT for 15 min and then at 45° C. for 1 h. The mixture was cooled to RT, extracted with DCM (3×800 mL), the organic layers combined, washed with water and brine, dried over $Na_2SO_4$, filtered and concentrated under vacuum. The crude was purified by chromatography on silica gel (1:10:20 EtOAc/petroleum ether/DCM) giving 7-bromo-2,5-dichloroquinazoline (52 g) as a solid. $^1$H NMR (300 MHz, DMSO-$d_6$) δ 9.61 (d, J=0.8 Hz, 1H), 8.11 (dd, J=1.7, 0.8 Hz, 1H), 7.84 (d, J=1.7 Hz, 1H). MS (EI) calc'd for $C_8H_4BrCl_2N_2$ [M+H]$^+$, 277, 279; found, 277, 279.

Preparation of Intermediate I-8 (7-bromo-6-fluoroquinazolin-2-amine)

Intermediate I-8 was prepared from 4-bromo-3-fluorobenzaldehyde via the route outlined below.

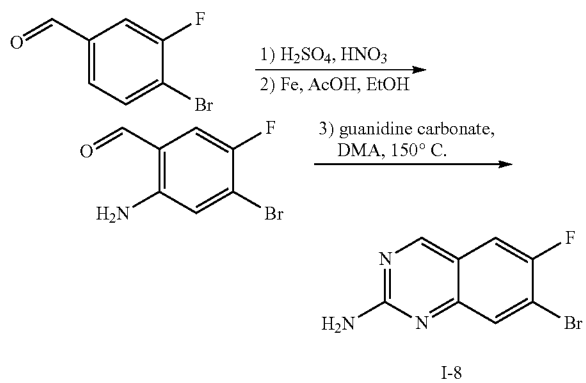

I-8

Step 1. Synthesis of 4-bromo-5-fluoro-2-nitrobenzaldehyde

Two 5 L three-necked round flasks were charged equally each with 4-bromo-3-fluorobenzaldehyde (500 g, 2.46 mol) and $H_2SO_4$ (2.5 L) and then cooled to 0° C. To each flask, $HNO_3$ (350 g, 5.55 mol) was added and the mixtures stirred for 1 h at RT. The reactions were quenched with ice water (15 L) and extracted with DCM (18 L). The organic layers from both reactions were combined, washed with brine, dried over $Na_2SO_4$, filtered and concentrated. The product, 4-bromo-5-fluoro-2-nitrobenzaldehyde, was obtained as a red solid (1.15 kg). $^1H$ NMR (400 MHz, $CDCl_3$) δ 10.41 (d, J=2.0 Hz, 1H), 8.44 (d, J=5.6 Hz, 1H), 7.68 (d, J=7.6 Hz, 1H).

Step 2. Synthesis of 2-amino-4-bromo-5-fluorobenzaldehyde

Four 5 L three-necked round flasks were equally charged each with 4-bromo-5-fluoro-2-nitrobenzaldehyde (300 g, 1.21 mol) in EtOH (2.1 L). Each were then treated with water (600 mL), AcOH (1.26 kg, 21.0 mol) and Fe (216 g, 3.87 mol). The reactions were stirred for 10 min, then combined by adding to ice water (40 L). The precipitate was filtered and the residue washed with EtOAc. The organic layer was concentrated and the resulting residue triturated with MTBE for 30 min. Filtration gave 2-amino-4-bromo-5-fluorobenzaldehyde (270 g) as a solid. $^1$HNMR (400 MHz, $CDCl_3$) δ 9.74 (d, J=22.8 Hz, 1H), 7.27 (d, J=10.8 Hz, 1H), 6.90 (d, J=5.2 Hz, 1H), 6.02 (s, 2H).

Step 3. Synthesis of 7-bromo-6-fluoroquinazolin-2-amine

Twelve 1 L three-necked round flasks were equally charged each with 2-amino-4-bromo-5-fluorobenzaldehyde (20 g, 92 mmol) in DMA (500 mL). To each was added guanidine carbonate (50 g, 275 mmol) and the reaction mixtures stirred for 1 h at 150° C. The twelve mixtures were combined by diluting with water (15 L) and the resulting suspension filtered. The residue was washed with MTBE to obtain 7-bromo-6-fluoroquinazolin-2-amine (96.0 g, 397 mmol) as a solid. $^1H$ NMR (400 MHz, DMSO-$d_6$) δ 9.11 (s, 1H), 7.79 (d, J=8.8 Hz, 1H), 7.77 (d, J=6.4 Hz, 1H), 7.04 (s, 2H). MS (EI) calc'd for $C_8H_6BrFN_3$ $[M+H]^+$, 242, 244; found 242, 244.

Preparation of Intermediate I-9 (7-bromo-2-chloro-6-fluoroquinazoline)

Intermediate I-9 was prepared from intermediate I-8.

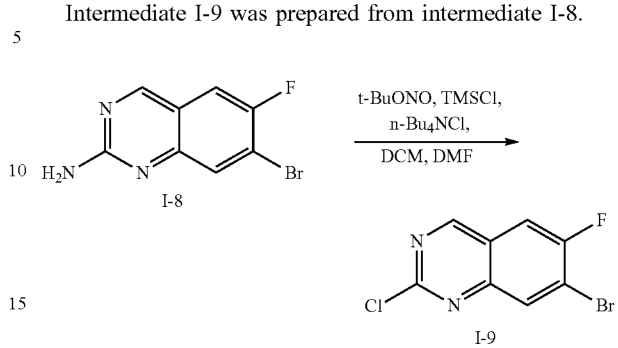

I-8

I-9

Two 5 L three necked round flasks were each equally charged with 7-bromo-6-fluoroquinazolin-2-amine (140 g, 578 mmol) in DCM (2.8 L) and DMF (280 mL). To each, TMSCl (251 g, 2.31 mol), n-$Bu_4$NCl (193 g, 694 mmol) were added and the mixtures cooled to 0° C. Next, each were treated dropwise with tert-butyl nitrite (328 g, 3.18 mol) and the mixtures stirred for 20 min at RT, then 3 h at 45° C. The reactions were combined in DCM (3 L), washed with sat'd $NaHCO_3$ (8 L), brine (2 L), dried over $Na_2SO_4$, filtered and concentrated. The residue was purified by column chromatography on $SiO_2$ (20:1 to 10:1 petroleum ether/EtOAc) to provide 7-bromo-2-chloro-6-fluoroquinazoline (102 g) as a solid. $^1H$ NMR (400 MHz, $CDCl_3$) δ 9.27 (s, 1H), 8.30 (d, J=6 Hz, 1H), 7.64 (d, J=7.2 Hz, 1H). MS (EI) calc'd for $C_8H_4BrClFN_2$ $[M+H]^+$, 261, 263; found 261, 263.

Preparation of Intermediate I-10 (7-bromo-6-chloroquinazolin-2-amine)

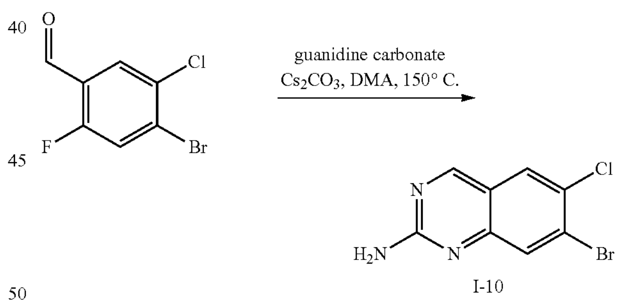

I-10

A solution of 4-bromo-5-chloro-2-fluorobenzaldehyde (2.10 g, 8.84 mmol), guanidine carbonate (1.59 g, 8.84 mmol), $Cs_2CO_3$ (2.88 g, 8.84 mmol) and DMA (30 mL) in three microwave vials was heated to 150° C. for 15 min. The mixtures were combined by pouring into water and the resulting precipitate filtered and collected giving 7-bromo-6-chloroquinazolin-2-amine (2.04 g) as a solid. $^1H$ NMR (500 MHz, DMSO-$d_6$) δ 9.12 (s, 1H), 8.12 (s, 1H), 7.81 (s, 1H), 7.19 (br s, 2H). MS (EI) calc'd for $C_8H_6BrClN_3$ $[M+H]^+$, 258, 260; found 258, 260.

Preparation of Intermediate I-11 (7-bromo-$N^5$,$N^5$-bis(4-methoxybenzyl)quinazoline-2,5-diamine)

Intermediate I-11 was prepared from 4-bromo-2,6-difluorobenzaldehyde via the route below.

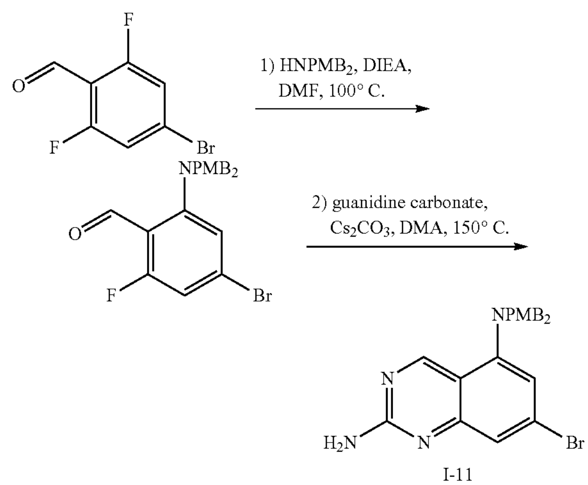

I-11

Step 1. Synthesis of 2-(Bis(4-methoxybenzyl)amino)-4-bromo-6-fluorobenzaldehyde A mixture of 4-bromo-2,6-difluorobenzaldehyde (1.38 g, 6.24 mmol) and bis(4-methoxybenzyl)amine (1.50 g, 5.83 mmol) in DMF (24 mL) was treated with i-$Pr_2NEt$ (5.1 mL, 29 mmol). The solution was stirred at 100° C. for 2 h and concentrated to dryness. The residue was carried forward without further purification. MS (EI) calc'd for $C_{23}H_2BrFNO_3Na$ $[M+Na]^+$, 480, 482; found 480, 482.

Step 2. Synthesis of 7-bromo-$N^5$,$N^5$-bis(4-methoxybenzyl)quinazoline-2,5-diamine A mixture containing 2-(bis(4-methoxybenzyl)amino)-4-bromo-6-fluorobenzaldehyde (crude residue from Step 1) in DMA (22 mL) was treated with guanidine carbonate (0.983 g, 5.45 mmol) and $Cs_2CO_3$ (1.78 g, 5.45 mmol). The reaction vessel was sealed and heated to 150° C. in a microwave for 30 min. The crude reaction was concentrated with heat under vacuo and the resulting residue was purified by chromatography on $SiO_2$ (12 g, 0-55% EtOAc/hexanes) to provide 7-bromo-$N^5$,$N^5$-bis(4-methoxybenzyl)quinazoline-2,5-diamine (879 mg, 1.83 mmol). MS (EI) calc'd for $C_{24}H_{24}BrN_4O_2$ $[M+H]^+$, 479, 481; found 479, 481.

Preparation of Intermediate I-12 (7-bromo-6-fluoro-$N^5$,$N^5$-bis(4-methoxybenzyl)quinazoline-2,5-diamine)

Intermediate I-12 was prepared from 1-bromo-2,3,5-trifluorobenzene as shown below.

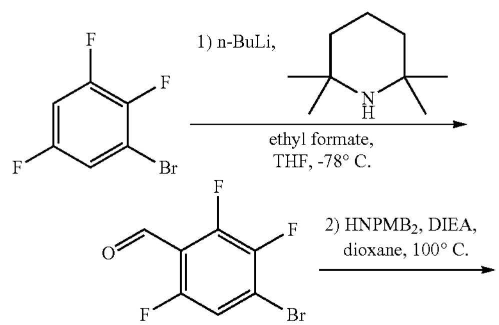

-continued

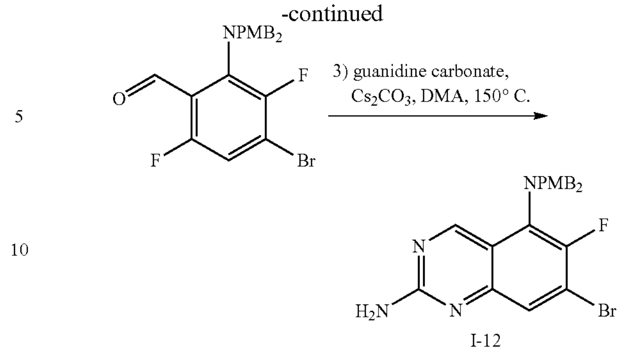

I-12

Step 1. Synthesis of 4-bromo-2,3,6-trifluorobenzaldehyde

A mixture of 2,2,6,6-tetramethylpiperidine (187 g, 1.33 mol) in THF (1.4 L) was cooled to −78° C., and treated dropwise with a 2.5 M solution of n-BuLi (400 mL, 1.00 mol) and stirred for 30 min. Next, 1-bromo-2,3,5-trifluorobenzene (140 g, 663 mmol) was added dropwise as a solution in THF (1.12 L) and the reaction mixture stirred for 1 h at −78° C. Next, a solution of ethyl formate (59 g, 796 mol) in THF (280 mL) was added dropwise and the reaction mixture stirred another 1 h. The mixture was finally quenched with the addition of aqueous $NH_4Cl$ (2 L) and extracted with EtOAc (3 L, 2 L, 1 L). The combined organic layers were concentrated and the residue purified by chromatography on $SiO_2$ (100:1 to 100:5 petroleum ether/EtOAc) to provide 4-bromo-2,3,6-trifluorobenzaldehyde (42 g) as a solid. $^1H$ NMR (400 MHz, $CDCl_3$) δ 10.13 (s, 1H), 7.86-7.90 (m, 1H).

Step 2. Synthesis of 2-(bis(4-methoxybenzyl)amino)-4-bromo-3,6-difluorobenzaldehyde A solution of 4-bromo-2,3,6-trifluorobenzaldehyde (50 g, 209 mmol), DIEA (55 g, 430 mmol), $HNPMB_2$ (63 g, 240 mmol) in 1,4-dioxane (500 mL) was warmed to 100° C., and stirred for 6 h. The mixture was concentrated and the residue purified by chromatography on $SiO_2$ (100:1 to 100:5, petroleum ether/EtOAc) to provide 2-(bis(4-methoxybenzyl)amino)-4-bromo-3,6-difluorobenzaldehyde (90 g) as an oil. $^1$HNMR (400 MHz, DMSO-$d_6$) δ 10.07 (s, 1H), 7.56-7.56 (m, 1H), 7.08-7.01 (m, 4H), 6.83-6.86 (m, 4H), 4.174 (s, 4H), 3.71 (s, 6H).

Step 3. Synthesis of 7-bromo-6-fluoro-$N^5$,$N^5$-bis(4-methoxybenzyl)quinazoline-2,5-diamine A solution of 2-(bis(4-methoxybenzyl)amino)-4-bromo-3,6-difluorobenzaldehyde (90 g, 189 mmol), $Cs_2CO_3$ (122 g, 374 mmol), guanidine carbonate (44 g, 242 mmol) in DMA (360 mL) was warmed to 150° C., and stirred for 30 min. The reaction mixture was cooled to RT, diluted with water (2 L) and extracted with EtOAc (2 L, 1 L). The organic layer was concentrated and the residue purified by chromatography on $SiO_2$ (100:1 to 2.5:1 petroleum ether/EtOAc) to provide 7-bromo-6-fluoro-$N^5$,$N^5$-bis(4-methoxybenzyl)quinazoline-2,5-diamine (31 g) as a solid. $^1H$ NMR (400 MHz, DMSO-$d_6$) δ 9.24 (s, 1H), 7.46-7.47 (d, J=4 Hz, 1H), 7.13-7.15 (d, J=8 Hz, 4H), 6.93 (s, 2H), 6.80-6.82 (d, J=8 Hz, 4H), 4.21 (s, 4H), 3.68 (s, 6H). MS (EI) calc'd for $C_{24}H_{23}BrFN_4O_2$ $[M+H]^+$, 497, 499; found 497, 499.

Preparation of Intermediate I-13 (7-bromo-N-(6-methoxy-2-methyl-1,2,3,4-tetrahydroisoquinolin-7-yl)quinazolin-2-amine)

Intermediate I-13 was prepared via the coupling of intermediates 1-2 and 7-bromo-2-chloroquinazoline.

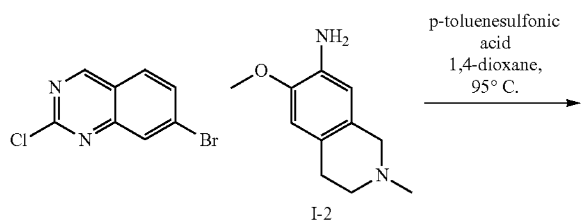

I-2

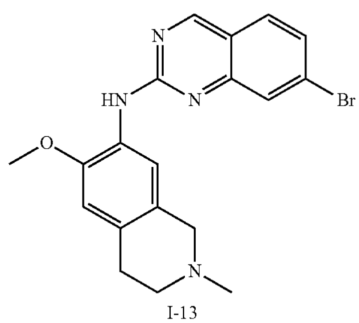

I-13

A mixture containing 7-bromo-2-chloroquinazoline (165 mg, 0.676 mmol), 6-methoxy-2-methyl-1,2,3,4-tetrahydroisoquinolin-7-amine (I-2) (100 mg, 0.520 mmol), and p-toluenesulfonic acid (134 mg, 0.780 mmol) was added 1,4-dioxane (2.6 mL). The reaction was stirred overnight at 95° C. The reaction was diluted with DCM and quenched with saturated $NaHCO_3$solution. The aqueous layer was extracted with DCM (3×25 mL). The combined organic layers were dried over $Na_2SO_4$ and after filtration, concentrated to dryness under reduced pressure. Chromatography on $SiO_2$ (gradient of 0-25% MeOH/DCM, 12 g silica gel) gave the desired product, I-13, as an oil that solidified upon standing. MS (EI) calc'd for $C_{19}H_2OBrN_4O$ $[M+H]^+$, 399, 401; found, 399, 401.

Preparation of Intermediate I-14 (7-bromo-N-(6-methoxy-2-methyl-1,2,3,4-tetrahydroisoquinolin-7-yl)quinazolin-2-amine)

Intermediate I-14 was prepared via the coupling of intermediates I-1 and 7-bromo-2-chloroquinazoline.

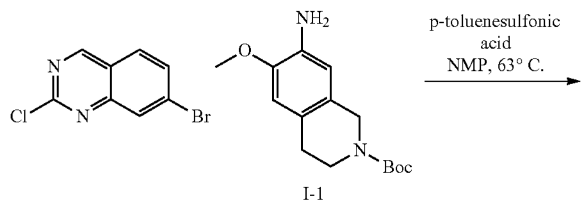

I-1

-continued

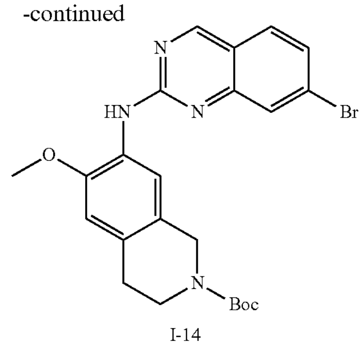

I-14

A mixture containing tert-butyl 7-amino-6-methoxy-3,4-dihydroisoquinoline-2(1H)-carboxylate (I-1) (514 mg, 1.85 mmol), 7-bromo-2-chloroquinazoline (495 mg, 2.03 mmol), and p-toluenesulfonic acid (63.6 mg, 0.369 mmol) was added NMP (6 mL). The mixture was stirred overnight at 63° C. The reaction was diluted with DCM and washed with 1:1 $H_2O$/brine solution (×3). The combined aqueous layers were extracted with DCM (3×25 mL). The combined organic layers were dried over $Na_2SO_4$ and after filtration, concentrated to dryness under reduced pressure. Chromatography on $SiO_2$ (gradient of 0-20% EtOAc/Hex, 12 g silica gel) gave the desired product. I-14, as an oil that solidified upon standing. MS (EI) calc'd for $C_{23}H_{26}BrN_4O_3$ $[M+H]^+$, 485, 487, found, 485, 487.

Preparation of Intermediate I-15 (tert-butyl 7-(2-Aminoquinazolin-7-yl)-8-methyl-2,3-dihydro-1H-pyrido[2,3-b][1,4]oxazine-1-carboxylate)

Intermediate I-15 was prepared via the coupling of intermediates I-6 and I-4.

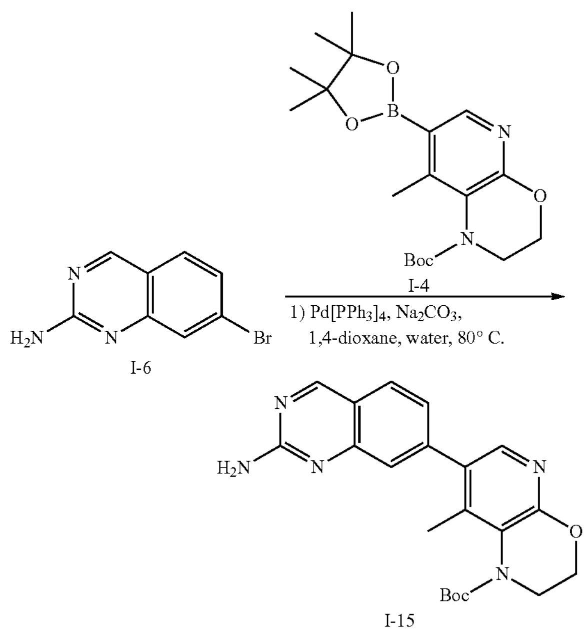

I-4

I-6

I-15

A mixture containing 7-bromoquinazolin-2-amine (I-6; 50 mg, 0.22 mmol), tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate (intermediate I-4; 100 mg, 0.27 mmol), $PdCl_2$(dppf) (16 mg, 0.022 mmol) and $Na_2CO_3$ (50 mg, 0.47 mmol) in 1,4-dioxane (1 mL) and water (0.2 mL) was stirred overnight at 80° C. The mixture was diluted with DCM, washed with water. Organic layer was dried ($Na_2SO_4$) and concentrated. Chromatography on $SiO_2$ (gradient of 0-20% MeOH/DCM, 25 g silica gel) gave the desired product I-15 as a beige solid. MS (EI) calc'd for $C_{21}H_{24}N_5O_3$ [M+H]$^+$, 416; found, 416.

Preparation of Intermediate I-16 (tert-butyl 7-(2-Amino-5-(bis(4-methoxybenzyl)amino)-6-fluoroquinazolin-7-yl)-8-methyl-2,3-dihydro-1H-pyrido[2,3-b][1,4]oxazine-1-carboxylate)

Intermediate I-16 was prepared via the coupling of intermediates I-12 and I-4.

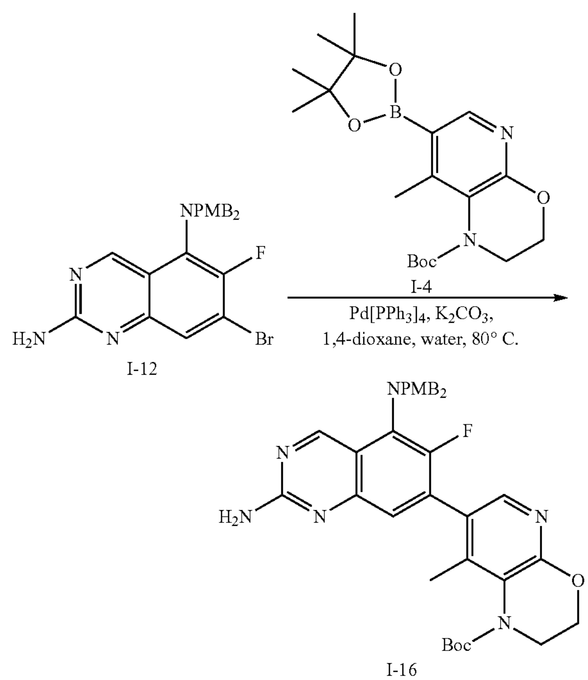

I-4

I-12

I-16

A mixture containing 7-bromo-6-fluoro-$N^5$,$N^5$-bis(4-methoxybenzyl)quinazoline-2,5-diamine (I-12) (5.0 g, 10 mmol), tert-butyl 8-methyl-7-(4,4,5,5-tetramethyl-1,3,2-dioxaborolan-2-yl)-2,3-dihydro-1H-pyrido[2,3-b][1,4]oxazine-1-carboxylate (I-4) (4.5 g, 12 mmol), $Pd(PPh_3)_4$ (1.16 g mg, 1.01 mmol), $K_2CO_3$ (2.8 g, 20 mmol) in 1,4-dioxane (15 mL) and water (5 mL) was stirred overnight at 80° C. The reaction mixture filtered, and the residue washed with EtOAc. The combined organic layers were concentrated under reduced pressure and purified by chromatography on $SiO_2$ (gradient of 0-20% MeOH/DCM, 120 g silica gel) to give the desired product, I-16, as an oil that solidified upon standing. $^1$H NMR (500 MHz, $CDCl_3$) δ 9.53 (s, 1H), 7.92 (s, 1H), 7.24 (m, 1H), 7.17 (2 d, 4H), 6.79 (2 d, 4H), 5.25 (br, 2H), 4.61 (br, 1H), 4.54 (br, 1H), 4.39 (br, 1H), 4.28 (s, 4H), 3.77 (s, 6H), 3.17 (br, 1H), 2.02 (s, 3H), 1.26 (s, 9H). MS (EI) calc'd for $C_{37}H_{40}FN_6O_5$ [M+H]$^+$, 667; found, 667.

Preparation of Intermediate I-17 (tert-butyl 7-(2-amino-6-fluoroquinazolin-7-yl)-8-methyl-2,3-dihydro-1H-pyrido[2,3-b][1,4]oxazine-1-carboxylate)

Intermediate I-17 was prepared via the coupling of intermediates I-4 and I-8.

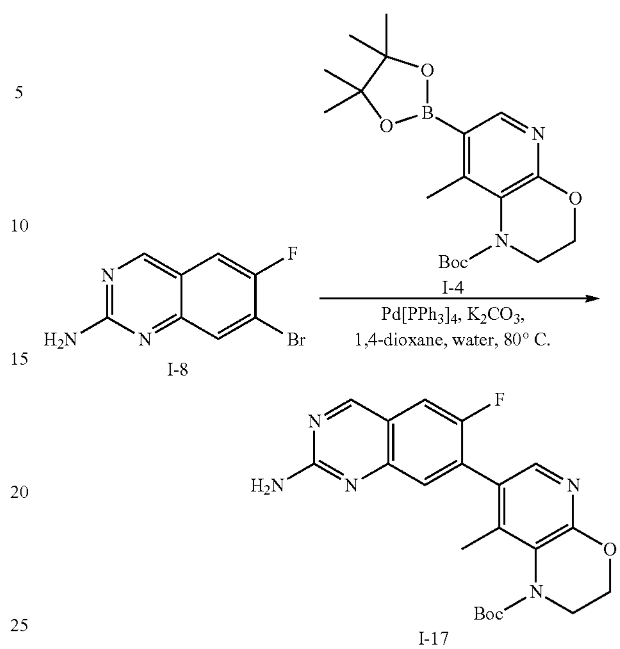

I-4

I-8

I-17

A vial charged with 7-bromo-6-fluoroquinazolin-2-amine (50 mg, 0.21 mmol) in 1,4-dioxane (1.5 mL) was added intermediate I-4 (85 mg, 0.23 mmol), $K_2CO_3$ (86 mg, 0.62 mmol) and $Pd[PPh_3]_4$ (48 mg, 0.041 mmol). The vial was sealed and added water (0.5 mL). The mixture was deoxygenated by bubbling argon for 3 min, then warmed to 70° C., and stirred overnight. After cooling to to RT, the reaction mixture was filtered and concentrated. Purified by chromatography on $SiO_2$ (0-50% EtOAc:Hex then 5% MeOH/DCM and then 25% MeOH/DCM in 4 g silica gel). The fractions containing the desired product mass were pooled and concentrated to dryness to afford tert-butyl 7-(2-amino-6-fluoroquinazolin-7-yl)-8-methyl-2,3-dihydro-1H-pyrido[2,3-b][1,4]oxazine-1-carboxylate. MS (EI) calc'd for $C_{21}H_{23}FN_5O_3$, [M+H]$^+$, 412; found, 412.

Preparation of Intermediate I-18 (7-(8-chloro-2,3-dihydro-1H-pyrido[2,3-b][1,4]oxazin-7-yl-6-fluoro-$N^5$,$N^5$-bis(4-methoxybenzyl)quinazoline-2,5-diamine)

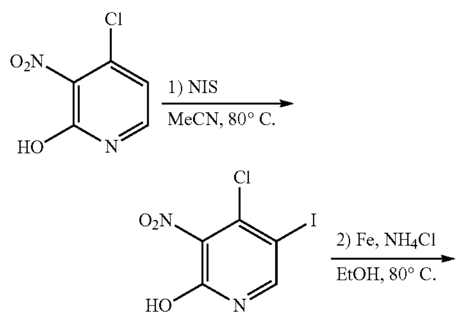

-continued

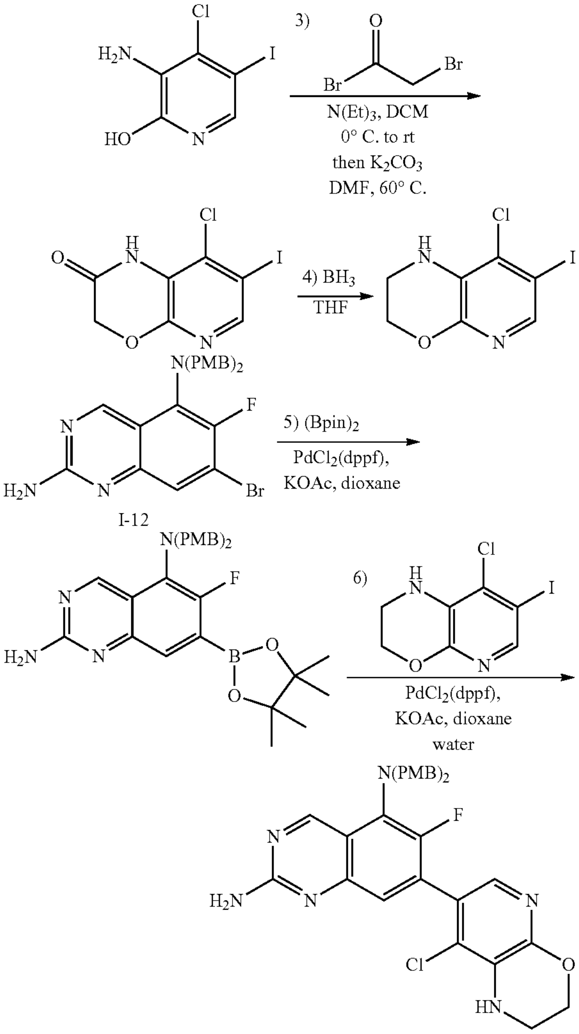

I-12

I-18

Step 1. Preparation of 4-chloro-5-iodo-3-nitropyridin-2-ol

A mixture of 4-chloro-3-nitropyridin-2-ol (2 g, 11.5 mmol) and NIS (2.84 g, 12.60 mmol) in MeCN (60 Ml) was stirred at 80° C. for 17 h to give a mixture. TLC showed that the starting material was consumed and new spot was formed. The solvent was removed under reduced pressure and the residue was dissolved in saturated $NaSO_3$ (100 Ml) and EtOAc (100 Ml). The organic layer was separated and the aqueous was re-extracted with EtOAc (3×100 Ml) and the combined organic layers were washed with brine (250 Ml), dried over anhydrous $Na_2SO_4$, filtered and concentrated under reduced pressure. The residue was purified by flash silica gel chromatography (ISCO®; 20 g SepaFlash® Silica Flash Column, eluent of 50% ethyl acetate/pet. Ether gradient at 30 Ml/min) to give 4-chloro-5-iodo-3-nitropyridin-2-ol (2.7 g, 8.54 mmol) as a solid.

Step 2. Preparation of 3-amino-4-chloro-5-iodopyridin-2-ol

To a stirred solution of 4-chloro-5-iodo-3-nitropyridin-2-ol (2 g, 6.66 mmol) in ethanol (30 mL) and water (30 mL) was added iron (1.86 g, 33.3 mmol) and ammonium chloride (1.78 g, 33.3 mmol) at 20° C., after the addition was finished, the reaction was stirred at 80° C. for 2 h. TLC showed the starting material was consumed and new spot was formed. The mixture was concentrated under reduced pressure and the residue was dissolved in EtOAc (50 mL) and water (50 mL). The mixture was extracted with EtOAc (3×50 mL), and the organic layer was washed with brine (50 mL) and added $Na_2SO_4$ to remove water, concentrated under reduced pressure to give the crude product. The residue was purified by Pre-TLC (silica gel, EtOAc) to give 3-amino-4-chloro-5-iodopyridin-2-ol (1.2 g, 3.77 mmol) as a solid.

Step 3. Preparation of 8-chloro-7-iodo-1H-pyrido[2,3-b][1,4]oxazin-2(3H)-one

To a mixture of 3-amino-4-chloro-5-iodopyridin-2-ol (2 g, 7.39 mmol) and N(Et)3 (3.09 Ml, 22.2 mmol) in DCM (40 Ml) was added 2-bromoacetyl bromide (1.29 Ml, 14.8 mmol) at 0° C. The mixture was stirred at 20° C. for 2 h. The mixture was diluted with DCM (100 Ml), washed with water (50 Ml). The organic layer was concentrated in vacuum. The residue was diluted with DMF (40 Ml), then $K_2CO_3$ (3.07 g, 22.2 mmol) was added. The mixture was stirred at 60° C. for 8 h. TLC showed desired product was formed. The mixture was quenched with water (80 Ml), extracted with EtOAc (3×100 Ml), the combined organic layers were dried over $Na_2SO_4$, filtered and the filtrate was concentrated in vacuo to afford crude 8-chloro-7-iodo-1H-pyrido[2,3-b][1,4]oxazin-2(3H)-one (2 g, 6.44 mmol) as a solid.

Step 4. Preparation of 8-chloro-7-iodo-2,3-dihydro-1H-pyrido[2,3-b][1,4]oxazine

To a solution of 8-chloro-7-iodo-1H-pyrido[2,3-b][1,4]oxazin-2(3H)-one (500 mg, 1.61 mmol) in THF (5 mL) was added $BH_3$THF (8.05 mL, 8.05 mmol) at 0° C. After the addition, the mixture was warmed to 25° C., and stirred at this temperature for 5 h. LCMS showed starting material was consumed. The mixture was cooled to room temperature, quenched with MeOH and stirred for 40 min until no gas formed. The residue mixture was adjust to pH=9 with NaOH (1 M). The mixture was extracted with EtOAc (3×50 mL). The combined organic layers were washed with water (50 mL), brine (50 mL). The organic layer was dried over $Na_2SO_4$, filtered and concentrated in vacuum to give 8-chloro-7-iodo-2,3-dihydro-1H-pyrido[2,3-b][1,4]oxazine (450 mg, 1.214 mmol) as a solid.

Step 5. Preparation of 6-fluoro-$N^5$,$N^5$-bis(4-methoxybenzyl)-7-(4,4,5,5-tetramethyl-1,3,2-dioxaborolan-2-yl)quinazoline-2,5-diamine A mixture of intermediate I-12 (50 mg, 0.101 mmol), $(Bpin)_2$ (51.1 mg, 0.201 mmol) and potassium acetate (39.5 mg, 0.402 mmol) in dioxane (1 Ml) was degassed and backfilled with $N_2$ (three times). $PdCl_2$(dppf) (7.36 mg, 10.05 μmol) was added under $N_2$. The mixture was heated to 100° C. for 12 h. LCMS showed that the desired product was formed. It was not worked up and was used for next step directly.

Step 6. Synthesis of Intermediate I-18 (7-(8-chloro-2,3-dihydro-1H-pyrido[2,3-b][1,4]oxazin-7-yl)-6-fluoro-$N^5$N-bis(4-methoxybenzyl)quinazoline-2,5-diamine)

A mixture of 8-chloro-7-iodo-2,3-dihydro-1H-pyrido[2,3-b][1,4]oxazine (27.2 mg, 0.092 mmol), 6-fluoro-$N^5$,$N^5$-bis (4-methoxybenzyl)-7-(4,4,5,5-tetramethyl-1,3,2-dioxaborolan-2-yl)quinazoline-2,5-diamine (50 mg, crude) and $K_2CO_3$ (38.1 mg, 0.276 mmol) $PdCl_2$(dppf) (6.72 mg, 9.18 μmol) in dioxane (1 mL) and water (0.2 mL) was degassed and backfilled with $N_2$ (three times). The mixture was heated to 70° C. for 3 h. LCMS showed desired product. The mixture was concentrated under reduced pressure to give the crude product. The residue was purified by Prep-TLC (silica gel, pet. $CH_2Cl_2$/MeOH=10/1], v/v, Rf=0.5) to give the desired product (30 mg, 0.046 mmol) as a solid. MS (EI) calc'd for $C_{31}H_{29}ClFN_6O_3$ $[M+H]^+$, 587; found, 587.

Preparation of Intermediate I-19 (6-fluoro-$N^5$,$N^5$-bis(4-methoxybenzyl)-7-(3,3,8-trimethyl-2,3-dihydro-1H-pyrido[2,3-b][1,4]oxazin-7-yl)quinazoline-2,5-diamine)

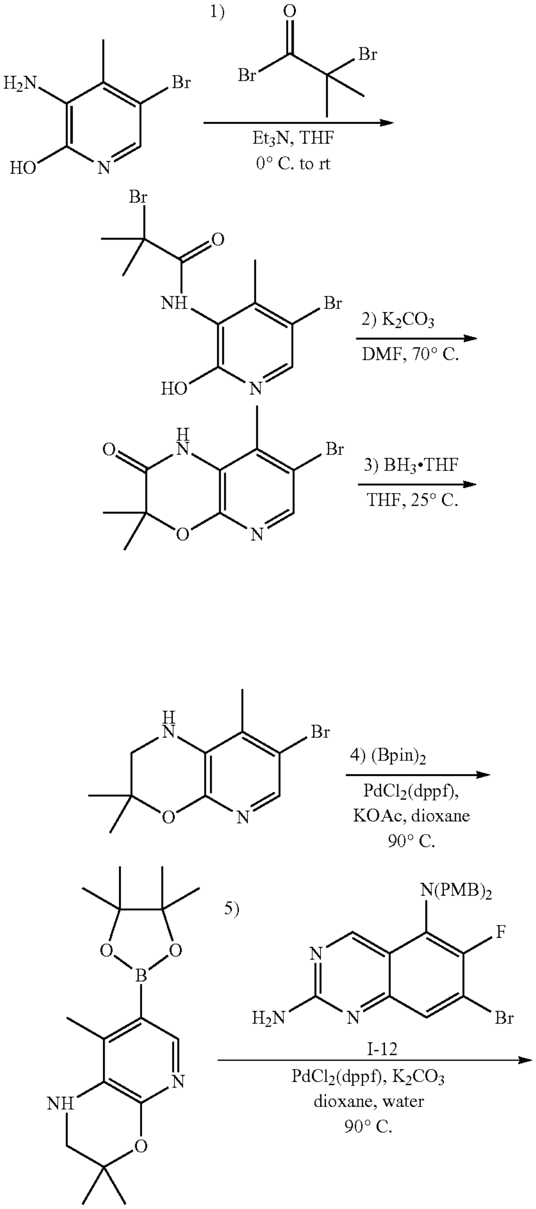

-continued

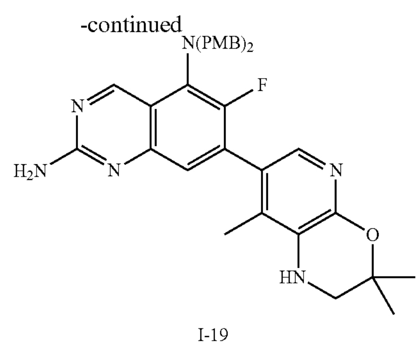

I-19

Step 1. Preparation of 2-bromo-N-(5-bromo-2-hydroxy-4-methylpyridin-3-yl)-2-methylpropanamide To a mixture of 3-amino-5-bromo-4-methylpyridin-2-ol (3 g, 14.8 mmol) and $Et_3N$ (6.18 mL, 44.3 mmol) in THF (60 mL) was added 2-bromo-2-methylpropanoyl bromide (3.74 g, 16.3 mmol) at 0° C. The mixture was stirred at 20° C. for 2 h. LCMS showed desired product was formed. The mixture was quenched with water (100 mL), extracted with EtOAc (3×70 mL), the combined organic layers were dried over $Na_2SO_4$, filtered and the filtrate was concentrated in vacuo to afford crude 2-bromo-N-(5-bromo-2-hydroxy-4-methylpyridin-3-yl)-2-methylpropanamide (5 g, 14.2 mmol) as a solid, which was used directly in next step without further purification.

Step 2. Preparation of 7-bromo-3,3,8-trimethyl-1H-pyrido[2,3-b][1,4]oxazin-2(3H)-one A mixture of 2-bromo-N-(5-bromo-2-hydroxy-4-methylpyridin-3-yl)-2-methylpropanamide (5 g, 14.2 mmol) and $K_2CO_3$ (5.89 g, 42.6 mmol) in DMF (100 mL) was stirred at 70° C. for 3 h, LCMS showed the product was formed. The mixture was washed with water (500 mL), extracted with EtOAc (2×250 mL), the combined organic layers were washed with brine, dried over $Na_2SO_4$, filtered and the filtrate was concentrated in vacuo. The residue was purified by flash silica gel chromatography ($SiO_2$, Eluent of 0~40% EtOAc/Pet. Ether) to give 7-bromo-3,3,8-trimethyl-1H-pyrido[2,3-b][1,4]oxazin-2(3H)-one (3 g, 9.41 mmol) as a solid. $^1H$ NMR (400 MHz, $CDCl_3$) δ 9.20 (br s, 1H) 8.04 (s, 1H) 2.41 (s, 3H) 1.59 (s, 6H).

Step 3. Preparation of 7-bromo-3,3,8-trimethyl-2,3-dihydro-1H-pyrido[2,3-b][1,4]oxazine To a solution of 7-bromo-3,3,8-trimethyl-1H-pyrido[2,3-b][1,4]oxazin-2(3H)-one (100 mg, 0.369 mmol) in THF (1 mL) was added $BH_3$·THF (1.84 mL, 1.84 mmol) at 25° C. After the addition, the mixture was warmed to 25° C., and stirred at this temperature for 4 h. LCMS showed starting material was consumed. The mixture was quenched with MeOH, and stirred for 40 min until no gas formed. The mixture was extracted with EtOAc (3×10 mL). The combined organic layers were washed with water (10 mL), brine (10 mL). The organic layer was dried over $Na_2SO_4$, filtered and concentrated in vacuum and purify by Prep-TLC (silica gel, pet. ether/ethyl acetate=1/1) to give 7-bromo-3,3,8-trimethyl-2,3-dihydro-1H-pyrido[2,3-b][1,4]oxazine (70 mg, 0.218 mmol) as a solid. $^1H$ NMR (400 MHz, $CDCl_3$) δ 7.75 (s, 1H) 3.15 (s, 2H) 2.23 (s, 3H) 1.38 (s, 6H).

Step 4. Preparation of 3,3,8-trimethyl-7-(4,4,5,5-tetramethyl-1,3,2-dioxaborolan-2-yl)-2,3-dihydro-1H-pyrido[2,3-b][1,4]oxazine A mixture of 7-bromo-3,3,8-trimethyl-2,3-dihydro-1H-pyrido[2,3-b][1,4]oxazine (500 mg, 1.95 mmol), $(Bpin)_2$ (988 mg, 3.89 mmol), KOAc (573 mg, 5.83 mmol) and $PdCl_2$(dppf) (71.1 mg, 0.097 mmol) in dioxane (15 mL) was stirred at 90° C. for 15 h, LCMS showed the product was formed. Solvent was filtered, purified by flash silica gel chromatography (ISCO®; 4 g SepaFlash® Silica Flash Column, eluent of [0~30]% ethyl acetate/pet. Ether gradient at 25 mL/min) to give 3,3,8-trimethyl-7-(4,4,5,5-tetramethyl-1,3,2-dioxaborolan-2-yl)-2,3-dihydro-1H-pyrido[2,3-b][1,4]oxazine (400 mg, 1.315 mmol) as an oil.

Step 5. Preparation of Intermediate I-19 (6-fluoro-$N^5$,$N^5$-bis(4-methoxybenzyl)-7-(3,3,8-trimethyl-2,3-dihydro-1H-pyrido[2,3-b][1,4]oxazin-7-yl)quinazoline-2,5-diamine)

To a mixture of intermediate I-12 (600 mg, 1.21 mmol), 3,3,8-trimethyl-7-(4,4,5,5-tetramethyl-1,3,2-dioxaborolan-2-yl)-2,3-dihydro-1H-pyrido[2,3-b][1,4]oxazine (550 mg, 1.810 mmol) and $K_2CO_3$ (500 mg, 3.62 mmol) in dioxane (10 mL) and water (2 mL) was added $PdCl_2$(dppf) (88 mg, 0.121 mmol) at 25° C. under $N_2$. Then the mixture was stirred at 90° C. for 15 h under $N_2$. LCMS showed that the reaction completed. The organic layer was separated and concentrated. The residue was purified by flash silica gel chromatography (OSCO®; 4 g SepaFlash® Silica Flash Column, eluent of [0~100]% ethyl acetate/pet. ether gradient at 30 mL/min) to give the desired product (600 mg, 1.01 mmol) as a solid. MS (EI) calc'd for $C_{34}H_6FN_6O_3$ $[M+H]^+$, 595; found, 595.

Preparation of Intermediate I-20 (7-(3,8-dimethyl-2,3-dihydro-1H-pyrido[2,3-b][1,4]oxazin-7-yl)-6-fluoro-$N^5$,N-bis(4-methoxybenzyl)quinazoline-2,5-diamine)

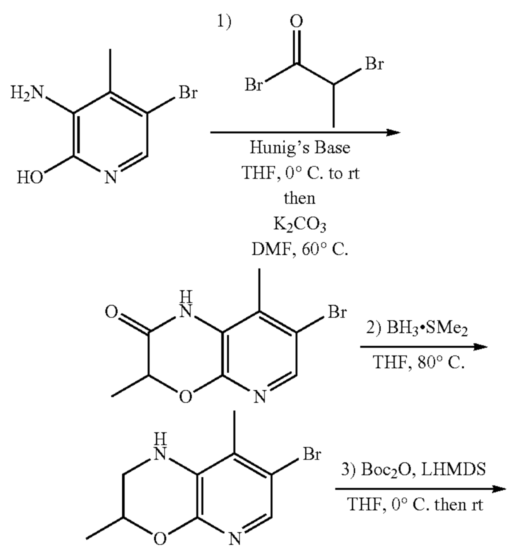

-continued

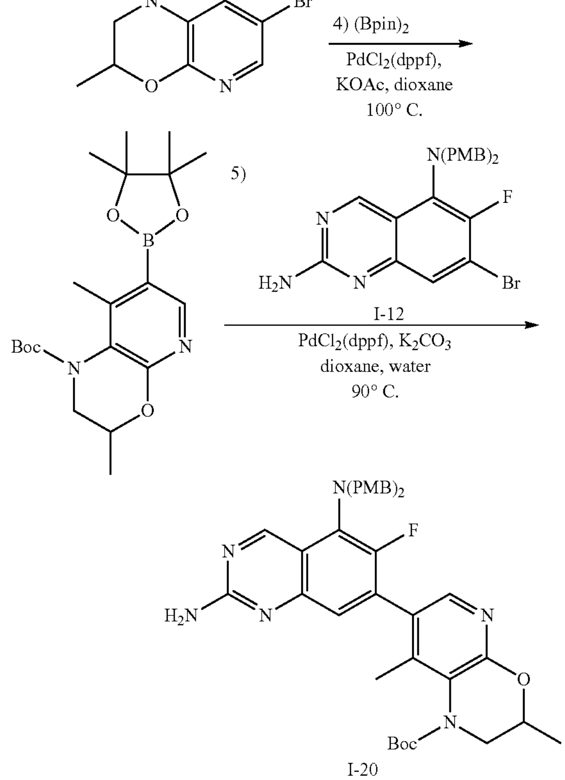

I-20

Step 1. Preparation of 7-bromo-3,8-dimethyl-1H-pyrido[2,3-b][1,4]oxazin-2(3H)-one To a mixture of 3-amino-5-bromo-4-methylpyridin-2-ol (7 g, 34.5 mmol) and Hunig's Base (15.05 mL, 86 mmol) in THF (60 mL) was added 2-bromopropanoyl bromide (5.42 mL, 51.7 mmol) at 0° C. The mixture was stirred at 20° C. for 3 h. Then DMF (20 mL) was added, followed by $K_2CO_3$ (9.53 g, 69.0 mmol). The mixture was stirred at 60° C. for 16 h. LCMS and TLC showed desired product was formed. The mixture was quenched with water (100 mL), extracted with EtOAc (3×80 mL). The combined organic layers were dried over $Na_2SO_4$, filtered and the filtrate was concentrated in vacuum. The residue was purified by column chromatography ($SiO_2$, Pet.ether:EtOAc=5:1~2:1) to give 7-bromo-3,8-dimethyl-1H-pyrido[2,3-b][1,4]oxazin-2(3H)-one (5 g, 19.45 mmol) as a solid.

Step 2. Preparation of 7-bromo-3,8-dimethyl-2,3-dihydro-1H-pyrido[2,3-b][1,4]oxazine To a solution of 7-bromo-3,8-dimethyl-1H-pyrido[2,3-b][1,4]oxazin-2(3H)-one (4.5 g, 17.5 mmol) in THF (45 mL) was added borane dimethyl sulfide complex (3.50 mL, 35.0 mmol) (10 M) at 0° C. After the additional, the mixture was warmed to 80° C., and stirred at this temperature for 2 h. LCMS showed starting material was consumed. The mixture was cooled to room temperature, quenched with MeOH and stirred for 40 min until no gas formed. The mixture was warmed to 80° C. for 2 h. Then it was concentrated in vacuum to give 7-bromo-3,8-dimethyl-2,3-dihydro-1H-pyrido[2,3-b][1,4]oxazine (3.7 g, 13.70 mmol) as a solid.

Step 3. Preparation of tert-butyl 7-bromo-3,8-dimethyl-2,3-dihydro-1H-pyrido[2,3-b][1.4]oxazine-1-carboxylate To a solution of 7-bromo-3,8-dimethyl-2,3-dihydro-1H-pyrido[2,3-b][1,4]oxazine (4.5 g, 18.5 mmol) and $Boc_2O$ (5.16 mL, 22.2 mmol) in THF (45 mL) was added LHMDS (22.2 mL, 22.2 mmol) at 0° C. The mixture was stirred at 20° C. for 2 h. TLC showed the desired product. The mixture was quenched with water (50 mL), extracted with EtOAc (2×50 mL). The combined organic layers were washed with brine (50 mL), dried over $Na_2SO_4$, filtered and concentrated in vacuum. The residue was purified by flash silica gel chromatography (ISCO®; 40 g SepaFlash®-Silica Flash Column, Eluent of 10~40% EtOAc/Pet.ether gradient at 30 mL/min) to give tert-butyl 7-bromo-3,8-dimethyl-2,3-dihydro-1H-pyrido[2,3-b][1,4]oxazine-1-carboxylate (3 g, 6.99 mmol) as an oil. $^1H$ NMR (500 MHz, $CD_3OD$) δ 8.06 (s, 1H), 4.41 (s, 1H), 3.28-3.33 (m, 2H), 2.25-2.32 (m, 3H), 1.47 (m, 9H).

Step 4. Preparation of tert-butyl 3,8-dimethyl-7-(4,4,5,5-tetramethyl-1,3,2-dioxaborolan-2-yl)-2,3-dihydro-1H-pyrido[2,3-b][1,4]oxazine-1-carboxylate A mixture of tert-butyl 7-bromo-3,8-dimethyl-2,3-dihydro-1H-pyrido[2,3-b][1,4]oxazine-1-carboxylate (2 g, 5.83 mmol), $(Bpin)_2$ (2.96 g, 11.65 mmol) and KOAc (2.288 g, 23.31 mmol) in dioxane (30 mL) was degassed and backfilled with $N_2$ (three times). $PdCl_2(dppf)$ (0.426 g, 0.583 mmol) was added under $N_2$. The mixture was heated to 100° C. for 12 h. LCMS showed the desired product. The mixture was quenched with water (30 mL), extracted with EtOAc (2×50 mL). The combined organic layers were washed with brine (30 mL), dried over $Na_2SO_4$, filtered and concentrated in vacuum and the residue was purified by silica gel (ISCO; 40 g SepaFlash; Silica Flash Column, eluent of [0-40]% EtOAc/PE gradient at 30 mL/min) to give the desired product (3.5 g, 5.38 mmol). As an oil. MS (EI) calc'd for $C_{20}H_{32}BN_2O_5$ $[M+H]^+$, 391; found, 391.

Step 5. Preparation of Intermediate I-20 (7-(3,8-dimethyl-2,3-dihydro-1H-pyrido[2,3-b][1,4]oxazin-7-yl)-6-fluoro-$N^5$,N-bis(4-methoxybenzyl)quinazoline-2,5-diamine)

To a mixture of tert-butyl 3,8-dimethyl-7-(4,4,5,5-tetramethyl-1,3,2-dioxaborolan-2-yl)-2,3-dihydro-1H-pyrido[2,3-b][1,4]oxazine-1-carboxylate (1.31 g, 2.01 mmol), $K_2CO_3$ (0.834 g, 6.03 mmol) and intermediate I-12 (1 g, 2.01 mmol) in dioxane (10 mL) and water (2 mL) was added $PdCl_2$ (dppf) (0.147 g, 0.201 mmol) at 20° C. under $N_2$. Then the reaction was stirred at 90° C. for 12 h. LCMS showed the desired product. Water (20 mL) and EtOAc (20 mL) was added. The organic layer was separated and the aqueous was re-extracted with EtOAc (3×20 mL). The combined organic layers were washed with brine (20 mL), dried over anhydrous $Na_2SO_4$, filtered and concentrated. The residue was purified by flash silica gel chromatography (ISCO®; 12 g SepaFlash®, Silica Flash Column, Eluent of 10~60% EtOAc/Pet.ether gradient at 30 mL/min) to give intermediate I-20 (1.2 g, 1.410 mmol) as an oil. MS (EI) calc'd for $C_{33}H_4FN_6O_3$ $[M+H]^+$, 681; found, 681.

Compound Examples of Table 1

Example 1A. Preparation of 1-4

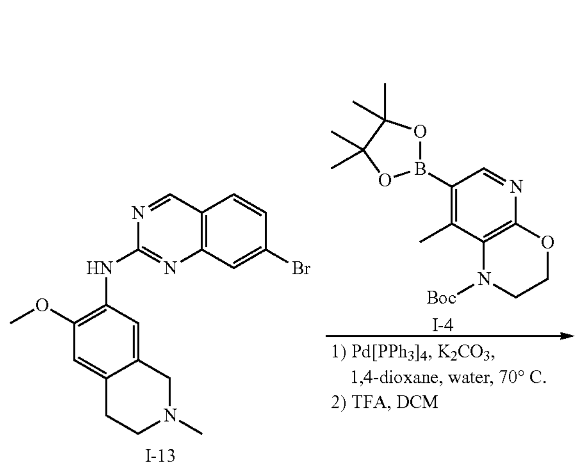

I-13

I-4

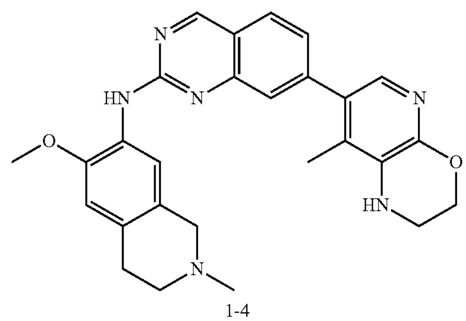

1-4

A mixture containing intermediate I-4 (52 mg, 0.14 mmol), intermediate I-13 (50 mg, 0.13 mmol), $Pd[PPh_3]_4$ (29 mg, 0.025 mmol), and $K_2CO_3$ (52 mg, 0.38 mmol) was taken-up in 1,4-dioxane (1.3 mL) and water (0.5 mL). The mixture was deoxygenated by bubbling argon gas through the reaction mixture for 3 min. then stirred overnight at 70° C. After cooling, the reaction was filtered and concentrated to dryness. The crude oil was taken up in 1 mL of DCM and treated with 1 mL of TFA. The solution was aged for 1 h at RT and then concentrated to dryness to give deprotected product. The residue was purified by reverse phase chromatography (gradient of 15-70% ACN/water with 0.1% $NH_4OH$) to provide 1-4 as a solid. $^1H$ NMR (500 MHz, DMSO-$d_6$) δ 9.33 (s, 1H), 8.33 (s, 1H), 8.26 (s, 1H), 7.98 (d, J=8.2 Hz, 1H), 7.56 (s, 1H), 7.39 (s, 1H), 7.34 (dd, J=8.2, 1.5 Hz, 1H), 6.90 (s, 1H), 5.73 (s, 1H), 4.34-4.24 (m, 2H), 3.88 (s, 3H), 3.37 (br, 2H), 3.33 (s, 2H), 3.14 (br, 1H), 2.97 (s, 2H), 2.70 (s, 3H), 2.03 (s, 3H), 1.92 (s, 1H). MS (EI) calc'd for $C_{27}H_{29}N_6O_2$ $[M+H]^+$, 469; found, 469.

Example 1B. Preparation of 1-94

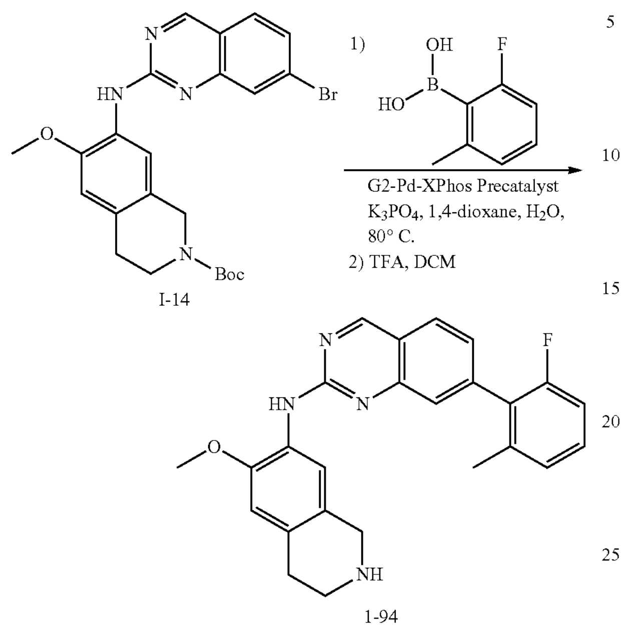

I-14

1-94

A vial charged with (2-fluoro-6-methylphenyl)boronic acid (13 mg, 0.082 mmol), Intermediate I-14 (33 mg, 0.068 mmol), G2-Pd-XPhos Precatalyst (11 mg, 0.014 mmol), and $K_3PO_4$ (43 mg, 0.20 mmol) was added 1,4-dioxane (0.9 mL) and water (90 μL). The mixture was deoxygenated by bubbling argon for 3 min, then warmed to 80° C., and stirred overnight. After cooling to to RT, the reaction mixture was filtered and concentrated. The crude residue was dissolved in 1 mL of DCM and 1 mL of TFA, and then aged for 2 h. After concentration and the crude mixture was purified by reverse phase chromatography (30-95% ACN/water with 0.1% $NH_4OH$) to afford compound 1-94. $^1H$ NMR (500 MHz, DMSO-$d_6$) δ 9.33 (s, 1H), 8.22 (s, 1H), 8.12 (s, 1H), 8.00 (d, J=8.2 Hz, 1H), 7.55 (s, 1H), 7.45-7.33 (m, 1H), 7.29 (d, J=8.0 Hz, 1H), 7.22 (d, J=7.6 Hz, 1H), 7.18 (t, J=8.9 Hz, 1H), 6.76 (s, 1H), 3.85 (s, 5H), 2.95 (t, J=5.6 Hz, 2H), 2.68 (t, J=5.4 Hz, 2H), 2.17 (s, 3H). MS (EI) calc'd for $C_{25}H_{24}FN_4O$, $[M+H]^+$, 415, found, 415.

Example 1C. Preparation of 1-95

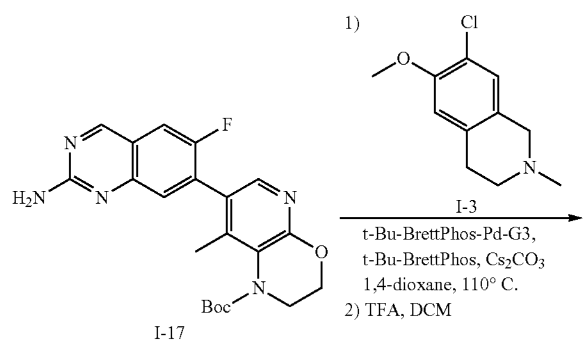

I-17

-continued

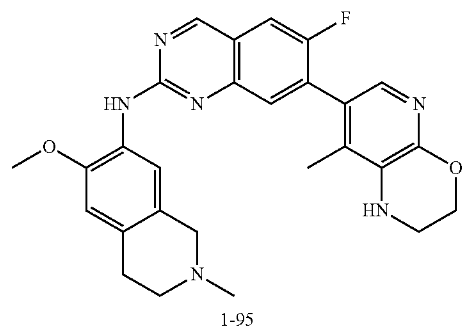

1-95

Steps 1 and 2. Synthesis of Compound 1-95 (6-fluoro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine)

A solution of 7-chloro-6-methoxy-2-methyl-1,2,3,4-tetrahydroisoquinoline (I-3) (87 mg, 0.41 mmol), intermediate I-17 (85 mg, 0.21 mmol), t-BuBrettPhos-Pd-G3 (88 mg, 0.10 mmol), t-BuBrettPhos (50 mg, 0.10 mmol), and $Cs_2CO_3$ (337 mg, 1.03 mmol) in 1,4-dioxane (4 mL) was deoxygenated by bubbling argon for 3 min. The mixture was heated to 110° C., and stirred overnight. After cooling, the reaction was filtered and concentrated to dryness. Purified by flash column chromatography (4 g, silica gel, 0-35% EtOAc:Hex then 0-25% MeOH:DCM). The fractions containing the desired product mass were pooled and concentrated to dryness. The product was taken in 1 mL DCM and added 1 mL TFA. After 2 h, the reaction was concentrated to dryness and purified by reverse phase chromatography (15-70% ACN/water with 0.1% $NH_4OH$) to afford compound 1-95. $^1H$ NMR (500 MHz, DMSO-$d_6$) δ 9.30 (s, 1H), 8.21 (s, 1H), 8.16 (s, 1H), 7.83 (d, J=8.9 Hz, 1H), 7.60 (d, J=6.7 Hz, 1H), 7.39 (s, 1H), 6.80 (s, 1H), 5.74 (s, 1H), 4.30 (s, 2H), 3.84 (s, 3H), 3.46 (s, 2H), 3.38 (s, 2H), 2.80 (s, 2H), 2.58 (s, 2H), 2.33 (s, 3H), 1.93 (s, 3H). MS (EI) calc'd for $C_{27}H_{28}FN_6O_2$, $[M+H]^+$, 487; found, 487.

Example 1D. Preparation of 1-96

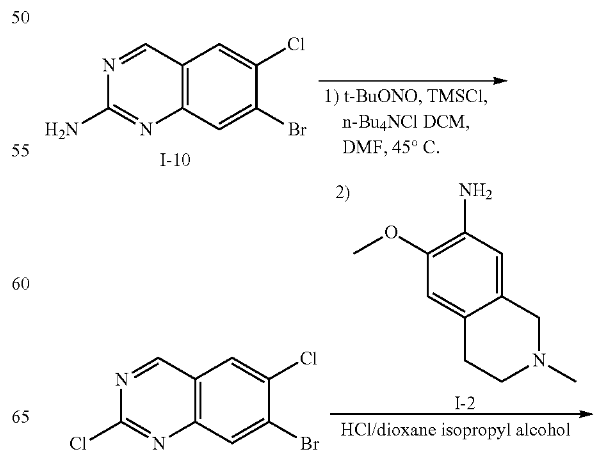

I-10

-continued

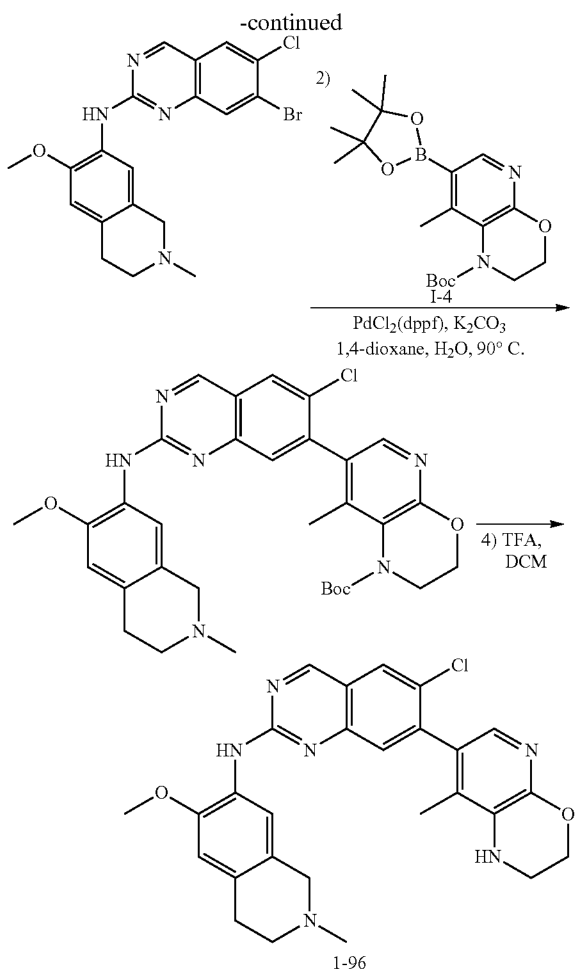

1-96

Step 1. Preparation of 7-bromo-2,6-dichloroquinazoline

To a solution of 7-bromo-6-chloroquinazolin-2-amine (2.0 g, 7.7 mmol), tetrabutylammonium chloride (4.3 g, 15 mmol), and chlorotrimethylsilane (3.9 mL, 31 mmol) in DCM (35 mL) and DMF (2 mL) was added tert-butyl nitrite (2.8 mL, 23 mmol), dropwise, via syringe. The reaction mixture was allowed to stir at RT for 30 minutes and then at 45° C. After 4 h. LC/MS indicated reaction has reached completion. Quenched with saturated aqueous $NaHCO_3$, extracted with DCM, washed with aqueous lithium chloride, dried over $MgSO_4$, filtered and concentrated to dryness. Purified by chromatography on $SiO_2$ (0-20% EtOAc/Hex in 40 g silica gel, dry loaded) to give 7-bromo-2,6-dichloroquinazoline product as a solid. MS (EI) calc'd for $C_8H_4BrCl_2N_2$, $[M+H]^+$, 278, 280; found, 278, 280.

Step 2. Preparation of 7-bromo-6-chloro-N-(6-methoxy-2-methyl-1,2,3,4-tetrahydroisoquinolin-7-yl)quinazolin-2-amine To a solution of 7-bromo-2,6-dichloroquinazoline (76 mg, 0.27 mmol) in isopropanol (1 mL) was added HCl/1,4-dioxane (4N) (0.1 mL), then 6-methoxy-2-methyl-1,2,3,4-tetrahydroisoquinolin-7-amine (58 mg, 0.30 mmol) was added at 15° C. The mixture was stirred at 110° C. for 2 h. LC/MS showed the product was formed. The mixture was cooled to RT and some solid was formed. The mixture was filtered to afford 7-bromo-6-chloro-N-(6-methoxy-2-methyl-1,2,3,4-tetrahydroisoquinolin-7-yl)quinazolin-2-amine as a solid, which was used directly in next step without further purification. MS (EI) calc'd for $C_{19}H_{19}BrClN_4O$, $[M+H]^+$, 433, 435; found, 433, 435.

Step 3. Synthesis of tert-butyl 7-(6-chloro-2-((6-methoxy-2-methyl-1,2,3,4-tetrahydroisoquinolin-7-yl)amino)quinazolin-7-yl)-8-methyl-2,3-dihydro-1H-pyrido[2,3-b][1,4]oxazine-1-carboxylate To a solution of 7-bromo-6-chloro-N-(6-methoxy-2-methyl-1,2,3,4-tetrahydroisoquinolin-7-yl)quinazolin-2-amine (60 mg, 0.14 mmol) and intermediate I-4 (63 mg, 0.17 mmol) in 1,4-dioxane (6 mL), water (1 mL) was added $K_2CO_3$ (29 mg, 0.21 mmol) and PdCl$_2$(dppf) (10 mg, 0.014 mmol). The mixture was stirred at 90° C. for 2 h. LC/MS showed starting material was consumed, desired product as main peak. The mixture was diluted with EtOAc (50 mL), washed with water (30 mL) and then with brine (30 mL). The organic layer was dried over $Na_2SO_4$, filtered and concentrated in vacuum. Chromatography on $SiO_2$ (20% MeOH/DCM) gave tert-butyl 7-(6-chloro-2-((6-methoxy-2-methyl-1,2,3,4-tetrahydroisoquinolin-7-yl)amino)quinazolin-7-yl)-8-methyl-2,3-dihydro-1H-pyrido[2,3-b][1,4]oxazine-1-carboxylate as a solid. MS (EI) calc'd for $C_{32}H_{36}ClN_6O_4$, $[M+H]^+$, 603; found, 603.

Step 4. Synthesis of Compound 1-96 (6-chloro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine)

To a solution of tert-butyl 7-(6-chloro-2-((6-methoxy-2-methyl-1,2,3,4-tetrahydroisoquinolin-7-yl)amino)quinazolin-7-yl)-8-methyl-2,3-dihydro-1H-pyrido[2,3-b][1,4]oxazine-1-carboxylate (30 mg, 0.050 mmol) in DCM (0.5 mL), TFA (0.5 mL) was added. The mixture was stirred at 20° C. for 3 h. LC/MS showed the reaction was completed. The mixture was concentrated to give crude product, it was purified by HPLC (TFA, Instrument ee Method Column YMC-Actus Triart C18 150*30 mm*5 um Condition water (0.1% TFA)-ACN Begin B 22 End B 52 Gradient Time (min) 11 100% B Hold Time (min) 1.1 FlowRate (mL/min) 40 Injections 1) to give compound 1-96 as a solid. $^1H$ NMR (400 MHz, $CD_3OD$) δ 9.24 (s, 1H), 8.57 (s, 1H), 8.09 (s, 1H), 7.67 (s, 1H), 7.42 (s, 1H), 6.93 (s, 1H), 4.50-4.58 (m, 3H), 4.19-4.31 (m, 1H), 3.95 (s, 3H), 3.73 (br s, 1H), 3.52-3.60 (m, 2H), 3.39 (br s, 1H), 3.11-3.25 (m, 2H), 3.03 (s, 3H), 2.01 (s, 3H). MS (EI) calc'd for $C_{27}H_{28}ClN_6O_2$, $[M+H]^+$, 503; found, 503.

Example 1E. Preparation of 1-97

Compound 1-97 was prepared from tert-butyl 7-(6-chloro-2-((6-methoxy-2-methyl-1,2,3,4-tetrahydroisoquinolin-7-yl)amino)quinazolin-7-yl)-8-methyl-2,3-dihydro-1H-pyrido[2,3-b][1,4]oxazine-1-carboxylate (synthesis described in Example 1D) as outlined below.

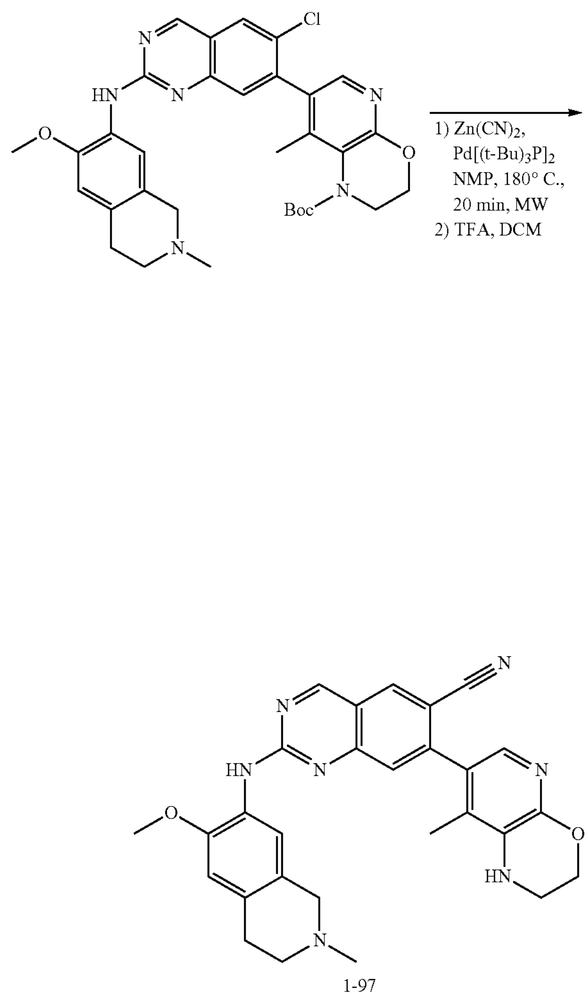

1-97

To a mixture of tert-butyl 7-(6-chloro-2-((6-methoxy-2-methyl-1,2,3,4-tetrahydroisoquinolin-7-yl)amino)quinazolin-7-yl)-8-methyl-2,3-dihydro-1H-pyrido[2,3-b][1,4]oxazine-1-carboxylate (30 mg, 0.050 mmol), $Pd[(t-Bu)_3P]_2$ (25.4 mg, 0.050 mmol) in NMP (1 mL) was added dicyanozinc (47 mg, 0.40 mmol). Then the mixture was stirred at 180° C. for 20 min under microwave. LC/MS showed that the desired target was formed. Water (10 mL) and EtOAc (15 mL) was added. The organic layer was separated and the aqueous was re-extracted with EtOAc (3×15 mL). The combined organic layers were washed with brine (10 mL), dried over anhydrous $Na_2SO_4$, filtered and concentrated. Chromatography on $SiO_2$ (DCM:MeOH=10:1) to give afford a solid which was taken up in DCM (1 mL) and added TFA (0.5 mL). The mixture was stirred at 20° C. for 2 h. LC/MS showed that the desired target was formed. The solvent was removed by concentrated to give crude product, the residue was purified by HPLC (Instrument ee Method Column YMC-Actus Triart C18 150*30 mm*5 um Condition water (0.1% TFA)-ACN Begin B 17, End B 47 Gradient Time (min) 11 100% B Hold Time (min) 1.1 FlowRate (mL/min) 40 Injections 1) to give compound 1-97 as a solid. $^1H$ NMR (400 MHz, $CD_3OD$) δ 9.27 (s, 1H), 8.42 (s, 1H), 8.34 (s, 1H), 7.62 (s, 1H), 7.38 (s, 1H), 6.82 (s, 1H), 4.42 (t, J=4.3 Hz, 2H), 3.92 (s, 3H), 3.64 (s, 2H), 3.49-3.51 (m, 2H), 2.92-2.95 (m, 2H), 2.77-2.79 (m, 2H), 2.47 (s, 3H), 2.03 (s, 3H). MS (EI) calc'd for $C_{28}H_{28}N_7O_2$, $[M+H]^+$, 494; found, 494.

Example 1F. Preparation of 1-111

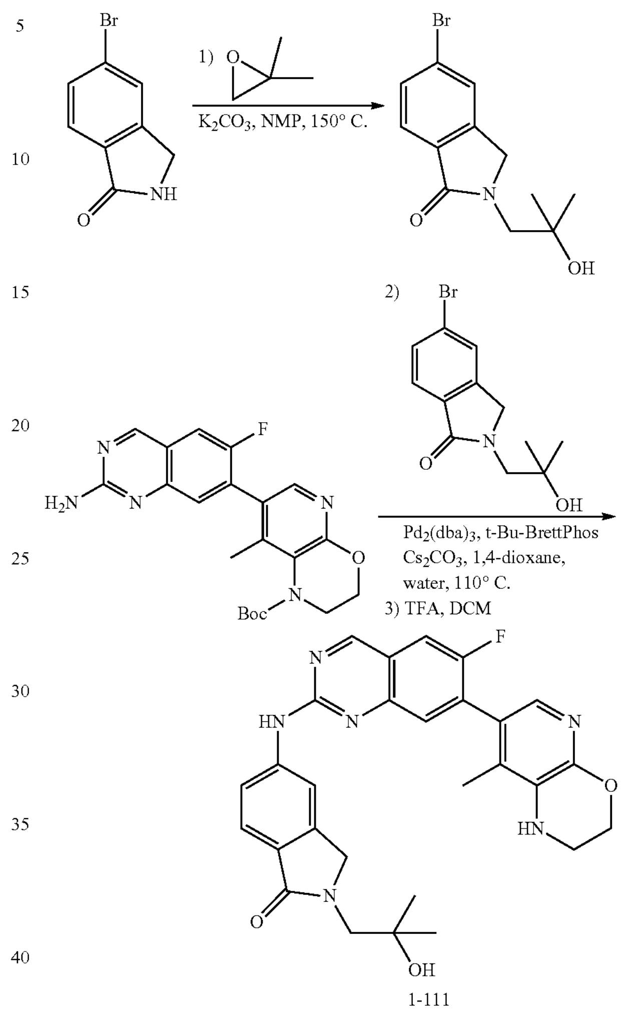

1-111

Step 1. Preparation of 5-bromo-2-(2-hydroxy-2-methylpropyl)isoindolin-1-one

A microwave vial charged with 5-bromoisoindolin-1-one (150 mg, 0.707 mmol) and isobutylene oxide (0.31 mL, 3.5 mmol) in NMP (0.7 mL) was added $K_2CO_3$ (200 mg, 1.4 mmol). The reaction was heated to 150° C. overnight. The reaction was allowed to cool, and then filtered and concentrated to dryness. Purified by flash column chromatography (silica gel, 4 g, 0-10% MeOH/DCM). After concentration, 5-bromo-2-(2-hydroxy-2-methylpropyl)isoindolin-1-one was afforded as a solid. MS (EI) calc'd for $C_{12}H_{15}BrNO_2$, $[M+H]^+$, 284; found, 284.

Steps 2 and 3. Synthesis of Compound 1-111 (5-{[6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one)

A vial charged with 5-bromo-2-(2-hydroxy-2-methylpropyl)isoindolin-1-one (41 mg, 0.15 mmol), tert-butyl 7-(2-amino-6-fluoroquinazolin-7-yl)-8-methyl-2,3-dihydro-1H- pyrido[2,3-b][1,4]oxazine-1-carboxylate (40 mg, 0.097 mmol), t-BuBrettPhos (19 mg, 0.039 mmol). $Pd_2(dba)_3$ (8.9 mg, 9.7 μmol), and $K_3PO_4$ (41 mg, 0.19 mmol) in toluene (1.0 mL) was treated with water (10 μL) and then purged with nitrogen gas for 5 min. The dark reaction mixture was heated to 110° C. overnight. After cooling, the reaction was filtered and concentrated to dryness. The crude residue was taken up in DCM (1.0 mL) and TFA (1.0 mL). After 2 h, the reaction was concentrated to dryness. The crude deprotected product was purified by reverse phase chromatography (15-70% ACN/water with 0.1% $NH_4OH$). After concentration, compound 1-111 was isolated as a pale solid. $^1H$ NMR (500 MHz, DMSO-$d_6$) δ 10.33 (s, 1H), 9.40 (s, 1H), 8.46 (s, 1H), 7.95-7.85 (m, 2H), 7.72 (d, J=6.7 Hz, 1H), 7.61 (d, J=8.3 Hz, 1H), 7.41 (s, 1H), 5.75 (s, 1H), 4.65 (d, J=2.8 Hz, 3H), 4.38-4.25 (m, 2H), 3.42 (s, 2H), 3.39 (s, 2H), 1.94 (d, J=1.4 Hz, 3H), 1.12 (s, 6H). MS (EI) calc'd for $C_{28}H_{28}FN_6O_3$, $[M+H]^+$, 515; found, 515.

Example 1G. Preparation of 1-115

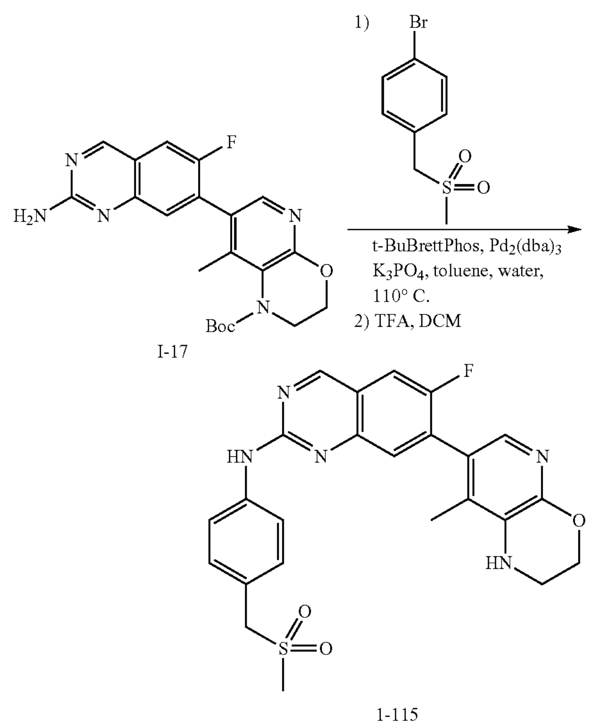

I-17

1-115

Steps 1 and 2. Synthesis of Compound 1-115

A vial charged with 1-bromo-4-((methylsulfonyl)methyl) benzene (52 mg, 0.21 mmol), intermediate I-17 (150 mg, 0.365 mmol), t-BuBrettPhos (71 mg, 0.15 mmol), $Pd_2(dba)_3$ (33 mg, 0.036 mmol), and $K_3PO_4$ (155 mg, 0.729 mmol) in toluene (3.5 mL) was added water (0.2 mL). The mixture was purged with nitrogen gas for 10 min and then heated to 110° C. overnight. After cooling, the reaction was filtered and concentrated to dryness. Purified by flash column chromatography (4 g, silica gel, 0-25% MeOH:DCM). The fractions containing the desired product mass were pooled and concentrated to dryness. The product was taken in 1 mL DCM and added 1 mL TFA. After 2 h, the reaction was concentrated to dryness and purified by reverse phase chromatography (15-70% ACN/water with 0.1% $NH_4OH$) to afford compound 1-115. $^1H$ NMR (500 MHz, DMSO-$d_6$) δ 10.05 (s, 1H), 9.36 (s, 1H), 8.01 (d, J=8.6 Hz, 2H), 7.86 (d, J=9.2 Hz, 1H), 7.62 (d, J=6.7 Hz, 1H), 7.40 (s, 1H), 7.35 (d, J=8.6 Hz, 2H), 5.74 (s, 1H), 4.42 (s, 2H), 4.35-4.25 (m, 2H), 3.39 (d, J=8.3 Hz, 2H), 2.88 (s, 3H), 1.94 (d, J=1.5 Hz, 3H). MS (EI) calc'd for $C_{24}H_{23}FN_5O_3S$, $[M+H]^+$, 480; found, 480.

Example 1H

Preparation of 1-116 and 1-117

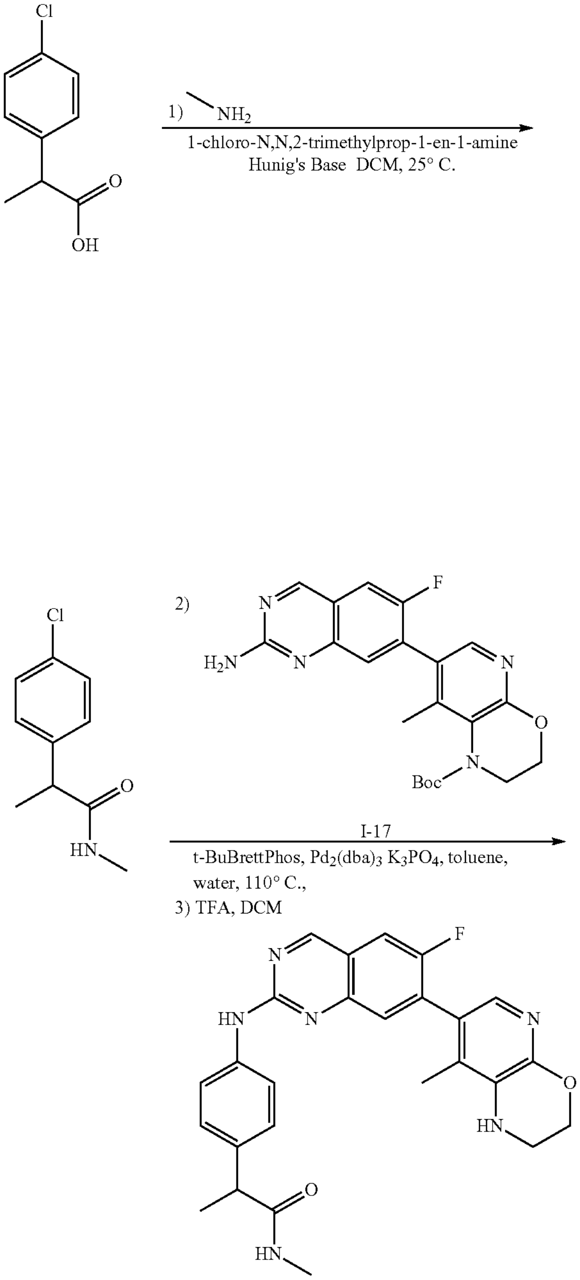

1-116

-continued

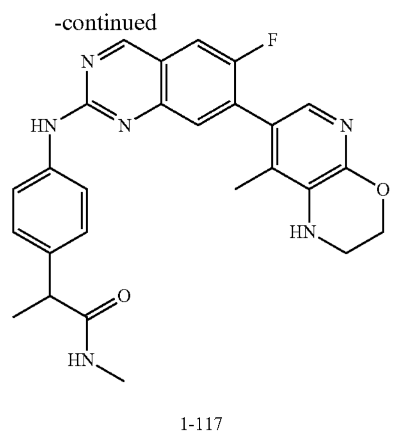

1-117

Step 1. Preparation of 2-(4-chlorophenyl)-N-methylpropanamide

A solution of 2-(4-chlorophenyl)propanoic acid (500 mg, 2.71 mmol) in DCM (18 mL) was added 1-chloro-N,N-2-trimethylpropenylamine (1.0 mL, 5.42 mmol). The mixture was allowed to stir at rt for 15 min. Then methanamine (168 mg, 5.42 mmol) and N,N-diisopropylethylamine (1.0 mL, 8.12 mmol) were added to the mixture and the reaction was allowed to stir at 25° C. for 15 min. The reaction was then diluted with DCM and quenched with saturated ammonium chloride. The organic layer was separated from the aqueous layer and concentrated to dryness. The crude product 2-(4-chlorophenyl)-N-methylpropanamide (396 mg, 2.00 mmol) was used in the next reaction without further purification. MS (EI) calc'd for $C_{10}H_{13}ClNO$ $[M+H]^+$, 198; found, 198.

Steps 2 and 3. Preparation of Compounds 1-116 and 1-117

A vial charged with 2-(4-chlorophenyl)-N-methylpropanamide (144 mg, 0.729 mmol), intermediate I-17 (100 mg, 0.243 mmol), t-BuBrettPhos (47.1 mg, 0.097 mmol), $Pd_2(dba)_3$ (22.26 mg, 0.024 mmol), and $K_3PO_4$ (103 mg, 0.486 mmol) in toluene (4.6 mL) was added Water (0.243 mL). The mixture was purged with nitrogen gas for 10 min and then heated to 110° C. overnight. The reaction was allowed to cool to rt, then filtered and concentrated. Purified by flash column chromatography (4 g, silica gel, 0-10% MeOH:DCM). The fractions containing the desired product were pooled and concentrated. The oil was taken up in 1 mL of DCM and added 1 mL of TFA—allowed to age at rt for 1 h. The solvent and excess TFA were concentrated under reduced pressure. The enantiomers were resolved by chiral-Prep-SFC [Column: AS-H, 21×250 mm; 30% (MeOH/0.1% $NH_4OH$)/$CO_2$; Flow rate: 70 mL/min; 220 nm] to provide compound 1-117 [RT: 5.3 min] and compound 1-116 [RT: 6.3 min].

Compound 1-116. $^1H$ NMR (500 MHz, DMSO-$d_6$) δ 9.86 (s, 1H), 9.32 (s, 1H), 7.92-7.77 (m, 4H), 7.55 (d, J=6.7 Hz, 1H), 7.39 (s, 1H), 7.24 (d, J=8.6 Hz, 2H), 5.75 (s, 1H), 4.35-4.27 (m, 2H), 3.52 (q, J=7.0 Hz, 1H), 3.39 (s, 2H), 2.55 (d, J=4.6 Hz, 3H), 1.93 (d, J=1.6 Hz, 3H), 1.31 (d, J=7.1 Hz, 3H). MS (EI) calc'd for $C_{26}H_{26}FN_6O_2$ $[M+H]^+$, 473; found, 473.

Compound 1-117. $^1H$ NMR (500 MHz, DMSO-$d_6$) δ 9.86 (s, 1H), 9.32 (s, 1H), 7.92-7.79 (m, 4H), 7.55 (d, J=6.7 Hz, 1H), 7.39 (s, 1H), 7.24 (d, J=8.6 Hz, 2H), 5.75 (s, 1H), 4.36-4.23 (m, 2H), 3.52 (q, J=7.0 Hz, 1H), 3.39 (s, 2H), 2.55 (d, J=4.6 Hz, 3H), 1.93 (d, J=1.5 Hz, 3H), 1.31 (d, J=7.1 Hz, 3H). MS (EI) calc'd for $C_{26}H_{26}FN_6O_2$ $[M+H]^+$, 473; found, 473.

Preparation of 1-118 and 1-119

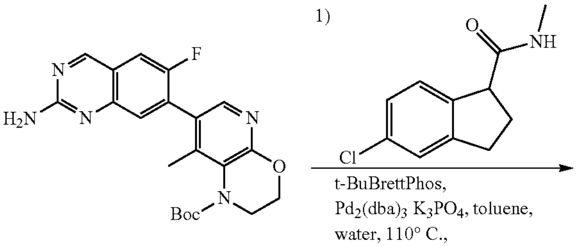

I-17

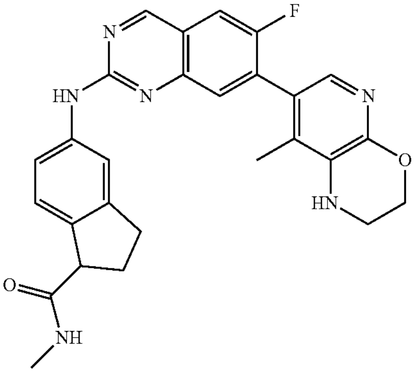

1-118

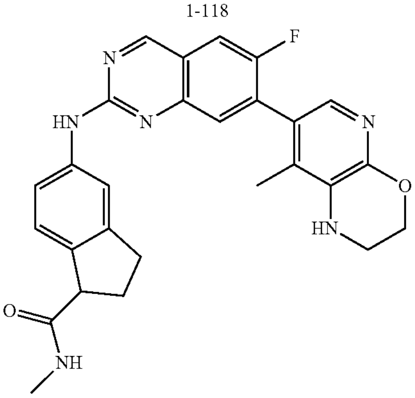

1-119

A vial charged with 5-chloro-N-methyl-2,3-dihydro-1H-indene-1-carboxamide (153 mg, 0.729 mmol), intermediate I-17 (100 mg, 0.243 mmol), t-BuBrettPhos (47.1 mg, 0.097 mmol), $Pd_2(dba)_3$ (22.26 mg, 0.024 mmol), and $K_3PO_4$ (103 mg, 0.486 mmol) in toluene (4.6 mL) was added Water (0.243 mL). The mixture was purged with nitrogen gas for 10 min and then heated to 110° C. overnight. The reaction was allowed to cool to rt, then filtered and concentrated. The adduct was purified by flash column chromatography (4 g, silica gel, 0-10% MeOH:DCM). The fractions containing the desired product were pooled and concentrated to dryness. The oil was then taken up in 1 mL of DCM and added 1 mL of TFA—allowed to age at rt for 1 h. The solvent and excess TFA were concentrated under reduced pressure. The enantiomers were resolved by chiral-Prep-SFC [Column:

OJ-H, 21×250 mm; 40% (MeOH/0.1% $NH_4OH$)/$CO_2$: Flow rate: 70 mL/min; 220 nm] to provide compound 1-119 [RT: 4.3 min] and compound 1-118 [RT: 5.3 min].

Compound 1-118. $^1H$ NMR (500 MHz, DMSO-$d_6$) 1H NMR (499 MHz, DMSO-$d_6$) δ 9.84 (s, 1H), 9.31 (s, 1H), 7.98 (q, J=4.4 Hz, 1H), 7.86 (s, 1H), 7.82 (d, J=9.2 Hz, 1H), 7.70 (d, J=7.9 Hz, 1H), 7.55 (d, J=6.7 Hz, 1H), 7.39 (s, 1H), 7.13 (d, J=8.2 Hz, 1H), 5.74 (s, 1H), 4.34-4.28 (m, 2H), 3.80 (s, 1H), 3.38 (s, 2H), 3.05-2.95 (m, 1H), 2.83 (dt, J=15.5, 7.8 Hz, 1H), 2.64 (d, J=4.6 Hz, 3H), 2.30-2.11 (m, 2H), 1.93 (d, J=1.3 Hz, 3H). MS (EI) calc'd for $C_{27}H_{26}FN_6O_2$ $[M+H]^+$, 485; found, 485.

Compound 1-119. $^1H$ NMR (500 MHz, DMSO-$d_6$) δ 9.84 (s, 1H), 9.31 (s, 1H), 7.98 (q, J=4.4 Hz, 1H), 7.86 (s, 1H), 7.82 (d, J=9.2 Hz, 1H), 7.70 (d, J=8.1 Hz, 1H), 7.55 (d, J=6.7 Hz, 1H), 7.39 (s, 1H), 7.13 (d, J=8.3 Hz, 1H), 5.74 (s, 1H), 4.35-4.26 (m, 2H), 3.80 (t, J=7.3 Hz, 1H), 3.38 (s, 2H), 2.99 (d, J=6.0 Hz, 1H), 2.83 (dt, J=15.7, 8.0 Hz, 1H), 2.64 (d, J=4.6 Hz, 3H), 2.31-2.12 (m, 2H), 1.93 (d, J=1.3 Hz, 3H). MS (EI) calc'd for $C_{27}H_{26}FN_6O_2$ $[M+H]^+$, 485; found, 485.

Example 1I. Preparation of Compound 1-123

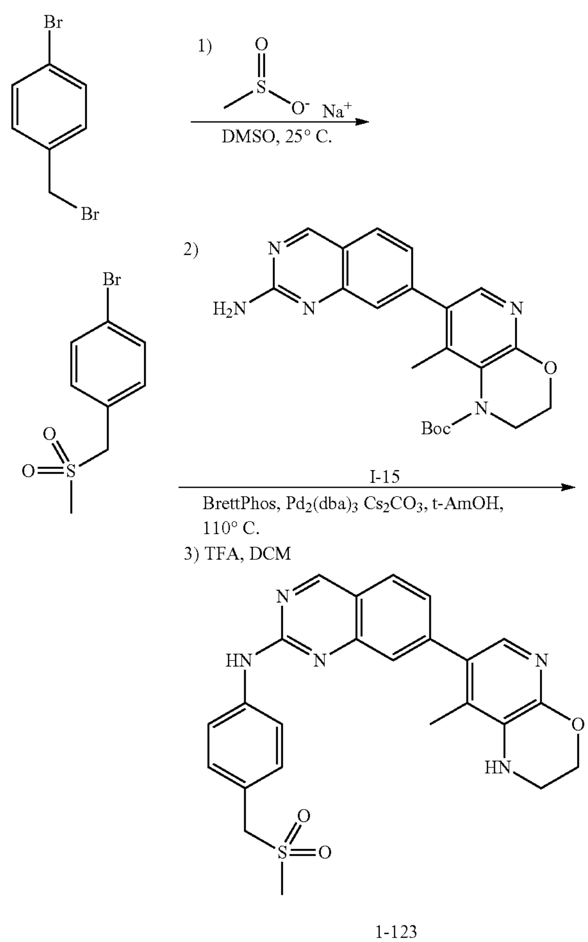

1-123

Step 1. Preparation of 1-bromo-4-((methylsulfonyl)methyl)benzene

To a mixture of 1-bromo-4-(bromomethyl) benzene (5 g, 20.01 mmol) in DMSO (50 mL) was added sodium methanesulfinate (3.06 g, 30.0 mmol). The reaction mixture was stirred at 25° C. for 13 h. TLC ($SiO_2$, EtOAc/Pet. ether=3/1) showed the starting material consumed completely. Water (100 mL) was added, the resulting mixture was added EtOAc (2×80 mL). The combined organic layers were washed with brine (100 mL), dried over anhydrous $Na_2SO_4$, filtered and concentrated to give 1-bromo-4-((methylsulfonyl)methyl)benzene (4.06 g, 16.30 mmol) as a solid, which was used directly in next step without further purification. $^1H$ NMR (500 MHz, $CDCl_3$) δ 7.51 (d, J=8.5 Hz, 2H), 7.25 (d, J=8.0 Hz, 2H), 4.14-4.19 (m, 2H), 2.70-2.77 (m, 3H).

Steps 2 and 3. Preparation of Compound 1-123

A mixture of intermediate I-15 (60 mg, 0.153 mmol), 1-bromo-4-((methylsulfonyl)methyl)benzene (68.4 mg, 0.275 mmol), $Cs_2CO_3$ (199 mg, 0.610 mmol), Brettphos (40.9 mg, 0.076 mmol) and $Pd_2(dba)_3$ (27.9 mg, 0.031 mmol) in tert-Amyl Alcohol (2 mL) was degassed and backfilled with $N_2$ (three times). The reaction mixture was stirred at 110° C. for 15 h. LCMS showed major desired product. The reaction mixture was quenched with water (15 mL), then the mixture was extracted with EtOAc (20 mL×3), the combined organic layers were washed with brine (15 mL), dried over anhydrous $Na_2SO_4$, filtered and concentrated to get a residue which was purified by prep-TLC (SiO2, EtOAc/Pet.ether=3/1) to give the desired adduct as an oil. The oil was taken up in DCM (2 mL) and TFA (2 mL) and stirred at 25° C. for 0.5 h. LCMS showed the desired product was formed. The mixture was concentrated in vacuo. The residue was purified by pre-HPLC (Column Agela DuraShell C18 150*25 mm*5 um Condition water (0.04% $NH_3H_2O$+10 mM $NH_4HCO_3$)—CAN Begin B 24 End B 54 Gradient Time (min) 10 100% B Hold Time (min) 2 Flow Rate (mL/min) 25 Injections 1) to 1-123 as a solid. $^1H$ NMR (400 MHz, CD3OD) δ 9.22 (s, 1H), 7.97 (d, J=8.8 Hz, 2H), 7.91 (d, J=8.0 Hz, 1H), 7.60-7.62 (m, 1H), 7.59 (s, 1H), 7.39-7.45 (m, 3H), 7.32 (dd, J=8.0, 1.6 Hz, 1H), 4.58 (s, 3H), 4.37-4.41 (m, 4H), 3.46-3.52 (m, 2H), 2.87 (s, 3H), 2.11 (s, 3H). MS (EI) calc'd for $C_{24}H_{24}N_5O_3S$ $[M+H]^+$, 462; found, 462.

Example 1J

Preparation of Compounds 1-124 and 1-126

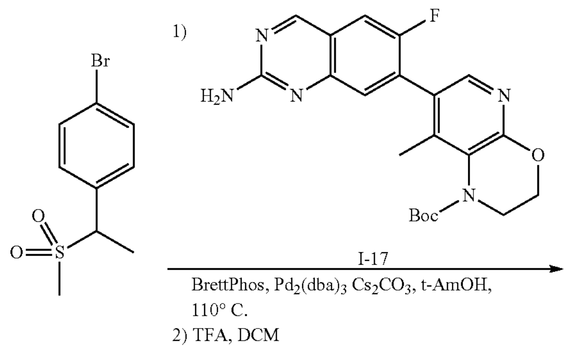

-continued

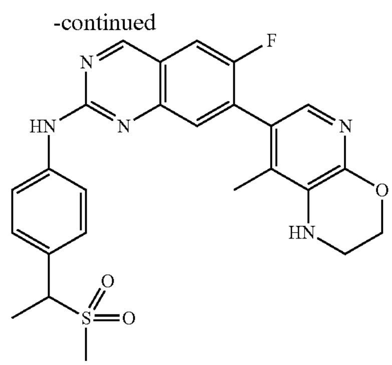

1-124

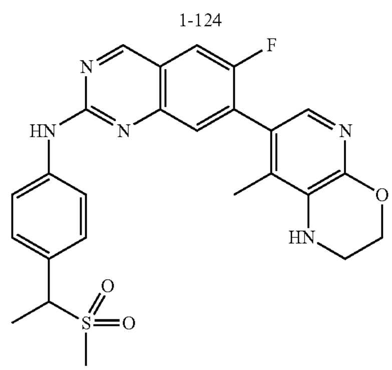

1-126

A mixture of intermediate I-17 (150 mg, 0.365 mmol), Brettphos (98 mg, 0.182 mmol), 1-bromo-4-(1-(methylsulfonyl)ethyl)benzene (144 mg, 0.547 mmol), $Cs_2CO_3$ (475 mg, 1.458 mmol) and $Pd_2(dba)_3$ (66.8 mg, 0.073 mmol)) in tert-Amyl Alcohol (3 mL) was stirred at 110° C. for 16 h under $N_2$. LCMS showed the product was formed. The mixture was purified by pre-TLC ($SiO_2$, EtOAc:MeOH=10:1) to afford the adduct as an oil. The oil was then taken up in DCM (2 mL) and TFA (2 mL) and stirred at 25° C. for 1 h. LCMS showed the desired product was formed. The reaction mixture was concentrated in vacuo. The residue was purified by Prep-HPLC (Column YMC-Actus Triart C18 100*30 mm*5 um, Condition water (0.1% TFA)-ACN Begin B 22, End B 52 Gradient Time (min) 11, 100% B Hold Time (min) 1.1 FlowRate (mL/min) 40, Injections 2) to afford the deprotected product as a solid. The enantiomers were resolved by chiral-Prep-SFC (Column DAICEL CHIRALCEL OJ-H (250 mm*30 mm, 5 um), Condition 0.1% $NH_3H_2O$ EtOH Begin B 40%, End B 40% Gradient Time (min), 100% B Hold Time (min) FlowRate (mL/min) 70, Injections 120) to give isomer 1-126 ($t_R$=6.6 min) and isomer 1-124 ($t_R$=8.3 min), both as solids.

Compound 1-124. $^1$H NMR (400 MHz, $CD_3OD$) δ 9.20 (s, 1H), 7.95 (d, J=7.6 Hz, 2H), 7.59-7.66 (m, 2H), 7.38-7.47 (m, 3H), 4.37-4.43 (m, 3H), 3.45-3.52 (m, 1H), 2.75 (s, 3H), 2.01 (d, J=2.0 Hz, 3H), 1.74 (d, J=7.2 Hz, 3H). MS (EI) calc'd for $C_{25}H_{25}FN_5O_3S$ $[M+H]^+$, 494; found, 494.

Compound 1-126. $^1$H NMR (400 MHz, $CD_3OD$) δ 9.20 (s, 1H), 7.95 (d, J=8.8 Hz, 2H), 7.57-7.68 (m, 2H), 7.44 (d, J=8.8 Hz, 2H), 7.38 (s, 1H), 4.36-4.42 (m, 3H), 3.45-3.52 (m, 2H), 2.75 (s, 3H), 2.01 (d, J=1.6 Hz, 3H), 1.74 (d, J=7.2 Hz, 3H). MS (EI) calc'd for $C_{25}H_{25}FN_5O_3S$ $[M+H]^+$, 494; found, 494.

Preparation of Compounds 1-125 and 1-127

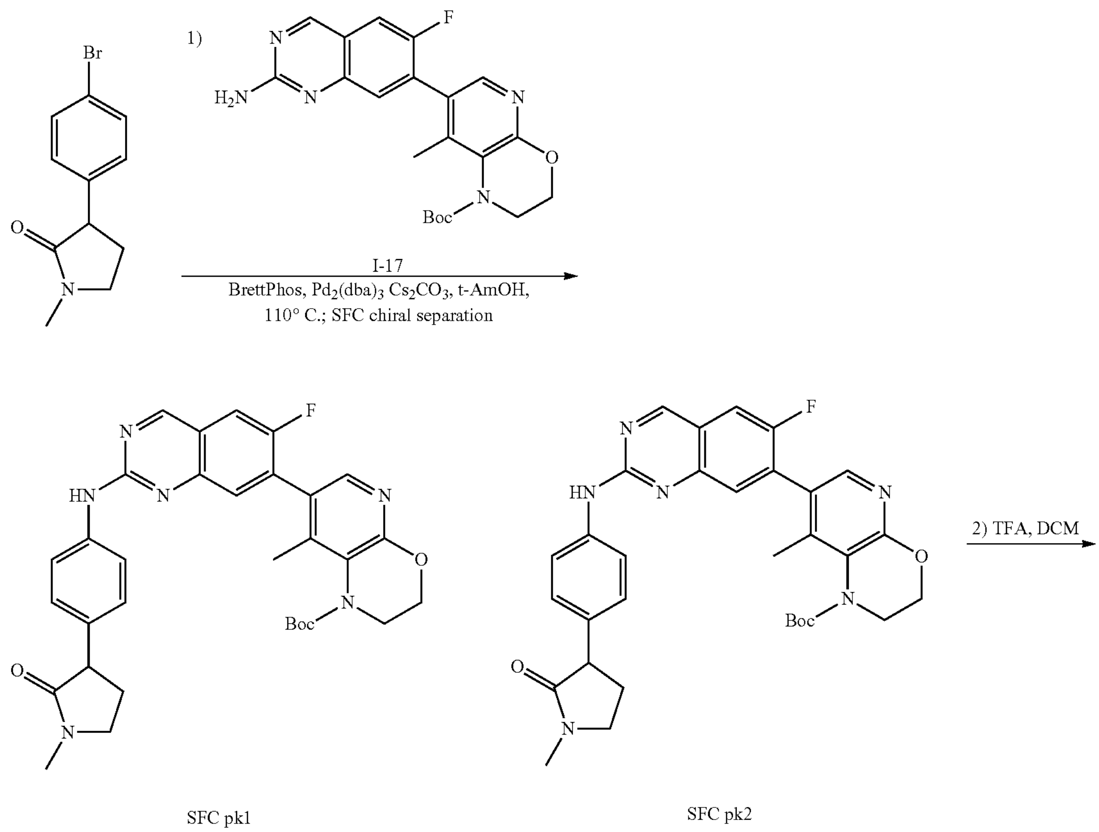

SFC pk1

SFC pk2

-continued

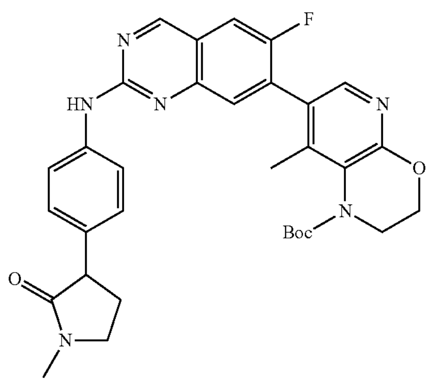

1-125

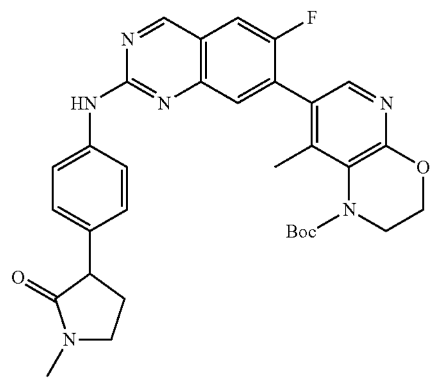

1-127

Step 1

A solution of Brettphos (65.2 mg, 0.122 mmol), 3-(4-bromophenyl)-1-methylpyrrolidin-2-one (124 mg, 0.486 mmol), $Pd_2(dba)_3$ (44.5 mg, 0.049 mmol), intermediate I-17 (100 mg, 0.243 mmol), $Cs_2CO_3$ (238 mg, 0.729 mmol) in t-AmOH (2 mL) was stirred at 110° C. under $N_2$ for 16 h. LCMS showed desired product was formed. The mixture was diluted with water (20 mL), and extracted with EtOAc (2×30 mL), the organic layer was washed with brine (20 mL), dried over $Na_2SO_4$, after filtration, the filtrate was concentrated under reduced pressure. The residue was purified by prep-TLC (MeOH/EtOAc=1:20) to give adduct as a solid. The enantiomers were resolved by SFC (Column: Phenomenex-Cellulose-2 (250 mm*30 mm, 5 um), Condition: 0.1% $NH_3H_2O$/IPA, Mobile phase: A: $CO_2$ B: IPA (0.1% $NH_3H_2O$), Gradient: from 5% to 40% of B in 5.5 min and hold 40% for 3 min, then 5% of B for 1.5 min, Flow rate: 70 mL/min, Column temp: 35° C.) to give SFC pk1 (Rt=1.5 min, UV=220 nm, EE=100%) ad SFC pk2 (Rt=4.6 min, UV=220 nm, EE=100%), both as solid.

Step 2

Preparation of Compound 1-125

To a solution of SFC pk1 in DCM (2 mL) was added TFA (1 mL) at 25° C. under $N_2$ atmosphere. The mixture was stirred at 25° C. for 1 h. The reaction was monitored by LCMS. LCMS showed the reaction was finished. The mixture was evaporated under reduced pressure to give the crude product. The residue was purified by reverse preparative HPLC (Column: Waters XSELECT C18 150*30 mm*5 um: Condition: water (0.1% TFA)-MeCN; Begin B-End B: 21-41; Gradient Time (min): 10; 100% B Hold Time (min): 1; Flow rate (mL/min): 25) to give compound 1-125 as a solid. $^1$H NMR (500 MHz, DMSO-$d_6$) δ 9.93 (s, 1H), 9.34 (s, 1H), 7.88 (dd, J=9.0, 16.0 Hz, 3H), 7.59 (d, J=6.5 Hz, 1H), 7.51 (s, 1H), 7.16 (d, J=8.5 Hz, 2H), 4.40 (t, J=4.0 Hz, 2H), 3.56 (t, J=9.0 Hz, 1H), 3.42-3.46 (m, 3H), 3.35-3.40 (m, 1H), 2.80 (s, 3H), 2.40-2.47 (m, 1H), 1.99-2.04 (m, 1H), 1.98 (s, 3H). MS (EI) calc'd for $C_{27}H_{26}FN_6O_2$ $[M+H]^+$, 485; found, 485.

Preparation of 1-127

Compound was prepared using the same deprotection method as 1-125 from SFC pk2.

Compound 1-127. $^1$H NMR (500 MHz, DMSO-$d_6$) δ 9.91 (s, 1H), 9.34 (s, 1H), 7.84-7.91 (m, 3H), 7.57 (d, J=6.5 Hz, 1H), 7.46 (s, 1H), 7.16 (d, J=8.5 Hz, 2H), 4.36 (t, J=4.0 Hz, 2H), 3.35-3.48 (m, 4H), 2.80 (s, 3H), 2.40-2.46 (m, 2H), 1.98-2.05 (m, 1H), 1.96 (s, 3H). MS (EI) calc'd for $C_{27}H_{26}FN_6O_2$ $[M+H]^+$, 485; found, 485.

Example 1K. Preparation of 1-135

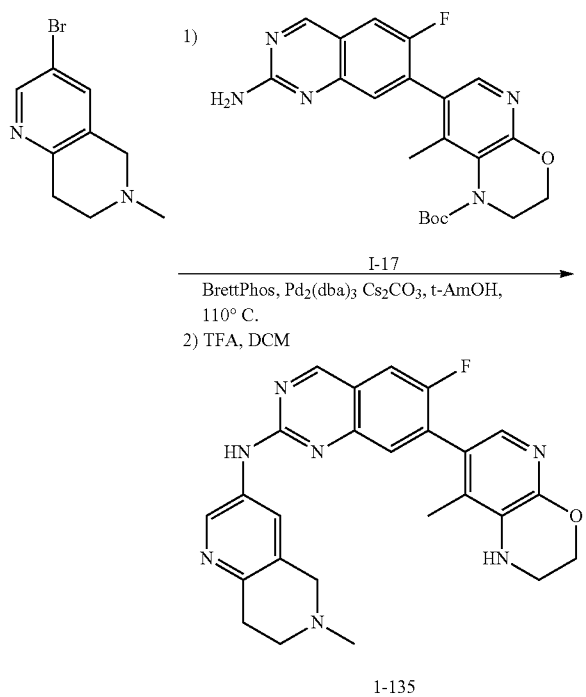

1-135

A mixture containing 3-bromo-6-methyl-5,6,7,8-tetrahydro-1,6-naphthyridine (220 mg, 0.969 mmol), intermediate I-17 (200 mg, 0.486 mmol), $Cs_2CO_3$ (500 mg, 1.535 mmol) and t-BuBrettPhos Pd G3 (50 mg, 0.059 mmol) in toluene (2 mL) and water (0.1 mL) was deoxygenated by bubbling nitrogen for 3 min with stirring. The mixture was stirred overnight at 110° C. After cooling to RT, the reaction was filtered and loaded onto column (80 g) and eluted with 0-50% MeOH/DCM. The fractions containing the desired adduct were pooled and concentrated to give a solid. The solid was dissolved in 2 mL of DCM and 2 mL of TFA—aged 2 hours. Concentrated, dissolved in 4:1 DCM/MeOH and extracted with sat'd $NaHCO_3$. Organic layer concentrated and the residue dissolved in 4:1 DCM/MeOH. Purified by chromatography on $SiO_2$ (gradient of 50% MeOH/DCM 40 g silica) to provide the desired product as a solid. $^1H$ NMR (500 MHz, DMSO-$d_6$) δ 10.01 (s, 1H), 9.35 (s, 1H), 8.75 (d, J=2.3 Hz, 1H), 8.23 (s, 1H), 7.85 (d, J=9.2 Hz, 1H), 7.64 (d, J=6.7 Hz, 1H), 7.39 (s, 1H), 5.75 (s, 1H), 4.36-4.26 (m, 2H), 3.54 (s, 2H), 3.38 (s, 2H), 2.85 (t, J=5.8 Hz, 2H), 2.69 (t, J=5.9 Hz, 2H), 2.37 (s, 3H), 2.08 (s, 1H), 1.93 (d, J=1.3 Hz, 3H). MS (EI) calc'd for $C_{25}H_{25}FN_7O$ $[M+H]^+$, 458; found, 458.

Compounds listed in the table below were prepared using the synthetic methods described in the aforementioned examples. The table provides the compound structure, the name, the calculated and observed masses, and the example method used for preparation.

TABLE 1

| Example Number | Structure | Name | Exact Mass $[M + H]^+$; Method |
|---|---|---|---|
| 1-1 | 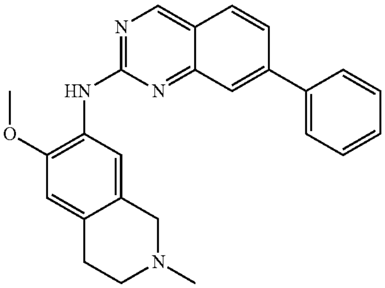 [SMILES: COc1cc2c(cc1Nc1ncc3ccc(-c4ccccc4)cc3n1)CN(C)CC2] | N-(6-methoxy-2-methyl-1,2,3,4-tetrahydroisoquinolin-7-yl)-7-phenylquinazolin-2-amine | Calc'd 397, found 397; 1A |
| 1-2 | 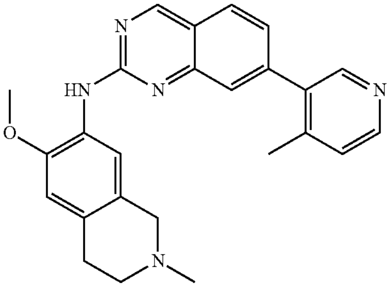 [SMILES: COc1cc2c(cc1Nc1ncc3ccc(-c4cnccc4C)cc3n1)CN(C)CC2] | N-(6-methoxy-2-methyl-1,2,3,4-tetrahydroisoquinolin-7-yl)-7-(4-methylpyridin-3-yl)quinazolin-2-amine | Calc'd 412, found 412; 1A |
| 1-3 | 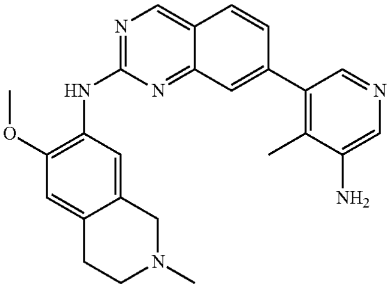 [SMILES: COc1cc2c(cc1Nc1ncc3ccc(-c4cncc(N)c4C)cc3n1)CN(C)CC2] | 7-(5-amino-4-methylpyridin-3-yl)-N-(6-methoxy-2-methyl-1,2,3,4-tetrahydroisoquinolin-7-yl)quinazolin-2-amine | Calc'd 427, found 426; 1A |
| 1-4 | 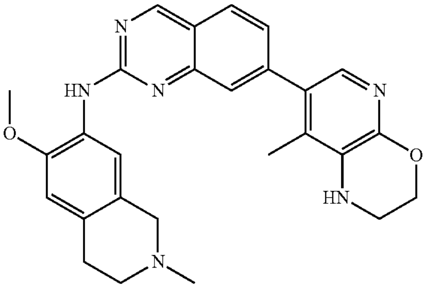 [SMILES: COc1cc2c(cc1Nc1ncc3ccc(-c4cnc5c(c4C)NCCO5)cc3n1)CN(C)CC2] | N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine | Calc'd 469, found 469; 1A |

TABLE 1-continued

| Example Number | Structure | Name | Exact Mass [M + H]+; Method |
|---|---|---|---|
| 1-5 | 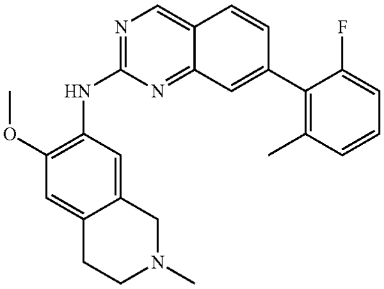 [SMILES: COc1cc2c(cc1Nc1ncc3ccc(-c4c(C)cccc4F)cc3n1)CN(C)CC2] | 7-(2-fluoro-6-methylphenyl)-N-(6-methoxy-2-methyl-1,2,3,4-tetrahydroisoquinolin-7-yl)quinazolin-2-amine | Calc'd 429, found 429; 1A |
| 1-6 | 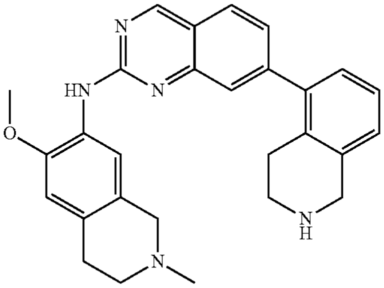 [SMILES: COc1cc2c(cc1Nc1ncc3ccc(-c4cccc5c4CCNC5)cc3n1)CN(C)CC2] | N-(6-methoxy-2-methyl-1,2,3,4-tetrahydroisoquinolin-7-yl)-7-(1,2,3,4-tetrahydroisoquinolin-5-yl)quinazolin-2-amine | Calc'd 452, found 452; 1A |
| 1-7 | 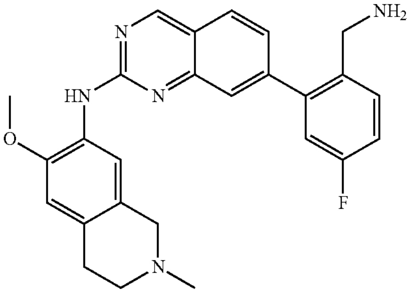 [SMILES: COc1cc2c(cc1Nc1ncc3ccc(-c4cc(F)ccc4CN)cc3n1)CN(C)CC2] | 7-[2-(aminomethyl)-5-fluorophenyl]-N-(6 methoxy-2-methyl-1,2,3,4-tetrahydroisoquinolin-7-yl)quinazolin-2-amine | Calc'd 444, found 444; 1A |
| 1-8 | 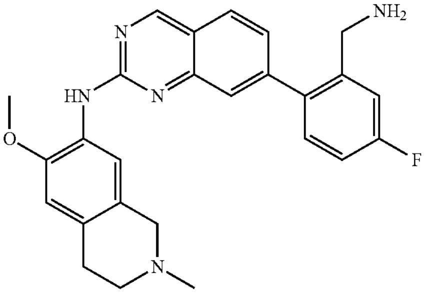 [SMILES: COc1cc2c(cc1Nc1ncc3ccc(-c4ccc(F)cc4CN)cc3n1)CN(C)CC2] | 7-[2-(aminomethyl)-4-fluorophenyl]-N-(6-methoxy-2-methyl-1,2,3,4-tetrahydroisoquinolin-7-yl)quinazolin-2-amine | Calc'd 444, found 444; 1A |
| 1-9 | 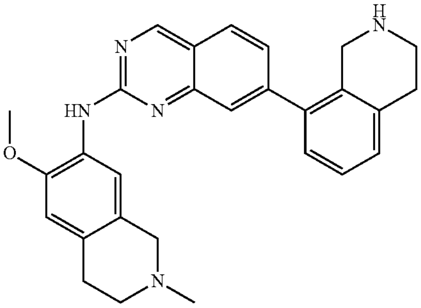 [SMILES: COc1cc2c(cc1Nc1ncc3ccc(-c4cccc5c4CNCC5)cc3n1)CN(C)CC2] | N-(6-methoxy-2-methyl-1,2,3,4-tetrahydroisoquinolin-7-yl)-7-(1,2,3,4-tetrahydroisoquinolin-8-yl)quinazolin-2-amine | Calc'd 452, found 452; 1A |

TABLE 1-continued

| Example Number | Structure | Name | Exact Mass [M + H]+; Method |
|---|---|---|---|
| 1-10 | 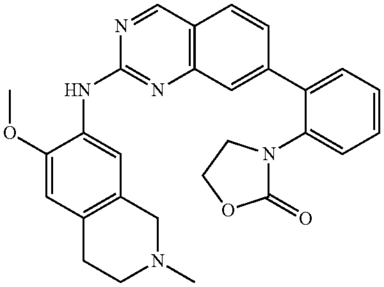 [SMILES: COc1cc2c(cc1Nc1ncc3ccc(-c4ccccc4N4CCOC4=O)cc3n1)CN(C)CC2] | 3-(2-{2-[(6-methoxy-2-methyl-1,2,3,4-tetrahydroisoquinolin-7-yl)amino]quinazolin-7-yl}phenyl)-1,3-oxazolidin-2-one | Calc'd 482, found 482 1A |
| 1-11 | 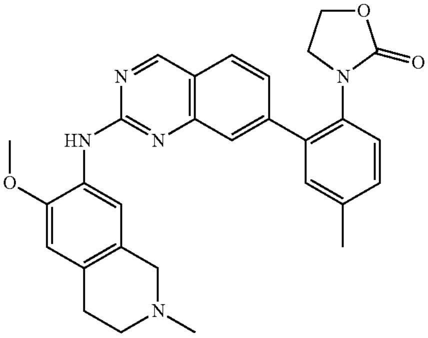 [SMILES: COc1cc2c(cc1Nc1ncc3ccc(-c4cc(C)ccc4N4CCOC4=O)cc3n1)CN(C)CC2] | 3-(2-{2-[(6-methoxy-2-methyl-1,2,3,4-tetrahydroisoquinolin-7-yl)amino]quinazolin-7-yl}-4-methylphenyl)-1,3-oxazolidin-2-one | Calc'd 496, found 496; 1A |
| 1-12 | 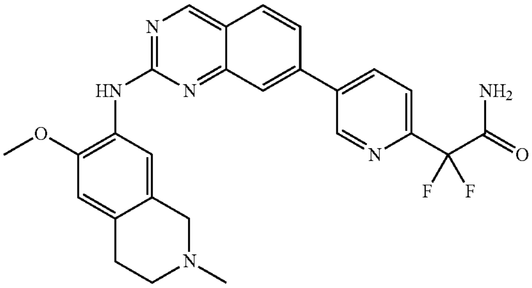 [SMILES: COc1cc2c(cc1Nc1ncc3ccc(-c4ccc(C(F)(F)C(N)=O)nc4)cc3n1)CN(C)CC2] | 2,2-difluoro-2-(5-{2-[(6-methoxy-2-methyl-1,2,3,4-tetrahydroisoquinolin-7-yl)amino]quinazolin-7-yl}pyridin-2-yl)acetamide | Calc'd 491, found 491; 1A |
| 1-13 | 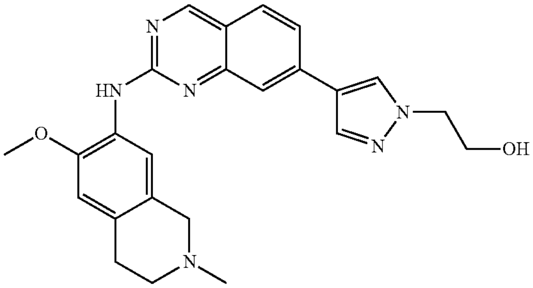 [SMILES: COc1cc2c(cc1Nc1ncc3ccc(-c4cnn(CCO)c4)cc3n1)CN(C)CC2] | 2-(4-{2-[(6-methoxy-2-methyl-1,2,3,4-tetrahydroisoquinazolin-7-yl)amino]quinazolin-7-yl}-1H-pyrazol-1-yl)ethan-1-ol | Calc'd 431, found 431; 1A |
| 1-14 | 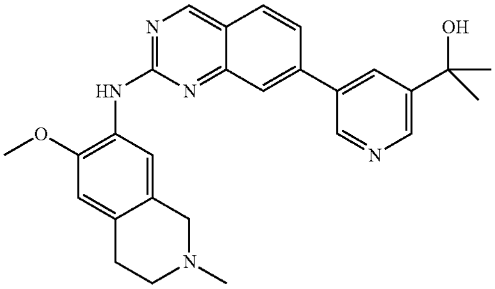 [SMILES: COc1cc2c(cc1Nc1ncc3ccc(-c4cncc(C(C)(C)O)c4)cc3n1)CN(C)CC2] | 2-(5-{2-[(6-methoxy-2-methyl-1,2,3,4-tetrahydroisoquinolin-7-yl)amino]quinazolin-7-yl}pyridin-3-yl)propan-2-ol | Calc'd 456, found 456; 1A |

TABLE 1-continued

| Example Number | Structure | Name | Exact Mass $[M + H]^+$; Method |
|---|---|---|---|
| 1-15 | 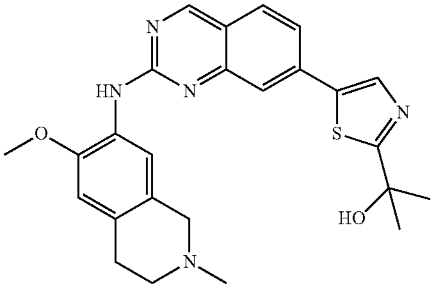 [SMILES: COc1cc2c(cc1Nc1ncc3ccc(-c4cnc(C(C)(C)O)s4)cc3n1)CN(C)CC2] | 2-(5-{2-[(6-methoxy-2-methyl-1,2,3,4-tetrahydroisoquinolin-7-yl)amino]quinazolin-7-yl}-1,3-thiazol-2-yl)propan-2-ol | Calc'd 462, found 462; 1A |
| 1-16 | 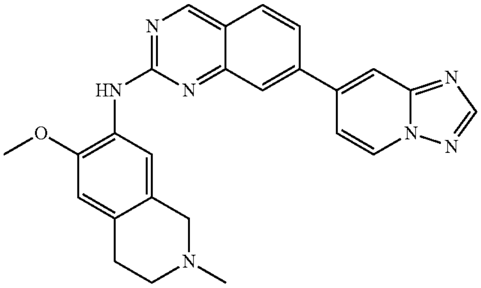 [SMILES: COc1cc2c(cc1Nc1ncc3ccc(-c4ccn5ncnc5c4)cc3n1)CN(C)CC2] | N-(6-methoxy-2-methyl-1,2,3,4-tetrahydroisoquinolin-7-yl)-7-([1,2,4]triazolo[1,5-a]pyridin-7-yl)quinazolin-2-amine | Calc'd 438, found 438; 1A |
| 1-17 | 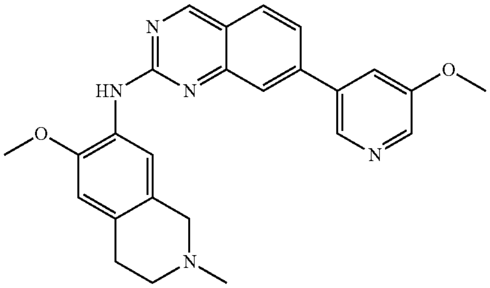 | N-(6-methoxy-2-methyl-1,2,3,4-tetrahydroisoquinolin-7-yl)-7-(5-methoxypyridin-3-yl)quinazolin-2-amine | Calc'd 428, found 428; 1A |
| 1-18 | 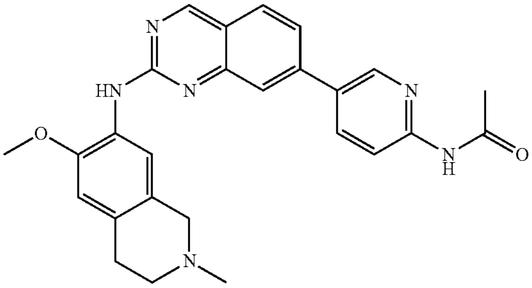 [SMILES: COc1cc2c(cc1Nc1ncc3ccc(-c4ccc(NC(C)=O)nc4)cc3n1)CN(C)CC2] | N-(5-{2-[(6-methoxy-2-methyl-1,2,3,4-tetrahydroisoquinolin-7-yl)amino]quinazolin-7-yl}pyridin-2-yl)acetamide | Calc'd 455, found 455; 1A |
| 1-19 | 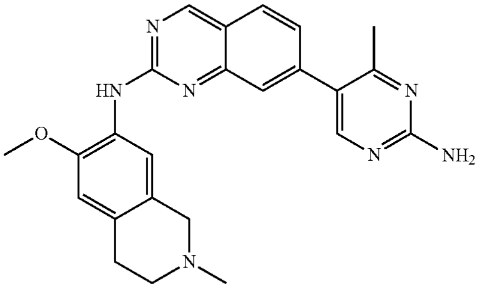 [SMILES: COc1cc2c(cc1Nc1ncc3ccc(-c4cnc(N)nc4C)cc3n1)CN(C)CC2] | 7-(2-amino-4-methylpyrimidin-5-yl)-N-(6-methoxy-2-methyl-1,2,3,4-tetrahydroisoquinazolin-7-yl)quinazolin-2-amine | Calc'd 428, found 428; 1A |

TABLE 1-continued

| Example Number | Structure | Name | Exact Mass [M + H]+; Method |
|---|---|---|---|
| 1-20 | 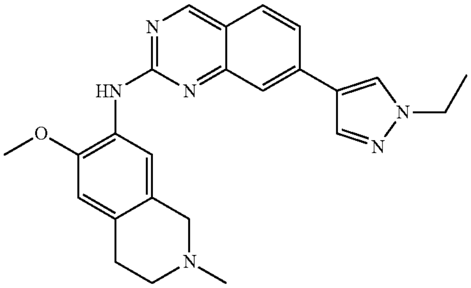 [SMILES: CCn1cc(-c2ccc3cnc(Nc4cc5c(cc4OC)CCN(C)C5)nc3c2)cn1] | 7-(1-ethyl-1H-pyrazol-4-yl)-N-(6-methoxy-2-methyl-1,2,3,4-tetrahydroisoquinolin-7-yl)quinazolin-2-amine | Calc'd 415, found 415; 1A |
| 1-21 | 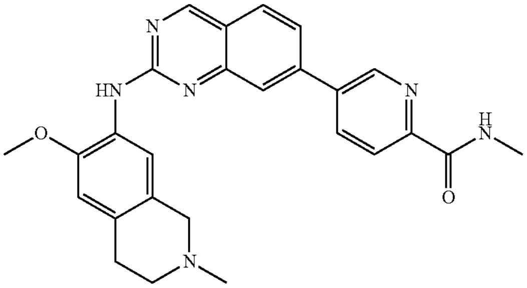 | 5-{2-[(6-methoxy-2-methyl-1,2,3,4-tetrahydroisoquinolin-7-yl)amino]quinazolin-7-yl}-N-methylpyridine-2-carboxamide | Calc'd 455, found 455; 1A |
| 1-22 | 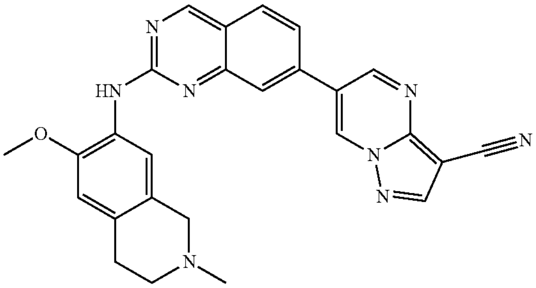 [SMILES: COc1cc2c(cc1Nc1ncc3ccc(-c4cnc5c(C#N)cnn5c4)cc3n1)CN(C)CC2] | 6-{2-[(6-methoxy-2-methyl-1,2,3,4-tetrahydroisoquinolin-7-yl)amino]quinazolin-7-yl}pyrazolo[1,5-a]pyrimidine-3-carbonitrile | Calc'd 463, found 463; 1A |
| 1-23 | 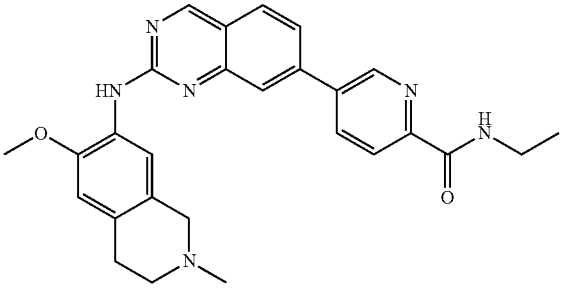 [SMILES: CCNC(=O)c1ccc(-c2ccc3cnc(Nc4cc5c(cc4OC)CCN(C)C5)nc3c2)cn1] | N-ethyl-5-{2-[(6-methoxy-2-methyl-1,2,3,4-tetrahydroisoquinolin-7-yl)amino]quinazolin-7-yl}pyridine-2-carboxamide | Calc'd 469, found 469; 1A |
| 1-24 | 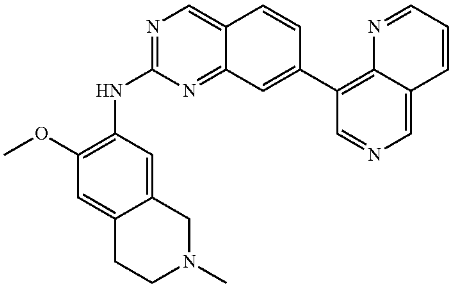 [SMILES: COc1cc2c(cc1Nc1ncc3ccc(-c4cncc5cccnc45)cc3n1)CN(C)CC2] | N-(6-methoxy-2-methyl-1,2,3,4-tetrahydroisoquinolin-7-yl)-7-(1,6-naphthyridin-8-yl)quinazolin-2-amine | Calc'd 449, found 449; 1A |

TABLE 1-continued

| Example Number | Structure | Name | Exact Mass [M + H]+; Method |
|---|---|---|---|
| 1-25 | 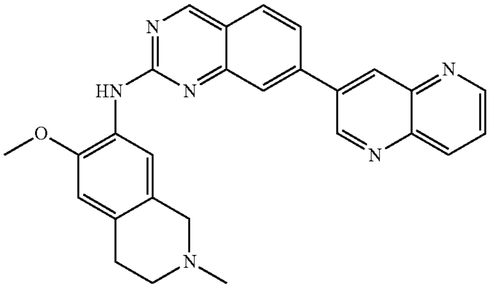 [SMILES: COc1cc2c(cc1Nc1ncc3ccc(-c4cnc5cccnc5c4)cc3n1)CN(C)CC2] | N-(6-methoxy-2-methyl-1,2,3,4-tetrahydroisoquinolin-7-yl)-7-(,15-naphthyridin-3-yl)quinazolin-2-amine | Calc'd 449, found 449; 1A |
| 1-26 | 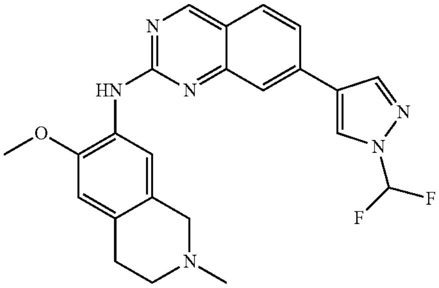 [SMILES: COc1cc2c(cc1Nc1ncc3ccc(-c4cnn(C(F)F)c4)cc3n1)CN(C)CC2] | 7-[1-(difluoromethyl)-1H-pyrazol-4-yl]-N-(6-methoxy-2-methyl-1,2,3,4-tetrahydroisoquinolin-7-yl)quinazolin-2-amine | Calc'd 437, found 437; 1A |
| 1-27 | 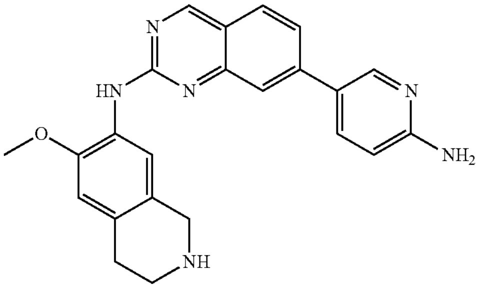 [SMILES: COc1cc2c(cc1Nc1ncc3ccc(-c4ccc(N)nc4)cc3n1)CNCC2] | 7-(6-aminopyridin-3-yl)-N-(6-methoxy-1,2,3,4-tetrahydroisoquinolin-7-yl)quinazolin-2-amine | Calc'd 399, found 399; 1B |
| 1-28 | 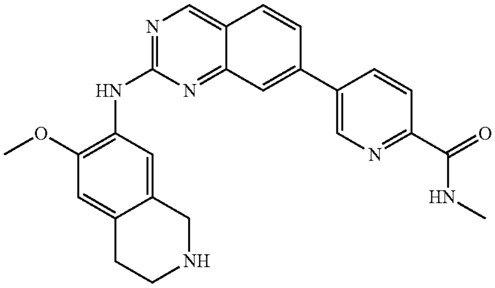 | 5-{2-[(6-methoxy-1,2,3,4-tetrahydroisoquinolin-7-yl)amino]quinazolin-7-yl}-N-methylpyridine-2-carboxamide | Calc'd 441, found 441; 1B |
| 1-29 | 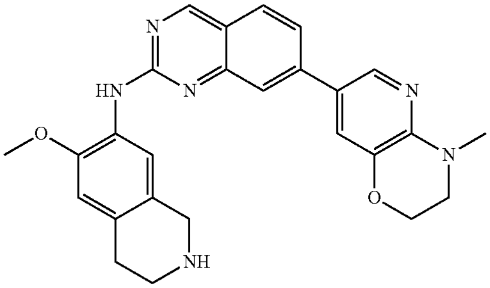 | N-(6-methoxy-1,2,3,4-tetrahydroisoquinolin-7-yl)-7-(4-methyl-3,4-dihydro-2H-pyrido[3,2-b][1,4]oxazin-7-yl)quinazolin-2-amine | Calc'd 455, found 455; 1B |

TABLE 1-continued

| Example Number | Structure | Name | Exact Mass $[M + H]^+$; Method |
|---|---|---|---|
| 1-30 | 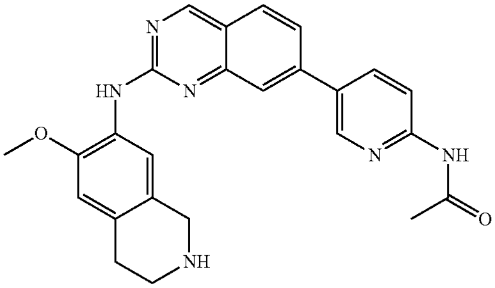 [SMILES: COc1cc2c(cc1Nc1ncc3ccc(-c4ccc(NC(C)=O)nc4)cc3n1)CNCC2] | N-(5-{2-[(6-methoxy-1,2,3,4-tetahydroisoquinolin-7-yl)amino]quinazolin-7-yl}pyridin-2-yl)acetamide | Calc'd 441, found 441; 1B |
| 1-31 | 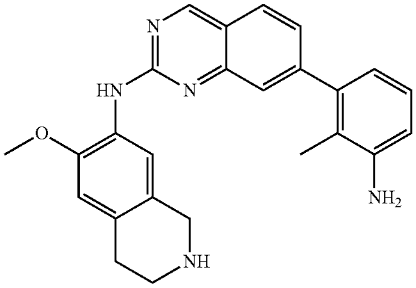 [SMILES: COc1cc2c(cc1Nc1ncc3ccc(-c4cccc(N)c4C)cc3n1)CNCC2] | 7-(3-amino-2-methylphenyl)-N-(6-methoxy-1,2,3,4-tetrahydroisoquinolin-7-yl)quinazolin-2-amine | Calc'd 412, found 412; 1B |
| 1-32 | 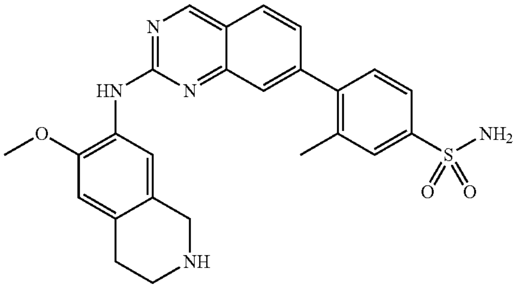 [SMILES: COc1cc2c(cc1Nc1ncc3ccc(-c4ccc(S(N)(=O)=O)cc4C)cc3n1)CNCC2] | 4-{2-[(6-methoxy-1,2,3,4-tetrahydroisoquinolin-7-yl)amino]quinazolin-7-yl}-3-methylbenzene-1-sulfonamide | Calc'd 476, found 476; 1B |
| 1-33 | 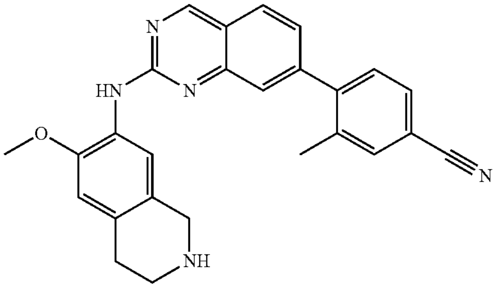 [SMILES: COc1cc2c(cc1Nc1ncc3ccc(-c4ccc(C#N)cc4C)cc3n1)CNCC2] | 4-{2-[(6-methoxy-1,2,3,4-tetrahydroisoquinolin-7-yl)amino]quinazolin-7-yl}-3-methylbenzonitrile | Calc'd 422, found 422; 1B |
| 1-34 | 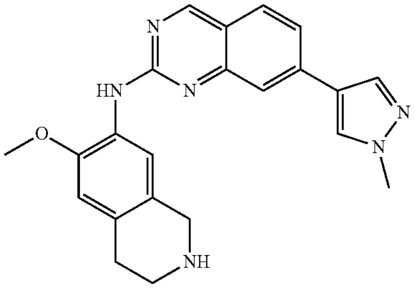 [SMILES: COc1cc2c(cc1Nc1ncc3ccc(-c4cnn(C)c4)cc3n1)CNCC2] | N-(6-methoxy-1,2,3,4-tetrahydroisoquinolin-7-yl)-7-(1-methyl-1H-pyrazol-4-yl)quinazolin-2-amine | Calc'd 387, found 387; 1B |

TABLE 1-continued

| Example Number | Structure | Name | Exact Mass $[M + H]^+$; Method |
|---|---|---|---|
| 1-35 | 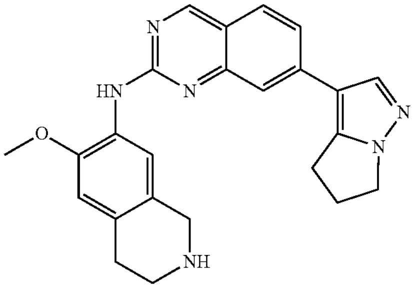 [SMILES: COc1cc2c(cc1Nc1ncc3ccc(-c4cnn5c4CCC5)cc3n1)CNCC2] | 7-(5,6-dihydro-4H-pyrrolo[1,2-b]pyrazol-3-yl)-N-(6-methoxy-1,2,3,4-tetrahydroisoquinolin-7-yl)quinazolin-2-amine | Calc'd 413, found 413; 1B |
| 1-36 | 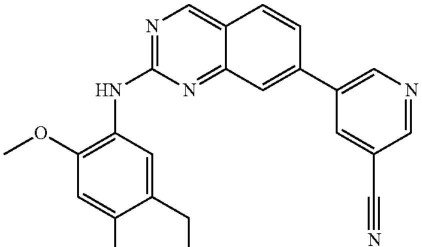 | 5-{2-[(6-methoxy-1,2,3,4-tetrahydroisoquinolin-7-yl)amino]quinazolin-7-yl}pyridine-3-carbonitrile | Calc'd 409, found 409; 1B |
| 1-37 | 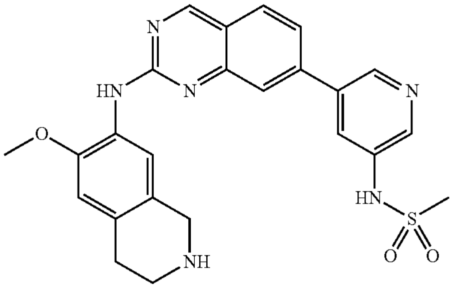 | N-(5-{2-[(6-methoxy-1,2,3,4-tetrahydroisoquinolin-7-yl)amino]quinazolin-7-yl}pyridin-3-yl)methanesulfonamide | Calc'd 477, found 477; 1B |
| 1-38 | 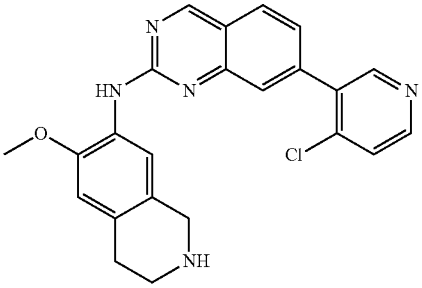 [SMILES: COc1cc2c(cc1Nc1ncc3ccc(-c4cnccc4Cl)cc3n1)CNCC2] | 7-(4-chloropyridin-3-yl)-N-(6-methoxy-1,2,3,4-tetrahydroisoquinolin-7-yl)quinazolin-2-amine | Calc'd 418, found 418; 1B |
| 1-39 | 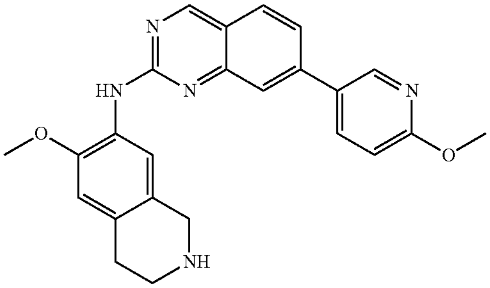 | 7-(6-methoxypyridin-3-yl)-N-(6-methoxy-1,2,3,4-tetrahydroisoquinolin-7-yl)quinazolin-2-amine | Calc'd 414, found 414; 1B |

TABLE 1-continued

| Example Number | Structure | Name | Exact Mass [M + H]$^+$; Method |
|---|---|---|---|
| 1-40 | 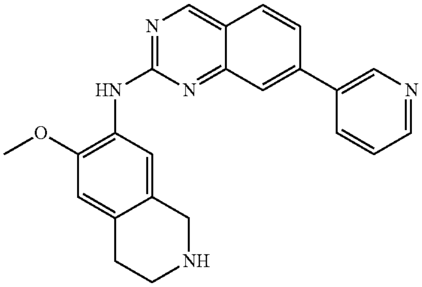 [SMILES: COc1cc2c(cc1Nc1ncc3ccc(-c4cccnc4)cc3n1)CNCC2] | N-(6-methoxy-1,2,3,4-tetrahydroisoquinolin-7-yl)-7-(pyridin-3-yl)quinazolin-2-amine | Calc'd 384, found 384; 1B |
| 1-41 | 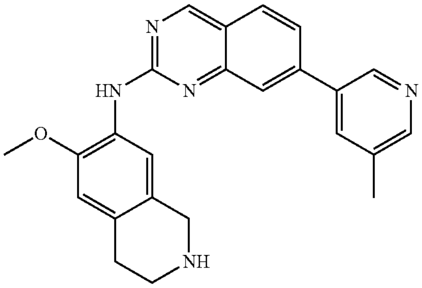 [SMILES: COc1cc2c(cc1Nc1ncc3ccc(-c4cncc(C)c4)cc3n1)CNCC2] | N-(6-methoxy-1,2,3,4-tetrahydroisoquinolin-7-yl)-7-(5-methylpyridin-3-yl)quinazolin-2-amine | Calc'd 398, found 398; 1B |
| 1-42 | 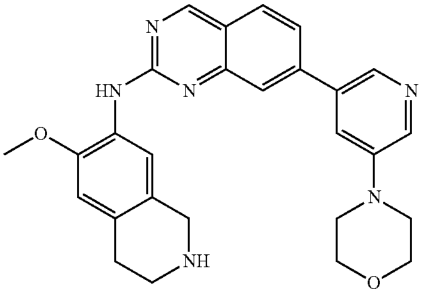 [SMILES: COc1cc2c(cc1Nc1ncc3ccc(-c4cncc(N5CCOCC5)c4)cc3n1)CNCC2] | N-(6-methoxy-1,2,3,4-tetrahydroisoquinolin-7-yl)-7-[5-(morpholin-4-yl)pyridin-3-yl]quinazolin-2-amine | Calc'd 469, found 469; 1B |
| 1-43 | 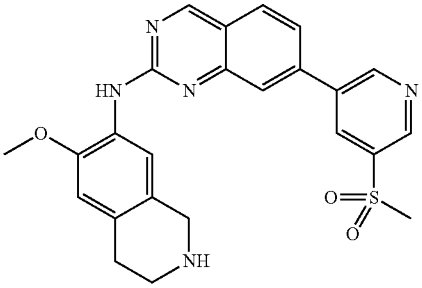 | N-(6-methoxy-1,2,3,4-tetrahydroisoquinolin-7-yl)-7-[5-(methylsulfonyl)pyridin-3-yl]quinazolin-2-amine | Calc'd 462, found 462; 1B |
| 1-44 | 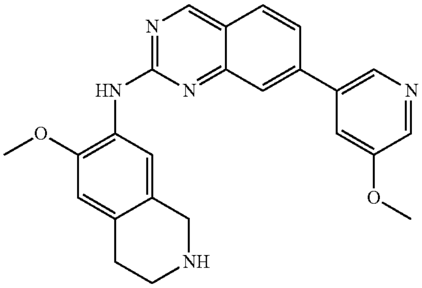 | 7-(5-methoxypyridin-3-yl)-N-(6-methoxy-1,2,3,4-tetrahydroisoquinolin-7-yl)quinazolin-2-amine | Calc'd 414, found 414; 1B |

TABLE 1-continued

| Example Number | Structure | Name | Exact Mass [M + H]+; Method |
|---|---|---|---|
| 1-45 | 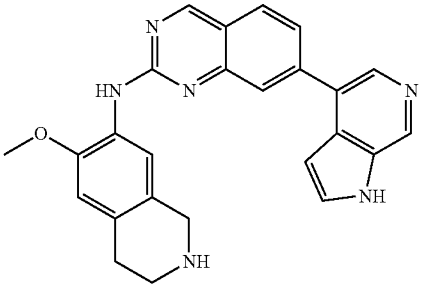 [SMILES: COc1cc2c(cc1Nc1ncc3ccc(-c4cncc5[nH]ccc45)cc3n1)CNCC2] | N-(6-methoxy-1,2,3,4-tetrahydroisoquinolin-7-yl)-7-(1H-pyrrolo[2,3-c]pyridin-4-yl)quinazolin-2-amine | Calc'd 423, found 423; 1B |
| 1-46 | 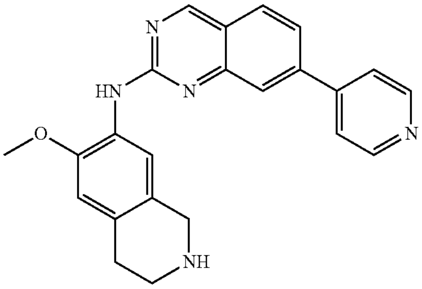 [SMILES: COc1cc2c(cc1Nc1ncc3ccc(-c4ccncc4)cc3n1)CNCC2] | N-(6-methoxy-1,2,3,4-tetrahydroisoquinolin-7-yl)-7-(pyridin-4-yl)quinazolin-2-amine | Calc'd 384, found 384; 1B |
| 1-47 | 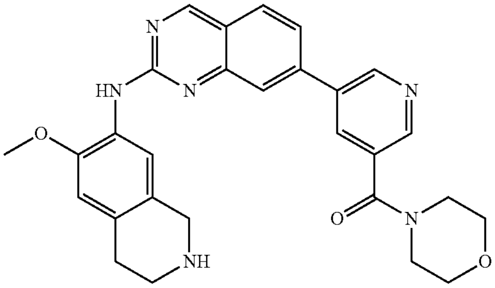 [SMILES: COc1cc2c(cc1Nc1ncc3ccc(-c4cncc(C(=O)N5CCOCC5)c4)cc3n1)CNCC2] | (5-{2-[(6-methoxy-1,2,3,4-tetrahydroisoquinolin-7-yl)amino]quinazolin-7-yl}pyridin-3-yl)(morpholin-4-yl)methanone | Calc'd 497, found 497; 1B |
| 1-48 | 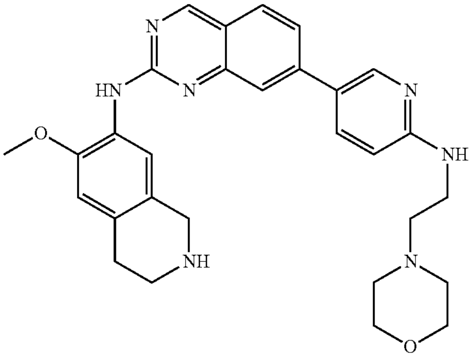 [SMILES: COc1cc2c(cc1Nc1ncc3ccc(-c4ccc(NCCN5CCOCC5)nc4)cc3n1)CNCC2] | N-(6-methoxy-1,2,3,4-tetrahydroisoquinolin-7-yl)-7-(6-{[2-(morpholin-4-yl)ethyl]amino}pyridin-3-yl)quinazolin-2-amine | Calc'd 512, found 512; 1B |
| 1-49 | 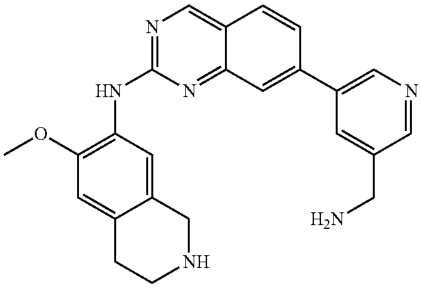 [SMILES: COc1cc2c(cc1Nc1ncc3ccc(-c4cncc(CN)c4)cc3n1)CNCC2] | 7-[5-(aminomethyl)pyridin-3-yl]-N-(6-methoxy-1,2,3,4-tetrahydroisoquinolin-7-yl)quinazolin-2-amine | Calc'd 413, found 413; 1B |

TABLE 1-continued

| Example Number | Structure | Name | Exact Mass [M + H]⁺; Method |
|---|---|---|---|
| 1-50 | 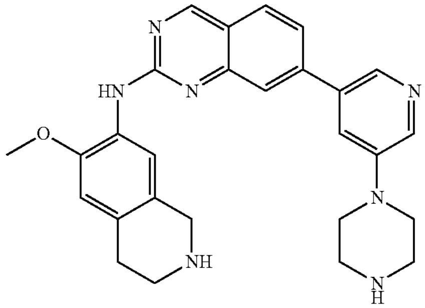 [SMILES: COc1cc2c(cc1Nc1ncc3ccc(-c4cncc(N5CCNCC5)c4)cc3n1)CNCC2] | N-(6-methoxy-1,2,3,4-tetrahydroisoquinolin-7-yl)-7-[5-(piperazin-1-yl)pyridin-3-yl]quinazolin-2-amine | Calc'd 468, found 468; 1B |
| 1-51 | 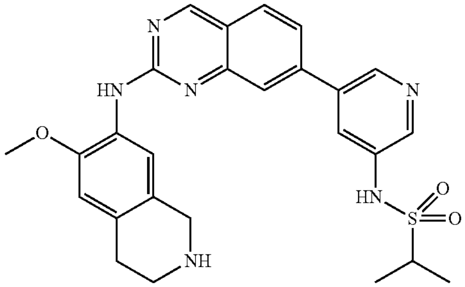 [SMILES: COc1cc2c(cc1Nc1ncc3ccc(-c4cncc(NS(=O)(=O)C(C)C)c4)cc3n1)CNCC2] | N-(5-{2-[(6-methoxy-1,2,3,4-tetrahydroisoquinolin-7-yl)amino]quinazolin-7-yl}pyridin-3-yl)propane-2-sulfonamide | Calc'd 505, found 505; 1B |
| 1-52 | 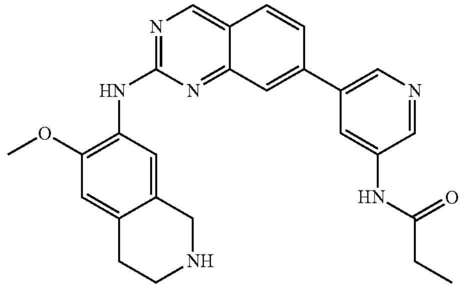 [SMILES: CCC(=O)Nc1cncc(-c2ccc3cnc(Nc4cc5c(cc4OC)CCNC5)nc3c2)c1] | N-(5-{2-[(6-methoxy-1,2,3,4-tetrahydroisoquinolin-7-yl)amino]quinazolin-7-yl}pyridin-3-yl)propanamide | Calc'd 455, found 455; 1B |
| 1-53 | 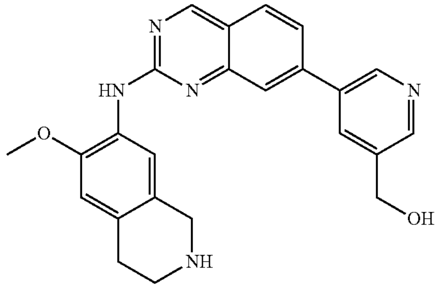 [SMILES: COc1cc2c(cc1Nc1ncc3ccc(-c4cncc(CO)c4)cc3n1)CNCC2] | (5-{2-[(6-methoxy-1,2,3,4-tetrahydroisoquinolin-7-yl)amino]quinazolin-7-yl}pyridin-3-yl)methanol | Calc'd 414, found 414; 1B |

TABLE 1-continued

| Example Number | Structure | Name | Exact Mass $[M + H]^+$; Method |
|---|---|---|---|
| 1-54 | 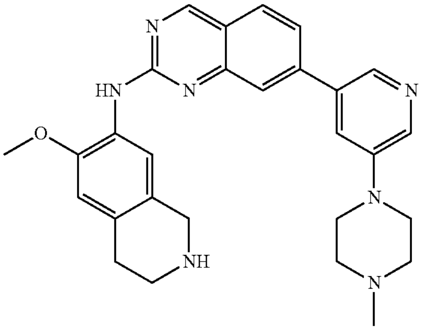 [SMILES: COc1cc2c(cc1Nc1ncc3ccc(-c4cncc(N5CCN(C)CC5)c4)cc3n1)CNCC2] | N-(6-methoxy-1,2,3,4-tetrahydroisoquinolin-7-yl)-7-[5-(4-methylpiperazin-1-yl)pyridin-3-yl]quinazolin-2-amine | Calc'd 482, found 482; 1B |
| 1-55 | 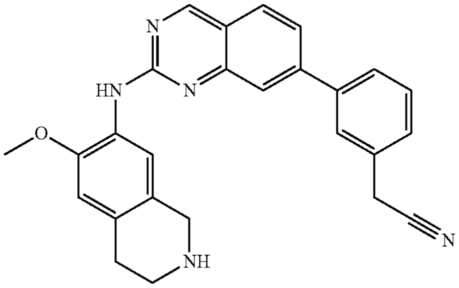 [SMILES: COc1cc2c(cc1Nc1ncc3ccc(-c4cccc(CC#N)c4)cc3n1)CNCC2] | (3-{2-[(6-methoxy-1,2,3,4-tetrahydroisoquinolin-7-yl)amino]quinazolin-7-yl}phenyl)acetonitrile | Calc'd 422, found 422; 1B |
| 1-56 | 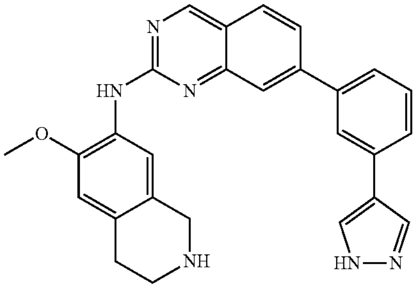 [SMILES: COc1cc2c(cc1Nc1ncc3ccc(-c4cccc(-c5cn[nH]c5)c4)cc3n1)CNCC2] | N-(6-methoxy-1,2,3,4-tetrahydroisoquinolin-7-yl)-7-[3-(1H-pyrazol-4-yl)phenyl]quinazolin-2-amine | Calc'd 449, found 449; 1B |
| 1-57 | 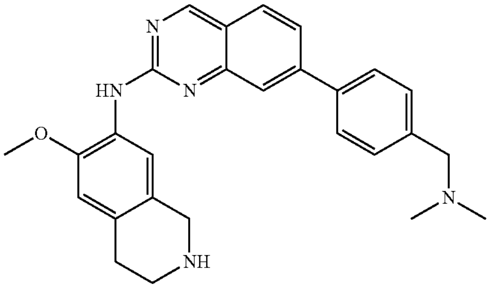 | 7-{4-[(dimethylamino)methyl]phenyl}-N-(6-methoxy-1,2,3,4-tetrahydroisoquinolin-7-yl)quinazolin-2-amine | Calc'd 440, found 440; 1B |
| 1-58 | 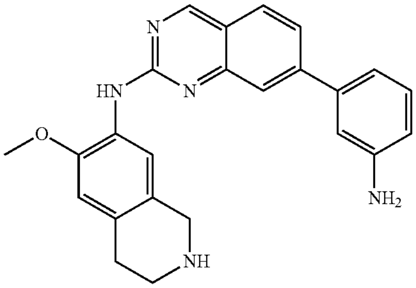 [SMILES: COc1cc2c(cc1Nc1ncc3ccc(-c4cccc(N)c4)cc3n1)CNCC2] | 7-(3-aminophenyl)-N-(6-methoxy-1,2,3,4-tetrahydroisoquinolin-7-yl)quinazolin-2-amine | Calc'd 398, found 398; 1B |

TABLE 1-continued

| Example Number | Structure | Name | Exact Mass $[M + H]^+$; Method |
|---|---|---|---|
| 1-59 | 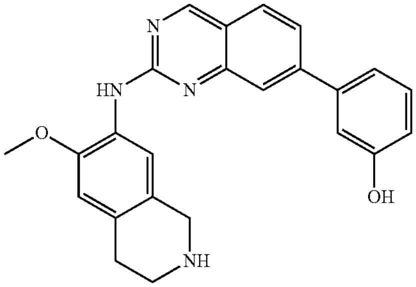 [SMILES: COc1cc2c(cc1Nc1ncc3ccc(-c4cccc(O)c4)cc3n1)CNCC2] | 3-{2-[(6-methoxy-1,2,3,4-tetrahydroisoquinolin-7-yl)amino]quinazolin-7-yl}phenol | Calc'd 399, found 399, 1B |
| 1-60 | 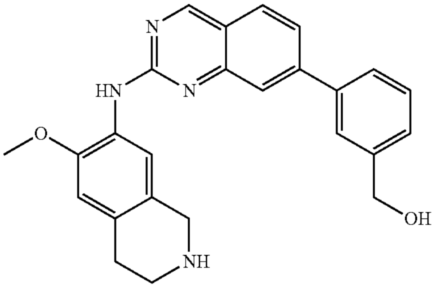 [SMILES: COc1cc2c(cc1Nc1ncc3ccc(-c4cccc(CO)c4)cc3n1)CNCC2] | (3-{2-[(6-methoxy-1,2,3,4-tetrahydroisoquinolin-7-yl)amino]quinazolin-7-yl}phenyl)methanol | Calc'd 413, found 413; 1B |
| 1-61 | 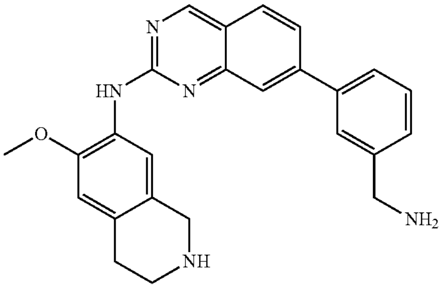 [SMILES: COc1cc2c(cc1Nc1ncc3ccc(-c4cccc(CN)c4)cc3n1)CNCC2] | 7-[3-(aminomethyl)phenyl]-N-(6-methoxy-1,2,3,4-tetrahydroisoquinolin-7-yl)quinazolin-2-amine | Calc'd 412, found 412; 1B |
| 1-62 | 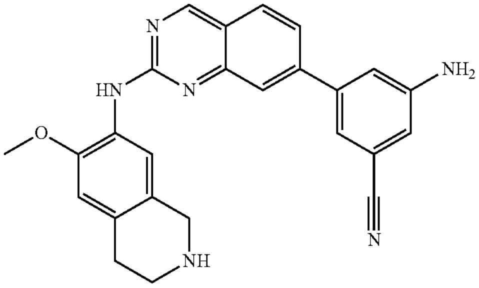 [SMILES: COc1cc2c(cc1Nc1ncc3ccc(-c4cc(N)cc(C#N)c4)cc3n1)CNCC2] | 3-amino-5-{2-[(6-methoxy-1,2,3,4-tetrahydroisoquinolin-7-yl)amino]quinazolin-7-yl}benzonitrile | Calc'd 423, found 423; 1B |
| 1-63 | 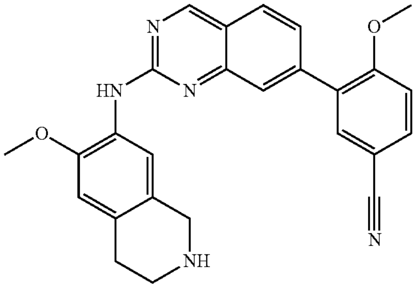 | 4-methoxy-3-{2-[(6-methoxy-1,2,3,4-tetrahydroisoquinolin-7-yl)amino]quinazolin-7-yl}benzonitrile | Calc'd 438, found 438; 1B |

TABLE 1-continued

| Example Number | Structure | Name | Exact Mass [M + H]+; Method |
|---|---|---|---|
| 1-64 | 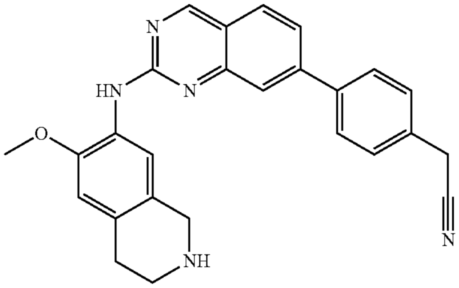 [SMILES: COc1cc2c(cc1Nc1ncc3ccc(-c4ccc(CC#N)cc4)cc3n1)CNCC2] | (4-{2-[(6-methoxy-1,2,3,4-tetrahydroisoquinolin-7-yl)amino]quinazolin-7-yl}phenyl)acetonitrile | Calc'd 422, found 422; 1B |
| 1-65 | 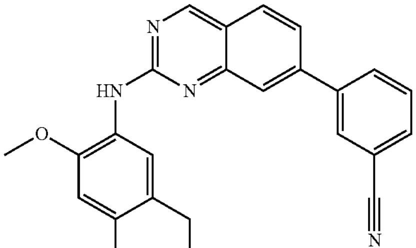 | 3-{2-[(6-methoxy-1,2,3,4-tetrahydroisoquinolin-7-yl)amino]quinazolin-7-yl}benzonitrile | Calc'd 408, found 408; 1B |
| 1-66 | 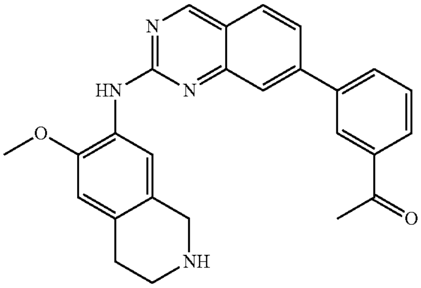 [SMILES: COc1cc2c(cc1Nc1ncc3ccc(-c4cccc(C(C)=O)c4)cc3n1)CNCC2] | 1-(3-{2-[(6-methoxy-1,2,3,4-tetrahydroisoquinolin-7-yl)amino]quinazolin-7-yl}phenyl)ethan-1-one | Calc'd 425, found 425; 1B |
| 1-67 | 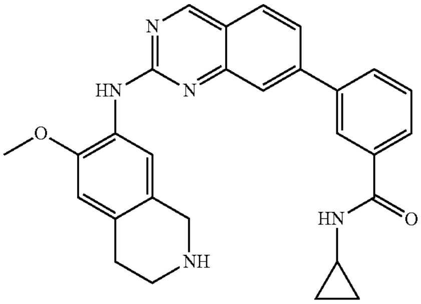 [SMILES: COc1cc2c(cc1Nc1ncc3ccc(-c4cccc(C(=O)NC5CC5)c4)cc3n1)CNCC2] | N-cyclopropyl-3-{2-[(6-methoxy-1,2,3,4-tetrahydroisoquinolin-7-yl)amino]quinazolin-7-yl}benzamide | Calc'd 466, found 466; 1B |
| 1-68 | 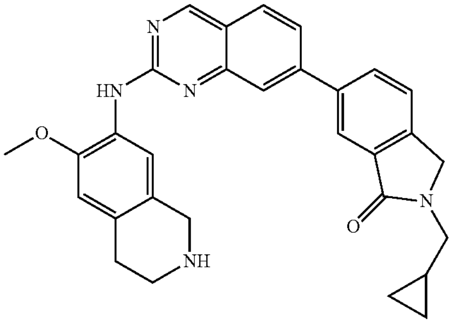 [SMILES: COc1cc2c(cc1Nc1ncc3ccc(-c4ccc5c(c4)C(=O)N(CC4CC4)C5)cc3n1)CNCC2] | 2-(cyclopropylmethyl)-6-{2-[(6-methoxy-1,2,3,4-tetrahydroisoquinolin-7-yl)amino]quinazolin-7-yl}-2,3-dihydro-1H-isoindol-1-one | Calc'd 492, found 492; 1B |

TABLE 1-continued

| Example Number | Structure | Name | Exact Mass [M + H]+; Method |
|---|---|---|---|
| 1-69 | 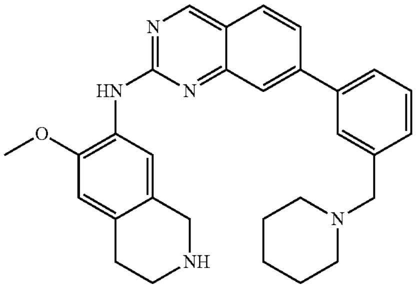 [SMILES: COc1cc2c(cc1Nc1ncc3ccc(-c4cccc(CN5CCCCC5)c4)cc3n1)CNCC2] | N-(6-methoxy-1,2,3,4-tetrahydroisoquinolin-7-yl)-7-{3-[(piperidin-1-yl)methyl]phenyl}quinazolin-2-amine | Calc'd 480, found 480; 1B |
| 1-70 | 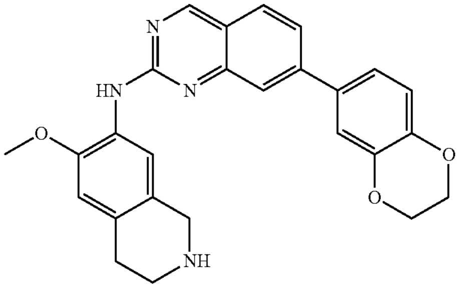 [SMILES: COc1cc2c(cc1Nc1ncc3ccc(-c4ccc5c(c4)OCCO5)cc3n1)CNCC2] | 7-(2,3-dihydro-1,4-benzodioxan-6-yl)-N-(6-methoxy-1,2,3,4-tetrahydroisoquinolin-7-yl)quinazolin-2-amine | Calc'd 441, found 441; 1B |
| 1-71 | 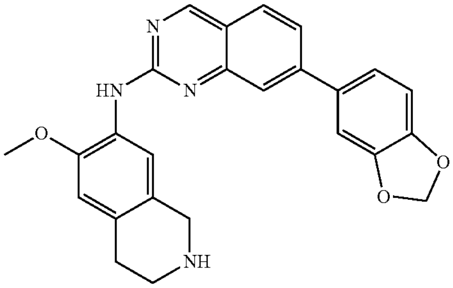 [SMILES: COc1cc2c(cc1Nc1ncc3ccc(-c4ccc5c(c4)OCO5)cc3n1)CNCC2] | 7-(2H-1,3-benzodioxol-5-yl)-N-(6-methoxy-1,2,3,4-tetrahydroisoquinolin-7-yl)quinazolin-2-amine | Calc'd 427, found 427; 1B |
| 1-72 | 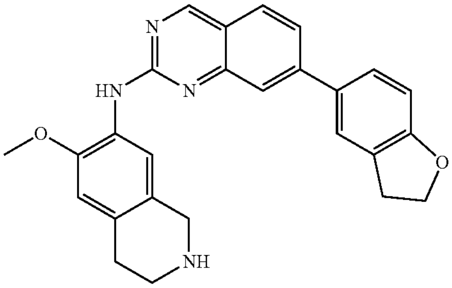 [SMILES: COc1cc2c(cc1Nc1ncc3ccc(-c4ccc5c(c4)CCO5)cc3n1)CNCC2] | 7-(2,3-dihydro-1-benzofuran-5-yl)-N-(6-methoxy-1,2,3,4-tetrahydroisoquinolin-7-yl)quinazolin-2-amine | Calc'd 425, found 425; 1B |
| 1-73 | 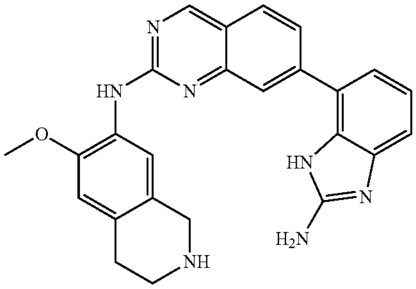 [SMILES: COc1cc2c(cc1Nc1ncc3ccc(-c4cccc5nc(N)[nH]c45)cc3n1)CNCC2] | 7-(2-amino-1H-benzimidazol-2-yl)-N-(6-methoxy-1,2,3,4-tetrahydroisoquinolin-7-yl)quinazolin-2-amine | Calc'd 438, found 438; 1B |

TABLE 1-continued

| Example Number | Structure | Name | Exact Mass [M + H]+; Method |
|---|---|---|---|
| 1-74 | 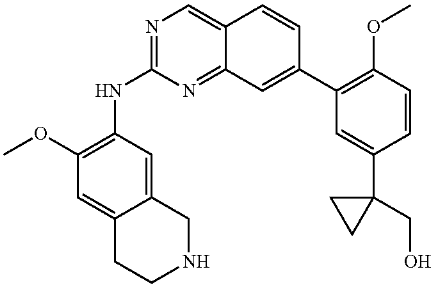 | [1-(4-methoxy-3-{2-[(6-methoxy-1,2,3,4-tetrahydroisoquinolin-7-yl)amino]quinazolin-7-yl}phenyl)cyclo-propyl]methanol | Calc'd 483, found 483; 1B |
| 1-75 | 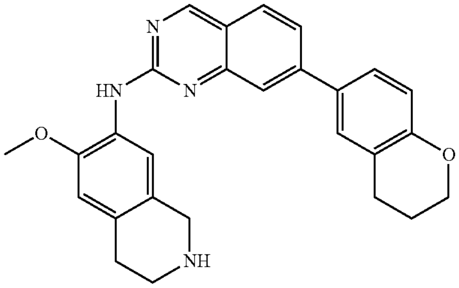 [SMILES: COc1cc2c(cc1Nc1ncc3ccc(-c4ccc5c(c4)CCCO5)cc3n1)CNCC2] | 7-(3,4-dihydro-2H-1-benzopyran-6-yl)-N-(6-methoxy-1,2,3,4-tetrahydroisoquinolin-7-yl)quinazolin-2-amine | Calc'd 439, found 439; 1B |
| 1-76 | 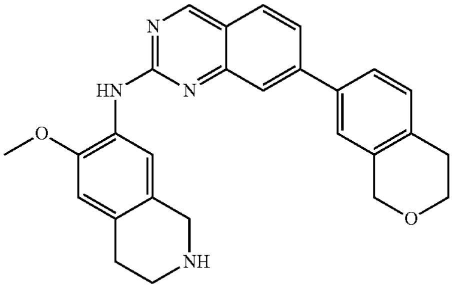 [SMILES: COc1cc2c(cc1Nc1ncc3ccc(-c4ccc5c(c4)COCC5)cc3n1)CNCC2] | 7-(3,4-dihydro-1H-2-benzopyran-7-yl)-N-(6-methoxy-1,2,3,4-tetrahydroisoquinolin-7-yl)quinazolin-2-amine | Calc'd 439, found 439; 1B |
| 1-77 | 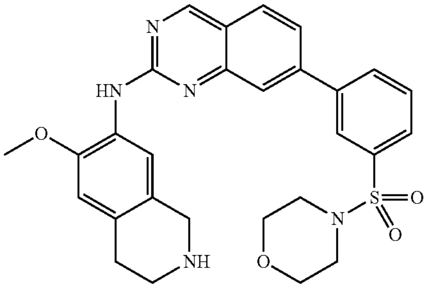 [SMILES: COc1cc2c(cc1Nc1ncc3ccc(-c4cccc(S(=O)(=O)N5CCOCC5)c4)cc3n1)CNCC2] | N-(6-methoxy-1,2,3,4-tetrahydroisoquinolin-7-yl)-7-{3-[(morpholin-4-yl)sulfonyl]phenyl}quinazo-lin-2-amine | Calc'd 532, found 532; 1B |
| 1-78 | 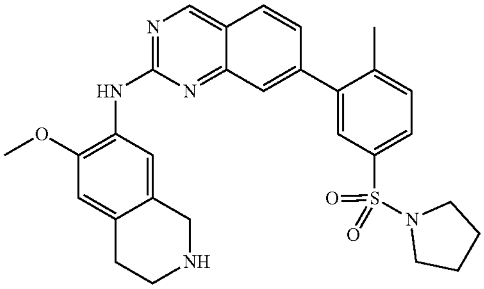 [SMILES: COc1cc2c(cc1Nc1ncc3ccc(-c4cc(S(=O)(=O)N5CCCC5)ccc4C)cc3n1)CNCC2] | N-(6-methoxy-1,2,3,4-tetrahydroisoquinolin-7-yl)-7-{2-methyl-5-[(pyrrolidin-1-yl)sulfonyl]phenyl}quinazo-lin-2-amine | Calc'd 530, found 530; 1B |

TABLE 1-continued

| Example Number | Structure | Name | Exact Mass [M + H]+; Method |
|---|---|---|---|
| 1-79 | 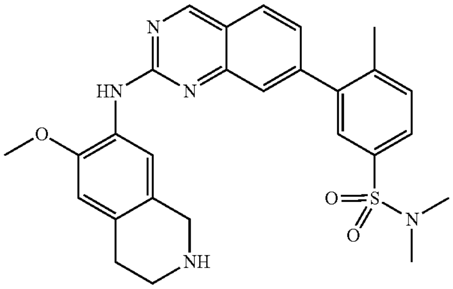 | 3-{2-[(6-methoxy-1,2,3,4-tetrahydroisoquinolin-7-yl)amino]quinazolin-7-yl}-N,N,4-trimethylbenzene-1-sulfonamide | Calc'd 504, found 504; 1B |
| 1-80 | 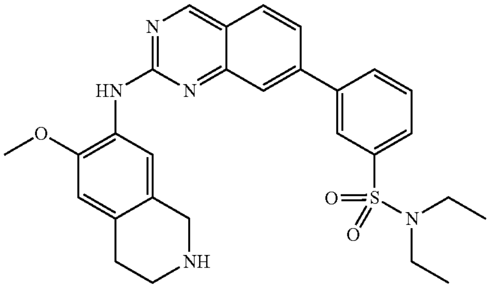 [SMILES: CCN(CC)S(=O)(=O)c1cccc(-c2ccc3cnc(Nc4cc5c(cc4OC)CCNC5)nc3c2)c1] | N,N-diethyl-3-{2-[(6-methoxy-1,2,3,4-tetrahydroisoquinolin-7-yl)amino]quinazolin-7-yl}benzene-1-sulfonamide | Calc'd 518, found 518; 1B |
| 1-81 | 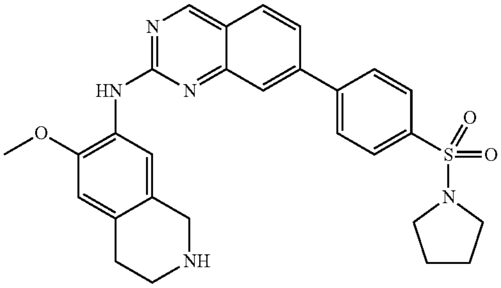 [SMILES: COc1cc2c(cc1Nc1ncc3ccc(-c4ccc(S(=O)(=O)N5CCCC5)cc4)cc3n1)CNCC2] | N-(6-methoxy-1,2,3,4-tetrahydroisoquinolin-7-yl)-7-{4-[(pyrrolidin-1-yl)sulfonyl]phenyl}quinazolin-2-amine | Calc'd 516, found 516; 1B |
| 1-82 | 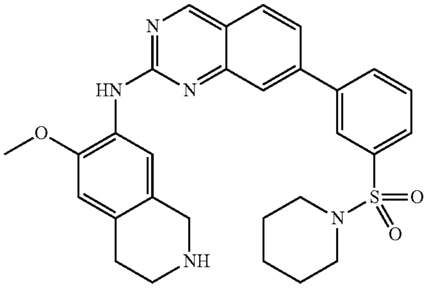 [SMILES: COc1cc2c(cc1Nc1ncc3ccc(-c4cccc(S(=O)(=O)N5CCCCC5)c4)cc3n1)CNCC2] | N-(6-methoxy-1,2,3,4-tetrahydroisoquinolin-7-yl)-7-{3-[(piperidin-1-yl)sulfonyl]phenyl}quinazoline-2-amine | Calc'd 530, found 530; 1B |

TABLE 1-continued

| Example Number | Structure | Name | Exact Mass [M + H]$^+$; Method |
|---|---|---|---|
| 1-83 | 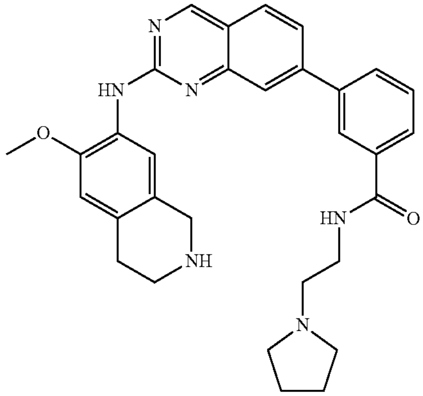 [SMILES: COc1cc2c(cc1Nc1ncc3ccc(-c4cccc(C(=O)NCCN5CCCC5)c4)cc3n1)CNCC2] | 3-{2-[(6-methoxy-1,2,3,4-tetrahydroisoquinolin-7-yl)amino]quinazolin-7-yl}-N-[2-(pyrrolidin-1-yl)ethyl]benzamide | Calc'd 523, found 523; 1B |
| 1-84 | 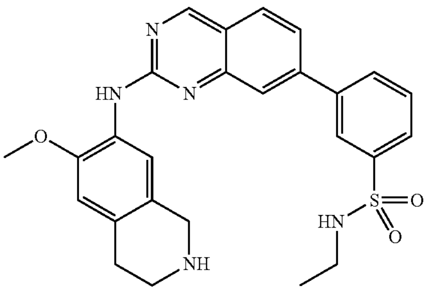 [SMILES: CCNS(=O)(=O)c1cccc(-c2ccc3cnc(Nc4cc5c(cc4OC)CCNC5)nc3c2)c1] | N-ethyl-3-{2-[(6-methoxy-1,2,3,4-tetrahydroisoquinolin-7-yl)amino]quinazolin-7-yl}benzene-1-sulfonamide | Calc'd 490, found 490; 1B |
| 1-85 | 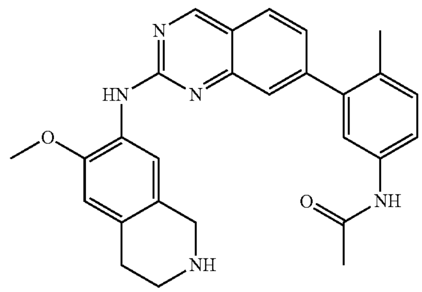 [SMILES: COc1cc2c(cc1Nc1ncc3ccc(-c4cc(NC(C)=O)ccc4C)cc3n1)CNCC2] | N-(3-{2-[(6-methoxy-1,2,3,4-tetrahydroisoquinolin-7-yl)amino]quinazolin-7-yl}-4-methylphenyl)acetamide | Calc'd 454, found 454; 1B |
| 1-86 | 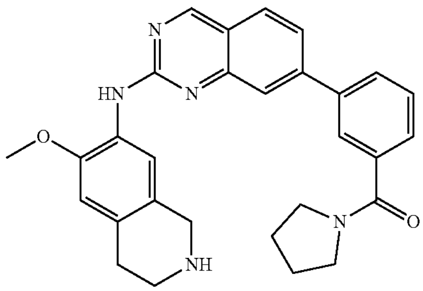 [SMILES: COc1cc2c(cc1Nc1ncc3ccc(-c4cccc(C(=O)N5CCCC5)c4)cc3n1)CNCC2] | (3-{2-[(6-methoxy-1,2,3,4-tetrahydroisoquinolin-7-yl)amino]quinazolin-7-yl}phenyl)(pyrrolidin-1-yl)methanone | Calc'd 480, found 480; 1B |

TABLE 1-continued

| Example Number | Structure | Name | Exact Mass $[M + H]^+$; Method |
|---|---|---|---|
| 1-87 | 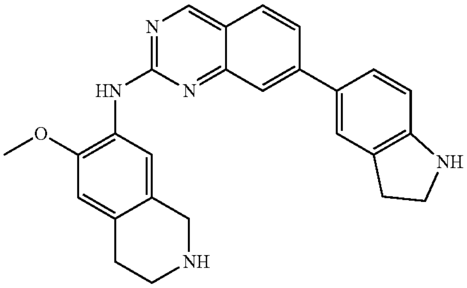 [SMILES: COc1cc2c(cc1Nc1ncc3ccc(-c4ccc5c(c4)CCN5)cc3n1)CNCC2] | 7-(2,3-dihydro-1H-indol-5-yl)-N-(6-methoxy-1,2,3,4-tetrahydroisoquinolin-7-yl)quinazolin-2-amine | Calc'd 424, found 424; 1B |
| 1-88 | 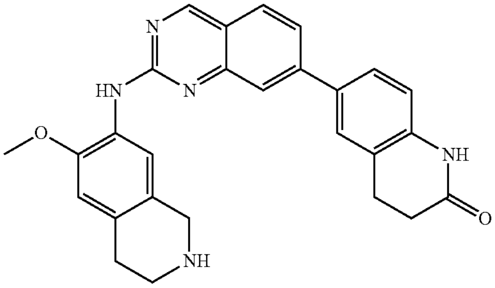 [SMILES: COc1cc2c(cc1Nc1ncc3ccc(-c4ccc5c(c4)CCC(=O)N5)cc3n1)CNCC2] | 6-{2-[(6-methoxy-1,2,3,4-tetrahydroisoquinolin-7-yl)amino]quinazolin-7-yl}-3,4-dihydroquinolin-2(1H)-one | Calc'd 452, found 452; 1B |
| 1-89 | 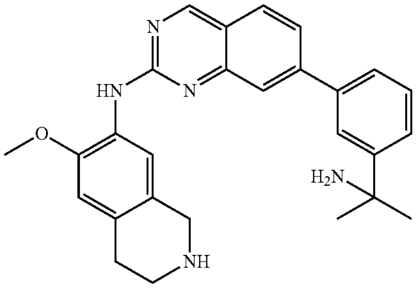 [SMILES: COc1cc2c(cc1Nc1ncc3ccc(-c4cccc(C(C)(C)N)c4)cc3n1)CNCC2] | 7-[3-(2-aminopropan-2-yl)phenyl]-N-(6-methoxy-1,2,3,4-tetrahydroisoquinolin-7-yl)quinazolin-2-amine | Calc'd 440, found 440; 1B |
| 1-90 | 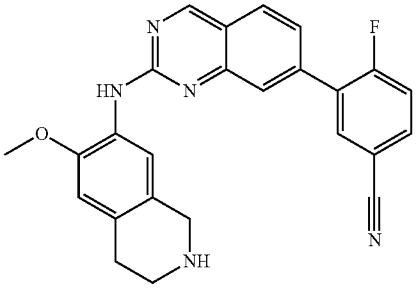 [SMILES: COc1cc2c(cc1Nc1ncc3ccc(-c4cc(C#N)ccc4F)cc3n1)CNCC2] | 4-fluoro-3-{2-[(6-methoxy-1,2,3,4-tetrahydroisoquinolin-7-yl)amino]quinazolin-7-yl}benzonitrile | Calc'd 426, found 426; 1B |
| 1-91 | 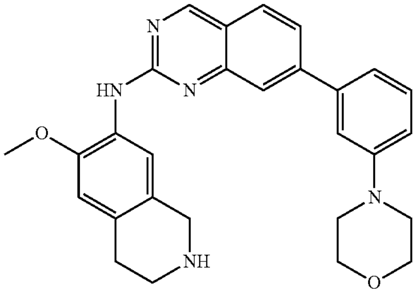 [SMILES: COc1cc2c(cc1Nc1ncc3ccc(-c4cccc(N5CCOCC5)c4)cc3n1)CNCC2] | N-(6-methoxy-1,2,3,4-tetrahydroisoquinolin-7-yl)-7-[3-(morpholin-4-yl)phenyl]quinazolin-2-amine | Calc'd 468, found 468; 1B |

TABLE 1-continued

| Example Number | Structure | Name | Exact Mass [M + H]+; Method |
|---|---|---|---|
| 1-92 | 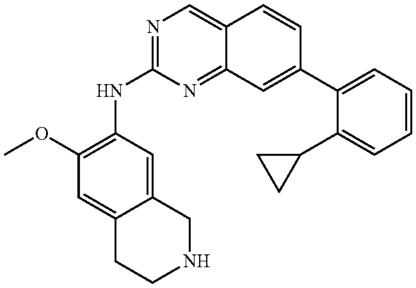 [SMILES: COc1cc2c(cc1Nc1ncc3ccc(-c4ccccc4C4CC4)cc3n1)CNCC2] | 7-(2-cyclopropylphenyl)-N-(6-methoxy-1,2,3,4-tetrahydroisoquinolin-7-yl)quinazolin-2-amine | Calc'd 423, found 423; 1B |
| 1-93 | 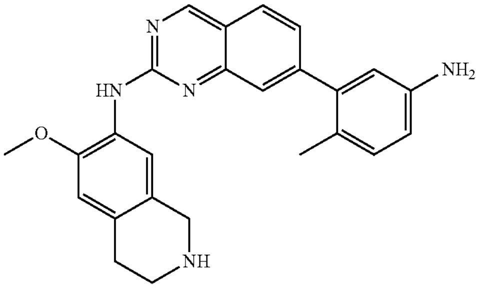 [SMILES: COc1cc2c(cc1Nc1ncc3ccc(-c4cc(N)ccc4C)cc3n1)CNCC2] | 7-(5-amino-2-methylphenyl)-N-(6-methoxy-1,2,3,4-tetrahydroisoquinolin-7-yl)quinazolin-2-amine | Calc'd 412, found 412; 1B |
| 1-94 | 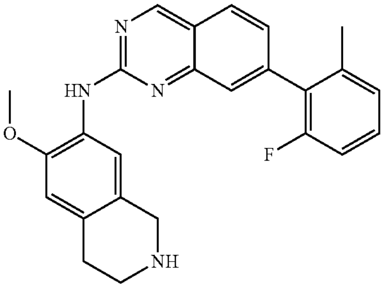 [SMILES: COc1cc2c(cc1Nc1ncc3ccc(-c4c(C)cccc4F)cc3n1)CNCC2] | 7-(2-fluoro-6-methylphenyl)-N-(6-methoxy-1,2,3,4-tetrahydroisoquinolin-7-yl)quinazolin-2-amine | Calc'd 415, found 415; 1B |
| 1-95 | 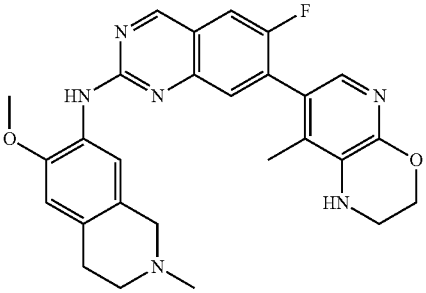 [SMILES: COc1cc2c(cc1Nc1ncc3cc(F)c(-c4cnc5c(c4C)NCCO5)cc3n1)CN(C)CC2] | 6-fluoro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine | Calc'd 487, found 487; 1C |
| 1-96 | 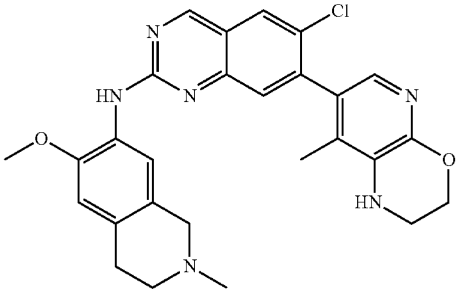 [SMILES: COc1cc2c(cc1Nc1ncc3cc(Cl)c(-c4cnc5c(c4C)NCCO5)cc3n1)CN(C)CC2] | 6-chloro-N-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazolin-2-amine | Calc'd 503, found 503; 1D |

TABLE 1-continued

| Example Number | Structure | Name | Exact Mass [M + H]+; Method |
|---|---|---|---|
| 1-97 | 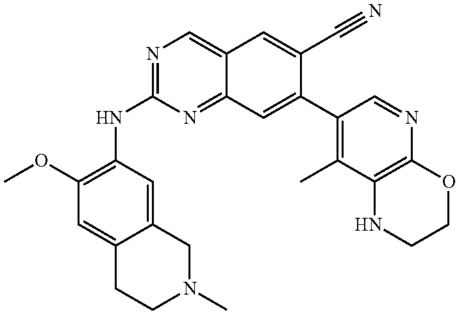 [SMILES: COc1cc2c(cc1Nc1ncc3cc(C#N)c(-c4cnc5c(c4C)NCCO5)cc3n1)CN(C)CC2] | 2-[(6-methoxy-2-methyl-1-1,2,3,4-tetrahydroisoquinolin-7-yl)amino]-7-(8-methyl-2,3-dihydro-1H-pyrido[2,3-b][1,4]oxazin-7-yl)quinazoline-6-carbonitrile | Calc'd 494, found 494; 1E |
| 1-98 | 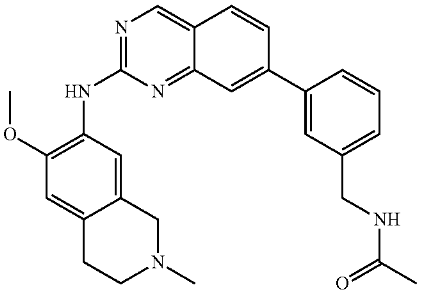 [SMILES: COc1cc2c(cc1Nc1ncc3ccc(-c4cccc(CNC(C)=O)c4)cc3n1)CN(C)CC2] | N-[(3-{2-[(6-methoxy-2-methyl-1,2,3,4-tetrahydroisoquinolin-7-yl)amino]quinazolin-7-yl}phenyl)methyl]acetamide | Calc'd 468, found 468; 1A |
| 1-99 | 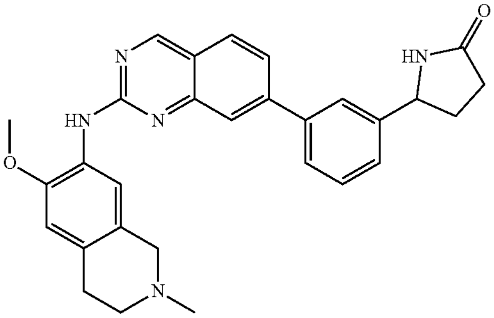 [SMILES: COc1cc2c(cc1Nc1ncc3ccc(-c4cccc(C5CCC(=O)N5)c4)cc3n1)CN(C)CC2] | (R and S)-5-(3-{2-[(6-methoxy-2-methyl-1,2,3,4-tetrahydroisoquinolin-7-yl)amino]quinazolin-7-yl}phenyl)pyrrolidin-2-one | Calc'd 480, found 480; 1A |
| 1-100 | 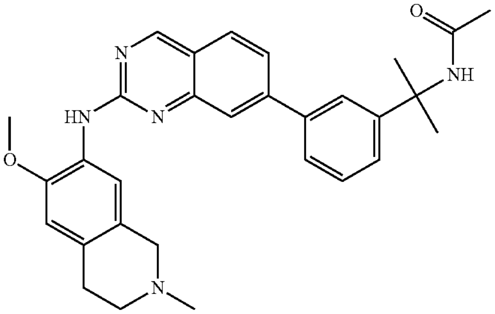 [SMILES: COc1cc2c(cc1Nc1ncc3ccc(-c4cccc(C(C)(C)NC(C)=O)c4)cc3n1)CN(C)CC2] | N-[2-(3-{2-[(6-methoxy-2-methyl-1,2,3,4-tetrahydroisoquinolin-7-yl)amino]quinazolin-7-yl}phenyl)propan-2-yl]acetamide | Calc'd 496, found 496; 1A |
| 1-101 | 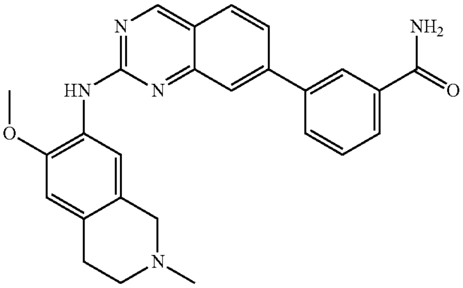 [SMILES: COc1cc2c(cc1Nc1ncc3ccc(-c4cccc(C(N)=O)c4)cc3n1)CN(C)CC2] | 3-{2-[(6-methoxy-2-methyl-1,2,3,4-tetrahydroisoquinolin-7-yl)amino]quinazolin-7-yl}benzamide | Calc'd 440, found 440; 1A |

TABLE 1-continued

| Example Number | Structure | Name | Exact Mass [M + H]+; Method |
|---|---|---|---|
| 1-102 | 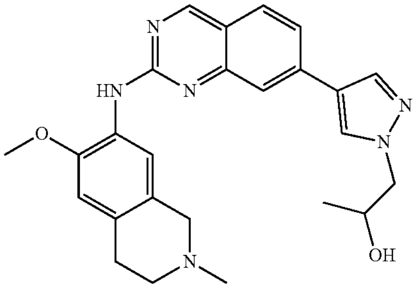 [SMILES: COc1cc2c(cc1Nc1ncc3ccc(-c4cnn(CC(C)O)c4)cc3n1)CN(C)CC2] | (R and S)-1-(4-{2-[(6-methoxy-2-methyl-1,2,3,4-tetrahydroisoquinolin-7-yl)amino]quinazolin-7-yl}-1H-pyrazol-1-yl)propan-2-ol | Calc'd 445, found 445; 1A |
| 1-103 | 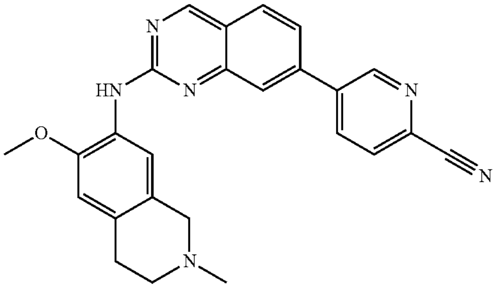 [SMILES: COc1cc2c(cc1Nc1ncc3ccc(-c4ccc(C#N)nc4)cc3n1)CN(C)CC2] | 5-{2-[(6-methoxy-2-methyl-1,2,3,4-tetrahydroisoquinolin-7-yl)amino]quinazolin-7-yl}pyridine-2-carbonitrile | Calc'd 423, found 423; 1A |
| 1-104 | 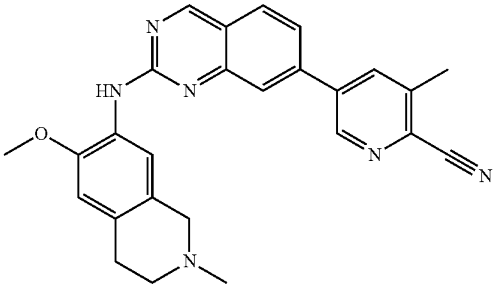 [SMILES: COc1cc2c(cc1Nc1ncc3ccc(-c4cnc(C#N)c(C)c4)cc3n1)CN(C)CC2] | 5-{2-[(6-methoxy-2-methyl-1,2,3,4-tetrahydroisoquinolin-7-yl)amino]quinazolin-7-yl}-3-methylpyridine-2-carbonitrile | Calc'd 437, found 437; 1A |
| 1-105 | 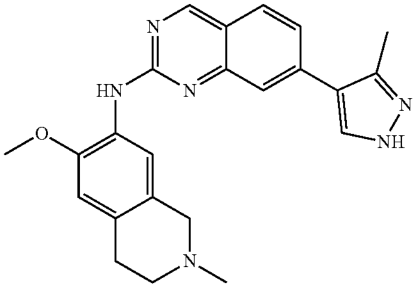 [SMILES: COc1cc2c(cc1Nc1ncc3ccc(-c4c[nH]nc4C)cc3n1)CN(C)CC2] | N-(6-methoxy-2-methyl-1,2,3,4-tetrahydroisoquinolin-7-yl)-7-(3-methyl-1H-pyrazol-4-yl)quinazolin-2-amine | Calc'd 401, found 401; 1A |
| 1-106 | 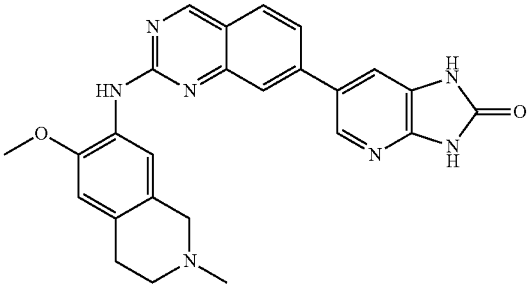 [SMILES: COc1cc2c(cc1Nc1ncc3ccc(-c4cnc5[nH]c(=O)[nH]c5c4)cc3n1)CN(C)CC2] | 6-{2-[(6-methoxy-2-methyl-1,2,3,4-tetrahydroisoquinolin-7-yl)amino]quinazolin-7-yl}-1,3-dihydro-2H-imidazo[4,5-b]pyridin-2-one | Calc'd 454, found 454; 1A |

TABLE 1-continued

| Example Number | Structure | Name | Exact Mass [M + H]$^+$; Method |
|---|---|---|---|
| 1-107 | 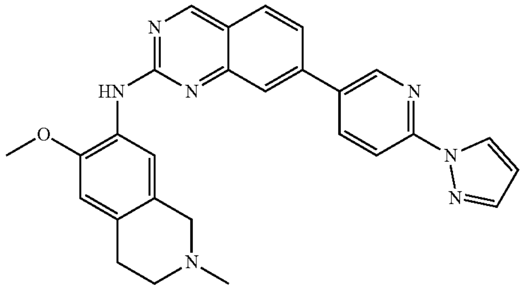 [SMILES: COc1cc2c(cc1Nc1ncc3ccc(-c4ccc(-n5cccn5)nc4)cc3n1)CN(C)CC2] | N-(6-methoxy-2-methyl-1,2,3,4-tetrahydroisoquinolin-7-yl)-7-[6-(1H-pyrazol-1-yl)pyridin-3-yl]quinazolin-2-amine | Calc'd 464, found 464; 1A |
| 1-108 | 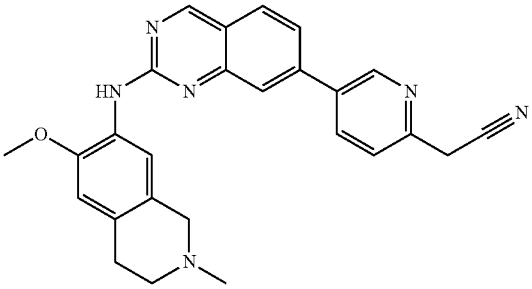 [SMILES: COc1cc2c(cc1Nc1ncc3ccc(-c4ccc(CC#N)nc4)cc3n1)CN(C)CC2] | (5-{2-[(6-methoxy-2-methyl-1,2,3,4-tetrahydroisoquinolin-7-yl)amino]quinazolin-7-yl}pyridin-2-yl)acetonitrile | Calc'd 437, found 437; 1A |
| 1-109 | 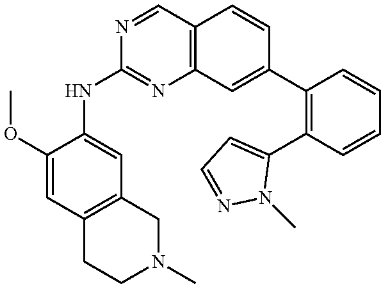 [SMILES: COc1cc2c(cc1Nc1ncc3ccc(-c4ccccc4-c4ccnn4C)cc3n1)CN(C)CC2] | N-(6-methoxy-2-methyl-1,2,3,4-tetrahydroisoquinolin-7-yl)-7-[2-(1-methyl-1H-pyrazol-5-yl)phenyl]quinazolin-2-amine | Calc'd 477, found 477; 1A |
| 1-110 | 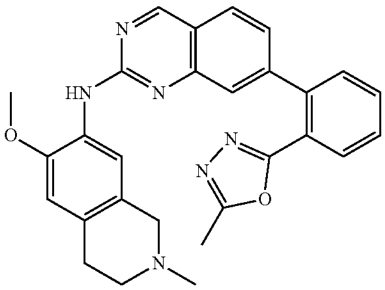 [SMILES: COc1cc2c(cc1Nc1ncc3ccc(-c4ccccc4-c4nnc(C)o4)cc3n1)CN(C)CC2] | N-(6-methoxy-2-methyl-1,2,3,4-tetrahydroisoquinolin-7-yl)-7-[2-(5-methyl-1,3,4-oxadiazol-2-yl)phenyl]quinazolin-2-amine | Calc'd 479, found 479; 1A |

TABLE 1-continued

| Example Number | Structure | Name | Exact Mass [M + H]+; Method |
|---|---|---|---|
| 1-111 | 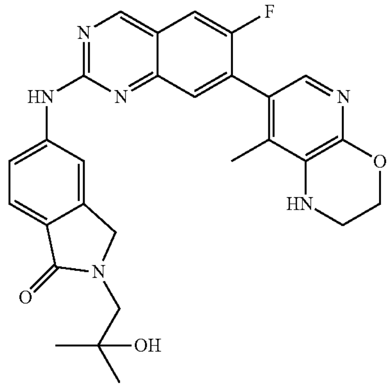 [SMILES: Cc1c(-c2cc3nc(Nc4ccc5c(c4)CN(CC(C)(C)O)C5=O)ncc3cc2F)cnc2c1NCCO2] | 5-{[6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one | Calc'd 515, found 515; 1F |
| 1-112 | 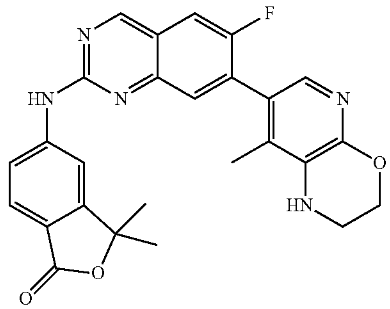 [SMILES: Cc1c(-c2cc3nc(Nc4ccc5c(c4)C(C)(C)OC5=O)ncc3cc2F)cnc2c1NCCO2] | 5-{[6-fluoro-7-(8-methyl-2,3-dihydro-1H-pyrido[2,3-b][1,4]oxazin-7-yl)quinazolin-2-yl]amino}-3,3-dimethyl-2-benzofuran-1(3H)-one | Calc'd 472, found 472; 1C |
| 1-113 | 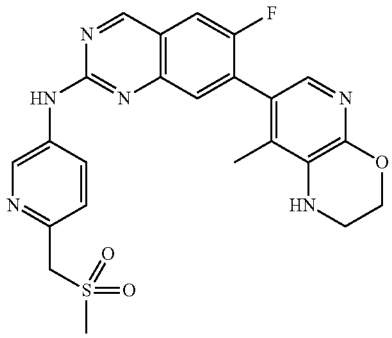 [SMILES: Cc1c(-c2cc3nc(Nc4ccc(CS(C)(=O)=O)nc4)ncc3cc2F)cnc2c1NCCO2] | 6-fluoro-7-(8-methyl-2,3-dihydro-1H-pyrido[2,3-b][1,4]oxazin-7-yl)-N-(6-((methylsulfonyl)methyl)pyridin-3-yl)quinazolin-2-amine | Calc'd 457, found 457; 1G |
| 1-114 | 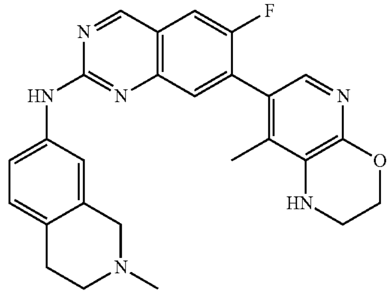 [SMILES: Cc1c(-c2cc3nc(Nc4ccc5c(c4)CN(C)CC5)ncc3cc2F)cnc2c1NCCO2] | 6-fluoro-7-(8-methyl-2,3-dihydro-1H-pyrido[2,3-b][1,4]oxazin-7-yl)-N-(2-methyl-1,2,3,4-tetrahydroisoquinolin-7-yl)quinazolin-2-amine | Calc'd 457, found 457; 1G |

TABLE 1-continued

| Example Number | Structure | Name | Exact Mass [M + H]+; Method |
|---|---|---|---|
| 1-115 | 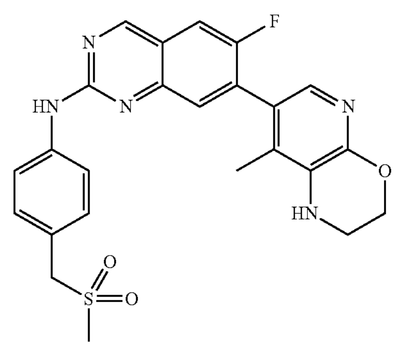 [SMILES: Cc1c(-c2cc3nc(Nc4ccc(CS(C)(=O)=O)cc4)ncc3cc2F)cnc2c1NCCO2] | 6-fluoro-7-(8-methyl-2,3-dihydro-1H-pyrido[2,3-b][1,4]oxazin-7-yl)-N-(4-[(methylsulfonyl)methyl]phenyl}quinazolin-2-amine | Calc'd 480, found 480; 1G |
| 1-116 | 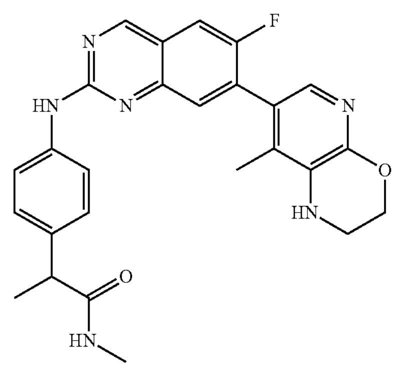 [SMILES: CNC(=O)C(C)c1ccc(Nc2ncc3cc(F)c(-c4cnc5c(c4C)NCCO5)cc3n2)cc1] | (R or S)-2-(4-{[6-fluoro-7-(8-methyl-2,3-dihydro-1H-pyrido[2,3-b][1,4]oxazin-7-yl)quinazolin-2-yl]amino}phenyl)-N-methylpropanamide | Calc'd 473, found 473; 1H |
| 1-117 | 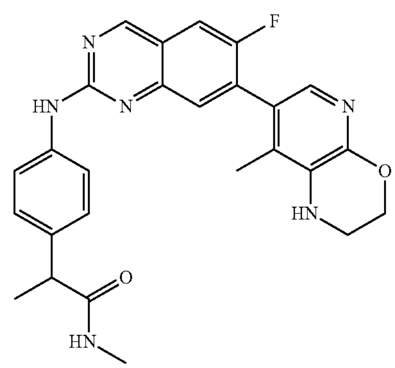 [SMILES: CNC(=O)C(C)c1ccc(Nc2ncc3cc(F)c(-c4cnc5c(c4C)NCCO5)cc3n2)cc1] | (R or S)-2-(4-{[6-fluoro-7-(8-methyl-2,3-dihydro-1H-pyrido[2,3-b][1,4]oxazin-7-yl)quinazolin-2-yl]amino}phenyl)-N-methylpropanamide | Calc'd 473, found 473; 1H |
| 1-118 | 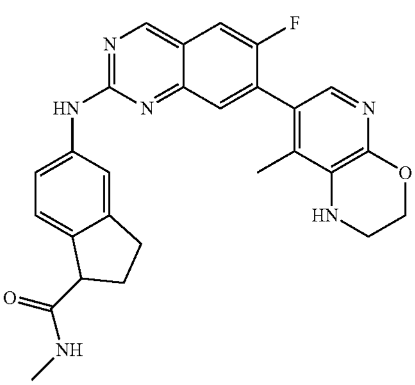 [SMILES: CNC(=O)C1CCc2cc(Nc3ncc4cc(F)c(-c5cnc6c(c5C)NCCO6)cc4n3)ccc21] | (R or S)-5-{[6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide | Calc'd 485, found 485; 1H |

TABLE 1-continued

| Example Number | Structure | Name | Exact Mass [M + H]+; Method |
|---|---|---|---|
| 1-119 | 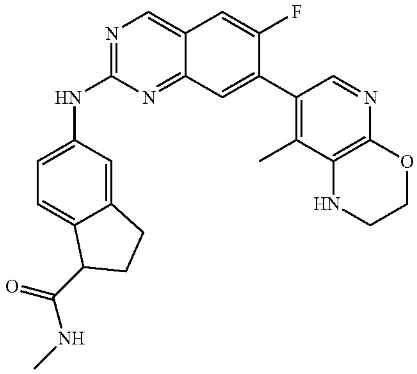 [SMILES: CNC(=O)C1CCc2cc(Nc3ncc4cc(F)c(-c5cnc6c(c5C)NCCO6)cc4n3)ccc21] | (R or S)-5-{[6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide | Calc'd 485, found 485; 1H |
| 1-120 | 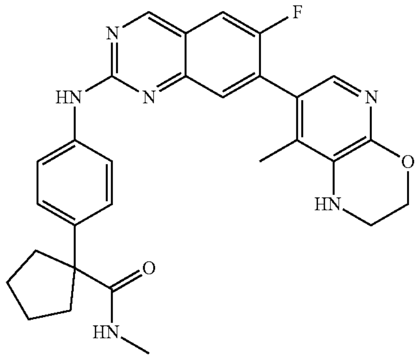 [SMILES: CNC(=O)C1(c2ccc(Nc3ncc4cc(F)c(-c5cnc6c(c5C)NCCO6)cc4n3)cc2)CCCC1] | 1-(4-{[6-fluoro-7-(8-methyl-2,3-dihydro-1H-pyrido[2,3-b][1,4]oxazin-7-yl)quinazolin-2-yl]amino}phenyl)-N-methylcyclopentane-1-carboxamide | Calc'd 513, found 513; 1H |
| 1-121 | 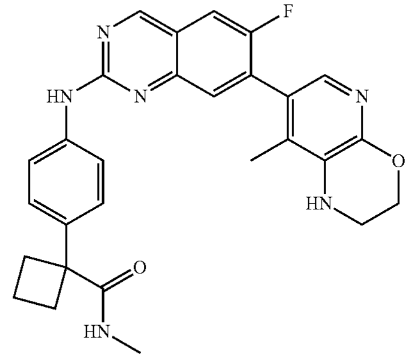 [SMILES: CNC(=O)C1(c2ccc(Nc3ncc4cc(F)c(-c5cnc6c(c5C)NCCO6)cc4n3)cc2)CCC1] | 1-(4-{[6-fluoro-7-(8-methyl-2,3-dihydro-1H-pyrido[2,3-b][1,4]oxazin-7-yl)quinazolin-2-yl]amino}phenyl)-N-methylcyclobutane-1-carboxamide | Calc'd 499, found 499; 1H |
| 1-122 | 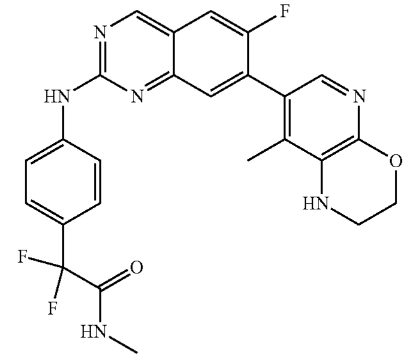 [SMILES: CNC(=O)C(F)(F)c1ccc(Nc2ncc3cc(F)c(-c4cnc5c(c4C)NCCO5)cc3n2)cc1] | 2,2-difluoro-2-(4-{[6-fluoro-7-(8-methyl-2,3-dihydro-1H-pyrido[2,3-b][1,4]oxazin-7-yl)quinazolin-2-yl]amino}phenyl)-N-methylacetamide | Calc'd 495, found 495; 1H |

TABLE 1-continued

| Example Number | Structure | Name | Exact Mass [M + H]+; Method |
|---|---|---|---|
| 1-123 | 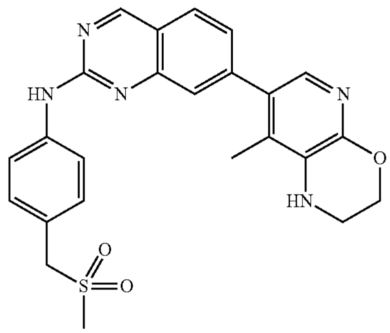 [SMILES: Cc1c(-c2ccc3cnc(Nc4ccc(CS(C)(=O)=O)cc4)nc3c2)cnc2c1NCCO2] | 7-(8-methyl-2,3-dihydro-1H-pyrido[2,3-b][1,4]oxazin-7-yl)-N-{4-[(methylsulfonyl)methyl]phenyl}quinazolin-2-amine | Calc'd 462, found 462; 1I |
| 1-124 | 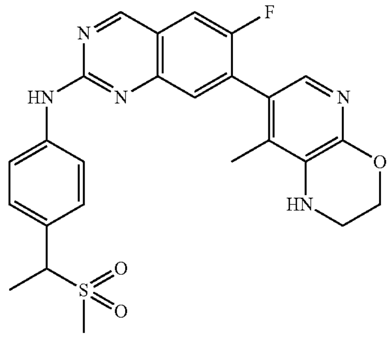 [SMILES: Cc1c(-c2cc3nc(Nc4ccc(C(C)S(C)(=O)=O)cc4)ncc3cc2F)cnc2c1NCCO2] | (R or S)-6-fluoro-7-(8-methyl-2,3-dihydro-1H-pyrido[2,3-b][1,4]oxazin-7-yl)-N-{4-[1-(methylsulfonyl)ethyl]phenyl}quinazolin-2-amine | Calc'd 494, found 494; 1J |
| 1-125 | 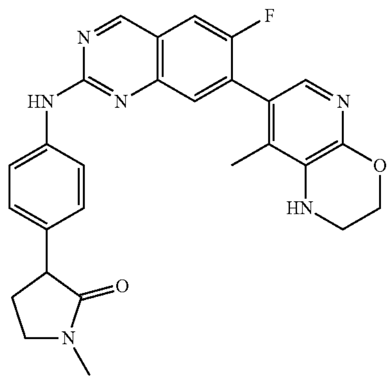 [SMILES: Cc1c(-c2cc3nc(Nc4ccc(C5CCN(C)C5=O)cc4)ncc3cc2F)cnc2c1NCCO2] | (R or S)-3-(4-{[6-fluoro-7-(8-methyl-2,3-dihydro-1H-pyrido[2,3-b][1,4]oxazin-7-yl)quinazolin-2-yl]amino}phenyl)-1-methylpyrrolidin-2-one | Calc'd 485, found 485; 1J |
| 1-126 | 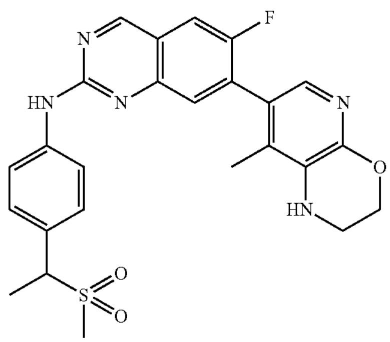 [SMILES: Cc1c(-c2cc3nc(Nc4ccc(C(C)S(C)(=O)=O)cc4)ncc3cc2F)cnc2c1NCCO2] | (R of S)-6-fluoro-7-(8-methyl-2,3-dihydro-1H-pyrido[2,3-b][1,4]oxazin-7-yl)-N-{4-[1-(methylsulfonyl)ethyl]phenyl}quinazolin-2-amine | Calc'd 494, found 494; 1J |

TABLE 1-continued

| Example Number | Structure | Name | Exact Mass [M + H]+; Method |
|---|---|---|---|
| 1-127 | 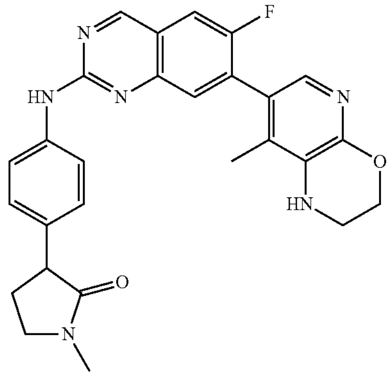 [SMILES: Cc1c(-c2cc3nc(Nc4ccc(C5CCN(C)C5=O)cc4)ncc3cc2F)cnc2c1NCCO2] | (R of S)-3-(4-{[6-fluoro-7-(8-methyl-2,3-dihydro-1H-pyrido[2,3-b][1,4]oxazin-7-yl)quinazolin-2-yl]amino}phenyl)-1-methylpyrrolidin-2-one | Calc'd 485, found 485; 1J |
| 1-128 | 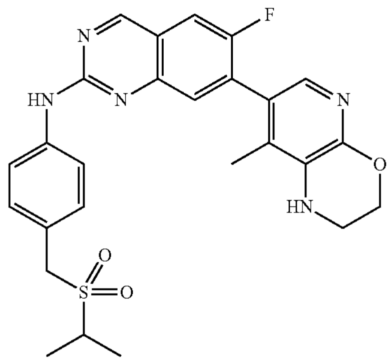 [SMILES: Cc1c(-c2cc3nc(Nc4ccc(CS(=O)(=O)C(C)C)cc4)ncc3cc2F)cnc2c1NCCO2] | 6-fluoro-N-(4-((isopropylsulfonyl)methyl)phenyl)-7-(8-methyl-2,3-dihydro-1H-pyrido[2,3-b][1,4]oxazin-7-yl)quinazolin-2-amine | Calc'd 508, found 508; 1J |
| 1-129 | 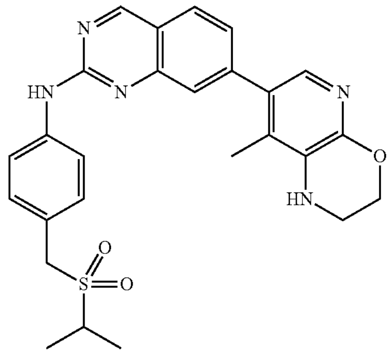 [SMILES: Cc1c(-c2ccc3cnc(Nc4ccc(CS(=O)(=O)C(C)C)cc4)nc3c2)cnc2c1NCCO2] | N-(4-((isopropylsulfonyl)methyl)phenyl)-7-(8-methyl-2,3-dihydro-1H-pyrido[2,3-b][1,4]oxazin-7-yl)quinazolin-2-amine | Calc'd 490, found 490; 1I |
| 1-130 | 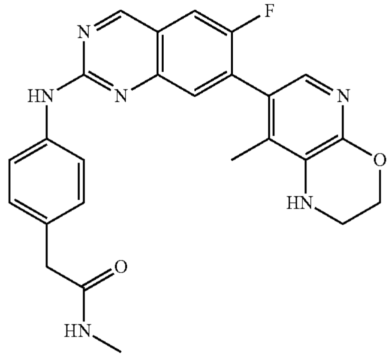 [SMILES: CNC(=O)Cc1ccc(Nc2ncc3cc(F)c(-c4cnc5c(c4C)NCCO5)cc3n2)cc1] | 2-(4-{[6-fluoro-7-(8-methyl-2,3-dihydro-1H-pyrido[2,3-b][1,4]oxazin-7-yl)quinazolin-2-yl]amino}phenyl)-N-methylacetamide | Calc'd 459, found 459; 1K |

TABLE 1-continued

| Example Number | Structure | Name | Exact Mass [M + H]+; Method |
|---|---|---|---|
| 1-131 | 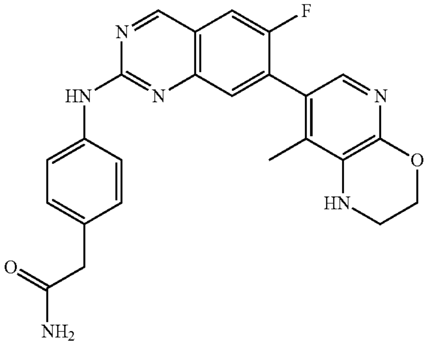 [SMILES: Cc1c(-c2cc3nc(Nc4ccc(CC(N)=O)cc4)ncc3cc2F)cnc2c1NCCO2] | 2-(4-{[6-fluoro-7-(8-methyl-2,3-dihydro-1H-pyrido[2,3-b][1,4]oxazin-7-yl)quinazolin-2-yl]amino}phenyl)acetamide | Calc'd 445, found 445; 1K |
| 1-132 | 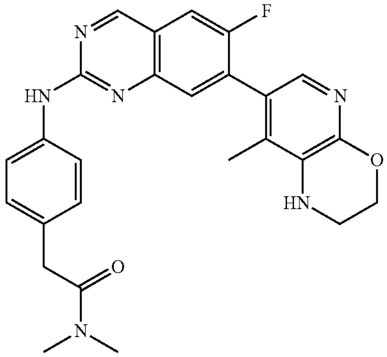 [SMILES: Cc1c(-c2cc3nc(Nc4ccc(CC(=O)N(C)C)cc4)ncc3cc2F)cnc2c1NCCO2] | 2-(4-{[6-fluoro-7-(8-methyl-2,3-dihydro-1H-pyrido[2,3-b][1,4]oxazin-7-yl)quinazolin-2-yl]amino}phenyl)-N,N-dimethylacetamide | Calc'd 473, found 473; 1K |
| 1-133 | 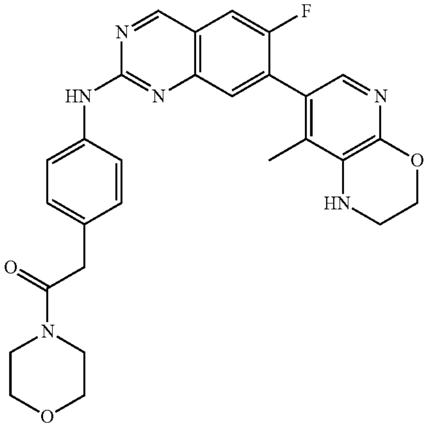 [SMILES: Cc1c(-c2cc3nc(Nc4ccc(CC(=O)N5CCOCC5)cc4)ncc3cc2F)cnc2c1NCCO2] | 2-(4-{[6-fluoro-7-(8-methyl-2,3-dihydro-1H-pyrido[2,3-b][1,4]oxazin-7-yl)quinazolin-2-yl]amino}phenyl)-1-(morpholin-4-yl)ethan-1-one | Calc'd 515, found 515; 1K |
| 1-134 | 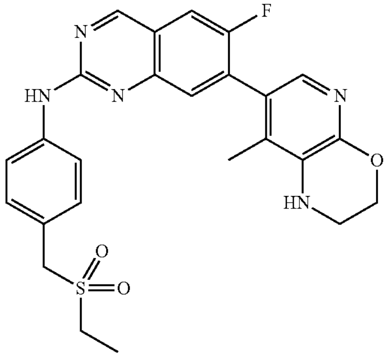 [SMILES: CCS(=O)(=O)Cc1ccc(Nc2ncc3cc(F)c(-c4cnc5c(c4C)NCCO5)cc3n2)cc1] | N-{4-[(ethylsulfonyl)methyl]phenyl}-6-fluoro-7-(8-methyl-2,3-dihydro-1H-pyrido[2,3-b][1,4]oxazin-7-yl)quinazolin-2-amine | Calc'd 494, found 494; 1K |

TABLE 1-continued

| Example Number | Structure | Name | Exact Mass $[M + H]^+$; Method |
|---|---|---|---|
| 1-135 | 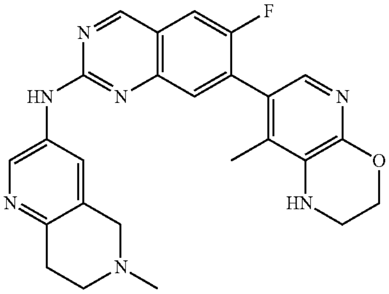 [SMILES: Cc1c(-c2cc3nc(Nc4cnc5c(c4)CN(C)CC5)ncc3cc2F)cnc2c1NCCO2] | 6-fluoro-7-(8-methyl-2,3-dihydro-1H-pyrido[2,3-b][1,4]oxazin-7-yl)-N-(6-methyl-5,6,7,8-tetrahydro-1,6-naphthyridin-3-yl)quinazolin-2-amine | Calc'd 458, found 458; 1K |

Compound Examples of Table 2

Example 2A

Preparation of Compound 2-2

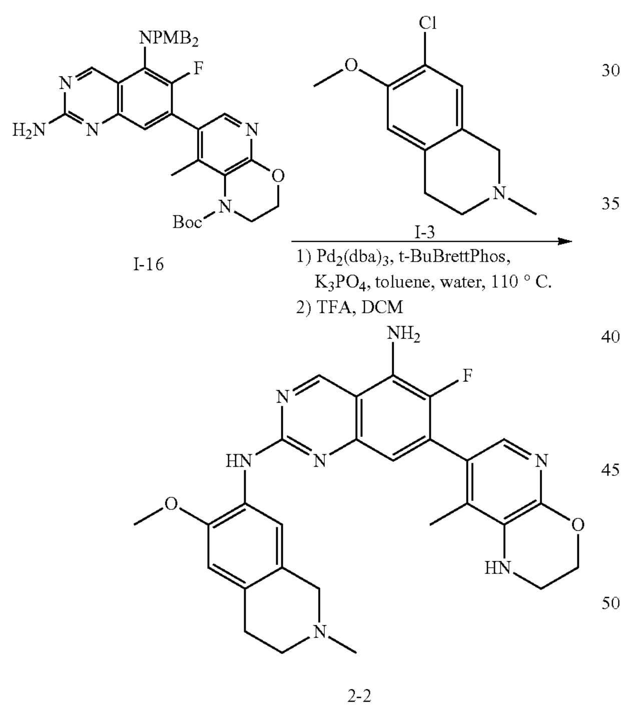

A mixture containing intermediate I-16 (200 mg, 0.30 mmol), intermediate I-3 (95 mg, 0.45 mmol), $K_3PO_4$ (190 mg, 0.900 mmol), $Pd_2(dba)_3$ (55 mg, 0.060 mmol), and t-BuBrettPhos (29 mg, 0.060 mmol) in toluene (3 mL) was treated with water (0.027 mL, 1.5 mmol). The mixture was deoxygenated by bubbling argon gas through the reaction mixture for 3 min. The reaction mixture was stirred overnight at 110° C. After cooling, the reaction was diluted with DCM and washed with water. The organic layer was then dried ($Na_2SO_4$) and concentrated. The residue was purified by chromatography on $SiO_2$ (gradient of 0-50% MeOH/DCM in 80 g silica) giving the protected coupling intermediate. The intermediate was then taken-up in 2 mL of DCM, treated with 0.5 mL of TFA and the solution allowed to age overnight, then concentrated to dryness. The residue was purified by reverse phase chromatography (gradient of 2-55% ACN/water with 0.1% $NH_4OH$) to provide 2-2 as a solid. $^1H$ NMR (500 MHz, DMSO-$d_6$) δ 9.54 (s, 1H), 8.22 (s, 1H), 7.97 (s, 1H), 7.34 (s, 1H), 6.77 (s, 1H), 6.64 (d, J=5 Hz, 1H), 6.35 (br s, 2H), 5.68 (s, 1H), 4.30 (m, 2H), 3.84 (s, 3H), 3.40-3.44 (br, 4H), 2.78 (m, 2H), 2.57 (m, 2H), 2.32 (s, 3H), 1.94 (s, 3H). MS (EI) calc'd for $C_{27}H_{29}FN_7O_2$ $[M+H]^+$, 502; found, 502.

Preparation of Compound 2-24 (6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine)

Compound 2-24 was prepared from intermediate I-16 and 1-bromo-4-((methylsulfonyl)methyl)benzene using coupling method from Example 2A.

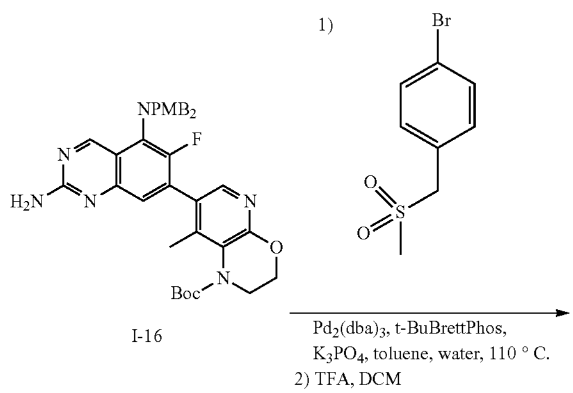

-continued
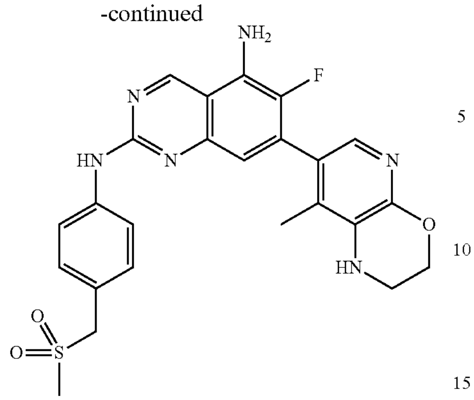
2-24
Compound 2-24. $^{1}H$ NMR (500 MHz, DMSO-$d_6$) δ 9.83 (s, 1H), 9.60 (s, 1H), 7.98 (d, J=8.6 Hz, 2H), 7.36 (s, 1H), 7.33 (d, J=8.6 Hz, 2H), 6.65 (d, J=5.7 Hz, 1H), 6.37 (s, 2H), 5.69 (s, 1H), 4.40 (s, 2H), 4.30 (t, J=4.2 Hz, 2H), 3.38 (s, 2H), 2.88 (s, 3H), 1.95 (s, 3H). MS (EI) calc'd for $C_{24}H_{24}FN_6O_3S$ $[M+H]^+$, 495; found, 495.
Preparation of Compounds 2-28 and 2-29
Compounds 2-28 and 2-29 were prepared from tert-butyl 2-(4-bromophenyl)pyrrolidine-1-carboxylate as outlined below.
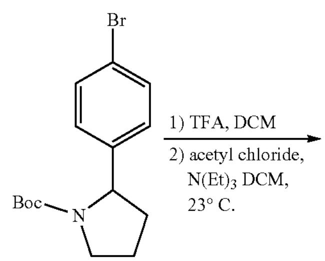
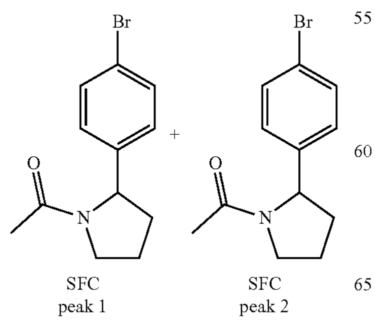
SFC peak 1 + SFC peak 2
-continued
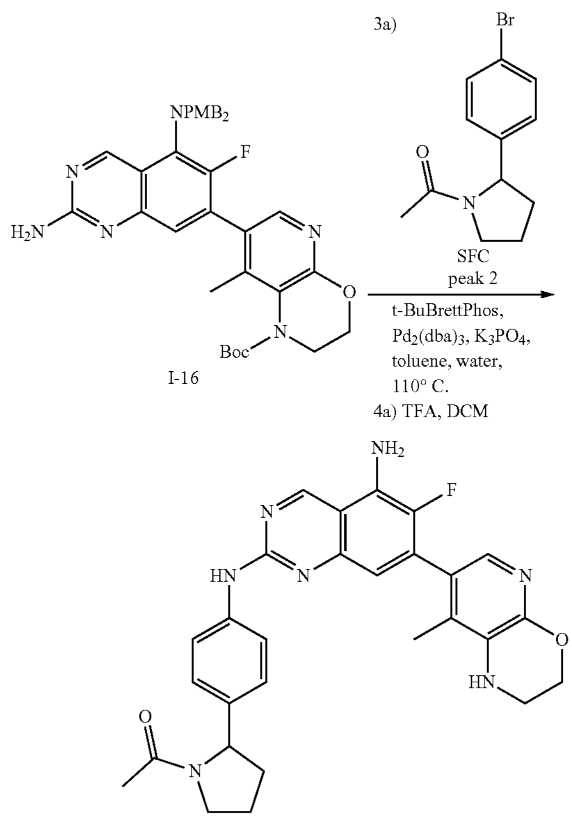
2-28
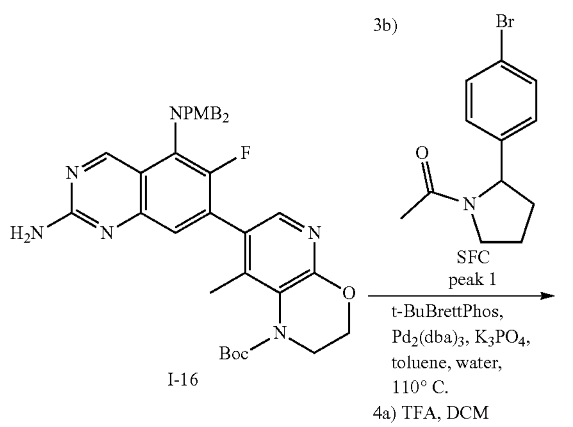
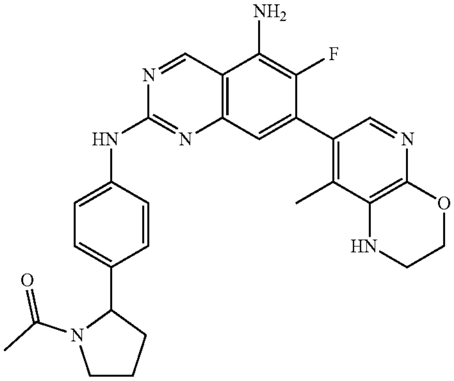
2-29

Steps 1 and 2. Preparation and Chiral Separation of 1-(2-(4-bromophenyl)pyrrolidin-1-yl)ethan-1-one A solution of (R and S)-tert-butyl 2-(4-bromophenyl) pyrrolidine-1-carboxylate (783 mg, 2.40 mmol) in DCM (12 mL) was treated with TFA (270 mg, 2.4 mmol). The solution was allowed to age at RT for 1 h. The solvent and excess TFA was then removed under reduced pressure to afford 2-(4-bromophenyl)pyrrolidine as a TFA salt. The crude residue was taken up in DCM (11 mL) and to it was added acetyl chloride (0.15 mL, 2.2 mmol). To this solution was added triethylamine (0.90 mL, 6.5 mmol) via dropwise addition. The reaction was allowed to stir at 23° C., and monitored by LC/MS. After 1 h, the reaction was diluted with DCM and added water. The mixture was transferred to a separatory funnel and shaken up vigorously. The organic layer was separated and the organic layer was extracted with DCM (3×25 mL). The combined organic layer was washed with brine and then separated. The organic layer was dried over $Na_2SO_4$ and then concentrated to dryness over reduced pressure. The crude residue was purified by flash column chromatography on $SiO_2$ (0-10% MeOH/DCM in 4 g silica gel) to give the desired product as a racemate. The enantiomers were resolved by chiral-Prep-SFC [Column: OJ, 21×250 mm; 10% (MeOH/0.1% $NH_4OH$)/$CO_2$; Flow rate: 70 mL/min: 220 nm] to provide SFC peak 1 [RT: 3.5 min] and SFC peak 2 [RT: 4.5 min].

Preparation of Compound 2-28 ((R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one)

Compound 2-28 was prepared from intermediate I-16 and SFC peak 2 (R or S)-1-(2-(4-bromophenyl)pyrrolidin-1-yl) ethan-1-one using coupling method from Example 2A.

Compound 2-28. $^1H$ NMR (500 MHz, DMSO-$d_6$) (rotamers) δ 9.73 and 9.63 (2s, 1H), 9.57 and 9.55 (2s, 1H), 7.87 (m, 2H), 7.35 (s, 1H), 7.08 (m, 2H), 6.59 (m, 1H), 6.36 and 6.34 (2s, 2H), 5.69 (s, 1H), 4.98 (t, J=8.5 Hz, 1H), 4.38-4.25 (m, 2H), 3.66-3.51 (m, 2H), 3.38 (s, 2H), 2.42-2.25 (m, 1H), 1.94 (s, 3H), 1.79 (m, 2H), 1.71 (s, 2H). MS (EI) calc'd for $C_{28}H_{29}FN_7O_2$ $[M+H]^+$, 514; found, 514.

Preparation of Compound 2-29 ((R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one)

Compound 2-29 was prepared from intermediate I-16 and SFC peak 1 (R or S)-1-(2-(4-bromophenyl)pyrrolidin-1-yl) ethan-1-one using coupling method from Example 2A.

Compound 2-29. $^1H$ NMR (500 MHz, DMSO-$d_6$) (rotamers) δ 9.73 and 9.63 (2s, 1H), 9.57 and 9.55 (2s, 1H), 7.86 (m, 2H), 7.35 (s, 1H), 7.08 (m, 2H), 6.59 (m, 1H), 6.36 and 6.34 (2s, 2H), 5.69 (s, 1H), 4.98 (t, J=8.7 Hz, 1H), 4.30 (t, J=4.3 Hz, 2H), 3.66-3.45 (m, 2H), 3.38 (s, 2H), 2.32 (s, 1H), 1.95 (s, 3H), 1.79 (m, 2H), 1.71 (s, 2H). MS (EI) calc'd for $C_{28}H_{29}FN_7O_2$ $[M+H]^+$, 514; found, 514.

Preparation of Compound 2-7 (1-[6-{[5-amino-6-fluoro-7-(8-methyl-2,3-dihydro-1H-pyrido[2,3-b][1,4]oxazin-7-yl)quinazolin-2-yl]amino}-3,4-dihydroquinolin-1(2H)-yl]ethan-1-one)

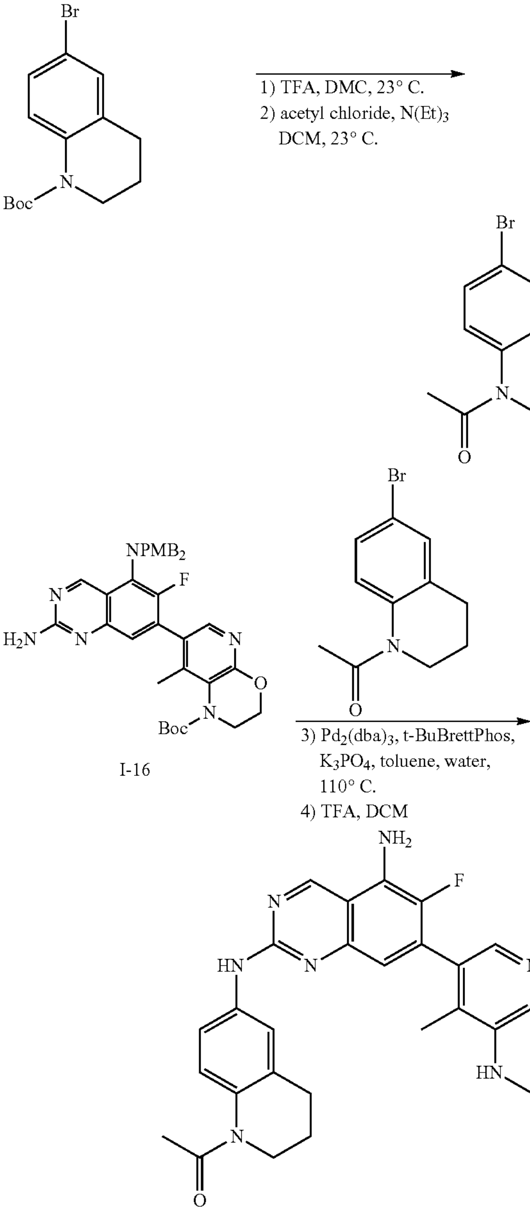

I-16

2-7

Steps 1 and 2. Preparation of 1-(6-bromo-3,4-dihydroquinolin-1(2H)-yl)ethan-1-one A solution of tert-butyl 6-bromo-3,4-dihydroquinoline-1(2H)-carboxylate, HCl (150 mg, 0.430 mmol) in DCM (2.2 mL) was treated with TFA (0.33 mL, 4.3 mmol). The reaction bubbled and allowed to age at RT for 2 h. The solvent was removed under reduced pressure to give 6-bromo-1,2,3,4-tetrahydroquinoline, TFA. The crude oil was taken up in DCM (2 mL) and added acetyl chloride (31

µL, 0.43 mmol). This was followed by the slow addition of triethylamine (0.18 mL, 1.3 mmol). The reaction was allowed to stir at 23° C. After 1 h, the reaction was diluted with DCM and added water. The mixture was transferred to a separatory funnel and shaken up vigorously. The organic layer was separated and the organic layer was extracted with DCM (3×25 mL). The combined organic layer was washed with brine and then separated. The organic layer was dried over $Na_2SO_4$ and then concentrated to dryness over reduced pressure. The residue was purified by chromatography on $SiO_2$ (gradient of 0-10% MeOH/DCM in 4 g silica gel) to afford 1-(6-bromo-3,4-dihydroquinolin-1(2H)-yl)ethan-1-one. MS (EI) calc'd for $C_{11}H_{13}BrNO$ $[M+H]^+$, 254, 256; found, 254, 256.

Steps 3 and 4. Synthesis of Compound 2-7

A mixture of 1-(6-bromo-3,4-dihydroquinolin-1(2H)-yl) ethan-1-one (29 mg, 0.11 mmol), intermediate I-16 (50 mg, 0.075 mmol), t-BuBrettPhos (15 mg, 0.030 mmol), $Pd_2(dba)_3$ (6.9 mg, 7.5 µmol), and $K_3PO_4$ (32 mg, 0.15 mmol) in toluene (0.75 mL) and water (10 µL) was deoxygenated by bubbling argon for 3 min, then warmed to 110° C., and stirred overnight. After cooling to to RT, filtered and concentrated. Crude reaction residue was dissolved in 1 mL of DCM, 1 mL of TFA, aged for 2 h. After concentration and the crude mixture was purified by reverse phase chromatography (15-70% ACN/water with 0.1% $NH_4OH$) to give the desired product, 2-7. $^1H$ NMR (500 MHz, DMSO-$d_6$) δ 9.69 (s, 1H), 9.57 (s, 1H), 7.84 (s, 1H), 7.70 (s, 2H), 7.35 (s, 1H), 6.62 (d, J=5.7 Hz, 1H), 6.35 (s, 2H), 5.69 (s, 1H), 4.39-4.21 (m, 2H), 3.66 (t, J=6.3 Hz, 2H), 3.38 (s, 2H), 2.69 (s, 2H), 2.14 (s, 3H), 1.94 (s, 3H), 1.86 (s, 2H). MS (EI) calc'd for $C_{27}H_{27}FN_7O_2$, $[M+H]^+$, 500; found, 500.

Preparation of Compounds 2-10 and 2-11

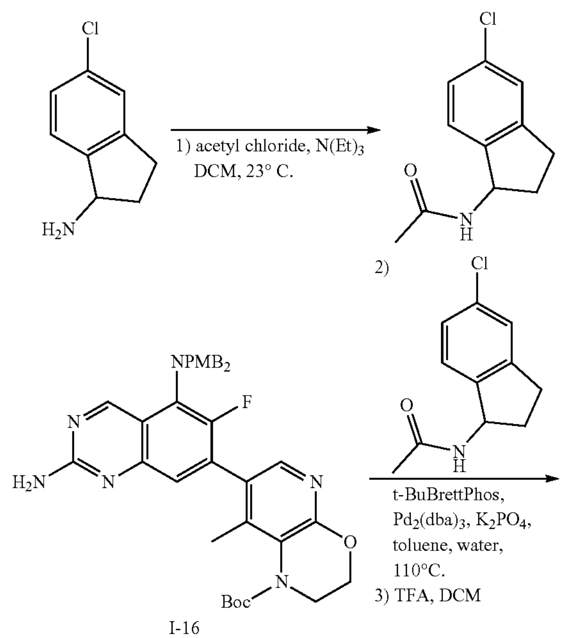

I-16

-continued

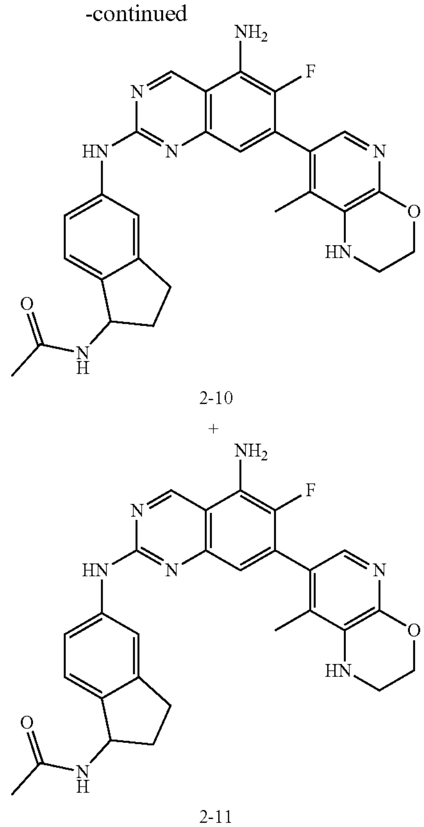

2-10

+

2-11

Step 1. Synthesis of (R and S)—N-(5-chloro-2,3-dihydro-1H-inden-1-yl)acetamide

A solution solution of 5-chloro-2,3-dihydro-1H-inden-1-amine (150 mg, 0.89 mmol) in DCM (4.5 mL) was added acetyl chloride (64 µL, 0.90 mmol). This was followed by the slow addition of triethylamine (0.31 mL, 2.2 mmol). The reaction was allowed to stir at 23° C. and monitored by LC/MS. After 1 h, the reaction was diluted with DCM and added water. The mixture was transferred to a separatory funnel and shaken up vigorously. The organic layer was separated and the organic layer was extracted with DCM (3×25 mL). The combined organic layer was washed with brine and then separated. The organic layer was dried over $Na_2SO_4$ and then concentrated to dryness over reduced pressure. The residue was purified by chromatography on $SiO_2$ (0-10% MeOH/DCM in 4 g silica gel) to afford (R and S)—N-(5-chloro-2,3-dihydro-1H-inden-1-yl)acetamide. MS (EI) calc'd for $C_{11}H_{13}ClNO$ $[M+H]^+$, 210, 212; found, 210, 212.

Steps 2-3. Synthesis of Compounds 2-10 and 2-11

A vial charged with (R and S)—N-(5-chloro-2,3-dihydro-1H-inden-1-yl)acetamide (24 mg, 0.11 mmol), intermediate I-16 (50 mg, 0.075 mmol), t-BuBrettPhos (15 mg, 0.030 mmol), $Pd_2(dba)_3$ (6.9 mg, 7.5 µmol), and $K_3PO_4$ (32 mg, 0.15 mmol) in toluene (0.75 mL) and water (10 µL) was deoxygenated by bubbling argon gas through the reaction mixture for 3 min. The mixture was stirred overnight at 110° C. After cooling, the reaction was filtered and concentrated to dryness. After concentration of the pooled fractions, the residual oil was taken up in 1 mL of DCM and added 1 mL TFA. After aging for 2 h, the reaction was concentrated to dryness to give the fully deprotected product. The crude mixture was purified by reverse phase chromatography (15-70% ACN/water with 0.1% $NH_4OH$) to afford the desired product as a racemate. The enantiomers were resolved by chiral-Prep-SFC [Column: CCO, 21×250 mm; 35% (MeOH/0.1% $NH_4OH$)/$CO_2$; Flow rate: 70 mL/min: 215 nm] to provide 2-10 [RT: 7.2 min] and 2-11 [RT: 8.4 min] as solids.

Compound 2-10 ((S or R)—N-(5-((5-amino-6-fluoro-7-(8-methyl-2,3-dihydro-1H-pyrido[2,3-b][1,4]oxazin-7-yl) quinazolin-2-yl)amino)-2,3-dihydro-1H-inden-1-yl)acetamide). $^1H$ NMR (500 MHz, DMSO-$d_6$) δ 9.67 (s, 1H), 9.56 (s, 1H), 8.16 (d, J=8.2 Hz, 1H), 7.90 (s, 1H), 7.69 (d, J=8.0 Hz, 1H), 7.35 (s, 1H), 7.10 (d, J=8.3 Hz, 1H), 6.60 (d, J=5.7 Hz, 1H), 6.35 (s, 2H), 5.69 (s, 1H), 5.21 (q, J=7.7 Hz, 1H), 4.37-4.20 (m, 2H), 3.38 (s, 2H), 2.98-2.84 (m, 1H), 2.84-2.72 (m, 1H), 2.42-2.31 (m, 1H), 1.94 (s, 3H), 1.86 (s, 3H), 1.82-1.69 (m, 1H). MS (EI) calc'd for $C_{27}H_{27}FN_7O_2$ $[M+H]^+$, 500; found, 500.

Compound 2-11 ((S or R)—N-(5-((5-amino-6-fluoro-7-(8-methyl-2,3-dihydro-1H-pyrido[2,3-b][1,4]oxazin-7-yl) quinazolin-2-yl)amino)-2,3-dihydro-1H-inden-1-yl)acetamide). $^1H$ NMR (500 MHz, DMSO-$d_6$) δ 9.67 (s, 1H), 9.56 (s, 1H), 8.16 (d, J=8.2 Hz, 1H), 7.90 (s, 1H), 7.69 (d, J=8.3 Hz, 1H), 7.35 (s, 1H), 7.10 (d, J=8.3 Hz, 1H), 6.60 (d, J=5.7 Hz, 1H), 6.35 (s, 2H), 5.69 (s, 1H), 5.21 (q, J=7.6 Hz, 1H), 4.37-4.21 (m, 2H), 3.38 (s, 2H), 2.98-2.85 (m, 1H), 2.85-2.71 (m, 1H), 2.42-2.30 (m, 1H), 1.94 (s, 3H), 1.86 (s, 3H), 1.81-1.68 (m, 1H). MS (EI) calc'd for $C_{27}H_{27}FN_7O_2$ $[M+H]^+$, 500; found, 500.

Preparation of Compound 2-58

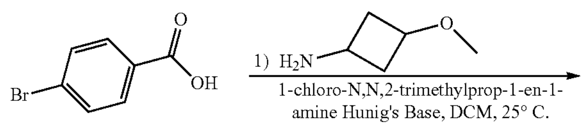

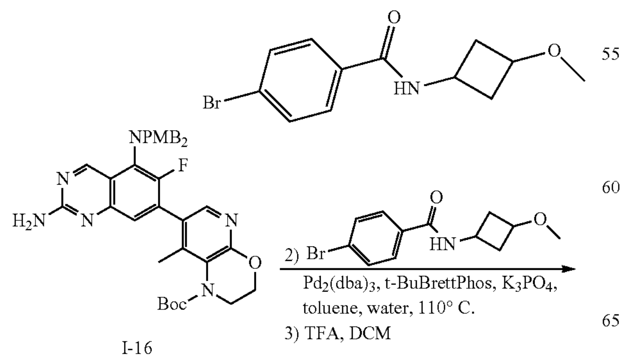

I-16

-continued

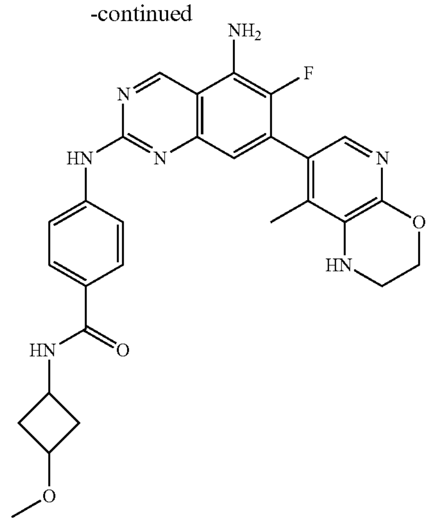

2-58

Step 1. Synthesis of 4-bromo-N-(3-methoxycyclobutyl)benzamide

A solution of 4-bromobenzoic acid (240 mg, 1.19 mmol) in DCM (8 mL) was treated with 1-chloro-N,N,2-trimethylpropenylamine (0.43 mL, 2.4 mmol). The mixture was allowed to stir at rt for 15 min. Then 3-methoxycyclobutan-1-amine (240 mg, 2.4 mmol) and Hunig's Base (0.46 mL, 3.6 mmol) were added to the mixture and the reaction was allowed to stir at 25° C. After 15 min, the reaction was diluted with DCM and added saturated $NH_4Cl$. The aqueous layer was extracted with DCM (3×20 mL). The combined organic layer was washed with brine, dried over $Na_2SO_4$ and filtered. After concentration at reduced pressure, the crude mixture was purified by flash column chromatography (4 g, silica gel, 0-10% MeOH) to give 4-bromo-N-(3-methoxycyclobutyl)benzamide as the desired product. MS (EI) calc'd for $C_{12}H_{15}BrNO_2$ $[M+H]^+$, 284; found, 284.

Steps 2 and 3. Synthesis of Compound 2-58

Compound 2-58 was prepared from intermediate I-16 and 4-bromo-N-(3-methoxycyclobutyl)benzamide using coupling method from Example 2A.

Compound 2-58. $^1H$ NMR (500 MHz, DMSO-$d_6$) δ 10.02 (s, 1H), 9.63 (s, 1H), 8.40 (d, J=7.7 Hz, 1H), 8.05-7.98 (m, 2H), 7.81 (d, J=8.8 Hz, 2H), 7.44 (s, 1H), 6.68 (d, J=5.7 Hz, 1H), 4.39-4.32 (m, 2H), 4.03 (dd, J=16.5, 8.8 Hz, 2H), 3.42 (s, 2H), 3.15 (s, 2H), 2.61-2.53 (m, 2H), 2.26 (t, J=6.2 Hz, 1H), 2.01-1.89 (m, 4H). MS (EI) calc'd for $C_{28}H_{29}FN_7O_3$ $[M+H]^+$, 530; found, 530.

Example 2B

Preparation of Compounds 2-35 and 2-36

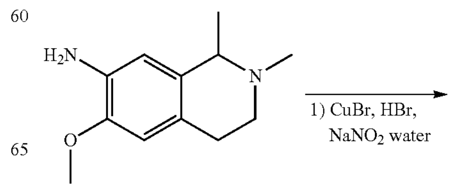

-continued

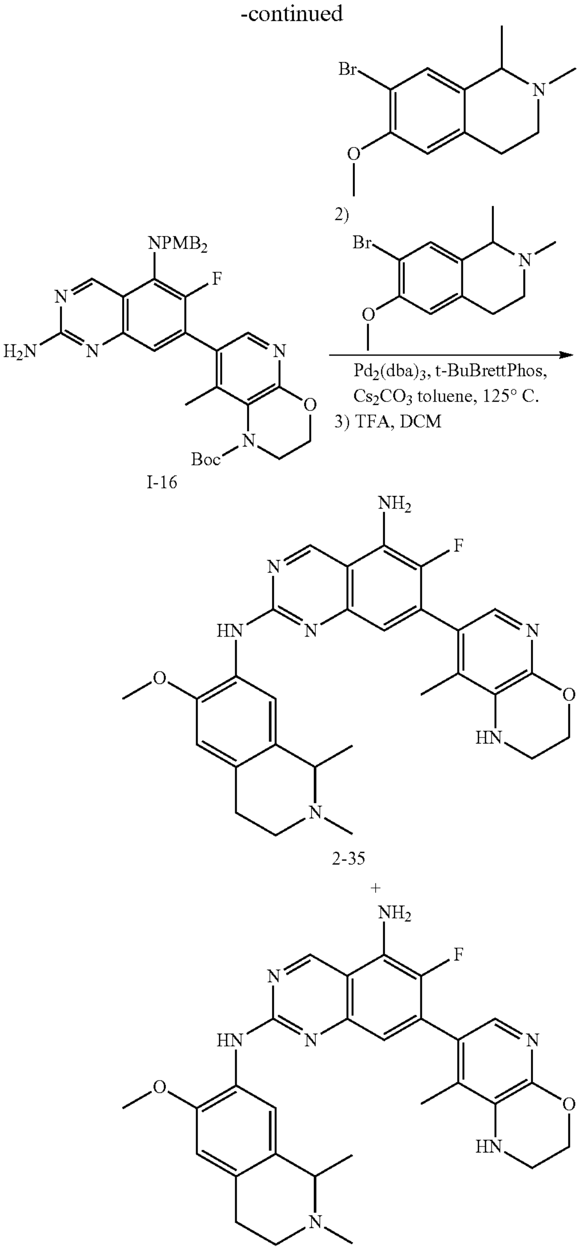

I-16

2-35

+

2-36

Steps 1. Preparation of (R and S)-7-bromo-6-methoxy-1,2-dimethyl-1,2,3,4-tetrahydroisoquinoline To 6-methoxy-1,2-dimethyl-1,2,3,4-tetrahydroisoquinolin-7-amine (100 mg, 0.485 mmol; see WO 2018/102366 for preparation) in 5% HBr (6 mL) was added $NaNO_2$ (40.1 mg, 0.582 mmol) in water (2.4 mL) at 0° C. for 2 h. This was followed by addition of CuBr (280 mg, 1.9 mmol) in 5% HBr (5 mL). The mixture was then stirred at 25° C. for 12 h. LC/MS showed desired product was formed. The residue was purified by reversed MPLC (Biotage; 20 g Agela, C18, 20~35 μm, Eluent of 10%~64% $H_2O$ (0.5% TFA)/ACN gradient at 30 mL/min) to give crude. The residue was purified by Pre-TLC (10% MeOH/DCM) to give (R and S)-7-bromo-6-methoxy-1,2-dimethyl-1,2,3,4-tetrahydroisoquinoline as an oil. $^1H$ NMR (400 MHz, $CDCl_3$) δ 7.28 (s, 1H), 6.60 (s, 1H), 3.86 (s, 3H), 3.55 (q, J=6.8 Hz, 1H), 2.99-3.10 (m, 1H), 2.77-2.91 (m, 2H), 2.61-2.70 (m, 1H), 2.47 (s, 3H), 1.37 (d, J=6.8 Hz, 3H). MS (EI) calc'd for $C_{12}H_{17}BrNO$ $[M+H]^+$, 272; found, 272.

Steps 2-3. Synthesis of Compounds 2-35 and 2-36

A mixture of intermediate I-16 (150 mg, 0.23 mmol), (R and S)-7-bromo-6-methoxy-1,2-dimethyl-1,2,3,4-tetrahydroisoquinoline (61 mg, 0.23 mmol), $Cs_2CO_3$ (220 mg, 0.68 mmol), $Pd_2(dba)_3$ (27 mg, 0.029 mmol) and t-BuBrettPhos (33 mg, 0.067 mmol) in toluene (2 mL) was stirred at 125° C. for 5 h under nitrogen. LC/MS showed the desired product was formed. Water (20 mL) was added, and was extracted with EtOAc (3×40 mL). The organic layers were washed with brine (50 mL), dried over $Na_2SO_4$, filtered and concentrated in vacuo to give a crude solid. The crude solid in DCM (1 mL) and TFA (1 mL) was stirred at 25° C. for 1 h. The LC/MS showed the desired product. The mixture was concentrated in vacuo, the residue was purified by prep-HPLC (Column: Boston Green ODS 150×30 mm×5 um; Condition water (0. % TFA)-ACN Begin B 5 End B 35 Gradient Time (min) 10; 100% B Hold Time (min) 2 FlowRate (mL/min) 25; Injections 8) to afford the desired product as a racemate. The enantiomers were resolved Chiral-SFC (Column: DAICEL CHIRALPAK IG (250 mm×30 mm, 10 um): Condition 0.1% $NH_3H_2O$ ETOH Begin B 55% End B 55% Gradient Time (min); 100% B Hold Time (min) FlowRate (mL/min) 60; Injections 120) to give 2-35 [RT: 3.1 min] and 2-36 [RT: 6.1 min]. The both targets were solids.

Compound 2-35 ((S or R)-6-fluoro-$N^2$-(6-methoxy-1,2-dimethyl-1,2,3,4-tetrahydroisoquinolin-7-yl)-7-(8-methyl-2,3-dihydro-1H-pyrido[2,3-b][14]oxazin-7-yl)quinazoline-2,5-diamine). $^1H$ NMR (400 MHz, $CD_3OD$) δ 9.40 (s, 1H), 8.50 (s, 1H), 7.36 (s, 1H), 6.68-6.80 (m, 2H), 4.35-4.45 (m, 2H), 3.91 (s, 3H), 3.58-3.66 (m, 1H), 3.46-3.52 (m, 2H), 3.05 (td, J=5.6, 11.6 Hz, 1H), 2.77-2.93 (m, 2H), 2.59-2.70 (m, 1H), 2.45 (s, 3H), 2.02 (s, 3H), 1.44 (br d, J=6.40 Hz, 3H). MS (EI) calc'd for $C_{28}H_{31}FN_7O_2$ $[M+H]^+$, 516; found, 516.

Compound 2-36 ((S or R)-6-fluoro-$N^2$-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine). $^1H$ NMR (400 MHz, $CD_3OD$) δ 9.40 (s, 1H), 8.50 (s, 1H), 7.36 (s, 1H), 6.68-6.80 (m, 2H), 4.35-4.45 (m, 2H), 3.91 (s, 3H), 3.58-3.66 (m, 1H), 3.46-3.52 (m, 2H), 3.05 (td, J=5.6, 11.6 Hz, 1H), 2.77-2.93 (m, 2H), 2.59-2.70 (m, 1H), 2.45 (s, 3H), 2.02 (s, 3H), 1.44 (br d, J=6.40 Hz, 3H). MS (EI) calc'd for $C_{28}H_{31}FN_7O_2$ $[M+H]^+$, 516; found, 516.

Preparation of Compound 2-45

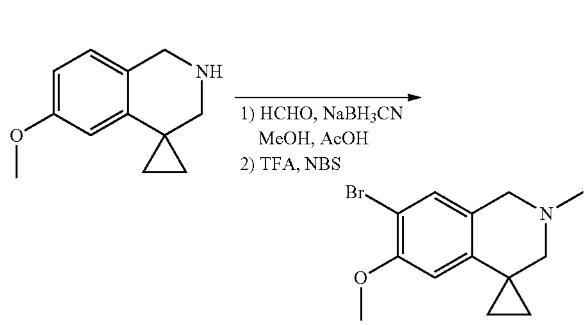

-continued

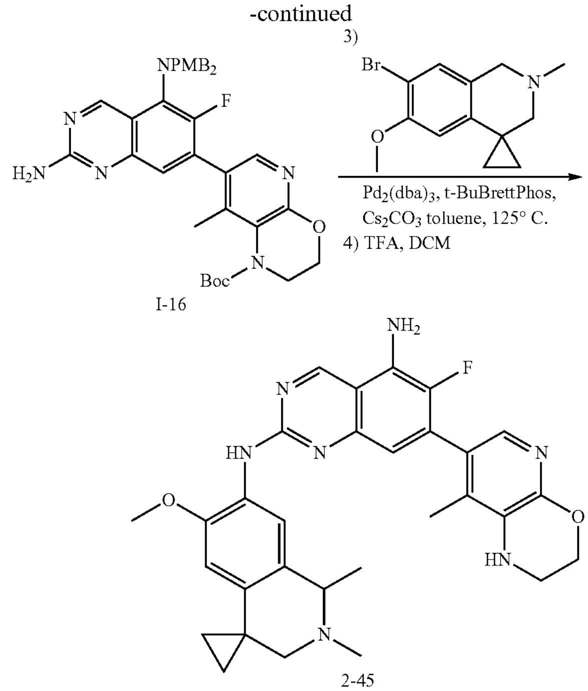

I-16

2-45

Steps 1 and 2. Preparation of 7'-bromo-6'-methoxy-2'-methyl-2',3'-dihydro-1'H-spiro[cyclopropane-1,4'-isoquinoline]

To a mixture of 6'-methoxy-2'3'-dihydro-1'H-spiro[cyclopropane-1,4'-isoquinoline] (500 mg, 2.64 mmol) in MeOH (5 mL) was added formaldehyde (37%) (860 mg, 11 mmol) and AcOH (0.5 mL). The mixture was stirred at 15° C. for 10 min, then $NaCNBH_3$ (498 mg, 7.93 mmol) was added and stirred at 15° C. for 4 h under nitrogen. Solvent was removed under reduced pressure. To the residue was added water (30 mL), and extracted with EtOAc (3×50 mL). The organic layers were washed with brine (50 mL), dried over $Na_2SO_4$, filtered and concentrated in vacuum to give the desired product which was used in next step directly. To the crude mixture (500 mg, crude) in TFA (5 mL) was added NBS (482 mg, 2.71 mmol) at 25° C. Then the mixture was stirred at 25° C. for 1 h. LC-MS showed desired product was formed. Then it was added water (10 mL) and $NaHCO_3$ to adjust the pH to 8-9, a solution of 10% MeOH/DCM (50 mL) was added. The organic layer was separated and the aqueous was re-extracted with 10% MeOH/DCM (2×30 mL). The combined organic layers were washed with brine (80 mL), dried over anhydrous $Na_2SO_4$, filtered and concentrated. The residue was purified by Pre-TLC (silica gel, DCM:MeOH=10:1) to give 7'-bromo-6'-methoxy-2'-methyl-2',3'-dihydro-1'H-spiro[cyclopropane-1,4'-isoquinoline] as a solid. $^1H$ NMR (400 MHz, $CDCl_3$) δ 7.19 (s, 1H), 6.16 (m, 11H), 3.80 (s, 3H), 3.62 (s, 2H), 2.50 (s, 2H), 2.43 (s, 3H), 0.99-1.06 (m, 2H), 0.88-0.98 (m, 2H).

Steps 3 and 4. Synthesis of 2-45

A mixture of intermediate I-16 (100 mg, 0.150 mmol), 7'-bromo-6'-methoxy-2'-methyl-2',3'-dihydro-1'H-spiro[cyclopropane-1,4'-isoquinoline] (50 mg, 0.18 mmol), $Cs_2CO_3$ (147 mg, 0.45 mmol), $Pd_2(dba)_3$ (28 mg, 0.030 mmol) and t-BuBrettphos (36 mg, 0.075 mmol) in toluene (2 mL) was stirred at 125° C. for 4 h under nitrogen. LC/MS showed the desired product was formed. Water (10 mL) and 10% MeOH/DCM (20 mL) was added. The organic layer was separated and the aqueous layer was re-extracted with 10% MeOH/DCM (3×10 mL). The combined organic layers were washed with brine (30 mL), dried over anhydrous $Na_2SO_4$, filtered and concentrated. The mixture was purified by Prep-TLC (silica gel, DCM/MeOH=10/1) to give the desired adduct as an oil. To a solution of this adduct in DCM (0.5 mL) was added TFA (0.5 mL). Then it was stirred at 25° C. for 1 h. LC/MS showed the desired product. The mixture was concentrated in vacuum, the residue was purified by prep-HPLC (Column Agela DuraShell C18 150*25 mm*5 um; Condition water (0.04% $NH_3H_2O$+10 mM $NH_4HCO_3$)-ACN Begin B 34 End B 49 Gradient Time (min) 14; 100% B Hold Time (min) 2 FlowRate (ml/min) 25; Injections 6) to afford compound 2-45 as a solid. $^1H$ NMR (400 MHz, $CD_3OD$) δ 9.40 (s, 1H), 8.38 (s, 1H), 7.38 (s, 1H), 6.79 (d, J=5.6 Hz, 1H), 6.32 (s, 1H), 4.40 (t, J=4.0 Hz, 2H), 3.89 (s, 3H), 3.72 (s, 2H), 3.49 (t, J=4.0 Hz, 2H), 2.57 (s, 2H), 2.43 (s, 3H), 2.03 (s, 3H), 1.02-1.09 (m, 2H), 0.88-0.95 (m, 2H). MS (EI) calc'd for $C_{29}H_{31}FN_7O_2$ $[M+H]^+$, 528; found, 528.

Preparation of Compound 2-46

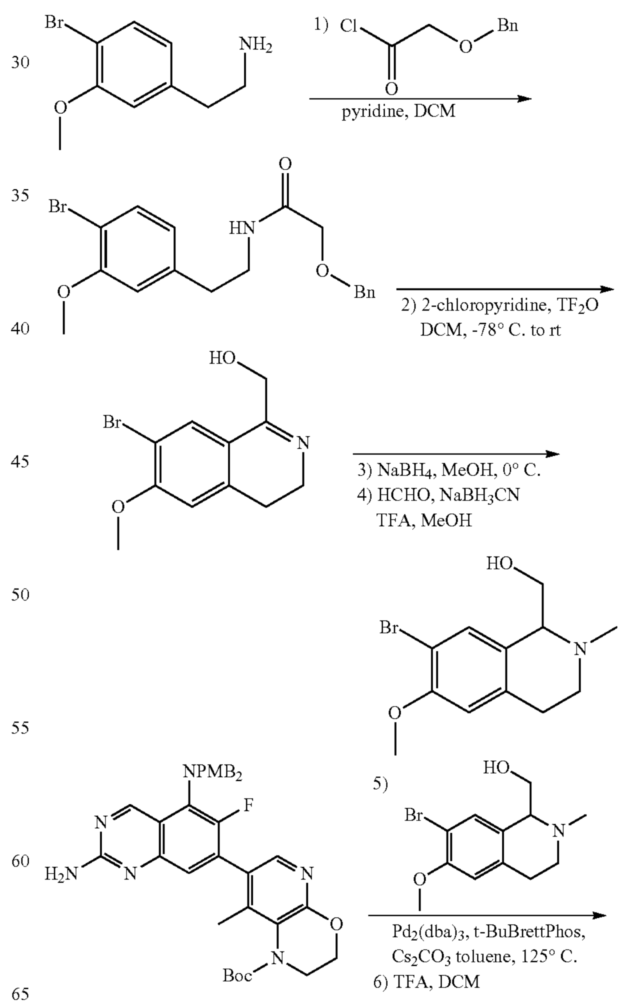

I-16

-continued

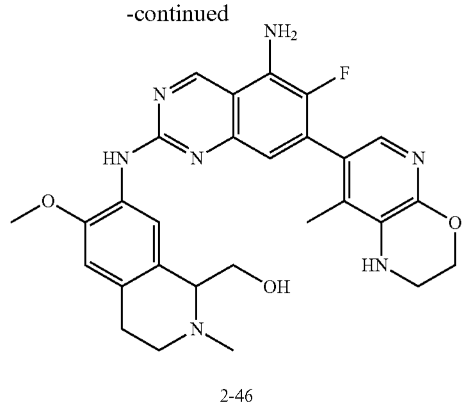

2-46

Step 1. Preparation of 2-(benzyloxy)-N-(4-bromo-3-methoxyphenethyl)acetamide

To a stirred solution of 2-(4-bromo-3-methoxyphenyl) ethanamine (500 mg, 2.17 mmol) in DCM (3 mL) was added pyridine (0.5 mL, 6.2 mmol) and 2-(benzyloxy)acetyl chloride (520 mg, 2.82 mmol) at 20° C., after the addition was finished, the reaction was stirred at 20° C. for 1 h. The mixture was treated with water (20 mL), extracted by EtOAc (3×30 mL). The organic layers were separated, washed with brine and dried over $Na_2SO_4$. After filtration, the filtrate was concentrated in vacuum. The crude product was purified by flash silica gel chromatography (ISCO®; Agela® Flash Column Silica-CS (4 g) Eluent of 0~60% EtOAc/Petroleum ether gradient at 35 mL/min) to give 2-(benzyloxy)-N-(4-bromo-3-methoxyphenethyl)acetamide as an oil. MS (EI) calc'd for $C_{18}H_{21}BrNO_3$ $[M+H]^+$, 380; found, 380.

Step 2. Preparation of (7-bromo-6-methoxy-3,4-dihydroisoquinolin-1-yl)methanol

To a stirred solution of 2-(benzyloxy)-N-(4-bromo-3-methoxyphenethyl)acetamide (250 mg, 0.66 mmol) in DCM (2 mL) was added 2-chloropyridine (150 mg, 1.32 mmol) and $Tf_2O$ (0.22 mL, 1.3 mmol) at −78° C. After the addition was finished, the reaction was stirred at 0° C. for 1 h. LC/MS showed the starting material was consumed and the desired MS was detected. The solution was added $Et_3N$ to adjust pH~7, and concentrated under reduced pressure to give crude product (7-bromo-6-methoxy-3,4-dihydroisoquinolin-1-yl)methanol which was used to the next step directly. MS (EI) calc'd for $C_{11}H_{13}BrNO_2$ $[M+H]^+$, 272; found, 272.

Steps 3 and 4. Preparation of (7-bromo-6-methoxy-2-methyl-1,2,3,4-tetrahydroisoquinolin-1-yl)methanol To a stirred solution of(7-bromo-6-methoxy-3,4-dihydroisoquinolin-1-yl)methanol (100 mg, crude) in MeOH (3 mL) was added $NaBH_4$ (28 mg, 0.74 mmol) at 0° C., after the addition was finished, the reaction was stirred at 0° C. for 1 h. LC/MS showed desired product was formed. The mixture was concentrated in vacuum, the residue was purified by prep-HPLC (Instrument EI Method Column Phenomenex Synergi C18 150*30 mm*4 um Condition water (0.225% FA)-ACN Begin B 35 End B 55 Gradient Time (min) 11 100% B Hold Time (min) 2 FlowRate (mL/min) 25 Injections 4) to give (7-bromo-6-methoxy-1,2,3,4-tetrahydroisoquinolin-1-yl)methanol as a solid. To a mixture of (7-bromo-6-methoxy-1,2,3,4-tetrahydroisoquinolin-1-yl) methanol (10 mg, 0.037 mmol) and formaldehyde (37%) (11 mg, 0.14 mmol) in MeOH (4 mL) was added a drop of AcOH (0.4 mL). The mixture was stirred at 15° C. for 10 min, then the mixture was added $NaCNBH_3$ (6 mg, 0.095 mmol) and stirred at 15° C. for 4 h under nitrogen. Solvent was removed under reduced pressure. To the residue was added water (30 mL), and extracted with EtOAc (3×50 mL). The organic layers were washed with brine (50 mL), dried over $Na_2SO_4$, filtered and concentrated in vacuo. The residue was purified by prep-HPLC (Instrument EI Method Column Phenomenex Synergi C18 150*30 mm*4 um Condition water (0.225% FA)-ACN Begin B 35 End B 55 Gradient Time (min) 11 100% B Hold Time (min) 2 Flow Rate (mL/min) 25 Injections 4) to give (7-bromo-6-methoxy-2-methyl-1,2,3,4-tetrahydroisoquinolin-1-yl) methanol as an oil. MS (EI) calc'd for $C_{12}H_{17}BrNO_2$ $[M+H]^+$, 287; found, 287.

Steps 5 and 6. Synthesis of 2-46

A mixture of intermediate I-16 (15 mg, 0.022 mmol), (7-bromo-6-methoxy-2-methyl-1,2,3,4-tetrahydroisoquinolin-1-yl)methanol (7 mg, 0.024 mmol), $Cs_2CO_3$ (22 mg, 0.068 mmol), $Pd_2(dba)_3$ (3 mg, 3.3 μmol) and t-BuBrettPhos (3 mg, 6.2 μmol) in toluene (1 mL) was stirred at 125° C. for 5 h under nitrogen. LC/MS showed the desired product was formed. After cooled to room temperature, water (15 mL) was added, and the mixture was extracted by DCM (3×20 mL). The combined organic layers were washed with brine, dried over $Na_2SO_4$, after filtration, the filtrate was concentrated in vacuum. The residue was purified by prep-TLC (10% MeOH/DCM) to give the desired adduct as a solid. The product was then taken up in DCM (2 mL) and then added TFA (0.2 mL) at 20° C. after the addition was finished, the reaction was stirred at 20° C. for 2 h. The mixture was concentrated in vacuum and purified by prep-HPLC (Instrument EI Method Column Phenomenex Synergi C18 150*30 mm*4 um Condition water (0.225% FA)-ACN Begin B 35 End B 55 Gradient Time (min) 11 100% B Hold Time (min) 2 FlowRate (mL/min) 25 Injections 4) to give compound 2-46 as a solid. $^1H$ NMR (400 MHz, $CD_3OD$) δ 9.40 (s, 1H), 8.50 (s, 1H), 7.35 (s, 1H), 6.74-6.78 (m, 2H), 4.37 (t, J=4.4 Hz, 2H), 3.90 (s, 3H), 3.80-3.86 (m, 2H), 3.66 (br s, 1H), 3.46 (t, J=4.4 Hz, 2H), 2.87-2.93 (m, 2H), 2.74-2.78 (m, 2H), 2.57 (s, 3H), 2.00 (s, 3H). MS (EI) calc'd for $C_{28}H_{31}FN_7O_3$ $[M+H]^+$, 532, found, 532.

Preparation of Compound 2-50

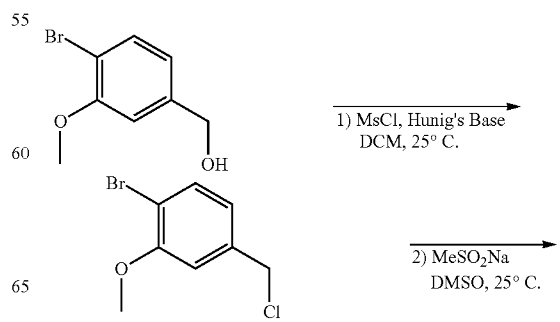

-continued

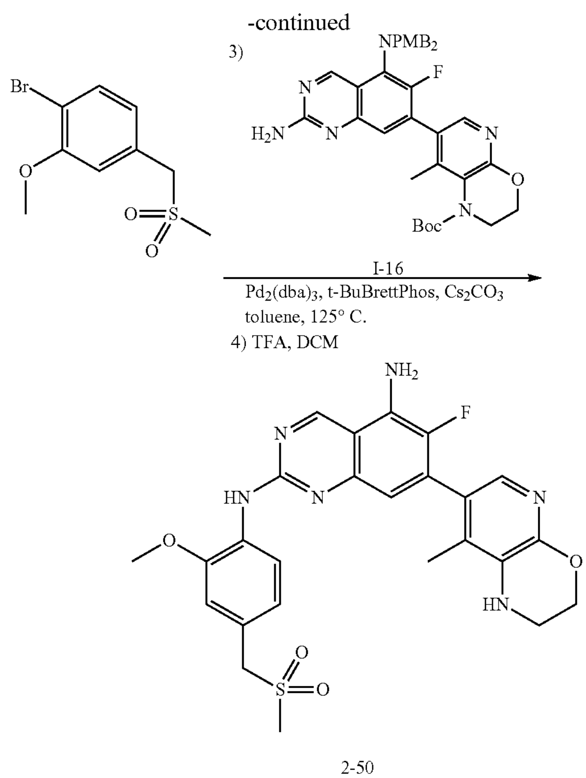

2-50

Step 1. Preparation of 1-bromo-4-(chloromethyl)-2-methoxybenzene

A mixture of (4-bromo-3-methoxyphenyl)methanol (0.750 g, 3.46 mmol) and Hunig's Base (1.81 mL, 10.4 mmol) was added MsCl (0.87 mL, 11 mmol) at 0° C. The reaction mixture was stirred at 25° C. for 2 h. TLC (silica gel, EtOAc/Pet. ether=1/5) showed the starting material was consumed completely, and new spots were generated. Water (20 mL) was added, the resulting mixture was added DCM (20 mL). The organic layer was separated and the aqueous was re-extracted with DCM (3×20 mL). The combined organic layers were washed with brine (40 mL), dried over anhydrous $Na_2SO_4$, filtered and concentrated to give a residue which was purified by flash silica gel chromatography (ISCO®; 12 g Agela® Silica Flash Column, Eluent of 0~5% EtOAc/Pet. ether gradient at 30 mL/min) to give 1-bromo-4-(chloromethyl)-2-methoxybenzene as an oil. $^1H$ NMR (400 MHz, $CDCl_3$) δ 7.52 (d, J=8.0 Hz, 1H), 6.94 (d, J=1.6 Hz, 1H), 6.87 (dd, J=1.2, 7.6 Hz, 1H), 4.55 (s, 2H), 3.93 (s, 3H).

Step 2. Preparation of 1-bromo-2-methoxy-4-((methylsulfonyl)methyl)benzene

A mixture of 1-bromo-4-(chloromethyl)-2-methoxybenzene (300 mg, 1.27 mmol) in DMSO (4 mL) was added sodium methanesulfinate (156 mg, 1.53 mmol) at 25° C. The reaction mixture was stirred at 25° C. for 18 h. TLC (silica gel, EtOAc/Pet. ether=3/1) showed the starting material was consumed completely, and new spot was generated. Water (20 mL) was added, the resulting mixture was added EtOAc (20 mL). The organic layer was separated and the aqueous was re-extracted with EtOAc (3×20 mL). The combined organic layers were washed with brine (40 mL), dried over anhydrous $Na_2SO_4$, filtered and concentrated to give a 1-bromo-2-methoxy-4-((methylsulfonyl)methyl)benzene as a solid. $^1H$ NMR (400 MHz, $CDCl_3$) δ 7.57 (d, J=8.0 Hz, 1H), 6.99 (d, J=1.6 Hz, 1H), 6.85 (dd, J=1.6, 8.0 Hz, 1H), 4.22 (s, 2H), 3.93 (s, 3H), 2.79 (s, 3H).

Steps 3 and 4. Synthesis of 2-50

A mixture of t-BuBrettPhos (25 mg, 0.052 mmol), $Pd_2(dba)_3$ (19 mg, 0.021 mmol), intermediate I-16 (70 mg, 0.11 mmol), $Cs_2CO_3$ (103 mg, 0.315 mmol) and I-bromo-2-methoxy-4-((methylsulfonyl)methyl)benzene (62 mg, 0.21 mmol) in toluene (2 mL) was degassed and backfilled with nitrogen (three times). The reaction mixture was stirred at 125° C. for 8 h. LC-MS showed major desired product and a little starting material. Water (20 mL) was added, the resulting mixture was added EtOAc (20 mL). The organic layer was separated and the aqueous was re-extracted with EtOAc (3×20 mL). The combined organic layers were washed with brine (40 mL), dried over anhydrous $Na_2SO_4$, filtered and concentrated to give a residue which was purified by prep-TLC (silica gel, 10% MeOH/DCM) to give the desired adduct as a solid. The adduct was taken up in DCM (1 mL) and added TFA (1 mL) at 20° C. The reaction mixture was stirred at 20° C. for 1 h. LC-MS showed major desired product. The mixture was concentrated to give a residue which was purified by Prep-HPLC (Instrument ee; Method Column YMC-Actus Triart C18 150 mm*30 mm*5 um: Condition water (0.1% TFA)-ACN Begin B 18 End B 48 Gradient Time (min) 11; 100% B Hold Time (min) 1.1 FlowRate (mL/min) 40: Injections 1) to give compound 2-50 as an orange solid. $^1H$ NMR (400 MHz, DMSO-$d_6$) δ 9.61 (s, 1H), 8.48 (br s, 1H), 7.40 (s, 1H), 7.12 (s, 1H), 7.03 (d, J=7.6 Hz, 1H), 6.67 (d, J=5.2 Hz, 1H), 4.44 (s, 2H), 4.32-4.34 (m, 2H), 3.89 (s, 3H), 3.49-3.51 (m, 2H), 2.90 (s, 3H), 1.96 (s, 3H). MS (EI) calc'd for $C_{25}H_{26}FN_6O_4S$ $[M+H]^+$, 525; found, 525.

Preparation of Compounds 2-55 and 2-56

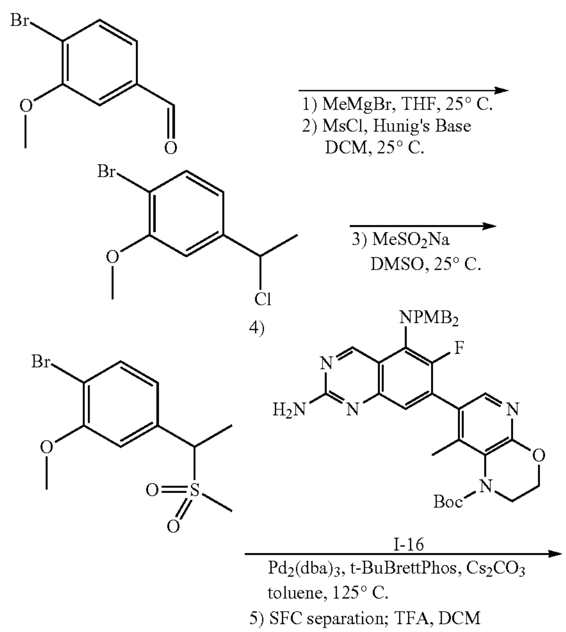

-continued

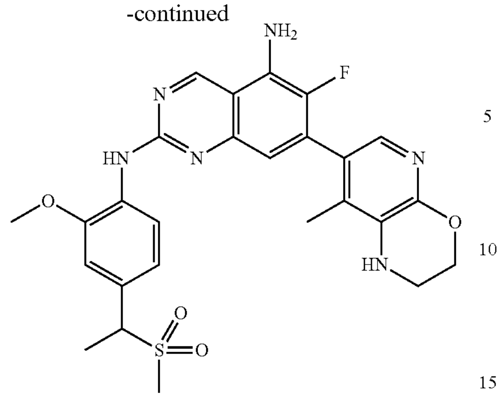

2-55

+

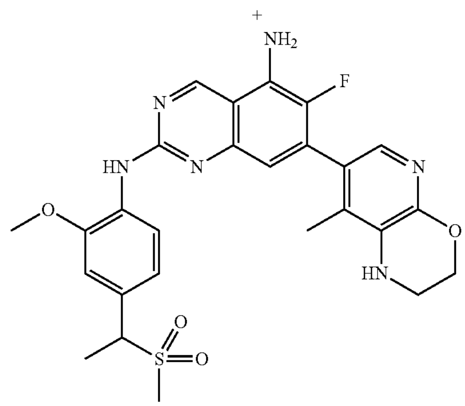

2-56

Steps 1 and 2. Preparation of 1-bromo-4-(1-chloroethyl)-2-methoxybenzene

To a mixture of 4-bromo-3-methoxybenzaldehyde (1.3 g, 6.05 mmol) in THF (15 mL) was added methylmagnesium bromide (4.0 mL, 12 mmol) at −30° C. The reaction mixture was slowly warmed to 25° C. and stirred at 25° C. for 4 h. TLC ($SiO_2$, EtOAc/Pet. ether=1/5) showed major desired product. Sat. $NH_4Cl$ (20 mL) was added, the resulting mixture was added EtOAc (20 mL). The organic layer was separated and the aqueous was re-extracted with EtOAc (3×20 mL). The combined organic layers were washed with brine (40 mL), dried over anhydrous $Na_2SO_4$, filtered and concentrated to give a residue which was purified by flash silica gel chromatography (ISCO®; 12 g Agela® Silica Flash Column, Eluent of 0-15% EtOAc/Pet. ether, gradient at 30 mL/min) to give 1-(4-bromo-3-methoxyphenyl)ethanol as an oil. The product was added DIEA (2.4 mL, 14 mmol) and to this mixture was added Ms-Cl (1.6 mL, 20 mmol) at 0° C. The reaction mixture was stirred at 25° C. for 4 h. TLC ($SiO_2$, EtOAc/Pet. ether=1/10) showed the starting material was consumed completely, and new spots were generated. Water (30 mL) was added, and to the resulting mixture was added DCM (30 mL). The organic layer was separated and the aqueous was re-extracted with DCM (3×30 mL). The combined organic layers were washed with brine (40 mL), dried over anhydrous $Na_2SO_4$, filtered and concentrated to give a residue which was purified by flash silica gel chromatography (ISCO®: 12 g Agela® Silica Flash Column, Eluent of 0~1% EtOAc/Pet. ether gradient at 30 mL/min) to give 1-bromo-4-(1-chloroethyl)-2-methoxybenzene as an oil. $^1H$ NMR (400 MHz, $CDCl_3$) δ 7.49 (d, J=8.0 Hz, 1H), 6.97 (d, J=1.2 Hz, 1H), 6.82 (dd, J=1.2, 8.0 Hz, 1H), 5.10 (q, J=6.4 Hz, 1H), 3.94 (s, 3H), 1.85 (d, J=6.4 Hz, 3H).

Step 3. Preparation of 1-bromo-2-methoxy-4-(1-(methylsulfonyl)ethyl)benzene

To a mixture of 1-bromo-4-(1-chloroethyl)-2-methoxybenzene (540 mg, 2.16 mmol) in DMSO (10 mL) was added sodium methanesulfinate (265 mg, 2.60 mmol) at 0° C. The reaction mixture was stirred at 25° C. for 18 h. TLC ($SiO_2$. EtOAc/Pet. Ether=5/1) showed the starting material was not consumed completely. Then the reaction mixture was stirred at 45° C. for 18 h. TLC ($SiO_2$, EtOAc/Pet. Ether=3/1) showed the starting material was consumed completely, and new spots were generated. Water (20 mL) was added, and to the resulting mixture was added EtOAc (20 mL). The organic layer was separated and the aqueous layer was re-extracted with EtOAc (3×20 mL). The combined organic layers were washed with brine (40 mL), dried over anhydrous $Na_2SO_4$, filtered and concentrated to give a residue which was purified by flash silica gel chromatography (ISCO®; 4 g Agela® Silica Flash Column, Eluent of 0~20% EtOAc/Pet. Ether gradient at 20 mL/min) to give 1-bromo-2-methoxy-4-(1-(methylsulfonyl)ethyl)benzene as a solid. $^1H$ NMR (400 MHz, $CDCl_3$) δ 7.56 (d, J=8.0 Hz, 1H), 7.01 (d, J=1.6 Hz, 1H), 6.88 (dd, J=2.0, 8.4 Hz, 1H), 4.16 (q, J=7.2 Hz, 1H), 3.93 (s, 3H), 2.68 (s, 3H), 1.79 (d, J=7.2 Hz, 3H).

Step 4. Preparation of (R and S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine A mixture of t-Bu-Brettphos (36 mg, 0.075 mmol), $Pd_2(dba)_3$ (28 mg, 0.030 mmol), intermediate I-16 (100 mg, 0.150 mmol), $Cs_2CO_3$ (147 mg, 0.450 mmol) and 1-bromo-2-methoxy-4-(1-(methylsulfonyl)ethyl)benzene (88 mg, 0.30 mmol) in toluene (2 mL) was degassed and backfilled with nitrogen (three times). The mixture was stirred at 125° C. for 18 h. The color turned brown. LC-MS major desired product and a little starting material. Water (20 mL) was added, the resulting mixture was added EtOAc (20 mL). The organic layer was separated and the aqueous was re-extracted with EtOAc (3×20 mL). The combined organic layers were washed with brine (40 mL), dried over anhydrous $Na_2SO_4$, filtered and concentrated to give a residue, which was purified by prep-TLC ($SiO_2$, $MeOH/CH_2Cl_2$=1/10) to give the desired racemate as a solid. The racemate was resolved using Prep-SFC, SFC Method Column DAICEL CHIRALPAK AD (250 mm*50 mm, 10 um); Condition 0.1% $NH_3H_2O$ ETOH Begin B 40% End B 40% Gradient Time (min) 100% B Hold Time (min) FlowRate (mL/min) 80; Injections 70 to give SFC-P1 [RT: 6.491 min] and SFC-P2 [RT: 7.013 min] both as solids.

Step 5. Synthesis of Compounds 2-55 and 2-56

Compound 2-55 (R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine SFC-P2 (37 mg, 0.042 mmol) was taken up in in DCM (1 mL) was added TFA (1 mL) at 20° C. The reaction mixture was stirred at 20° C. for 1 h. The color turned yellow. LC-MS showed major desired product. The mixture was concentrated to give a residue which was purified by Prep-Hplc (Instrument ee: Method Column YMC-Actus Triart C18 150*30 mm*5 um; Condition water (0.1% TFA)-ACN Begin B 22 End B 52 Gradient Time (min) 11; 100% B Hold Time (min) 1.1 FlowRate (mL/min) 40; Injections 1) to give compound 2-55 as an orange solid. $^1$H NMR (400 MHz, DMSO-$d_6$) δ 9.61 (s, 1H), 8.47 (br s, 1H), 7.40 (s, 1H), 7.14 (s, 1H), 7.07 (d, J=8.0 Hz, 1H), 6.67 (d, J=5.6 Hz, 1H), 4.48-4.53 (m, 1H), 4.34 (t, J=4.0 Hz, 2H), 3.90 (t, 3H), 3.40 (t, J=4.0 Hz, 2H), 2.82 (s, 3H), 1.96 (s, 3H), 1.65 (d, J=7.6 Hz, 3H). MS (EI) calc'd for $C_{26}H_{28}FN_6O_4S$ $[M+H]^+$, 539; found, 539.

Compound 2-56 ((R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine)

SFC-P1 (40 mg, 0.045 mmol) in DCM (1 mL) was added TFA (1 mL) at 20° C. The reaction mixture was stirred at 20° C. for 1 h. The color turned yellow. LC-MS showed major desired product. The mixture was concentrated to give a residue which was purified by Prep-Hplc (Instrument ee: Method Column YMC-Actus Triart C18 150*30 mm*5 um; Condition water (0.1% TFA)-ACN Begin B 22 End B 52 Gradient Time (min) 11; 100% B Hold Time (min) 1.1 FlowRate (mL/min) 40; Injections 1) to give compound 2-56 as an orange solid. $^1$H NMR (400 MHz, DMSO-$d_6$) δ 9.61 (s, 1H), 8.48 (br s, 1H), 7.40 (s, 1H), 7.14 (s, 1H), 7.07 (d, J=6.8 Hz, 1H), 6.67 (d, J=5.6 Hz, 1H), 4.47-4.53 (m, 1H), 4.34 (t, J=4.0 Hz, 2H), 3.90 (s, 3H), 3.40 (t, J=4.0 Hz, 2H), 2.82 (s, 3H), 1.96 (s, 3H), 1.65 (d, J=7.2 Hz, 3H). MS (EI) calc'd for $C_{26}H_{28}FN_6O_4S$ $[M+H]^+$, 539; found, 539.

Preparation of Compound 2-59

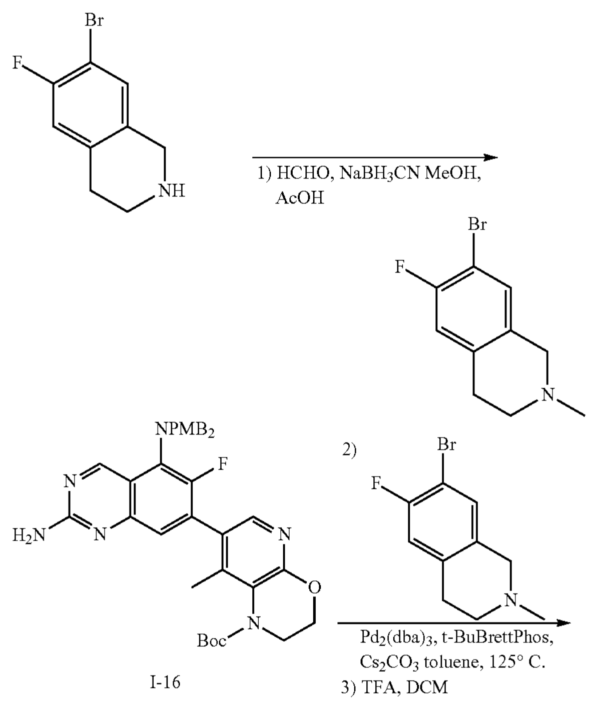

I-16

-continued

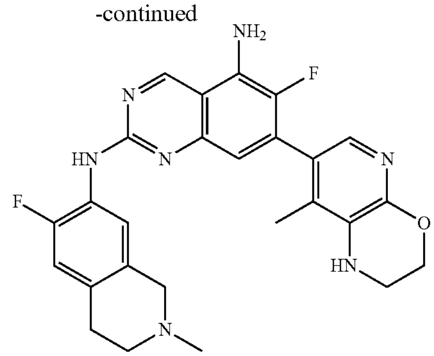

2-59

Step 1. Preparation of 7-bromo-6-fluoro-2-methyl-1,2,3,4-tetrahydroisoquinoline

A mixture of 7-bromo-6-fluoro-1,2,3,4-tetrahydroisoquinoline (60 mg, 0.26 mmol) and formaldehyde (85 mg, 1.0 mmol) was added dropwise AcOH (0.2 mL) in MeOH (2 mL). The mixture was stirred at 15° C. for 10 min, then the mixture was added $NaBH_3CN$ (49 mg, 0.78 mmol) and stirred at 15° C. for 4 h under nitrogen. TLC showed the starting material was consumed. Then solvent was removed under reduced pressure. To the residue was added water (5 mL), and extracted with EtOAc (3×5 mL). The organic layers were washed with brine (5 mL), dried over $Na_2SO_4$, filtered and concentrated in vacuum to give crude 7-bromo-6-fluoro-2-methyl-1,2,3,4-tetrahydroisoquinoline as an oil which was used directly for next step. MS (EI) calc'd for $C_{10}H_{12}BrFN$ $[M+H]^+$, 244, 246; found, 244, 246.

Steps 2 and 3. Synthesis of 2-59

A mixture of intermediate I-16 (100 mg, 0.150 mmol), 7-bromo-6-fluoro-2-methyl-1,2,3,4-tetrahydroisoquinoline (40 mg, 0.17 mmol), $Cs_2CO_3$ (147 mg, 0.451 mmol), $Pd_2(dba)_3$ (28 mg, 0.030 mmol) and t-BuBrettPhos (36 mg, 0.075 mmol) in toluene (2 mL) was stirred at 125° C. for 6 h under nitrogen. LC/MS showed the desired product was formed. Water (10 mL) and EtOAc:MeOH=10:1 (10 mL) was added. The organic layer was separated and the aqueous was re-extracted with EtOAc:MeOH=10:1 (3×10 mL). The combined organic layers were washed with brine (10 mL), dried over anhydrous $Na_2SO_4$, filtered and concentrated. The mixture was purified by Prep-TLC (silica gel, EtOAc/MeOH=10/1], v/v, Rf=0.4) to give the desired adduct as a solid. To this adduct (60 mg, 0.072 mmol) in DCM (1.5 mL) was added TFA (1.5 mL). Then the solution was stirred at 25° C. for 2 h. The LC/MS showed the desired product. The mixture was concentrated in vacuum to give crude product which was purified by Pre-HPLC (Column YMC-Actus Triart C18 150*30 mm*5 um Condition water (0.1% TFA)-ACN Begin B 17 End B 47 Gradient Time (min) 11 100% B Hold Time (min) 1.1 FlowRate (mL/min) 40 Injections 2) to give compound 2-59 as a solid. $^1$H NMR (400 MHz, DMSO-$d_6$) δ 9.95 (br s, 1H), 9.54 (s, 1H), 9.17 (s, 1H), 8.02 (brd, J=7.6 Hz, 1H), 7.33 (s, 1H), 7.16 (d, J=11.2 Hz, 1H), 6.54 (d, J=6.0 Hz, 1H), 4.48 (br d, J=14.8 Hz, 1H), 4.28 (br s, 2H), 4.19-4.25 (m, 2H), 3.64 (br d, J=11.6 Hz, 1H), 3.35 (br s, 2H), 3.22-3.29 (m, 1H), 2.96-3.12 (m, 3H), 2.90 (s, 3H), 1.90 (s, 3H). MS (EI) calc'd for $C_{26}H_{26}F_2N_7O$ $[M+H]^+$, 490; found, 490.

Preparation of Compounds 2-62 and 2-63

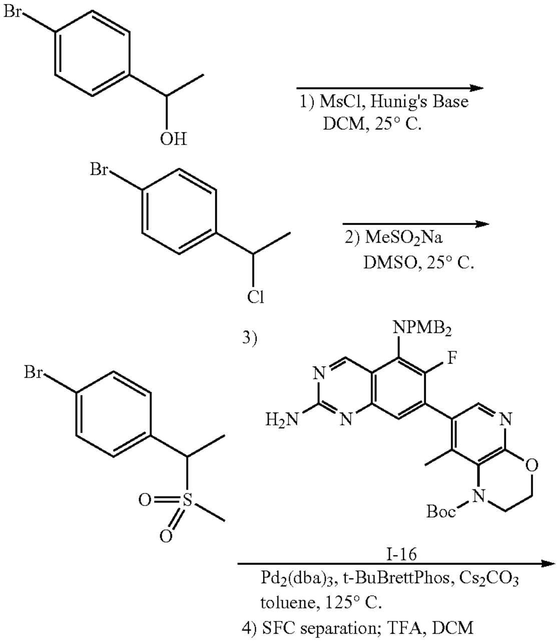

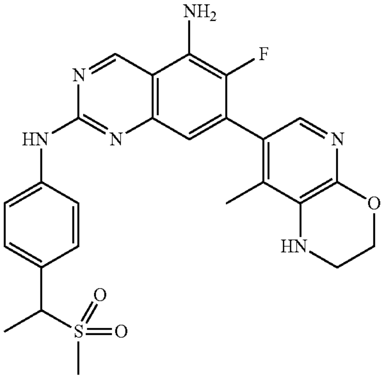

2-62

+

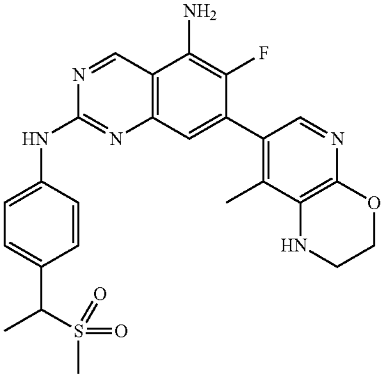

2-63

Step 1. Preparation of 1-bromo-4-(1-chloroethyl) benzene

To a mixture of 1-(4-bromophenyl) ethanol (1.0 g, 4.97 mmol) and Hunig's Base (2.61 mL, 14.9 mmol) in DCM (12 mL) was added Ms-Cl (1.20 mL, 15.4 mmol) at 0° C. The reaction mixture was stirred at 25° C. for 4 h. TLC ($SiO_2$, EtOAc/Pet. Ether=1/10) showed the starting material was consumed completely, and new spots were generated. Water (30 mL) was added, the resulting mixture was added DCM (30 mL). The organic layer was separated and the aqueous was re-extracted with DCM (3×30 mL). The combined organic layers were washed with brine (40 mL), dried over anhydrous $Na_2SO_4$, filtered and concentrated to give a residue which was purified by flash silica gel chromatography (ISCO®; 4 g Agela® Silica Flash Column, Eluent of 0~1% EtOAc/Pet. Ether gradient at 20 mL/min) to give 1-bromo-4-(1-chloroethyl) benzene as an oil. $^1H$ NMR (500 MHz, $CDCl_3$) δ 7.47-7.52 (m, 2H), 7.30 (d, J=8.5 Hz, 2H), 5.05 (q, J=7.0 Hz, 1H), 1.83 (d, J=6.5 Hz, 3H).

Step 2. Preparation of 1-bromo-4-(1-(methylsulfonyl)ethyl)benzene

A mixture of 1-bromo-4-(1-chloroethyl)benzene (1.0 g, 3.9 mmol) in DMSO (10 mL) was added sodium methanesulfinate (0.593 g, 5.81 mmol) at 0° C. The reaction mixture was stirred at 45° C. for 18 h. TLC ($SiO_2$, EtOAc/Pet. Ether=3/1) showed the starting material was consumed completely, and new spots were generated. Water (20 mL) was added, the resulting mixture was added EtOAc (20 mL). The organic layer was separated and the aqueous was re-extracted with EtOAc (3×20 mL). The combined organic layers were washed with brine (40 mL), dried over anhydrous $Na_2SO_4$, filtered and concentrated to give a residue which was purified by flash silica gel chromatography (ISCO®; 12 g Agela® Silica Flash Column, Eluent of 0~25% EtOAc/Pet. ether gradient at 30 mL/min) to give 1-bromo-4-(1-(methylsulfonyl)ethyl)benzene as a solid. $^1H$ NMR (400 MHz, $CDCl_3$) δ 7.53-7.59 (m, 2H), 7.33 (d, J=8.4 Hz, 2H), 4.16 (q, J=7.2 Hz, 1H), 2.68 (s, 3H), 1.79 (d, J=7.2 Hz, 3H).

Steps 3-4. Synthesis of Compounds 2-62 and 2-63

A mixture of t-BuBrettPhos (36 mg, 0.075 mmol), $Pd_2(dba)_3$ (28 mg, 0.030 mmol), intermediate I-16 (100 mg, 0.150 mmol), $Cs_2CO_3$ (147 mg, 0.450 mmol) and 1-bromo-4-(1-(methylsulfonyl)ethyl)benzene (79 mg, 0.30 mmol) in toluene (2 mL) was degassed and backfilled with nitrogen (3×). The reaction was stirred at 125° C. for 8 h. The color turned brown. LC-MS showed the major of product and a little material. Diluted with water (20 mL) and extracted with EtOAc (20 mL). The organic layer was concentrated to give a residue which was purified by prep-TLC ($SiO_2$, MeOH/DCM=1/10) to give the fully protected adduct as a racemate, a solid was isolated. The fully protected products were by SFC (Column: Phenomenex-Cellulose-2 (250 mm*30 mm, 5 um), Condition: 0.1% $NH_3H_2O$/IPA, Mobile phase: A: $CO_2$ B: IPA (0.1% $NH_3H_2O$), Gradient: from 5% to 40% of B in 5.5 min and hold 40% for 3 min, then 5% of B for 1.5 min, Flow rate: 70 mL/min, Column temp: 35° C.) to give SFC-P1 [RT: 10.732 min] and SFC-P2 [RT: 11.894 min] both as solids.

Synthesis of Compound 2-62 ((R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine)

SFC-P1 (19 mg, 0.022 mmol) in DCM (2 mL) was added TFA (2.0 mL) at 25° C. The mixture was stirred at 25° C. for 3 h. The mixture was concentrated under reduced pressure. The residue was purified by reversed phase HPLC fitted with Waters XSELECT C18 150*30 mm*5 um using water (0.1% TFA)-MeCN as eluents (Mobile phase A water (0.1% TFA), Mobile phase B acetonitrile, Detective wavelength 220 nm) and concentration to give 6-fluoro-7-(8-methyl-2,3-dihydro-1H-pyrido[2,3-b][1,4]oxazin-7-yl)-N2-(4-(1-(methylsulfonyl)ethyl)phenyl)quinazoline-2,5-diamine as a solid. $^{1}$H NMR (400 MHz, $CD_3OD$) δ 9.50 (s, 1H), 7.83 (d, J=8.4 Hz, 2H), 7.51 (s, 1H), 7.45 (d, J=8.4 Hz, 2H), 6.79 (d, J=5.2 Hz, 1H), 4.58 (t, J=4.4 Hz, 2H), 4.41 (q, J=7.2 Hz, 1H), 3.60 (t, J=4.4 Hz, 2H), 2.8 (s, 3H), 2.1 (d, J=1.2 Hz, 3H), 1.73 (d, J=7.2 Hz, 3H). MS (EI) calc'd for $C_{25}H_{26}FN_6O_3S$ $[M+H]^+$, 509; found, 509.

Synthesis of Compound 2-63 ((R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine)

Compound 2-63 was synthesized using the same deprotection and purification method as the above for compound 2-62.

Compound 2-63. $^{1}$H NMR (400 MHz, $CD_3OD$) δ 9.50 (s, 1H), 7.83 (d, J=8.4 Hz, 2H), 7.51 (s, 1H), 7.45 (d, J=8.4 Hz, 2H), 6.79 (d, J=5.2 Hz, 1H), 4.58 (t, J=4.4 Hz, 2H), 4.41 (q, J=7.2 Hz, 1H), 3.60 (t, J=4.4 Hz, 2H), 2.8 (s, 3H), 2.1 (d, J=1.2 Hz, 3H), 1.73 (d, J=7.2 Hz, 3H). MS (EI) calc'd for $C_{25}H_{26}FN_6O_3S$ $[M+H]^+$, 509; found, 509.

Preparation of Compound 2-67

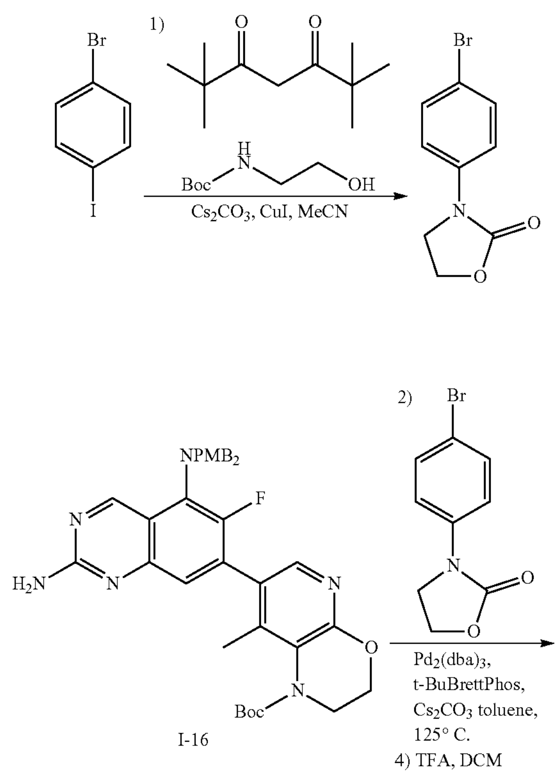

-continued

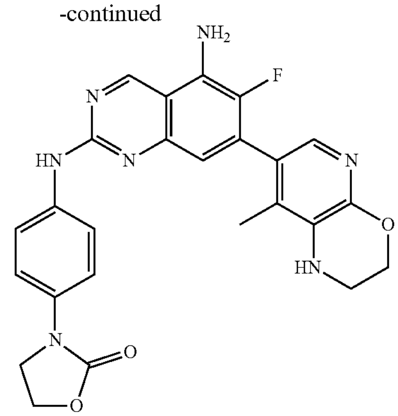

2-67

Step 1. Preparation of 3-(4-bromophenyl)oxazolidin-2-one

A mixture of 1-bromo-4-iodobenzene (1.0 g, 3.5 mmol), N-boc-ethanolamine (0.63 g, 3.9 mmol), 2,2,6,6-tetramethyl-3,5-heptanedione (0.13 g, 0.71 mmol), $Cs_2CO_3$ (3.5 g, 10.6 mmol) and Copper(I) Iodide (0.067 g, 0.35 mmol) in ACN (10 mL) was stirred at 100° C. under nitrogen for 20 h. LC/MS showed desired product. TLC ($SiO_2$; Rf=0.2, petroleum ether:ethyl acetate=3:1) showed the new spot. The mixture was concentrated in vacuo. The residue was purified by flash silica gel chromatography (ISCO; 4 g Agela Silica Flash Column, Eluent of 60% EA/PE gradient at 30 mL/min) to afford 3-(4-bromophenyl)oxazolidin-2-one as a solid. MS (EI) calc'd for $C_9H_9BrNO_2$ $[M+H]^+$, 242; found, 242.

Steps 2 and 3. Synthesis of 2-67

Compound 2-67 was prepared from intermediate I-16 and 3-(4-bromophenyl)oxazolidin-2-one using the same coupling method in Example 2B.

Compound 2-67. $^{1}$H NMR (400 MHz, DMSO-$d_6$) δ 9.76 (s, 1H), 9.56 (s, 1H), 7.93 (d, J=9.2 Hz, 2H), 7.47 (d, J=9.6 Hz, 2H), 7.38 (s, 1H), 6.61 (d, J=5.2 Hz, 1H), 4.41 (t, J=8.0 Hz, 2H), 4.32 (br s, 2H), 4.03 (t, J=7.6 Hz, 2H), 3.47-3.64 (m, 2H), 1.95 (s, 3H). MS (EI) calc'd for $C_{25}H_{23}FN_7O_3$ $[M+H]^+$, 488; found, 488.

Preparation of Compound 2-87

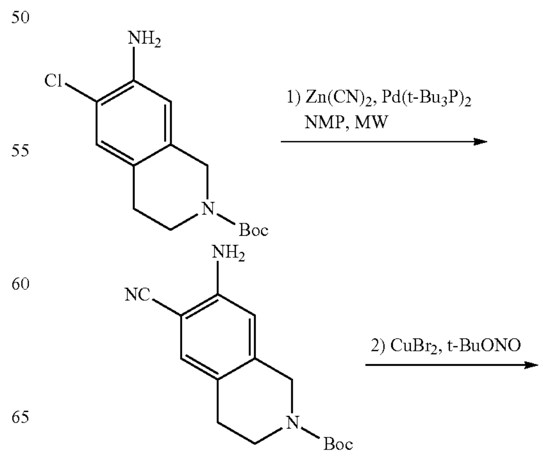

-continued

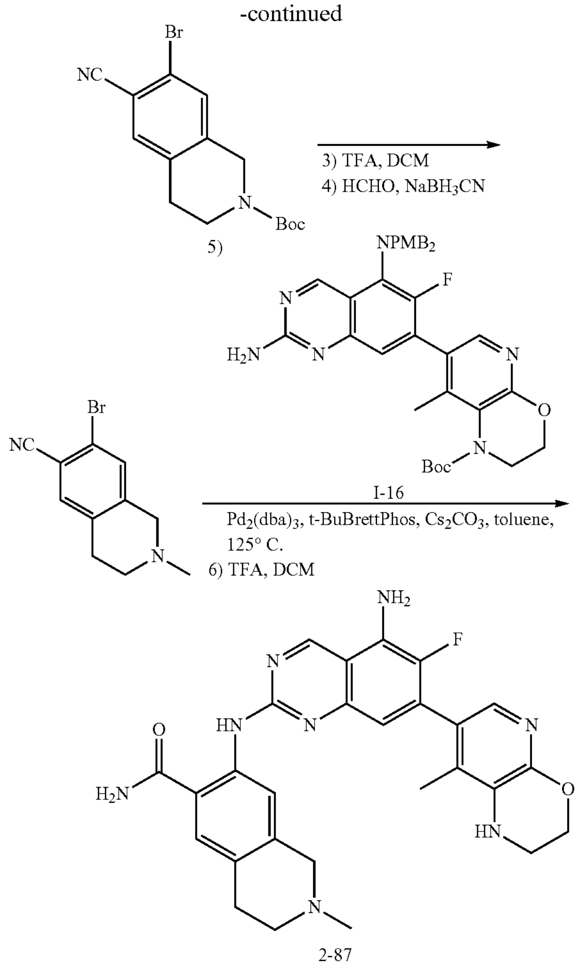

2-87

Step 1. Preparation of tert-butyl 7-amino-6-cyano-3,4-dihydroisoquinoline-2(1H)-carboxylate To a mixture of tert-butyl 7-amino-6-chloro-3,4-dihydroisoquinoline-2(1H)-carboxylate (500 mg, 1.77 mmol), bis(tri-tert-butylphosphine)palladium(0) (361 mg, 0.707 mmol) in NMP (10 mL) was added dicyanozinc (623 mg, 5.30 mmol). Then the mixture was stirred at 180° C. for 20 min under microwave. LC/MS showed that the desired target was formed. Water (100 mL) and EtOAc (80 mL) was added. The organic layer was separated and the aqueous was re-extracted with EtOAc (3×50 mL). The combined organic layers were washed with brine (100 mL), dried over anhydrous $Na_2SO_4$, filtered and concentrated. The residue was purified by column chromatography (Eluent of 20~50% EtOAc/Pet. ether) to give tert-butyl 7-amino-6-cyano-3,4-dihydroisoquinoline-2(1H)-carboxylate as a solid. MS (EI) calc'd for $C_{15}H_{20}N_3O_2$ [M+H]$^+$, 274; found, 218 (M−56+H).

Step 2. Preparation of tert-butyl 7-bromo-6-cyano-3,4-dihydroisoquinoline-2(1H)-carboxylate To a mixture of tert-butyl 7-amino-6-cyano-3,4-dihydroisoquinoline-2(1H)-carboxylate (480 mg, 1.76 mmol) and copper(II) bromide (590 mg, 2.6 mmol) in ACN (10 mL) was added tert-butyl nitrite (0.25 mL, 2.1 mmol) dropwised at 25° C., the mixture was stirred at 25° C. for 6 h. LC/MS showed desired product. Sat. $NH_4Cl$ (10 mL) and sat. $Na_2SO_3$ (10 mL) was added to adjust the pH to 5~7. The mixture was diluted with EtOAc (80 mL), washed with water (50 mL), brine (50 mL), dried over anhydrous $Na_2SO_4$, filtered and concentrated in vacuum to give crude tert-butyl 7-bromo-6-cyano-3,4-dihydroisoquinoline-2(1H)-carboxylate (590 mg, crude) as an oil, which was used directly in next step without further purification. MS (EI) calc'd for $C_{15}H_{18}BrN_2O_2$ [M+H]$^+$, 334; found, 281 (M−56+H).

Steps 3 and 4. Preparation of 7-bromo-2-methyl-1,2,3,4-tetrahydroisoquinoline-6-carbonitrile A mixture of tert-butyl 7-bromo-6-cyano-3,4-dihydroisoquinoline-2(1H)-carboxylate (590 mg, 1.750 mmol) in DCM (5 mL) and TFA (5 mL) was stirred at 25° C. for 0.5 h. LC/MS showed desired product. The mixture was concentrated in vacuo to give 7-bromo-1,2,3,4-tetrahydroisoquinoline-6-carbonitrile (415 mg, crude) as an oil, which was used directly in next step without further purification.

A mixture of 7-bromo-1,2,3,4-tetrahydroisoquinoline-6-carbonitrile (415 mg, 1.75 mmol) and formaldehyde (568 mg, 7.00 mmol) was added a drop of AcOH (0.5 mL) in MeOH (8 mL). The mixture was stirred at 25° C. for 20 min, then $NaBH_3CN$ (330 mg, 5.25 mmol) was added. The mixture was stirred at 25° C. for 12 h under nitrogen. Solvent was removed under reduced pressure. To the residue was added water (30 mL), basified by addition of $NaHCO_3$aqueous solution to pH~9, and extracted with EtOAc (3×50 mL). The organic layers were washed with brine (50 mL), dried over $Na_2SO_4$, filtered and concentrated in vacuo. The residue was purified by pre-TLC (Pet. ether: EtOAc=1:2) to afford 7-bromo-2-methyl-1,2,3,4-tetrahydroisoquinoline-6-carbonitrile as a solid. $^1H$ NMR (400 MHz, $CDCl_3$) δ ppm 7.41 (s, 1H), 7.33 (s, 1H), 3.58 (s, 2H), 2.85-2.91 (m, 2H), 2.66-2.72 (m, 2H), 2.46 (s, 3H).

Steps 5 and 6. Synthesis of 2-87

Compound 2-87 was prepared from intermediate I-16 and 7-bromo-2-methyl-1,2,3,4-tetrahydroisoquinoline-6-carbonitrile using the same coupling method in Example 2B.

$^1H$ NMR (400 MHz, $CD_3OD$) δ 7.91 (s, 1H), 7.80 (s, 1H), 7.60 (s, 1H), 7.30 (s, 1H), 6.39 (d, J=6.4 Hz, 1H), 4.36-4.38 (m, 2H), 3.83 (s, 2H), 3.46-3.47 (m, 2H), 3.05-3.12 (m, 2H), 2.83 (t, J=6.4 Hz, 2H), 2.52 (s, 3H), 2.02 (s, 3H). MS (EI) calc'd for $C_{27}H_{28}FN_8O_2$ [M+H]$^+$, 515; found, 515.

Example 2C. Preparation of 2-37

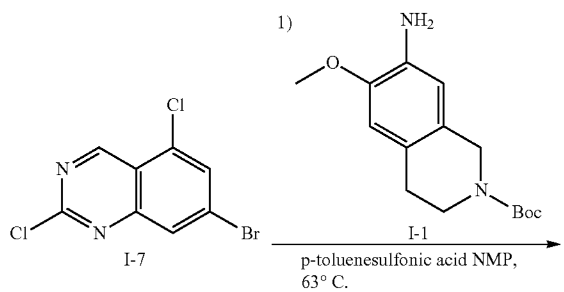

-continued

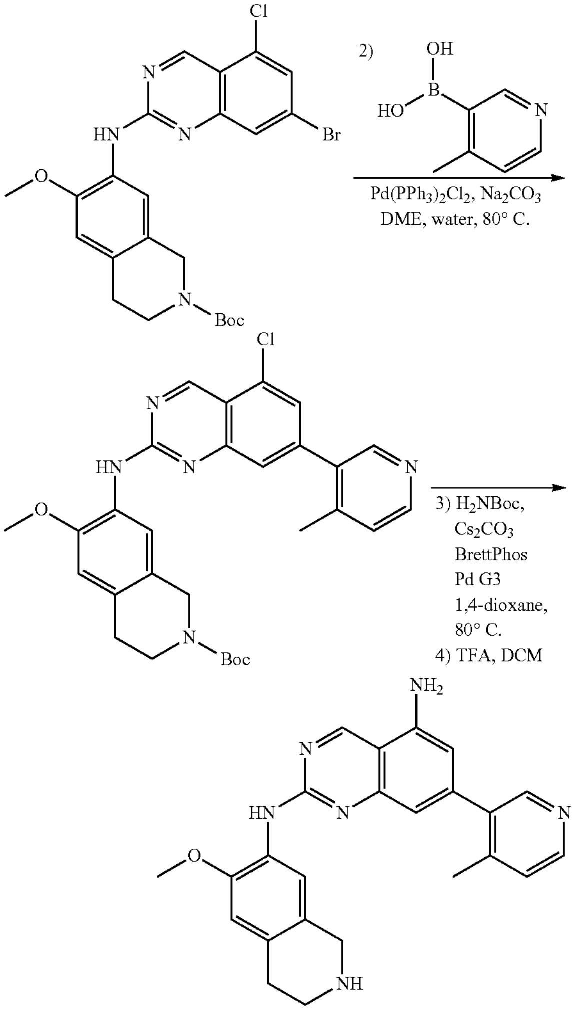

2-37

Step 1. Synthesis of tert-butyl 7-((7-Bromo-5-chloroquinazolin-2-yl)amino)-6-methoxy-3,4-dihydroisoquinoline-2(1H)-carboxylate A mixture of intermediate I-1 (124 mg, 0.445 mmol), intermediate I-7 (103 mg, 0.371 mmol), and p-toluenesulfonic acid (96 mg, 0.56 mmol) in NMP (1.2 mL) was heated to 63° C. and stirred overnight. The reaction was allowed to cool to rt, filtered, and concentrated to dryness. Chromatography on $SiO_2$ (gradient of 0-40% EtOAc/Hex, 4 g silica gel) gave the desired intermediate tert-butyl 7-((7-bromo-5-chloroquinazolin-2-yl)amino)-6-methoxy-3,4-dihydroisoquinoline-2(1H)-carboxylate as an oil that solidified upon standing. MS (EI) calc'd for $C_{23}H_{25}BrClN_4O_3$ $[M+H]^+$, 519, 521; found, 519, 521.

Step 2. Synthesis of tert-butyl 7-((5-chloro-7-(4-methylpyridin-3-yl)quinazolin-2-yl)amino)-6-methoxy-3,4-dihydroisoquinoline-2(1H)-carboxylate A solution of (4-methylpyridin-3-yl)boronic acid (20 mg, 0.14 mmol), intermediate I-16 (68 mg, 0.13 mmol) and $Pd(PPh_3)_2Cl_2$ (9.2 mg, 0.013 mmol) in DME (0.44 mL) was treated with 2 M aqueous solution of $Na_2CO_3$ (200 µl, 0.39 mmol). The reaction was deoxygenated by bubbling argon gas through the reaction mixture for 3 min, and then heated to 80° C. overnight. After cooling, the reaction was filtered and concentrated to dryness. Chromatography on $SiO_2$ (gradient of 0-80% EtOAc/Hex, 4 g silica gel) gave the desired tert-butyl 7-((5-chloro-7-(4-methylpyridin-3-yl)quinazolin-2-yl)amino)-6-methoxy-3,4-dihydroisoquinoline-2(1H)-carboxylate as an oil. MS (EI) calc'd for $C_{29}H_{31}ClN_5O_3$ $[M+H]^+$, 532; found, 532.

Steps 3 and 4. Synthesis of 3-37 ($N^2$-(6-methoxy-1,2,3,4-tetrahydroisoquinolin-7-yl)-7-(4-methylpyridin-3-yl)quinazoline-2,5-diamine)

A solution of tert-butyl 7-((5-chloro-7-(4-methylpyridin-3-yl)quinazolin-2-yl)amino)-6-methoxy-3,4-dihydroisoquinoline-2(1H)-carboxylate (35 mg, 0.066 mmol), tert-butyl carbamate (193 mg, 1.65 mmol), $Cs_2CO_3$ (107 mg, 0.329 mmol), and BrettPhos Pd G3 (12 mg, 0.013 mmol) in 1,4-dioxane (6.5 mL) was deoxygenated by bubbling argon gas through the reaction mixture for 3 min and then heated to 80° C. overnight. After cooling, the reaction was filtered and concentrated to dryness. Chromatography on $SiO_2$ (gradient of 0-80% EtOAc/Hex, 4 g silica gel) gave the protected coupling intermediate. The intermediate was then taken-up in 2 mL of DCM, treated with 2 mL of TFA and the solution allowed to age for 1 h, then concentrated to dryness. The residue was purified by reverse phase chromatography (gradient of 15-70% ACN/water with 0.1% $NH_4OH$) to provide 2-37 as a solid. $^1H$ NMR (500 MHz, DMSO-$d_6$) δ 9.47 (s, 1H), 8.47 (d, J=5.0 Hz, 1H), 8.41 (s, 1H), 8.35 (s, 1H), 8.03 (s, 1H), 7.36 (d, J=5.0 Hz, 1H), 6.86 (s, 1H), 6.75 (s, 1H), 6.48 (s, 2H), 6.42 (d, J=1.2 Hz, 1H), 4.11 (s, 2H), 3.88 (s, 3H), 3.23 (t, J=6.1 Hz, 2H), 2.87 (t, J=5.9 Hz, 2H), 2.30 (s, 3H). MS (EI) calc'd for $C_{24}H_{25}N_6O$ $[M+H]^+$, 413; found, 413.

Example 2D. Preparation of 2-38

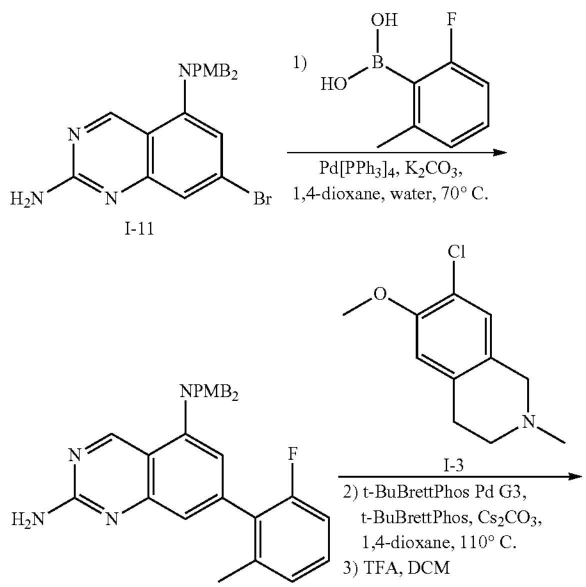

-continued

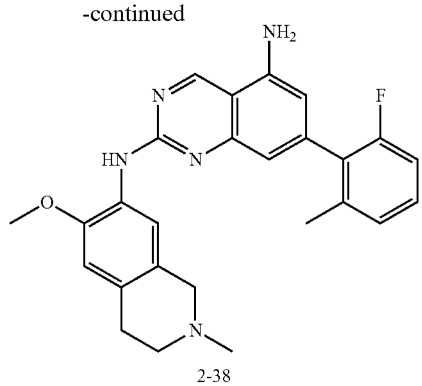

2-38

Step 1. Synthesis of 7-(2-fluoro-6-methylphenyl)-$N^5$,$N^5$-bis(4-methoxybenzyl)quinazoline-2,5-diamine A solution of intermediate I-11 (75 mg, 0.16 mmol) in 1,4-dioxane (1.7 mL) was treated with (2-fluoro-6-methylphenyl)boronic acid (27 mg, 0.17 mmol), $K_2CO_3$ (65 mg, 0.47 mmol), tetrakis(triphenylphosphine)palladium(0) (36 mg, 0.031 mmol) and water (0.6 mL). The mixture was deoxygenated by bubbling argon gas through the reaction mixture for 3 min, then heated to 70° C. overnight. After cooling, the reaction is filtered and concentrated to dryness. Chromatography on $SiO_2$ (gradient of 0-55% EtOAc/Hex, 4 g silica gel) gave 7-(2-fluoro-6-methylphenyl)-$N^5$,$N^5$-bis(4-methoxybenzyl)quinazoline-2,5-diamine. MS (EI) calc'd for $C_{31}H_{30}FN_4O_2$ $[M+H]^+$, 509, found, 509.

Steps 2 and 3. Synthesis of 2-38 ((7-(2-fluoro-6-methylphenyl)-$N^2$-(6-methoxy-2-methyl-1,2,3,4-tetrahydroisoquinolin-7-yl)quinazoline-2,5-diamine))

A solution of intermediate I-3 (33 mg, 0.15 mmol), 7-(2-fluoro-6-methylphenyl)-N,N-bis(4-methoxybenzyl) quinazoline-2,5-diamine (65 mg, 0.13 mmol), t-BuBrettPhos-Pd-G3 (22 mg, 0.026 mmol), t-BuBrettPhos (12 mg, 0.026 mmol), and $Cs_2CO_3$ (208 mg, 0.639 mmol) in 1,4-dioxane (1.3 mL) was deoxygenated by bubbling argon gas through the reaction mixture for 3 min. The mixture was stirred overnight at 110° C. After cooling to rt, the reaction was filtered and concentrated to dryness. The intermediate was then taken up in 2 mL of DCM, treated with 2 mL of TFA and the solution allowed to age for 30 min. The mixture is then concentrated to dryness. The residue was purified by reverse phase chromatography (gradient of 30-95% ACN/water with 0.1% $NH_4OH$) to provide 2-38 as a solid. $^1H$ NMR (500 MHz, DMSO-$d_6$) δ 9.45 (s, 1H), 8.27 (s, 1H), 7.95 (s, 1H), 7.42-7.27 (m, 1H), 7.24-7.06 (m, 2H), 6.78 (s, 1H), 6.63 (s, 1H), 6.43 (s, 2H), 6.31 (s, 1H), 3.86 (s, 3H), 3.46 (s, 2H), 2.79 (s, 2H), 2.59 (s, 2H), 2.33 (s, 3H), 2.17 (s, 3H). MS (EI) calc'd for $C_{26}H_{27}FN_5O$ $[M+H]^+$, 444; found, 444.

Example 2E. Preparation of 2-49

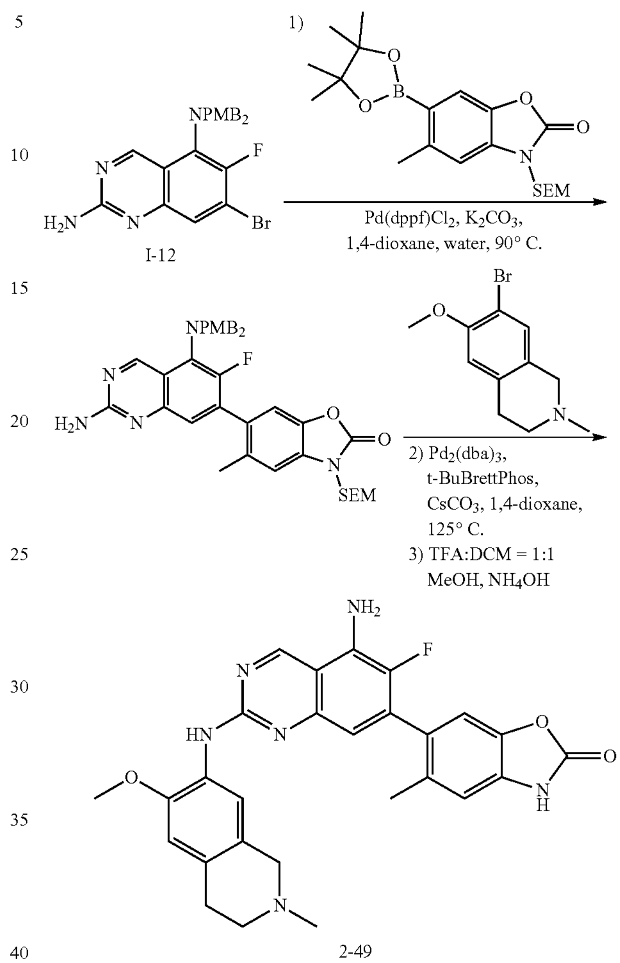

I-12

2-49

Step 1. Preparation of 6-(2-amino-5-(bis(4-methoxybenzyl)amino)-6-fluoroquinazolin-7-yl)-5-methyl-3-((2-(trimethylsilyl)ethoxy)methyl)benzo[d]oxazol-2(3H)-one To a mixture of intermediate I-12 (200 mg, 0.402 mmol), 5-methyl-6-(4,4,5,5-tetramethyl-1,3,2-dioxaborolan-2-yl)-3-((2-(trimethylsilyl)ethoxy)methyl)benzo[d]oxazol-2(3H)-one (187 mg, 0.462 mmol) and $K_2CO_3$ (111 mg, 0.804 mmol) in 1,4-dioxane (5 mL) and water (1 mL) was added $Pd(dppf)Cl_2$ (29 mg, 0.040 mmol) at 25° C. under nitrogen. Then the mixture was stirred at 90° C. for 2 h. LC/MS showed that the reaction completed. Water (20 mL) and DCM (30 mL) was added. The organic layer was separated and the aqueous was re-extracted with DCM (2×20 mL). The combined organic layers were washed with brine (50 mL), dried over anhydrous $Na_2SO_4$, filtered and concentrated. The residue was purified by pre-TLC (silica gel, EtOAc) to give 6-(2-amino-5-(bis(4-methoxybenzyl)amino)-6-fluoroquinazolin-7-yl)-5-methyl-3-((2-(trimethylsilyl)ethoxy)methyl)benzo[d]oxazol-2(3H)-one as a solid. MS (EI) calc'd for $C_{38}H_{43}FN_5O_5Si$ $[M+H]^+$, 696; found, 696.

Steps 2 and 3. Synthesis of Compound 2-49

A mixture of 6-(2-amino-5-(bis(4-methoxybenzyl)amino)-6-fluoroquinazolin-7-yl)-5-methyl-3-((2-(trimethylsilyl)ethoxy)methyl)benzo[d]oxazol-2(3H)-one (170 mg, 0.244 mmol), 7-bromo-6-methoxy-2-methyl-1,2,3,4-tetrahydroisoquinoline (81 mg, 0.32 mmol), $Cs_2CO_3$ (240 mg, 0.73 mmol), $Pd_2(dba)_3$ (45 mg, 0.049 mmol) and t-BuBrettphos (59 mg, 0.12 mmol) in toluene (2 mL) was stirred at 125° C. for 3 h under nitrogen. LC/MS showed the desired product was formed. Water (10 mL) and EtOAc:MeOH=10:1 (20 mL) was added. The organic layer was separated and the aqueous was re-extracted with EtOAc:MeOH=10:1 (3×10 mL). The combined organic layers were washed with brine (30 mL), dried over anhydrous $Na_2SO_4$, filtered and concentrated. The mixture was purified by Prep-TLC (silica gel, EtOAc/MeOH=10:1) to give the desired intermediate as an oil. This was taken up in a mixture in DCM/TFA (1:1) (1 mL) solution and then stirred at 25° C. for 1 h. Then the reaction mixture was concentrated under reduced pressure. The residue was dissolved in MeOH (3 mL) and added $NH_3 \cdot H_2O$ (2 mL) (28% in $H_2O$). The mixture was stirred at 25° C. for 0.5 h. LC/MS showed that the reaction completed and the mixture was concentrated under reduced pressure. The residue was purified by Prep-HPLC (Column Agela DuraShell C18 150*25 mm*5 um; Condition water (0.04% $NH_3H_2O$+10 mM $NH_4HCO_3$)-ACN Begin B 35 End B 65 Gradient Time (min) 10; 100% B Hold Time (min) 0 FlowRate (mL/min) 25; Injections 4) to give 2-49 as a solid. $^1H$ NMR (400 MHz, DMSO-$d_6$) δ 9.41 (s, 1H), 8.38 (s, 1H), 7.12 (s, 1H), 7.04 (s, 1H), 6.79 (d, J=6.0 Hz, 1H), 6.78 (s, 1H), 3.92 (s, 3H), 3.61 (s, 2H), 2.88-2.98 (m, 2H), 2.70-2.79 (m, 2H), 2.44 (s, 3H), 2.22 (s, 3H). MS (EI) calc'd for $C_{27}H_{26}FN_6O_3$ $[M+H]^+$, 501; found, 501.

Example 2F

Preparation of Compound 2-48

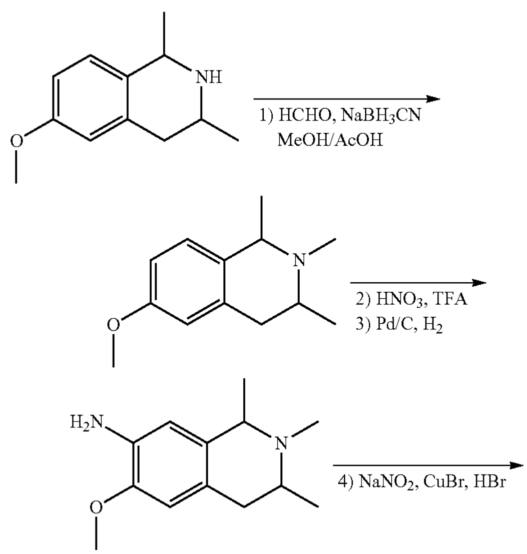

-continued

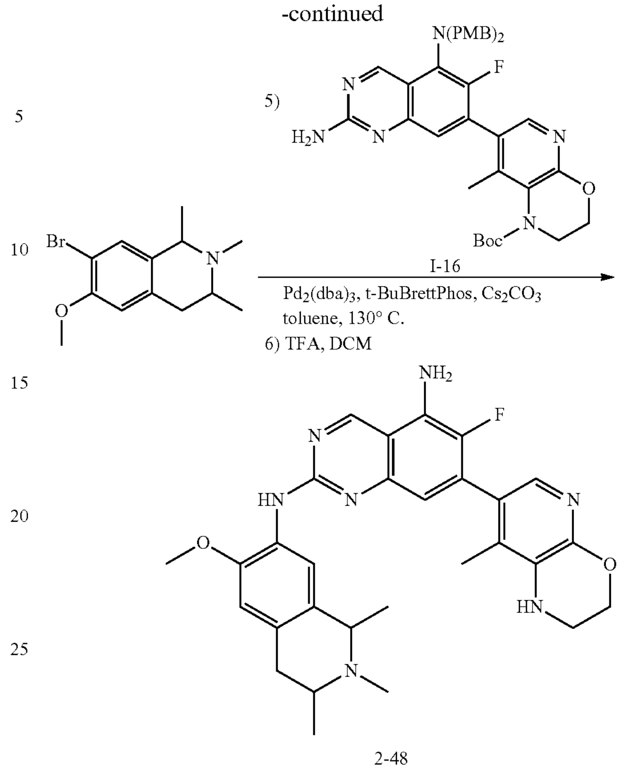

2-48

Step 1. Preparation of 6-methoxy-1,2,3-trimethyl-1,2,3,4-tetrahydroisoquinoline

To a mixture of 6-methoxy-1,3-dimethyl-1,2,3,4-tetrahydroisoquinoline (500 mg, 2.61 mmol) was added formaldehyde (314 mg, 10.5 mmol) and AcOH (0.5 mL) in MeOH (5 mL) and then stirred at 25° C. for 30 min, then the mixture was treated with sodium cyanotrihydroborate (493 mg, 7.84 mmol) and stirred at 25° C. for 1 h under nitrogen. Solvent was removed under reduced pressure. To the residue was added water (30 mL), and extracted with DCM/MeOH (10:1) (3×30 mL). The organic layers were washed with brine (20 mL), dried over $Na_2SO_4$, filtered and concentrated to give 6-methoxy-1,2,3-trimethyl-1,2,3,4-tetrahydroisoquinoline as an oil. MS (EI) calc'd for $C_{13}H_{20}NO$ $[M+H]^+$, 206; found, 206.

Steps 2 and 3. Preparation of 6-methoxy-1,2,3-trimethyl-1,2,3,4-tetrahydroisoquinolin-7-amine To a solution of 6-methoxy-1,2,3-trimethyl-1,2,3,4-tetrahydroisoquinoline (500 mg, 2.44 mmol) in TFA (5 mL) was added nitric acid (0.17 mL, 2.7 mmol) in TFA (0.5 mL) slowly. The temperature was hold on 0-20° C. The mixture was stirred at 0° C. for 2 h. TLC showed starting material was consumed and desired product formed. The mixture was quenched with water (10 mL) based to pH=13~14 with aq. NaOH (1N) and was extracted with DCM/MeOH (10:1) (3×40 mL). The organic layers were washed with brine (30 mL), dried over $Na_2SO_4$, filtered and concentrated in vacuum. The residue was purified by silica gel (ISCO; 12 g SepaFlash; Silica Flash Column, eluent of [0-10]% EtOAc/MeOH, gradient at 30 mL/min) to give 6-methoxy-1,2,3-trimethyl-7-nitro-1,2,3,4-tetrahydroisoquinoline (230 mg, 0.919 mmol) which was taken up in MeOH (5 mL) and added Pd/C (98 mg, 0.092 mmol). The mixture was stirred at 25° C. for 2 h under a hydrogen balloon (15 psi). LC/MS showed starting material was consumed and desired product formed. The mixture was filtered and concentrated to give 6-methoxy-1,2,3-trimethyl-1,2,3,4-tetrahydroisoquinolin-7-amine as an oil. MS (EI) calc'd for $C_{13}H_{21}N_2O$ $[M+H]^+$, 221; found, 221.

Step 4. Preparation of 7-bromo-6-methoxy-1,2,3-trimethyl-1,2,3,4-tetrahydroisoquinoline To a mixture of 6-methoxy-1,2,3-trimethyl-1,2,3,4-tetrahydroisoquinolin-7-amine (200 mg, 0.91 mmol) in 5% HBr (in water) (12 mL) was added sodium nitrite (81 mg, 1.2 mmol) in water (5 mL) at 0° C. for 1 h. This was followed by addition of Copper(I) Bromide (456 mg, 3.18 mmol) in 5% HBr (in water) (10 mL). The mixture was then stirred at 25° C. for 12 h. LC-MS showed desired product was formed. The reaction was concentrated to give the residue. The residue was purified by pre-HPLC (TFA) to give 7-bromo-6-methoxy-1,2,3-trimethyl-1,2,3,4-tetrahydroisoquinoline (80 mg, 0.28 mmol) as an oil. HPLC condition: Instrument ee, Method: TFA, Column YMC-Actus Triart C18 150*30 mm*5 um, Condition water (0.1% TFA)-ACN Begin B 14 End B 44 Gradient Time (min) 11 100% B Hold Time (min) 1.1 FlowRate (mL/min) 40, Injections 5. MS (EI) calc'd for $C_{13}H_{19}BrNO$ $[M+H]^+$, 284, 286; found, 284, 286.

Steps 5 and 6. Synthesis of 2-48

To a solution of intermediate I-16 (120 mg, 0.180 mmol), 7-bromo-6-methoxy-1,2,3-trimethyl-1,2,3,4-tetrahydroisoquinoline (77 mg, 0.27 mmol), $Cs_2CO_3$ (176 mg, 0.540 mmol) was added $Pd_2(dba)_3$ (21 mg, 0.023 mmol) and i-BuBrettPhos (26 mg, 0.054 mmol) in toluene (4 mL) was stirred at 130° C. for 6 h under nitrogen. LC/MS showed the desired product was formed. The mixture was quenched with water (20 mL), then the mixture was extracted with EtOAc (3×30 mL), the combined organic layer was washed with brine, dried over anhydrous $Na_2SO_4$, filtered and concentrated to get the residue. It was further purified by pre-TLC (EtOAc/MeOH=2:1) to give the desired adduct as an oil. The adduct was taken up in DCM (1 mL) and added TFA (1 mL). The resulting mixture was then stirred at 25° C. for 2 h. LC/MS showed the material was consumed and the desired product was found. The mixture was concentrated to get the residue. The crude mixture was purified by pre-HPLC(basic) to afford Compound 2-48 as a solid. HPLC condition: Instrument ed, Method: basic, Column Agela DuraShell C18 150*25 mm*5 um, Condition water (0.04% $NH_3H_2O$+10 mM $NH_4HCO_3$)-ACN Begin B 27 End B 57 Gradient Time (min) 10 100% B Hold Time (min) 2 FlowRate (mL/min) 25 Injections 2. $^1H$ NMR (400 MHz, $CD_3OD$) δ 9.40 (s, 1H), 8.56 (s, 1H), 7.36 (s, 1H), 6.68-6.73 (m, 2H), 4.40 (t, J=4.4 Hz, 2H), 3.91 (s, 3H), 3.48 (t, J=4.4 Hz, 2H), 2.60-2.87 (m, 4H), 2.33 (s, 3H), 2.02 (s, 3H), 1.56 (d, J=6.8 Hz, 3H), 1.27 (d, J=6.4 Hz, 3H). MS (EI) calc'd for $C_{29}H_{33}FN_7O_2$ $[M+H]^+$, 530; found, 530.

Preparation of Compounds 2-54 and 2-57

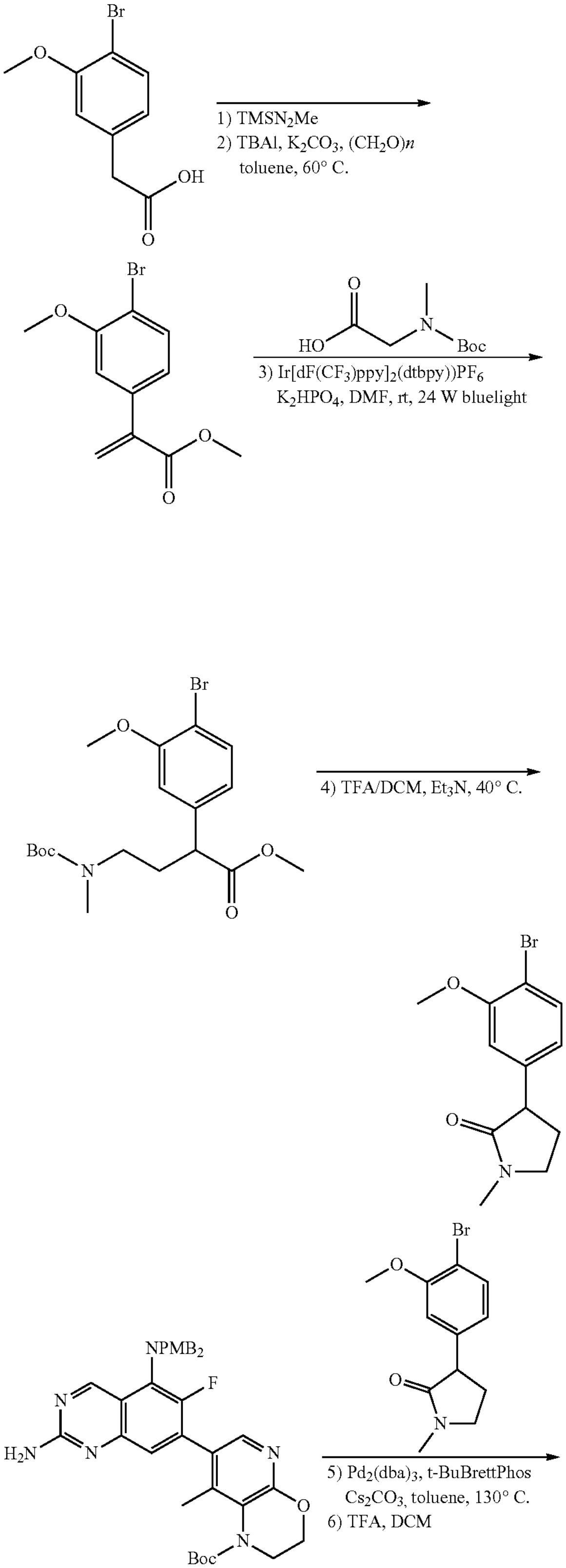

I-16

-continued

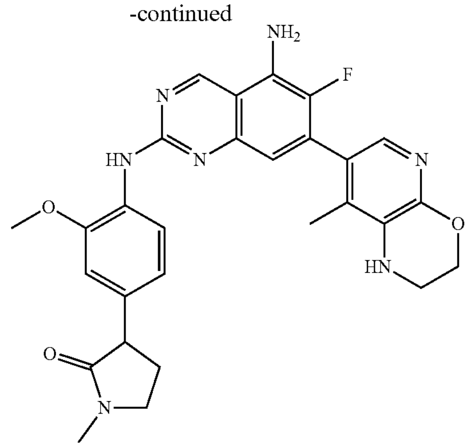

2-54

+

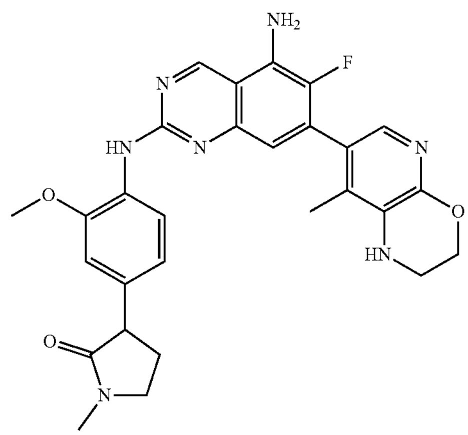

2-57

Steps 1 and 2. Synthesis of methyl 2-(4-bromo-3-methoxyphenyl)acrylate

To a solution of 2-(4-bromo-3-methoxyphenyl)acetic acid (600 mg, 2.45 mmol) in DCM (5 mL) and MeOH (1 mL) was added TMS-Diazomethane (2.45 mL, 4.90 mmol) portionwise at 0° C., then the mixture was stirred at 0° C. for 30 min. TLC showed finished. It was concentrated to give crude, the crude was purified by flash silica gel chromatography (ISCO®; 4 g SepaFlash® Silica Flash Column, eluent of 0-18% ethyl acetate/pet. ether gradient at 30 mL/min) to give methyl 2-(4-bromo-3-methoxyphenyl)acetate as an oil. This product (600 mg, 2.32 mmol) was taken up in toluene (20 mL) and added formaldehyde (209 mg, 6.95 mmol), $K_2CO_3$ (960 mg, 6.95 mmol) and TBAI (43 mg, 0.12 mmol). Then it was stirred at 60° C. for 15 h. TLC showed finished. The mixture was filtered and purified by flash silica gel chromatography (ISCO®; 4 g SepaFlash®, Silica Flash Column, eluent of [0~5]% ethyl acetate/pet. ether gradient at 30 mL/min) to give methyl 2-(4-bromo-3-methoxyphenyl) acrylate as an oil. $^1$H NMR (400 MHz, $CDCl_3$) δ 7.51 (d, J=8.0 Hz, 1H), 6.98 (d, J=2.0 Hz, 1H), 6.88 (dd, J=8.0, 2.0 Hz, 1H), 6.40 (d, J=0.8 Hz, 1H), 5.93 (d, J=1.2 Hz, 1H), 3.91 (s, 3H), 3.83 (s, 3H).

Step 3. Synthesis of methyl 2-(4-bromo-3-methoxyphenyl)-4-((tert-butoxycarbonyl)(methyl)amino) butanoate To a mixture of 2-((tert-butoxycarbonyl)(methyl)amino) acetic acid (94 mg, 0.50 mmol), methyl 2-(4-bromo-3-methoxyphenyl)acrylate (135 mg, 0.498 mmol), $K_2HPO_4$ (104 mg, 0.598 mmol), $(Ir[dF(CF_3)ppy]_2(dtbpy))PF_6$ (28 mg, 0.025 mmol) was added DMF (2 mL). Then it was stirred at 20° C. for 1 h under (34W, Blue LED). TLC showed finished. It was dissolved in water (20 mL) and EtOAc (20 mL). The organic layer was separated and the aqueous was re-extracted with EtOAc (3×20 mL). The combined organic layers were washed with brine (20 mL), dried over anhydrous $Na_2SO_4$, filtered and the filtrate was evaporated in vacuum to give crude, the crude was purified by Prep-TLC (silica gel: pet. ether/ethyl acetate=4/1) to give methyl 2-(4-bromo-3-methoxyphenyl)-4-((tert-butoxycarbonyl)(methyl)amino)butanoate as an oil. $^1$H NMR (400 MHz, $CDCl_3$) δ 7.46 (d, J=8.0 Hz, 1H), 6.83 (s, 1H), 6.77 (dd, J=8.4 Hz, 1.6 Hz, 1H), 3.89 (s, 3H), 3.66 (s, 3H), 3.46-3.56 (m, 1H), 3.19 (s, 2H), 2.80 (br s, 3H), 2.31 (dq, J=14.4, 7.6 Hz, 1H), 1.92 (dq, J=14.4, 7.2 Hz, 1H), 1.43 (s, 9H).

Step 4. Synthesis of 3-(4-bromo-3-methoxyphenyl)-1-methylpyrrolidin-2-one

To a solution of methyl 2-(4-bromo-3-methoxyphenyl)-4-((tert-butoxycarbonyl)(methyl)amino)butanoate (80 mg) in DCM (3 mL) was added TFA (1 mL), then it was stirred at 20° C. for 1 h. LC/MS showed a product, then it was concentrated to give a residue. The residue was dissolved in MeOH (2 mL), then $Et_3N$ (0.13 mL, 0.96 mmol) was added and stirred at 40° C. for 15 h. LC/MS showed the desired product was formed. It was concentrated to give crude, the crude was purified by Prep. TLC (EtOAc) to give 3-(4-bromo-3-methoxyphenyl)-1-methylpyrrolidin-2-one as an oil. $^1$H NMR (500 MHz, $CDCl_3$) δ 7.48 (d, J=8.0 Hz, 1H), 6.86 (d, J=1.5 Hz, 1H), 6.72 (dd, J=8.0, 2.0 Hz, 1H), 3.90 (s, 3H), 3.63 (t, J=9.0 Hz, 1H), 3.40-3.51 (m, 2H), 2.94 (s, 3H), 2.52-2.56 (m, 1H), 2.07-2.17 (m, 1H).

Steps 5 and 6. Synthesis of Compounds 2-54 and 2-57

To a mixture of 3-(4-bromo-3-methoxyphenyl)-1-methylpyrrolidin-2-one (25 mg, 0.088 mmol), intermediate I-16 (59 mg, 0.088 mmol), $Cs_2CO_3$ (115 mg, 0.352 mmol) in Toluene (2 mL) was added t-BuBrettPhos (13 mg, 0.026 mmol) and $Pd_2(dba)_3$ (10 mg, 0.011 mmol). The mixture was stirred at 130° C. for 5 h under nitrogen. LC/MS showed desired product was formed. The mixture was purified by Prep. TLC (silica gel: MeOH:EtOAc=1:15) to give the desired adduct as an oil. The product was taken up in DCM (3 mL) and added TFA (1.5 mL). Then it was stirred at 10° C. for 1 h. LC/MS showed the reaction was finished. It was concentrated to give crude, the crude was purified by HPLC (YMC-Actus Triart C18 150*30 mm*5 um Condition water (0.1% TFA)-ACN Begin B 20 End B 50 Gradient Time (min) 11 100% B Hold Time (min) 1.1 FlowRate (mL/min) 40 Injections 1) to give the racemate as a solid. The enantiomers were resolved by Prep-SFC, SFC (DAICEL CHIRALPAK AD (150 mm*30 mm, 10 um) Condition 0.1% $NH_3H_2O$ IPA B 55 End B 55 FlowRate (mL/min) 80) to give 2-54 [RT: 2.504 min] and 2-57 [RT: 3.239 min] all as solids.

Compound 2-54 (R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one. $^1$H NMR (400 MHz, DMSO-$d_6$) δ 9.51 (s, 1H), 8.36 (d, J=8.4 Hz, 1H), 8.00 (s, 1H), 7.30 (s, 1H), 6.87 (d, J=1.2 Hz, 1H), 6.76 (dd, J=8.4, 1.2 Hz, 1H), 6.56 (d, J=5.6 Hz, 1H), 6.34 (s, 2H), 5.64 (br s, 1H), 4.25 (br t, J=4.4 Hz, 2H), 3.84 (s, 3H), 3.55 (t, J=8.8 Hz, 1H), 3.33-3.45 (m, 4H), 2.76 (s, 3H), 2.34-2.42 (m, 1H), 1.95-2.05 (m, 1H), 1.90 (s, 3H). MS (EI) calc'd for $C_{28}H_{29}FN_7O_3$ [M+H]$^+$, 530; found, 530.

Compound 2-57 (R or S)-3-(4-{[5-amino-6-fluoro-7-(8-methyl-2,3-dihydro-1H-pyrido[2,3-b][1,4]oxazin-7-ylquinazolin-2-yl]amino}-3-methoxyphenyl)-1-methylpyrrolidin-2-one. $^1$H NMR (400 MHz, $CD_3OD$) δ 9.37 (s, 1H), 8.58 (d, J=8.4 Hz, 1H), 7.35 (s, 1H), 6.86 (d, J=1.2 Hz, 1H), 6.81 (dd, J=8.4, 1.2 Hz, 1H), 6.74 (d, J=5.6 Hz, 1H), 4.33-4.41 (m, 2H), 3.92 (s, 3H), 3.67 (t, J=8.8 Hz, 1H), 3.47-3.58 (m, 2H), 3.42-3.47 (m, 2H), 2.89-2.94 (m, 3H), 2.45-2.57 (m, 1H), 2.07-2.17 (m, 1H), 2.00 (d, J=1.6 Hz, 3H). MS (EI) calc'd for $C_{28}H_{29}FN_7O_3$ [M+H]$^+$, 530; found, 530.

Preparation of Compound 2-75

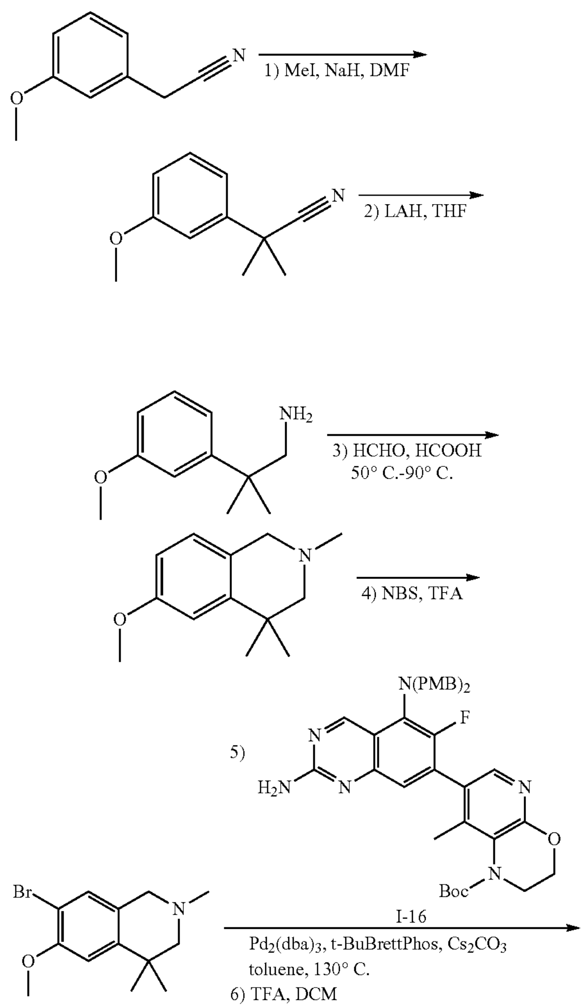

-continued

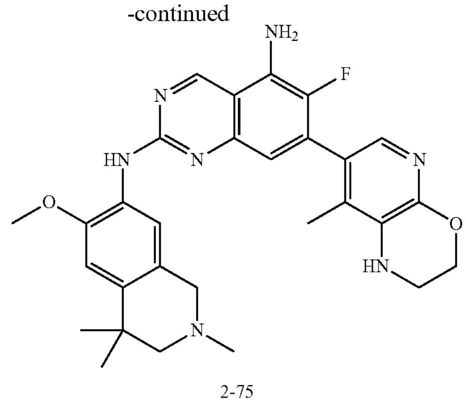

2-75

Step 1. Preparation of 2-(3-methoxyphenyl)-2-methylpropanenitrile

To a mixture of 2-(3-methoxyphenyl)acetonitrile (2.0 g, 14 mmol) in DMF (20 mL) was added NaH (60% in mineral oil) (1.63 g, 41 mmol) at 0° C. under nitrogen. Then the mixture was stirred at 0° C. for 0.5 h. Iodomethane (6.32 g, 44.5 mmol) was added at 0° C. The mixture was stirred at 25° C. for 12 h. LC/MS showed that the reaction completed. Water (200 mL) and EtOAc (100 mL) was added. The organic layer was separated and the aqueous was re-extracted with EtOAc (3×100 mL). The combined organic layers were washed with brine (200 mL), dried over anhydrous $Na_2SO_4$, filtered and concentrated. The residue was purified by flash silica gel chromatography (ISCO®; 40 g Agela Silica Flash Column, eluent of 60% EtOAc/pet. ether gradient at 40 mL/min) to give 2-(3-methoxyphenyl)-2-methylpropanenitrile as light oil. MS (EI) calc'd for $C_{11}H_{14}NO$ [M+H]$^+$, 176; found, 176.

Step 2. Preparation of 2-(3-methoxyphenyl)-2-methylpropan-1-amine

To a solution of 2-(3-methoxyphenyl)-2-methylpropanenitrile (2.3 g, 13 mmol) in THF (20 mL) was added LAH (450 mg, 11.9 mmol) at 25° C. After the addition, the mixture was stirred at this temperature for 5 h. LC/MS showed starting material was consumed. The mixture was cooled to room temperature, quenched with MeOH and stirred for 40 min until no gas formed. The residual mixture was adjusted to pH=9 with NaOH (1 M). The mixture was extracted with EtOAc (3×50 mL). The combined organic layers were washed with water (50 mL), brine (50 mL). The organic layer was dried over $Na_2SO_4$, filtered and concentrated in vacuum and purified by flash silica gel chromatography (ISCO®; 120 g SepaFlash® Silica Flash Column, Eluent of 10~60% EtOAc/Pet.ether gradient at 25 mL/min) to give 2-(3-methoxyphenyl)-2-methylpropan-1-amine as a solid. MS (EI) calc'd for $C_{11}H_{18}NO$ [M+H]$^+$, 180; found, 180.

Step 3. Preparation of 6-methoxy-2,4,4-trimethyl-1,2,3,4-tetrahydroisoquinoline

To a stirred solution of 2-(3-methoxyphenyl)-2-methylpropan-1-amine (1.1 g, 6.14 mmol) in HCOOH (10 mL) was added paraformaldehyde (500 mg, 5.39 mmol) at 20° C. After the addition was finished, the reaction was stirred at 50° C. for 2 h. LC/MS showed starting material was consumed. The mixture was warmed to 90° C. for another 1 h. LC/MS showed desired product as main peak. The resulting mixture was cooled to rt, diluted with water and extracted with DCM. The aqueous phase was separated, and basified with 4 N NaOH solution, then was extracted with DCM (3×50 mL). The combined organics were dried over anhydrous sodium sulfate, filtered, and concentrated to afford 6-methoxy-2,4,4-trimethyl-1,2,3,4-tetrahydroisoquinoline as an oil. MS (EI) calc'd for $C_{13}H_{20}NO$ $[M+H]^+$, 206; found, 206.

Step 4. Preparation of 7-bromo-6-methoxy-2,4,4-trimethyl-1,2,3,4-tetrahydroisoquinoline To a stirred solution of 6-methoxy-2,4,4-trimethyl-1,2,3,4-tetrahydroisoquinoline (700 mg, 3.41 mmol) in TFA (5 mL) was added NBS (546 mg, 3.07 mmol) at 0° C. After the addition was finished, the reaction was stirred at 25° C. for 3 h. LC/MS showed the reaction was finished. 2 N NaOH was added to the mixture to adjust pH>9. The mixture was extracted by DCM (3×20 mL), the organic layers were collected, washed with brine, dried over $Na_2SO_4$. After filtration, the filtrate was concentrated in vacuo. The crude product was purified by flash silica gel chromatography (ISCO®; Agela® Flash Column Silica-CS (4 g), eluent of 0-50% Ethyl acetate/Petroleum ether gradient at 35 mL/min) to give 7-bromo-6-methoxy-2,4,4-trimethyl-1,2,3,4-tetrahydroisoquinoline as an oil. MS (EI) calc'd for $C_{13}H_{19}BrNO$ $[M+H]^+$, 284; found, 284.

Steps 5 and 6. Synthesis of 2-75

Compound 2-75 was prepared from intermediate I-16 and 7-bromo-6-methoxy-2,4,4-trimethyl-1,2,3,4-tetrahydroisoquinoline using coupling method from Example 2F.

Compound 2-75. $^1H$ NMR (400 MHz, DMSO-$d_6$) δ 9.56 (s, 1H), 9.49-9.54 (m, 1H), 8.38 (s, 1H), 8.14 (br s, 1H), 7.34 (s, 1H), 7.08 (s, 1H), 6.67 (br d, J=5.6 Hz, 1H), 4.39-4.43 (m, 2H), 4.25-4.28 (m, 4H), 3.91 (s, 3H), 2.18-3.24 (m, 2H), 2.93 (br d, J=3.6 Hz, 3H), 1.92 (s, 3H), 1.40 (s, 3H), 1.35 (s, 3H). MS (EI) calc'd for $C_{29}H_{33}FN_7O_2$ $[M+H]^+$, 530; found, 530.

Preparation of Compound 2-88

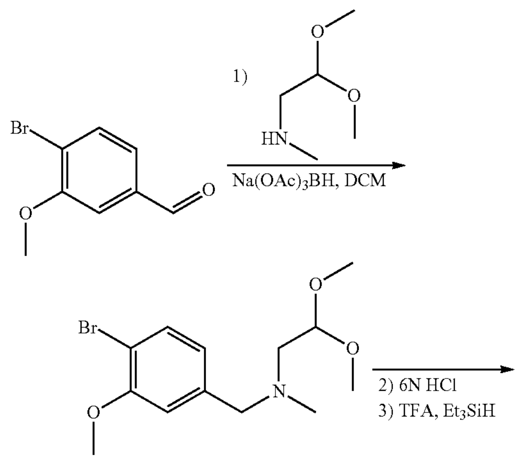

-continued

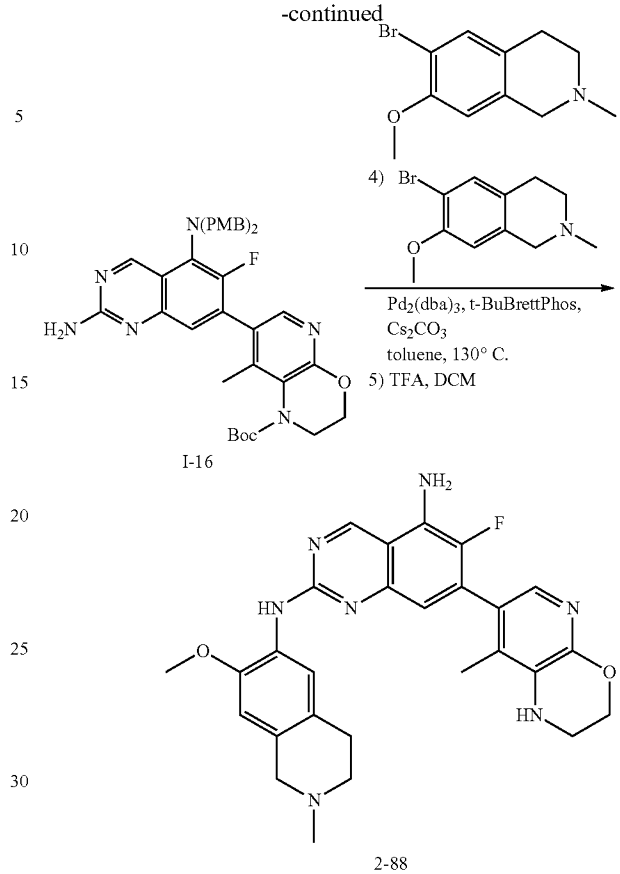

I-16

2-88

Step 1. Preparation of N-(4-bromo-3-methoxybenzyl)-2,2-dimethoxy-N-methylethanamine To a stirred solution of 4-bromo-3-methoxybenzaldehyde (1.0 g, 4.65 mmol) in DCM (5 mL) was added sodium cyanoborohydride (0.70 g, 11 mmol) and 2,2-dimethoxy-N-methylethanamine (1.11 g, 9.30 mmol) at 25° C. After the addition was finished, the reaction was stirred at 25° C. for 16 h. LC/MS showed the reaction was finished. The mixture was added 1 N NaOH solution to adjust pH>9, extracted by DCM (3×20 mL). The organic layers were collected, washed with brine, dried over $Na_2SO_4$, after filtration, the filtrate was concentrated in vacuo. The crude product was purified by flash silica gel chromatography (ISCO®; Agela® Flash Column Silica-CS (4 g) Eluent of 0~30% Ethyl acetate/Petroleum ether gradient at 35 mL/min) to give N-(4-bromo-3-methoxybenzyl)-2,2-dimethoxy-N-methylethanamine as an oil. $^1H$ NMR (500 MHz, $CDCl_3$) δ 7.44 (d, J=8.0 Hz, 1H), 6.94-6.98 (m, 2H), 6.77-6.83 (m, 2H), 5.30 (s, 1H), 3.90 (s, 3H), 3.52 (s, 2H), 3.33 (s, 6H), 2.70 (d, J=5.5 Hz, 2H), 2.31 (s, 3H).

Steps 2 and 3. Preparation of 6-bromo-7-methoxy-2-methyl-1,2,3,4-tetrahydroisoquinoline A mixture of N-(4-bromo-3-methoxybenzyl)-2,2-dimethoxy-N-methylethanamine (1.0 g, 3.14 mmol) in HCl (8 mL, 48 mmol) was stirred at 40° C. for 18 h. LC/MS showed the reaction was finished. The mixture was added 1 N NaOH solution to adjust pH>13. The mixture was extracted with DCM (3×30 mL) and concentrated under reduced pressure to give 6-bromo-7-methoxy-2-methyl-1,2,3,4-tetrahydroisoquinolin-4-ol (700 mg, 2.57 mmol) as an oil which was then taken up in DCM (2 mL) and added TFA (2 mL, 2.6 mmol). Triethylsilane (3.0 g, 26 mmol) was added to the mixture at 25° C. After the addition was finished, the reaction was stirred at 25° C. for 3 h. LC/MS showed the reaction was finished. The mixture was added 2 N NaOH solution to adjust pH>9. The mixture was extracted with DCM (3×20 mL). The organic layers were collected and washed with brine, dried over $Na_2SO_4$. After filtration, the filtrate was concentrated in vacuo to give 6-bromo-7-methoxy-2-methyl-1,2,3,4-tetrahydroisoquinoline (crude) as an oil. MS (EI) calc'd for $C_{11}H_{15}BrNO$ $[M+H]^+$, 256; found, 256.

Steps 4 and 5. Synthesis of Compound 2-88

Compound 2-88 was prepared from intermediate I-16 and 6-bromo-7-methoxy-2-methyl-1,2,3,4-tetrahydroisoquinoline using coupling method from Example 2F.

Compound 2-88. $^1H$ NMR (500 MHz, DMSO-$d_6$) δ 9.55 (s, 1H), 8.25 (s, 1H), 7.98 (s, 1H), 7.35 (s, 1H), 6.73 (s, 1H), 6.62 (d, J=5.5 Hz, 1H), 6.37 (s, 2H), 5.69 (br s, 1H), 4.30 (br s, 2H), 3.84 (s, 3H), 3.43-3.47 (m, 2H), 3.37-3.39 (m, 2H), 2.77-2.78 (m, 2H), 2.57-2.60 (m, 2H), 2.34 (s, 3H), 1.94 (s, 3H). MS (EI) calc'd for $C_{27}H_{29}FN_7O_2$ $[M+H]^+$, 502; found, 502.

Preparation of Compound 2-141

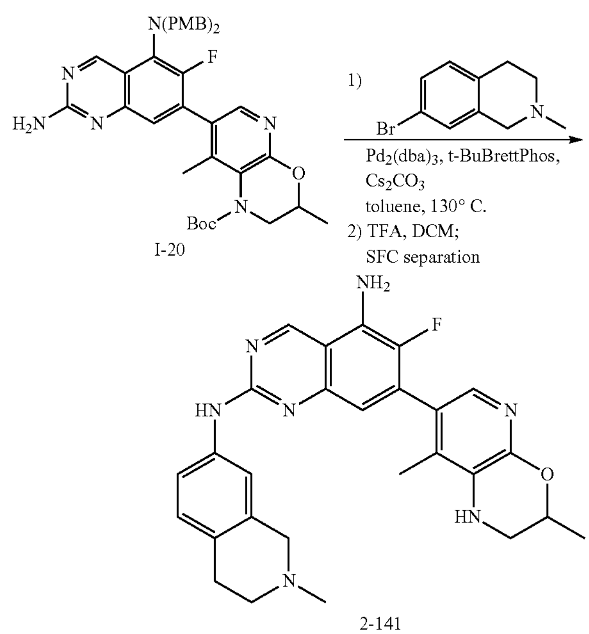

I-20

2-141

Steps 1 and 2. Synthesis of Compound 2-141

A mixture of intermediate I-20 (400 mg, 0.588 mmol), 7-bromo-2-methyl-1,2,3,4-tetrahydroisoquinoline (266 mg, 1.175 mmol), $Cs_2CO_3$ (574 mg, 1.763 mmol), $Pd_2(dba)_3$ (53.8 mg, 0.059 mmol) and t-BuBrettPhos (85 mg, 0.176 mmol) in toluene (8 mL). Then it was stirred at 130° C. for 5 h under $N_2$. LCMS showed the desired product. The mixture was added water (10 mL), and extracted with EtOAc (3×10 mL). The organic layers were washed with brine (10 mL), dried over $Na_2SO_4$, filtered and concentrated in vacuo and purified by flash silica gel chromatography (ISCO®; 4 g SepaFlash® Silica Flash Column, eluent of [0~100]% ethyl acetate/pet. ether gradient at 30 mL/min) to give the desired adduct (240 mg, 0.215 mmol) as a solid. The product was taken up in DCM (3 ml) and added TFA (3 ml). Then the solution was stirred at 30° C. for 1 h. The LCMS showed the desired product. The mixture was purified by Prep-HPLC (Column YMC-Actus Triart C18 100*30 mm*5 um Condition water (0.1% TFA)-ACN Begin B 10 End B 40 Gradient Time (min) 11 100% B Hold Time (min) 1.1 FlowRate (ml/min) 40 Injections 5) to give the fully deprotected product (a solid) as a mixture of enantiomers (100 mg, 0.189 mmol).

Compound 2-141 was separated by SFC to afford as a solid (18.20 mg, 0.036 mmol). The SFC method was Instrument ACSSH-CG, Column DAICEL CHIRALPAK IG(250 mm*50 mm, 10 um) Condition Heptane-EtOH Begin B 50 End B 100 Gradient Time (min) 10 100% B Hold Time (min) 20 FlowRate (ml/min) 25 Injections 5. $^1H$ NMR (400 MHz, $CD_3OD$) δ 9.39 (s, 1H), 7.63 (s, 1H), 7.57 (d, J=8.4 Hz, 1H), 7.38 (s, 1H), 7.09 (d, J=8.4 Hz, 1H), 6.75 (d, J=5.6 Hz, 1H), 4.37-4.41 (m, 1H), 3.70 (s, 2H), 3.49-3.52 (m, 1H), 3.12 (d, J=4.4 Hz, 1H), 2.91-2.95 (m, 2H), 2.80-2.84 (m, 2H), 2.50 (s, 3H), 2.03 (s, 3H), 1.44 (d, J=6.4 Hz, 3H). MS (EI) calc'd for $C_{27}H_{27}FN_7O$ $[M+H]^+$, 486; found, 486.

Preparation of Compound 2-145

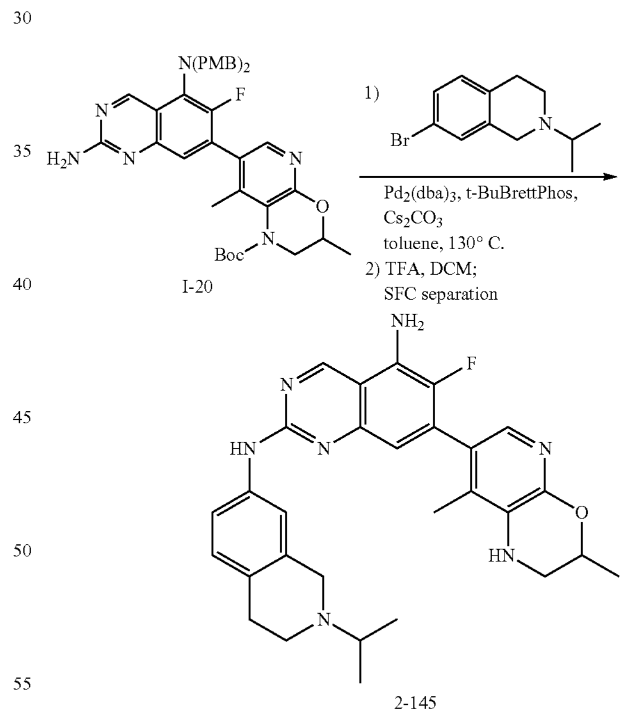

I-20

2-145

Steps 1 and 2. Synthesis of Compound 2-145

A mixture of intermediate I-20 (400 mg, 0.588 mmol), 7-bromo-2-isopropyl-1,2,3,4-tetrahydroisoquinoline (299 mg, 1.175 mmol), $Cs_2CO_3$ (574 mg, 1.763 mmol), $Pd_2(dba)_3$ (53.8 mg, 0.059 mmol) and t-BuBrettPhos (85 mg, 0.176 mmol) in toluene (8 ml). Then it was stirred at 130° C. for 5 h under $N_2$. LCMS showed the desired product was formed. The mixture was added water (10 mL), and extracted with EtOAc (3×10 mL). The organic layers were washed with brine (10 mL), dried over $Na_2SO_4$, filtered and concentrated in vacuum and purified by flash silica gel chromatography (ISCO®; 4 g SepaFlash® Silica Flash Column, eluent of [0~100]% ethyl acetate/pet. ether gradient at 30 mL/min) to give the desired adduct (200 mg, 0.176 mmol) as a solid. The product was taken up in DCM (2 mL) and added TFA (2 mL). Then the solution was stirred at 30° C. for 1 h. The LCMS showed the desired product. The mixture was purified by Prep-HPLC (Column YMC-Actus Triart C18 100*30 mm*5 um Condition water (0.1% TFA)-ACN Begin B 12 End B 42 Gradient Time (min) 11 100% B Hold Time (min) 1.1 FlowRate (ml/min) 40 Injections 4) to give the fully deprotected product (a solid) (100 mg, 0.190 mmol) as a mixture of enantiomers.

Compound 2-145 (18.30 mg, 0.032 mmol) was resolved by SFC to give a solid. The SFC method was Instrument ACSSH-CG, Column DAICEL CHIRALPAK IG(250 mm*50 mm, 10 um) Condition Heptane-EtOH Begin B 50 End B 100 Gradient Time (min) 10 100% B Hold Time (min) 20 FlowRate (ml/min) 25 Injections 5. $^1$H NMR (400 MHz, CD3OD) δ 9.38 (s, 1H), 7.68 (s, 1H), 7.54 (d, J=8.4 Hz, 1H), 7.36 (s, 1H), 7.07 (d, J=8.0 Hz, 1H), 6.77 (d, J=5.6 Hz, 1H), 4.36-4.40 (m, 1H), 3.84 (s, 2H), 3.50 (d, J=12.0 Hz 1H), 3.11 (d, J=12.0 Hz, 1H), 2.96-3.01 (m, 1H), 2.91 (s, 4H), 2.01 (s, 3H), 1.44 (d, J=6.4 Hz, 3H), 1.19 (d, J=6.8 Hz, 6H). MS (EI) calc'd for $C_{29}H_{33}FN_7O$ [M+H]$^+$, 514; found, 514.

Example 2G

Preparation of Compound 2-68

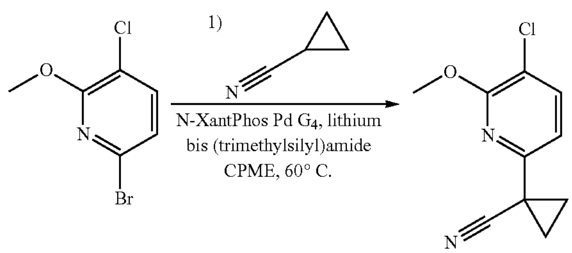

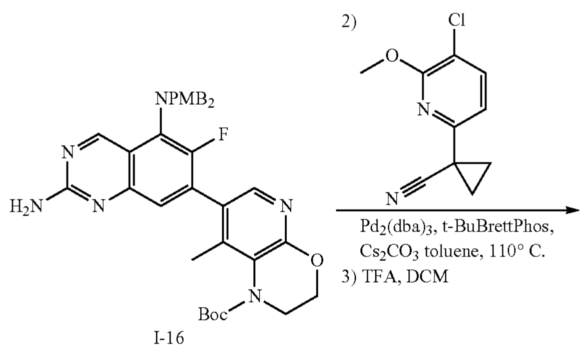

I-16

-continued

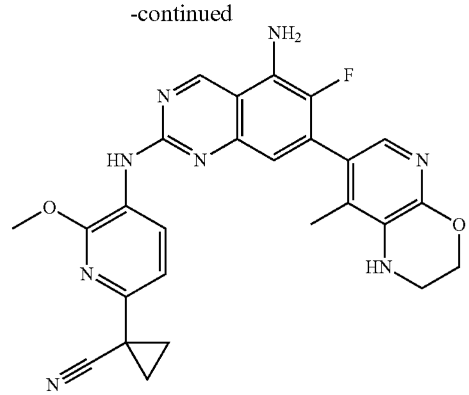

2-68

Step 1. Preparation of 1-(5-chloro-6-methoxy pyridin-2-yl)cyclopropane-1-carbonitrile To a vial containing 6-bromo-3-chloro-2-methoxypyridine (500 mg, 2.25 mmol) was added cyclopropanecarbonitrile (0.25 mL, 3.4 mmol) and N-XantPhos Pd G4 (105 mg, 0.112 mmol). The mixture was dissolved in CPME (11 mL) and degassed with nitrogen for 5 min. To the reaction mixture, under nitrogen, was added lithium bis(trimethylsilyl)amide (6.74 mL, 6.74 mmol). The mixture was heated to 60° C., and allowed to stir for 2 h. LC/MS indicated complete conversion to desired product. The reaction mixture was concentrated under reduced pressure. The crude residue was purified by normal phase column chromatography (gradient elution of DCM/EtOAc) to afford 1-(5-chloro-6-methoxypyridin-2-yl)cyclopropane-1-carbonitrile as orange solid. MS (EI) calc'd for $C_{10}H_{10}ClN_2O$ [M+H]$^+$, 209, 211; found, 209, 211.

Steps 2 and 3. Synthesis of 2-68

To a vial containing intermediate I-16 (100 mg, 0.150 mmol) was added 1-(5-chloro-6-methoxypyridin-2-yl)cyclopropane-1-carbonitrile (47 mg, 0.23 mmol), $Pd_2(dba)_3$ (28 mg, 0.030 mmol), t-BuBrettPhos (29 mg, 0.060 mmol) and $Cs_2CO_3$ (147 mg, 0.450 mmol). The mixture was dissolved in toluene (3 mL) and degassed with nitrogen gas for 5 min. The reaction was heated to 90° C., and allowed to stir for 14 h. LC/MS indicated desired product: SM was still observed. The reaction mixture was filtered and concentrated under reduced pressure. The crude residue was purified by normal phase column chromatography (gradient elution of 0-100% DCM/EtOAc) to afford the protected product as an oil. The oil was dissolved in 1 mL of DCM and 0.5 mL of TFA. The reaction mixture was allowed to stir at RT for 1 h. The reaction mixture was concentrated under reduced pressure. The crude residue was dissolved in DMSO and filtered. The solution was purified by reverse phase column chromatography (gradient elution of 15-70% Acetonitrile/Water+0.1% TFA) to afford 2-68 as orange solid. $^1$H NMR (500 MHz, DMSO-$d_6$) δ 9.61 (s, 1H), 8.75 (d, J=8.0 Hz, 1H), 8.34 (s, 1H), 7.40 (s, 1H), 7.19 (d, J=8.0 Hz, 1H), 6.67 (d, J=5.7 Hz, 1H), 4.35 (s, 2H), 3.93 (s, 3H), 3.41 (s, 2H), 1.96 (s, 3H), 1.81-1.62 (m, 4H). MS (EI) calc'd for $C_{26}H_{24}FN_8O_2$ [M+H]$^+$, 499; found, 499.

Preparation of Compound 2-70 (6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine)

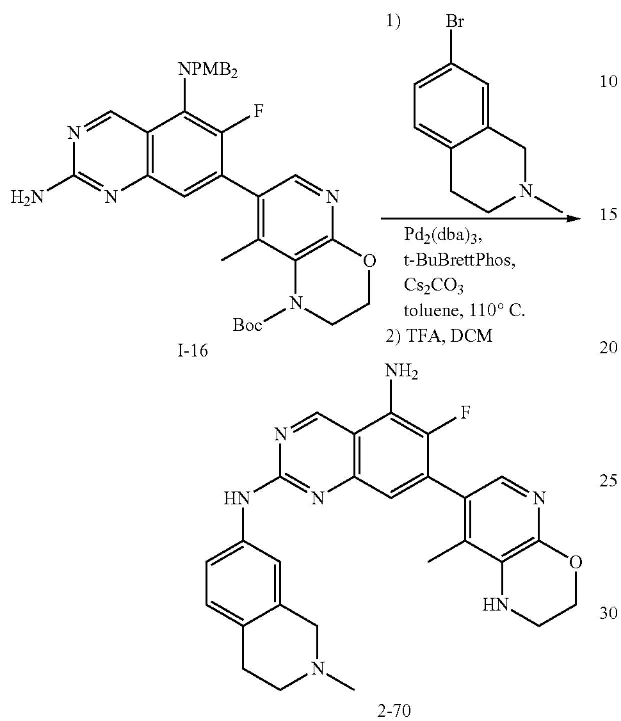

I-16

2-70

Steps 1 and 2. Synthesis of 2-70

A mixture containing $Cs_2CO_3$ (800 mg, 2.455 mmol), $Pd_2(dba)_3$ (110 mg, 0.120 mmol), t-BuBrettPhos (120 mg, 0.248 mmol), 7-bromo-2-methyl-1,2,3,4-tetrahydroisoquinoline (500 mg, 2.211 mmol), intermediate I-16 (8(0) mg, 1.20 mmol) in toluene (5 mL) was deoxygenated by bubbling nitrogen for 3 min, then warmed to 110° C., and stirred overnight. After cooling, the reaction was filtered and concentrated to dryness. The crude oil was purified by chromatography on $SiO_2$ (80 g silica gel, gradient of 0-50% MeOH/DCM) to provide the desired adduct as an oil. The oil was dissolved in 2 mL of DCM and 2 mL of TFA and aged for 2 hours. After 2 h, the reaction was concentrated and purified by reverse phase chromatography (gradient of 2-55% ACN/water with 0.1% TFA) to provide compound 2-70 as a light orange solid. $^1$H NMR (500 MHz, DMSO-$d_6$) δ 9.92 (s, 1H), 9.85 (s, 1H), 9.59 (s, 1H), 8.03 (s, 1H), 7.68 (d, J=8.5 Hz, 1H), 7.41 (s, 1H), 7.18 (d, J=8.5 Hz, 1H), 6.67 (d, J=5.7 Hz, 1H), 4.52 (d, J=14.9 Hz, 2H), 4.39-4.26 (m, 4H), 3.66 (s, 1H), 3.47-3.25 (m, 3H), 3.14-2.88 (m, 5H), 1.97 (s, 3H). MS (EI) calc'd for $C_{26}H_{27}FN_7O$ [M+H]$^+$, 472; found, 472.

Preparation of Compound 2-148

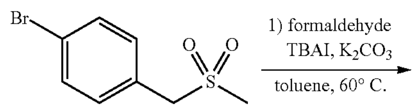

-continued

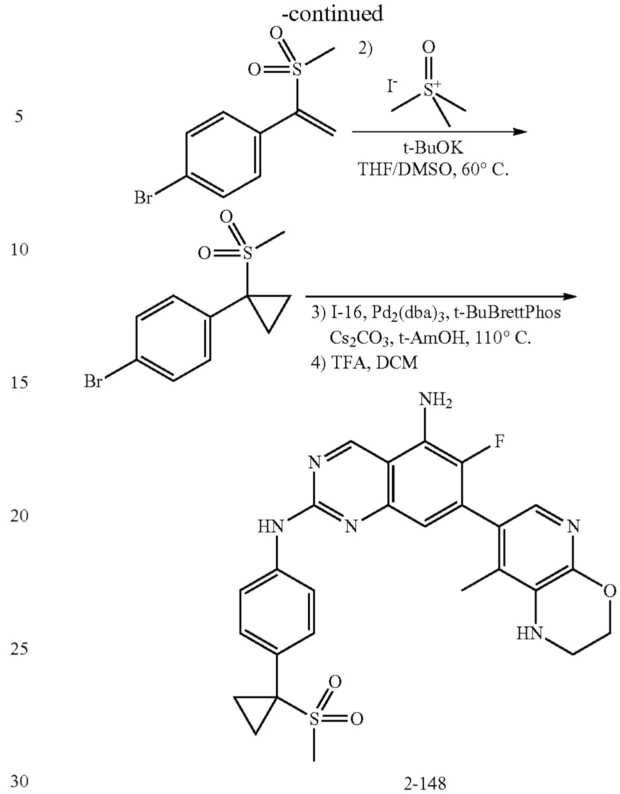

2-148

Step 1. Preparation of 1-bromo-4-(1-(methylsulfonyl)vinyl)benzene

To a solution of 1-bromo-4-((methylsulfonyl) methyl) benzene (3 g, 12.04 mmol) in Toluene (20 mL) was added formaldehyde (1.085 g, 36.1 mmol), $K_2CO_3$ (4.99 g, 36.1 mmol) and TBAI (0.222 g, 0.602 mmol). Then it was stirred at 60° C. for 15 h. TLC showed finished, it was filtered and purified by flash silica gel chromatography (ISCO®; 4 g SepaFlash® Silica Flash Column, eluent of [0~5]% ethyl acetate/pet. ether gradient at 30 mL/min) to give 1-bromo-4-(1-(methylsulfonyl)vinyl)benzene (340 mg, 1.302 mmol) as an oil. $^1$H NMR (400 MHz, $CDCl_3$) δ 7.59 (d, J=8.0 Hz, 2H), 7.52 (d, J=8.0 Hz, 2H), 6.56 (s, 1H), 6.04 (s, 1H), 2.81 (s, 3H).

Step 2. Preparation of 1-bromo-4-(1-(methylsulfonyl)cyclopropyl)benzene

Trimethylsulfoxonium iodide (337 mg, 1.532 mmol) in DMSO (1 mL) were sequentially added to a 100 mL single-mouth bottle, potassium tert-butoxide (172 mg, 1.532 mmol) in THF (5 mL), the two peak mix together and stirred at 25° C. for 20 minutes, then 1-bromo-4-(1-(methylsulfonyl)vinyl)benzene (200 mg, 0.766 mmol) was added to the mixture. The reaction was monitored by TLC (Pe.ether/EA=2:1), after stirring at 25° C. for 1 h, the reaction was finished. Followed by addition of 1 M hydrochloric acid (10 mL), ethyl acetate (20 mL) and water (15 mL), still separated, the aqueous phase with ethyl acetate (20 mL) and the combined organic phases, the organic phase was washed with a saturated sodium chloride solution, dried over anhydrous sodium sulfate, filtered, and concentrated under reduced pressure, the resulting residue was purified by silica gel column chromatography (PE/EtOAc=10/1) was purified to give the title 1-bromo-4-(1-(methylsulfonyl)cyclopropyl) benzene (200 mg, 0.727 mmol) as an oil. $^1$H NMR (400 MHz, $CDCl_3$) δ 7.49-7.53 (m, 2H), 7.39-7.44 (m, 2H), 2.74 (s, 3H), 1.80-1.85 (m, 2H), 1.23-1.27 (m, 2H).

Steps 3 and 4. Preparation of Compound 2-148

A mixture of t-BuBrettPhos (40.3 mg, 0.075 mmol), 1-bromo-4-(1-(methylsulfonyl)cyclopropyl)benzene (124 mg, 0.450 mmol), $Cs_2CO_3$ (147 mg, 0.450 mmol), intermediate I-16 (100 mg, 0.150 mmol) and $Pd_2(dba)_3$ (27.5 mg, 0.030 mmol) in t-AmOH (3 mL) was degassed and back-filled with $N_2$ (three times). The reaction mixture was stirred at 110° C. for 16 h. LCMS showed the desired product. The reaction mixture was quenched with water (15 mL), then the mixture was extracted with EtOAc (20 mL×3), the combined organic layer was washed with brine (15 mL), dried over anhydrous $Na_2SO_4$, filtered and concentrated to give the desired adduct (50 mg, 0.058 mmol). The product was taken up in DCM (3 mL) was added TFA (1.5 mL) at 25° C. The reaction was stirred at 25° C. for 1 h. The mixture was added 2 N NaOH solution to adjust pH>9, extracted by DCM (3×20 mL), the organic layers were collected, washed with brine, dried over $Na_2SO_4$, after filtration, the filtrate was concentrated in vacuo. The crude product was purified by prep-HPLC (Instrument EI Method Column Phenomenex Synergi C18 150*30 mm*4 um Condition water (0.225% FA)-ACN Begin B 35 End B 55 Gradient Time (min) 11 100% B Hold Time (min) 2 FlowRate (mL/min) 25 Injections 4) to give 2-148 (19.58 mg, 0.037 mmol) as a solid. $^1$H NMR (400 MHz, $CDCl_3$): δ 9.21 (s, 1H), 7.85 (d, J=8.8 Hz, 2H), 7.62 (s, 1H), 7.54 (d, J=8.8 Hz, 2H), 7.37 (s, 1H), 7.06 (d, J=6.0 Hz, 1H), 4.46-4.49 (m, 2H), 4.44 (s, 2H), 3.75 (br s, 1H), 3.55 (br s, 2H), 2.79 (s, 3H), 2.02 (s, 3H), 1.80-1.86 (m, 2H), 1.26-1.31 (m, 2H). MS (EI) calc'd for $C_{26}H_{26}FN_6O_3S$ [M+H]$^+$, 521; found, 521.

Example 2H

Preparation of Compounds 2-85 and 2-86

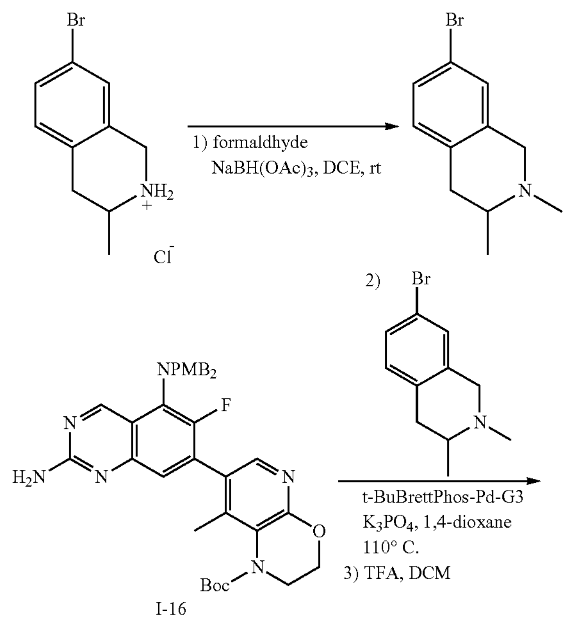

I-16

-continued

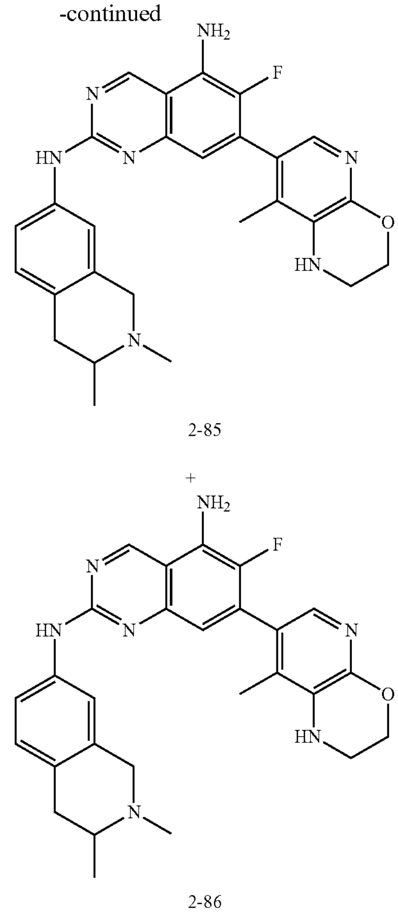

2-85

+

2-86

Steps 1. Preparation of 7-bromo-2,3-dimethyl-1,2,3,4-tetrahydroisoquinoline

A solution of 7-bromo-3-methyl-1,2,3,4-tetrahydroisoquinoline hydrochloride in DCE (60 mL) was treated with formaldehyde (3 mL, 40 mmol, 37 wt %) at room temperature and the reaction was stirred for 15 minutes. Sodium triacetoxyborohydride (12.1 g, 57.1 mmol) was then added and the reaction was stirred overnight. The reaction was quenched by the addition of sodium hydroxide (30 mL, 1M) and stirred for 15 minutes. The layers were separated and the aqueous layer was extracted with DCM (1×30 mL), the organic fractions were dried over sodium sulfate, filtered and concentrated. This provided 7-bromo-2,3-dimethyl-1,2,3,4-tetrahydroisoquinoline which was used without further purification. MS (EI) calc'd for $C_{11}H_{15}BrN$ [M+H]$^+$, 240, 242; found, 240, 242.

Steps 2-3. Synthesis of Compounds 2-85 and 2-86

A vial charged with 7-bromo-2,3-dimethyl-1,2,3,4-tetrahydroisoquinoline (216 mg, 0.900 mmol), tert-butyl 7-(2-amino-5-(bis(4-methoxybenzyl)amino)-6-fluoroquinazolin-7-yl)-8-methyl-2,3-dihydro-1H-pyrido[2,3-b][1.4]oxazine-1-carboxylate (500 mg, 0.750 mmol), tBuBrettPhos-Pd-G3 (64 mg, 0.075 mmol), and $K_3PO_4$ (318 mg, 1.50 mmol) was evacuated and backfilled with argon, dioxane (7.5 mL) was added and the reaction was stirred overnight at 110° C. After cooling, the reaction was diluted with DCM (5 mL) filtered through celite and concentrated to dryness. The residual oil was taken up in DCM (7 mL) and treated with TFA (3 mL). The reaction was stirred overnight and concentrated. The crude mixture was purified by reverse phase chromatography (15-70% ACN/water with 0.1% TFA) to afford the desired product. The enantiomers were resolved by chiral-Prep-SFC [Column OD-H, 21×250 mm; 45% (MeOH/0.1% $NH_4OH$)/$CO_2$; Flow rate: 70 mL/min; 220 nm] to provide 2-85 [RT: 4.5 min] and 2-86 [RT: 5.8 min].

Compound 2-85 ((R or S)—$N_2$-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine). $^1H$ NMR (499 MHz, DMSO-$d_6$) δ 9.55 (s, 1H), 9.54 (s, 1H), 7.72 (s, 1H), 7.58 (dd, J=8.3, 1.9 Hz, 1H), 7.34 (s, 1H), 6.97 (d, J=8.3 Hz, 1H), 6.59 (d, J=5.7 Hz, 1H), 6.32 (s, 2H), 5.70-5.65 (m, 1H), 4.31-4.26 (m, 2H), 3.70 (d, J=15.7 Hz, 1H), 3.43 (d, J=15.7 Hz, 1H), 3.39-3.35 (m, 2H), 2.74 (dd, J=15.6, 3.4 Hz, 1H), 2.60-2.44 (m, 2H), 2.29 (s, 3H), 1.93 (s, 3H), 1.06 (d, J=6.1 Hz, 3H). MS (EI) calc'd for $C_{27}H_{29}FN_7O$ $[M+H]^+$, 486; found, 486.

Compound 2-86 ((R or S)—$N_2$-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine). $^1H$ NMR (499 MHz, DMSO-$d_6$) δ 9.55 (s, 1H), 9.54 (s, 1H), 7.72 (s, 1H), 7.58 (dd, J=8.3, 1.9 Hz, 1H), 7.34 (s, 1H), 6.97 (d, J=8.3 Hz, 1H), 6.59 (d, J=5.7 Hz, 1H), 6.32 (s, 2H), 5.70-5.65 (m, 1H), 4.31-4.26 (m, 2H), 3.70 (d, J=15.7 Hz, 1H), 3.43 (d, J=15.7 Hz, 1H), 3.39-3.35 (m, 2H), 2.74 (dd, J=15.6, 3.4 Hz, 1H), 2.60-2.44 (m, 2H), 2.29 (s, 3H), 1.93 (s, 3H), 1.06 (d, J=6.1 Hz, 3H). MS (EI) calc'd for $C_{27}H_{29}FN_7O$ $[M+H]^+$, 486; found, 486.

Example 21

Preparation of Compound 2-133

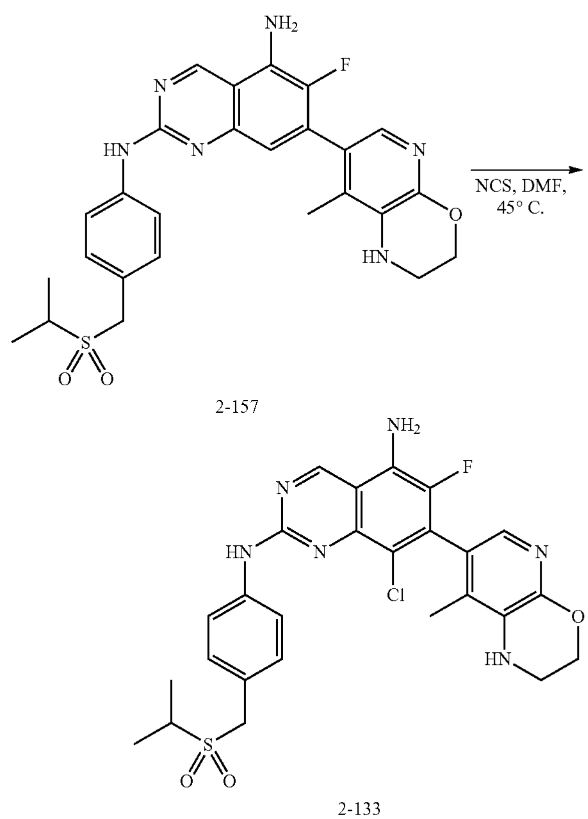

2-157

2-133

Compound 2-157 was prepared using coupling method exemplified in Example 2O with intermediate I-16 and 1-bromo-4-((isopropylsulfonyl)methyl)benzene. After deprotection (also exemplified in Example 2O) compound 2-157 was isolated. MS (ESI) m/z calc'd for $C_{26}H_{28}FN_6O_3S$ $[M+H]^+$, 523, found 523.

Upon isolation, compound 2-133 were prepared from compound 2-157.

To a mixture of compound 2-157 (43 mg, 0.081 mmol) in DMF (1 mL) was added N-chlorosuccinimide (10.77 mg, 0.081 mmol). The reaction mixture was stirred at 40° C. for 1 h. The color turned yellow. LC-MS showed major desired product. The mixture was concentrated to give a residue which was purified by Prep-Hplc (Instrument ee: Method Column YMC-Actus Triart C18 100 mm*30 mm*5 um; Condition water (0.1% TFA)-ACN Begin B 27 End B 57 Gradient Time (min) 11; 100% B Hold Time (min) 1.1 FlowRate (mL/min) 40; Injections 1) to give 2-133 (11.21 mg, 0.019 mmol), a solid, as a mixture of atropisomers.

Compound 2-133. $^1H$ NMR (400 MHz, DMSO-$d_6$): δ 10.11 (s, 1H), 9.61 (s, 1H), 8.14 (br d, J=8.4 Hz, 2H), 7.13-7.40 (m, 3H), 4.29-4.42 (m, 4H), 3.50-3.51 (m, 1H), 3.07-3.14 (m, 1H), 1.87 (s, 3H), 1.25 (d, J=6.8 Hz, 6H). MS (ESI) m/z calc'd for $C_{26}H_{27}ClFN_6O_3S$ $[M+H]^+$, 557, found 557.

Example 2J

Preparation of Compound 2-72

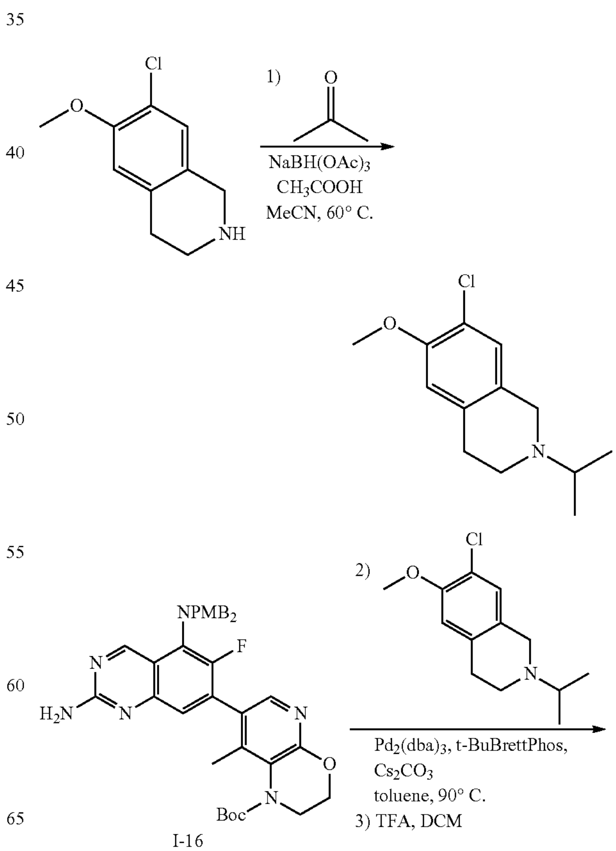

I-16

-continued

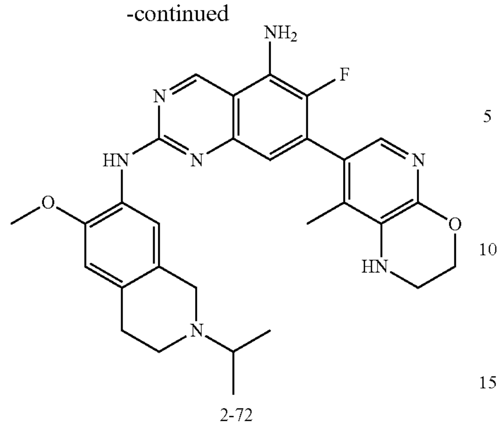

2-72

Step 1. Preparation of 7-chloro-2-isopropyl-6-methoxy-1,2,3,4-tetrahydroisoquinoline A mixture of 7-chloro-6-methoxy-1,2,3,4-tetrahydroisoquinoline (1.50 g, 7.59 mmol) and propan-2-one (2.8 mL, 38 mmol) in ACN (15 mL) and acetic acid (0.10 mL, 1.7 mmol) was stirred for 30 min. To this, sodium triacetoxyborohydride (4.83 g, 22.8 mmol) was added and stirred overnight. Excess solvent was removed in vacuo and this was directly purified on a silica gel column using DCM-MeOH. Appropriate fractions were pooled together, excess solvent was removed under reduced pressure and this was vacuum-dried to give the desired compound as an oil. MS (EI) calc'd for $C_{13}H_{19}ClNO$ $[M+H]^+$, 240; found, 240.

Steps 2 and 3. Synthesis of 2-72

To a vial, intermediate I-16, 7-chloro-2-isopropyl-6-methoxy-1,2,3,4-tetrahydroisoquinoline (342 mg, 1.43 mmol) and t-BuBrettPhos (33 mg, 0.067 mmol) and $Pd_2(dba)_3$ (31 mg, 0.034 mmol) and ground $Cs_2CO_3$ (501 mg, 1.54 mmol) and toluene (4 mL) were added. The vial was thoroughly flushed with nitrogen and then stirred at 90° C. overnight. The reaction mixture was filtered through a bed of celite and washed with DCM. Excess solvent was removed under reduced pressure and the residue was directly purified on a silica gel column using 10% MeOH-DCM. Appropriate fractions were pooled together and excess solvent was removed under reduced pressure and the oil obtained was vacuum dried to give the desired adduct as a solid. The product (404 mg, 0.464 mmol) in DCM (3 mL) was added TFA (1.00 mL, 0.464 mmol) and stirred overnight. Excess solvent was removed under reduced pressure. The oil obtained was co-evaporated several times with DCM/ethyl ether. The reaction mixture was neutralized with aq. $NaHCO_3$ soln and extracted with DCM. The org. layer was separated, washed with brine, dried over anhydrous magnesium sulfate, filtered and excess solvent was removed under reduced pressure. This was purified on HPLC using gradient elution with ACN-water and TFA as a modifier. Appropriate fractions were pooled together, excess solvent was removed under reduced pressure and this was lyophilized to give the title compound as an orange solid. $^1H$ NMR (500 MHz, DMSO-$d_6$) δ 9.59 (s, 1H), 8.53 (s, 1H), 8.11 (s, 1H), 7.36 (s, 1H), 6.97 (s, 1H), 6.84-6.70 (m, 1H), 6.59-6.36 (m, 1H), 4.43-4.35 (m, 2H), 4.35-4.28 (m, 3H), 3.7-3.6 (m, 2H), 3.46-3.34 (m, 4H), 3.34-3.22 (m, 2H), 3.22-3.09 (m, 2H), 3.09-2.96 (m, 1H), 1.94 (s, 3H), 1.40-1.30 (m, 6H). MS (EI) calc'd for $C_{29}H_{33}FN_7O_2$ $[M+H]^+$, 530; found, 530.

Preparation of Compound 2-76 (6-fluoro-7-(8-methyl-2,3-dihydro-11H-pyrido[2,3-b][1,4]oxazin-7-yl)-N~2~-[2-(propan-2-yl)-1,2,3,4-tetrahydroisoquinolin-7-yl]quinazoline-2,5-diamine)

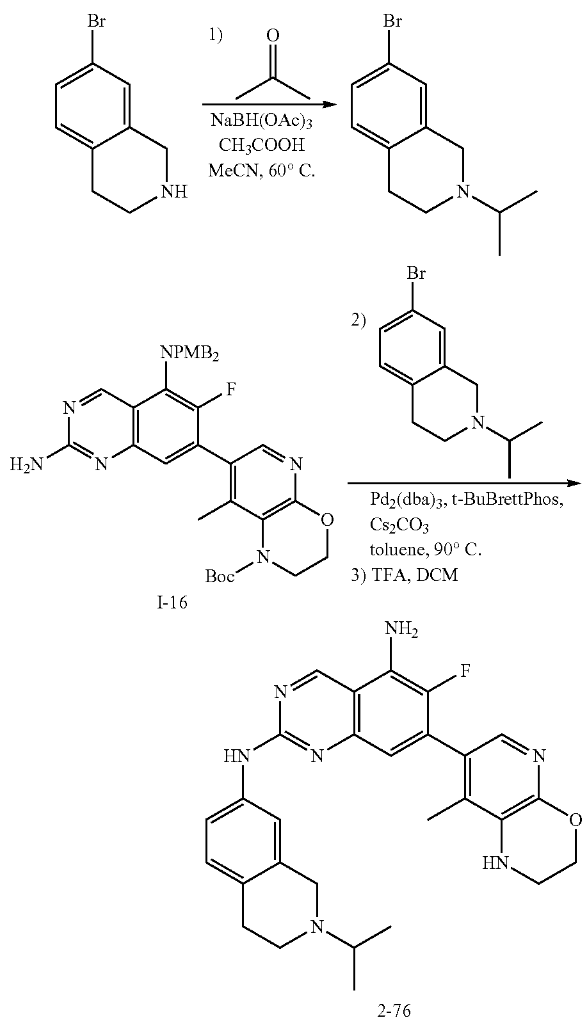

I-16

2-76

Step 1. Preparation of 7-bromo-2-isopropyl-1,2,3,4-tetrahydroisoquinoline

To 7-bromo-1,2,3,4-tetrahydroisoquinoline (2.00 g, 9.43 mmol) and propan-2-one (3.5 mL, 47 mmol) in ACN (16 mL), acetic acid (0.12 mL, 2.2 mmol) was added and stirred for 30 min. To this sodium triacetoxyborohydride (6.0) g, 28.3 mmol) was added and the suspension was stirred overnight at room temperature. This was directly purified on a silica gel column using 10% DCM-MeOH. Appropriate fractions were pooled together, excess solvent was removed under reduced pressure and vacuum dried to give the desired compound as an oil. MS (EI) calc'd for $C_{12}H_{17}BrN$ $[M+H]^+$, 254, 256; found, 254, 256.

Steps 2 and 3. Synthesis of Compound 2-76

Compound 2-76 was prepared from intermediate I-16 and 7-bromo-2-isopropyl-1,2,3,4-tetrahydroisoquinoline using coupling method from Example 2J.

Compound 2-76. $^1$H NMR (500 MHz, DMSO-$d_6$) δ 9.59 (s, 1H), 8.53 (s, 1H), 8.11 (s, 1H), 7.36 (s, 1H), 6.97 (s, 1H), 6.84-6.70 (m, 1H), 6.59-6.36 (m, 1H), 4.43-4.35 (m, 2H), 4.35-4.28 (m, 3H), 3.46-3.34 (m, 4H), 3.34-3.22 (m, 2H), 3.22-3.09 (m, 2H), 3.09-2.96 (m, 1H), 1.94 (s, 3H), 1.40-1.30 (m, 6H). MS (EI) calc'd for $C_{21}H_{31}FN_7O$ [M+H]$^+$, 500; found, 500.

Example 2K

Preparation of Compounds 2-91 and 2-92

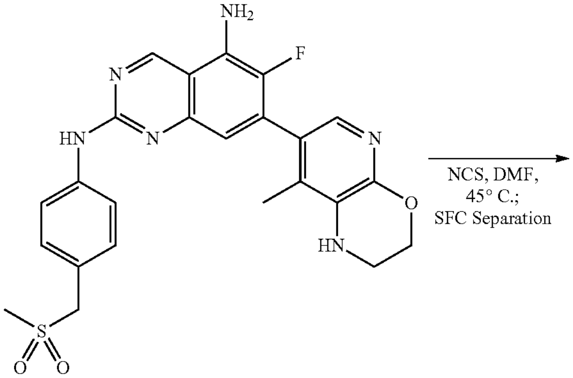

2-24

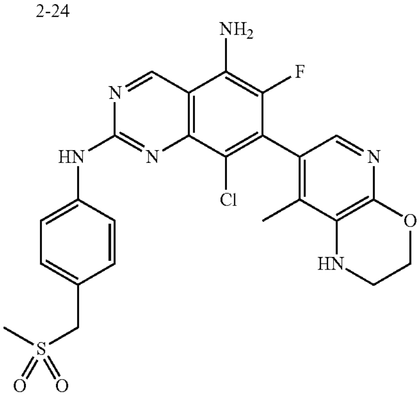

2-91

+

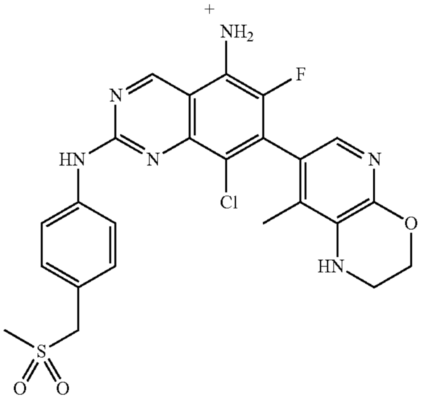

2-92

A solution of compound 2-24 (200 mg, 0.405 mmol) in DMF (8 mL) was treated with N-chlorosuccinimide (54 mg, 0.41 mmol). The reaction was heated to 45° C. for 1 h and 40 min. Notable amounts of starting material was still present. The reaction was allowed to stir for additional 1 h. The reaction was diluted in DMSO/MeOH and purified by reverse phase chromatography (15-70% ACN/water with 0.1% $NH_4OH$). After concentration, the atropisomers were resolved by chiral SFC [Column AS-H, 21×250 mm; 45% (MeOH/0.1% $NH_4OH$)/$CO_2$; Flow rate: 70 mL/min: 220 nm] to provide 2-91 [RT: 4.3 min] and 2-92 [RT: 6.0 min].

Compound 2-91. $^1$H NMR (500 MHz, DMSO-$d_6$) δ 10.11 (s, 1H), 9.65 (s, 1H), 8.17 (d, J=8.6 Hz, 2H), 7.36 (d, J=8.7 Hz, 2H), 7.29 (s, 1H), 6.54 (s, 2H), 4.40 (s, 2H), 4.37-4.26 (m, 2H), 3.42-3.38 (m, 2H), 2.87 (s, 3H), 1.86 (s, 3H). MS (EI) calc'd for $C_{24}H_{23}ClFN_6O_3S$ [+H]$^+$, 529, 531; found, 529, 531.

Compound 2-92. $^1$H NMR (500 MHz, DMSO-$d_6$) δ 10.11 (s, 1H), 9.65 (s, 1H), 8.17 (d, J=8.5 Hz, 2H), 7.36 (d, J=8.6 Hz, 2H), 7.28 (s, 1H), 6.53 (s, 2H), 5.72 (s, 1H), 4.40 (s, 2H), 4.32 (s, 2H), 3.44-3.37 (m, 2H), 2.87 (s, 3H), 1.86 (s, 3H). MS (EI) calc'd for $C_{24}H_{23}ClFN_6O_3S$ [M+H]$^+$, 529, 531; found, 529, 531.

Preparation of Compounds 2-90, 2-93, and 2-94

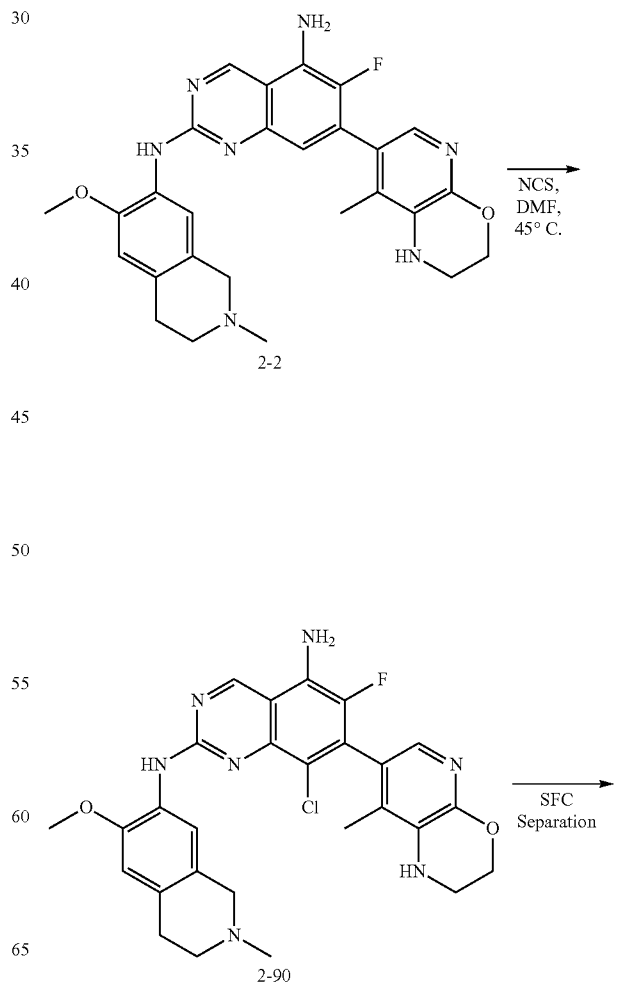

2-2

2-90

-continued

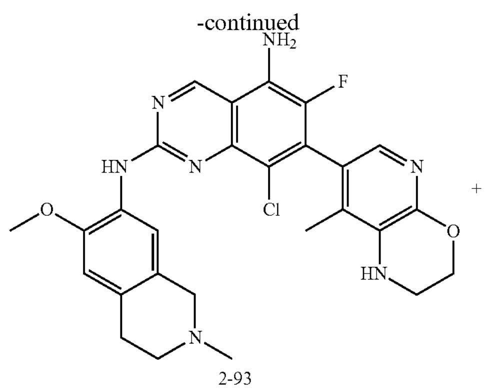

2-93

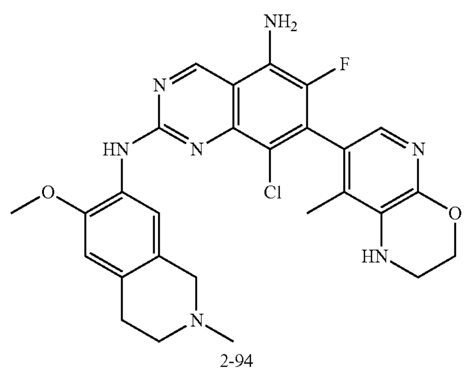

2-94

A solution of compound 2-2 (447 mg, 0.726 mmol) in DMF (3 mL) was treated at RT with NCS (100 mg, 0.749 mmol) and the reaction warmed to 45° C. Stirred for 60 min. LC/MS analysis indicates good conversion to a halogenated product. Quenched with 0.5 mL of 1 M $Na_2S_2O_3$ solution. Stirred for 10 min, filtered and purified by reverse phase chromatography (gradient of 2-55% ACN/water with 0.1% TFA) gave 2-90.

Compound 2-90. $^1$H NMR (500 MHz, DMSO-$d_6$) δ 9.93 (s, 1H), 9.65 (s, 1H), 8.83 (d, J=6.1 Hz, 1H), 8.33 (s, 1H), 7.32 (s, 1H), 6.97 (s, 1H), 4.45-4.17 (m, 6H), 3.92 (s, 3H), 3.66 (s, 1H), 3.46-3.26 (m, 3H), 3.19-2.85 (m, 5H), 1.87 (s, 3H). MS (EI) calc'd for $C_{27}H_{28}ClFN_7O_2$ $[M+H]^+$, 536; found, 536.

The atropisomers were resolved by chiral SFC [Column CCA F4, 21×250 mm; 35% (MeOH/0.1% $NH_4OH$)/$CO_2$; Flow rate: 70 mL/min; 220 nm] to provide 2-94 [RT: 3.4 min] and 2-93 [RT: 4.6 min].

Compound 2-93. $^1$H NMR (600 MHz, DMSO-$d_6$) δ 9.62 (s, 1H), 8.69 (s, 1H), 8.20 (s, 1H), 7.28 (s, 1H), 6.84 (s, 1H), 6.56 (s, 2H), 5.72 (s, 1H), 4.31 (s, 2H), 3.89 (s, 3H), 3.70 (d, J=75.8 Hz, 2H), 3.39 (s, 2H), 2.86 (s, 3H), 2.47 (s, 2H), 2.08 (s, 1H), 1.86 (s, 3H). MS (EI) calc'd for $C_{27}H_{28}ClFN_7O_2$ $[M+H]^+$, 536; found, 536.

Compound 2-94. $^1$H NMR (500 MHz, DMSO-$d_6$) δ 9.61 (s, 1H), 8.65 (s, 1H), 8.16 (s, 1H), 7.28 (s, 1H), 6.80 (s, 1H), 6.55 (s, 2H), 5.71 (s, 1H), 4.39-4.24 (m, 2H), 3.88 (s, 3H), 3.41 (d, J=19.3 Hz, 4H), 2.80 (t, J=5.6 Hz, 2H), 2.32 (s, 3H), 1.86 (s, 3H). MS (EI) calc'd for $C_{27}H_{28}ClFN_7O_2$ $[M+H]^+$, 536; found, 536.

Preparation of Compounds 2-97 and 2-98

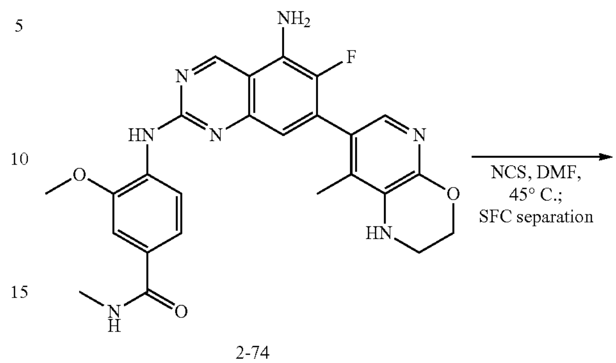

2-74

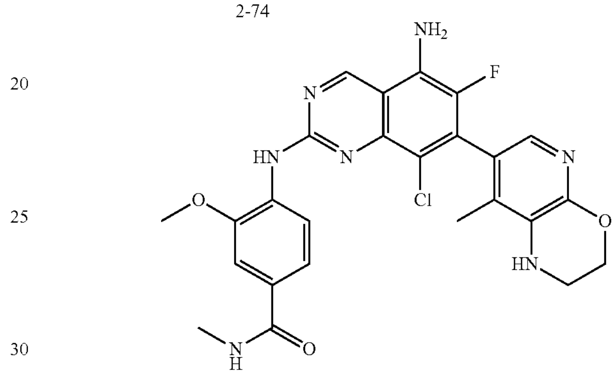

2-97

+

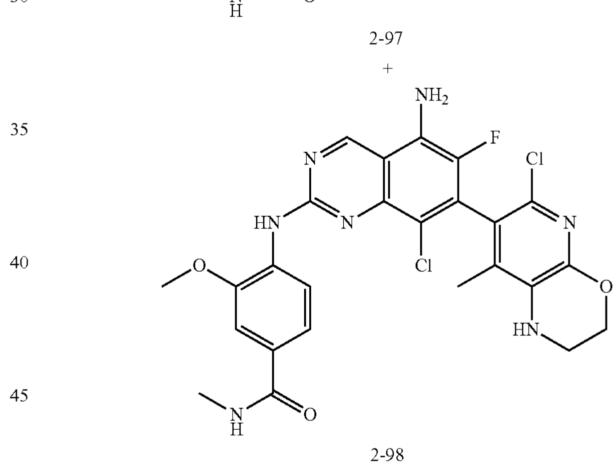

2-98

To a vial containing 2-74 (495 mg, 1.01 mmol) in DMF (10.1 mL) was added N-chlorosuccinimide (149 mg, 1.11 mmol). The reaction mixture was heated to 45° C., and allowed to stir for 100 min. The reaction mixture was quenched by the addition of saturated aqueous $Na_2S_2O_3$ and concentrated under reduced pressure. The mixture was azeotroped with toluene 3×. The residue was dissolved in a 1:1 acetonitrile/MeOH mixture and filtered. The supernatant was concentrated under reduced pressure. The residue was dissolved in DMSO and filtered. The solution was purified by reverse phase column chromatography (gradient elution of 15-70% acetonitrile/Water+0.05% $NH_4OH$) to afford compounds 2-97 and 2-98 as solids.

Compound 2-97. $^1$H NMR (500 MHz, DMSO-$d_6$) δ 9.68 (s, 1H), 9.01 (d, J=8.9 Hz, 1H), 8.38 (s, 1H), 8.37 (m, 1H), 7.55 (s, 1H), 7.54 (s, 1H), 7.29 (s, 1H), 6.61 (s, 2H), 5.73 (s, 1H), 4.32 (s, 2H), 3.99 (s, 3H), 3.41-3.38 (m, 2H), 2.79 (d, J=4.5 Hz, 3H), 1.86 (s, 3H). MS (EI) calc'd for $C_{25}H_{24}Cl_2FN_7O_3$ $[M+H]^+$, 524, found, 524.

Compound 2-98. $^1H$ NMR (500 MHz, DMSO-$d_6$) δ 9.69 (s, 1H), 8.99 (d, J=8.8 Hz, 1H), 8.41 (s, 1H), 8.37 (d, J=4.6 Hz, 1H), 7.55 (s, 1H), 7.54 (s, 1H), 6.66 (s, 2H), 5.89 (s, 1H), 4.35 (s, 2H), 3.99 (s, 3H), 3.41-3.38 (m, 2H), 2.79 (d, J=4.5 Hz, 3H), 1.84 (s, 3H). MS (EI) calc'd for $C_{25}H_{23}Cl_2FN_7O_3$ $[M+H]^+$, 558; found, 558.

Preparation of Compounds 2-99 and 2-101

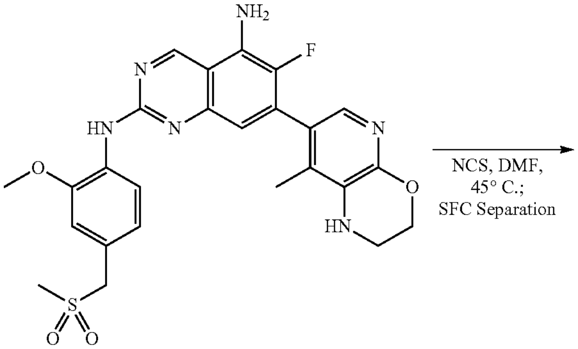

2-50

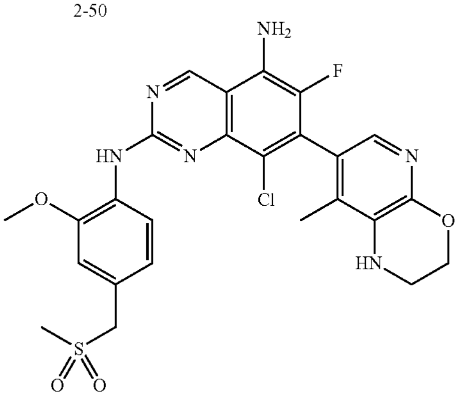

2-99

+

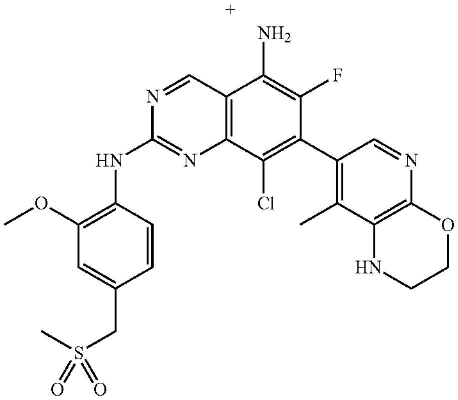

2-101

To a solution of compound 2-50 (866 mg, 1.65 mmol) in DMF (10 mL) was added N-chlorosuccinimide (220 mg, 1.65 mmol). The reaction was heated to 45° C. for 1 h and 40 min. The reaction was diluted in DMSO/MeOH and purified by reverse phase chromatography (15-70% ACN/water with 0.1% $NH_4OH$). After concentration, the atropisomers were resolved by chiral SFC [Column CCA F4, 21×250 mm; 35% (MeOH/0.1% $NH_4OH$)/$CO_2$; Flow rate: 70 mL/min; 220 nm] to provide 2-99 [RT: 4.3 min] and 2-101 [RT: 5.5 min].

Compound 2-99. $^1H$ NMR (500 MHz, DMSO-$d_6$) δ 9.65 (s, 1H), 8.91 (d, J=8.2 Hz, 1H), 8.30 (s, 1H), 7.28 (s, 1H), 7.14 (s, 1H), 7.06 (d, J=8.2 Hz, 1H), 6.58 (s, 2H), 5.72 (s, 1H), 4.43 (s, 2H), 4.32 (s, 2H), 3.93 (s, 3H), 3.39 (s, 2H), 2.90 (s, 3H), 1.85 (s, 3H). MS (EI) calc'd for $C_{25}H_{25}ClFN_6O_4S$ $[M+H]^+$, 529, 531; found, 529, 531.

Compound 2-101. $^1H$ NMR (500 MHz, DMSO-$d_6$) δ 9.65 (s, 1H), 8.91 (d, J=8.2 Hz, 1H), 8.30 (s, 1H), 7.28 (s, 1H), 7.14 (s, 1H), 7.06 (d, J=8.6 Hz, 1H), 6.58 (s, 2H), 5.72 (s, 1H), 4.43 (s, 2H), 4.32 (s, 2H), 3.93 (s, 3H), 3.37 (m, 2H), 2.90 (s, 3H), 1.85 (s, 3H). MS (EI) calc'd for $C_{25}H_{25}ClFN_6O_4S$ $[M+H]^+$, 559, 561; found, 559, 561.

Preparation of Compounds 2-100 and 2-108

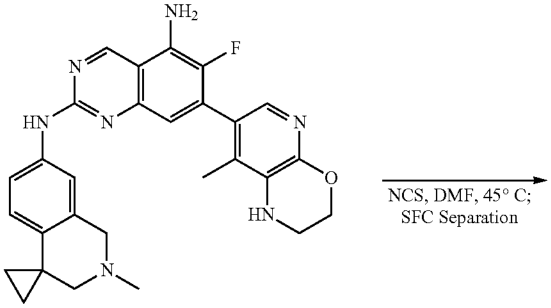

2-73

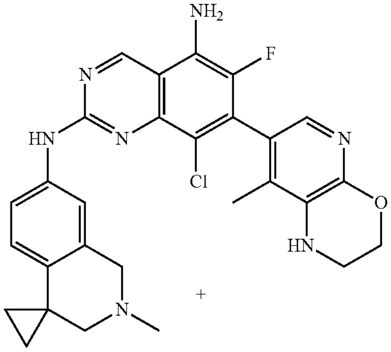

+

2-100

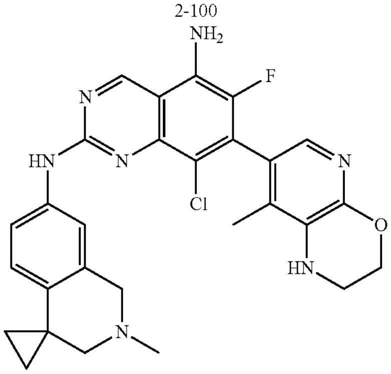

2-108

A solution of Compound 2-73 (102 mg, 0.205 mmol) in DMF (10 mL) was treated with N-chlorosuccinimide (27 mg, 0.21 mmol). The reaction was heated to 45° C. for 15 min. The reaction was diluted in DMSO/MeOH and purified by reverse phase chromatography (15-70% ACN/water with 0.1% $NH_4OH$). After concentration, the atropisomers were resolved by chiral SFC [Column CCA F4, 21×250 mm; 35% (MeOH/0.1% $NH_4OH$)/$CO_2$: Flow rate: 70 mL/min; 220 nm] to provide 2-100 [RT: 5.0 min] and 2-108 [RT: 6.3 min].

Compound 2-100. $^1$H NMR (500 MHz, DMSO-$d_6$) δ 9.86 (s, 1H), 9.60 (s, 1H), 8.05 (s, 1H), 7.71 (d, J=8.3 Hz, 1H), 7.28 (s, 1H), 6.65 (d, J=8.5 Hz, 1H), 6.48 (s, 1H), 5.71 (s, 1H), 4.31 (s, 2H), 3.55 (s, 2H), 3.37 (d, J=6.9 Hz, 2H), 2.42 (s, 1H), 2.30 (s, 2H), 1.86 (s, 2H), 1.24 (s, 3H), 0.85 (d, J=40.3 Hz, 4H). MS (EI) calc'd for $C_{28}H_{28}ClFN_7O$ [M+H]$^+$, 532; found, 532.

Compound 2-108. $^1$H NMR (500 MHz, DMSO-$d_6$) δ 9.86 (s, 1H), 9.60 (s, 1H), 8.05 (s, 1H), 7.71 (dd, J=8.5, 1.9 Hz, 1H), 7.28 (s, 1H), 6.65 (d, J=8.7 Hz, 1H), 6.48 (s, 1H), 5.71 (s, 1H), 4.36-4.26 (m, 2H), 3.55 (s, 2H), 3.42-3.36 (m, 2H), 2.42 (s, 2H), 2.30 (s, 3H), 1.86 (s, 3H), 0.94-0.75 (m, 4H). MS (EI) calc'd for $C_{28}H_{28}ClFN_7O$ [M+H]$^+$, 532; found, 532.

Preparation of Compounds 2-102, 2-105 and 2-106

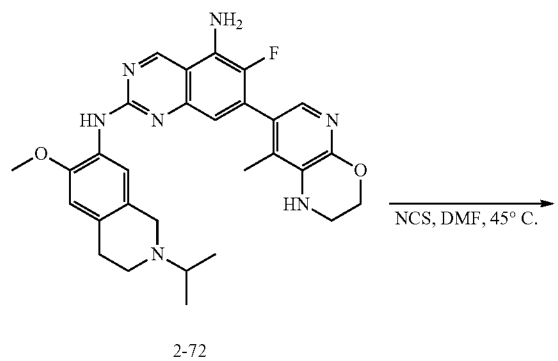

2-72

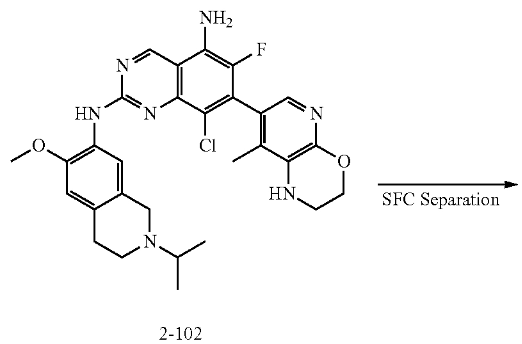

2-102

-continued

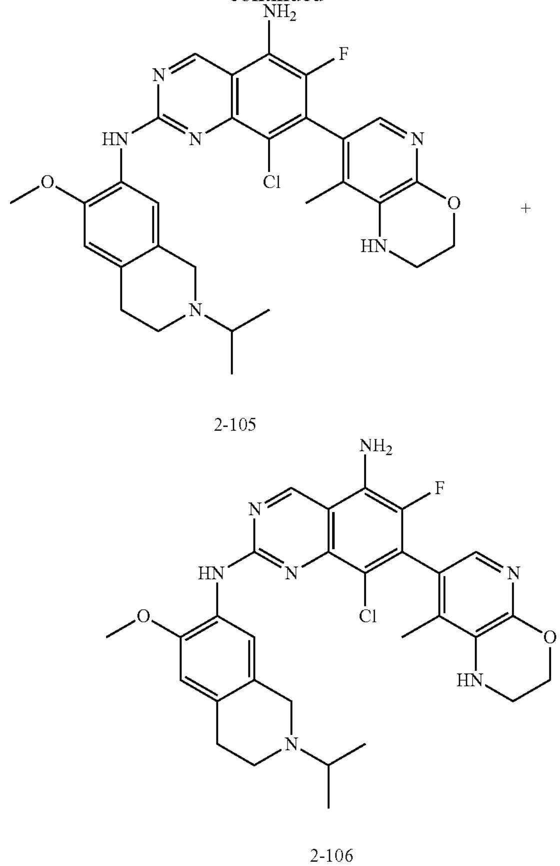

+

2-105

2-106

To compound 2-72 (190 mg, 0.359 mmol) in DMF (7 mL), N-chlorosuccinimide (48 mg, 0.36 mmol) was added and this was allowed to stir at 45° C. for 90 mm. The reaction was cooled in ice-water and very carefully quenched with MeOH. This was directly purified by HPLC using gradient elution with ACN-water using TFA as a modifier. Appropriate fractions were pooled together, excess solvent was removed under reduced pressure and this was lyophilyzed to give compound 2-102.

Compound 2-102. $^1$H NMR (500 MHz, DMSO-$d_6$) δ 9.61 (s, 1H), 8.63 (s, 1H), 8.16 (s, 1H), 7.27 (s, 1H), 6.77 (s, 1H), 6.54 (s, 2H), 5.71 (s, 1H), 4.30 (s, 2H), 3.87 (s, 3H), 3.56 (s, 2H), 2.67 (s, 4H), 1.85 (s, 3H), 1.30-1.21 (m, 4H), 1.04 (s, 6H). MS (EI) calc'd for $C_{29}H_{32}ClFN_7O_2$ [M+H]$^+$, 564; found, 564.

Subsequently, atropisomers were resolved by SFC [Column OD-H, 21×250 mm; 40% (MeOH/0.1% $NH_4OH$)/$CO_2$; Flow rate: 70 mL/min; 220 nm] to provide 2-106 [RT: 4.5 min] and 2-105 [RT: 5.7 min]. The products were collected and then lyophilized to give solids.

Compound 2-105. $^1$H NMR (500 MHz, DMSO-$d_6$) δ 9.61 (s, 1H), 8.63 (s, 1H), 8.16 (s, 1H), 7.27 (s, 1H), 6.77 (s, 1H), 6.54 (s, 2H), 5.71 (s, 1H), 4.30 (s, 2H), 3.87 (s, 3H), 3.56 (s, 2H), 2.67 (s, 4H), 1.85 (s, 3H), 1.30-1.21 (m, 4H), 1.04 (s, 6H). MS (EI) calc'd for $C_{29}H_{32}ClFN_7O_2$ [M+H]$^+$, 564; found, 564.

Compound 2-106. $^1$H NMR (500 MHz, DMSO-$d_6$) δ 9.61 (s, 1H), 8.63 (s, 1H), 8.16 (s, 1H), 7.27 (s, 1H), 6.77 (s, 1H), 6.54 (s, 2H), 5.71 (s, 1H), 4.30 (s, 2H), 3.87 (s, 3H), 3.56 (s, 2H), 2.67 (s, 4H), 1.85 (s, 3H), 1.30-1.21 (m, 4H), 1.04 (s, 6H). MS (EI) calc'd for $C_{29}H_{32}ClFN_7O_2$ [M+H]$^+$, 564; found, 564.

Preparation of Compounds 2-112 and 2-113

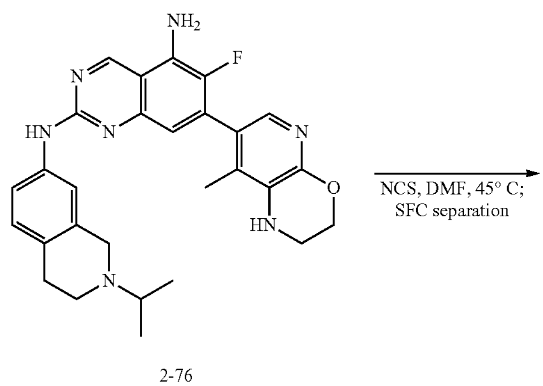

2-76

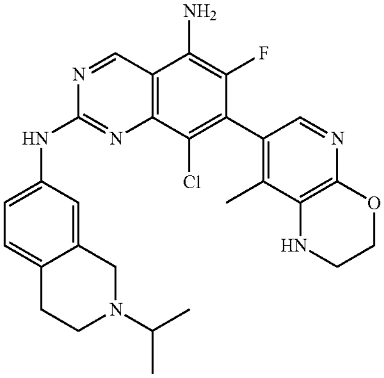

2-112

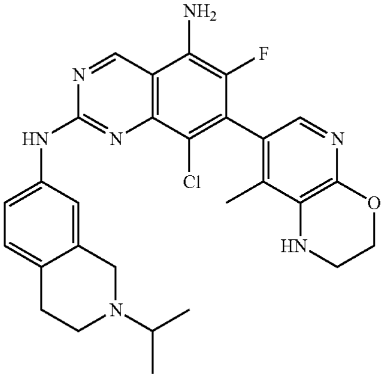

2-113

To compound 2-76 (210.0 mg, 0.420 mmol) in DMF (2.00 mL), N-chlorosuccinimide (61.7 mg, 0.462 mmol) was added and this was allowed to stir at 45° C. for an hour. The reaction mixture was cooled in ice-water. Quenched with 1 mL cold water. LCMS showed only a peak. This was directly purified on silica gel column using 10% MeOH-DCM. Appropriate fractions were pooled together, excess solvent was removed under reduced pressure and this was vacuum dried to give the chlorinated product, (+ and −)-8-chloro-6-fluoro-$N_2$-(2-isopropyl-1,2,3,4-tetrahydroisoquinolin-7-yl)-7-(8-methyl-2,3-dihydro-1H-pyrido[2,3-b][1,4]oxazin-7-yl)quinazoline-2,5-diamine, as a foamy solid. Subsequently, atropisomers were resolved by SFC [Column OD-H, 21×250 mm: 40% (MeOH/0.1% $NH_4OH$)/$CO_2$; Flow rate: 70 mL/min: 220 nm] to provide 2-112 [RT: 5.3 min] and 2-113 [RT: 6.5 min]. The products were collected and then lyopholized to give solids.

Compound 2-112. $^1H$ NMR (500 MHz, DMSO-$d_6$) δ 10.13 (s, 1H), 9.65 (s, 1H), 8.29 (d, J=17.5 Hz, 1H), 7.86 (d, J=8.6 Hz, 1H), 7.28 (s, 1H), 7.22 (d, J=14.1 Hz, 1H), 7.10 (s, 1H), 7.00 (s, 1H), 6.54 (s, 2H), 4.55-4.39 (m, 1H), 4.35-4.24 (m, 2H), 3.75-3.61 (m, 2H), 3.31-2.94 (m, 5H), 1.86 (s, 3H), 1.34 (s, 6H). MS (EI) calc'd for $C_{28}H_{30}ClFN_7O$ $[M+H]^+$, 534; found, 534.

Compound 2-113. $^1H$ NMR (500 MHz, DMSO-$d_6$) δ 9.86 (s, 1H), 9.60 (s, 1H), 8.06 (s, 1H), 7.71 (d, J=9.6 Hz, 1H), 7.28 (s, 1H), 7.01 (d, J=8.3 Hz, 1H), 6.49 (s, 2H), 5.71 (s, 1H), 4.31 (s, 2H), 3.61 (s, 2H), 3.39 (s, 3H), 2.80-2.63 (m, 5H), 1.86 (s, 3H), 1.05 (d, J=6.4 Hz, 6H). MS (EI) calc'd for $C_{21}H_{30}ClFN_7O$ $[M+H]^+$, 534; found, 534.

Preparation of Compounds 2-131 and 2-135

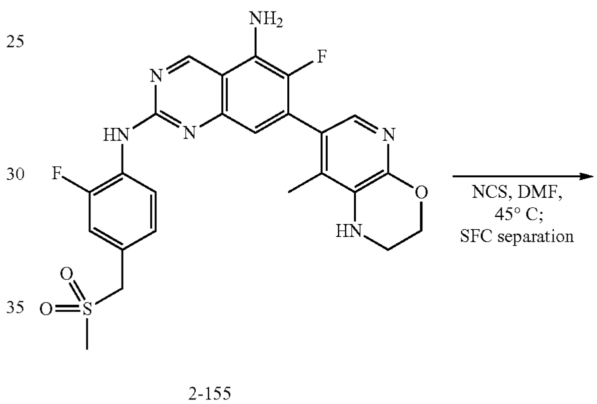

2-155

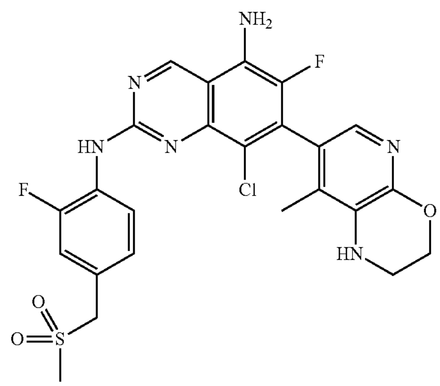

2-131

-continued

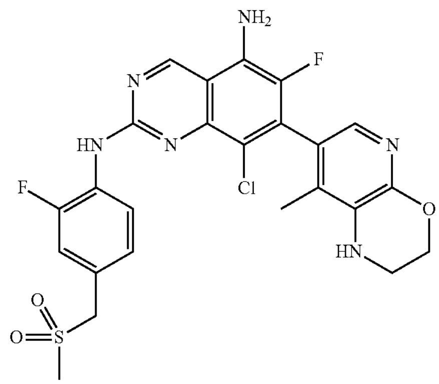

2-135

Compound 2-155 was prepared using coupling method exemplified in Example 2O with intermediate I-16 and 1-bromo-2-fluoro-4-((methylsulfonyl)methyl)benzene. After deprotection (also exemplified in Example 2O) compound 2-155 was isolated. MS (ESI) m/z calc'd for $C_{24}H_{23}F_2N_6O_3S$ $[M+H]^+$, 513, found 513.

Upon isolation, compounds 2-131 and 2-135 were prepared from compound 2-155.

To a solution of compound 2-155 (178 mg, 0.347 mmol)) in DMF (2 mL) was added N-chlorosuccinimide (46.4 mg, 0.347 mmol) at 25° C., the mixture was stirred at 40° C. for 1 h. LCMS showed the product was formed. The mixture was purified by pre-HPLC (Column YMC-Actus Triart C18 100*30 mm*5 um, Condition water (0.1% TFA)-ACN Begin B 20, End B 50 Gradient Time (min) 11, 100% B Hold Time (min) 1.1 FlowRate (ml/min) 40, Injections 4) to afford (+ and −)-8-chloro-6-fluoro-N2-(2-fluoro-4-((methylsulfonyl)methyl)phenyl)-7-(8-methyl-2,3-dihydro-1H-pyrido[2,3-b][1,4]oxazin-7-yl)quinazoline-2,5-diamine (60 mg, 0.110 mmol) as an oil. The mixture of atropisomers were separated by SFC (Column DAICEL CHIRALPAK AS(250 mm*30 mm, 10 um), Condition 0.1% NH3H2O ETOH Begin B 55%, End B 55% Gradient Time (min), 100% B Hold Time (min) FlowRate (ml/min) 70, Injections 70) to give 2-135 (17.01 mg, 0.031 mmol) (tR=2.596 min) and 2-131 (20.03 mg, 0.035 mmol) (tR=3.354 min), both as solids.

Compound 2-131. $^1$H NMR (400 MHz, CD3OD) δ ppm 9.52 (s, 1H), 9.07 (t, J=8.4 Hz, 1H), 7.47 (s, 1H), 7.24-7.34 (m, 2H), 4.57 (t, J=4.4 Hz, 2H), 4.41 (s, 2H), 3.59 (t, J=4.4 Hz, 2H), 2.88 (s, 4H), 2.03 (s, 3H). MS (ESI) m/z calc'd for $C_{24}H_{22}ClF_2N_6O_3S$ $[M+H]^+$, 547, found 547.

Compound 2-135. $^1$H NMR (400 MHz, CD3OD) δ ppm 9.50 (s, 1H), 9.07 (t, J=8.8 Hz, 1H), 7.41 (s, 1H), 7.22-7.32 (m, 2H), 4.50 (t, J=4.4 Hz, 2H), 4.40 (s, 2H), 3.55 (t, J=4.4 Hz, 2H), 2.88 (s, 3H), 1.98 (s, 3H). MS (ESI) m/z calc'd for $C_{24}H_{22}ClF_2N_6O_3S$ $[M+H]^+$, 547, found 547.

Preparation of Compounds 2-132 and 2-137

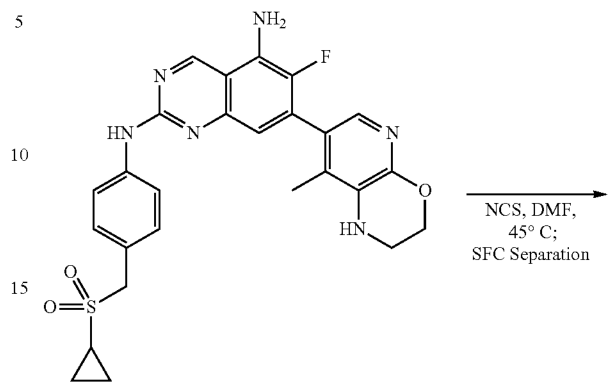

2-136

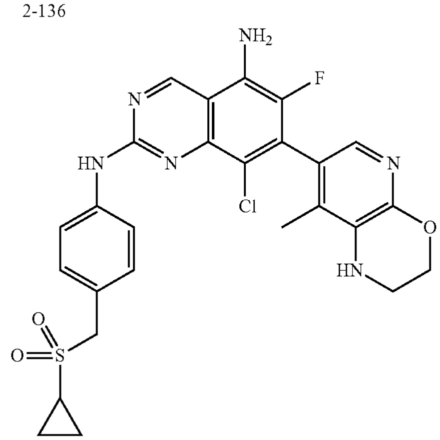

2-132

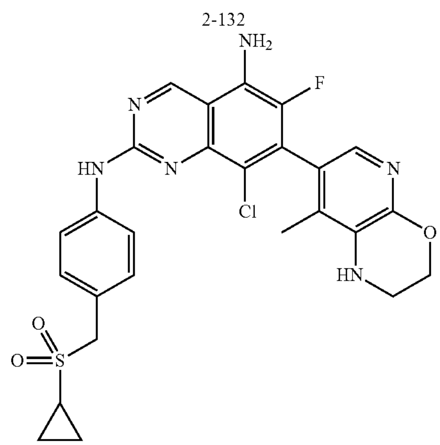

2-137

Compound 2-136 was prepared using coupling method exemplified in Example 2O with intermediate I-16 and 1-bromo-4-((cyclopropylsulfonyl)methyl)benzene. After deprotection (also exemplified in Example 2O) compound 2-136 was isolated. MS (ESI) m/z calc'd for $C_{26}H_{26}FN_6O_3S$ $[M+H]^+$, 521, found 521.

Upon isolation, compounds 2-132 and 2-137 were prepared from compound 2-136.

To a solution of compound 2-136 (110 mg, 0.211 mmol) in DMF (2 mL) was added N-chlorosuccinimide (28.2 mg, 0.211 mmol) at 25° C., the mixture was stirred at 40° C. for 1 h. LCMS showed the product was formed. The mixture was purified by pre-HPLC (Column YMC-Actus Triart C18 100*30 mm*5 um, Condition water (0.1% TFA)-ACN Begin B 20, End B 50 Gradient Time (min) 11, 100% B Hold Time (min) 1.1 FlowRate (ml/min) 40, Injections 4) to afford (+ and −)-8-chloro-N2-(4-((cyclopropylsulfonyl)methyl) phenyl)-6-fluoro-7-(8-methyl-2,3-dihydro-1H-pyrido[2,3-b][1,4]oxazin-7-yl)quinazoline-2,5-diamine (25 mg, 0.044 mmol) as an oil. The mixture of atropisomers were separated by SFC (Column DAICEL CHIRALPAK Chiralpak AS-3 100 ¡Á4.6 mm I.D., 3 um, Mobile phase: A: CO2 B: ethanol (0.05% DEA) Isocratic: 40% B Flow rate: 2.8 mL/min Column temp.: 35 ¡æ ABPR: 1500 psi) to afford 2-137 (6.26 mg, 10.84 μmol) as a solid (Rt=4.486 min) and 2-132 (6.22 mg, 10.58 μmol) as a solid (Rt=6.798 min).

Compound 2-132. $^1$H NMR (400 MHz, $CD_3OD$) δ ppm 9.46 (s, 1H), 8.14 (d, J=8.8 Hz, 2H), 7.41 (d, J=8.8 Hz, 2H), 7.30 (s, 1H), 4.36-4.46 (m, 4H), 3.46-3.53 (m, 2H), 2.43 (quin, J=6.4 Hz, 1H), 1.94 (s, 3H), 0.96-1.03 (m, 4H). MS (ESI) m/z calc'd for $C_{26}H_{25}ClFN_6O_3S$ $[M+H]^+$, 555, found 555.

Compound 2-137. $^1$H NMR (400 MHz, CD3OD) δ ppm 9.46 (s, 1H), 8.14 (d, J=8.8 Hz, 2H), 7.41 (d, J=8.8 Hz, 2H), 7.30 (s, 1H), 4.35-4.45 (m, 4H), 3.50 (dd, J=5.2, 3.6 Hz, 2H), 2.39-2.47 (m, 1H), 1.94 (s, 3H), 0.97-1.03 (m, 4H). MS (ESI) m/z calc'd for $C_{26}H_{25}ClFN_6O_3S$ $[M+H]^+$, 555, found 555.

Preparation of Compounds 2-134 and 2-140

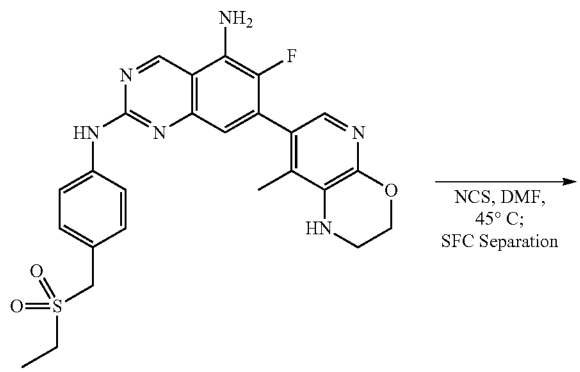

2-89

-continued

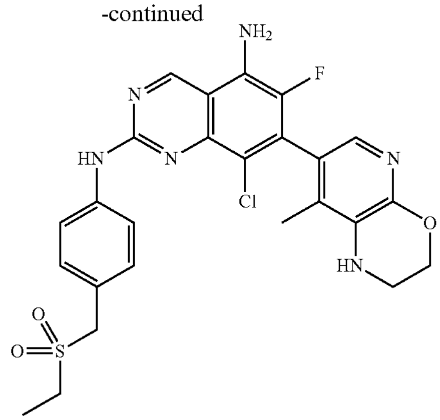

2-134

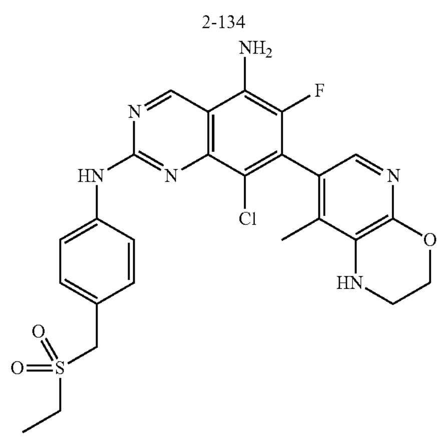

2-140

To a stirred solution of 2-89 (180 mg, 0.354 mmol) in DMF (3 mL) was added NCS (47.3 mg, 0.354 mmol) at 25° C., after the addition was finished, the reaction was stirred at 45° C. The reaction was monitored by LC-MS, after stirring at 45° C. for 1 h, the reaction was finished. The mixture was filtered and purified by prep-HPLC (Instrument EI Method Column Phenomenex Synergi C 18 150*30 mm*4 um Condition water (0.225% FA)-ACN Begin B 35 End B 55 Gradient Time (min) 11 100% B Hold Time (min) 2 Flow Rate (mL/min) 25 Injections 4) to give the title compound a mixture of atropisomers (90 mg, 0.166 mmol) as a solid. The mixture was resolved by SFC (Column DAICEL CHIRALPAK AS(250 mm*30 mm, 10 um), Condition 0.1% $NH_3H_2O$ MEOH Begin B 55%, End B 55% Gradient Time (min), 100% B Hold Time (min) FlowRate (ml/min) 70, Injections 50) to afford 2-134 (23.86 mg, 0.042 mmol) as a solid (Rt=3.156 min) and 2-140 (24.41 mg, 0.044 mmol) as a solid (Rt=4.466 min).

Compound 2-134. $^1$H NMR (400 MHz, $CD_3OD$) δ ppm 9.48 (s, 1H), 8.13 (d, J=8.8 Hz, 2H), 7.53 (s, 1H), 7.39 (d, J=9.2 Hz, 2H), 4.62 (t, J=4.4 Hz, 2H), 4.35 (s, 2H), 3.63 (t, J=4.4 Hz, 2H), 2.99 (q, J=7.6 Hz, 2H), 2.07 (s, 3H), 1.32 (t, J=7.6 Hz, 3H). MS (ESI) m/z calc'd for $C_{23}H_{25}ClFN_6O_3S$ $[M+H]^+$, 543, found 543.

Compound 2-140. $^1$H NMR (400 MHz, $CD_3OD$) δ ppm 9.48 (s, 1H), 8.13 (d, J=8.8 Hz, 2H), 7.54 (s, 1H), 7.39 (d, J=8.8 Hz, 2H), 4.63 (t, J=4.4 Hz, 2H), 4.34 (s, 2H), 3.63 (t, J=4.4 Hz, 2H), 2.99 (q, J=7.6 Hz, 2H), 2.07 (s, 3H), 1.32 (t, J=7.6 Hz, 3H). MS (ESI) m/z calc'd for $C_{25}H_{25}ClFN_6O_3S$ $[M+H]^+$, 543, found 543.

Preparation of Compounds 2-156 and 2-159

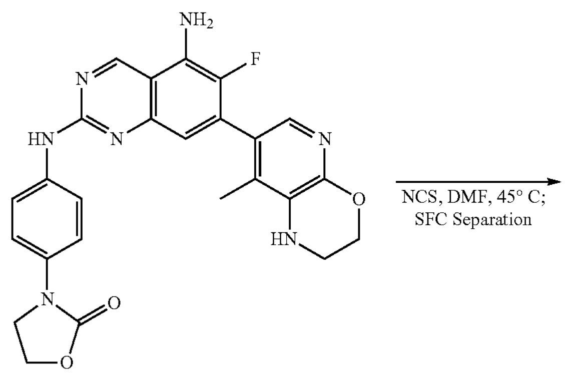

2-67

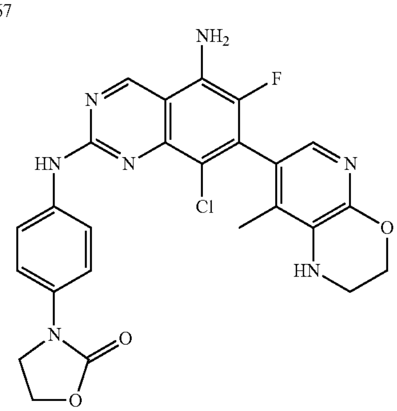

2-156

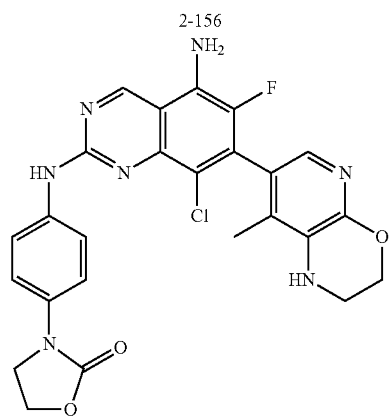

2-159

To a solution of compound 2-67 (55 mg, 0.113 mmol) in DMF (1.5 mL) was added NCS (12.81 mg, 0.096 mmol). The mixture was stirred at 40° C. for 1 h. LCMS showed the desired MS. The residue was purified by reverse preparative HPLC (Column: Waters XSELECT C18 150*30 mm*5 um; Condition: water (0.1% TFA)-MeCN; Begin B-End B: 21-41; Gradient Time (mm): 10; 100% B Hold Time (min): 1; FlowRate (mL/min): 25) to give the desired product (42 mg, 0.080 mmol) as a mixture of atropisomers. The isomers were resolved by SFC (DAICEL CHIRALPAK AS (250 mm*30 mm, 10 um) Condition 0.1% NH3H2O MEOH Begin B 60% End B 60% Gradient Time (min) 100% B Hold Time (min) FlowRate (mL/min) 60 Injections 90) to give 2-159 (6.99 mg, 0.013 mmol) (t=4.362 min, ee=100%) and 2-156 (5.76 mg, 10.62 μmol) (t=9.648 min, ee=100%) both as a solids.

Compound 2-156. $^1$H NMR (DMSO-$d_6$, 400 MHz) δ 9.99 (s, 1H), 9.60 (s, 1H), 8.13 (br d, J=8.8 Hz, 2H), 7.49 (d, J=9.6 Hz, 2H), 7.26 (s, 1H), 6.49 (s, 2H), 5.70 (br s, 1H), 4.41 (t, J=8.0 Hz, 2H), 4.30 (br s, 2H), 4.04 (t, J=8.0 Hz, 2H), 3.37-3.41 (m, 2H), 1.84 ppm (s, 3H). MS (ESI) m/z calc'd for $C_{25}H_{22}ClFN_7O_3$ [M+H]$^+$, 522, found 522.

Compound 2-159. $^1$H NMR (DMSO-$d_6$, 400 MHz) δ 9.99 (s, 1H), 9.60 (s, 1H), 8.13 (br d, J=8.8 Hz, 2H), 7.49 (d, J=9.2 Hz, 2H), 7.26 (s, 1H), 6.49 (s, 2H), 5.70 (br s, 1H), 4.37-4.45 (m, 2H), 4.30 (br s, 2H), 3.68-4.08 (m, 3H), 3.38-3.48 (m, 2H), 1.84 ppm (s, 3H). MS (ESI) m/z calc'd for $C_{25}H_{22}ClFN7O_3$ [M+H]$^+$, 522, found 522.

Preparation of Compounds 2-163 and 2-169

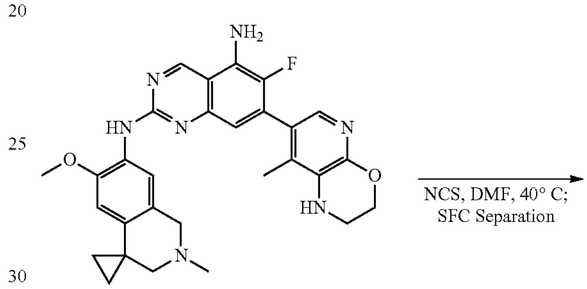

2-45

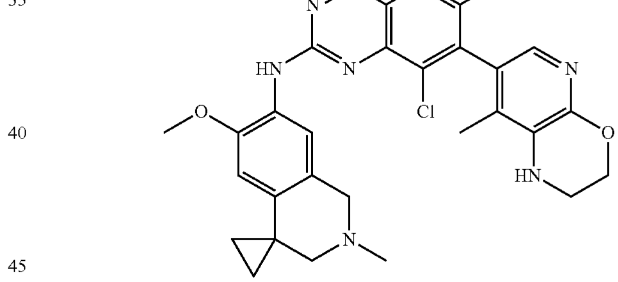

2-163

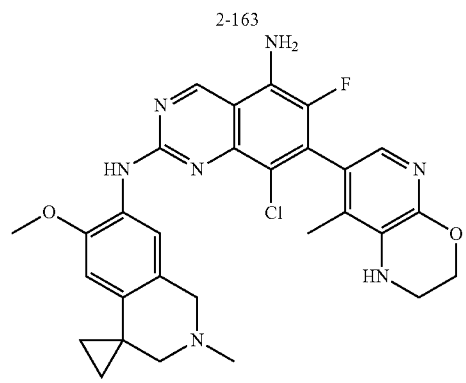

2-169

To mixture of compound 2-45 (550 mg, 1.042 mmol) in DMF (1 ml) was added NCS (139 mg, 1.042 mmol). Then the solution was stirred at 40° C. for 1 h. The LCMS showed the desired product. The mixture was purified by Pre-HPLC (Column Agela DuraShell C18 150*25 mm*5 um Condition water (0.04% $NH_3H_2O$+10 mM NH4HCO3)-ACN Begin B 39 End B 69 Gradient Time (min) 10 100% B Hold Time (min) 2 FlowRate (ml/min) 25 Injections 19) to give the desired product (a solid) (240 mg, 0.425 mmol) as a mixture of atropisomers. The isomers were resolved by SFC to afford 2-169 (105.04 mg, 0.184 mmol) (Rt=3.292 min) and 2-163 (91.92 mg, 0.160 mmol) (Rt=8.588 min) both as solids. The SFC method was Instrument SFC-MS, Column DAICEL CHIRALPAK AD (250 mm*30 mm, 10 um) Condition 0.1% NH3H2O MEOH Begin B 55% End B 55% Gradient Time (min) 100% B Hold Time (min) FlowRate (ml/min) 80 Injections 80.

Compound 2-163. $^1H$ NMR (500 MHz, CD3OD) δ 9.43 (s, 1H), 8.83 (s, 1H), 7.31 (s, 1H), 6.32 (s, 1H), 4.42 (br t, J=4.0 Hz, 2H), 3.91 (s, 3H), 3.68 (s, 2H), 3.50 (br t, J=4.0 Hz, 2H), 2.53-2.57 (m, 2H), 2.41 (s, 3H), 1.95 (s, 3H), 1.05 (br s, 2H), 0.92 (br s, 2H). MS (ESI) m/z calc'd for $C_{29}H_{30}ClFN7O_2$ $[M+H]^+$, 562, found 562.

Compound 2-169. $^1H$ NMR (500 MHz, $CD_3OD$) δ 9.43 (s, 1H), 8.83 (s, 1H), 7.31 (s, 1H), 6.32 (s, 1H), 4.42 (br t, J=4.0 Hz, 2H), 3.91 (s, 3H), 3.68 (s, 2H), 3.50 (br t, J=4.0 Hz, 2H), 2.53-2.57 (m, 2H), 2.41 (s, 3H), 1.95 (s, 3H), 1.05 (br s, 2H), 0.92 (br s, 2H). MS (ESI) m/z calc'd for $C_{29}H_{30}ClFN7O_2$ $[M+H]^+$, 562, found 562.

Preparation of Compounds 2-164 and 2-167

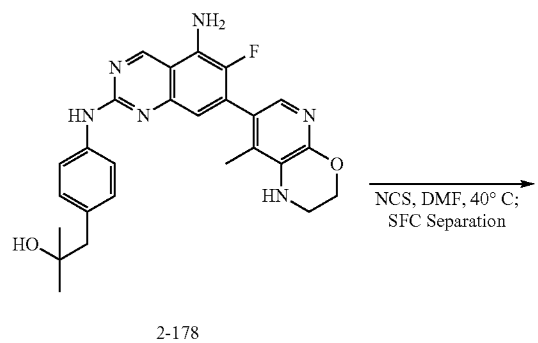

2-178

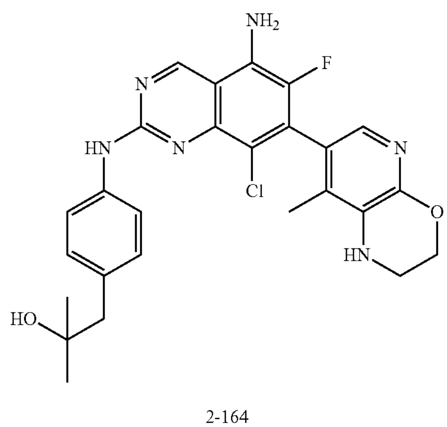

2-164

-continued

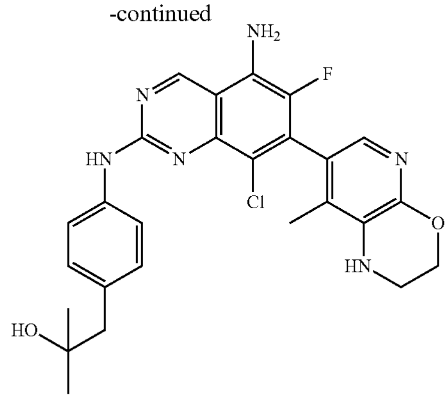

2-167

To a solution of compound 2-178 (40 mg, 0.084 mmol) in DMF (1 mL) was added N-chlorosuccinimide (9.57 mg, 0.072 mmol). The mixture was stirred at 40° C. for 1 h. LCMS showed the desired MS. The residue was purified by reverse preparative HPLC (Column: Waters XSELECT C18 150*30 mm*5 um: Condition: water (0.1% TFA)-MeCN; Begin B-End B: 21-41; Gradient Time (min): 10; 100% B Hold Time (min): 1: FlowRate (mL/min): 25) to give the desired product as a mixture of atropisomers (25 mg, 0.047 mmol) as an oil. Subsequently, the atropisomers were resolved by SFC (DAICEL CHIRALPAK AS(250 mm*30 mm, 10 um) Condition 0.1% NH3H2O ETOH Begin B 50% End B 50% Gradient Time (min) 100% B Hold Time (min) FlowRate (mL/min) 60 Injections 50) to give 2-167 (2.80 mg, 5.36 μmol) (t=4.362 min, ee=100%) as a solid and 2-164 (1.92 mg, 3.64 μmol) (t=5.745 min, ee=100%) all as solid.

Compound 2-164. $^1H$ NMR (CD3OD, 400 MHz) δ 9.43 (s, 1H), 7.98 (d, J=8.4 Hz, 2H), 7.29 (s, 1H), 7.19 (d, J=8.4 Hz, 2H), 4.42 (br t, J=4.0 Hz, 2H), 3.49 (br s, 2H), 2.72 (s, 2H), 1.94 (s, 3H), 1.18 ppm (s, 6H). MS (ESI) m/z calc'd for $C_{26}H_{27}ClFN_6O_2$ $[M+H]^+$, 509, found 509.

Compound 2-167. $^1H$ NMR (CD3OD, 400 MHz) δ 9.44 (s, 1H), 7.97 (d, J=8.4 Hz, 2H), 7.35 (s, 1H), 7.19 (d, J=8.4 Hz, 2H), 4.43-4.50 (m, 2H), 3.53 (br s, 2H), 2.72 (s, 2H), 1.97 (s, 3H), 1.18 ppm (s, 6H). MS (ESI) m/z calc'd for $C_{26}H_{27}ClFN_6O_2$ $[M+H]^+$, 509, found 509.

Preparation of Compounds 2-179 and 2-180

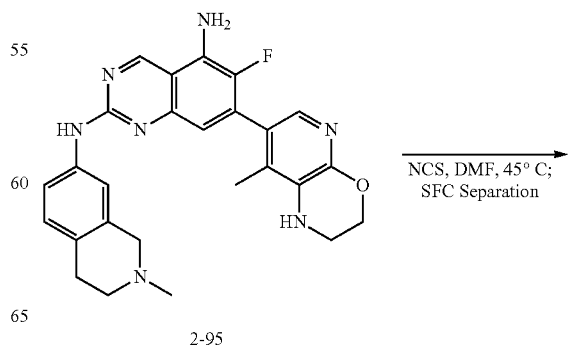

2-95

-continued

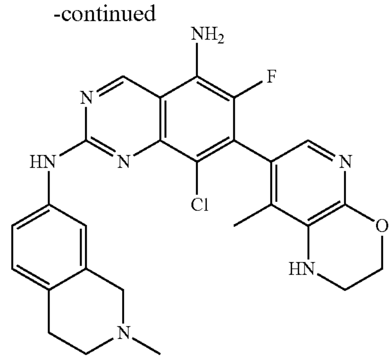

2-179

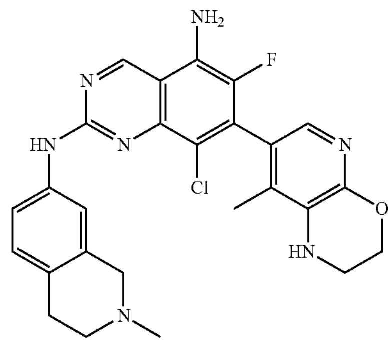

2-180

To a vial containing compound 2-95 (1.04 g, 2.206 mmol) in DMF (22.06 ml) was added N-chlorosuccinimide (0.324 g, 2.426 mmol). The reaction was allowed to proceed at 45° C. for 1 h. The reaction was then cooled to RT and quenched by the addition of saturated aqueous $Na_2S_2O_3$. The mixture was concentrated under reduced pressure and azeotroped with toluene. The residue was dissolved in a 1:1 mixture of acetonitrile/MeOH, filtered and concentrated. The racemic mixture was separated by SFC purification to afford the two peaks (chiral-Prep-SFC [Column CCA F4, 21×250 mm; 35% (MeOH/0.1% $NH_4OH$)/$CO_2$; Flow rate: 70 mL/min; 220 nm] to provide 2-179 [RT: 5.0-5.7 min] and 2-180 [RT: 6.2-7.5 min]).

Compound 2-179. $^1H$ NMR (499 MHz, DMSO-$d_6$) δ 9.88 (s, 1H), 9.60 (s, 1H), 8.08 (s, 1H), 7.70 (d, J=6.8 Hz, 1H), 7.28 (s, 1H), 7.03 (d, J=8.4 Hz, 1H), 6.50 (s, 2H), 5.72 (s, 1H), 4.39-4.23 (m, 2H), 3.45 (s, 2H), 3.39 (s, 2H), 2.76 (t, J=5.6 Hz, 2H), 2.57 (q, J=8.3, 7.0 Hz, 2H), 2.32 (s, 3H), 1.86 (s, 3H). MS (ESI) m/z calc'd for $C_{26}H_{26}ClFN_7O$ $[M+H]^+$, 506, found 506.

Compound 2-180. $^1H$ NMR (499 MHz, DMSO-$d_6$) δ 9.88 (s, 1H), 9.61 (s, 1H), 8.08 (s, 1H), 7.71 (d, J=8.4 Hz, 1H), 7.28 (s, 1H), 7.03 (d, J=8.4 Hz, 1H), 6.50 (s, 2H), 5.72 (s, 1H), 4.32 (s, 2H), 3.46 (s, 2H), 3.38 (s, 2H), 2.76 (d, J=5.6 Hz, 2H), 2.62-2.55 (m, 2H), 2.33 (s, 3H), 1.86 (s, 3H). MS (ESI) m/z calc'd for $C_{26}H_{26}ClFN_7O$ $[M+H]^+$, 506, found 506.

Preparation of Compounds 2-181 and 2-182

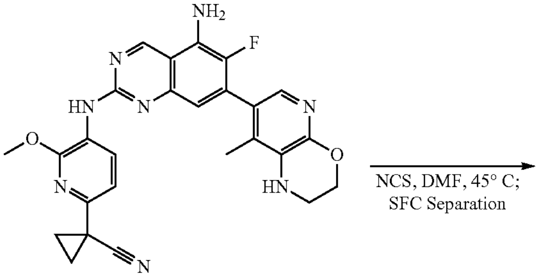

2-68

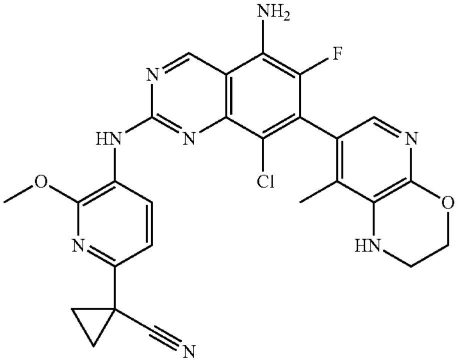

2-181

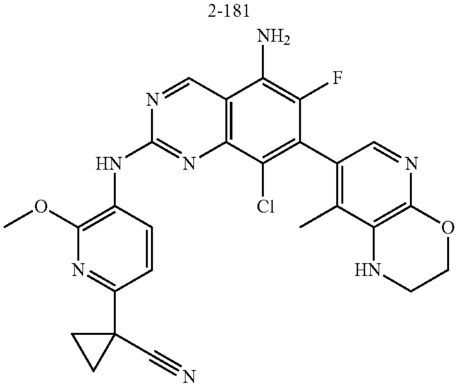

2-182

To a vial containing compound 2-68 (86.6 mg, 0.174 mmol) in DMF (1737 μl) was added N-chlorosuccinimide (23.20 mg, 0.174 mmol). The reaction mixture was heated to 45° C. and allowed to stir for 50 min. LCMS indicated ~1:1 of SM to chlorinated product. The reaction was allowed to proceed for an additional 50 min at 45° C., at which time the reaction had become cloudy. LCMS indicated insignificant change to the conversion to the desired product. The reaction mixture was quenched by the addition of saturated aqueous $Na_2S_2O_3$ and concentrated under reduced pressure. The mixture was azeotroped with toluene 3× to remove DMF. The residue was dissolved in a 1:1 acetonitrile/MeOH mixture and filtered. The supernatant was concentrated under reduced pressure. The crude residue was subjected to SFC separation (chiral-Prep-SFC [Column OJ-H, 21×250 mm; 40% (MeOH/0.1% $NH_4OH$)/$CO_2$: Flow rate: 70 mL/min; 220 nm]) to afford 2-181 [RT: 5.5 min] and 2-182 [RT: 7.0 min].

Compound 2-181. $^1H$ NMR (499 MHz, DMSO-$d_6$) δ 9.66 (s, 1H), 9.08 (d, J=7.9 Hz, 1H), 8.43 (s, 1H), 7.28 (s, 1H), 7.18 (d, J=8.1 Hz, 1H), 6.60 (s, 2H), 5.73 (s, 1H), 4.35-4.27 (m, 2H), 3.96 (s, 3H), 3.41-3.37 (m, 2H), 1.85 (s, 3H), 1.77-1.66 (m, 4H). MS (ESI) m/z calc'd for $C_{26}H_{23}ClFN_8O_2$ $[M+H]^+$, 533, found 533.

Compound 2-182. $^1H$ NMR (499 MHz, DMSO-$d_6$) δ 9.66 (s, 1H), 9.08 (d, J=7.9 Hz, 1H), 8.43 (s, 1H), 7.28 (s, 1H), 7.18 (d, J=8.1 Hz, 1H), 6.60 (s, 2H), 5.73 (s, 1H), 4.35-4.27 (m, 2H), 3.96 (s, 3H), 3.41-3.37 (m, 2H), 1.85 (s, 3H), 1.77-1.66 (m, 4H). MS (ESI) m/z calc'd for $C_{26}H_{23}ClFN_8O_2$ $[M+H]^+$, 533, found 533.

Preparation of Compounds 2-184 and 2-185

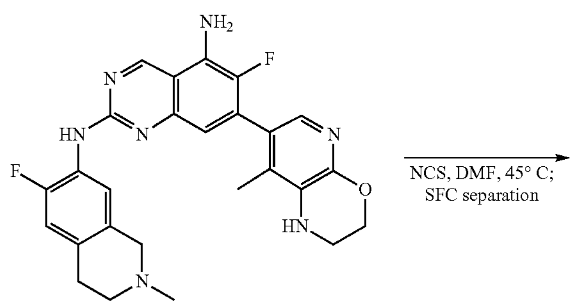

2-59

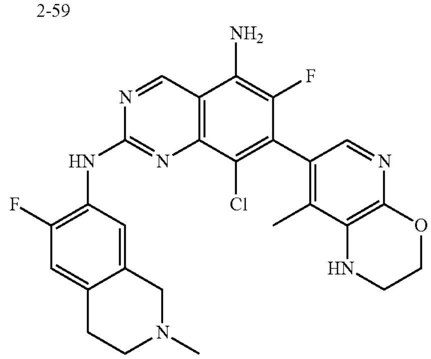

2-184

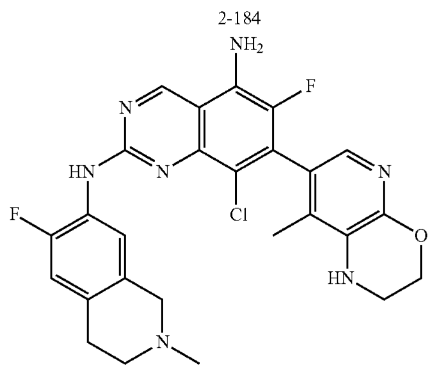

2-185

To a vial containing a solution of compound 2-59 (504.1 mg, 1.030 mmol) in DMF (10.300 mL) was added N-chlorosuccinimide (144 mg, 1.081 mmol). The solution was heated to 45° C., and allowed to stir for 50 min. LCMS indicated complete consumption of starting material. The reaction was quenched by the addition of saturated aqueous $Na_2S_2O_3$ and diluted with toluene. The mixture was concentrated under reduced pressure. The remaining residue was dissolved in a 1:1 acetonitrile:MeOH mixture, filtered and concentrated under reduced pressure. ~20% of the residue was dissolved in DMSO and filtered. The solution was purified by reverse phase column chromatography (gradient elution of 15-70% Acetonitrile/Water+0.05% $NH_3$) to afford a mixture of atropisomers (25.4 mg, 0.048 mmol) as solid. Subsequently, atropisomers were resolved by SFC [Column CCA F4, 21×250 mm; 35% (MeOH/0.1% $NH_4OH$)/$CO_2$; Flow rate: 70 mL/min; 220 nm] to provide 2-184 [RT: 3.0 min] and 2-185 [RT: 4.5 min]. The products were collected and then lyopholized to give solids.

Compound 2-184. $^1H$ NMR (499 MHz, DMSO-$d_6$) δ 9.62 (s, 1H), 9.22 (s, 1H), 7.27 (s, 1H), 6.99 (d, J=11.5 Hz, 1H), 6.53 (s, 2H), 5.71 (s, 1H), 4.31 (s, 2H), 3.43 (s, 3H), 2.79 (s, 2H), 2.57 (s, 2H), 2.32 (s, 3H), 1.85 (s, 3H). MS (EI) calc'd for $C_{26}H_{25}ClF_2N_7O$ $[M+H]^+$, 524; found, 524.

Compound 2-185. $^1H$ NMR (499 MHz, DMSO-d6) δ 9.62 (s, 1H), 9.22 (s, 1H), 7.27 (s, 1H), 6.99 (d, J=11.5 Hz, 1H), 6.53 (s, 2H), 5.71 (s, 1H), 4.31 (s, 2H), 3.43 (s, 3H), 2.79 (s, 2H), 2.57 (s, 2H), 2.32 (s, 3H), 1.85 (s, 3H). MS (EI) calc'd for $C_{26}H_{28}ClF_2N_7O$ $[M+H]^+$, 524; found, 524.

Example 2L

Preparation of Compound 2-109

Compound 2-109 was prepared from compound 2-111 as outlined below.

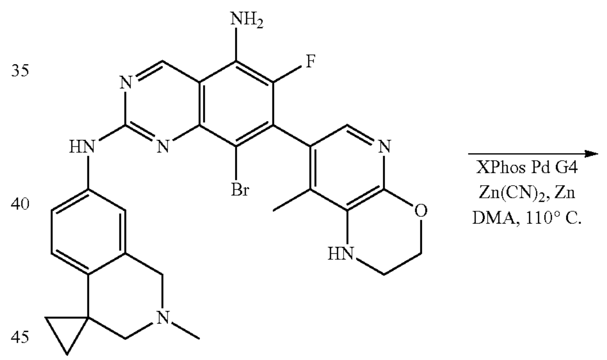

2-111

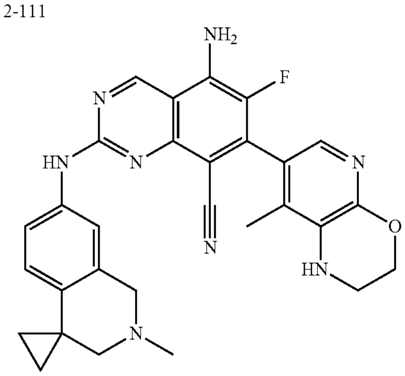

2-109

To a vial was added compound 2-111 (105 mg, 0.182 mmol), Zinc (1.19 mg, 0.018 mmol), zinc cyanide (12.8 mg, 0.109 mmol), and XPhos Pd G4 (157 mg, 0.182 mmol). DMA (1.5 mL) was added and the mixture was degassed with nitrogen for 5 min (bubbling). The mixture was sealed and heated to 110° C. overnight. The mixture was cooled and the residue was purified by column chromatography on silica gel (12 g) eluting with 3:1 EtOAc/MeOH in hexanes (50-100%) to give the title compound as an insufficiently pure mixture. The residue was purified by preparative HPLC Reverse phase (C-18), eluting with Acetonitrile/Water+0.05% $NH_3$. The residue was purified by achiral SFC ([Column EP, 21×250 mm: 30% (MeOH/0.1% $NH_4OH$)/$CO_2$; Flow rate: 70 mL/min; 220 nm] to provide 2-109 [RT: 4.7 min] as a mixture of atropisomers. $^1H$ NMR (500 MHz, DMSO-$d_6$) δ 10.01 (s, 1H), 9.62 (s, 1H), 8.19 (s, 1H), 7.55 (dd, J=8.5, 1.8 Hz, 1H), 7.47 (s, 2H), 7.39 (s, 1H), 6.63 (d, J=8.6 Hz, 1H), 5.80 (s, 1H), 4.33 (s, 2H), 3.55 (s, 2H), 3.45-3.36 (m, 2H), 2.42 (s, 2H), 2.27 (s, 3H), 1.94 (s, 3H), 0.93-0.86 (m, 2H), 0.81 (t, J=5.0 Hz, 2H). MS (ESI) m/z calc'd for $C_{29}H_{28}FN_8O$ $[M+H]^+$, 523, found 523.

Example 2M

Preparation of Compound 2-110

Compound 2-110 was prepared from compound 2-111 as outlined below.

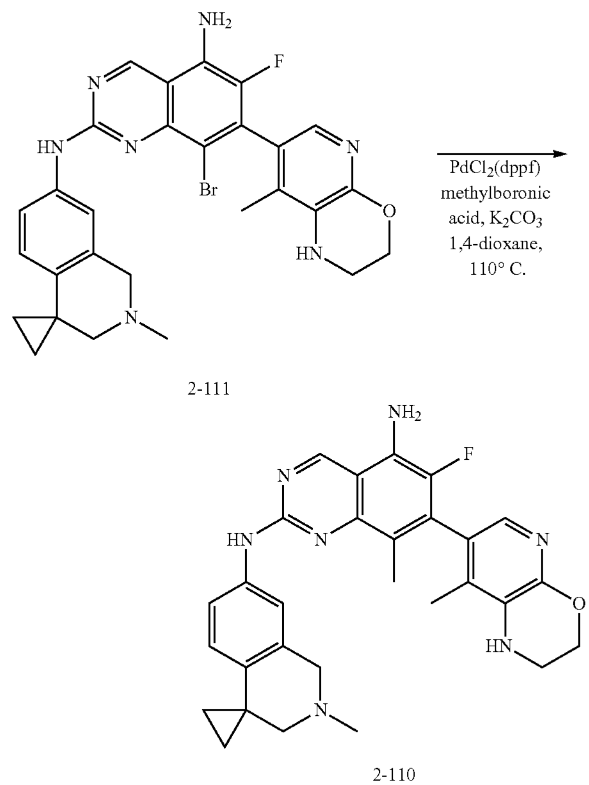

2-111

2-110

Compound 2-111 (105 mg, 0.182 mmol), methylboronic acid (55 mg, 0.91 mmol), $PdCl_2$(dppf)-DCM (100 mg, 0.122 mmol), and $K_2CO_3$ (76 mg, 0.55 mmol) were added to a 20 mL vial in dioxane (1.5 mL). The mixture was degassed with nitrogen for 5 min (bubbling) and sealed. The mixture was heated to 110° C. overnight. The mixture cooled and purified by column chromatography on silica gel (12 g), eluting with 3:1 EtOAc/MeOH in hexanes (40-100%) to give the title compound as a mixture. This mixture was purified by preparative HPLC Reverse phase (C-18), eluting with Acetonitrile/Water+0.05% $NH_3$, to give compound 2-110 as a mixture of atropisomers. $^1H$ NMR (500 MHz, DMSO-$d_6$) δ 9.60 (s, 1H), 9.53 (s, 1H), 7.84 (s, 1H), 7.65 (d, J=7.2 Hz, 1H), 7.22 (s, 1H), 6.65 (d, J=8.6 Hz, 1H), 6.02 (s, 2H), 5.67 (s, 1H), 4.31 (s, 2H), 3.55 (s, 2H), 3.38 (m, 11H), 2.43 (s, 2H), 2.30 (s, 3H), 2.16 (s, 3H), 1.82 (s, 3H), 0.89 (s, 2H), 0.80 (s, 2H). MS (ESI) m/z calc'd for $C_{29}H_{31}FN_7O$ $[M+H]^+$, 512, found 512.

Example 2N

Preparation of Compound 2-111

Compound 2-111 was prepared from compound 2-73 as outlined below.

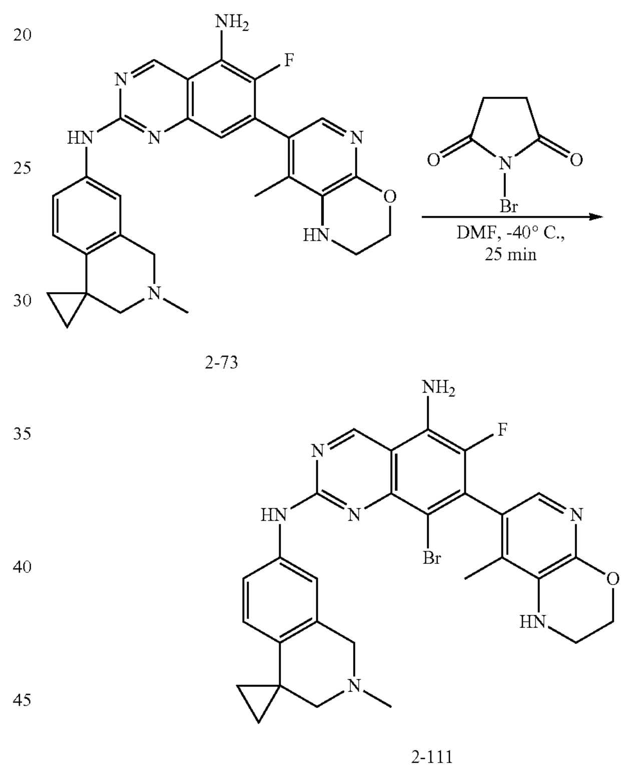

2-73

2-111

Compound 2-73 (407 mg, 0.818 mmol) was added to a 2 dram vial in DMF (4 mL) and chilled to −40° C. (dry ice in MeCN). NBS (138 mg, 0.777 mmol) was added portionwise and the mixture was stirred at −40° C. for 25 min until complete consumption of starting material. The mixture was quenched with sat. aq. $Na_2S_2O_6$ while cold and slowly allowed to warm to RT. The mixture was diluted with water (~10 mL) at ~0° C., and the product began to precipitate as an orange solid. After stirring for 20 min, the mixture was filtered with water (2×10 mL) and then $Et_2O$ (5×10 mL), and the solid was dried under vacuum in the oven (60° C.) for 5 h. The residue was purified by preparative HPLC Reverse phase (C-18), eluting with Acetonitrile/Water+0.05% $NH_3$, to give compound 2-111, as a mixture of atropisomers. $^1H$ NMR (500 MHz, DMSO-$d_6$) δ 9.87 (s, 1H), 9.57 (s, 1H), 8.14 (s, 1H), 7.72 (dd, J=8.6, 1.8 Hz, 1H), 7.25 (s, 1H), 6.65 (d, J=8.7 Hz, 1H), 6.52 (s, 2H), 5.71 (s, 1H), 4.39-4.24 (m, 2H), 3.56 (s, 2H), 3.39 (s, 2H), 2.42 (s, 2H), 2.29 (s, 3H), 1.85 (s, 3H), 0.89 (t, J=4.8 Hz, 2H), 0.81 (t, J=4.8 Hz, 2H). MS (ESI) m/z calc'd for $C_{28}H_{28}BrFN_7O$ [M+H]$^+$, 576, found 576.

Example 2O

Preparation of Compound 2-123

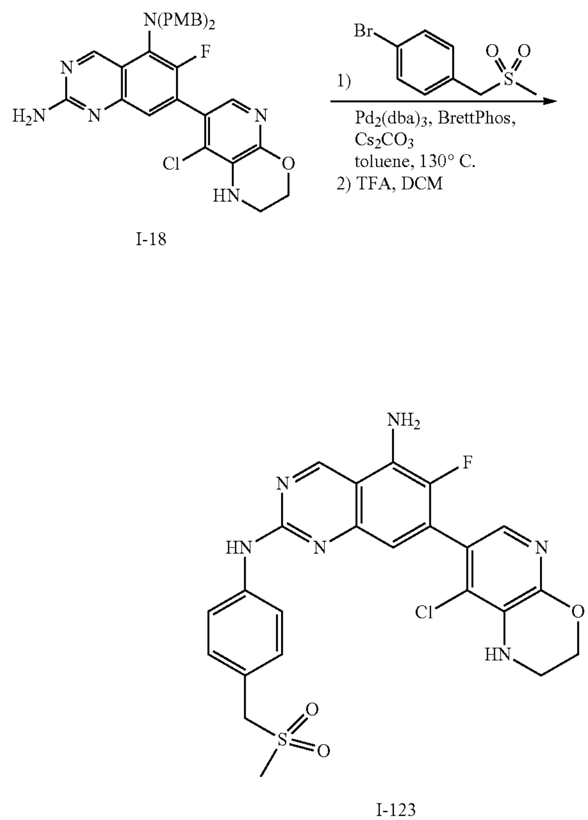

I-18

I-123

A mixture of intermediate I-18 (250 mg, 0.426 mmol), 1-bromo-4-((methylsulfonyl)methyl)benzene (212 mg, 0.852 mmol), $Cs_2CO_3$ (416 mg, 1.278 mmol), $Pd_2(dba)_3$ (78 mg, 0.085 mmol) and Brettphos (114 mg, 0.213 mmol) in toluene (5 mL) was stirred at 130° C. for 5 h under $N_2$. LCMS showed the desired product was formed. The mixture was purified by pre-TLC (EtOAc/Pet. ether=4/1) to afford the desired adduct as a solid. The product was taken up in DCM (2 mL) and TFA (1 mL) was stirred at 20° C. for 0.5 h. LCMS showed the desired product was formed. The mixture was concentrated in vacuo. The residue was purified by pre-HPLC (Column YMC-Actus Triart C18 100*3 (mm*5 um, Condition water (0.1% TFA)-ACN Begin B 24, End B 54 Gradient Time (min) 11, 100% B Hold Time (min) 1.1 FlowRate (mL/min) 40, Injections 4) to afford 7-(8-chloro-2,3-dihydro-1H-pyrido[2,3-b][1,4]oxazin-7-yl)-6-fluoro-N2-(4-((methylsulfonyl)methyl)phenyl)quinazoline-2,5-diamine (100.96 mg, 0.196 mmol) a solid. $^1H$ NMR (400 MHz, DMSO-d6) δ 9.88 (s, 1H), 9.57 (s, 1H), 7.92 (d, J=8.4 Hz, 2H), 7.40 (s, 1H), 7.29 (d, J=8.4 Hz, 2H), 6.67 (d, J=5.6 Hz, 1H), 4.28-4.41 (m, 4H), 3.38 (br s, 2H), 2.84 (s, 3H). MS (EI) calc'd for $C_{23}H_{21}ClFN_6O_3S$ [M+H]$^+$, 515; found, 515.

Preparation of Compound 2-122

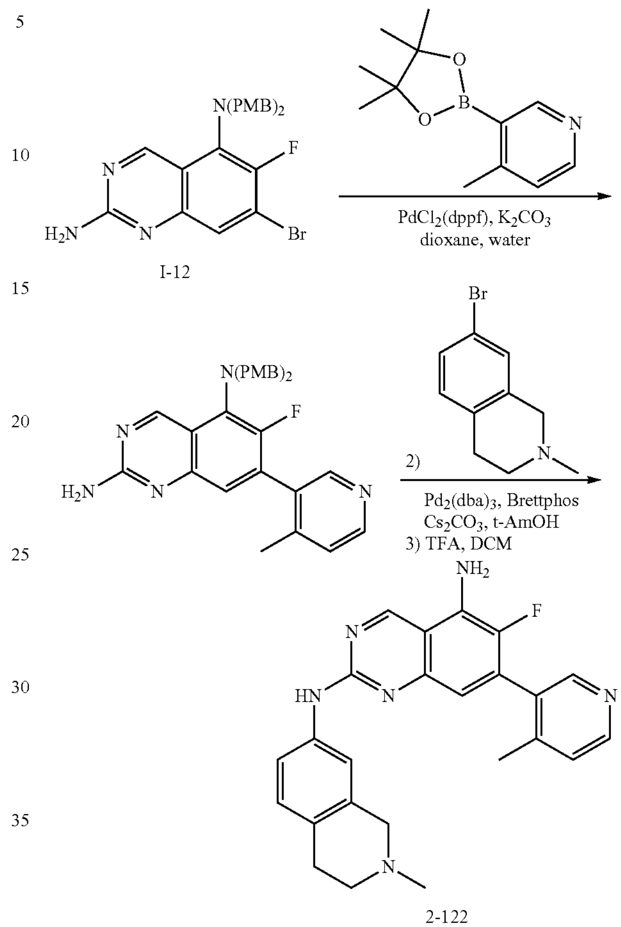

I-12

2-122

Step 1. Preparation of 6-fluoro-N$^5$,N$^5$-bis(4-methoxybenzyl)-7-(4-methylpyridin-3-yl)quinazoline-2,5-diamine To a mixture of intermediate I-12 (200 mg, 0.402 mmol), 4-methyl-3-(4,4,5,5-tetramethyl-1,3,2-dioxaborolan-2-yl)pyridine (101 mg, 0.462 mmol) and $K_2CO_3$ (111 mg, 0.804 mmol) in dioxane (3 mL) and water (0.6 mL) was added $PdCl_2$(dppf) (29.4 mg, 0.040 mmol) at 25° C. under $N_2$. Then the mixture was stirred at 90° C. 2 h. LCMS showed that the reaction completed. Water (50 mL) and DCM: MeOH=10:1 (50 mL) was added. The organic layer was separated and the aqueous was re-extracted with DCM: MeOH=10:1 (2×50 mL). The combined organic layers were washed with brine (50 mL), dried over anhydrous $Na_2SO_4$, filtered and concentrated. The residue was purified by pre-TLC ($SiO_2$, EtOAc:MeOH=10:1) to give 6-fluoro-N$^5$,N$^5$-bis(4-methoxybenzyl)-7-(4-methylpyridin-3-yl)quinazoline-2,5-diamine (168 mg, 0.286 mmol) as a solid. MS (ESI) m/z calc'd for $C_{30}H_{29}FN_5O_2$ [M+H]$^+$, 510, found 510.

Steps 2 and 3

A mixture of Brettphos (79 mg, 0.147 mmol), 6-fluoro-N$^5$,N$^5$-bis(4-methoxybenzyl)-7-(4-methylpyridin-3-yl)quinazoline-2,5-diamine (150 mg, 0.294 mmol), 7-bromo-2- methyl-1,2,3,4-tetrahydroisoquinoline (133 mg, 0.589 mmol), $Pd_2(dba)_3$ (53.9 mg, 0.059 mmol) and $Cs_2CO_3$ (384 mg, 1.177 mmol) in tert-Amyl Alcohol (3 mL) was stirred at 110° C. for 16 h under $N_2$. LCMS showed the product was formed. The mixture was purified by pre-TLC (EtOAc: MeOH=8:1) to afford the desired adduct as an oil. The oil was taken up in DCM (2 mL) and TFA (2 mL) was stirred at 25° C. for 1 h. LCMS showed the desired product was formed. The reaction mixture was concentrated in vacuo. The residue was purified by Prep-HPLC (Column YMC-Actus Triart C18 100*30 mm*5 um Condition water (0.1% TFA)-CAN Begin B 5 End B 35 Gradient Time (mm) 11 100% B Hold Time (mm) 1.1 Flow Rate(mL/min) 40, Injections 3) to give 2-122 (85.79 mg, 0.207 mmol) as a solid. $^1H$ NMR (400 MHz, DMSO-$d_6$) δ ppm 10.11 (br s, 1H), 9.90 (s, 1H), 9.62 (s, 1H), 8.67-8.77 (m, 2H), 7.96 (s, 1H), 7.69-7.80 (m, 2H), 7.16 (d, J=8.8 Hz, 1H), 6.77 (d, J=5.6 Hz, 1H), 4.51 (br s, 1H), 4.47 (br s, 1H), 3.64 (br s, 1H), 3.31 (br s, 1H), 2.94-3.13 (m, 2H), 2.92 (br s, 3H), 2.35 (s, 3H). MS (ESI) m/z calc'd for $C_{24}H_{24}FN_6$ $[M+H]^+$, 415, found 415.

Preparation of Compounds 2-125 and 2-129

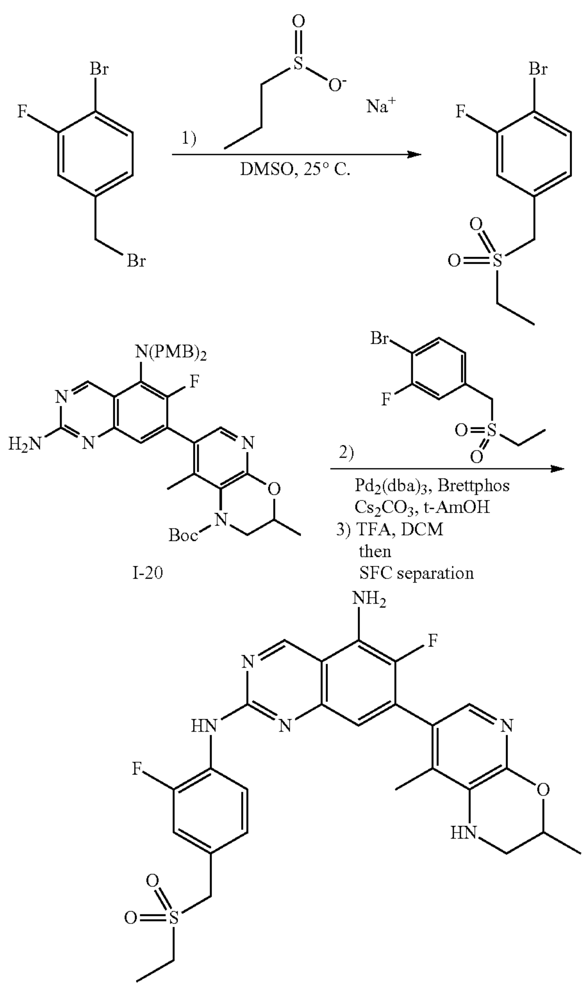

I-20

2-125

-continued

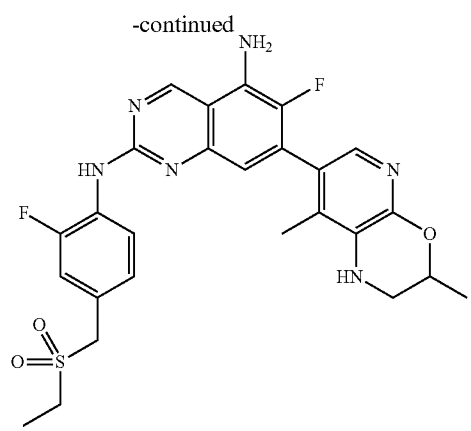

2-129

Step 1. Preparation of 1-bromo-4-((ethylsulfonyl)methyl)-2-fluorobenzene

To a mixture of 1-bromo-4-(bromomethyl)-2-fluorobenzene (2.5 g, 9.33 mmol) in DMSO (15 mL) was added sodium ethanesulfinate (1.300 g, 11.20 mmol) at 0° C. The reaction mixture was stirred at 25° C. for 18 h. TLC showed the starting material was consumed completely, and a new spot was generated. Water (60 mL) was added, the resulting mixture was extracted with EtOAc (3×40 mL). The combined organic layers were washed with brine (80 mL), dried over anhydrous $Na_2SO_4$, filtered and concentrated to give a residue which was purified by flash silica gel chromatography (ISCO®; 20 g Agela® Silica Flash Column, Eluent of 0-25% EtOAc/Pet. ether gradient at 30 mL/min) to give 1-bromo-4-((ethylsulfonyl)methyl)-2-fluorobenzene (2.2 g, 7.83 mmol) as a solid.

Steps 2 and 3. Preparation of Compounds 2-125 and 2-129

A mixture of intermediate I-20 (200 mg, 0.294 mmol), 1-bromo-4-((ethylsulfonyl)methyl)-2-fluorobenzene (149 mg, 0.529 mmol), $Cs_2CO_3$ (287 mg, 0.881 mmol), Brettphos and $Pd_2(dba)_3$ (53.8 mg, 0.059 mmol) in tert-AmOH (3 mL) was degassed and backfilled with $N_2$ (three times). The reaction mixture was stirred at 110° C. for 16 h. LCMS showed the desired product. The reaction mixture was quenched with water (15 mL), then the mixture was extracted with EtOAc (3×20 mL), the combined organic layer was washed with brine (15 mL), dried over anhydrous $Na_2SO_4$, filtered and concentrated to give the desired adduct. The oil was then taken up in DCM (1.5 mL) and added TFA (1.5 mL). Then the solution was stirred at 25° C. for 0.5 h. The LCMS showed the desired product. The mixture was concentrated in vacuum to give crude product which was purified by Pre-HPLC (Column YMC-Actus Triart C18 100*30 mm*5 um Condition water (0.1% TFA)-I Begin B 15 End B 45 Gradient Time (min) 11 100% B Hold Time (min) 1.1 Flow rate(mL/min) 40 Injections 3) to give the fully deprotected product as a mixture of enantiomers (a solid).

Subsequently, the enantiomers were resolved by SFC (Column: Chiralpak AD-3 50 ¡Á4.6 mm I.D., 3 um), Condition: A: CO2 B: ethanol (0.05% DEA), Gradient: from 5% to 40% of B in 5.5 min and hold 40% for 3 min, then 5% of B for 1.5 min, Flow rate: 4 mL/min, Column temp: 40° C.)

to give 1-125 ($t_R$=3.910 min, UV=220 nm, ee=100%) and 1-129 ($t_R$=5.567 min, UV=220 nm, ee=96.14%), both as solid.

Compound 2-125. $^1H$ NMR (500 MHz, DMSO-$d_6$) δ 9.61 (s, 1H), 9.28 (s, 1H), 8.15 (t, J=8.4 Hz, 1H), 7.45 (s, 1H), 7.19-7.33 (m, 2H), 6.62 (d, J=5.5 Hz, 1H), 4.48 (s, 2H), 4.43 (d, J=14.9 Hz, 1H), 3.50 (d, J=12.4 Hz, 1H), 3.06 (q, J=7.5 Hz, 3H), 1.99 (s, 3H), 1.39 (d, J=6.3 Hz, 3H), 1.24 (t, J=7.4 Hz, 3H). MS (EI) calc'd for $C_{26}H_{27}F_2N_6O_3S$ $[M+H]^+$, 541; found, 541.

Compound 2-129. $^1H$ NMR (500 MHz, DMSO-$d_6$) δ 9.60 (s, 1H), 9.22 (s, 1H), 8.12-8.21 (m, 1H), 7.40 (s, 1H), 7.19-7.33 (m, 2H), 6.60 (d, J=5.5 Hz, 1H), 4.48 (s, 2H), 4.35 (s, 1H), 3.05 (q, J=7.6 Hz, 4H), 1.97 (s, 3H), 1.38 (d, J=6.2 Hz, 3H), 1.24 (t, J=7.4 Hz, 3H). MS (EI) calc'd for $C_{26}H_{27}F_2N_6O_3S$ $[M+H]^+$, 541, found, 541.

Preparation of Compounds 2-126, 2-127, and 2-128

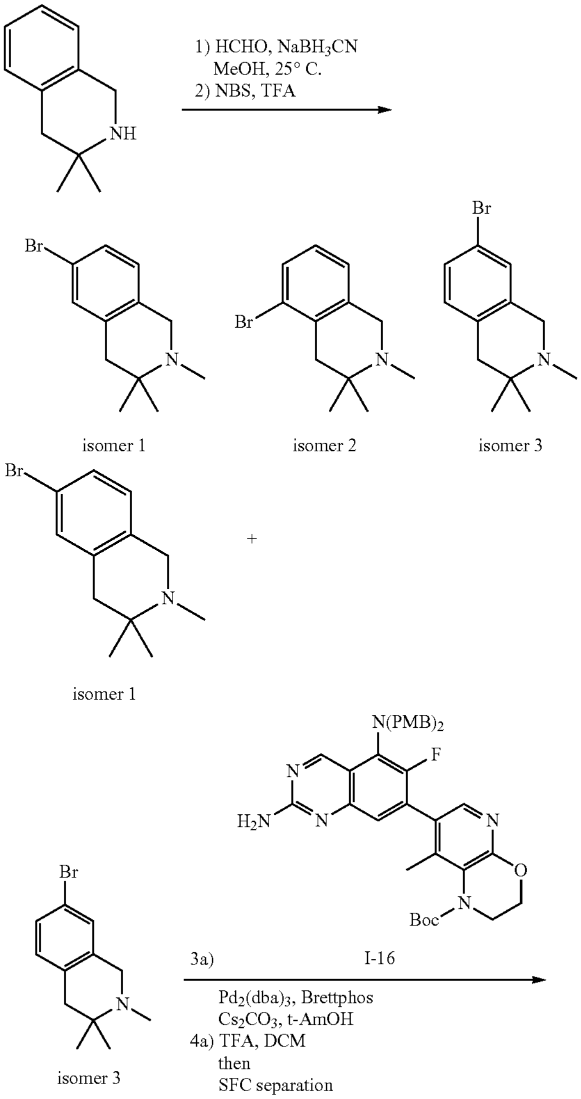

isomer 1 isomer 2 isomer 3 isomer 1 isomer 3

2-126 + 2-128

-continued

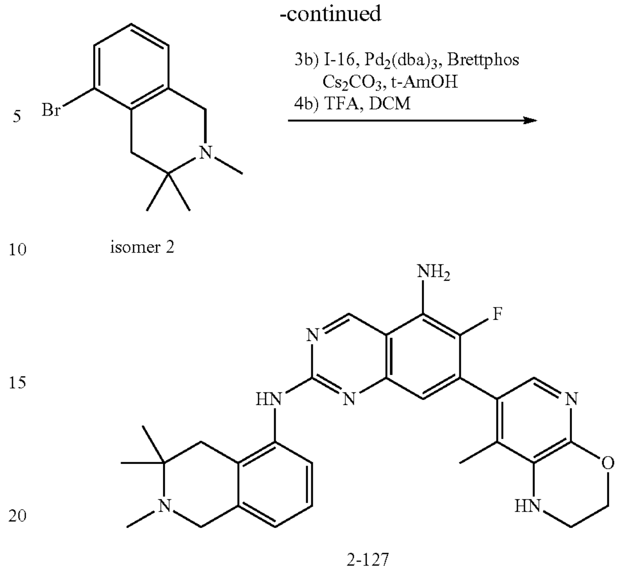

isomer 2

2-127

Steps 1 and 2. Preparation of 7-bromo-2,3,3-trimethyl-1,2,3,4-tetrahydroisoquinoline, 6-bromo-2,3,3-trimethyl-1,2,3,4-tetrahydroquinoline and 5-bromo-2,3,3-trimethyl-1,2,3,4-tetrahydroisoquinoline A mixture of 3,3-dimethyl-1,2,3,4-tetrahydroisoquinoline (500 mg, 3.10 mmol) and formaldehyde (1007 mg, 12.40 mmol) was added a drop of AcOH (1.6 mL) in MeOH (8 mL). The mixture was stirred at 25° C. for 20 min, then the mixture was added $NaCNBH_4$ (585 mg, 9.30 mmol) and stirred at 25° C. for 12 h under $N_2$. LCMS showed the product was formed. Solvent was removed under reduced pressure. To the residue was added water (50 mL), basified by $NaHCO_3$ aqueous solution to pH~9, and extracted with EtOAc (3×50 mL). The organic layers were washed with brine (50 mL), dried over $Na_2SO_4$, filtered and concentrated in vacuo to afford 2,3,3-trimethyl-1,2,3,4-tetrahydroisoquinoline (430 mg, 2.085 mmol) as an oil.

NBS (385 mg, 2.165 mmol) was added to a solution of 2,3,3-trimethyl-1,2,3,4-tetrahydroisoquinoline (330 mg, 1.883 mmol) in DCM (10.5 mL) and TFA (3 mL) at 20'° C. The mixture was stirred at 40° C. for 8 h, LCMS showed the product was formed. The mixture was purified by pre-HPLC (Column YMC-Actus Triart C18 100*30 mm*5 um, Condition water (0.1% TFA)-I Begin B 13, End B 43 Gradient Time (min) 11, 100% B Hold Time (min) 1.1 FlowRate (ml/min) 40, Injections 7) to afford 190 mg mixture of 6-bromo-2,3,3-trimethyl-1,2,3,4-tetrahydroisoquinoline (isomer 1), 5-bromo-2,3,3-trimethyl-1,2,3,4-tetrahydroisoquinoline (isomer 2), and 7-bromo-2,3,3-trimethyl-1,2,3,4-tetrahydroisoquinoline (isomer 3) as colourless oil. The oil was separated by SFC (Column Phenomenex-Cellulose-2 (250 mm*30 mm, 10 um), Condition 0.1% $NH_3H_2O$ ETOH Begin B 25%, End B 25% Gradient Time (min), 100% B Hold Time (min) FlowRate (mL/min) 60, Injections 50) to afford 68 mg mixture of 7-bromo-2,3,3-trimethyl-1,2,3,4-tetrahydroisoquinoline and 6-bromo-2,3,3-trimethyl-1,2,3,4-tetrahydroisoquinoline as colourless oil and 5-bromo-2,3,3-trimethyl-1,2,3,4-tetrahydroisoquinoline (37 mg, 0.131 mmol) as colourless oil.

Steps 3a and 4a. Synthesis of Compounds 2-126 and 2-128

A mixture of intermediate I-16 (60 mg, 0.090 mmol), 7-bromo-2,3,3-trimethyl-1,2,3,4-tetrahydroisoquinoline (isomer 3) and 6-bromo-2,3,3-trimethyl-1,2,3,4-tetrahydroisoquinoline (isomer 1) (34.3 mg, 0.135 mmol), $Pd_2(dba)_3$ (16.48 mg, 0.018 mmol), $Cs_2CO_3$ (88 mg, 0.270 mmol) and Brettphos (24.15 mg, 0.045 mmol) in tert-Amyl Alcohol (2 mL) was stirred at 110° C. for 13 h under $N_2$. TLC showed the starting material was consumed and new spots were formed. The mixture was concentrated in vacuo. The residue was purified by pre-TLC (MeOH/EtOAc=1:10) to afford a mixture of adducts as a solid. The mixture was taken up in DCM (1 mL) and TFA (1 mL) was stirred at 25° C. for 0.5 h. LCMS showed the desired product was formed. The mixture was concentrated in vacuo. The residue was purified by pre-HPLC (Column Agela DuraShell C18 150*25 mm*5 um, Condition water (0.05% NH3H2O+10 mM NH4HCO3)-I Begin B 36, End B 66 Gradient Time (min) 10, 100% B Hold Time (min) 2 FlowRate (mL/min) 25, Injections 1) to afford a mixture of isomers as a solid, which was confirmed by 2D NMR to be desired product. SFC showed two peaks.

The desired enantiomers were resolved by SFC (Instrument SFC-11, Method Column DAICEL CHIRALPAK AD (250 mm*30 mm, 10 um), Condition 0.1% NH3H2O IPA Begin B 50%, End B 50% Gradient Time (min), 100% B Hold Time (min). FlowRate (ml/min) 80, Injections 80) to afford 2-126 (2.03 mg, 3.54 μmol) as a solid (Rt=2.878 min) and 2-128 (5.24 mg, 10.22 μmol) as a solid (Rt=4.110 min).

Compound 2-126. $^1H$ NMR (400 MHz, $CD_3OD$) δ 9.39 (s, 1H), 7.56-7.65 (m, 2H), 7.37 (s, 1H), 7.01-7.08 (m, 1H), 6.69-6.78 (m, 1H), 6.69-6.78 (m, 1H), 4.37-4.44 (m, 2H), 3.75 (s, 2H), 3.48 (br s, 2H), 2.77 (s, 2H), 2.39 (s, 3H), 2.02 (d, J=1.6 Hz, 3H), 1.14 (s, 6H). MS (EI) calc'd for $C_{28}H_{31}FN_7O$ $[M+H]^+$, 500, found, 500.

Compound 2-128. $^1H$ NMR (400 MHz, $CD_3OD$) δ 9.39 (s, 1H), 7.62 (s, 1H), 7.50-7.56 (m, 1H), 7.36 (s, 1H), 7.03 (d, J=8.4 Hz, 1H), 6.74 (d, J=6.0 Hz, 1H), 4.39 (t, J=4.4 Hz, 2H), 3.76 (s, 2H), 3.45-3.52 (m, 2H), 2.70 (s, 2H), 2.37 (s, 3H), 2.01 (d, J=1.6 Hz, 3H), 1.12 (s, 6H). MS (EI) calc'd for $C_{28}H_{31}FN_7O$ $[M+H]^+$, 500; found, 500.

Steps 3b and 4b. Synthesis of Compound 2-127

Compound 2-127 was prepared from intermediate I-16 and 5-bromo-2,3,3-trimethyl-1,2,3,4-tetrahydroisoquinoline (isomer 2) using coupling and deprotection method from Example 2O.

Compound 2-127. $^1H$ NMR (400 MHz, $CD_3OD$) δ 9.38 (d, J=0.8 Hz, 1H), 7.64 (d, J=8.0 Hz, 1H), 7.33 (s, 1H), 7.18 (t, J=8.0 Hz, 1H), 6.92 (d, J=7.6 Hz, 1H), 6.64 (d, J=6.0 Hz, 1H), 4.33-4.41 (m, 2H), 3.79 (s, 2H), 3.42-3.49 (m, 2H), 2.70 (s, 2H), 2.36 (s, 3H), 1.99 (d, J=1.6 Hz, 3H), 1.11 (s, 6H). MS (EI) calc'd for $C_{28}H_{31}FN_7O$ $[M+H]^+$, 500; found, 500.

Preparation of Compounds 2-146 and 2-147

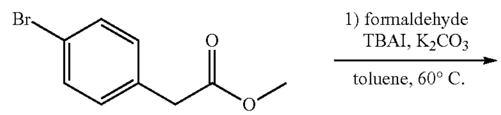

-continued

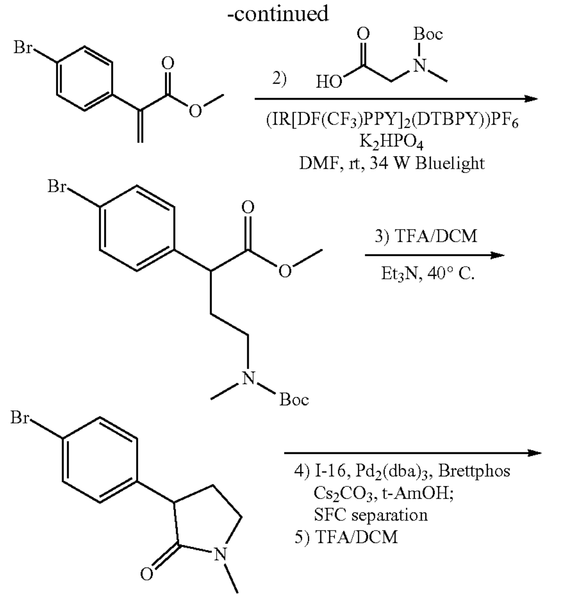

2-146

+

2-147

Step 1. Preparation of methyl 2-(4-bromophenyl)acrylate

To a solution of methyl 2-(4-bromophenyl) acetate (6 g, 26.2 mmol) in toluene (60 mL) was added formaldehyde (1.573 g, 52.4 mmol), $K_2CO_3$ (10.86 g, 79 mmol) and TBAI (0.5 g, 1.354 mmol). Then it was stirred at 60° C. for 15 h. TLC showed the reaction was finished, it was filtered and purified by flash silica gel chromatography (ISCO®, 40 g SepaFlash®, Silica Flash Column, eluent of (0~9)% ethyl acetate/petether gradient at 30 mL/min) to give methyl 2-(4-bromophenyl)acrylate (2.72 g, 11.26 mmol) as an oil.

Step 2. Preparation of methyl 2-(4-bromophenyl)-4-((tert-butoxycarbonyl)(methyl) amino) butanoate To a mixture of 2-((tert-butoxycarbonyl)(methyl)amino) acetic acid (1.177 g, 6.22 mmol), methyl 2-(4-bromophenyl) acrylate (1.5 g, 6.22 mmol). $K_2HPO_4$ (1.300 g, 7.47 mmol), (IR[DF($CF_3$)PPY]$_2$(DTBPY))$PF_6$ (0.070 g, 0.062 mmol) was added DMF (15 mL). Then it was stirred at 20° C. for 18 h, 1 cms showed the product was approved, it was dissolved in water (200 mL) and EtOAc (100 mL). The organic layer was separated and the aqueous was re-extracted with EtOAc (3×50 mL). The combined organic layers were washed with brine (100 mL), dried over anhydrous $Na_2SO_4$, filtered and the filtrate was evaporated in vacuum to give crude product, and it was purified by Prep-TLC (silica gel, pet. Ether/ethyl acetate=10/1) to give methyl 2-(4-bromophenyl)-4-((tert-butoxycarbonyl) (methyl) amino) butanoate (1.1 g, 2.71 mmol) as an oil. MS (EI) calc'd for $C_{17}H_{25}BrNO_4$ $[M+H]^+$, 388; found, 388.

Step 3. Preparation of 3-(4-bromophenyl)-1-methylpyrrolidin-2-one

To a solution of methyl 2-(4-bromophenyl)-4-((tert-butoxycarbonyl)(methyl)amino) butanoate (1.1 g, 2.85 mmol)

in DCM (12 mL) was added TFA (4 mL, 51.9 mmol) at 25° C. under $N_2$ atmosphere. The mixture was stirred at 25° C. for 30 min. TLC ($SiO_2$: $R_f$=0.2, petroleum ether:ethyl acetate=10:1) showed the reaction is complete. The SM was consumed and a new spot was observed. The mixture was evaporated under reduced pressure to give the product of methyl 2-(4-bromophenyl)-4-(methylamino) butanoate (0.8 g, 2.52 mmol) as an oil, then added the product in MeOH (12 mL) and added $Et_3N$ (1.948 mL, 13.98 mmol) at 25° C. under $N_2$ atmosphere. The mixture was stirred at 40° C. for 15 h. TLC ($SiO_2$; $R_f$=0.5, petroleum ether:ethyl acetate=1:1) showed the reaction is complete. The SM was consumed and a new spot was observed. The mixture was cooled, diluted with $NH_4Cl$ (30 mL), extracted with EtOAc (3×20 mL), dried over $Na_2SO_4$, filtered and the solvent was evaporated under reduced pressure to give the product of 3-(4-bromophenyl)-1-methylpyrrolidin-2-one (800 mg, 2.68 mmol) as an oil. $^1H$ NMR (400 MHz, $CD_3OD$) δ 7.43-7.50 (m, 2H), 7.15 (d, J=8.4 Hz, 2H), 3.69 (br t, J=9.2 Hz, 1H), 3.44-3.55 (m, 2H), 2.90 (s, 3H), 2.49-2.58 (m, 1H), 2.02-2.11 (m, 1H).

Steps 4 and 5. Synthesis of Compounds 2-146 and 2-147

To a solution of I-16 (300 mg, 0.450 mmol), $Pd_2(dba)_3$ (82 mg, 0.090 mmol), $Cs_2CO_3$ (440 mg, 1.350 mmol) 3-(4-bromophenyl)-1-methylpyrrolidin-2-one (172 mg, 0.675 mmol), Brettphos (121 mg, 0.225 mmol) in t-AmOH (6 mL) at 25° C., after the addition was finished, the mixture was stirred at 110° C.; The reaction was monitored by LCMS after stirring at 110° C. for 16 h. The mixture was diluted with water (100 mL), and extracted with DCM (50 mL*2), the organic layer was washed with brine (50 mL), dried over $Na_2SO_4$, after filtration, the filtrate was concentrated under reduced pressure. The residue was purified by P-TLC (EtOAc/MeOH=10:1) to give the desired adduct (a solid) as a mixture of enantiomers (280 mg, 0.290 mmol). The enantiomers were separated by SFC (Column: Chiralpak AS-3 100 ¡Á4.6 mm I.D., 3 um), Condition: ethanol (0.05% DEA) ethanol (0.05% DEA), Mobile phase: A: $CO_2$ B: ethanol (0.05% DEA), Gradient: from 5% to 40% of B in 4 min and hold 40% for 2.5 min, then 5% of B for 1.5 min, Flow rate: 2.8 mL/min, Column temp: 35° C.) to give isomer 1 (135 mg, 0.153 mmol) ($t_R$=4.336 min, UV=220 nm, ee=100%) and isomer 2 (172 mg, 0.195 mmol) ($t_R$=4.804 min, UV=220 nm, ee=99.32%), both as solids.

Isolation of Compound 2-147

The chirally resolved isomer 1 was taken up in DCM (4 mL) and added TFA (2 mL, 26.0 mmol) at 25° C., after the addition was finished, the mixture was stirred at 25° C. The reaction was monitored by LCMS after stirring at 25° C. for 1 h. The mixture was concentrated under reduced pressure. The residue was purified by reversed phase HPLC fitted with Waters XSELECT C18 150*30 mm*5 um using water (0.1% TFA)-Me CN as eluents (Mobile phase A water (0.1% TFA), Mobile phase B acetonitrile, detective wavelength 220 nm) and concentration to give 2-147 (77.31 mg, 0.155 mmol) as solid. $^1H$ NMR (500 MHz, DMSO-$d_6$) δ 9.80 (s, 1H), 9.59 (s, 1H), 7.84 (d, J=8.5 Hz, 2H), 7.46 (s, 1H), 7.15 (d, J=8.5 Hz, 2H), 6.63 (d, J=5.5 Hz, 1H), 4.39 (t, J=4.0 Hz, 2H), 3.56 (t, J=8.5 Hz, 1H), 3.41-3.47 (m, 3H), 3.35-3.40 (m, 1H), 2.80 (s, 3H), 2.39-2.44 (m, 2H), 1.99 (s, 3H). MS (EI) calc'd for $C_{27}H_{27}FN_7O_2$ $[M+H]^+$, 500; found, 500.

Isolation of Compound 2-146.

The chirally resolved isomer 2 was taken up in DCM (4 mL) and then added TFA (2 mL, 26.0 mmol) at 25° C., after the addition was finished, the mixture was stirred at 25° C.; The reaction was monitored by LCMS after stirring at 25° C. for 1 h. The mixture was concentrated under reduced pressure to give the crude product. The residue was purified by reversed phase HPLC fitted with Waters XSELECT C18 150*30 mm*5 um using water (0.1% TFA)-MeCN as eluents (Mobile phase A water (0.1% TFA), Mobile phase B acetonitrile, Detective wavelength 220 nm) and concentration to 2-146 (87.43 mg, 0.174 mmol) as solid. $^1H$ NMR (500 MHz, DMSO-$d_6$) δ 9.75 (s, 1H), 9.59 (s, 1H), 7.85 (d, J=8.5 Hz, 2H), 7.43 (s, 1H), 7.15 (d, J=8.5 Hz, 2H), 6.62 (d, J=6.0 Hz, 1H), 4.35-4.37 (m, 2H), 3.43 (d, J=3.5 Hz, 4H), 3.37 (s, 1H), 2.80 (s, 3H), 2.39-2.46 (m, 2H), 1.98 (s, 3H). MS (EI) calc'd for $C_{27}H_{27}FN_7O_2$ $[M+H]^+$, 500; found, 500.

Preparation of Compound 2-154

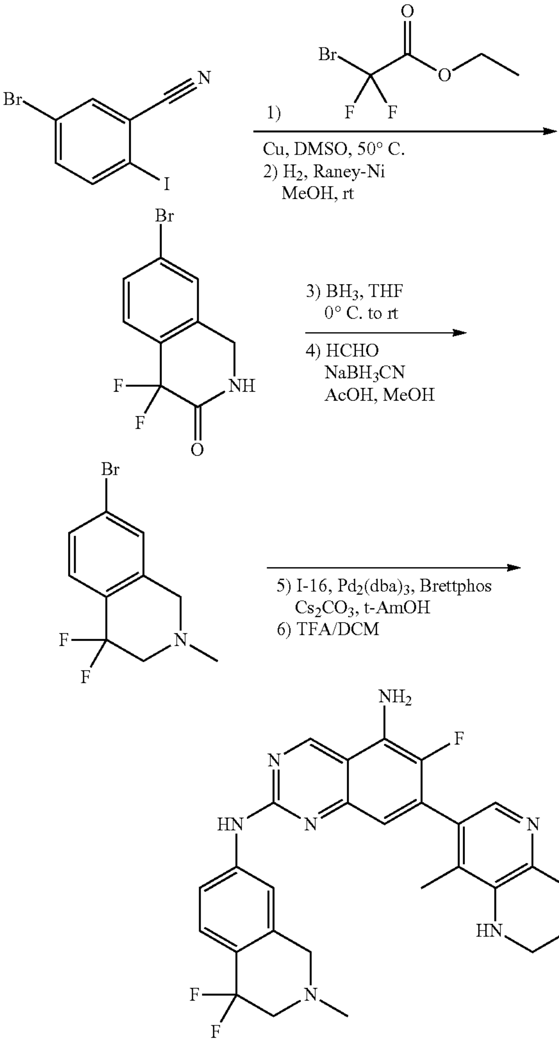

2-154

Steps 1 and 2. Preparation of 7-bromo-4,4-difluoro-1,4-dihydroisoquinolin-3(2H)-one To a suspension of copper (2.322 g, 36.5 mmol) in DMSO (45 mL) was added ethyl 2-bromo-2,2-difluoroacetate (3.30 g, 16.24 mmol). The mixture was stirred at 25° C. for 1 h.

Then 5-bromo-2-iodobenzonitrile (2.5 g, 8.12 mmol) was added. The mixture was stirred at 50° C. for 6 h. TLC ($SiO_2$, Pet.ether:EtOAc=3:1) showed that the reaction completed. Water (10 mL) and EtOAc (10 mL) was added. The organic layer was separated and the aqueous was re-extracted with EtOAc (3×80 mL). The combined organic layers were washed with brine (60 mL), dried over anhydrous $Na_2SO_4$, filtered and concentrated. The residue was purified by flash silica gel chromatography (ISCO®; 5 g Agela Silica Flash Column, eluent of 30% ethyl acetate/pet. Ether gradient at 50 mL/min) to give ethyl 2-(4-bromo-2-cyanophenyl)-2,2-difluoroacetate (130 mg, 0.428 mmol) as an oil.

To a solution of ethyl 2-(4-bromo-2-cyanophenyl)-2,2-difluoroacetate (1 g, 1.973 mmol) in MeOH (40 mL) was added platinum(IV) oxide (0.224 g, 0.987 mmol) at 25° C. with $H_2$ balloon (15 psi) for 2 h, LCMS showed desired product was formed and no staring material. The mixture was filtered and the filtrate was concentrated in vacuo to afford a crude residue which was purified by flash silica gel chromatography (ISCO®; 20 g Agela® Silica Flash Column. Eluent of 0~50% EtOAc/Pet. Ether gradient at 35 mL/min) to give 7-bromo-4,4-difluoro-1,2-dihydroisoquinolin-3(4H)-one (200 mg, 0.725 mmol) as a solid. $^1$H NMR (400 MHz, $CDCl_3$): δ 7.84 (br s, 1H), 7.67-7.73 (m, 1H), 7.60-7.67 (m, 1H), 7.49 (s, 1H), 4.63 (br d, J=2.4 Hz, 2H).

Steps 3 and 4. Preparation of 7-bromo-4,4-difluoro-2-methyl-1,2,3,4-tetrahydroisoquinoline To a solution of 7-bromo-4,4-difluoro-1,2-dihydroisoquinolin-3(4H)-one (200 mg, 0.763 mmol) in THF (4 mL) was added $BH_3$·THF (4.58 mL, 4.58 mmol) at 0° C. After the additional, the mixture was warmed to 25° C., and stirred at this temperature for 18 h. LC-MS showed no starting material. Aq. HCl (1 M, 1 mL) was added, the mixture was warmed to 70° C., then the resulting material was stirred at 70° C. for 2 h. Cooling to r.t., sat. $NaHCO_3$was added, the pH was adjusted to ~8. EtOAc (20 mL) was added, the resulting mixture was extracted with ethyl acetate (3×30 mL). The combined organic fractions were washed with brine (30 mL), dried over $Na_2SO_4$, filtered and the solvent was evaporated under reduced pressure to give 7-bromo-4,4-difluoro-1,2,3,4-tetrahydroisoquinoline (190 mg, 0.766 mmol) as a crude solid which was used directly.

To a solution of 7-bromo-4,4-difluoro-1,2,3,4-tetrahydroisoquinoline (190 mg, 0.643 mmol) in MeOH (2 mL) was added formaldehyde (261 mg, 3.22 mmol) and a drop of AcOH at 25° C. under $N_2$. After stirring at 25° C. for 0.5 h, $NaCNBH_3$ (81 mg, 1.287 mmol) was added. The mixture was stirred at 25° C. for 1 h. LC-MS showed major desired product. Sat. $NaHCO_3$was added, the pH was adjusted to ~8. EtOAc (20 mL) was added, the resulting mixture was extracted with ethyl acetate (3×20 mL). The combined organic fractions were washed with brine (30 mL), dried over $Na_2SO_4$, filtered and the solvent was evaporated under reduced pressure to give a residue which was purified by prep-TLC ($SiO_2$, EtOAc/Pet. Ether=1/3) to give 7-bromo-4,4-difluoro-2-methyl-1,2,3,4-tetrahydroisoquinoline (130 mg, 0.436 mmol) as an oil. MS (EI) calc'd for $C_{10}H_{11}BrF_2N$ $[M+H]^+$, 262, 264; found, 262, 264.

Steps 5 and 6. Synthesis of Compound 2-154

Compound 2-154 was prepared from intermediate I-16 and 7-bromo-4,4-difluoro-2-methyl-1,2,3,4-tetrahydroisoquinoline using coupling and deprotection methods exemplified in Example 2O.

Compound 2-154. $^1$H NMR (400 MHz, CD3OD): δ 9.44 (s, 1H), 7.90 (s, 1H), 7.81 (br d. J=8.4 Hz, 1H), 7.58 (d, J=8.8 Hz, 1H), 7.38 (s, 1H), 6.82 (d, J=6.0 Hz, 1H), 4.40 (t, J=4.4 Hz, 2H), 3.67 (br s, 2H), 3.44-3.54 (m, 2H), 2.99-3.09 (m, 2H), 2.49 (s, 3H), 2.03 (d, J=0.98 Hz, 2H), 1.98-2.09 (m, 1H). MS (EI) calc'd for $C_{26}H_{25}F_3N_7O$ $[M+H]^+$, 508; found, 508.

Example 2P

Preparation of Compound 2-171

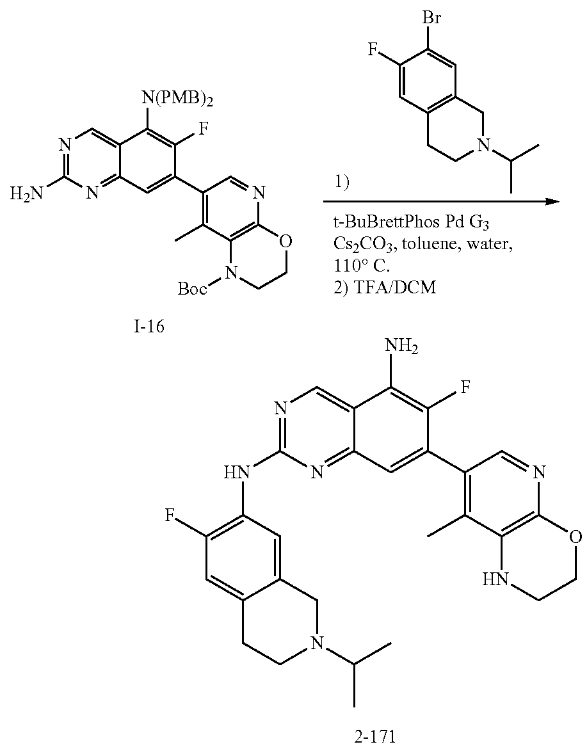

I-16

2-171

Steps 1 and 2. Synthesis of Compound 2-171

A mixture of 7-bromo-6-fluoro-2-isopropyl-1,2,3,4-tetrahydroisoquinoline (0.4 g, 1.470 mmol), intermediate I-16 (500 mg, 0.750 mmol), $Cs_2CO_3$ (0.5 g, 1.535 mmol), t-BuBrettPhos Pd G3 (0.12 g, 0.140 mmol) in toluene (5 mL) and water (0.25 mL) was stirred for 5 min at RT with nitrogen bubbling through the mixture. Next, the mixture was warmed to 110° C., and stirred for 15 h at this temperature. The mixture was cooled, diluted with DCM and extracted with water. The organic layer was dried ($Na_2SO_4$) and concentrated. The oil was then dissolved in DCM and purified by chromatography on $SiO_2$ (120 g column, 10-50% EtOAc/DCM and then 0-30% MeOH/DCM). The intermediate protected product weight: 560 mg, 0.650 mmol. The oil was then dissolved in 5 mL of DCM and 5 mL of TFA. The solution was aged for two hours and concentrated. Dissolved the oil in 50 mL of 5:1 DCM/MeOH, extracted with 2 N NaOH. Organic layer dried ($Na_2SO_4$), conc. Chromatography on $SiO_2$ (20-60% MeOH/DCM; 80 g silica gel) and then after concentration of fractions gave the desired product as a solid (125 mg, 0.24 mmol). $^1$H NMR (499 MHz, DMSO-$d_6$) δ 9.53 (s, 1H), 8.91 (s, 1H), 7.69 (d, J=8.1 Hz, 1H), 7.32 (s, 1H), 6.95 (d, J=11.5 Hz, 1H), 6.53 (d, J=5.7 Hz, 1H), 6.35 (s, 2H), 5.68 (s, 1H), 4.29 (t, J=4.1 Hz, 2H), 3.60 (s, 2H), 3.37 (s, 2H), 2.85 (dq, J=12.8, 6.4 Hz, 1H), 2.75 (t, J=5.4 Hz, 2H), 2.67 (t, J=5.7 Hz, 2H), 1.93 (s, 3H), 1.05 (d, J=6.5 Hz, 6H). MS (EI) calc'd for $C_{28}H_{30}F_2N_7O$ $[M+H]^+$, 518; found, 518.

Compounds listed in the table below were prepared using the synthetic methods described in the aforementioned examples. The table provides the compound structure, the name, the calculated and observed masses, and the example method used for preparation.

TABLE 2

| Example Number | Structure | Name | Exact Mass [M + H]+; Method |
|---|---|---|---|
| 2-1 | 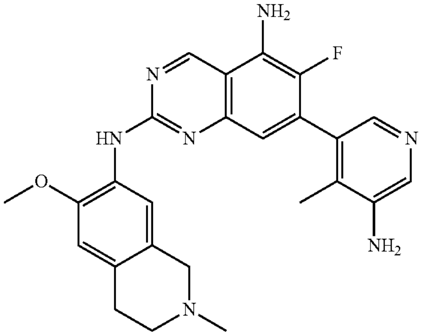 [SMILES: COc1cc2c(cc1Nc1ncc3c(N)c(F)c(-c4cncc(N)c4C)cc3n1)CN(C)CC2] | 7-(5-amino-4-methylpyridin-3-yl)-6-fluoro-N~2~-(6-methoxy-2-methyl-1,2,3,4-tetrahydroisoquinolin-7-yl)quinazoline-2,5-diamine | Calc'd 460, found 460; 2A |
| 2-2 | 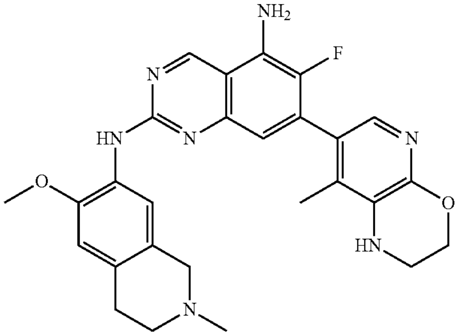 [SMILES: COc1cc2c(cc1Nc1ncc3c(N)c(F)c(-c4cnc5c(c4C)NCCO5)cc3n1)CN(C)CC2] | 6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 502, found 502; 2A |
| 2-3 | 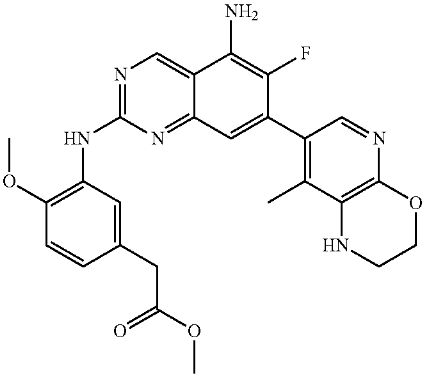 [SMILES: COC(=O)Cc1ccc(OC)c(Nc2ncc3c(N)c(F)c(-c4cnc5c(c4C)NCCO5)cc3n2)c1] | methyl (3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetate | Calc'd 505, found 505; 2A |
| 2-4 | 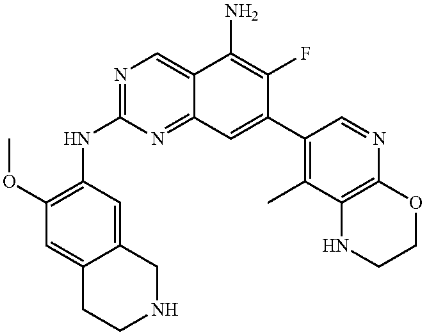 [SMILES: COc1cc2c(cc1Nc1ncc3c(N)c(F)c(-c4cnc5c(c4C)NCCO5)cc3n1)CNCC2] | 6-fluoro-N~2~-(6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 488, found 488; 2A |

TABLE 2-continued

| Example Number | Structure | Name | Exact Mass [M + H]+; Method |
|---|---|---|---|
| 2-5 | 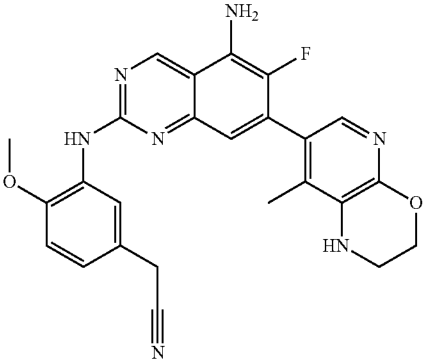 [SMILES: COc1ccc(CC#N)cc1Nc1ncc2c(N)c(F)c(-c3cnc4c(c3C)NCCO4)cc2n1] | (3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetonitrile | Calc'd 472, found 472; 2A |
| 2-6 | 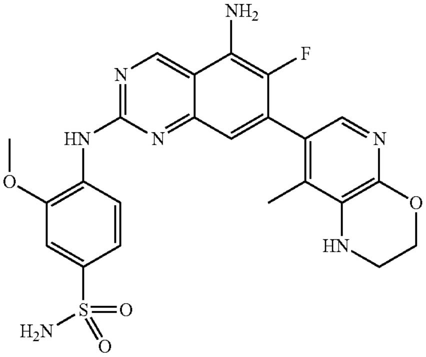 [SMILES: COc1cc(S(N)(=O)=O)ccc1Nc1ncc2c(N)c(F)c(-c3cnc4c(c3C)NCCO4)cc2n1] | 4-{[5-amino-6-fluoro-7-(8-methyl-2,3-dihydro-1H-pyrido[2,3-b][1,4]oxazin-7-yl)quinazolin-2-yl]amino}-3-methoxybenzene-1-sulfonamide | Calc'd 512, found 512; 2A |
| 2-7 | 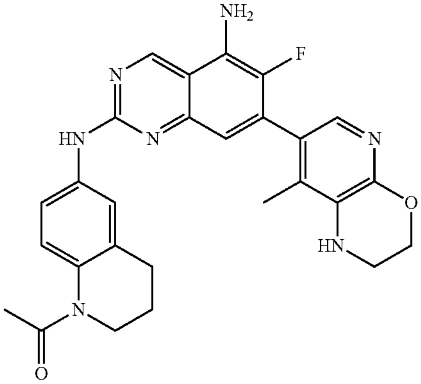 [SMILES: CC(=O)N1CCCc2cc(Nc3ncc4c(N)c(F)c(-c5cnc6c(c5C)NCCO6)cc4n3)ccc21] | 1-[6-{[5-amino-6-fluoro-7-(8-methyl-2,3-dihydro-1H-pyrido[2,3-b][1,4]oxazin-7-yl)quinazolin-2-yl]amino}-3,4-dihydroquinolin-1(2H)-yl]ethan-1-one | Calc'd 500, found 500; 2A |
| 2-8 | 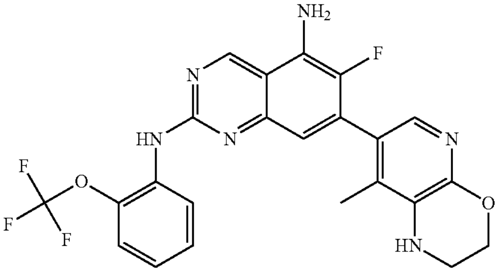 [SMILES: Cc1c(-c2cc3nc(Nc4ccccc4OC(F)(F)F)ncc3c(N)c2F)cnc2c1NCCO2] | 6-fluoro-7-(8-methyl-2,3-dihydro-1H-pyrido[2,3-b][1,4]oxazin-7-yl)-N~2~-[2-(trifluoromethoxy)phenyl]quinazoline-2,5-diamine | Calc'd 487, found 487; 2A |

TABLE 2-continued

| Example Number | Structure | Name | Exact Mass [M + H]$^+$; Method |
|---|---|---|---|
| 2-9 | 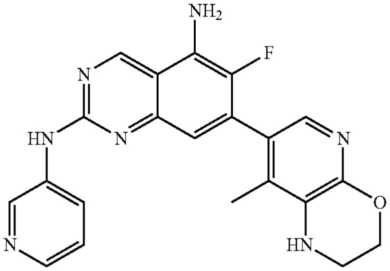 [SMILES: Cc1c(-c2cc3nc(Nc4cccnc4)ncc3c(N)c2F)cnc2c1NCCO2] | 6-fluoro-7-(8-methyl-2,3-dihydro-1H-pyrido[2,3-b][1,4]oxazin-7-yl)-N~2~-(pyridin-3-yl)quinazoline-2,5-diamine | Calc'd 404, found 404: 2A |
| 2-10 | 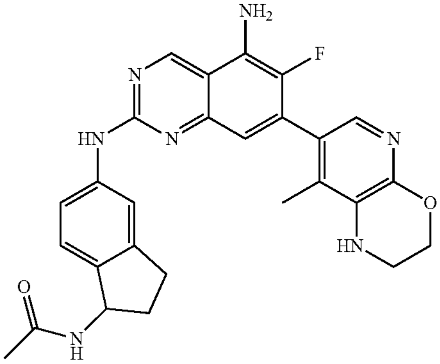 [SMILES: CC(=O)NC1CCc2cc(Nc3ncc4c(N)c(F)c(-c5cnc6c(c5C)NCCO6)cc4n3)ccc21] | (R or S)-N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide | Calc'd 500, found 500; 2A |
| 2-11 | 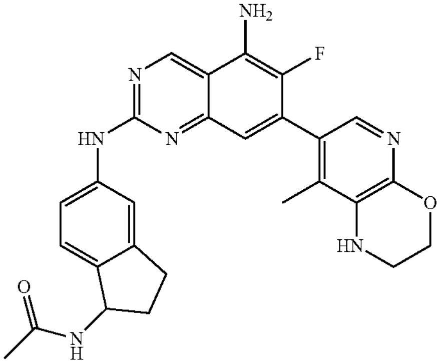 [SMILES: CC(=O)NC1CCc2cc(Nc3ncc4c(N)c(F)c(-c5cnc6c(c5C)NCCO6)cc4n3)ccc21] | (R or S)-N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide | Calc'd 500, found 500; 2A |
| 2-12 | 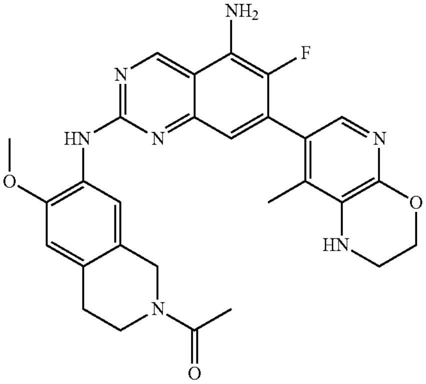 [SMILES: COc1cc2c(cc1Nc1ncc3c(N)c(F)c(-c4cnc5c(c4C)NCCO5)cc3n1)CN(C(C)=O)CC2] | 1-[7-{[5-amino-6-fluoro-7-(8-methyl-2,3-dihydro-1H-pyrido[2,3-b][1,4]oxazin-7-yl)quinazolin-2-yl]amino}-6-methoxy-3,4-dihydroisoquinolin-2(1H)-yl]ethan-1-one | Calc'd 530, found 530; 2A |

TABLE 2-continued

| Example Number | Structure | Name | Exact Mass [M + H]+; Method |
|---|---|---|---|
| 2-13 | 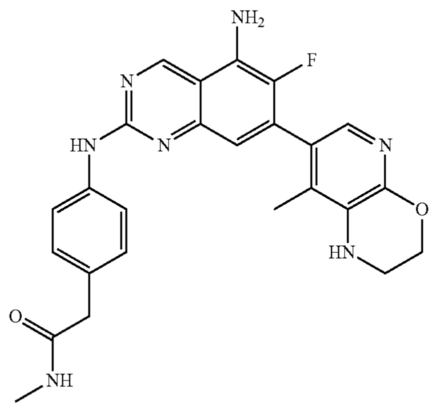 [SMILES: CNC(=O)Cc1ccc(Nc2ncc3c(N)c(F)c(-c4cnc5c(c4C)NCCO5)cc3n2)cc1] | 2-(4-{[5-amino-6-fluoro-7-(8-methyl-2,3-dihydro-1H-pyrido[2,3-b][1,4]oxazin-7-yl)quinazolin-2-ylamino}phenyl)-N-methylacetamide | Calc'd 474, found 474; |
| 2-14 | 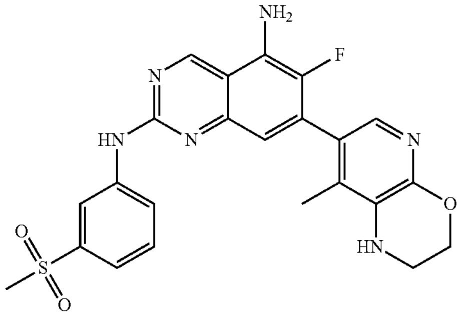 [SMILES: Cc1c(-c2cc3nc(Nc4cccc(S(C)(=O)=O)c4)ncc3c(N)c2F)cnc2c1NCCO2] | 6-fluoro-7-(8-methyl-2,3-dihydro-1H-pyrido[2,3-b][1,4]oxazin-7-yl)-N~2~-[3-(methylsulfonyl)phenyl] quinazoline-2,5-diamine | 2A Calc'd 481, found 481; 2A |
| 2-15 | 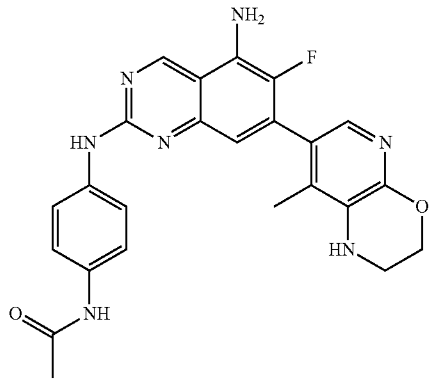 [SMILES: CC(=O)Nc1ccc(Nc2ncc3c(N)c(F)c(-c4cnc5c(c4C)NCCO5)cc3n2)cc1] | N-(4-{[5-amino-6-fluoro-7-(8-methyl-2,3-dihydro-1H-pyrido[2,3-b][1,4]oxazin-7-yl)quinazolin-2-ylamino}phenyl)acetamide | Calc'd 460, found 460; 2A |
| 2-16 | 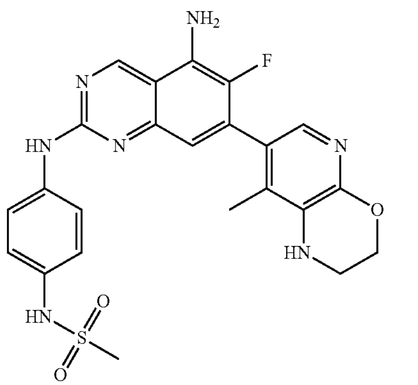 [SMILES: Cc1c(-c2cc3nc(Nc4ccc(NS(C)(=O)=O)cc4)ncc3c(N)c2F)cnc2c1NCCO2] | N-(4-{[5-amino-6-fluoro-7-(8-methyl-2,3-dihydro-1H-pyrido[2,3-b][1,4]oxazin-7-yl)quinazolin-2-yl]amino}phenyl)methane-sulfonamide | Calc'd 496, found 496; 2A |

TABLE 2-continued

| Example Number | Structure | Name | Exact Mass [M + H]+; Method |
|---|---|---|---|
| 2-17 | 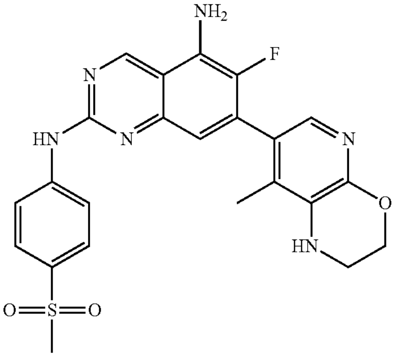 [SMILES: Cc1c(-c2cc3nc(Nc4ccc(S(C)(=O)=O)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-[4-(methylsulfonyl)phenyl] quinazoline-2,5-diamine | Calc'd 481, found 481; 2A |
| 2-18 | 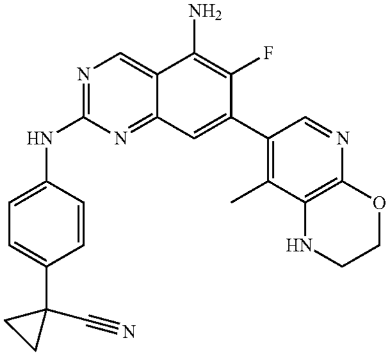 [SMILES: Cc1c(-c2cc3nc(Nc4ccc(C5(C#N)CC5)cc4)ncc3c(N)c2F)cnc2c1NCCO2] | 1-(4-{[5-amino-6-fluoro-7-(8-methyl-2,3-dihydro-1H-pyrido[2,3-b][1,4]oxazin-7-yl)quinazolin-2-yl]amino}phenyl)cyclo-propane-1-carbonitrile | Calc'd 468, found 468; 2A |
| 2-19 | 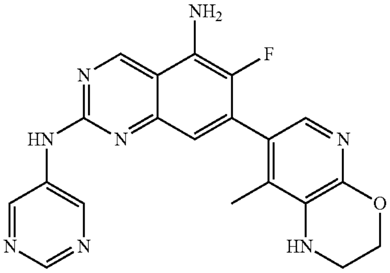 [SMILES: Cc1c(-c2cc3nc(Nc4cncnc4)ncc3c(N)c2F)cnc2c1NCCO2] | 6-fluoro-7-(8-methyl-2,3-dihydro-1H-pyrido[2,3-b][1,4]oxazin-7-yl)-N~2~-(pyrimidin-5-yl)quinazoline-2,5-diamine | Calc'd 405, found 405; 2A |
| 2-20 | 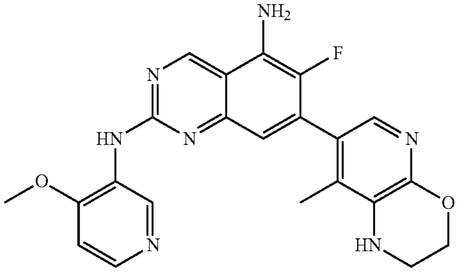 [SMILES: COc1ccncc1Nc1ncc2c(N)c(F)c(-c3cnc4c(c3C)NCCO4)cc2n1] | 6-fluoro-N~2~-(4-methoxypyridin-3-yl)-7-(8-methyl-2,3-dihydro-1H-pyrido[2,3-b][1,4]oxazin-7-yl)quinazoline-2,5-diamine | Calc'd 434, found 434: 2A |

TABLE 2-continued

| Example Number | Structure | Name | Exact Mass [M + H]+; Method |
|---|---|---|---|
| 2-21 | 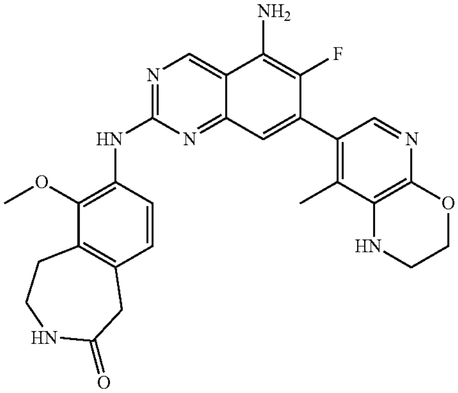 [SMILES: COc1c(Nc2ncc3c(N)c(F)c(-c4cnc5c(c4C)NCCO5)cc3n2)ccc2c1CCNC(=O)C2] | 7-{[5-amino-6-fluoro-7-(8-methyl-2,3-dihydro-1H-pyrido[2,3-b][1,4]oxazin-7-yl)quinazolin-2-ylamino}-6-methoxy-1,3,4,5-tetrahydro-2H-3-benzazepin-2-one | Calc'd 516, found 516; 2A |
| 2-22 | 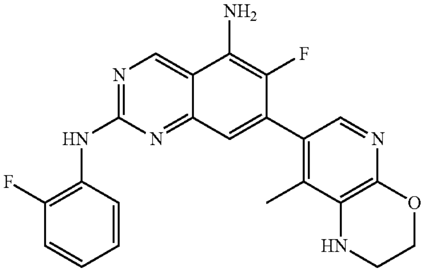 [SMILES: Cc1c(-c2cc3nc(Nc4ccccc4F)ncc3c(N)c2F)cnc2c1NCCO2] | 6-fluoro-N~2~-(2-fluorophenyl)-7-(8-methyl-2,3-dihydro-1H-pyrido[2,3-b][1,4]oxazin-7-yl)quinazoline-2,5-diamine | Calc'd 421, found 421; 2A |
| 2-23 | 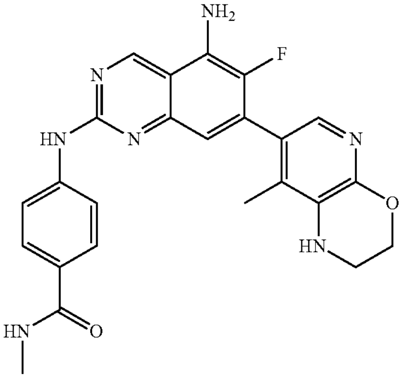 [SMILES: CNC(=O)c1ccc(Nc2ncc3c(N)c(F)c(-c4cnc5c(c4C)NCCO5)cc3n2)cc1] | 4-{[5-amino-6-fluoro-7-(8-methyl-2,3-dihydro-1H-pyrido[2,3-b][1,4]oxazin-7-yl)quinazolin-2-yl]amino}-N-methylbenzamide | Calc'd 460, found 460; 2A |
| 2-24 | 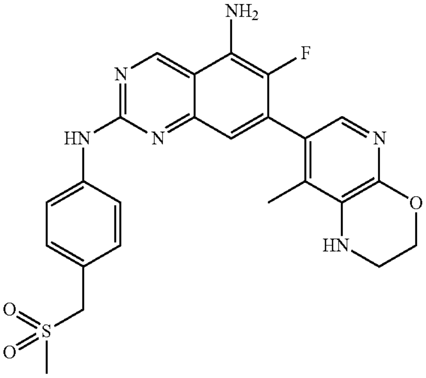 [SMILES: Cc1c(-c2cc3nc(Nc4ccc(CS(C)(=O)=O)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine | Calc'd 495, found 495; 2A |

TABLE 2-continued

| Example Number | Structure | Name | Exact Mass [M + H]+; Method |
|---|---|---|---|
| 2-25 | 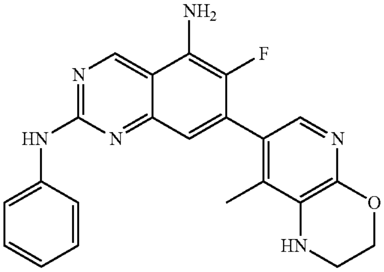 [SMILES: Cc1c(-c2cc3nc(Nc4ccccc4)ncc3c(N)c2F)cnc2c1NCCO2] | 6-fluoro-7-(8-methyl-2,3-dihydro-1H-pyrido[2,3-b][1,4]oxazin-7-yl)-N~2~-phenylquinazoline-2,5-diamine | Calc'd 403, found 403; 2A |
| 2-26 | 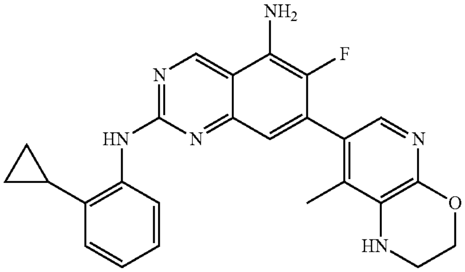 [SMILES: Cc1c(-c2cc3nc(Nc4ccccc4C4CC4)ncc3c(N)c2F)cnc2c1NCCO2] | N~2~-(2-cyclopropylphenyl)-6-fluoro-7-(8-methyl-2,3-dihydro-1H-pyrido[2,3-b][1,4]oxazin-7-yl)quinazoline-2,5-diamine | Calc'd 443, found 443; 2A |
| 2-27 | 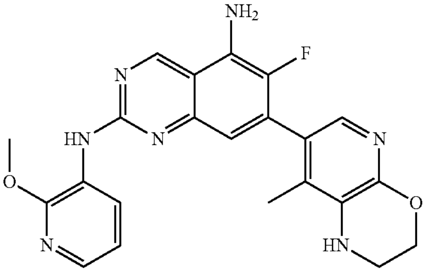 [SMILES: COc1ncccc1Nc1ncc2c(N)c(F)c(-c3cnc4c(c3C)NCCO4)cc2n1] | 6-fluoro-N~2~-(2-methoxypyridin-3-yl)-7-(8-methyl-2,3-dihydro-1H-pyrido[2,3-b][1,4]oxazin-7-yl)quinazoline-2,5-diamine | Calc'd 434, found 434; 2A |
| 2-28 | 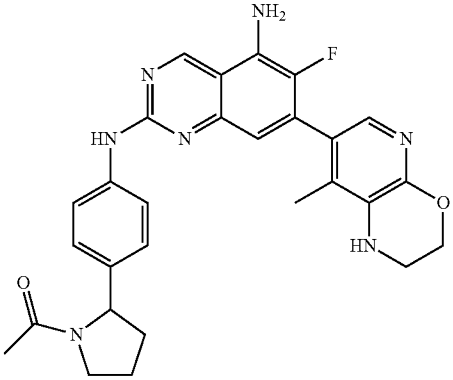 [SMILES: CC(=O)N1CCCC1c1ccc(Nc2ncc3c(N)c(F)c(-c4cnc5c(c4C)NCCO5)cc3n2)cc1] | (R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one | Calc'd 514, found 514; 2A |

TABLE 2-continued

| Example Number | Structure | Name | Exact Mass $[M + H]^+$; Method |
|---|---|---|---|
| 2-29 | 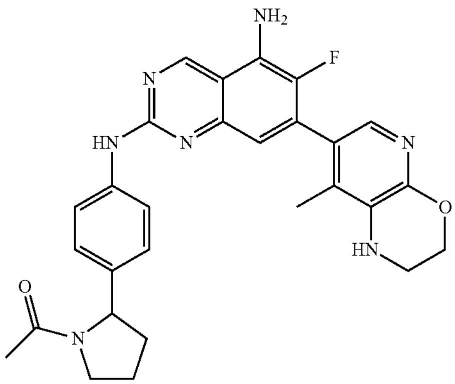 [SMILES: CC(=O)N1CCCC1c1ccc(Nc2ncc3c(N)c(F)c(-c4cnc5c(c4C)NCCO5)cc3n2)cc1] | (R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one | Calc'd 514, found 514; 2A |
| 2-30 | 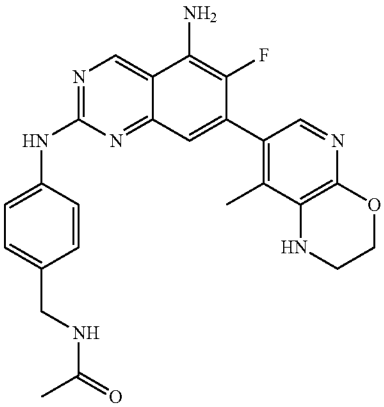 [SMILES: CC(=O)NCc1ccc(Nc2ncc3c(N)c(F)c(-c4cnc5c(c4C)NCCO5)cc3n2)cc1] | N-[(4-{[5-amino-6-fluoro-7-(8-methyl-2,3-dihydro-1H-pyrido[2,3-b][1,4]oxazin-7-yl)quinazolin-2-yl]amino}phenyl)methyl] acetamide | Calc'd 474, found 474; 2A |
| 2-31 | 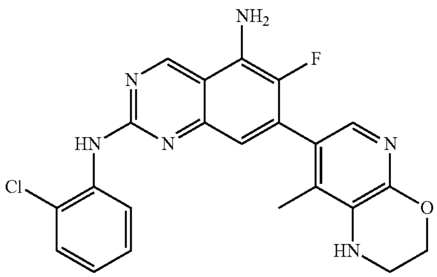 [SMILES: Cc1c(-c2cc3nc(Nc4ccccc4Cl)ncc3c(N)c2F)cnc2c1NCCO2] | N~2~-(2-chlorophenyl)-6-fluoro-7-(8-methyl-2,3-dihydro-1H-pyrido[2,3-b][1,4]oxazin-7-yl)quinazoline-2,5-diamine | Calc'd 437, found 437; 2A |
| 2-32 | 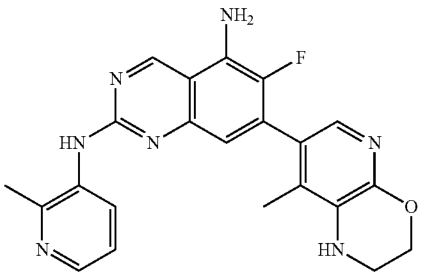 [SMILES: Cc1ncccc1Nc1ncc2c(N)c(F)c(-c3cnc4c(c3C)NCCO4)cc2n1] | 6-fluoro-7-(8-methyl-2,3-dihydro-1H-pyrido[2,3-b][1,4]oxazin-7-yl)-N~2~-(2-methylpyridin-3-yl)quinazoline-2,5-diamine | Calc'd 418, found 418; 2A |

TABLE 2-continued

| Example Number | Structure | Name | Exact Mass $[M + H]^+$; Method |
|---|---|---|---|
| 2-33 | 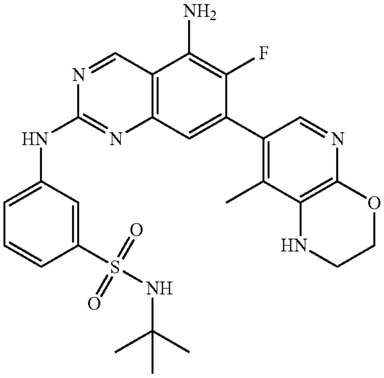 [SMILES: Cc1c(-c2cc3nc(Nc4cccc(S(=O)(=O)NC(C)(C)C)c4)ncc3c(N)c2F)cnc2c1NCCO2] | 3-{[5-amino-6-fluoro-7-(8-methyl-2,3-dihydro-1H-pyrido[2,3-b][1,4]oxazin-7-yl)quinazolin-2-yl]amino}-N-tert-butylbenzene-1-sulfonamide | Calc'd 538, found 538; 2A |
| 2-34 | 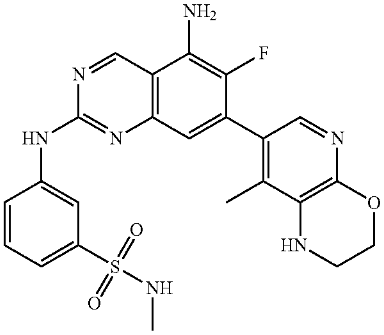 [SMILES: CNS(=O)(=O)c1cccc(Nc2ncc3c(N)c(F)c(-c4cnc5c(c4C)NCCO5)cc3n2)c1] | 3-{[5-amino-6-fluoro-7-(8-methyl-2,3-dihydro-1H-pyrido[2,3-b][1,4]oxazin-7-yl)quinazolin-2-ylamino}-N-methylbenzene-1-sulfonamide | Calc'd 496, found 496; 2A |
| 2-35 | 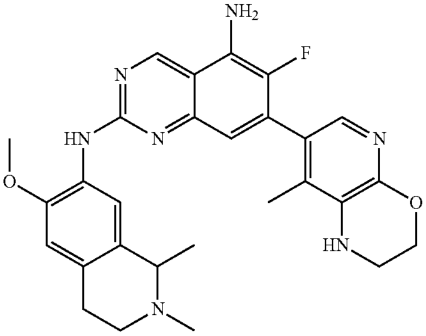 [SMILES: COc1cc2c(cc1Nc1ncc3c(N)c(F)c(-c4cnc5c(c4C)NCCO5)cc3n1)C(C)N(C)CC2] | (R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 516, found 516; 2B |
| 2-36 | 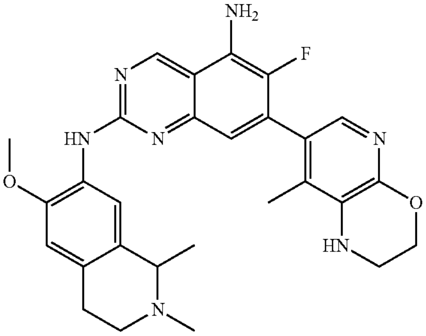 [SMILES: COc1cc2c(cc1Nc1ncc3c(N)c(F)c(-c4cnc5c(c4C)NCCO5)cc3n1)C(C)N(C)CC2] | (R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 516, found 516; 2B |

TABLE 2-continued

| Example Number | Structure | Name | Exact Mass [M + H]+; Method |
|---|---|---|---|
| 2-37 | 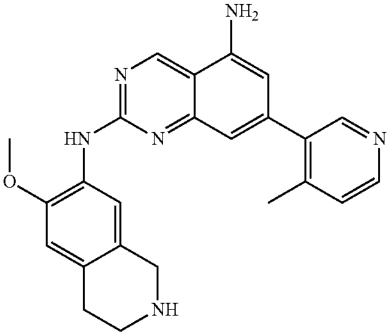 [SMILES: COc1cc2c(cc1Nc1ncc3c(N)cc(-c4cnccc4C)cc3n1)CNCC2] | N~2~-(6-methoxy-1,2,3,4-tetrahydroisoquinolin-7-yl)-7-(4-methylpyridin-3-yl)quinazoline-2,5-diamine | Calc'd 413, found 413; 2C |
| 2-38 | 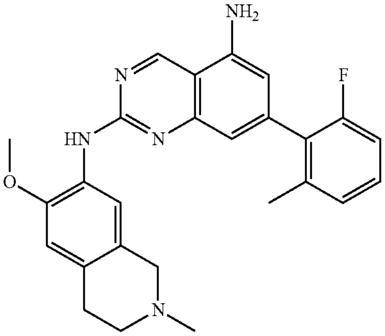 [SMILES: COc1cc2c(cc1Nc1ncc3c(N)cc(-c4c(C)cccc4F)cc3n1)CN(C)CC2] | 7-(2-fluoro-6-methylphenyl)-N~2~-(6-methoxy-2-methyl-1,2,3,4-tetrahydroisoquinolin-7-yl)quinazoline-2,5-diamine | Calc'd 444, found 444; 2D |
| 2-39 | 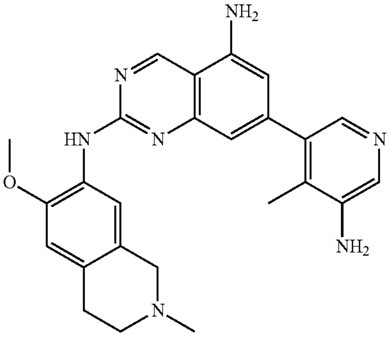 [SMILES: COc1cc2c(cc1Nc1ncc3c(N)cc(-c4cncc(N)c4C)cc3n1)CN(C)CC2] | 7-(5-amino-4-methylpyridin-3-yl)-N~2~-(6-methoxy-2-methyl-1,2,3,4-tetrahydroisoquinolin-7-yl)quinazoline-2,5-diamine | Calc'd 442, found 442; 2D |
| 2-40 | 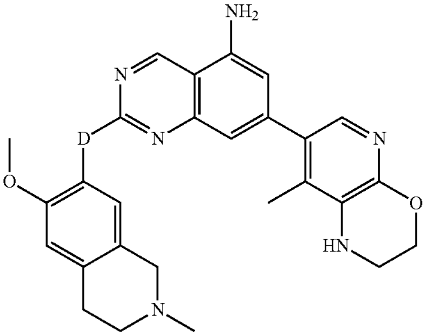 | N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 484, found 484; 2D |

TABLE 2-continued

| Example Number | Structure | Name | Exact Mass $[M + H]^+$; Method |
|---|---|---|---|
| 2-41 | 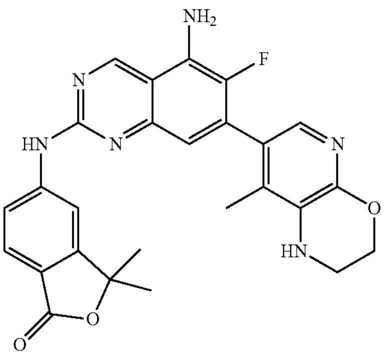 [SMILES: Cc1c(-c2cc3nc(Nc4ccc5c(c4)C(C)(C)OC5=O)ncc3c(N)c2F)cnc2c1NCCO2] | 5-{[5-amino-6-fluoro-7-(8-methyl-2,3-dihydro-1H-pyrido[2,3-b][1,4]oxazin-7-yl)quinazolin-2-yl]amino}-3,3-dimethyl-2-benzofuran-1(3H)-one | Calc'd 487, found 487; 2A |
| 2-42 | 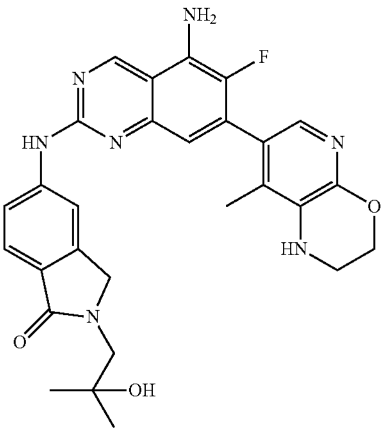 [SMILES: Cc1c(-c2cc3nc(Nc4ccc5c(c4)CN(CC(C)(C)O)C5=O)ncc3c(N)c2F)cnc2c1NCCO2] | 5-{[5-amino-6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one | Calc'd 530, found 530; 2A |
| 2-43 | 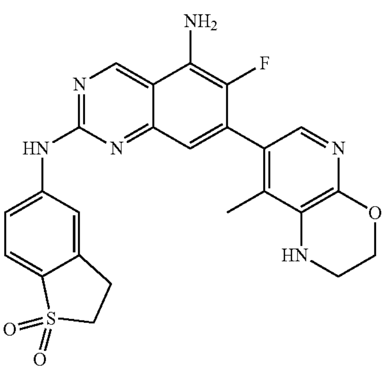 [SMILES: Cc1c(-c2cc3nc(Nc4ccc5c(c4)CCS5(=O)=O)ncc3c(N)c2F)cnc2c1NCCO2] | 5-{[5-amino-6-fluoro-7-(8-methyl-2,3-dihydro-1H-pyrido[2,3-b][1,4]oxazin-7-yl)quinazolin-2-yl]amino}-2,3-dihydro-1H-1-benzothiophene-1,1-dione | Calc'd 493, found 493; 2A |
| 2-44 | 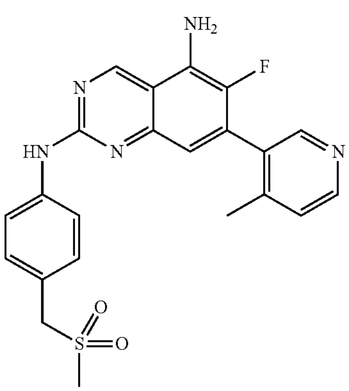 [SMILES: Cc1ccncc1-c1cc2nc(Nc3ccc(CS(C)(=O)=O)cc3)ncc2c(N)c1F] | 6-fluoro-7-(4-methylpyridin-3-yl)-N~2~-{4-[(methylsulfonyl)methyl]phenyl}quinazoline-2,5-diamine | Calc'd 438, found 438; 2A |

TABLE 2-continued

| Example Number | Structure | Name | Exact Mass [M + H]+; Method |
|---|---|---|---|
| 2-45 | 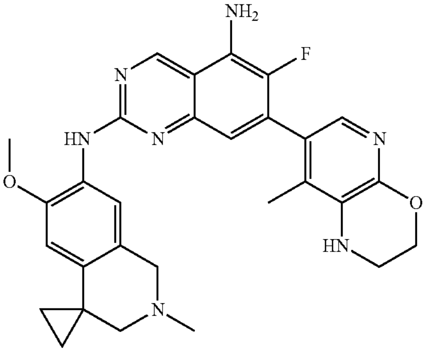 [SMILES: COc1cc2c(cc1Nc1ncc3c(N)c(F)c(-c4cnc5c(c4C)NCCO5)cc3n1)CN(C)CC21CC1] | 6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine | Calc'd 528, found 528; 2B |
| 2-46 | 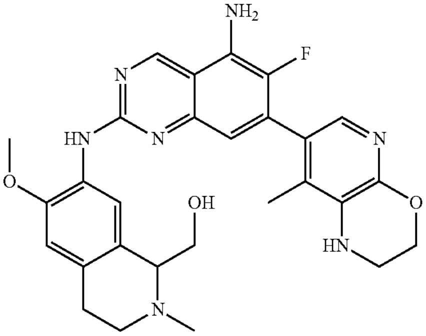 [SMILES: COc1cc2c(cc1Nc1ncc3c(N)c(F)c(-c4cnc5c(c4C)NCCO5)cc3n1)C(CO)N(C)CC2] | (R and S)-(7-{[5-amino-6-fluoro-7-(8-methyl-2,3-dihydro-1H-pyrido[2,3-b][1,4]oxazin-7-yl)quinazolin-2-yl]amino}-6-methoxy-2-methyl-1,2,3,4-tetrahydroisoquinolin-1-yl)methanol | Calc'd 532, found 532; 2B |
| 2-47 | 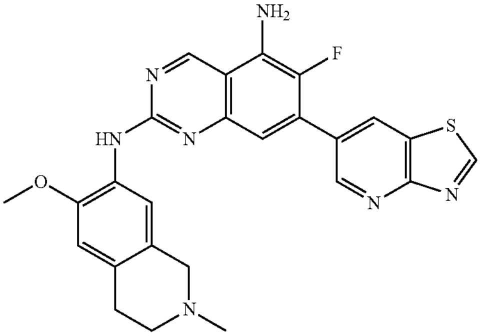 [SMILES: COc1cc2c(cc1Nc1ncc3c(N)c(F)c(-c4cnc5ncsc5c4)cc3n1)CN(C)CC2] | 6-fluoro-N~2~-(6-methoxy-2-methyl-1,2,3,4-tetrahydroisoquinolin-7-yl)-7-([1,3]thiazolo[4,5-b]pyridin-6-yl)quinazoline-2,5-diamine | Calc'd 488, found 488; 2B |
| 2-48 | 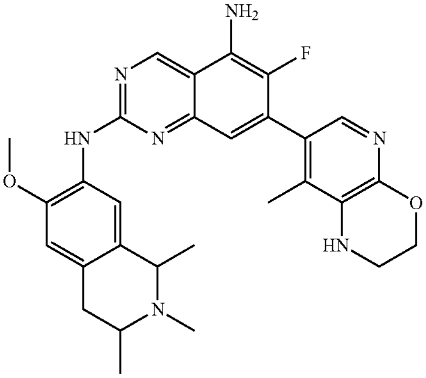 [SMILES: COc1cc2c(cc1Nc1ncc3c(N)c(F)c(-c4cnc5c(c4C)NCCO5)cc3n1)C(C)N(C)C(C)C2] | (R,R and S,S)-6-fluoro-N~2~-(6-methoxy-1,2,3-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 530, found 530; 2F |

TABLE 2-continued

| Example Number | Structure | Name | Exact Mass [M + H]+; Method |
|---|---|---|---|
| 2-49 | 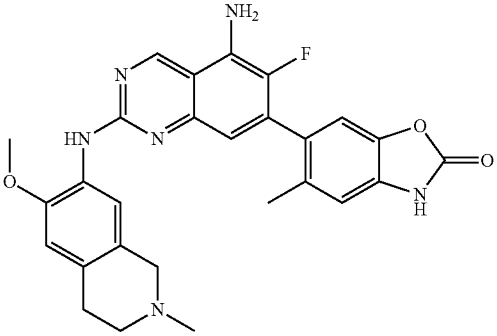 [SMILES: COc1cc2c(cc1Nc1ncc3c(N)c(F)c(-c4cc5oc(=O)[nH]c5cc4C)cc3n1)CN(C)CC2] | 6-(5-amino-6-fluoro-2-((6-methoxy-2-methyl-1,2,3,4-tetrahydroisoquinolin-7-yl)amino)quinazolin-7-yl)-5-methylbenzo[d]oxazol-2(3H)-one | Calc'd 501, found 501; 2E |
| 2-50 | 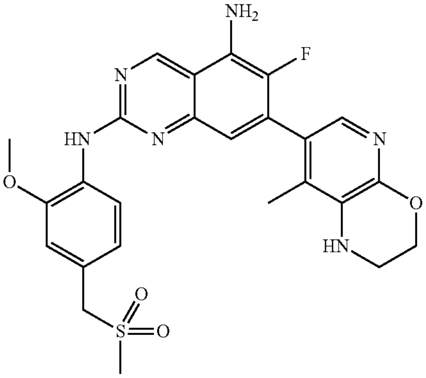 [SMILES: COc1cc(CS(C)(=O)=O)ccc1Nc1ncc2c(N)c(F)c(-c3cnc4c(c3C)NCCO4)cc2n1] | 6-fluoro-N2-(2-methoxy-4-((methylsulfonyl)methyl)phenyl)-7-(8-methyl-2,3-dihydro-1H-pyrido[2,3-b][1,4]oxazin-7-yl)quinazoline-2,5-diamine | Calc'd 525, found 525; 2B |
| 2-51 | 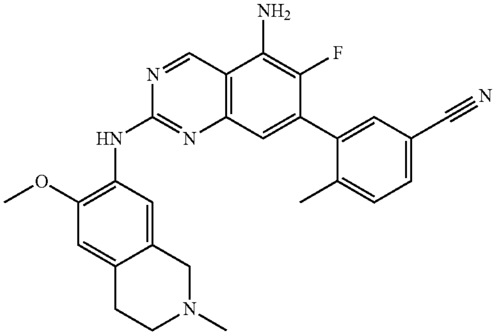 [SMILES: COc1cc2c(cc1Nc1ncc3c(N)c(F)c(-c4cc(C#N)ccc4C)cc3n1)CN(C)CC2] | 3-(5-amino-6-fluoro-2-((6-methoxy-2-methyl-1,2,3,4-tetrahydroisoquinolin-7-yl)amino)quinazolin-7-yl)-4-methylbenzonitrile | Calc'd 469, found 469; 2A |
| 2-52 | 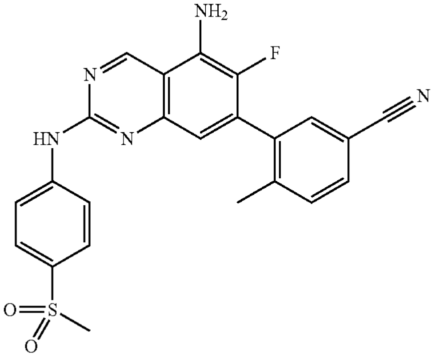 [SMILES: Cc1ccc(C#N)cc1-c1cc2nc(Nc3ccc(S(C)(=O)=O)cc3)ncc2c(N)c1F] | 3-(5-amino-6-fluoro-2-{[4-(methylsulfonyl)phenyl]amino}quinazolin-7-yl)-4-methylbenzonitrile | Calc'd 448, found 448; 2A |

TABLE 2-continued

| Example Number | Structure | Name | Exact Mass $[M + H]^+$; Method |
|---|---|---|---|
| 2-53 | 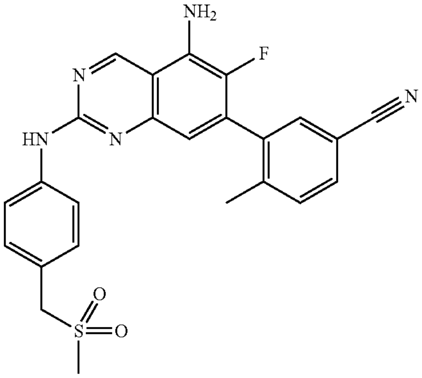 [SMILES: Cc1ccc(C#N)cc1-c1cc2nc(Nc3ccc(CS(C)(=O)=O)cc3)ncc2c(N)c1F] | 3-[5-amino-6-fluoro-2-({4-[(methylsulfonyl)methyl]phenyl}amino)quinazolin-7-yl]-4-methylbenzonitrile | Calc'd 462, found 462; 2A |
| 2-54 | 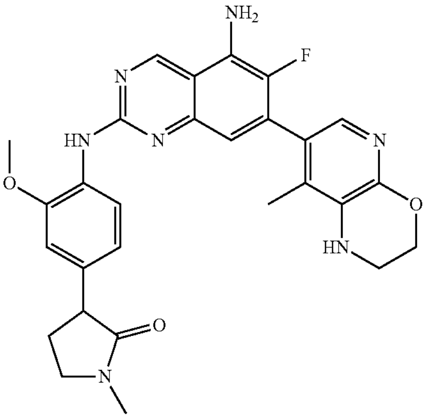 [SMILES: COc1cc(C2CCN(C)C2=O)ccc1Nc1ncc2c(N)c(F)c(-c3cnc4c(c3C)NCCO4)cc2n1] | (R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one | Calc'd 530, found 530; 2F |
| 2-55 | 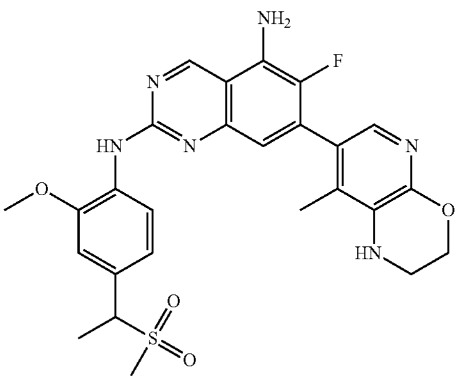 [SMILES: COc1cc(C(C)S(C)(=O)=O)ccc1Nc1ncc2c(N)c(F)c(-c3cnc4c(c3C)NCCO4)cc2n1] | (R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine | Calc'd 539, found 539; 2B |
| 2-56 | 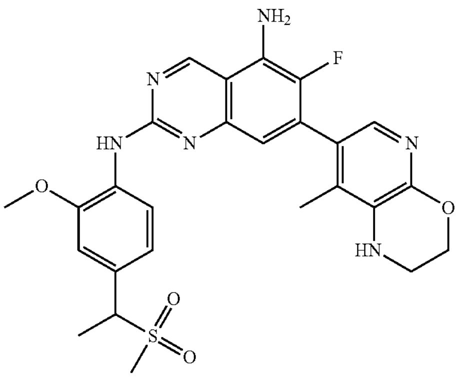 [SMILES: COc1cc(C(C)S(C)(=O)=O)ccc1Nc1ncc2c(N)c(F)c(-c3cnc4c(c3C)NCCO4)cc2n1] | (R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine | Calc'd 539, found 539; 2B |

TABLE 2-continued

| Example Number | Structure | Name | Exact Mass [M + H]+; Method |
|---|---|---|---|
| 2-57 | 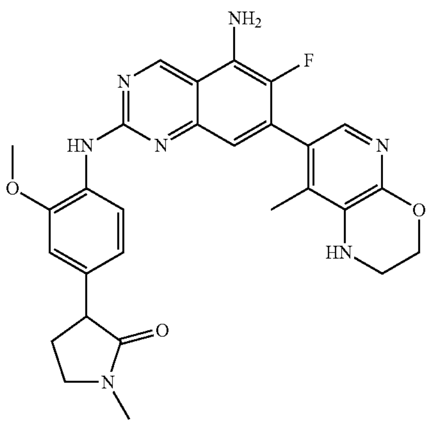 [SMILES: COc1cc(C2CCN(C)C2=O)ccc1Nc1ncc2c(N)c(F)c(-c3cnc4c(c3C)NCCO4)cc2n1] | (R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one | Calc'd 530, found 530; 2F |
| 2-58 | 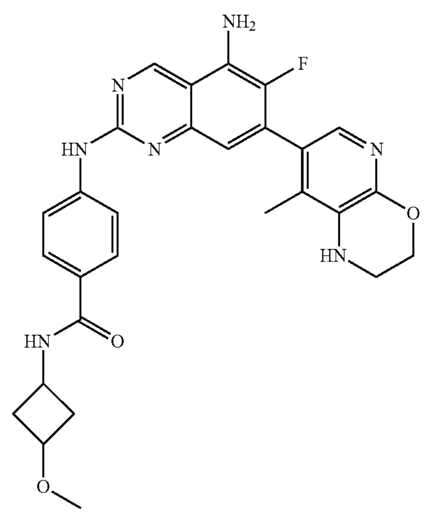 [SMILES: COC1CC(NC(=O)c2ccc(Nc3ncc4c(N)c(F)c(-c5cnc6c(c5C)NCCO6)cc4n3)cc2)C1] | 4-{[5-amino-6-fluoro-7-(8-methyl-2,3-dihydro-1H-pyrido[2,3-b][1,4]oxazin-7-yl)quinazolin-2-yl]amino}-N-(3-methoxycyclobutyl) benzamide | Calc'd 530, found 530; 2A |
| 2-59 | 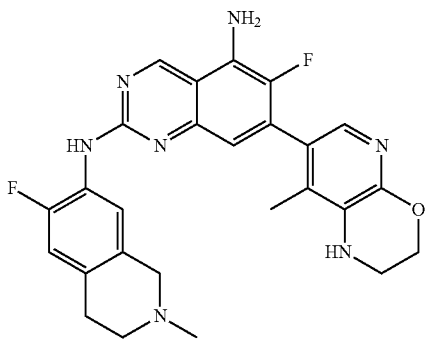 [SMILES: Cc1c(-c2cc3nc(Nc4cc5c(cc4F)CCN(C)C5)ncc3c(N)c2F)cnc2c1NCCO2] | 6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 490, found 490; 2B |

TABLE 2-continued

| Example Number | Structure | Name | Exact Mass [M + H]+; Method |
| --- | --- | --- | --- |
| 2-60 | 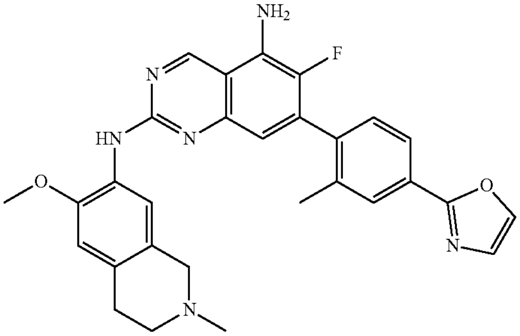 [SMILES: COc1cc2c(cc1Nc1ncc3c(N)c(F)c(-c4ccc(-c5ncco5)cc4C)cc3n1)CN(C)CC2] | 6-fluoro-N~2~-(6-methoxy-2-methyl-1,2,3,4-tetrahydroisoquinolin-7-yl)-7-[2-methyl-4-(1,3-oxazol-2-yl)phenyl]quinazoline-2,5-diamine | Calc'd 511, found 511; 2G |
| 2-61 | 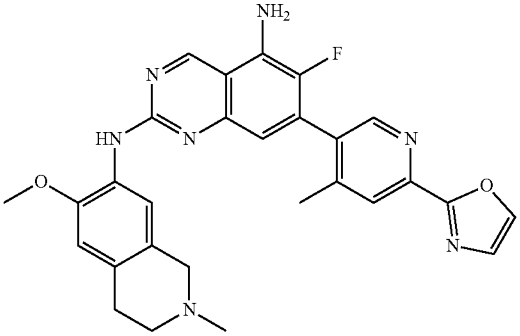 [SMILES: COc1cc2c(cc1Nc1ncc3c(N)c(F)c(-c4cnc(-c5ncco5)cc4C)cc3n1)CN(C)CC2] | 6-fluoro-N~2~-(6-methoxy-2-methyl-1,2,3,4-tetrahydroisoquinolin-7-yl)-7-[4-methyl-6-(1,3-oxazol-2-yl)pyridin-3-yl]quinazoline-2,5-diamine | Calc'd 512, found 512; 2G |
| 2-62 | 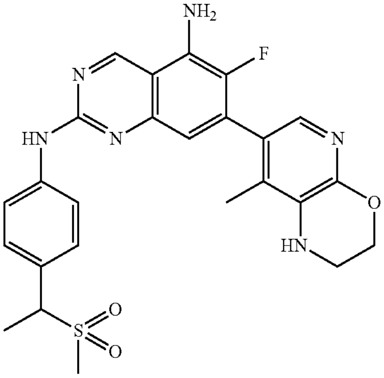 [SMILES: Cc1c(-c2cc3nc(Nc4ccc(C(C)S(C)(=O)=O)cc4)ncc3c(N)c2F)cnc2c1NCCO2] | (R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine | Calc'd 509, found 509; 2B |
| 2-63 | 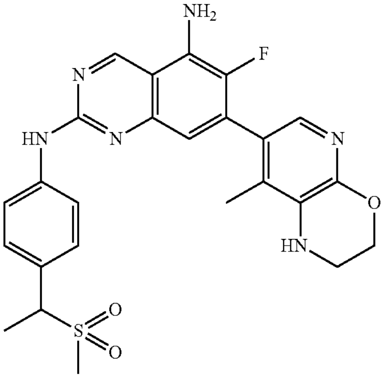 [SMILES: Cc1c(-c2cc3nc(Nc4ccc(C(C)S(C)(=O)=O)cc4)ncc3c(N)c2F)cnc2c1NCCO2] | (R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine | Calc'd 509, found 509; 2B |

TABLE 2-continued

| Example Number | Structure | Name | Exact Mass [M + H]+; Method |
|---|---|---|---|
| 2-64 | 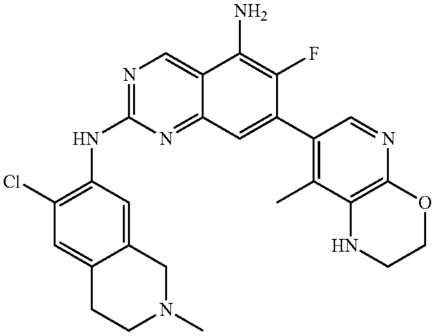 [SMILES: Cc1c(-c2cc3nc(Nc4cc5c(cc4Cl)CCN(C)C5)ncc3c(N)c2F)cnc2c1NCCO2] | N~2~-(6-chloro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine | Calc'd 506, found 506; 2B |
| 2-65 | 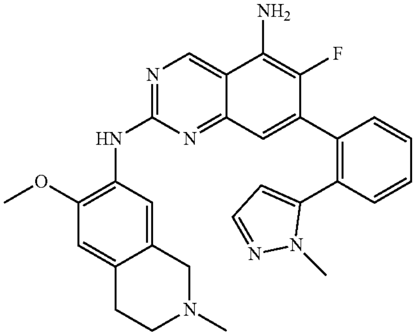 [SMILES: COc1cc2c(cc1Nc1ncc3c(N)c(F)c(-c4ccccc4-c4ccnn4C)cc3n1)CN(C)CC2] | 6-fluoro-N~2~-(6-methoxy-2-methyl-1,2,3,4-tetrahydroisoquinolin-7-yl)-7-[2-(1-methyl-1H-pyrazol-5-yl)phenyl]quinazoline-2,5-diamine | Calc'd 510, found 510; 2B |
| 2-66 | 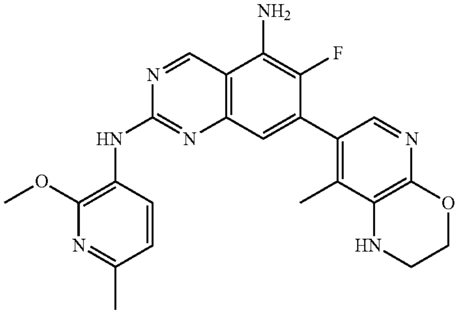 | 6-fluoro-N~2~-(2-methoxy-6-methylpyridin-3-yl)-7-(8-methyl-2,3-dihydro-1H-pyrido[2,3-b][1,4]oxazin-7-yl)quinazoline-2,5-diamine | Calc'd 448, found 448; 2B |
| 2-67 | 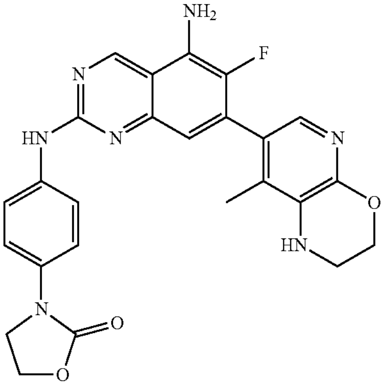 [SMILES: Cc1c(-c2cc3nc(Nc4ccc(N5CCOC5=O)cc4)ncc3c(N)c2F)cnc2c1NCCO2] | 3-(4-{[5-amino-6-fluoro-7-(8-methyl-2,3-dihydro-1H-pyrido[2,3-b][1,4]oxazin-7-yl)quinazolin-2-yl]amino}phenyl)-1,3-oxazolidin-2-one | Calc'd 488, found 488; 2B |

TABLE 2-continued

| Example Number | Structure | Name | Exact Mass [M + H]+; Method |
|---|---|---|---|
| 2-68 | 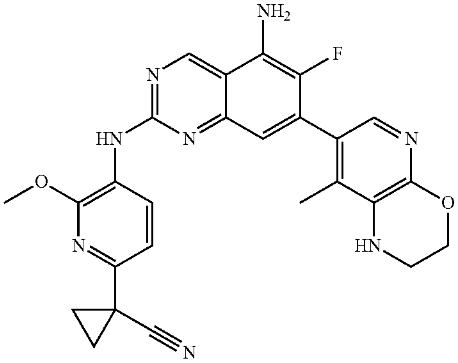 | 1-(5-{[5-amino-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile | Calc'd 499, found 499; 2G |
| 2-69 | 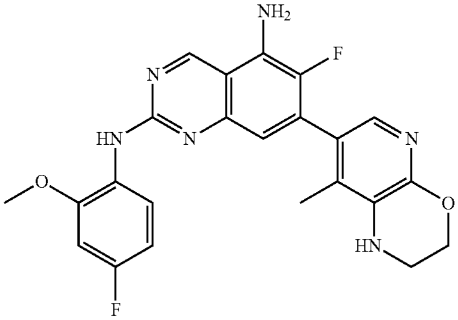 [SMILES: COc1cc(F)ccc1Nc1ncc2c(N)c(F)c(-c3cnc4c(c3C)NCCO4)cc2n1] | 6-fluoro-N~2~-(4-fluoro-2-methoxyphenyl)-7-(8-methyl-2,3-dihydro-1H-pyrido[2,3-b][1,4]oxazin-7-yl)quinazoline-2,5-diamine | Calc'd 451, found 451; 2G |
| 2-70 | 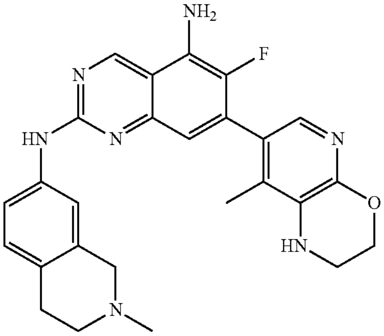 [SMILES: Cc1c(-c2cc3nc(Nc4ccc5c(c4)CN(C)CC5)ncc3c(N)c2F)cnc2c1NCCO2] | 6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine | Calc'd 472, found 472; 2G |
| 2-71 | 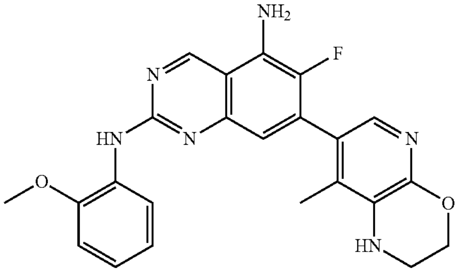 [SMILES: COc1ccccc1Nc1ncc2c(N)c(F)c(-c3cnc4c(c3C)NCCO4)cc2n1] | 6-fluoro-N~2~-(2-methoxyphenyl)-7-(8-methyl-2,3-dihydro-1H-pyrido[2,3-b][1,4]oxazin-7-yl)quinazoline-2,5-diamine | Calc'd 433, found 433; 2G |

TABLE 2-continued

| Example Number | Structure | Name | Exact Mass [M + H]+; Method |
|---|---|---|---|
| 2-72 | 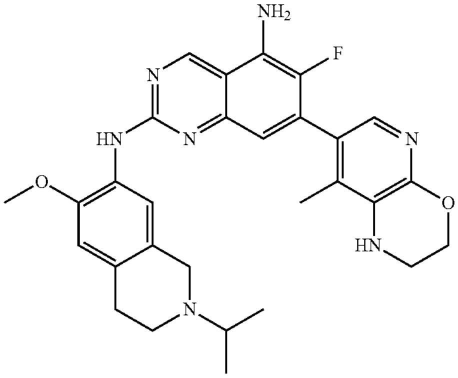 [SMILES: COc1cc2c(cc1Nc1ncc3c(N)c(F)c(-c4cnc5c(c4C)NCCO5)cc3n1)CN(C(C)C)CC2] | 6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine | Calc'd 530, found 530; 2J |
| 2-73 | 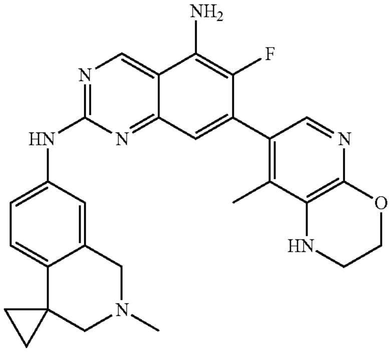 [SMILES: Cc1c(-c2cc3nc(Nc4ccc5c(c4)CN(C)CC54CC4)ncc3c(N)c2F)cnc2c1NCCO2] | 6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine | Calc'd 498, found 498; 2A |
| 2-74 | 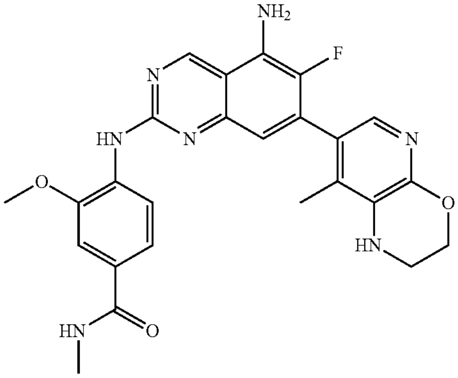 [SMILES: CNC(=O)c1ccc(Nc2ncc3c(N)c(F)c(-c4cnc5c(c4C)NCCO5)cc3n2)c(OC)c1] | 4-{[5-amino-6-fluoro-7-(8-methyl-2,3-dihydro-1H-pyrido[2,3-b][1,4]oxazin-7-yl)quinazolin-2-yl]amino}-3-methoxy-N-methylbenzamide | Calc'd 490, found 490; 2G |
| 2-75 | 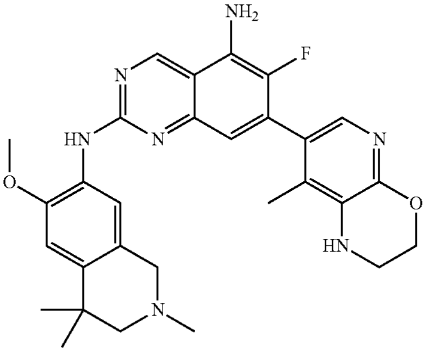 [SMILES: COc1cc2c(cc1Nc1ncc3c(N)c(F)c(-c4cnc5c(c4C)NCCO5)cc3n1)CN(C)CC2(C)C] | 6-fluoro-N~2~-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 530, found 530; 2F |

TABLE 2-continued

| Example Number | Structure | Name | Exact Mass $[M + H]^+$; Method |
|---|---|---|---|
| 2-76 | 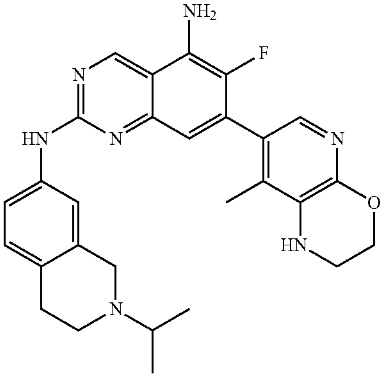 [SMILES: Cc1c(-c2cc3nc(Nc4ccc5c(c4)CN(C(C)C)CC5)ncc3c(N)c2F)cnc2c1NCCO2] | 6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine | Calc'd 500, found 500; 2J |
| 2-77 | 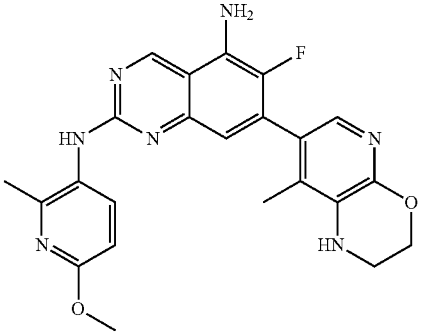 [SMILES: COc1ccc(Nc2ncc3c(N)c(F)c(-c4cnc5c(c4C)NCCO5)cc3n2)c(C)n1] | 6-fluoro-N~2~-(6-methoxy-2-methylpyridin-3-yl)-7-(8-methyl-2,3-dihydro-1H-pyrido[2,3-b][1,4]oxazin-7-yl)quinazoline-2,5-diamine | Calc'd 448, found 448; 2A |
| 2-78 | 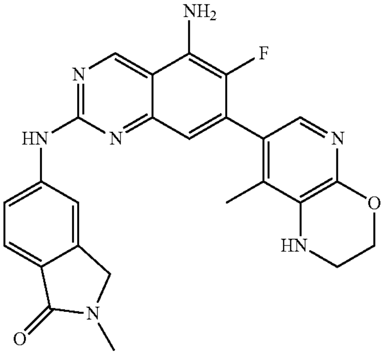 [SMILES: Cc1c(-c2cc3nc(Nc4ccc5c(c4)CN(C)C5=O)ncc3c(N)c2F)cnc2c1NCCO2] | 5-{[5-amino-6-fluoro-7-(8-methyl-2,3-dihydro-1H-pyrido[2,3-b][1,4]oxazin-7-yl)quinazolin-2-yl]amino}-2-methyl-2,3-dihydro-1H-isoindol-1-one | Calc'd 472, found 472; 2A |
| 2-79 | 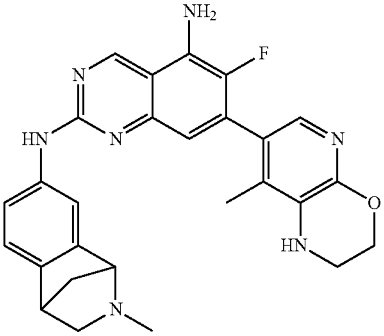 [SMILES: Cc1c(-c2cc3nc(Nc4ccc5c(c4)C4CC5CN4C)ncc3c(N)c2F)cnc2c1NCCO2] | (R,S and S,R)-6-fluoro-N2-(2-methyl-1,2,3,4-tetrahydro-1,4-methanoisoquinolin-7-yl)-7-(8-methyl-2,3-dihydro-1H-pyrido[2,3-b][1,4]oxazin-7-yl)quinazoline-2,5-diamine | Calc'd 484, found 482; 2H |

TABLE 2-continued

| Example Number | Structure | Name | Exact Mass [M + H]+; Method |
|---|---|---|---|
| 2-80 | 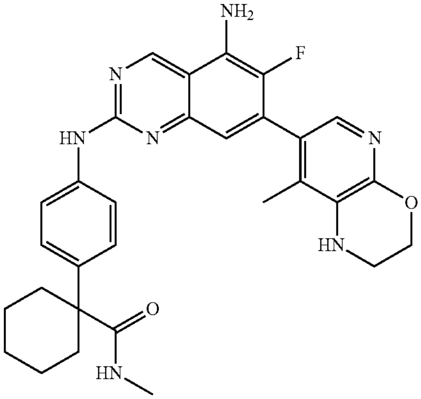 [SMILES: CNC(=O)C1(c2ccc(Nc3ncc4c(N)c(F)c(-c5cnc6c(c5C)NCCO6)cc4n3)cc2)CCCCC1] | 1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclohexane-1-carboxamide | Calc'd 542, found 542; 2A |
| 2-81 | 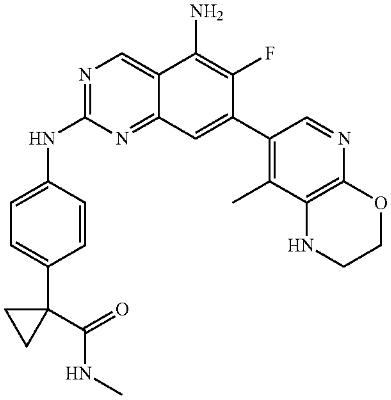 | 1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopropane-1-carboxamide | Calc'd 500, found 500; 2A |
| 2-82 | 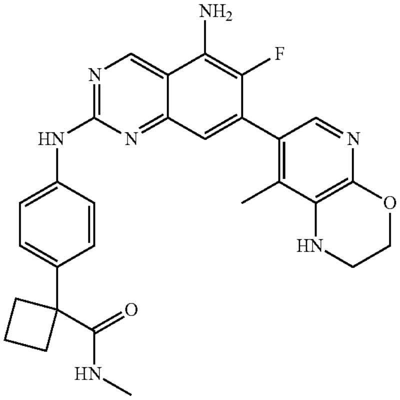 [SMILES: CNC(=O)C1(c2ccc(Nc3ncc4c(N)c(F)c(-c5cnc6c(c5C)NCCO6)cc4n3)cc2)CCC1] | 1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclobutane-1-carboxamide | Calc'd 514, found 514; 2A |

TABLE 2-continued

| Example Number | Structure | Name | Exact Mass $[M + H]^+$; Method |
|---|---|---|---|
| 2-83 | 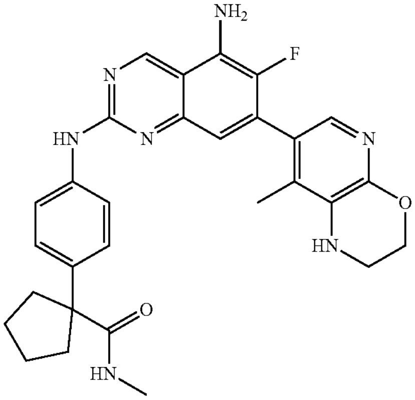 [SMILES: CNC(=O)C1(c2ccc(Nc3ncc4c(N)c(F)c(-c5cnc6c(c5C)NCCO6)cc4n3)cc2)CCCC1] | 1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopentane-1-carboxamide | Calc'd 528, found 528; 2A |
| 2-84 | 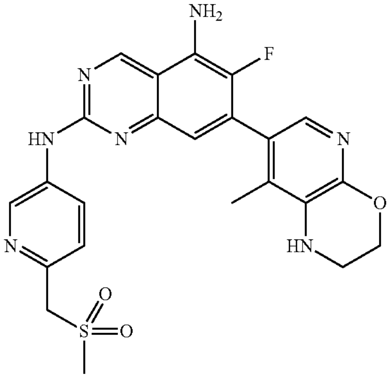 [SMILES: Cc1c(-c2cc3nc(Nc4ccc(CS(C)(=O)=O)nc4)ncc3c(N)c2F)cnc2c1NCCO2] | 6-fluoro-7-(8-methyl-2,3-dihydro-1H-pyrido[2,3-b][1,4]oxazin-7-yl)-N2-(6-((methylsulfonyl)methyl)pyridin-3-yl)quinazoline-2,5-diamine | Calc'd 496, found 496; 2A |
| 2-85 | 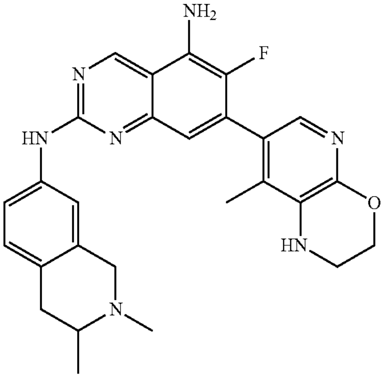 [SMILES: Cc1c(-c2cc3nc(Nc4ccc5c(c4)CN(C)C(C)C5)ncc3c(N)c2F)cnc2c1NCCO2] | (R or S)-N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine | Calc'd 486, found 486; 2H |
| 2-86 | 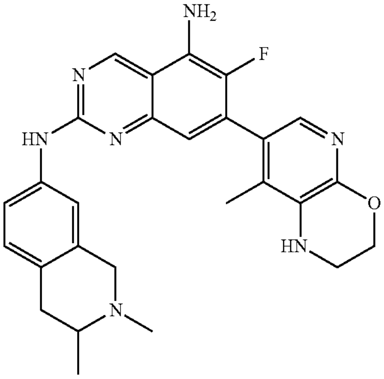 [SMILES: Cc1c(-c2cc3nc(Nc4ccc5c(c4)CN(C)C(C)C5)ncc3c(N)c2F)cnc2c1NCCO2] | (R or S)-N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine | Calc'd 486, found 486; 2H |

TABLE 2-continued

| Example Number | Structure | Name | Exact Mass $[M + H]^+$; Method |
|---|---|---|---|
| 2-87 | 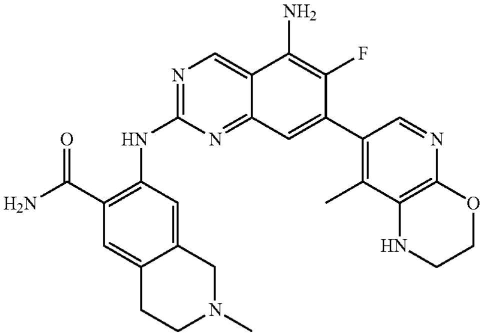 [SMILES: Cc1c(-c2cc3nc(Nc4cc5c(cc4C(N)=O)CCN(C)C5)ncc3c(N)c2F)cnc2c1NCCO2] | 7-((5-amino-6-fluoro-7-(8-methyl-2,3-dihydro-1H-pyrido[2,3-b][1,4]oxazin-7-yl)quinazolin-2-yl)amino)-2-methyl-1,2,3,4-tetrahydroisoquinoline-6-carboxamide | Calc'd 515, found 515; 2B |
| 2-88 | 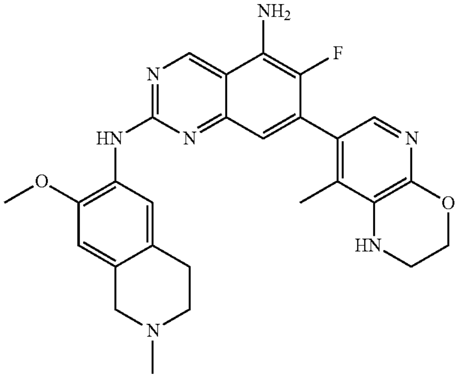 [SMILES: COc1cc2c(cc1Nc1ncc3c(N)c(F)c(-c4cnc5c(c4C)NCCO5)cc3n1)CCN(C)C2] | 6-fluoro-N2-(7-methoxy-2-methyl-1,2,3,4-tetrahydroisoquinolin-6-yl)-7-(8-methyl-2,3-dihydro-1H-pyrido[2,3-b][1,4]oxazin-7-yl)quinazoline-2,5-diamine | Calc'd 502, found 502; 2F |
| 2-89 | 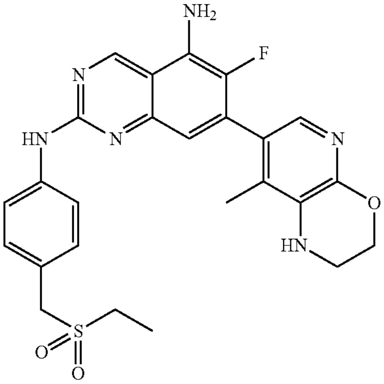 [SMILES: CCS(=O)(=O)Cc1ccc(Nc2ncc3c(N)c(F)c(-c4cnc5c(c4C)NCCO5)cc3n2)cc1] | N2-(4-((ethylsulfonyl)methyl) phenyl)-6-fluoro-7-(8-methyl-2,3-dihydro-1H-pyrido[2,3-b][1,4]oxazin-7-yl)quinazoline-2,5-diamine | Calc'd 509, found 509; 2A |
| 2-90 | 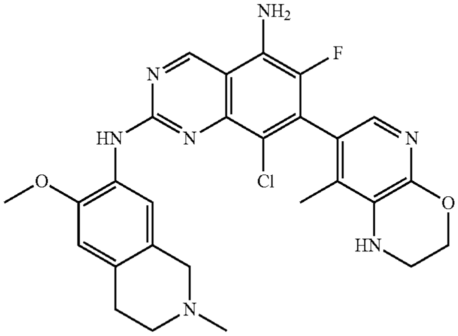 [SMILES: COc1cc2c(cc1Nc1ncc3c(N)c(F)c(-c4cnc5c(c4C)NCCO5)c(Cl)c3n1)CN(C)CC2] | (+ and −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 536, found 536; 2K |

TABLE 2-continued

| Example Number | Structure | Name | Exact Mass $[M + H]^+$; Method |
|---|---|---|---|
| 2-91 | 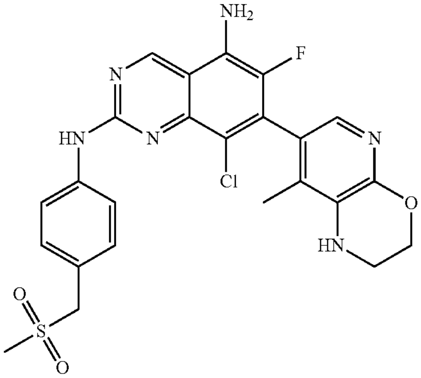 [SMILES: Cc1c(-c2c(F)c(N)c3cnc(Nc4ccc(CS(C)(=O)=O)cc4)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine | Calc'd 529, found 529; 2K |
| 2-92 | 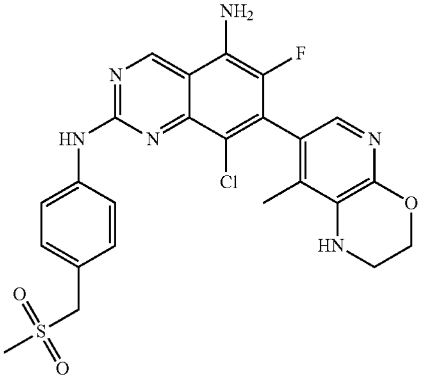 [SMILES: Cc1c(-c2c(F)c(N)c3cnc(Nc4ccc(CS(C)(=O)=O)cc4)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine | Calc'd 529, found 529; 2K |
| 2-93 | 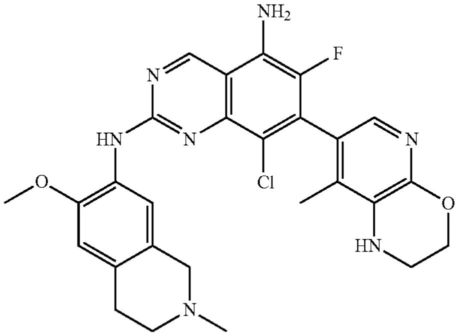 [SMILES: COc1cc2c(cc1Nc1ncc3c(N)c(F)c(-c4cnc5c(c4C)NCCO5)c(Cl)c3n1)CN(C)CC2] | (+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 536, found 536; 2K |
| 2-94 | 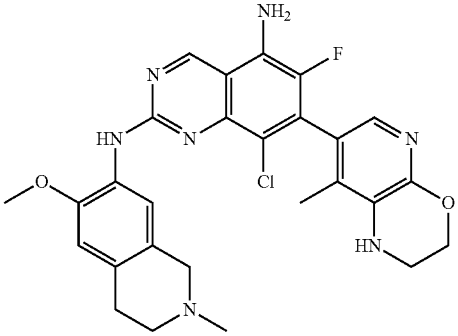 [SMILES: COc1cc2c(cc1Nc1ncc3c(N)c(F)c(-c4cnc5c(c4C)NCCO5)c(Cl)c3n1)CN(C)CC2] | (+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 536, found 536; 2K |

TABLE 2-continued

| Example Number | Structure | Name | Exact Mass [M + H]+; Method |
|---|---|---|---|
| 2-95 | 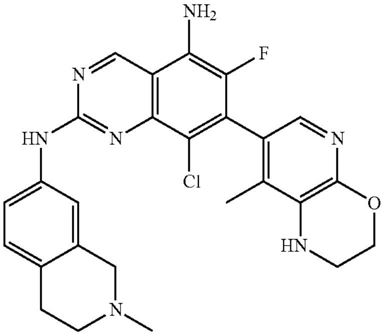 [SMILES: Cc1c(-c2c(F)c(N)c3cnc(Nc4ccc5c(c4)CN(C)CC5)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine | Calc'd 506, found 506; 2K |
| 2-96 | 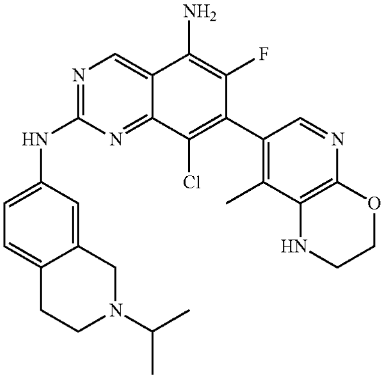 [SMILES: Cc1c(-c2c(F)c(N)c3cnc(Nc4ccc5c(c4)CN(C(C)C)CC5)nc3c2Cl)cnc2c1NCCO2] | (+ or −)-8-chloro-6-fluoro-7-(8-methyl-2,3-dihydro-1H-pyrido[2,3-b[1,4]oxazin-7-yl)-N~2~-[2-(propan-2-yl)-1,2,3,4-tetrahydroisoquinolin-7-yl]quinazoline-2,5-diamine | Calc'd 534, found 534; 2K |
| 2-97 | 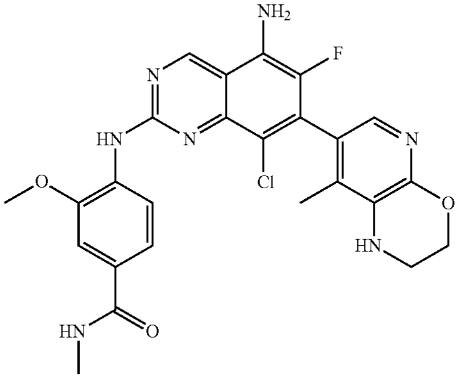 [SMILES: CNC(=O)c1ccc(Nc2ncc3c(N)c(F)c(-c4cnc5c(c4C)NCCO5)c(Cl)c3n2)c(OC)c1] | (+ or −)-4-{[5-amino-8-chloro-6-fluoro-7-(8-methyl-2,3-dihydro-1H-pyrido[2,3-b][1,4]oxazin-7-yl)quinazolin-2-yl]amino}-3-methoxy-N-methylbenzamide | Calc'd 524, found 524; 2K |
| 2-98 | 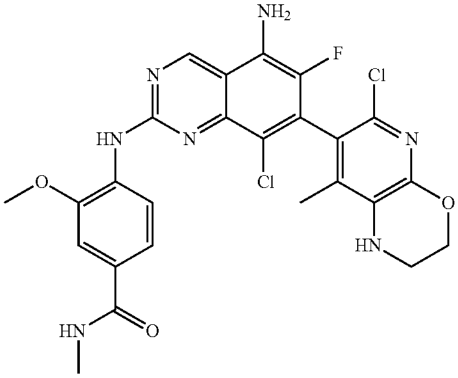 [SMILES: CNC(=O)c1ccc(Nc2ncc3c(N)c(F)c(-c4c(Cl)nc5c(c4C)NCCO5)c(Cl)c3n2)c(OC)c1] | (+ or −)-4-{[5-amino-8-chloro-7-(6-chloro-8-methyl-2,3-dihydro-1H-pyrido[2,3-b][1,4]oxazin-7-yl)-6-fluoroquinazolin-2-yl]amino}-3-methoxy-N-methylbenzamide | Calc'd 558, found 558; 2K |

TABLE 2-continued

| Example Number | Structure | Name | Exact Mass [M + H]+; Method |
|---|---|---|---|
| 2-99 | 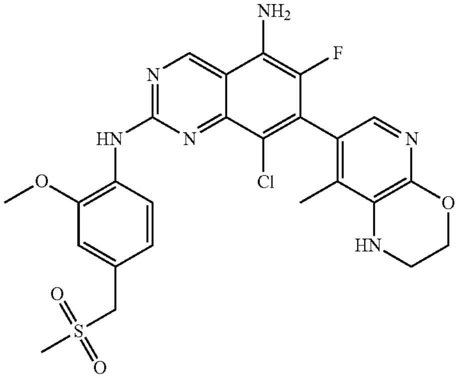 [SMILES: COc1cc(CS(C)(=O)=O)ccc1Nc1ncc2c(N)c(F)c(-c3cnc4c(c3C)NCCO4)c(Cl)c2n1] | (+ or −)-8-chloro-6-fluoro-N~2~-{2-methoxy-4-[(methylsulfonyl)methyl]phenyl}-7-(8-methyl-2,3-dihydro-1H-pyrido[2,3-b][1,4]oxazin-7-yl)quinazoline-2,5-diamine | Calc'd 559, found 559; 2K |
| 2-100 | 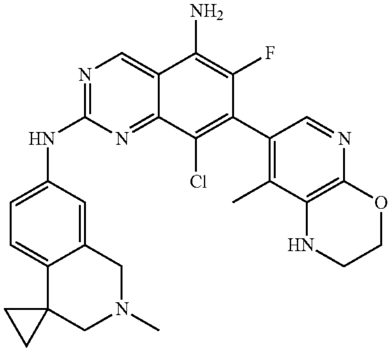 | (+ or −)-8-chloro-6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine | Calc'd 532, found 532; 2K |
| 2-101 | 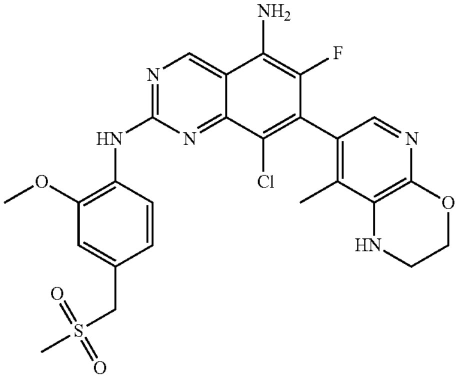 [SMILES: COc1cc(CS(C)(=O)=O)ccc1Nc1ncc2c(N)c(F)c(-c3cnc4c(c3C)NCCO4)c(Cl)c2n1] | (+ or −)-8-chloro-6-fluoro-N~2~-{2-methoxy-4-[(methylsulfony])methyl]phenyl}-7-(8-methyl-2,3-dihydro-1H-pyrido[2,3-b][1,4]oxazin-7-yl)quinazoline-2,5-diamine | Calc'd 559, found 559; 2K |
| 2-102 | 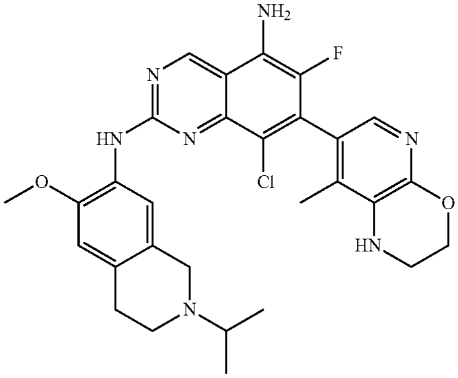 [SMILES: COc1cc2c(cc1Nc1ncc3c(N)c(F)c(-c4cnc5c(c4C)NCCO5)c(Cl)c3n1)CN(C(C)C)CC2] | (+ or −)-8-chloro-6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine | Calc'd 564, found 564; 2K |

TABLE 2-continued

| Example Number | Structure | Name | Exact Mass [M + H]+; Method |
|---|---|---|---|
| 2-103 | 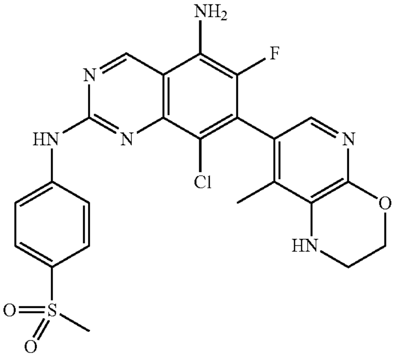 [SMILES: Cc1c(-c2c(F)c(N)c3cnc(Nc4ccc(S(C)(=O)=O)cc4)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-[4-(methylsulfonyl)phenyl] quinazoline-2,5-diamine | Calc'd 515, found 515; 2K |
| 2-104 | 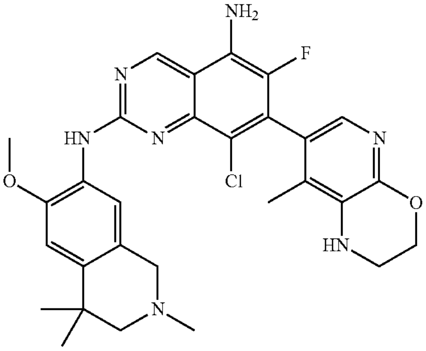 [SMILES: COc1cc2c(cc1Nc1ncc3c(N)c(F)c(-c4cnc5c(c4C)NCCO5)c(Cl)c3n1)CN(C)CC2(C)C] | 8-chloro-6-fluoro-N2-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 564, found 564; 2K |
| 2-105 | 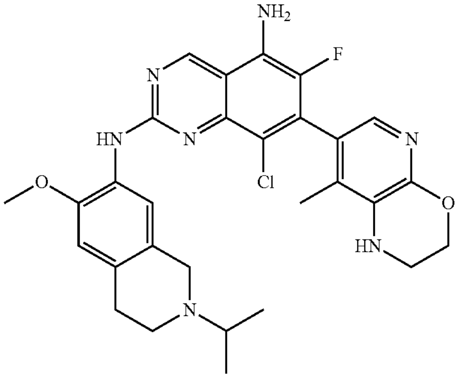 [SMILES: COc1cc2c(cc1Nc1ncc3c(N)c(F)c(-c4cnc5c(c4C)NCCO5)c(Cl)c3n1)CN(C(C)C)CC2] | (+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 564, found 564; 2K |
| 2-106 | 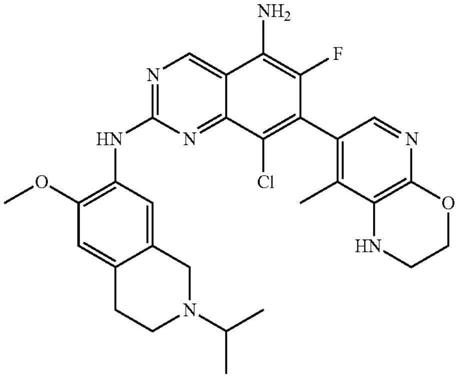 [SMILES: COc1cc2c(cc1Nc1ncc3c(N)c(F)c(-c4cnc5c(c4C)NCCO5)c(Cl)c3n1)CN(C(C)C)CC2] | (+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 564, found 564; 2K |

TABLE 2-continued

| Example Number | Structure | Name | Exact Mass [M + H]+; Method |
|---|---|---|---|
| 2-107 | 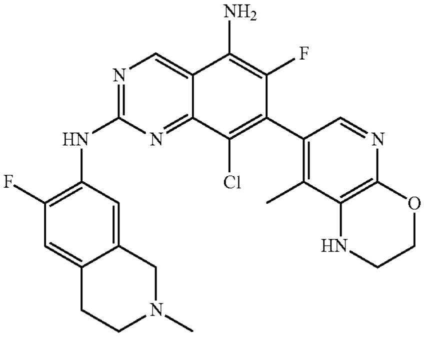 [SMILES: Cc1c(-c2c(F)c(N)c3cnc(Nc4cc5c(cc4F)CCN(C)C5)nc3c2Cl)cnc2c1NCCO2] | (+ or −)-8-chloro-6-fluoro-N2-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 524, found 524; 2K |
| 2-108 | 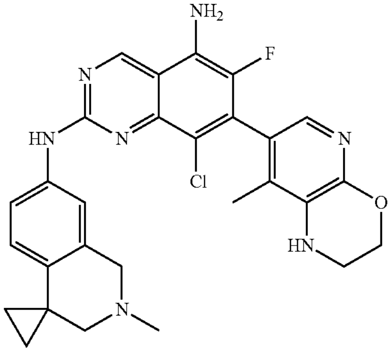 [SMILES: Cc1c(-c2c(F)c(N)c3cnc(Nc4ccc5c(c4)CN(C)CC54CC4)nc3c2Cl)cnc2c1NCCO2] | (+ or −)-8-chloro-6-fluoro-N2-(2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine | Calc'd 532, found 532; 2K |
| 2-109 | 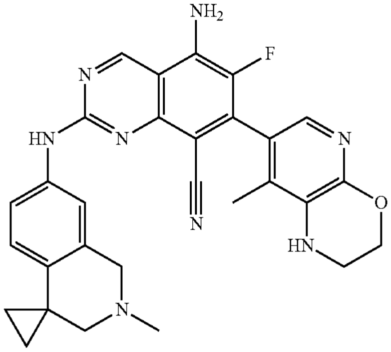 [SMILES: Cc1c(-c2c(F)c(N)c3cnc(Nc4ccc5c(c4)CN(C)CC54CC4)nc3c2C#N)cnc2c1NCCO2] | (+ or −)-5-amino-6-fluoro-2-((2'-methyl-2',3'-dihydro-1'H-spiro[cyclopropane-1,4'-isoquinolin]-7'-yl)amino)-7-(8-methyl-2,3-dihydro-1H-pyrido[2,3-b][1,4]oxazin-7-yl)quinazoline-8-carbonitrile | Calc'd 523, found 523; 2L |
| 2-110 | 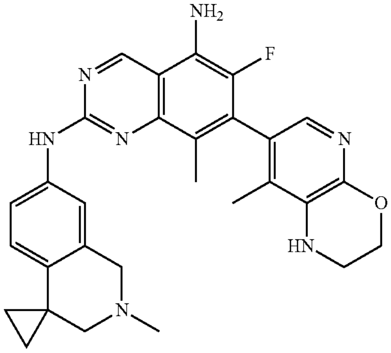 [SMILES: Cc1c(-c2c(F)c(N)c3cnc(Nc4ccc5c(c4)CN(C)CC54CC4)nc3c2C)cnc2c1NCCO2] | (+ or −)-6-fluoro-8-methyl-N2-(2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine | Calc'd 512, found 512; 2M |

TABLE 2-continued

| Example Number | Structure | Name | Exact Mass [M + H]+; Method |
|---|---|---|---|
| 2-111 | 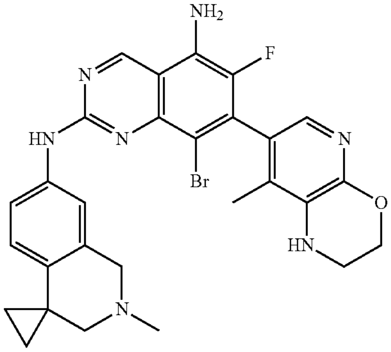 [SMILES: Cc1c(-c2c(F)c(N)c3cnc(Nc4ccc5c(c4)CN(C)CC54CC4)nc3c2Br)cnc2c1NCCO2] | (+ or −)-8-bromo-6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine | Calc'd 576, found 576; 2N |
| 2-112 | 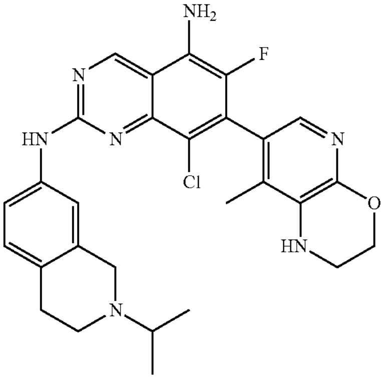 [SMILES: Cc1c(-c2c(F)c(N)c3cnc(Nc4ccc5c(c4)CN(C(C)C)CC5)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine | Calc'd 534, found 534; 2K |
| 2-113 | 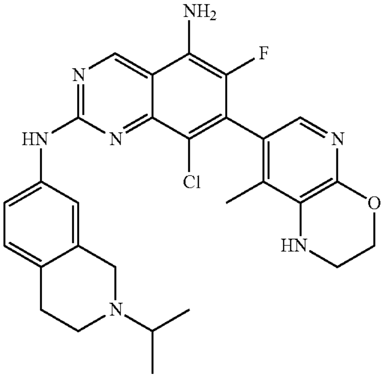 [SMILES: Cc1c(-c2c(F)c(N)c3cnc(Nc4ccc5c(c4)CN(C(C)C)CC5)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine | Calc'd 534, found 534; 2K |
| 2-114 | 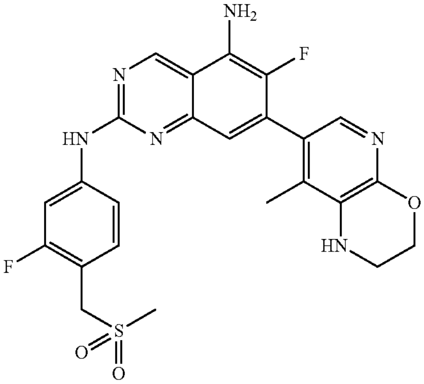 [SMILES: Cc1c(-c2cc3nc(Nc4ccc(CS(C)(=O)=O)c(F)c4)ncc3c(N)c2F)cnc2c1NCCO2] | 6-fluoro-N~2~-{3-fluoro-4-[(methanesulfonyl)methyl]phenyl}-7-(8-methyl-2,3-dihydro-1H-pyrido[2,3-b][1,4]oxazin-7-yl)quinazoline-2,5-diamine | Calc'd 513, found 513; 2A |

TABLE 2-continued

| Example Number | Structure | Name | Exact Mass [M + H]+; Method |
|---|---|---|---|
| 2-115 | 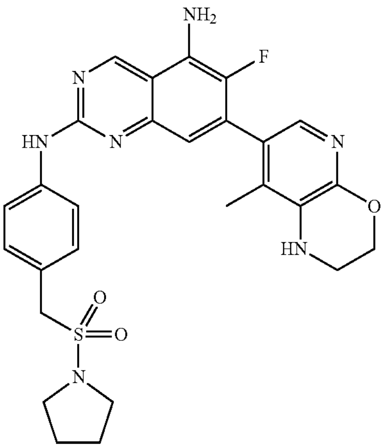 [SMILES: Cc1c(-c2cc3nc(Nc4ccc(CS(=O)(=O)N5CCCC5)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-{4-[(pyrrolidine-1-sulfonyl)methyl]phenyl}quinazoline-2,5-diamine | Calc'd 550, found 550; 2A |
| 2-116 | 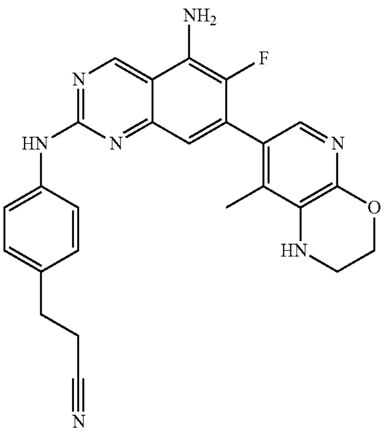 [SMILES: Cc1c(-c2cc3nc(Nc4ccc(CCC#N)cc4)ncc3c(N)c2F)cnc2c1NCCO2] | 3-(4-{[5-amino-6-fluoro-7-(8-methyl-2,3-dihydro-1H-pyrido[2,3-b][1,4]oxazin-7-yl)quinazolin-2-yl]amino}phenyl)propanenitrile | Calc'd 456, found 456; 2A |
| 2-117 | 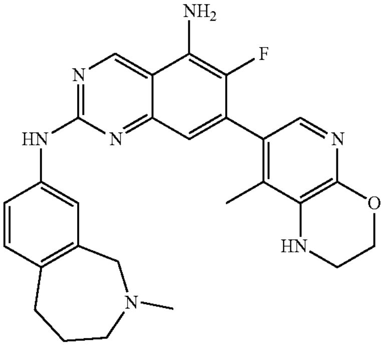 [SMILES: Cc1c(-c2cc3nc(Nc4ccc5c(c4)CN(C)CCC5)ncc3c(N)c2F)cnc2c1NCCO2] | 6-fluoro-7-(8-methyl-2,3-dihydro-1H-pyrido[2,3-b][1,4]oxazin-7-yl)-N~2~-(2-methyl-2,3,4,5-tetrahydro-1H-2-benzazepin-8-yl)quinazoline-2,5-diamine | Calc'd 486, found 486; 2A |

TABLE 2-continued

| Example Number | Structure | Name | Exact Mass $[M + H]^+$; Method |
|---|---|---|---|
| 2-118 | 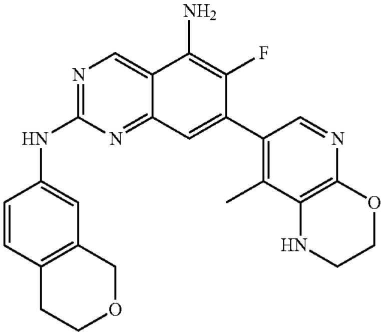 [SMILES: Cc1c(-c2cc3nc(Nc4ccc5c(c4)COCC5)ncc3c(N)c2F)cnc2c1NCCO2] | N~2~-(3,4-dihydro-1H-2-benzopyran-7-yl)-6-fluoro-7-(8-methyl-2,3-dihydro-1H-pyrido[2,3-b][1,4]oxazin-7-yl)quinazoline-2,5-diamine | Calc'd 459, found 459; 2A |
| 2-119 | 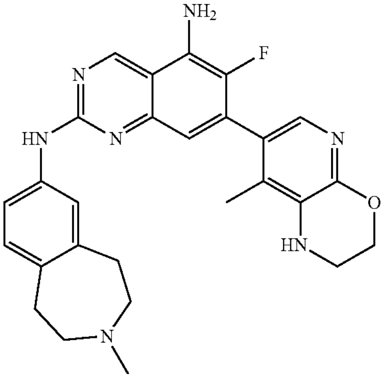 [SMILES: Cc1c(-c2cc3nc(Nc4ccc5c(c4)CCN(C)CC5)ncc3c(N)c2F)cnc2c1NCCO2] | 6-fluoro-7-(8-methyl-2,3-dihydro-1H-pyrido[2,3-b][1,4]oxazin-7-yl)-N~2~-(3-methyl-2,3,4,5-tetrahydro-1H-3-benzazepin-7-yl)quinazoline-2,5-diamine | Calc'd 486, found 486; 2A |
| 2-120 | 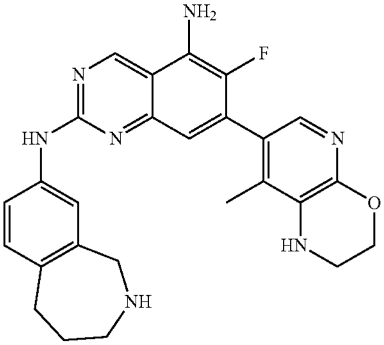 [SMILES: Cc1c(-c2cc3nc(Nc4ccc5c(c4)CNCCC5)ncc3c(N)c2F)cnc2c1NCCO2] | 6-fluoro-7-(8-methyl-2,3-dihydro-1H-pyrido[2,3-b][1,4]oxazin-7-yl)-N~2~-(2,3,4,5-tetrahydro-1H-2-benzazepin-8-yl)quinazoline-2,5-diamine | Calc'd 472, found 472; 2A |
| 2-121 | 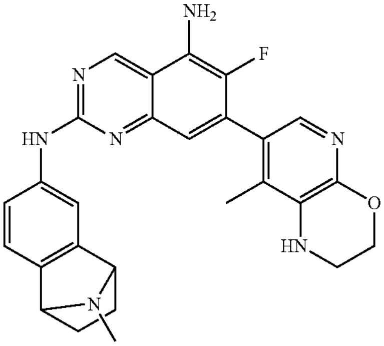 [SMILES: Cc1c(-c2cc3nc(Nc4ccc5c(c4)C4CCC5N4C)ncc3c(N)c2F)cnc2c1NCCO2] | 6-fluoro-7-(8-methyl-2,3-dihydro-1H-pyrido[2,3-b][1,4]oxazin-7-yl)-N~2~-(9-methyl-1,2,3,4-tetrahydro-1,4-epiminonaphthalen-6-yl)quinazoline-2,5-diamine | Calc'd 484, found 484; 2A |

TABLE 2-continued

| Example Number | Structure | Name | Exact Mass [M + H]+; Method |
|---|---|---|---|
| 2-122 | 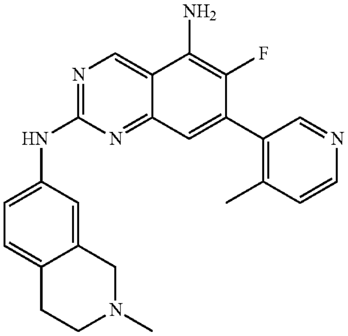 [SMILES: Cc1ccncc1-c1cc2nc(Nc3ccc4c(c3)CN(C)CC4)ncc2c(N)c1F] | 6-fluoro-7-(4-methylpyridin-3-yl)-N~2~-(2-methyl-1,2,3,4-tetrahydroisoquinolin-7-yl)quinazoline-2,5-diamine | Calc'd 415, found 415; 2O |
| 2-123 | 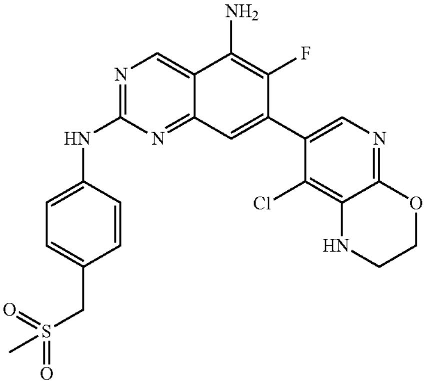 [SMILES: CS(=O)(=O)Cc1ccc(Nc2ncc3c(N)c(F)c(-c4cnc5c(c4Cl)NCCO5)cc3n2)cc1] | 7-(8-chloro-2,3-dihydro-1H-pyrido[2,3-b][1,4]oxazin-7-yl)-6-fluoro-N~2~-{4-[(methylsulfonyl)methyl]phenyl}quinazoline-2,5-diamine | Calc'd 515, found 515; 2O |
| 2-124 | 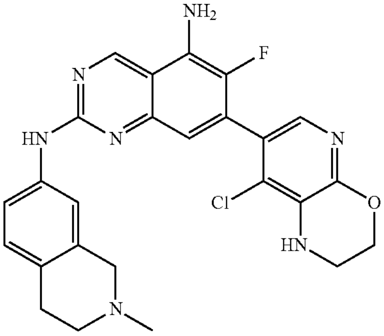 [SMILES: CN1CCc2ccc(Nc3ncc4c(N)c(F)c(-c5cnc6c(c5Cl)NCCO6)cc4n3)cc2C1] | 7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine | Calc'd 492, found 492; 2O |
| 2-125 | 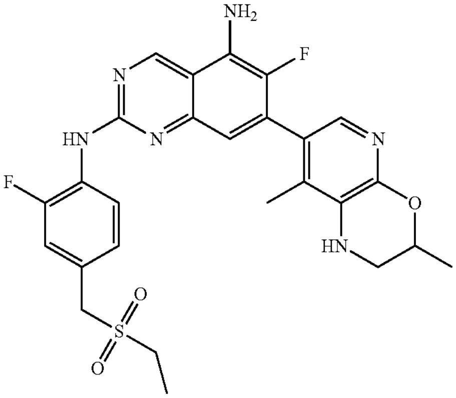 [SMILES: CCS(=O)(=O)Cc1ccc(Nc2ncc3c(N)c(F)c(-c4cnc5c(c4C)NCC(C)O5)cc3n2)c(F)c1] | (R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine | Calc'd 541, found 541; 2O |

TABLE 2-continued

| Example Number | Structure | Name | Exact Mass [M + H]+; Method |
|---|---|---|---|
| 2-126 | 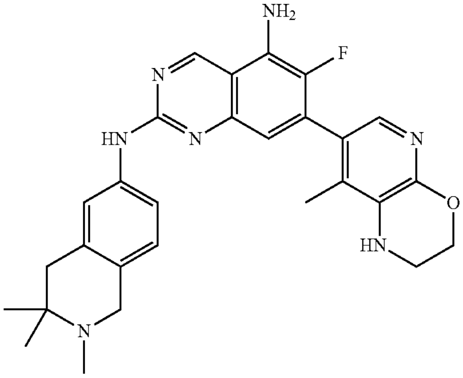 [SMILES: Cc1c(-c2cc3nc(Nc4ccc5c(c4)CC(C)(C)N(C)C5)ncc3c(N)c2F)cnc2c1NCCO2] | 6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-6-yl)quinazoline-2,5-diamine | Calc'd 500, found 500; 2O |
| 2-127 | 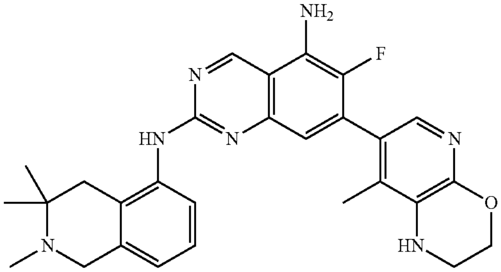 [SMILES: Cc1c(-c2cc3nc(Nc4cccc5c4CC(C)(C)N(C)C5)ncc3c(N)c2F)cnc2c1NCCO2] | 6-fluoro-7-(8-methyl-2,3-dihydro-1H-pyrido[2,3-b][1,4]oxazin-7-y])-N2-(2,3,3-trimethyl-1,2,3,4-tetrahydroisoquinolin-5-yl)quinazoline-2,5-diamine | Calc'd 500, found 500; 2O |
| 2-128 | 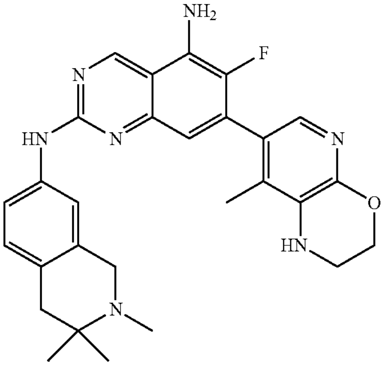 [SMILES: Cc1c(-c2cc3nc(Nc4ccc5c(c4)CN(C)C(C)(C)C5)ncc3c(N)c2F)cnc2c1NCCO2] | 6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-7-yl)quinazoline-2,5-diamine | Calc'd 500, found 500; 2C |
| 2-129 | 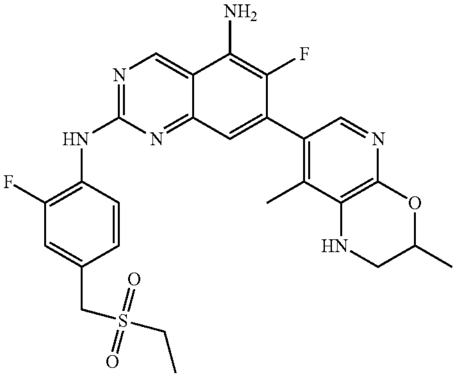 [SMILES: CCS(=O)(=O)Cc1ccc(Nc2ncc3c(N)c(F)c(-c4cnc5c(c4C)NCC(C)O5)cc3n2)c(F)c1] | (R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine | Calc'd 541, found 541; 2O |

TABLE 2-continued

| Example Number | Structure | Name | Exact Mass [M + H]$^+$; Method |
|---|---|---|---|
| 2-130 | 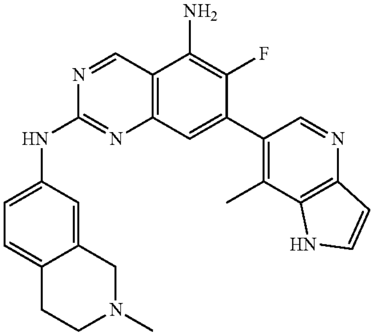 [SMILES: Cc1c(-c2cc3nc(Nc4ccc5c(c4)CN(C)CC5)ncc3c(N)c2F)cnc2cc[nH]c12] | 6-fluoro-7-(7-methyl-1H-pyrrolo[3,2-b]pyridin-6-yl)-N~2~-(2-methyl-1,2,3,4-tetrahydroisoquinolin-7-yl)quinazoline-2,5-diamine | Calc'd 454, found 454; 2O |
| 2-131 | 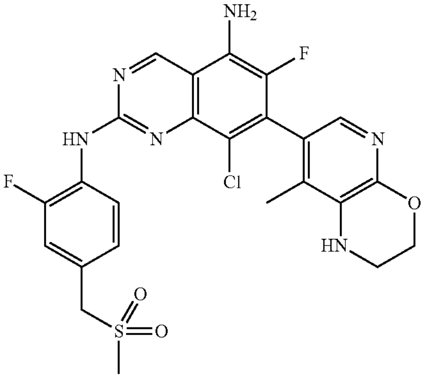 [SMILES: Cc1c(-c2c(F)c(N)c3cnc(Nc4ccc(CS(C)(=O)=O)cc4F)nc3c2Cl)cnc2c1NCCO2] | (+ or −)-8-chloro-6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine | Calc'd 547, found 547; 2K |
| 2-132 | 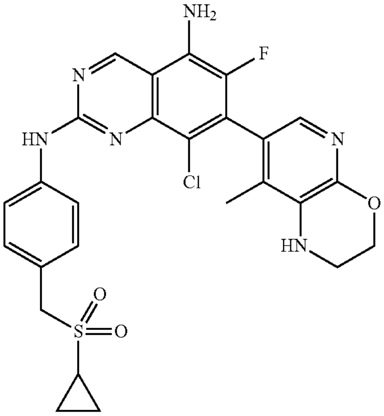 [SMILES: Cc1c(-c2c(F)c(N)c3cnc(Nc4ccc(CS(=O)(=O)C5CC5)cc4)nc3c2Cl)cnc2c1NCCO2] | (+ or −)-8-chloro-N~2~-{4-[(cyclopropylsulfony])methyl]phenyl}-6-fluoro-7-(8-methyl-2,3-dihydro-1H-pyrido[2,3-b][1,4]oxazin-7-yl)quinazoline-2,5-diamine | Calc'd 555, found 555; 2K |
| 2-133 | 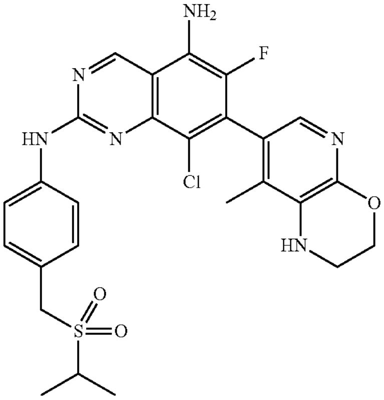 [SMILES: Cc1c(-c2c(F)c(N)c3cnc(Nc4ccc(CS(=O)(=O)C(C)C)cc4)nc3c2Cl)cnc2c1NCCO2] | (+ and −)-8-chloro-6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine | Calc'd 557, found 557; 2I |

TABLE 2-continued

| Example Number | Structure | Name | Exact Mass [M + H]+; Method |
|---|---|---|---|
| 2-134 | 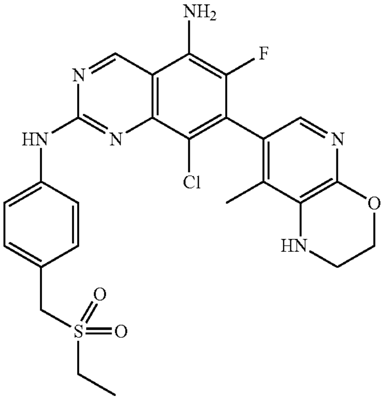 [SMILES: CCS(=O)(=O)Cc1ccc(Nc2ncc3c(N)c(F)c(-c4cnc5c(c4C)NCCO5)c(Cl)c3n2)cc1] | 8-chloro-N~2~-{4-[(ethylsulfony])methyl] phenyl}-6-fluoro-7-(8-methyl-2,3-dihydro-1H-pyrido[2,3-b][1,4]oxazin-7-yl)quinazoline-2,5-diamine | Calc'd 543, found 543; 2K |
| 2-135 | 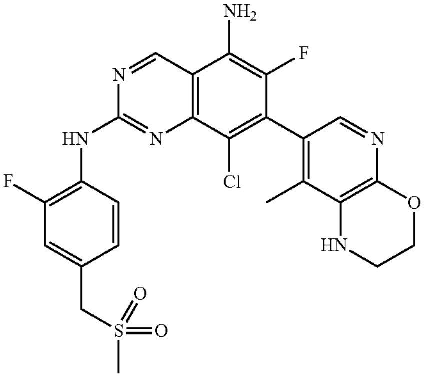 [SMILES: Cc1c(-c2c(F)c(N)c3cnc(Nc4ccc(CS(C)(=O)=O)cc4F)nc3c2Cl)cnc2c1NCCO2] | 8-chloro-6-fluoro-N~2~-{2-fluoro-4-[(methylsulfonyl)methyl] phenyl}-7-(8-methyl-2,3-dihydro-1H-pyrido[2,3-b][1,4]oxazin-7-yl)quinazoline-2,5-diamine | Calc'd 547, found 547; 2K |
| 2-136 | 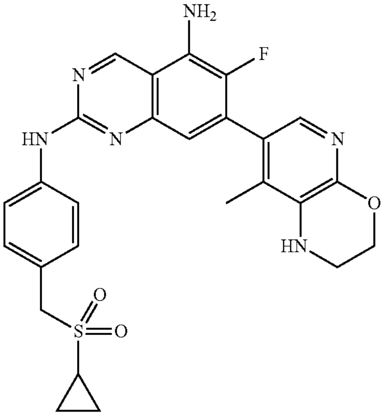 [SMILES: Cc1c(-c2cc3nc(Nc4ccc(CS(=O)(=O)C5CC5)cc4)ncc3c(N)c2F)cnc2c1NCCO2] | N~2~-{4-[(cyclopropylsulfony])methyl] phenyl}-6-fluoro-7-(8-methyl-2,3-dihydro-1H-pyrido[2,3-b][1,4]oxazin-7-yl)quinazoline-2,5-diamine | Calc'd 521, found 521; 2O |

TABLE 2-continued

| Example Number | Structure | Name | Exact Mass [M + H]+; Method |
|---|---|---|---|
| 2-137 | 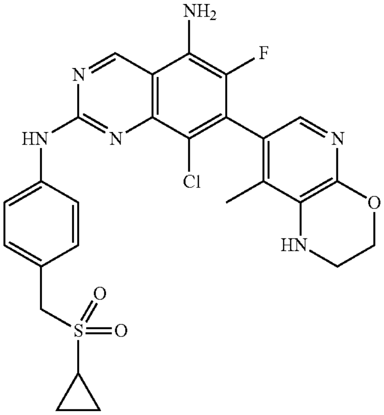 [SMILES: Cc1c(-c2c(F)c(N)c3cnc(Nc4ccc(CS(=O)(=O)C5CC5)cc4)nc3c2Cl)cnc2c1NCCO2] | (+ or −)-8-chloro-N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine | Calc'd 555, found 555; 2K |
| 2-138 | 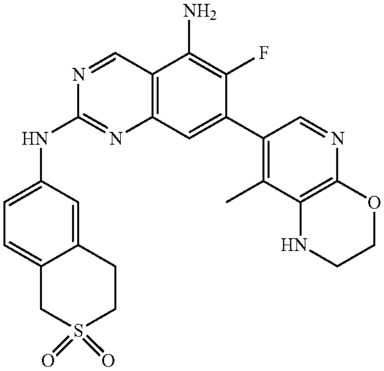 [SMILES: Cc1c(-c2cc3nc(Nc4ccc5c(c4)CCS(=O)(=O)C5)ncc3c(N)c2F)cnc2c1NCCO2] | 6-{[5-amino-6-fluoro-7-(8-methyl-2,3-dihydro-1H-pyrido[2,3-b][1,4]oxazin-7-yl)quinazolin-2-yl]amino}-3,4-dihydro-2-benzothiopyran-2,2(1H)-dione | Calc'd 507, found 507; 2O |
| 2-139 | 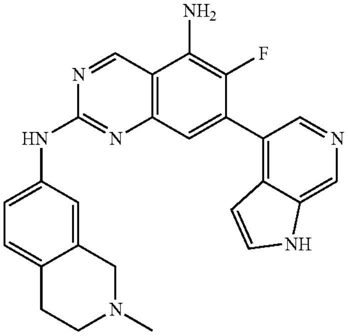 [SMILES: CN1CCc2ccc(Nc3ncc4c(N)c(F)c(-c5cncc6[nH]ccc56)cc4n3)cc2C1] | 6-fluoro-N~2~-(2-methyl-1,2,3,4-tetrahydroisoquinolin-7-yl)-7-(1H-pyrrolo[2,3-c]pyridin-4-yl)quinazoline-2,5-diamine | Calc'd 440, found 440; 2O |
| 2-140 | 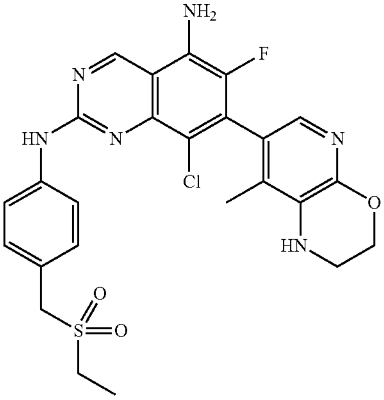 [SMILES: CCS(=O)(=O)Cc1ccc(Nc2ncc3c(N)c(F)c(-c4cnc5c(c4C)NCCO5)c(Cl)c3n2)cc1] | 8-chloro-N~2~-{4-[(ethylsulfonyl)methyl]phenyl}-6-fluoro-7-(8-methyl-2,3-dihydro-1H-pyrido[2,3-b][1,4]oxazin-7-yl)quinazoline-2,5-diamine | Calc'd 543, found 543; 2K |

TABLE 2-continued

| Example Number | Structure | Name | Exact Mass [M + H]+; Method |
|---|---|---|---|
| 2-141 | 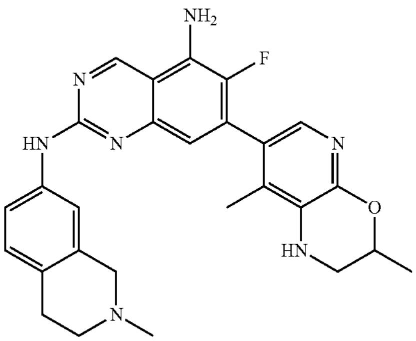 [SMILES: Cc1c(-c2cc3nc(Nc4ccc5c(c4)CN(C)CC5)ncc3c(N)c2F)cnc2c1NCC(C)O2] | (R or S)-7-(3,8-dimethyl-2,3-dihydro-1H-pyrido[2,3-b][1,4]oxazin-7-yl)-6-fluoro-N2-(2-methyl-1,2,3,4-tetrahydroisoquinolin-7-yl)quinazoline-2,5-diamine | Calc'd 486, found 486; 2F |
| 2-142 | 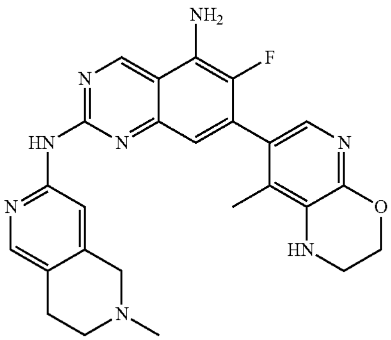 [SMILES: Cc1c(-c2cc3nc(Nc4cc5c(cn4)CCN(C)C5)ncc3c(N)c2F)cnc2c1NCCO2] | 6-fluoro-7-(8-methyl-2,3-dihydro-1H-pyrido[2,3-b][1,4]oxazin-7-yl)-N~2~-(6-methyl-5,6,7,8-tetrahydro-2,6-naphthyridin-3-yl)quinazoline-2,5-diamine | Calc'd 473, found 473; 2O |
| 2-143 | 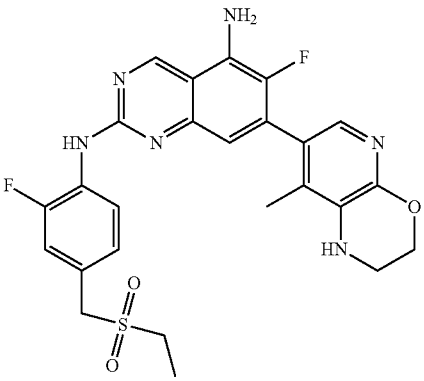 [SMILES: CCS(=O)(=O)Cc1ccc(Nc2ncc3c(N)c(F)c(-c4cnc5c(c4C)NCCO5)cc3n2)c(F)c1] | N~2~-{4-[(ethylsulfonyl)methyl]-2-fluorophenyl}-6-fluoro-7-(8-methyl-2,3-dihydro-1H-pyrido[2,3-b][1,4]oxazin-7-yl)quinazoline-2,5-diamine | Calc'd 527, found 527; 2O |
| 2-144 | 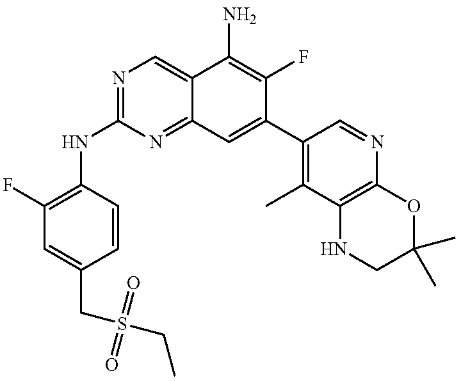 [SMILES: CCS(=O)(=O)Cc1ccc(Nc2ncc3c(N)c(F)c(-c4cnc5c(c4C)NCC(C)(C)O5)cc3n2)c(F)c1] | N~2~-{4-[(ethylsulfonyl)methyl]-2-fluorophenyl}-6-fluoro-7-(3,3,8-trimethyl-2,3-dihydro-1H-pyrido[2,3-b][1,4]oxazin-7-yl)quinazoline-2,5-diamine | Calc'd 555, found 555; 2O |

TABLE 2-continued

| Example Number | Structure | Name | Exact Mass $[M + H]^+$; Method |
|---|---|---|---|
| 2-145 | 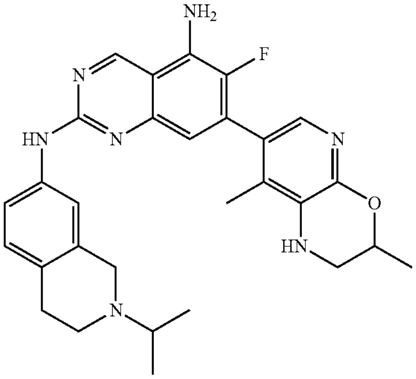 [SMILES: Cc1c(-c2cc3nc(Nc4ccc5c(c4)CN(C(C)C)CC5)ncc3c(N)c2F)cnc2c1NCC(C)O2] | 7-(3,8-dimethyl-2,3-dihydro-1H-pyrido[2,3-b][1,4]oxazin-7-yl)-6-fluoro-N2-(2-isopropyl-1,2,3,4-tetrahydroisoquinolin-7-yl)quinazoline-2,5-diamine | Calc'd 514, found 514; 2F |
| 2-146 | 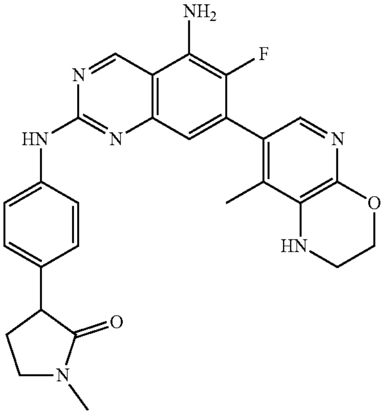 [SMILES: Cc1c(-c2cc3nc(Nc4ccc(C5CCN(C)C5=O)cc4)ncc3c(N)c2F)cnc2c1NCCO2] | (R or S)-3-(4-{[5-amino-6-fluoro-7-(8-methyl-2,3-dihydro-1H-pyrido[2,3-b][1,4]oxazin-7-yl)quinazolin-2-ylamino}phenyl)-1-methylpyrrolidin-2-one | Calc'd 500, found 500; 2O |
| 2-147 | 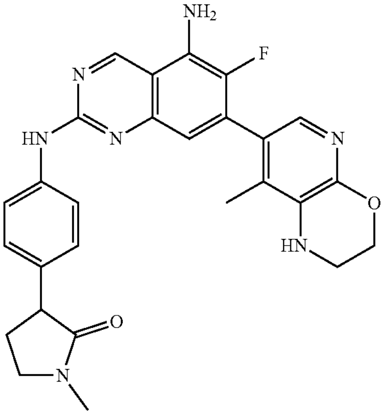 [SMILES: Cc1c(-c2cc3nc(Nc4ccc(C5CCN(C)C5=O)cc4)ncc3c(N)c2F)cnc2c1NCCO2] | (R or S)-3-(4-{[5-amino-6-fluoro-7-(8-methyl-2,3-dihydro-1H-pyrido[2,3-b][1,4]oxazin-7-yl)quinazolin-2-yl]amino}phenyl)-1-methylpyrrolidin-2-one | Calc'd 500, found 500; 2O |

TABLE 2-continued

| Example Number | Structure | Name | Exact Mass [M + H]+; Method |
|---|---|---|---|
| 2-148 | 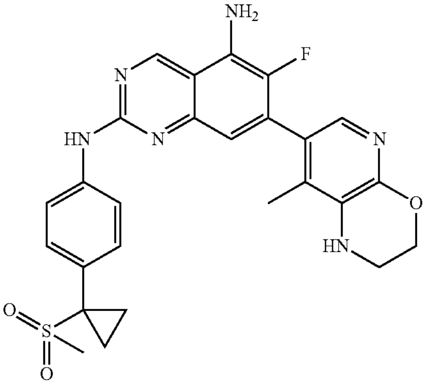 [SMILES: Cc1c(-c2cc3nc(Nc4ccc(C5(S(C)(=O)=O)CC5)cc4)ncc3c(N)c2F)cnc2c1NCCO2] | 6-fluoro-N~2~-{4-[1-(methanesulfonyl)cyclo-propyl]phenyl}-7-(8-methyl-2,3-dihydro-1H-pyrido[2,3-b][1,4]oxazin-7-yl)quinazoline-2,5-diamine | Calc'd 521, found 521; 2G |
| 2-149 | 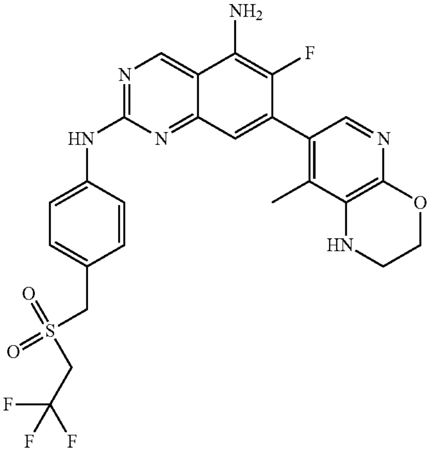 [SMILES: Cc1c(-c2cc3nc(Nc4ccc(CS(=O)(=O)CC(F)(F)F)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-{4-[(2,2,2-trifluoroethanesulfonyl) methyl]phenyl}quinazoline-2,5-diamine | Calc'd 563, found 563; 2O |
| 2-150 | 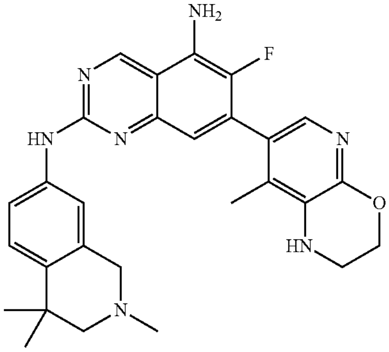 [SMILES: Cc1c(-c2cc3nc(Nc4ccc5c(c4)CN(C)CC5(C)C)ncc3c(N)c2F)cnc2c1NCCO2] | 6-fluoro-7-(8-methyl-2,3-dihydro-1H-pyrido[2,3-b][1,4]oxazin-7-yl)-N~2~-(2,4,4-trimethyl-1,2,3,4-tetrahydroisoquinolin-7-yl)quinazoline-2,5-diamine | Calc'd 500, found 500; 2G |

TABLE 2-continued

| Example Number | Structure | Name | Exact Mass [M + H]+; Method |
|---|---|---|---|
| 2-151 | 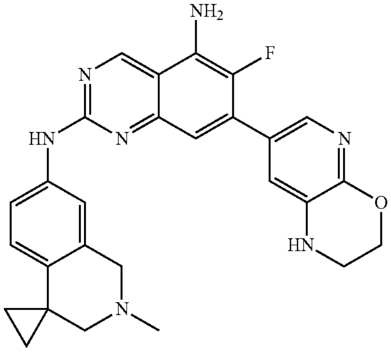 [SMILES: CN1Cc2cc(Nc3ncc4c(N)c(F)c(-c5cnc6c(c5)NCCO6)cc4n3)ccc2C2(CC2)C1] | 7-(2,3-dihydro-1H-pyrido[2,3-b][1,4]oxazin-7-yl)-6-fluoro-N~2~-(2'-methyl-2',3'-dihydro-1'H-spiro[cyclopropane-1,4'-isoquinolin]-7'-yl)quinazoline-2,5-diamine | Calc'd 484, found 484; 2F |
| 2-152 | 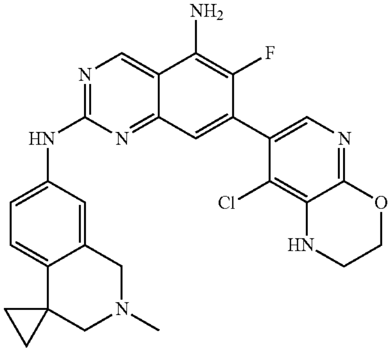 [SMILES: CN1Cc2cc(Nc3ncc4c(N)c(F)c(-c5cnc6c(c5Cl)NCCO6)cc4n3)ccc2C2(CC2)C1] | 7-(8-chloro-2,3-dihydro-1H-pyrido[2,3-b][1,4]oxazin-7-yl)-6-fluoro-N~2~-(2'-methyl-2',3'-dihydro-1'H-spiro[cyclopropane-1,4'-isoquinolin]-7'-yl)quinazoline-2,5-diamine | Calc'd 518, found 518; 2F |
| 2-153 | 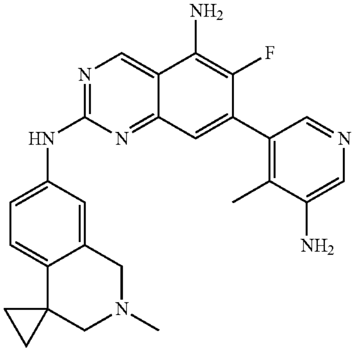 [SMILES: Cc1c(N)cncc1-c1cc2nc(Nc3ccc4c(c3)CN(C)CC43CC3)ncc2c(N)c1F] | 7-(5-amino-4-methylpyridin-3-yl)-6-fluoro-N~2~-(2'-methyl-2',3'-dihydro-1'H-spiro[cyclopropane-1,4'-isoquinolin]-7'-yl)quinazoline-2,5-diamine | Calc'd 456, found 456; 2O |
| 2-154 | 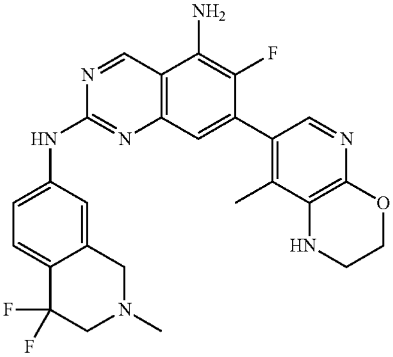 [SMILES: Cc1c(-c2cc3nc(Nc4ccc5c(c4)CN(C)CC5(F)F)ncc3c(N)c2F)cnc2c1NCCO2] | N~2~-(4,4-difluoro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine | Calc'd 508, found 508; 2O |

TABLE 2-continued

| Example Number | Structure | Name | Exact Mass $[M + H]^+$; Method |
|---|---|---|---|
| 2-155 | 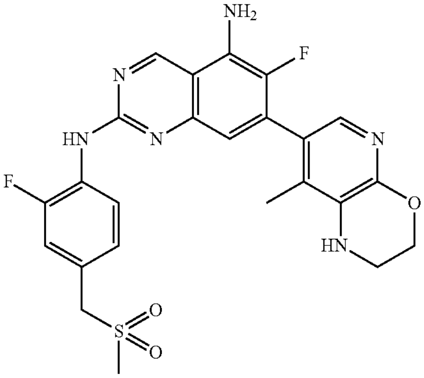 [SMILES: Cc1c(-c2cc3nc(Nc4ccc(CS(C)(=O)=O)cc4F)ncc3c(N)c2F)cnc2c1NCCO2] | 6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine | Calc'd 513, found 513; 2O |
| 2-156 | 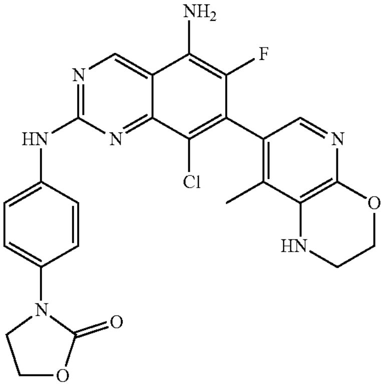 [SMILES: Cc1c(-c2c(F)c(N)c3cnc(Nc4ccc(N5CCOC5=O)cc4)nc3c2Cl)cnc2c1NCCO2] | 3-(4-{[5-amino-8-chloro-6-fluoro-7-(8-methyl-2,3-dihydro-1H-pyrido[2,3-b][1,4]oxazin-7-yl)quinazolin-2-ylamino}phenyl)-1,3-oxazolidin-2-one | Calc'd 522, found 522; 2K |
| 2-157 | 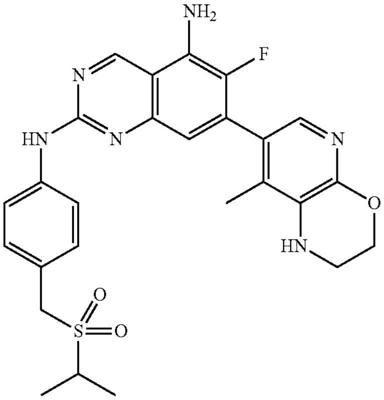 [SMILES: Cc1c(-c2cc3nc(Nc4ccc(CS(=O)(=O)C(C)C)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine | Calc'd 523, found 523; 2O |
| 2-158 | 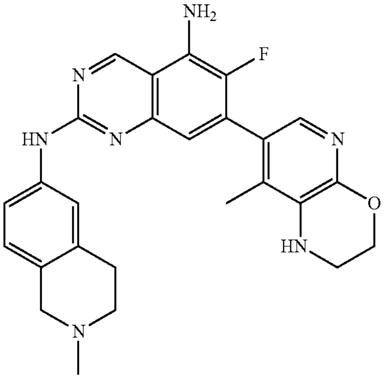 [SMILES: Cc1c(-c2cc3nc(Nc4ccc5c(c4)CCN(C)C5)ncc3c(N)c2F)cnc2c1NCCO2] | 6-fluoro-7-(8-methyl-2,3-dihydro-1H-pyrido[2,3-b][1,4]oxazin-7-yl)-N~2~-(2-methyl-1,2,3,4-tetrahydroisoquinolin-6-yl)quinazoline-2,5-diamine | Calc'd 472, found 472: 2F |

TABLE 2-continued

| Example Number | Structure | Name | Exact Mass [M + H]⁺; Method |
|---|---|---|---|
| 2-159 | 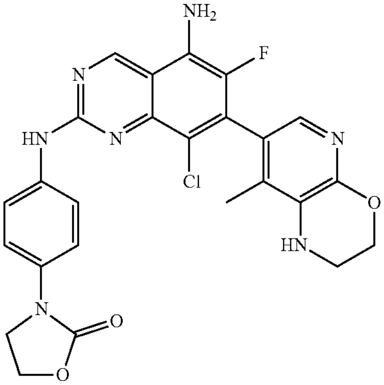 [SMILES: Cc1c(-c2c(F)c(N)c3cnc(Nc4ccc(N5CCOC5=O)cc4)nc3c2Cl)cnc2c1NCCO2] | 3-(4-{[5-amino-8-chloro-6-fluoro-7-(8-methyl-2,3-dihydro-1H-pyrido[2,3-b][1,4]oxazin-7-yl)quinazolin-2-ylamino}phenyl)-1,3-oxazolidin-2-one | Calc'd 522, found 522; 2K |
| 2-160 | 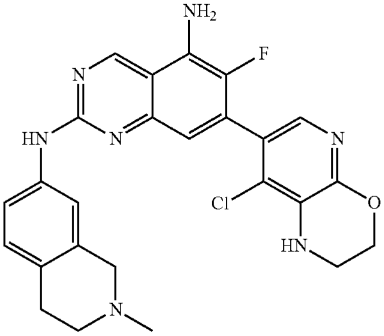 [SMILES: CN1CCc2ccc(Nc3ncc4c(N)c(F)c(-c5cnc6c(c5Cl)NCCO6)cc4n3)cc2C1] | 7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine | Calc'd 492, found 492; 2F |
| 2-161 | 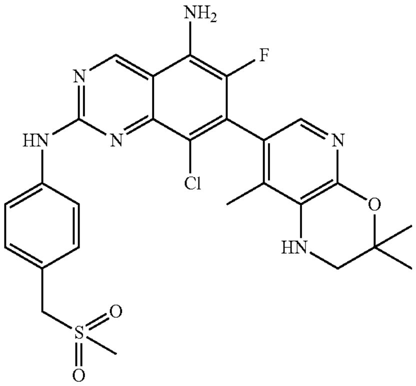 [SMILES: Cc1c(-c2c(F)c(N)c3cnc(Nc4ccc(CS(C)(=O)=O)cc4)nc3c2Cl)cnc2c1NCC(C)(C)O2] | (+ and −)-8-chloro-6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine | Calc'd 557, found 557; 2I |
| 2-162 | 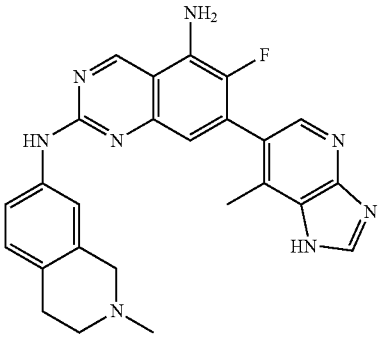 [SMILES: Cc1c(-c2cc3nc(Nc4ccc5c(c4)CN(C)CC5)ncc3c(N)c2F)cnc2nc[nH]c12] | 6-fluoro-7-(7-methyl-1H-imidazo[4,5-b]pyridin-6-yl)-N~2~-(2-methyl-1,2,3,4-tetrahydroisoquinolin-7-yl)quinazoline-2,5-diamine | Calc'd 455, found 455; 2F |

TABLE 2-continued

| Example Number | Structure | Name | Exact Mass [M + H]+; Method |
|---|---|---|---|
| 2-163 | 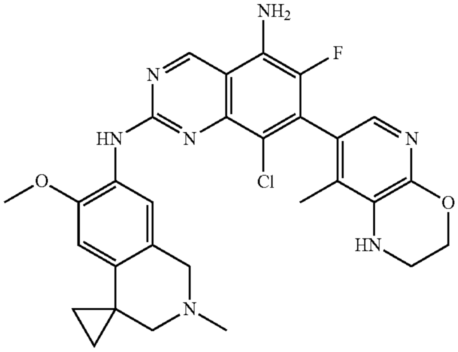 [SMILES: COc1cc2c(cc1Nc1ncc3c(N)c(F)c(-c4cnc5c(c4C)NCCO5)c(Cl)c3n1)CN(C)CC21CC1] | 8-chloro-6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine | Calc'd 562, found 562; 2K |
| 2-164 | 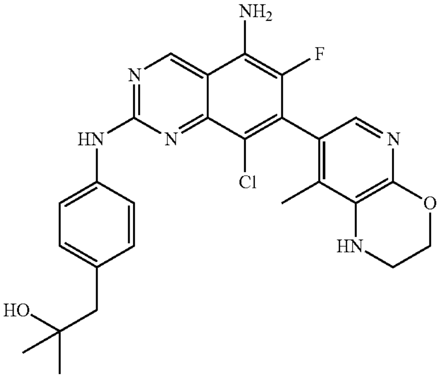 [SMILES: Cc1c(-c2c(F)c(N)c3cnc(Nc4ccc(CC(C)(C)O)cc4)nc3c2Cl)cnc2c1NCCO2] | 1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol | Calc'd 509, found 509; 2K |
| 2-165 | 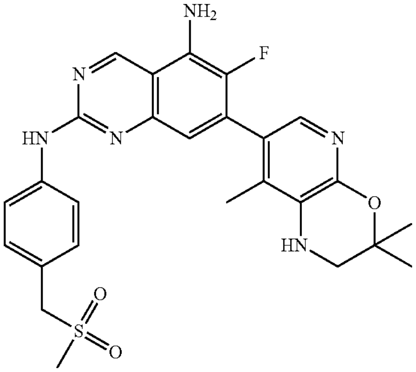 [SMILES: Cc1c(-c2cc3nc(Nc4ccc(CS(C)(=O)=O)cc4)ncc3c(N)c2F)cnc2c1NCC(C)(C)O2] | 6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine | Calc'd 523, found 523; 2G |
| 2-166 | 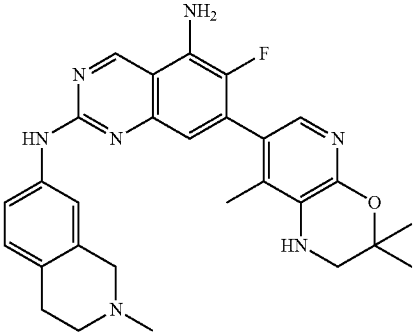 [SMILES: Cc1c(-c2cc3nc(Nc4ccc5c(c4)CN(C)CC5)ncc3c(N)c2F)cnc2c1NCC(C)(C)O2] | 6-fluoro-N~2~-(2-methyl-1,2,3,4-tetrahydroisoquinolin-7-yl)-7-(3,3,8-trimethyl-2,3-dihydro-1H-pyrido[2,3-b][1,4]oxazin-7-yl)quinazoline-2,5-diamine | Calc'd 500, found 500; 2F |

TABLE 2-continued

| Example Number | Structure | Name | Exact Mass [M + H]+; Method |
|---|---|---|---|
| 2-167 | 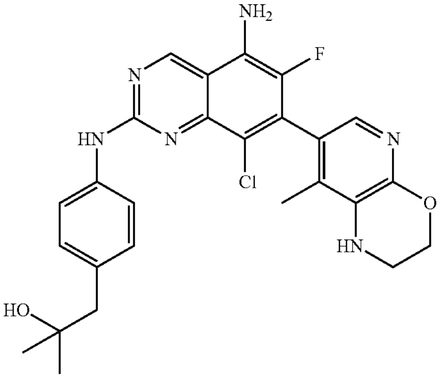 [SMILES: Cc1c(-c2c(F)c(N)c3cnc(Nc4ccc(CC(C)(C)O)cc4)nc3c2Cl)cnc2c1NCCO2] | 1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol | Calc'd 509, found 509; 2K |
| 2-168 | 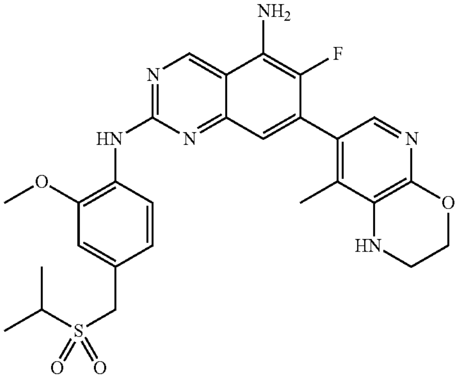 [SMILES: COc1cc(CS(=O)(=O)C(C)C)ccc1Nc1ncc2c(N)c(F)c(-c3cnc4c(c3C)NCCO4)cc2n1] | 6-fluoro-N~2~-(2-methoxy-4-{[(propan-2-yl)sulfonyl]methyl}phenyl)-7-(8-methyl-2,3-dihydro-1H-pyrido[2,3-b][1,4]oxazin-7-yl)quinazoline-2,5-diamine | Calc'd 553, found 553; 2F |
| 2-169 | 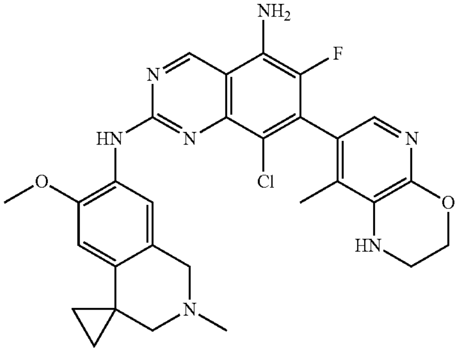 [SMILES: COc1cc2c(cc1Nc1ncc3c(N)c(F)c(-c4cnc5c(c4C)NCCO5)c(Cl)c3n1)CN(C)CC21CC1] | 8-chloro-6-fluoro-N~2~-(6'-methoxy-2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine | Calc'd 562, found 562; 2K |
| 2-170 | 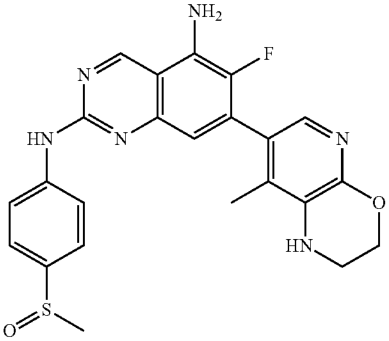 [SMILES: Cc1c(-c2cc3nc(Nc4ccc(S(C)=O)cc4)ncc3c(N)c2F)cnc2c1NCCO2] | 6-fluoro-7-(8-methyl-2,3-dihydro-1H-pyrido[2,3-b][1,4]oxazin-7-yl)-N~2~-[4-(methylsulfinyl)phenyl] quinazoline-2,5-diamine | Calc'd 465, found 465; 2F |

TABLE 2-continued

| Example Number | Structure | Name | Exact Mass [M + H]+; Method |
|---|---|---|---|
| 2-171 | 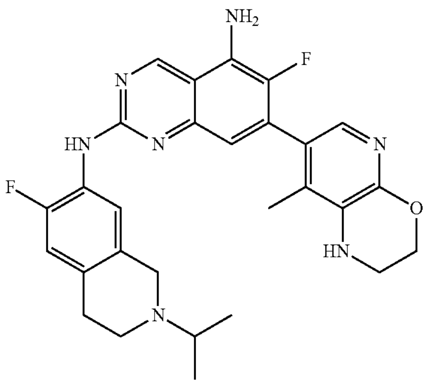 [SMILES: Cc1c(-c2cc3nc(Nc4cc5c(cc4F)CCN(C(C)C)C5)ncc3c(N)c2F)cnc2c1NCCO2] | 6-fluoro-N~2~-[6-fluoro-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine | Calc'd 518, found 518; 2P |
| 2-172 | 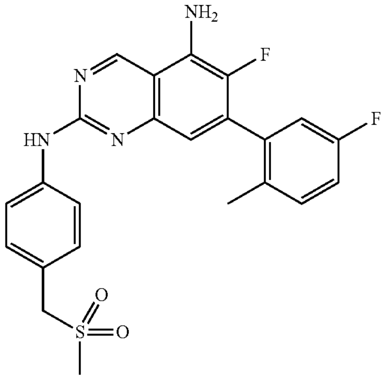 [SMILES: Cc1ccc(F)cc1-c1cc2nc(Nc3ccc(CS(C)(=O)=O)cc3)ncc2c(N)c1F] | 6-fluoro-7-(5-fluoro-2-methylphenyl)-N~2~-{4-[(methylsulfonyl)methyl]phenyl}quinazoline-2,5-diamine | Calc'd 455, found 455; 2G |
| 2-173 | 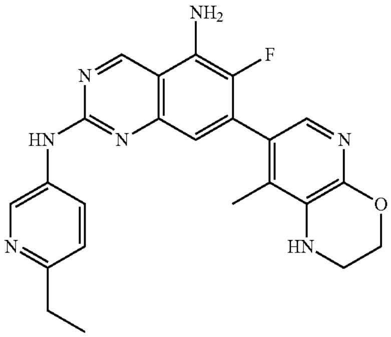 [SMILES: CCc1ccc(Nc2ncc3c(N)c(F)c(-c4cnc5c(c4C)NCCO5)cc3n2)cn1] | N~2~-(6-ethylpyridin-3-yl)-6-fluoro-7-(8-methyl-2,3-dihydro-1H-pyrido[2,3-b][1,4]oxazin-7-yl)quinazoline-2,5-diamine | Calc'd 432, found 432; 2G |
| 2-174 | 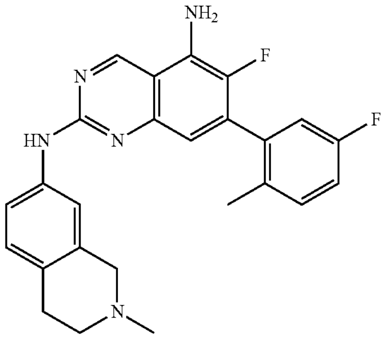 [SMILES: Cc1ccc(F)cc1-c1cc2nc(Nc3ccc4c(c3)CN(C)CC4)ncc2c(N)c1F] | 6-fluoro-7-(5-fluoro-2-methylphenyl)-N~2~-(2-methyl-1,2,3,4-tetrahydroisoquinolin-7-yl)quinazoline-2,5-diamine | Calc'd 432, found 432; 2G |

TABLE 2-continued

| Example Number | Structure | Name | Exact Mass [M + H]+; Method |
|---|---|---|---|
| 2-175 | 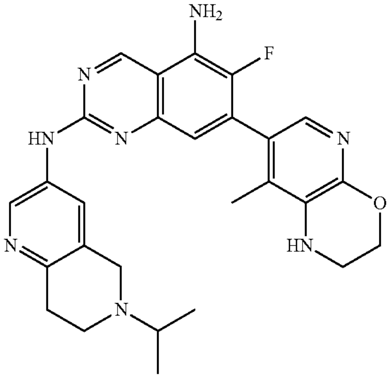 [SMILES: Cc1c(-c2cc3nc(Nc4cnc5c(c4)CN(C(C)C)CC5)ncc3c(N)c2F)cnc2c1NCCO2] | 6-fluoro-7-(8-methyl-2,3-dihydro-1H-pyrido[2,3-b][1,4]oxazin-7-yl)-N~2~-[6-(propan-2-yl)-5,6,7,8-tetrahydro-1,6-naphthyridin-3-yl]quinazoline-2,5-diamine | Calc'd 501, found 501; 2P |
| 2-176 | 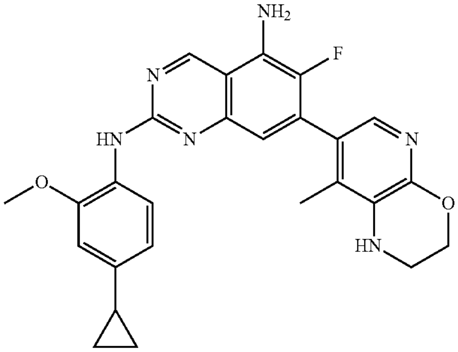 [SMILES: COc1cc(C2CC2)ccc1Nc1ncc2c(N)c(F)c(-c3cnc4c(c3C)NCCO4)cc2n1] | N~2~-(4-cyclopropyl-2-methoxyphenyl)-6-fluoro-7-(8-methyl-2,3-dihydro-1H-pyrido[2,3-b][1,4]oxazin-7-yl)quinazoline-2,5-diamine | Calc'd 473, found 473; 2G |
| 2-177 | 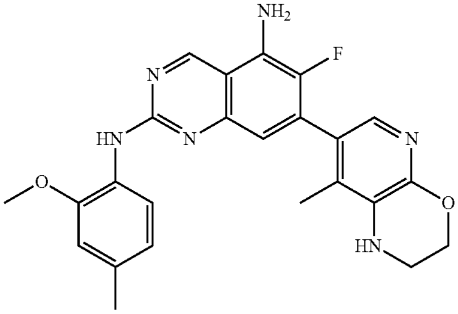 [SMILES: COc1cc(C)ccc1Nc1ncc2c(N)c(F)c(-c3cnc4c(c3C)NCCO4)cc2n1] | 6-fluoro-N~2~-(2-methoxy-4-methylphenyl)-7-(8-methyl-2,3-dihydro-1H-pyrido[2,3-b][1,4]oxazin-7-yl)quinazoline-2,5-diamine | Calc'd 447, found 447; 2G |
| 2-178 | 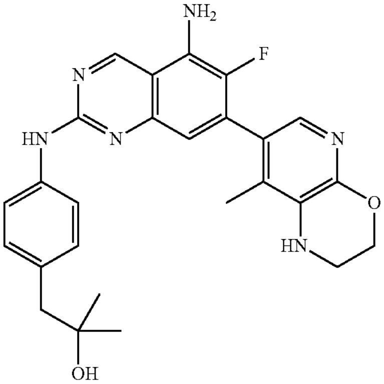 [SMILES: Cc1c(-c2cc3nc(Nc4ccc(CC(C)(C)O)cc4)ncc3c(N)c2F)cnc2c1NCCO2] | 1-(4-{[5-amino-6-fluoro-7-(8-methyl-2,3-dihydro-1H-pyrido[2,3-b][1,4]oxazin-7-yl)quinazolin-2-yl]amino}phenyl)-2-methylpropan-2-ol | Calc'd 475, found 475; 2G |

TABLE 2-continued

| Example Number | Structure | Name | Exact Mass [M + H]+; Method |
|---|---|---|---|
| 2-179 | 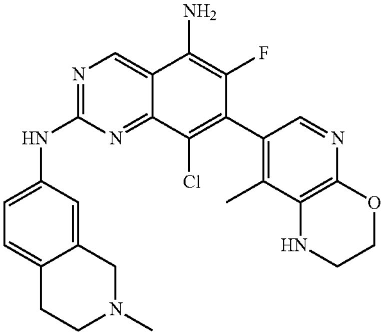 [SMILES: Cc1c(-c2c(F)c(N)c3cnc(Nc4ccc5c(c4)CN(C)CC5)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine | Calc'd 506, found 506; 2K |
| 2-180 | 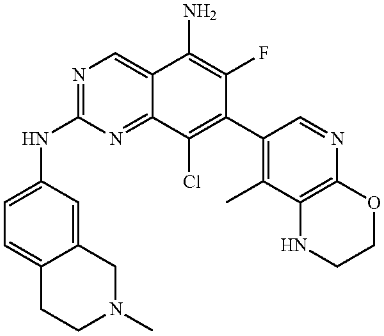 [SMILES: Cc1c(-c2c(F)c(N)c3cnc(Nc4ccc5c(c4)CN(C)CC5)nc3c2Cl)cnc2c1NCCO2] | (+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine | Calc'd 506, found 506; 2K |
| 2-181 | 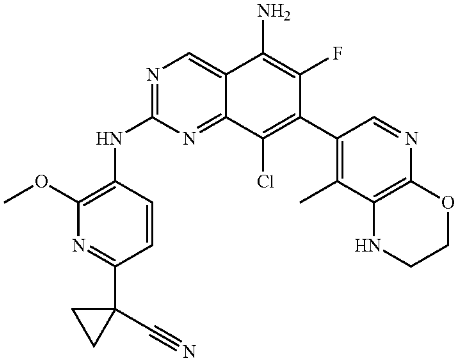 [SMILES: COc1nc(C2(C#N)CC2)ccc1Nc1ncc2c(N)c(F)c(-c3cnc4c(c3C)NCCO4)c(Cl)c2n1] | (+ or −)-1-(5-{[5-amino-8-chloro-6-fluoro-7-(8-methyl-2,3-dihydro-1H-pyrido[2,3-b][1,4]oxazin-7-yl)quinazolin-2-ylamino}-6-methoxypyridin-2-yl)cyclopropane-1-carbonitrile | Calc'd 533, found 533; 2K |
| 2-182 | 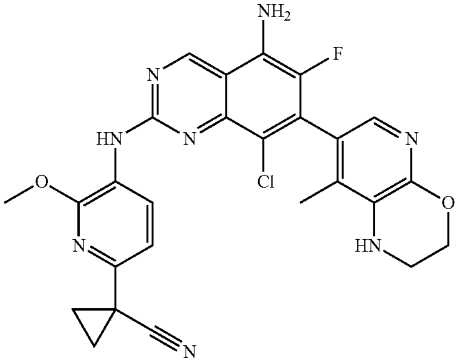 [SMILES: COc1nc(C2(C#N)CC2)ccc1Nc1ncc2c(N)c(F)c(-c3cnc4c(c3C)NCCO4)c(Cl)c2n1] | (+ or −)-1-(5-{[5-amino-8-chloro-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile | Calc'd 533, found 533; 2K |

TABLE 2-continued

| Example Number | Structure | Name | Exact Mass [M + H]+; Method |
|---|---|---|---|
| 2-183 | 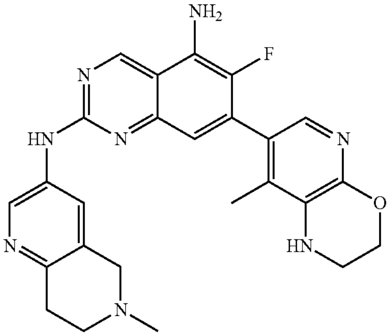 [SMILES: Cc1c(-c2cc3nc(Nc4cnc5c(c4)CN(C)CC5)ncc3c(N)c2F)cnc2c1NCCO2] | 6-fluoro-7-(8-methyl-2,3-dihydro-1H-pyrido[2,3-b][1,4]oxazin-7-yl)-N~2~-(6-methyl-5,6,7,8-tetrahydro-1,6-naphthyridin-3-yl)quinazoline-2,5-diamine | Calc'd 473, found 473; 2G |
| 2-184 | 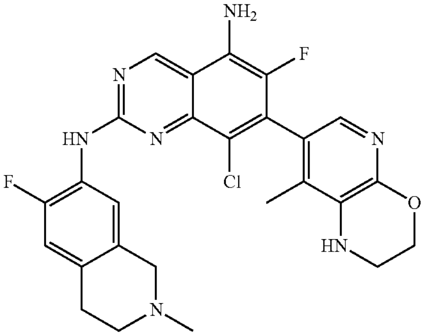 [SMILES: Cc1c(-c2c(F)c(N)c3cnc(Nc4cc5c(cc4F)CCN(C)C5)nc3c2Cl)cnc2c1NCCO2] | (+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 524, found 524; 2K |
| 2-185 | 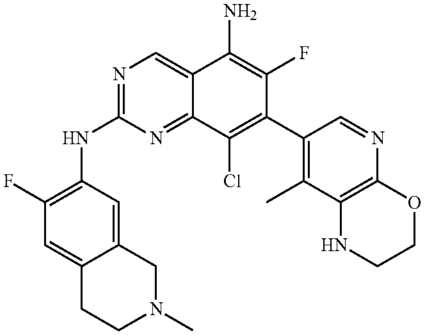 [SMILES: Cc1c(-c2c(F)c(N)c3cnc(Nc4cc5c(cc4F)CCN(C)C5)nc3c2Cl)cnc2c1NCCO2] | (+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine | Calc'd 524, found 524; 2K |
| 2-186 | 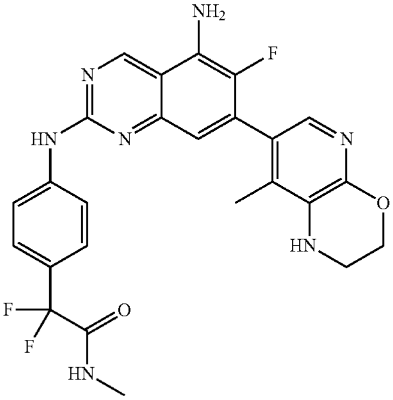 | 2-(4-{[5-amino-6-fluoro-7-(8-methyl-2,3-dihydro-1H-pyrido[2,3-b][1,4]oxazin-7-yl)quinazolin-2-yl]amino}phenyl)-2,2-difluoro-N-methylacetamide | Calc'd 510, found 510; 2G |

TABLE 2-continued

| Example Number | Structure | Name | Exact Mass [M + H]+; Method |
|---|---|---|---|
| 2-187 | 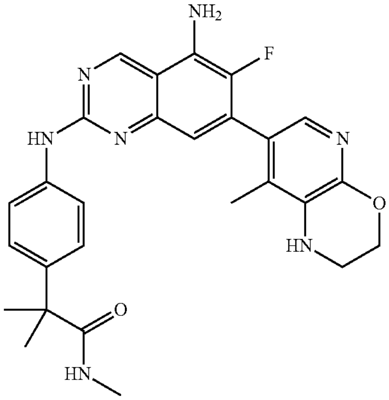 [SMILES: CNC(=O)C(C)(C)c1ccc(Nc2ncc3c(N)c(F)c(-c4cnc5c(c4C)NCCO5)cc3n2)cc1] | 2-(4-{[5-amino-6-fluoro-7-(8-methyl-2,3-dihydro-1H-pyrido[2,3-b][1,4]oxazin-7-yl)quinazolin-2-yl]amino}phenyl)-N,2-dimethylpropanamide | Calc'd 502, found 502: 2G |
| 2-188 | 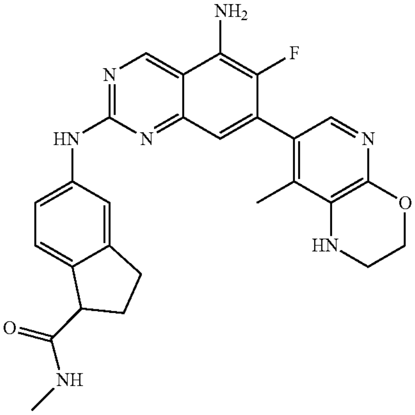 [SMILES: CNC(=O)C1CCc2cc(Nc3ncc4c(N)c(F)c(-c5cnc6c(c5C)NCCO6)cc4n3)ccc21] | 5-{[5-amino-6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide | Calc'd 500, found 500; 2G |

Compound Examples of Table 3

Example 3A. Preparation of 3-2

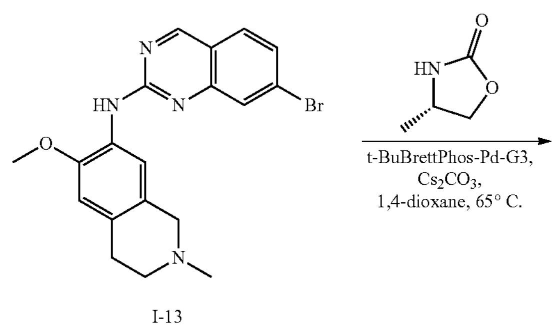

I-13

-continued

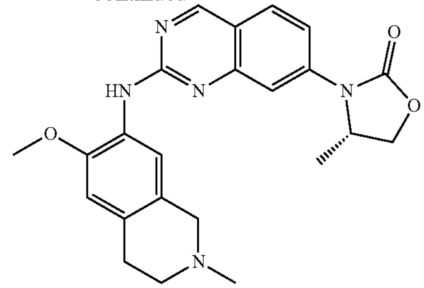

3-2

A solution of intermediate I-13 (60 mg, 0.15 mmol), t-BuBrettPhos-Pd-G3 (39 mg, 0.045 mmol), $Cs_2CO_3$ (150 mg, 0.45 mmol), and 4-methyl-1,3-oxazolidin-2-one (38 mg, 0.38 mmol) in 1,4-dioxane (2 mL) and deoxygenated by bubbling argon gas through the reaction mixture for 3 min. The mixture was stirred overnight at 65° C. After cooling, the reaction is filtered and concentrated to dryness. The residue was purified by achiral-Prep-SFC [Column: EP, 21×250 mm; (15% MeOH/0.1% $NH_4OH$)/$CO_2$; Flow rate: 70 mL/min; 220 nm: RT: 3.9 min] to provide 5-2 as a solid. $^1H$ NMR (500 MHz, DMSO-$d_6$) δ 9.18 (s, 1H), 8.17 (s, 1H), 8.06 (s, 1H), 7.93 (d, J=8.6 Hz, 1H), 7.65 (dd, J=10.7, 1.9

Hz, 2H), 6.80 (s, 1H), 4.98-4.81 (m, 1H), 4.61 (t, J=8.3 Hz, 1H), 4.12 (dd, J=8.4, 4.7 Hz, 1H), 3.80 (s, 3H), 3.48 (s, 2H), 2.81 (t, J=5.7 Hz, 2H), 2.59 (t, J=5.9 Hz, 2H), 2.36 (s, 3H), 1.31 (d, J=6.2 Hz, 3H). MS (EI) calc'd for $C_{23}H_{26}N_5O_3$ $[M+H]^+$, 420; found, 420.

Example 3B. Preparation of 3-13 and 3-14

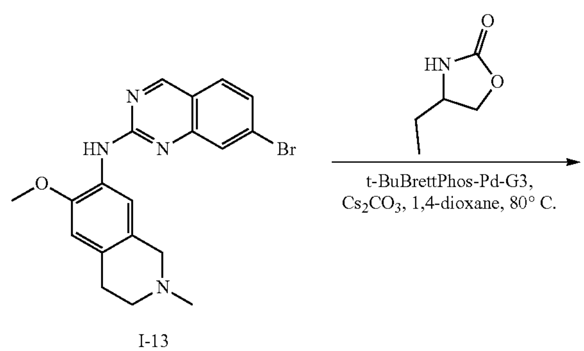

I-13

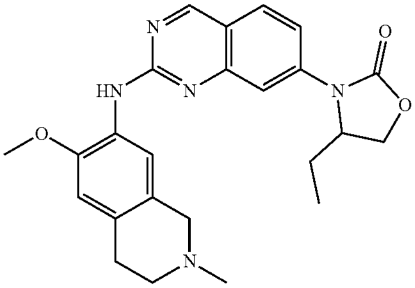

3-13

+

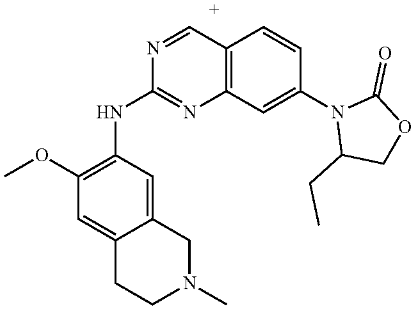

3-14

A vial charged with intermediate I-13 (100 mg, 0.250 mmol) in 1,4-dioxane (3.3 mL) was added 4-ethyloxazolidin-2-one (72 mg, 0.63 mmol), t-BuBrettPhos-Pd-G3 (64 mg, 0.075 mmol), and $Cs_2CO_3$ (408 mg, 1.25 mmol). The mixture was deoxygenated by bubbling argon gas through the reaction mixture for 3 min. The mixture was stirred overnight at 80° C. After cooling, the reaction is filtered and concentrated to dryness. The crude material was purified by chromatography on $SiO_2$ (0-100% EtOAc/hexanes, 4 g silica gel) to give the desired product as a racemate. The enantiomers were separated by chiral-Prep-SFC [Column: CCA, 21×250 mm; (45% MeOH/0.1% $NH_4OH$)/$CO_2$; Flow rate: 70 mL/min; 220 nm] to provide 3-13 [RT: 3.5 min] and 3-14 [RT: 4.3 min] as solids.

Compound 3-13 ((S or R)-4-ethyl-3-{2-[(6-methoxy-2-methyl-1,2,3,4-tetrahydroisoquinolin-7-yl)amino]quinazolin-7-yl}-1,3-oxazolidin-2-one). $^1H$ NMR (500 MHz, DMSO-$d_6$) δ 9.18 (s, 1H), 8.18 (s, 1H), 8.05 (s, 1H), 7.94 (d, J=8.8 Hz, 1H), 7.72 (s, 1H), 7.64 (d, J=8.8 Hz, 1H), 6.81 (s, 1H), 4.84 (s, 1H), 4.57 (t, J=8.5 Hz, 1H), 4.32-4.19 (m, 1H), 3.84 (s, 3H), 3.48 (s, 2H), 2.81 (s, 2H), 2.60 (t, J=5.2 Hz, 2H), 2.36 (s, 3H), 1.81-1.54 (m, 2H), 0.84 (t, J=7.3 Hz, 3H). MS (EI) calc'd for $C_{24}H_{28}N_5O_3$ $[M+H]^+$, 434; found, 434.

Compound 3-14 ((S or R)-4-ethyl-3-{2-[(6-methoxy-2-methyl-1,2,3,4-tetrahydroisoquinolin-7-yl)amino]quinazolin-7-yl}-1,3-oxazolidin-2-one). $^1H$ NMR (500 MHz, DMSO-$d_6$) δ 9.18 (d, J=2.1 Hz, 1H), 8.18 (s, 1H), 8.06 (s, 1H), 7.93 (dd, J=8.7, 2.4 Hz, 1H), 7.73 (s, 1H), 7.64 (d, J=8.8 Hz, 1H), 6.81 (s, 1H), 4.84 (s, 1H), 4.58 (t, J=8.4 Hz, 1H), 4.35-4.21 (m, 1H), 3.84 (d, J=2.2 Hz, 3H), 3.51 (s, 2H), 2.82 (s, 2H), 2.62 (s, 2H), 2.38 (s, 3H), 1.77-1.57 (m, 2H), 0.84 (t, J=6.2 Hz, 3H). MS (EI) calc'd for $C_{24}H_{28}N_5O_3$ $[M+H]^+$, 434; found, 434.

Example 3C. Preparation of 3-15 and 3-16

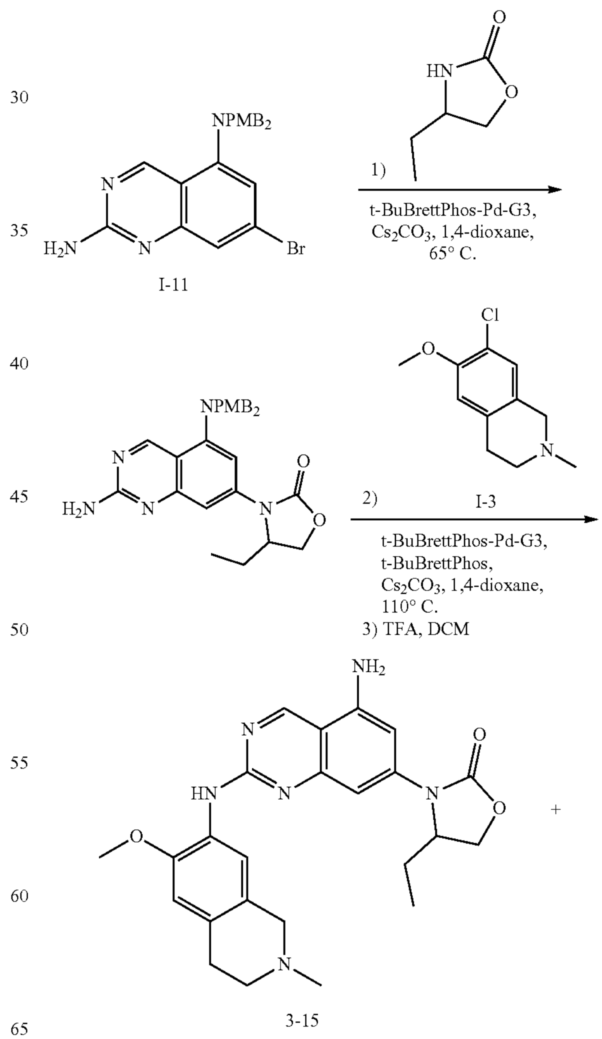

+

3-15

-continued

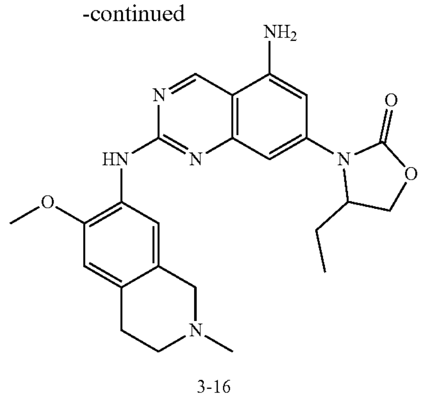

3-16

Step 1. Synthesis of (S and R)-3-(2-amino-5-(bis(4-methoxy-benzyl)amino)quinazolin-7-yl)-4-ethyloxazolidin-2-one A vial charged with intermediate I-11 (300 mg, 0.626 mmol) in 1,4-dioxane (6.3 mL) was added 4-ethyloxazolidin-2-one (180 mg, 1.565 mmol), t-BuBrettPhos-Pd-G3 (160 mg, 0.188 mmol), and $Cs_2CO_3$ (1.0 g, 3.13 mmol). The mixture was deoxygenated by bubbling argon gas through the reaction mixture for 3 min. The mixture was stirred overnight at 80° C. After cooling, the reaction is filtered and concentrated to dryness. Chromatography on $SiO_2$ (0-30% EtOAc/hexanes, then 0-20% EtOAc/DCM for the desired product, 4 g silica gel). The fractions containing the desired product mass were pooled and concentrated to dryness to afford (S and R)-3-(2-amino-5-(bis(4-methoxybenzyl)amino)quinazolin-7-yl)-4-ethyloxazolidin-2-one. MS (EI) calc'd for $C_{29}H_{32}N_5O_4$ $[M+H]^+$, 514; found, 514.

Steps 2-3. Synthesis of Compounds 3-15 and 3-16

A vial charged with intermediate I-3 (93 mg, 0.44 mmol), (S and R)-3-(2-amino-5-(bis(4-methoxybenzyl)amino)quinazolin-7-yl)-4-ethyloxazolidin-2-one (150 mg, 0.292 mmol), t-BuBrettPhos (57 mg, 0.12 mmol), $Pd_2(dba)_3$ (27 mg, 0.029 mmol), and $K_3PO_4$ (124 mg, 0.584 mmol) in toluene (2.9 mL) was deoxygenated by bubbling argon gas through the reaction mixture for 3 min. The mixture was stirred overnight at 110° C. After cooling, the reaction was filtered and concentrated to dryness. After concentration of the pooled fractions, the residual oil was taken up in 1 mL of DCM and added 1 mL TFA. After aging for 2 h, the reaction was concentrated to dryness to give the fully deprotected product. The crude mixture was purified by reverse phase chromatography (15-70% ACN/water with 0.1% $NH_4OH$) to give the desired product as a racemate. The enantiomers were resolved by chiral-Prep-SFC [Column: IA, 21×250 mm; 40% (MeOH/0.1% $NH_4OH$)/$CO_2$; Flow rate: 70 mL/min: 220 nm] to provide 3-15 [RT: 6.9 min] and 3-16 [RT: 7.9 min] as solids.

Compound 3-15 ((S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one). $^1H$ NMR (500 MHz, DMSO-$d_6$) δ 9.31 (s, 1H), 8.15 (s, 1H), 7.90 (s, 1H), 6.84 (s, 1H), 6.79 (s, 2H), 6.45 (s, 2H), 4.72-4.60 (m, 1H), 4.52 (t, J=8.5 Hz, 1H), 4.22 (dd, J=8.6, 3.9 Hz, 1H), 3.85 (s, 3H), 3.56 (s, 2H), 2.82 (t, J=5.5 Hz, 2H), 2.68 (s, 2H), 2.42 (s, 3H), 1.67 (s, 2H), 0.84 (t, J=7.4 Hz, 3H). MS (EI) calc'd for $C_{24}H_{29}N_6O_3$ $[M+H]^+$, 449; found, 449.

Compound 3-16 ((S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one). $^1H$ NMR (500 MHz, DMSO-$d_6$) δ 9.30 (s, 1H), 8.13 (s, 1H), 7.89 (s, 1H), 6.83 (s, 1H), 6.79 (d, J=8.0 Hz, 2H), 6.44 (s, 2H), 4.65 (s, 1H), 4.52 (t, J=8.1 Hz, 1H), 4.22 (d, J=8.4 Hz, 1H), 3.84 (s, 3H), 3.47 (s, 2H), 2.80 (s, 2H), 2.59 (s, 2H), 2.36 (s, 3H), 1.76-1.60 (m, 2H), 0.84 (t, J=7.0 Hz, 3H). MS (EI) calc'd for $C_{24}H_{29}N_6O_3$ $[M+H]^+$, 449; found, 449.

Example 3D. Preparation of 3-78

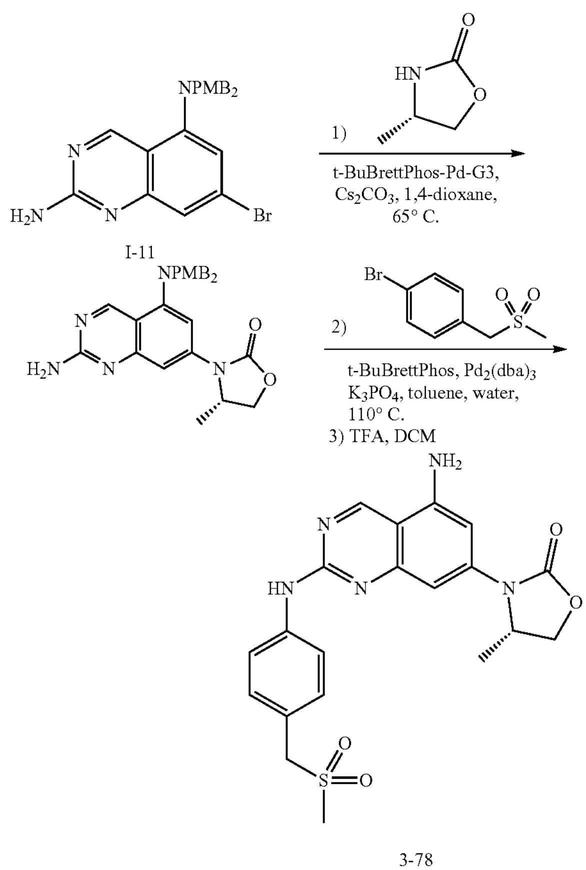

3-78

Step 1. Synthesis of (S)-3-(2-Amino-5-(bis(4-methoxybenzyl)amino)quinazolin-7-yl)-4-methyloxazolidin-2-one A solution of intermediate I-11 (100 mg, 0.209 mmol) in 1,4-dioxane (2.8 mL) was treated with (S)-4-methyl-1,3-oxazolidin-2-one (53 mg, 0.52 mmol), t-BuBrettPhos-Pd-G3 (54 mg, 0.063 mmol), and $Cs_2CO_3$ (340 mg, 1.04 mmol) and deoxygenated by bubbling argon gas through the reaction mixture for 3 min. The mixture was stirred overnight at 65° C. After cooling, the reaction is filtered and concentrated to dryness. Chromatography on $SiO_2$ (0-30% EtOAc/hexanes, then 0-20% EtOAc/DCM for the desired product, 4 g silica gel). The fractions containing the desired product mass were pooled and concentrated to dryness to afford (S)-3-(2-amino-5-(bis(4-methoxybenzyl)amino)quinazolin-7-yl)-4-methyloxazolidin-2-one. MS (EI) calc'd for $C_{28}H_{30}N_5O_4$ $[M+H]^+$, 500; found, 500.

Steps 2-3. Synthesis of 3-78

A vial charged with 1-bromo-4-((methylsulfonyl)methyl) benzene (20 mg, 0.080 mmol), (S)-3-(2-amino-5-(bis(4-methoxybenzyl)amino)quinazolin-7-yl)-4-methyloxazolidin-2-one (40 mg, 0.080 mmol), t-BuBrettPhos (16 mg, 0.032 mmol). $Pd_2(dba)_3$ (7.3 mg, 8.0 μmol), and $K_3PO_4$ (34 mg, 0.16 mmol) in Toluene (0.8 mL) was added water (40 μL). The reaction was deoxygenated by bubbling nitrogen gas through the reaction mixture for 3 min. The mixture was stirred overnight at 110° C. After cooling, the reaction was filtered and concentrated to dryness. Chromatography on $SiO_2$ (4 g, silica gel, 0-10% MeOH/DCM) to give the protected intermediate. After concentration of the pooled fractions, the residual oil was taken up in 1 mL of DCM and added 1 mL TFA. After aging for 2 h, the reaction was concentrated to dryness to give the fully deprotected product. The residue was purified by reverse phase column chromatography (gradient elution of 2-55% Acetonitrile/Water+0.1% $NH_4OH$) to give compound 3-78 as the desired product. $^1H$ NMR (500 MHz, DMSO-$d_6$) δ 9.72 (s, 1H), 9.35 (s, 1H), 7.97 (d, J=8.5 Hz, 2H), 7.34 (d, J=8.5 Hz, 2H), 6.84 (d, J=7.8 Hz, 2H), 6.44 (s, 2H), 4.74 (d, J=5.8 Hz, 1H), 4.55 (t, J=8.2 Hz, 1H), 4.40 (s, 2H), 4.07 (dd, J=8.3, 4.3 Hz, 1H), 2.88 (s, 3H), 1.32 (d, J=6.1 Hz, 3H). MS (EI) calc'd for $C_{20}H_{22}N_5O_4S$ $[M+H]^+$, 428; found, 428.

Example 3E. Preparation of 3-43

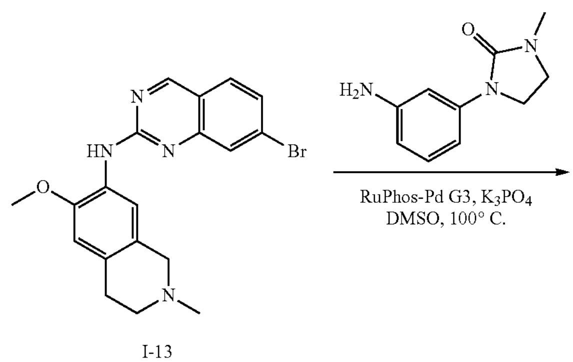

I-13

-continued

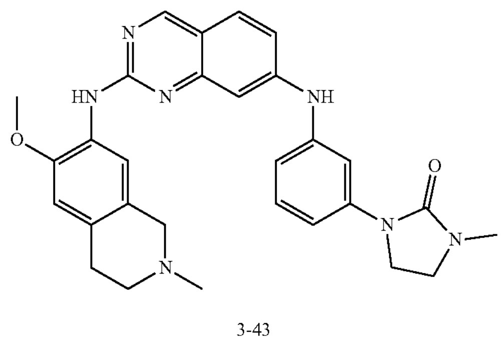

3-43

A solution of intermediate I-13 (13 mg, 0.033 mmol), t-RuPhos-Pd-G3 (5.5 mg, 0.007 mmol) in DMSO (0.3 mL) was added to a vial with $K_3PO_4$ (28 mg, 0.13 mmol) and 1-(3-aminophenyl)-3-methylimidazolidin-2-one (9.3 mg, 0.049 mmol). The mixture was stirred overnight at 80° C. After cooling, the reaction is diluted with 1 mL DMSO and filtered. The residue was purified by Reversed column (C18) $NH_4$-35% ACN-70% ACN in water over 8 mins, Flow rate: 25 mL/min; RT: 0.69 min] to provide desired product as a solid. $^1H$ NMR (500 MHz, DMSO-$d_6$) δ 8.96 (s, 1H), 8.89 (s, 1H), 8.15 (s, 1H), 7.86 (s, 1H), 7.75 (s, 1H), 7.70 (d, J=8.7 Hz, 1H), 7.30 (t, J=8.1 Hz, 1H), 7.10 (s, 1H), 7.08 (s, 1H), 7.06 (s, 1H), 6.92-6.88 (m, 1H), 6.77 (s, 1H), 3.83 (s, 3H), 3.82-3.77 (m, 2H), 2.78 (d, J=4.7 Hz, 5H), 2.57 (t, J=5.8 Hz, 2H), 2.55 (s, 4H), 2.33 (s, 3H). MS (EI) calc'd for $C_{29}H_{32}N_7O_2$ $[M+H]^+$, 510; found, 510.

Compounds listed in the table below were prepared using the synthetic methods described in the aforementioned examples. The table provides the compound structure, the name, the calculated and observed masses, and the example method used for preparation.

TABLE 3

| Example Number | Structure | Name | Exact Mass $[M + H]^+$; Method |
|---|---|---|---|
| 3-1 | 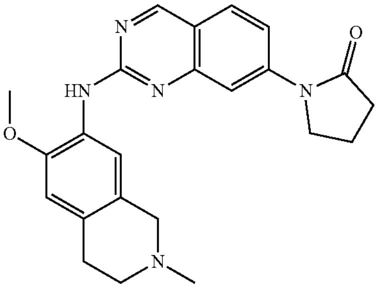 [SMILES: COc1cc2c(cc1Nc1ncc3ccc(N4CCCC4=O)cc3n1)CN(C)CC2] | 1-{2-[(6-methoxy-2-methyl-1,2,3,4-tetrahydroisoquinolin-7-yl)amino]quinazolin-7-yl}-pyrrolidin-2-one | Calc'd 404, found 404; 3A |

TABLE 3-continued

| Example Number | Structure | Name | Exact Mass [M + H]+; Method |
|---|---|---|---|
| 3-2 | 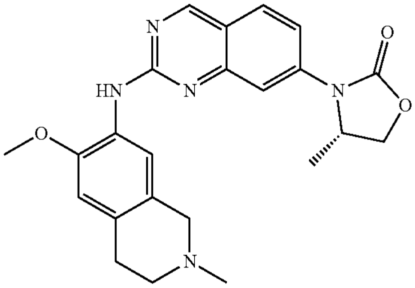 [SMILES: COc1cc2c(cc1Nc1ncc3ccc(N4C(=O)OC[C@@H]4C)cc3n1)CN(C)CC2] | (S)-3-{2-[(6-methoxy-2-methyl-1,2,3,4-tetrahydroisoquinolin-7-yl)amino]quinazolin-7-yl}-4-methyl-1,3-oxazolidin-2-one | Calc'd 420, found 420; 3A |
| 3-3 | 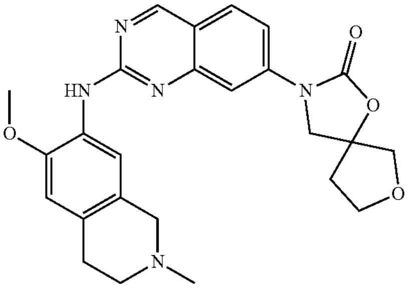 [SMILES: COc1cc2c(cc1Nc1ncc3ccc(N4CC5(CCOC5)OC4=O)cc3n1)CN(C)CC2] | (S and R)-3-{2-[(6-methoxy-2-methyl-1,2,3,4-tetrahydroiso-quinolin-7-yl)amino]quinazolin-7-yl}-1,7-dioxa-3-azaspiro[4.4]-nonan-2-one | Calc'd 462, found 462; 3A |
| 3-4 | 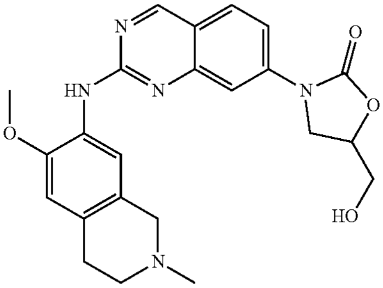 [SMILES: COc1cc2c(cc1Nc1ncc3ccc(N4CC(CO)OC4=O)cc3n1)CN(C)CC2] | (S and R)-5-(hydroxymethyl)-3-{2-[(6-methoxy-2-methyl-1,2,3,4-tetrahydroisoquinolin-7-yl)amino]quinazolin-7-yl}-1,3-oxazolidin-2-one | Calc'd 436, found 436; 3A |
| 3-5 | 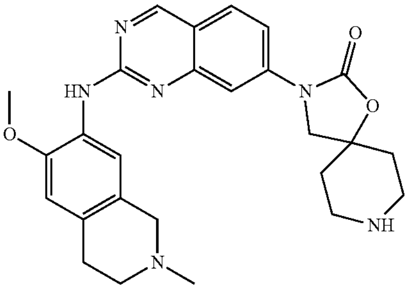 [SMILES: COc1cc2c(cc1Nc1ncc3ccc(N4CC5(CCNCC5)OC4=O)cc3n1)CN(C)CC2] | 3-{2-[(6-methoxy-2-methyl-1,2,3,4-tetrahydroisoquinolin-7-yl)amino]quinazolin-7-yl}-1-oxa-3,8-diazaspiro[4.5]decan-2-one | Calc'd 475, found 475; 3A |
| 3-6 | 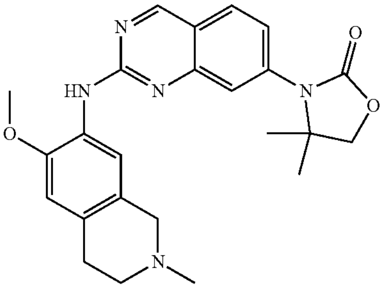 [SMILES: COc1cc2c(cc1Nc1ncc3ccc(N4C(=O)OCC4(C)C)cc3n1)CN(C)CC2] | 3-{2-[(6-methoxy-2-methyl-1,2,3,4-tetrahydroisoquinolin-7-yl)amino]quinazolin-7-yl}-4,4-dimethyl-1,3-oxazolidin-2-one | Calc'd 434, found 434; 3A |

TABLE 3-continued

| Example Number | Structure | Name | Exact Mass $[M + H]^+$; Method |
|---|---|---|---|
| 3-7 | 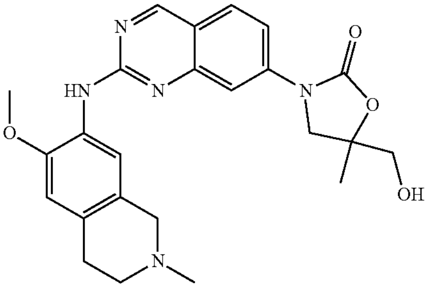 [SMILES: COc1cc2c(cc1Nc1ncc3ccc(N4CC(C)(CO)OC4=O)cc3n1)CN(C)CC2] | (S and R)-5-(hydroxymethyl)-3-{2-[(6-methoxy-2-methyl-1,2,3,4-tetrahydroisoquinolin-7-yl)amino]quinazolin-7-yl}-5-methyl-1,3-oxazolidin-2-one | Calc'd 450, found 450; 3A |
| 3-8 | 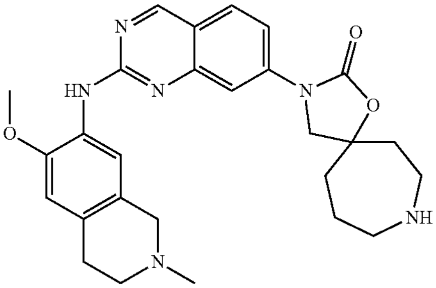 [SMILES: COc1cc2c(cc1Nc1ncc3ccc(N4CC5(CCCNCC5)OC4=O)cc3n1)CN(C)CC2] | (S and R)-3-{2-[(6-methoxy-2-methyl-1,2,3,4-tetrahydroiso-quinolin-7-yl)amino]quinazolin-7-yl}-1-oxa-3,8-diazaspiro[4.6]-undecan-2-one | Calc'd 489, found 489; 3A |
| 3-9 | 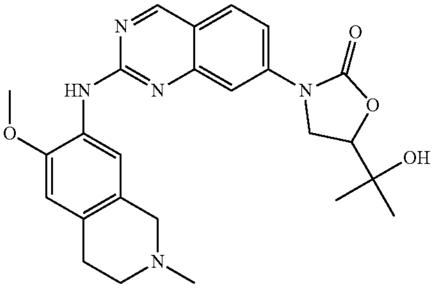 [SMILES: COc1cc2c(cc1Nc1ncc3ccc(N4CC(C(C)(C)O)OC4=O)cc3n1)CN(C)CC2] | (S and R)-5-(2-hydroxypropan-2-yl)-3-{2-[(6-methoxy-2-methyl-1,2,3,4-tetrahydroisoquinolin-7-yl)amino]quinazolin-7-yl}-1,3-oxazolidin-2-one | Calc'd 464, found 464; 3A |
| 3-10 | 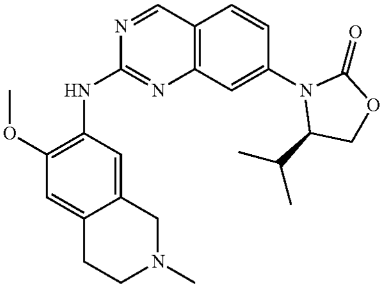 [SMILES: COc1cc2c(cc1Nc1ncc3ccc(N4C(=O)OC[C@H]4C(C)C)cc3n1)CN(C)CC2] | (4R)-3-{2-[(6-methoxy-2-methyl-1,2,3,4-tetrahydroisoquinolin-7-yl)amino]quinazolin-7-yl}-4-(propan-2-yl)-1,3-oxazolidin-2-one | Calc'd 448, found 448; 3A |
| 3-11 | 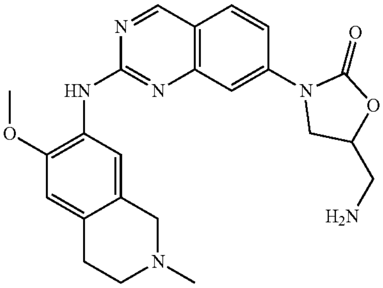 [SMILES: COc1cc2c(cc1Nc1ncc3ccc(N4CC(CN)OC4=O)cc3n1)CN(C)CC2] | (S and R)-5-(aminomethyl)-3-{2-[(6-methoxy-2-methyl-1,2,3,4-tetrahydroisoquinolin-7-yl)amino]quinazolin-7-yl}-1,3-oxazolidin-2-one | Calc'd 435, found 435; 3A |

TABLE 3-continued

| Example Number | Structure | Name | Exact Mass $[M + H]^+$; Method |
|---|---|---|---|
| 3-12 | 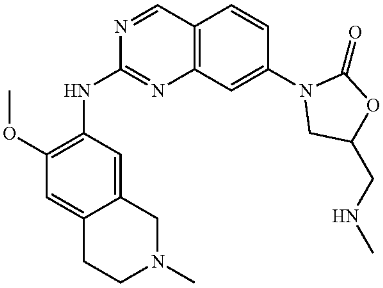 [SMILES: CNCC1CN(c2ccc3cnc(Nc4cc5c(cc4OC)CCN(C)C5)nc3c2)C(=O)O1] | (S and R)-3-12-[(6-methoxy-2-methyl-1,2,3,4-tetrahydroisoquinolin-7-yl)amino]quinazolin-7-yl}-5-[(methylamino)methyl]-1,3-oxazolidin-2-one | Calc'd 449, found 449; 3A |
| 3-13 | 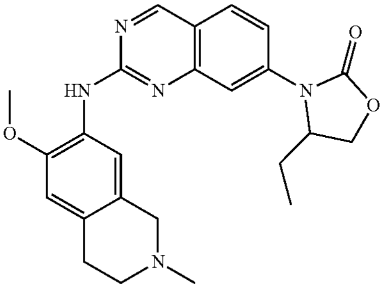 [SMILES: CCC1COC(=O)N1c1ccc2cnc(Nc3cc4c(cc3OC)CCN(C)C4)nc2c1] | (S or R)-4-ethyl-3-{2-[(6-methoxy-2-methyl-1,2,3,4-tetrahydroisoquinolin-7-yl)amino]quinazolin-7-yl}-1,3-oxazolidin-2-one | Calc'd 434, found 434; 3B |
| 3-14 | 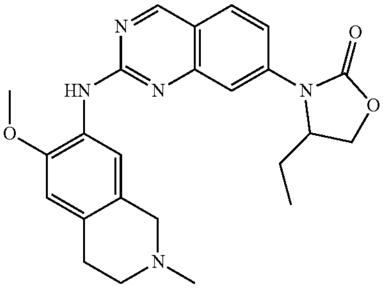 [SMILES: CCC1COC(=O)N1c1ccc2cnc(Nc3cc4c(cc3OC)CCN(C)C4)nc2c1] | (S or R)-4-ethyl-3-{2-[(6-methoxy-2-methyl-1,2,3,4-tetrahydroisoquinolin-7-yl)amino]quinazolin-7-yl}-1,3-oxazolidin-2-one | Calc'd 434, found 434; 3B |
| 3-15 | 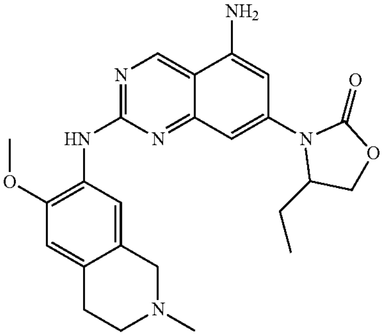 [SMILES: CCC1COC(=O)N1c1cc(N)c2cnc(Nc3cc4c(cc3OC)CCN(C)C4)nc2c1] | (S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one | Calc'd 449, found 449; 3C |
| 3-16 | 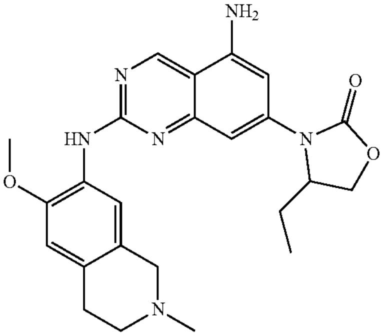 [SMILES: CCC1COC(=O)N1c1cc(N)c2cnc(Nc3cc4c(cc3OC)CCN(C)C4)nc2c1] | (S or R)-3-{5-amino-2-[(6-methoxy-2-methyl-1,2,3,4-tetrahydroisoquinolin-7-yl)amino]quinazolin-7-yl}-4-ethyl-1,3-oxazolidin-2-one | Calc'd 449, found 449; 3C |

TABLE 3-continued

| Example Number | Structure | Name | Exact Mass [M + H]+; Method |
|---|---|---|---|
| 3-17 | 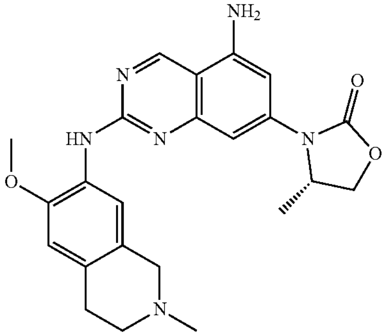 [SMILES: COc1cc2c(cc1Nc1ncc3c(N)cc(N4C(=O)OC[C@@H]4C)cc3n1)CN(C)CC2] | (S)-3-{5-amino-2-[(6-methoxy-2-methyl-1,2,3,4-tetrahydroiso-quinolin-7-yl)amino]quinazolin-7-yl}-4-methyl-1,3-oxazolidin-2-one | Calc'd 435, found 435; 3D |
| 3-18 | 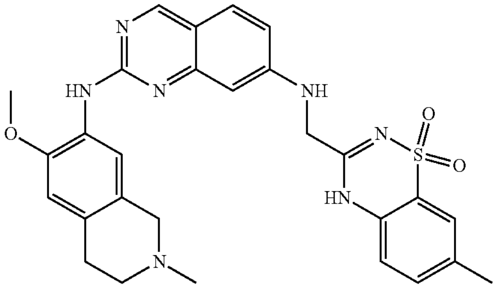 [SMILES: COc1cc2c(cc1Nc1ncc3ccc(NCC4=NS(=O)(=O)c5cc(C)ccc5N4)cc3n1)CN(C)CC2] | 3-[({2-[(6-methoxy-2-methyl-1,2,3,4-tetrahydroisoquinolin-7-yl)amino]quinazolin-7-yl}-amino)methyl]-7-methyl-1lambda~6~,2,4-benzothia-diazine-1,1(4H)-dione | Calc'd 544, found 544; 3E |
| 3-19 | 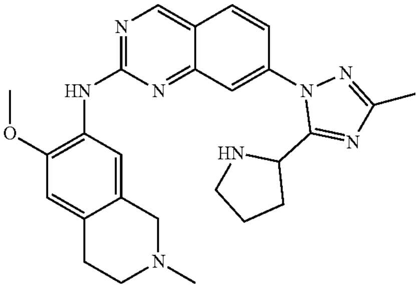 [SMILES: COc1cc2c(cc1Nc1ncc3ccc(-n4nc(C)nc4C4CCCN4)cc3n1)CN(C)CC2] | (S and R)-N-(6-methoxy-2-methyl-1,2,3,4-tetrahydroisoquinolin-7-yl)-7-[3-methyl-5-(pyrrolidin-2-yl)-1H-1,2,4-triazol-1-yl]quinazolin-2-amine | Calc'd 471, found 471; 3E |
| 3-20 | 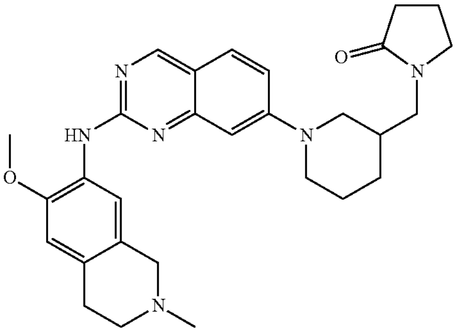 [SMILES: COc1cc2c(cc1Nc1ncc3ccc(N4CCCC(CN5CCCC5=O)C4)cc3n1)CN(C)CC2] | (S and R)-1-1(1-12-[(6-methoxy-2-methyl-1,2,3,4-tetrahydroiso-quinolin-7-yl)amino]quinazolin-7-yl}piperidin-3-yl)methyl]-pyrrolidin-2-one | Calc'd 501, found 501; 3E |

TABLE 3-continued

| Example Number | Structure | Name | Exact Mass [M + H]+; Method |
|---|---|---|---|
| 3-21 | 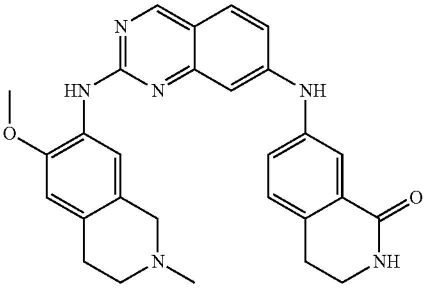 [SMILES: COc1cc2c(cc1Nc1ncc3ccc(Nc4ccc5c(c4)C(=O)NCC5)cc3n1)CN(C)CC2] | 7-({2-[(6-methoxy-2-methyl-1,2,3,4-tetrahydroisoquinolin-7-yl)amino]quinazolin-7-yl}-amino)-3,4-dihydroisoquinolin-1(2H)-one | Calc'd 481, found 481; 3E |
| 3-22 | 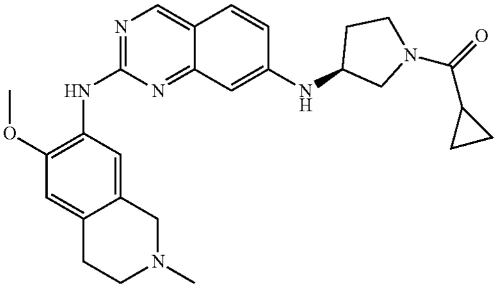 [SMILES: COc1cc2c(cc1Nc1ncc3ccc(N[C@H]4CCN(C(=O)C5CC5)C4)cc3n1)CN(C)CC2] | cyclopropyl[(3S)-3-({2-[(6-methoxy-2-methyl-1,2,3,4-tetrahydro-isoquinolin-7-yl)amino]quinazolin-7-yl}amino)pyrrolidin-1-yl]-methanone | Calc'd 473, found 473; 3E |
| 3-23 | 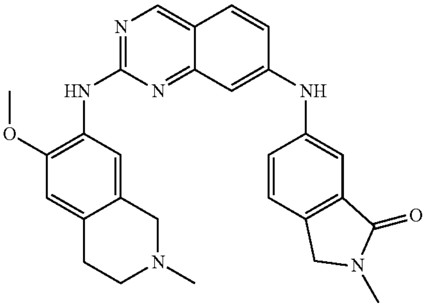 [SMILES: COc1cc2c(cc1Nc1ncc3ccc(Nc4ccc5c(c4)C(=O)N(C)C5)cc3n1)CN(C)CC2] | 6-({2-[(6-methoxy-2-methyl-1,2,3,4-tetrahydroisoquinolin-7-yl)amino]quinazolin-7-yl}-amino)-2-methyl-2,3-dihydro-1H-isoindol-1-one | Calc'd 481, found 481; 3E |
| 3-24 | 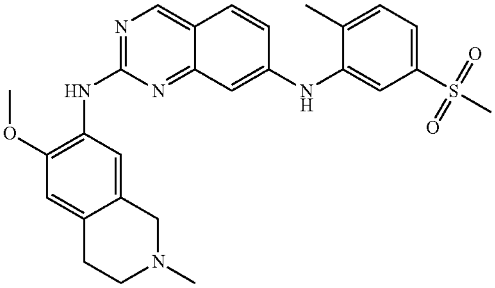 [SMILES: COc1cc2c(cc1Nc1ncc3ccc(Nc4cc(S(C)(=O)=O)ccc4C)cc3n1)CN(C)CC2] | N~2~-(6-methoxy-2-methyl-1,2,3,4-tetrahydroisoquinolin-7-yl)-N~7~-[2-methyl-5-(methylsulfonyl)phenyl]quinazoline-2,7-diamine | Calc'd 504, found 504; 3E |
| 3-25 | 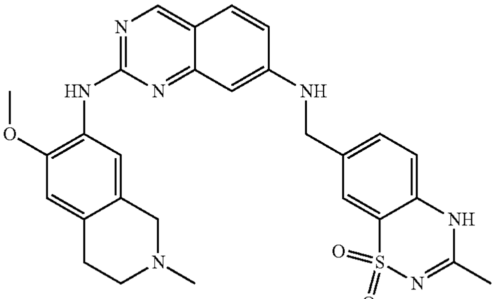 | 7-[({2-[(6-methoxy-2-methyl-1,2,3,4-tetrahydroisoquinolin-7-yl)amino]quinazolin-7-yl}-amino)methyl]-3-methyl-1lambda~6~,2,4-benzothiadiazine-1,1(4H)-dione | Calc'd 544, found 544; 3E |

TABLE 3-continued

| Example Number | Structure | Name | Exact Mass [M + H]+; Method |
|---|---|---|---|
| 3-26 | 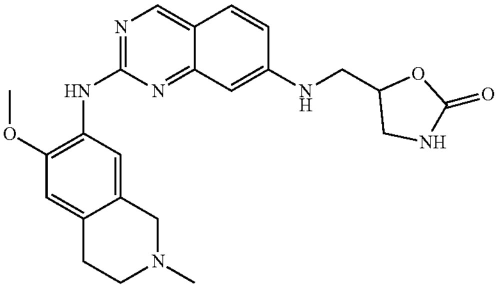 [SMILES: COc1cc2c(cc1Nc1ncc3ccc(NCC4CNC(=O)O4)cc3n1)CN(C)CC2] | (S and R)-5-[({2-1(6-methoxy-2-methyl-1,2,3,4-tetrahydroiso-quinolin-7-yl)amino]quinazolin-7-yl}amino)methyl]-1,3-oxazol-idin-2-one | Calc'd 435, found 435; 3E |
| 3~27 | 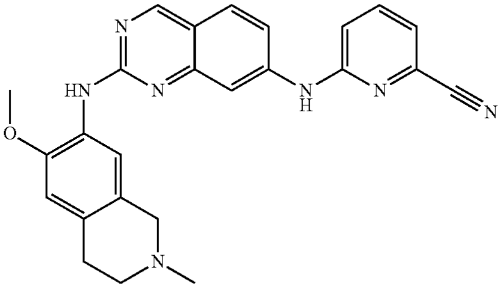 [SMILES: COc1cc2c(cc1Nc1ncc3ccc(Nc4cccc(C#N)n4)cc3n1)CN(C)CC2] | 6-({2-[(6-methoxy-2-methyl-1,2,3,4-tetrahydroisoquinolin-7-yl)amino]quinazolin-7-yl}-amino)-pyridine-2-carbonitrile | Calc'd 438, found 438; 3E |
| 3-28 | 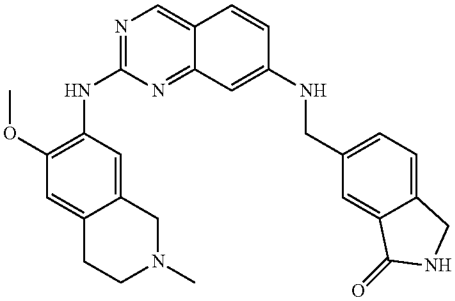 [SMILES: COc1cc2c(cc1Nc1ncc3ccc(NCc4ccc5c(c4)C(=O)NC5)cc3n1)CN(C)CC2] | 6-[({2-[(6-methoxy-2-methyl-1,2,3,4-tetrahydroisoquinolin-7-yl)amino]quinazolin-7-yl}-amino)methyl]-2,3-dihydro-1H-isoindol-1-one | Calc'd 481, found 481; 3E |
| 3-29 | 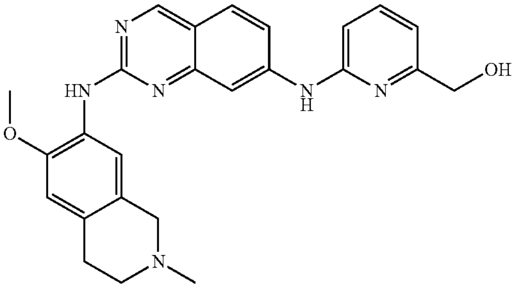 [SMILES: COc1cc2c(cc1Nc1ncc3ccc(Nc4cccc(CO)n4)cc3n1)CN(C)CC2] | [6-({2-[(6-methoxy-2-methyl-1,2,3,4-tetrahydroisoquinolin-7-yl)amino]quinazolin-7-yl}-amino)pyridin-2-yl]methanol | Calc'd 443, found 443; 3E |
| 3-30 | 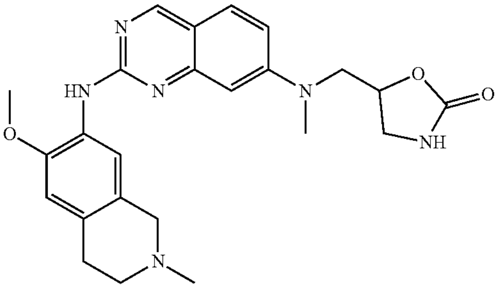 [SMILES: COc1cc2c(cc1Nc1ncc3ccc(N(C)CC4CNC(=O)O4)cc3n1)CN(C)CC2] | (S and R)-5-1112-1(6-methoxy-2-methyl-1,2,3,4-tetrahydroiso-quinolin-7-yl)amino]quinazolin-7-yl}(methyl)amino]methyl}-1,3-oxazolidin-2-one | Calc'd 449, found 449; 3E |

TABLE 3-continued

| Example Number | Structure | Name | Exact Mass $[M + H]^+$; Method |
|---|---|---|---|
| 3-31 | 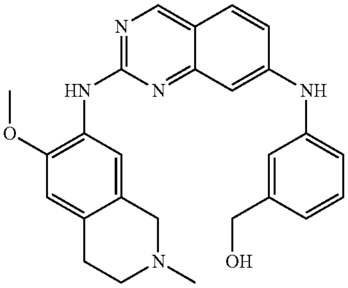 [SMILES: COc1cc2c(cc1Nc1ncc3ccc(Nc4cccc(CO)c4)cc3n1)CN(C)CC2] | [3-({2-[(6-methoxy-2-methyl-1,2,3,4-tetrahydroisoquinolin-7-yl)amino]quinazolin-7-yl}-amino)phenyl]methanol | Calc'd 442, found 442; 3E |
| 3-32 | 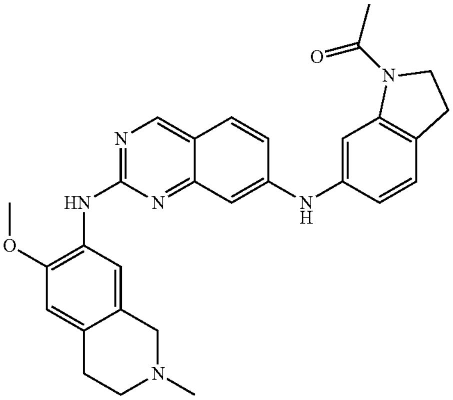 [SMILES: COc1cc2c(cc1Nc1ncc3ccc(Nc4ccc5c(c4)N(C(C)=O)CC5)cc3n1)CN(C)CC2] | 1-[6-({2-[(6-methoxy-2-methyl-1,2,3,4-tetrahydroisoquinolin-7-yl)amino]quinazolin-7-yl}-amino)-2,3-dihydro-1H-indol-1-yl]ethan-1-one | Calc'd 495, found 495; 3E |
| 3-33 | 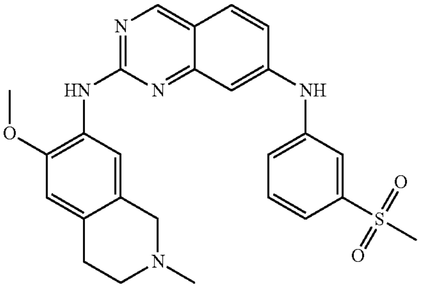 [SMILES: COc1cc2c(cc1Nc1ncc3ccc(Nc4cccc(S(C)(=O)=O)c4)cc3n1)CN(C)CC2] | N~2~-(6-methoxy-2-methyl-1,2,3,4-tetrahydroisoquinolin-7-yl)-N~7~-[3-(methylsulfonyl)phenyl]quinazoline-2,7-diamine | Calc'd 490, found 490; 3E |
| 3-34 | 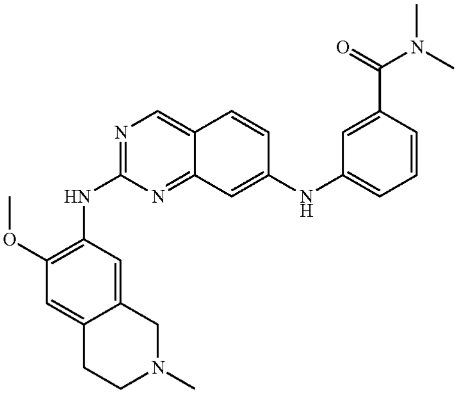 [SMILES: COc1cc2c(cc1Nc1ncc3ccc(Nc4cccc(C(=O)N(C)C)c4)cc3n1)CN(C)CC2] | 3-({2-[(6-methoxy-2-methyl-1,2,3,4-tetrahydroisoquinolin-7-yl)amino]quinazolin-7-yl}-amino)-N,N-dimethylbenzamide | Calc'd 483, found 483; 3E |

TABLE 3-continued

| Example Number | Structure | Name | Exact Mass [M + H]+; Method |
|---|---|---|---|
| 3-35 | 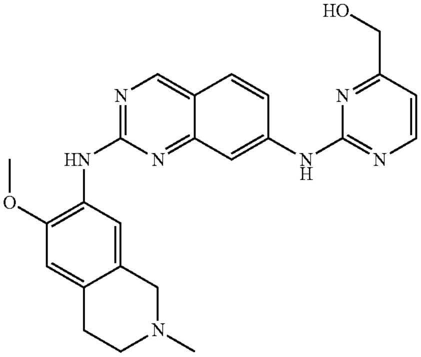 [SMILES: COc1cc2c(cc1Nc1ncc3ccc(Nc4nccc(CO)n4)cc3n1)CN(C)CC2] | [2-({2-[(6-methoxy-2-methyl-1,2,3,4-tetrahydroisoquinolin-7-yl)amino]quinazolin-7-yl}-amino)pyrimidin-4-yl]methanol | Calc'd 444, found 444; 3E |
| 3-36 | 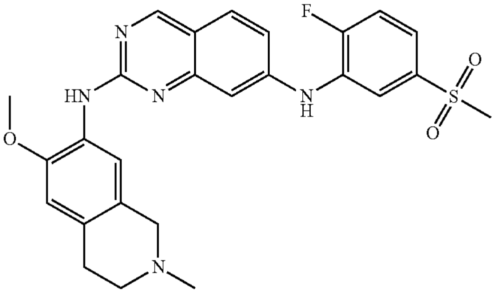 [SMILES: COc1cc2c(cc1Nc1ncc3ccc(Nc4cc(S(C)(=O)=O)ccc4F)cc3n1)CN(C)CC2] | N~7~-[2-fluoro-5-(methyl-sulfonyl)phenyl]-N~2~-(6-methoxy-2-methyl-1,2,3,4-tetra-hydroisoquinolin-7-yl)quinaz-oline-2,7-diamine | Calc'd 508, found 508; 3E |
| 3-37 | 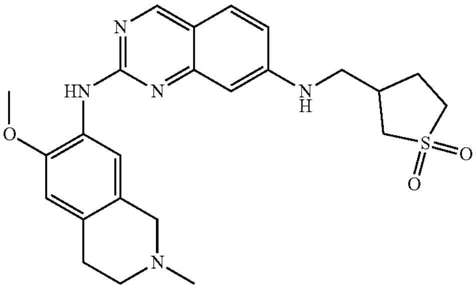 [SMILES: COc1cc2c(cc1Nc1ncc3ccc(NCC4CCS(=O)(=O)C4)cc3n1)CN(C)CC2] | (S and R)-3-1({2-[(6-methoxy-2-methyl-1,2,3,4-tetrahydroiso-quinolin-7-yl)amino]quinazolin-7-yl}amino)methyl]-1lambda~6~-thiolane-1,1-dione | Calc'd 468, found 468; 3E |
| 3-38 | 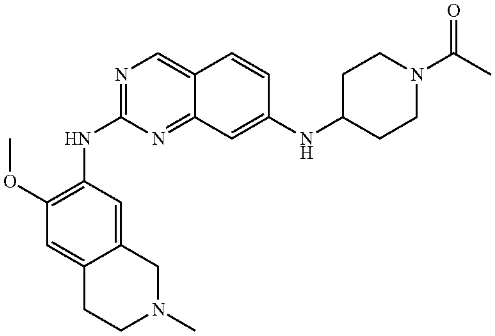 [SMILES: COc1cc2c(cc1Nc1ncc3ccc(NC4CCN(C(C)=O)CC4)cc3n1)CN(C)CC2] | 1-[4-({2-[(6-methoxy-2-methyl-1,2,3,4-tetrahydroisoquinolin-7-yl)amino]quinazolin-7-yl}-amino)piperidin-1-yl]ethan-1-one | Calc'd 461, found 461; 3E |

TABLE 3-continued

| Example Number | Structure | Name | Exact Mass $[M + H]^+$; Method |
|---|---|---|---|
| 3-39 | 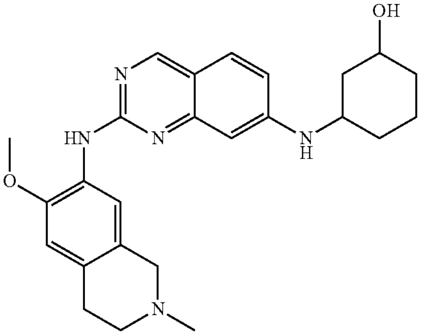 [SMILES: COc1cc2c(cc1Nc1ncc3ccc(NC4CCCC(O)C4)cc3n1)CN(C)CC2] | (±)-3-({2-[(6-methoxy-2-methyl-1,2,3,4-tetrahydroisoquinolin-7-yl)amino]quinazolin-7-yl}-amino)cyclohexan-1-ol | Calc'd 434, found 434; 3E |
| 3-40 | 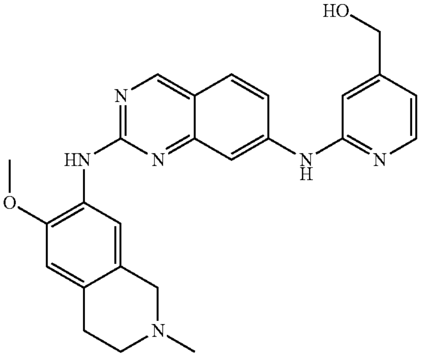 [SMILES: COc1cc2c(cc1Nc1ncc3ccc(Nc4cc(CO)ccn4)cc3n1)CN(C)CC2] | [2-({2-[(6-methoxy-2-methyl-1,2,3,4-tetrahydroisoquinolin-7-yl)amino]quinazolin-7-yl}-amino)pyridin-4-yl]methanol | Calc'd 443, found 443; 3E |
| 3-41 | 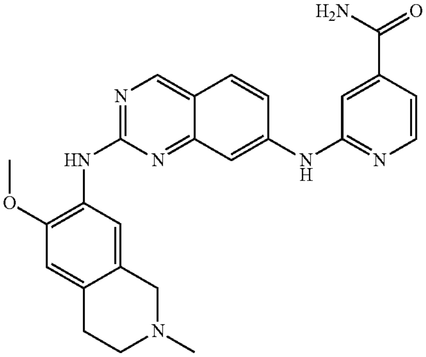 [SMILES: COc1cc2c(cc1Nc1ncc3ccc(Nc4cc(C(N)=O)ccn4)cc3n1)CN(C)CC2] | 2-({2-[(6-methoxy-2-methyl-1,2,3,4-tetrahydroisoquinolin-7-yl)amino]quinazolin-7-yl}-amino)pyridine-4-carboxamide | Calc'd 456, found 456; 3E |
| 3-42 | 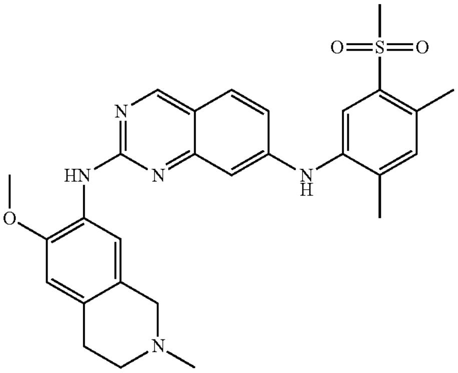 [SMILES: COc1cc2c(cc1Nc1ncc3ccc(Nc4cc(S(C)(=O)=O)c(C)cc4C)cc3n1)CN(C)CC2] | N~7~-[2,4-dimethyl-5-(methyl-sulfonyl)phenyl]-N~2~-(6-methoxy-2-methyl-1,2,3,4-tetra-hydroisoquinolin-7-yl)quinaz-oline-2,7-diamine | Calc'd 518, found 518; 3E |

TABLE 3-continued

| Example Number | Structure | Name | Exact Mass $[M + H]^+$; Method |
|---|---|---|---|
| 3-43 | 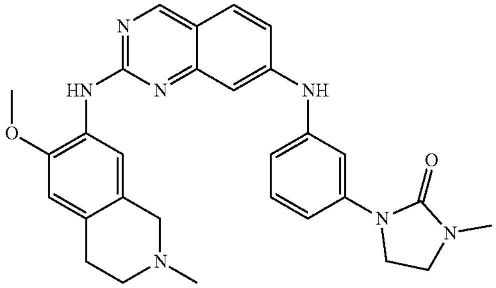 [SMILES: COc1cc2c(cc1Nc1ncc3ccc(Nc4cccc(N5CCN(C)C5=O)c4)cc3n1)CN(C)CC2] | 1-[3-({2-[(6-methoxy-2-methyl-1,2,3,4-tetrahydroisoquinolin-7-yl)amino]quinazolin-7-yl}-amino)phenyl]-3-methylimidaz-olidin-2-one | Calc'd 510, found 510; 3E |
| 3-44 | 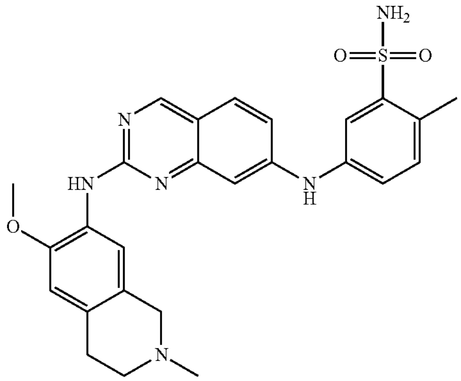 [SMILES: COc1cc2c(cc1Nc1ncc3ccc(Nc4ccc(C)c(S(N)(=O)=O)c4)cc3n1)CN(C)CC2] | 5-({2-[(6-methoxy-2-methyl-1,2,3,4-tetrahydroisoquinolin-7-yl)amino]quinazolin-7-yl}-amino)-2-methylbenzene-1-sulfonamide | Calc'd 505, found 505; 3E |
| 3-45 | 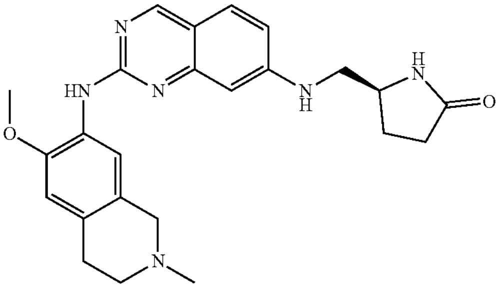 [SMILES: COc1cc2c(cc1Nc1ncc3ccc(NC[C@@H]4CCC(=O)N4)cc3n1)CN(C)CC2] | (5S)-5-[({2-[(6-methoxy-2-meth-yl-1,2,3,4-tetrahydroisoquinolin-7-yl)amino]quinazolin-7-yl}-amino)methyl]pyrrolidin-2-one | Calc'd 433, found 433; 3E |
| 3-46 | 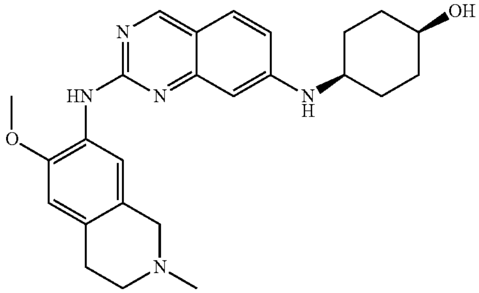 [SMILES: COc1cc2c(cc1Nc1ncc3ccc(N[C@H]4CC[C@@H](O)CC4)cc3n1)CN(C)CC2] | (1s,4s)-4-((2-((6-methoxy-2-methyl-1,2,3,4-tetrahydroiso-quinolin-7-yl)amino)quinazolin-7-yl)amino)cyclohexan-1-ol | Calc'd 434, found 434; 3E |
| 3-47 | 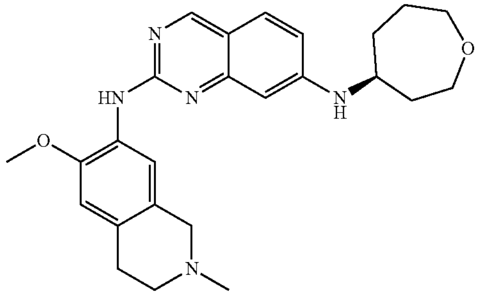 [SMILES: COc1cc2c(cc1Nc1ncc3ccc(N[C@H]4CCCOCC4)cc3n1)CN(C)CC2] | (S)-N2-(6-methoxy-2-methyl-1,2,3,4-tetrahydroisoquinolin-7-yl)-N7-(oxepan-4-yl)quinaz-oline-2,7-diamine | Calc'd 434, found 434; 3E |

TABLE 3-continued

| Example Number | Structure | Name | Exact Mass [M + H]+; Method |
|---|---|---|---|
| 3-48 | 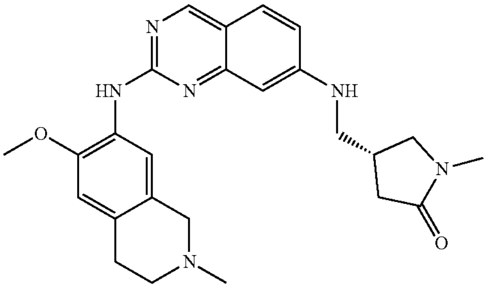 | (4S)-4-[({2-[(6-methoxy-2-methyl-1,2,3,4-tetrahydroisoquinolin-7-yl)amino]quinazolin-7-yl}-amino)methyl]-1-methylpyrrolidin-2-one | Calc'd 447, found 447; 3E |
| 3-49 | 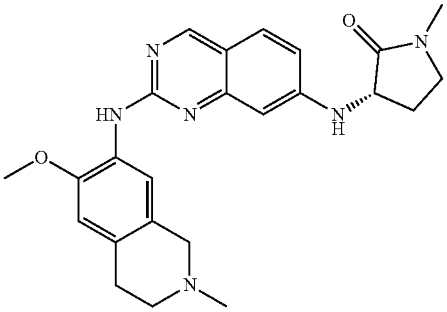 | (3S)-3-({2-[(6-methoxy-2-methyl-1,2,3,4-tetrahydroisoquinolin-7-yl)amino]quinazolin-7-yl}-amino)-1-methylpyrrolidin-2-one | Calc'd 433, found 433; 3E |
| 3-50 | 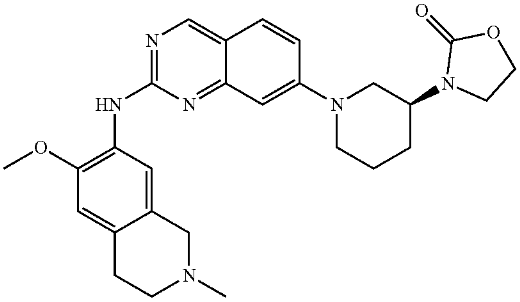 [SMILES: COc1cc2c(cc1Nc1ncc3ccc(N4CCC[C@H](N5CCOC5=O)C4)cc3n1)CN(C)CC2] | 3-[(3S)-1-{2-[(6-methoxy-2-methyl-1,2,3,4-tetrahydroisoquinolin-7-yl)amino]quinazolin-7-yl}piperidin-3-yl]-1,3-oxazolidin-2-one | Calc'd 489, found 489; 3E |
| 3-51 | 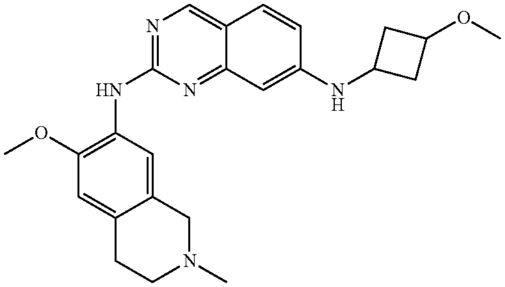 | N~7~-(3-methoxycyclobutyl)-N~2~-(6-methoxy-2-methyl-1,2,3,4-tetrahydroisoquinolin-7-yl)quinazoline-2,7-diamine | Calc'd 420, found 420; 3E |
| 3-52 | 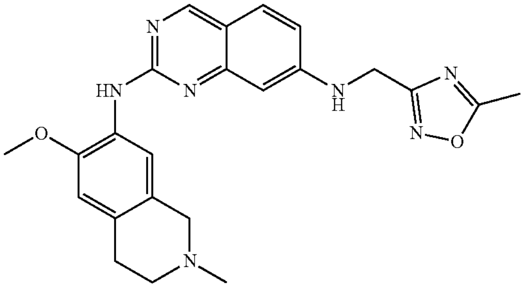 | N~2~-(6-methoxy-2-methyl-1,2,3,4-tetrahydroisoquinolin-7-yl)-N~7~-[(5-methyl-1,2,4-oxadiazol-3-yl)methyl]quinazoline-2,7-diamine | Calc'd 432, found 432; 3E |

TABLE 3-continued

| Example Number | Structure | Name | Exact Mass [M + H]$^+$; Method |
| --- | --- | --- | --- |
| 3-53 | 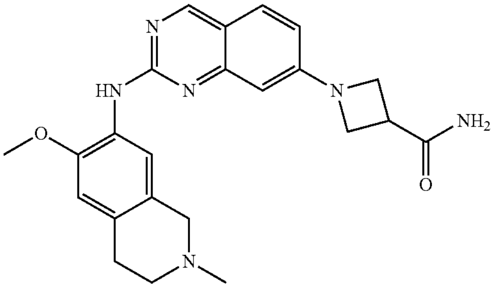 [SMILES: COc1cc2c(cc1Nc1ncc3ccc(N4CC(C(N)=O)C4)cc3n1)CN(C)CC2] | 1-{2-[(6-methoxy-2-methyl-1,2,3,4-tetrahydroisoquinolin-7-yl)amino]quinazolin-7-yl}-azetidine-3-carboxamide | Calc'd 419, found 419; 3E |
| 3-54 | 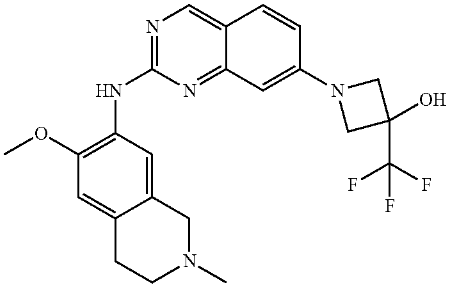 [SMILES: COc1cc2c(cc1Nc1ncc3ccc(N4CC(O)(C(F)(F)F)C4)cc3n1)CN(C)CC2] | (S and R)-1-12-[(6-methoxy-2-methyl-1,2,3,4-tetrahydroiso-quinolin-7-yl)amino]quinazolin-7-yl}-3-(trifluoromethyl)azet-idin-3-ol | Calc'd 460, found 460; 3E |
| 3-55 | 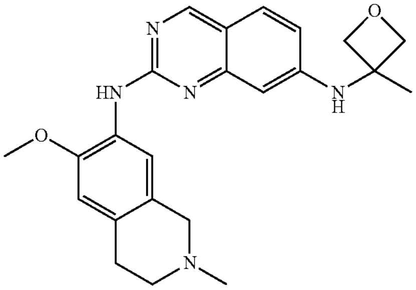 | N~2~-(6-methoxy-2-methyl-1,2,3,4-tetrahydroisoquinolin-7-yl)-N~7~-(3-methyloxetan-3-yl)quinazoline-2,7-diamine | Calc'd 406, found 406; 3E |
| 3-56 | 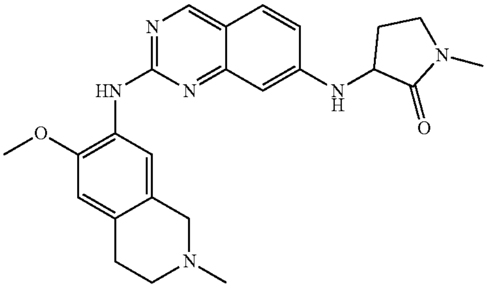 | (S and R)-3-({2-[(6-methoxy-2-methyl-1,2,3,4-tetrahydroiso-quinolin-7-yl)amino]quinazolin-7-yl}amino)-1-methylpyrrolidin-2-one | Calc'd 433, found 434; 3E |
| 3-57 | 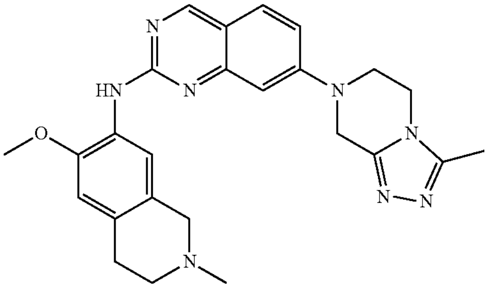 | N-(6-methoxy-2-methyl-1,2,3,4-tetrahydroisoquinolin-7-yl)-7-(3-methyl-5,6-dihydro[1,2,4]-triazolo[4,3-a]pyrazin-7(8H)-yl)quinazolin-2-amine | Calc'd 457, found 457; 3E |

TABLE 3-continued

| Example Number | Structure | Name | Exact Mass [M + H]+; Method |
|---|---|---|---|
| 3-58 | 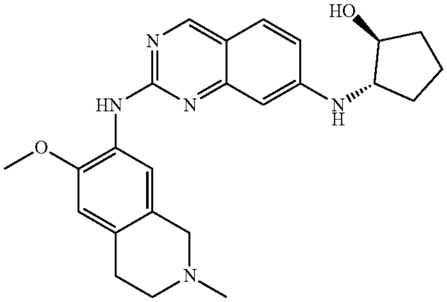 [SMILES: COc1cc2c(cc1Nc1ncc3ccc(N[C@H]4CCC[C@@H]4O)cc3n1)CN(C)CC2] | (1S,2S)-2-({2-[(6-methoxy-2-methyl-1,2,3,4-tetrahydroiso-quinolin-7-yl)amino]quinazolin-7-yl}amino)cyclopentan-1-ol | Calc'd 420, found 420; 3E |
| 3-59 | 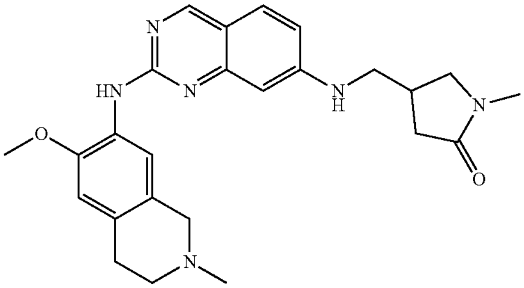 | (S and R)-4-[({2-[(6-methoxy-2-methyl-1,2,3,4-tetrahydroiso-quinolin-7-yl)amino]quinazolin-7-yl}amino)methyl]-1-methyl-pyrrolidin-2-one | Calc'd 447, found 447; 3E |
| 3-60 | 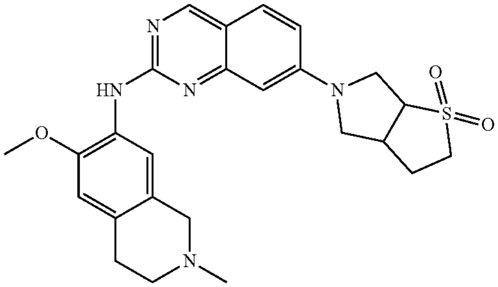 [SMILES: COc1cc2c(cc1Nc1ncc3ccc(N4CC5CCS(=O)(=O)C5C4)cc3n1)CN(C)CC2] | (±)-5-{2~-[(6-methoxy-2-methyl-1,2,3,4-tetrahydroisoquinolin-7-yl)amino]quinazolin-7-yl}-hexahydro-1lambda~6~-thieno-[2,3-c]pyrrole-1,1(2H)-dione | Calc'd 480, found 480; 3E |
| 3-61 | 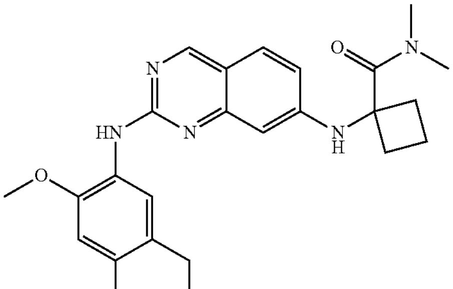 | 1-({2-[(6-methoxy-2-methyl-1,2,3,4-tetrahydroisoquinolin-7-yl)amino]quinazolin-7-yl}-amino)-N,N-dimethylcyclo-butane-1-carboxamide | Calc'd 461, found 461; 3E |
| 3-62 | 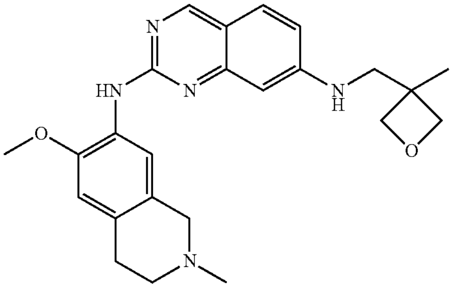 | N~2~-(6-methoxy-2-methyl-1,2,3,4-tetrahydroisoquinolin-7-yl)-N~7-[(3-methyloxetan-3-yl)-methyl]quinazoline-2,7-diamine | Calc'd 420, found 420; 3E |

TABLE 3-continued

| Example Number | Structure | Name | Exact Mass [M + H]+; Method |
|---|---|---|---|
| 3-63 | 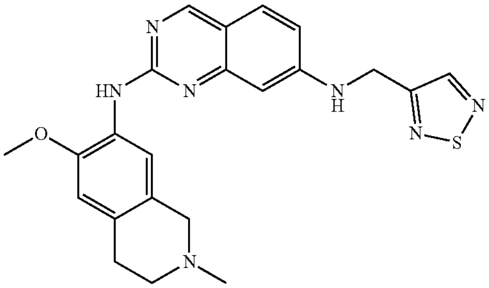 [SMILES: COc1cc2c(cc1Nc1ncc3ccc(NCc4cnsn4)cc3n1)CN(C)CC2] | N~2~-(6-methoxy-2-methyl-1,2,3,4-tetrahydroisoquinolin-7-yl)-N~7-[(1,2,5-thiadiazol-3-yl)-methyl]quinazoline-2,7-diamine | Calc'd 434, found 434; 3E |
| 3-64 | 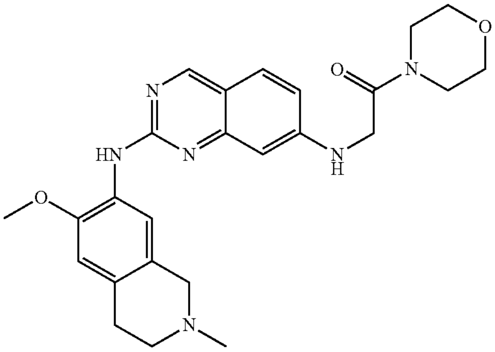 [SMILES: COc1cc2c(cc1Nc1ncc3ccc(NCC(=O)N4CCOCC4)cc3n1)CN(C)CC2] | 2-({2-[(6-methoxy-2-methyl-1,2,3,4-tetrahydroisoquinolin-7-yl)amino]quinazolin-7-yl}-amino)-1-(morpholin-4-yl)ethan-1-one | Calc'd 463, found 463; 3E |
| 3-65 | 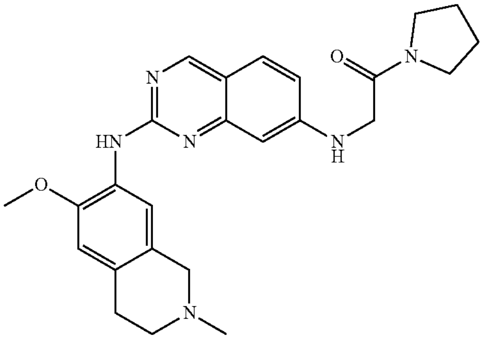 [SMILES: COc1cc2c(cc1Nc1ncc3ccc(NCC(=O)N4CCCC4)cc3n1)CN(C)CC2] | 2-({2-[(6-methoxy-2-methyl-1,2,3,4-tetrahydroisoquinolin-7-yl)amino]quinazolin-7-yl}-amino)-1-(pyrrolidin-1-yl)ethan-1-one | Calc'd 447, found 447; 3E |
| 3-66 | 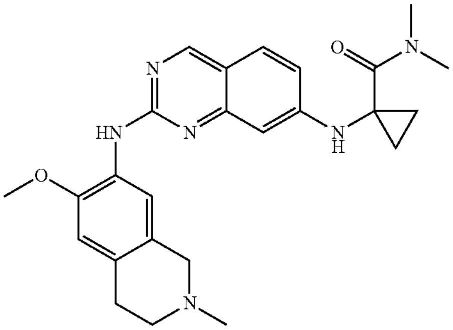 | 1-({2-[(6-methoxy-2-methyl-1,2,3,4-tetrahydroisoquinolin-7-yl)amino]quinazolin-7-yl}-amino)-N,N-dimethylcyclopropane-1-carboxamide | Calc'd 447, found 447; 3E |

TABLE 3-continued

| Example Number | Structure | Name | Exact Mass [M + H]+; Method |
|---|---|---|---|
| 3-67 | 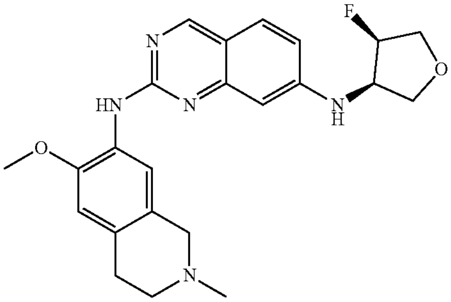 [SMILES: COc1cc2c(cc1Nc1ncc3ccc(N[C@@H]4COC[C@@H]4F)cc3n1)CN(C)CC2] | N~7~-[(3R,4R)-4-fluorooxolan-3-yl]-N~2~-(6-methoxy-2-methyl-1,2,3,4-tetrahydroisoquinolin-7-yl)quinazoline-2,7-diamine | Calc'd 424, found 424; 3E |
| 3-68 | 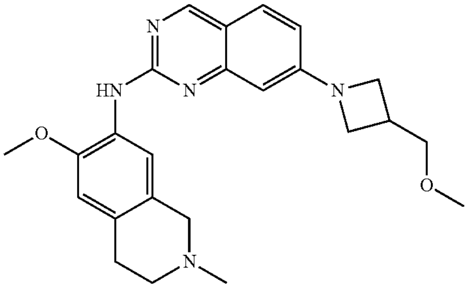 | 7-[3-(methoxymethyl)azetidin-1-yl]-N-(6-methoxy-2-methyl-1,2,3,4-tetrahydroisoquinolin-7-yl)quinazolin-2-amine | Calc'd 420, found 420; 3E |
| 3-69 | 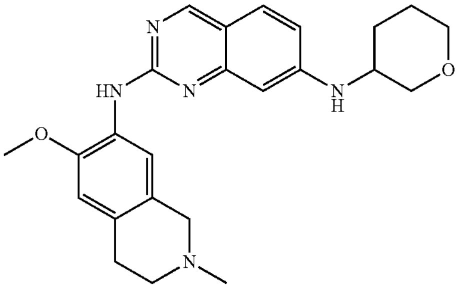 [SMILES: COc1cc2c(cc1Nc1ncc3ccc(NC4CCCOC4)cc3n1)CN(C)CC2] | (S and R)-N-2~-(6-methoxy-2-methyl-1,2,3,4-tetrahydroisoquinolin-7-yl)-N~7~-(oxan-3-yl)quinazoline-2,7-diamine | Calc'd 420, found 420; 3E |
| 3-70 | 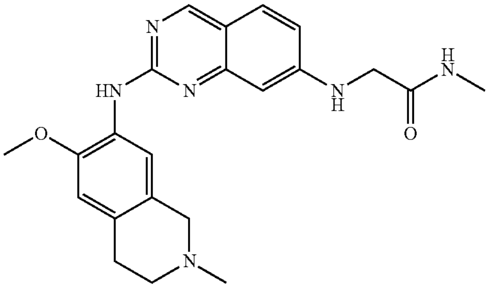 | N~2~-{2-[(6-methoxy-2-methyl-1,2,3,4-tetrahydroisoquinolin-7-yl)amino]quinazolin-7-yl}-N-methylglycinamide | Calc'd 407, found 407; 3E |
| 3-71 | 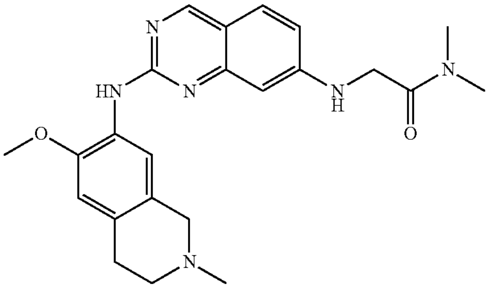 | N~2~-{2-[(6-methoxy-2-methyl-1,2,3,4-tetrahydroisoquinolin-7-yl)amino]quinazolin-7-yl}-N,N-dimethylglycinamide | Calc'd 421, found 421; 3E |

TABLE 3-continued

| Example Number | Structure | Name | Exact Mass [M + H]+; Method |
|---|---|---|---|
| 3-72 | 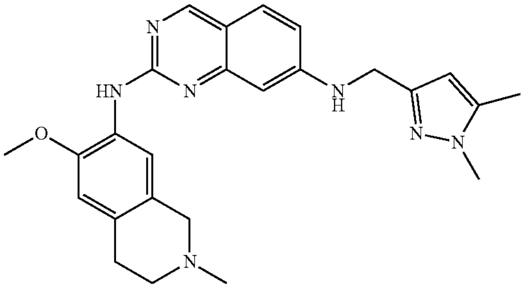 | N~7~-[(1,5-dimethyl-1H-pyrazol-3-yl)methyl]-N~2~-(6-methoxy-2-methyl-1,2,3,4-tetrahydroisoquinolin-7-yl)quinazoline-2,7-diamine | Calc'd 444, found 444; 3E |
| 3-73 | 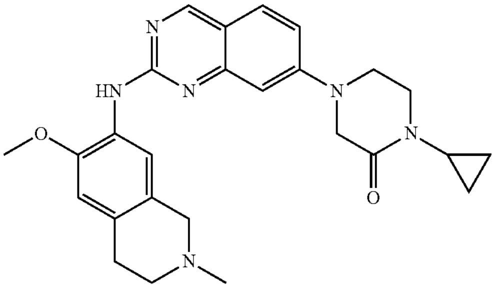 [SMILES: COc1cc2c(cc1Nc1ncc3ccc(N4CCN(C5CC5)C(=O)C4)cc3n1)CN(C)CC2] | 1-cyclopropyl-4-{2-[(6-methoxy-2-methyl-1,2,3,4-tetrahydroisoquinolin-7-yl)amino]quinazolin-7-yl}piperazin-2-one | Calc'd 459, found 459; 3E |
| 3-74 | 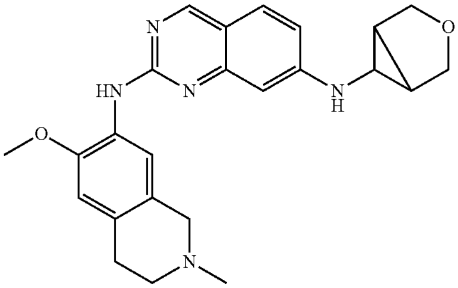 [SMILES: COc1cc2c(cc1Nc1ncc3ccc(NC4C5COCC54)cc3n1)CN(C)CC2] | N~2~-(6-methoxy-2-methyl-1,2,3,4-tetrahydroisoquinolin-7-yl)-N~7~-(3-oxabicyclo[3.1.0]-hexan-6-yl)quinazoline-2,7-diamine | Calc'd 418, found 418; 3E |
| 3-75 | 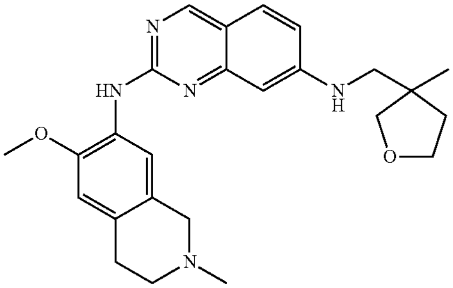 | (S and R)-N~2~-(6-methoxy-2-methyl-1,2,3,4-tetrahydroisoquinolin-7-yl)-N~7~-[(3-methyloxolan-3-yl)methyl]quinazoline-2,7-diamine | Calc'd 434, found 434; 3E |
| 3-76 | 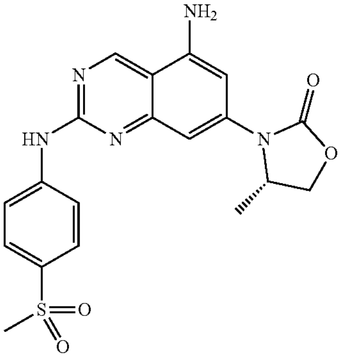 [SMILES: C[C@H]1COC(=O)N1c1cc(N)c2cnc(Nc3ccc(S(C)(=O)=O)cc3)nc2c1] | (S)-3-(5-amino-2-((4-(methylsulfonyl)phenyl)amino)quinazolin-7-yl)-4-methyloxazolidin-2-one | Calc'd 414, found 414; 3D |

TABLE 3-continued

| Example Number | Structure | Name | Exact Mass $[M + H]^+$; Method |
| --- | --- | --- | --- |
| 3-77 | 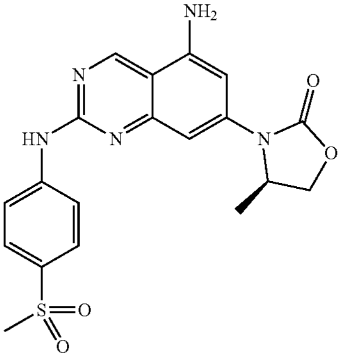 [SMILES: C[C@@H]1COC(=O)N1c1cc(N)c2cnc(Nc3ccc(S(C)(=O)=O)cc3)nc2c1] | (R)-3-(5-amino-2-((4-(methylsulfonyl)phenyl)amino)quinazolin-7-yl)-4-methyloxazolidin-2-one | Calc'd 414, found 414; 3D |
| 3-78 | 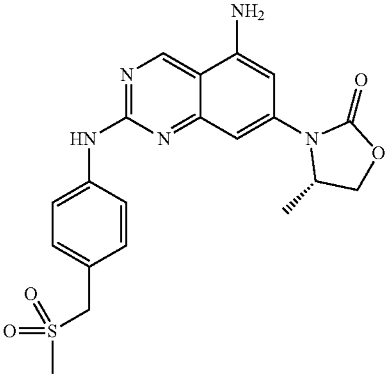 [SMILES: C[C@H]1COC(=O)N1c1cc(N)c2cnc(Nc3ccc(CS(C)(=O)=O)cc3)nc2c1] | (S)-3-(5-amino-2-((4-((methylsulfonyl)methyl)phenyl)amino)-quinazolin-7-yl)-4-methyloxazolidin-2-one | Calc'd 428, found 428; 3D |
| 3-79 | 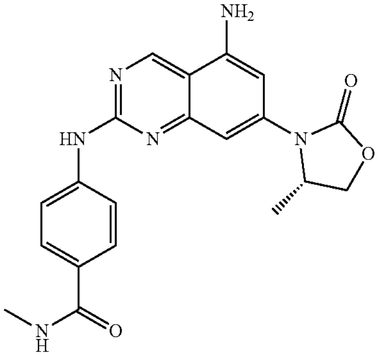 [SMILES: CNC(=O)c1ccc(Nc2ncc3c(N)cc(N4C(=O)OC[C@@H]4C)cc3n2)cc1] | 4-({5-amino-7-[(4S)-4-methyl-2-oxo-1,3-oxazolidin-3-yl-[quinazolin-2-yl}amino)-N-methylbenzamide | Calc'd 393, found 393; 3D |
| 3-80 | 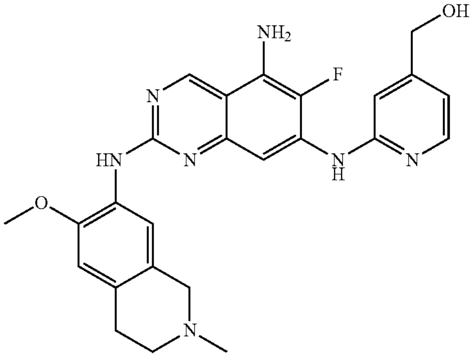 [SMILES: COc1cc2c(cc1Nc1ncc3c(N)c(F)c(Nc4cc(CO)ccn4)cc3n1)CN(C)CC2] | [2-({5-amino-6-fluoro-2-[(6-methoxy-2-methyl-1,2,3,4-tetrahydroisoquinolin-7-yl)amino]-quinazolin-7-yl}amino)pyridin-4-yl]methanol | Calc'd 476, found 476; 3E |

Compound Examples of Table 4

Example 4A. Preparation of 4-2

I-14

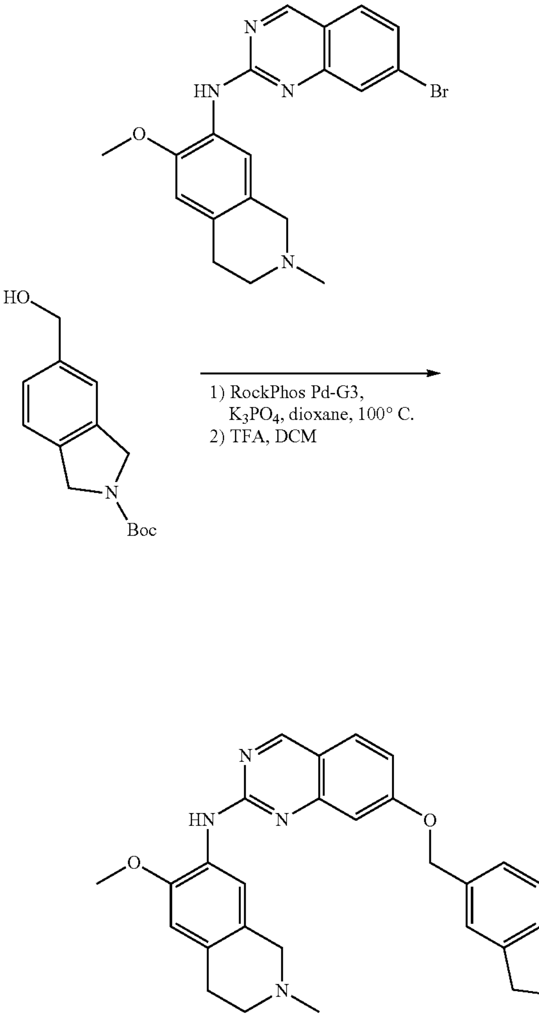

4-2

A solution of 7-bromo-N-(6-methoxy-2-methyl-1,2,3,4-tetrahydroisoquinolin-7-yl)quinazolin-2-amine (5.0 mg, 0.013 mmol), tert-butyl 5-(hydroxymethyl)isoindoline-2-carboxylate (4.4 mg, 0.019 mmol), $K_3PO_4$ (8 mg, 0.04 mmol) in 1,4-dioxane (1.3 mL) was treated with RockPhos-Pd-G3 (5 mg) and stirred overnight at 100° C. The reaction mixture was diluted with DCM and washed with brine. The organic layer was then concentrated, taken-up in DCM/TFA and concentrated, then finally purified by reverse phase chromatography to provide the desired product, 4-2. $^1$H NMR (500 MHz, DMSO-$d_6$) δ 9.11 (s, 1H), 8.55 (m, 1H), 8.30 (s, 1H), 8.27 (br, 1H), 8.20 (s, 1H), 7.85 (d, J=8 Hz, 1H), 7.06 (s, 1H), 7.02 (d, J=8 Hz, 1H), 6.96 (s, 1H), 4.49 (m, 1H), 4.20 (m, 1H), 4.04 (m, 1H), 3.87 (s, 3H), 3.35 (m, 2H), 3.10 (m, 1H), 3.05 (s, 3H), 2.93 (m, 1H), 2.13 (m, 1H), 1.96 (m, 2H), 1.54 (m, 2H). MS calc'd for $C_{28}H_{30}N_5O_2$ $[M+H]^+$, 468; found, 468.

Example 4B. Preparation of 4-9

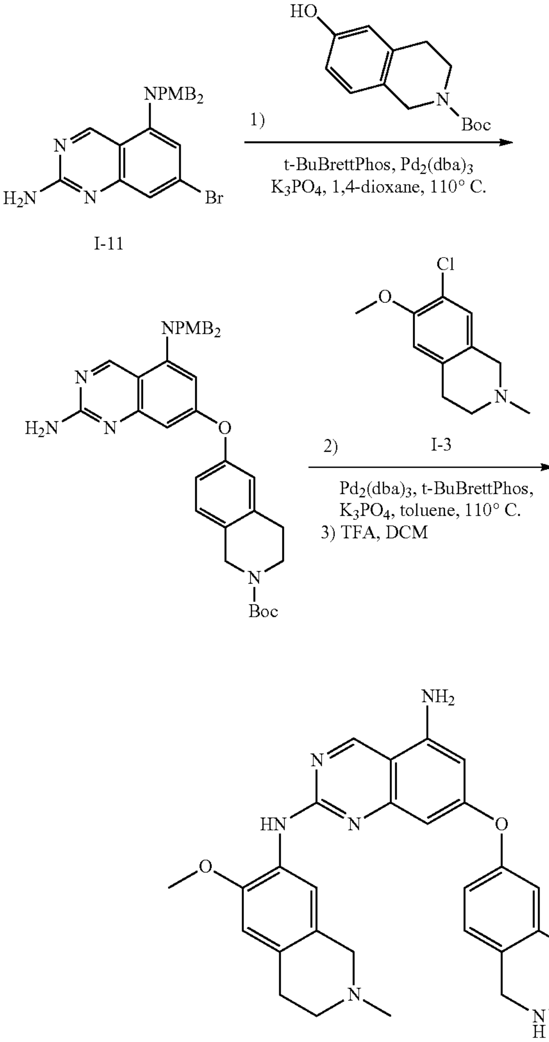

4-9

Step 1. Synthesis of tert-Butyl 6-((2-Amino-5-(bis(4-methoxybenzyl)amino)quinazolin-7-yl)oxy)-3,4-dihydroisoquinoline-2(1H)-carboxylate A solution of intermediate I-11 (100 mg, 0.209 mmol), tert-butyl 6-hydroxy-3,4-dihydroisoquinoline-2(1H)-carboxylate (78 mg, 0.31 mmol), t-BuBrettPhos (20 mg, 0.042 mmol), $Pd_2(dba)_3$ (19 mg, 0.021 mmol), and $K_3PO_4$ (133 mg, 0.626 mmol) in 1,4-dioxane (2.1 mL) and deoxygenated by bubbling argon gas through the reaction mixture for 3 min. The mixture was stirred overnight at 110° C. After cooling, the reaction was filtered and concentrated to dryness. Chromatography on $SiO_2$ (0-5% MeOH/DCM, 12 g silica gel). The fractions containing the desired product mass were pooled and concentrated to dryness to afford tert-butyl 6-((2-amino-5-(bis(4-methoxybenzyl)amino)quinazolin-7-yl)oxy)-3,4-dihydroisoquinoline-2(1H)-carboxylate. MS (EI) calc'd for $C_{31}H_{42}N_5O_5$ $[M+H]^+$, 648; found, 648.

Steps 2-3. Synthesis of 4-9 (N2-(6-Methoxy-2-methyl-1,2,3,4-tetrahydroisoquinolin-7-yl)-7-((1,2,3,4-tetrahydroisoquinolin-6-yl)oxy)quinazoline-2,5-diamine)

A solution of intermediate I-3 (24 mg, 0.12 mmol), tert-butyl 6-((2-amino-5-(bis(4-methoxybenzyl)amino)quinazolin-7-yl)oxy)-3,4-dihydroisoquinoline-2(1H)-carboxylate (50 mg, 0.077 mmol), t-BuBrettPhos (15 mg, 0.031 mmol), $Pd_2(dba)_3$ (7 mg, 0.008 mmol), and $K_3PO_4$ (33 mg, 0.15 mmol) in toluene (0.8 mL) was deoxygenated by bubbling argon gas through the reaction mixture for 3 min. The mixture was stirred overnight at 110° C. After cooling to rt, the reaction was filtered and concentrated to dryness. The intermediate was then taken up in 2 mL of DCM, treated with 2 mL of TFA and the solution allowed to age for 30 min. The mixture is then concentrated to dryness. The residue was purified by reverse phase chromatography (gradient of 15-75% ACN/water with 0.1% $NH_4OH$) to provide 4-9 as a solid. $^1H$ NMR (500 MHz, DMSO-$d_6$) δ 9.25 (s, 1H), 8.03 (s, 1H), 7.85 (s, 1H), 7.08 (d, J=8.1 Hz, 1H), 6.88 (d, J=8.1 Hz, 1H), 6.84 (s, 1H), 6.76 (s, 1H), 6.45 (s, 2H), 6.13 (s, 1H), 6.05 (s, 1H), 3.85 (s, 2H), 3.82 (s, 3H), 3.42 (s, 2H), 2.94 (d, J=5.3 Hz, 2H), 2.78 (s, 2H), 2.69 (s, 2H), 2.57 (t, J=5.3 Hz, 2H), 2.33 (s, 3H). MS (EI) calc'd for $C_{28}H_{31}N_6O_2$ $[M+H]^+$, 483; found, 483.

Compounds listed in the table below were prepared using the synthetic methods described in the aforementioned examples. The table provides the compound structure, the name, the calculated and observed masses, and the example method used for preparation.

TABLE 4

| Example Number | Structure | Name | Exact Mass $[M + H]^+$; Method |
|---|---|---|---|
| 4-1 | 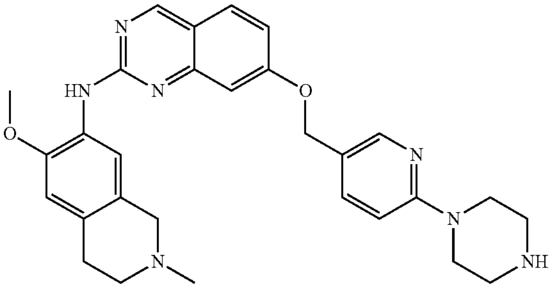 [SMILES: COc1cc2c(cc1Nc1ncc3ccc(OCc4ccc(N5CCNCC5)nc4)cc3n1)CN(C)CC2] | N-(6-methoxy-2-methyl-1,2,3,4-tetrahydroisoquinolin-7-yl)-7-{[6-(piperazin-1-yl)pyridin-3-yl]methoxy}-quinazolin-2-amine | Calc'd 512, found 512; 4A |
| 4-2 | 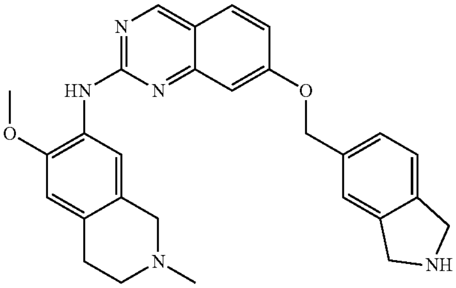 [SMILES: COc1cc2c(cc1Nc1ncc3ccc(OCc4ccc5c(c4)CNC5)cc3n1)CN(C)CC2] | 7-[(2,3-dihydro-1H-isoindol-5-yl)methoxy]-N-(6-methoxy-2-methyl-1,2,3,4-tetrahydroisoquinolin-7-yl)-quinazolin-2-amine | Calc'd 468, found 468; 4A |
| 4-3 | 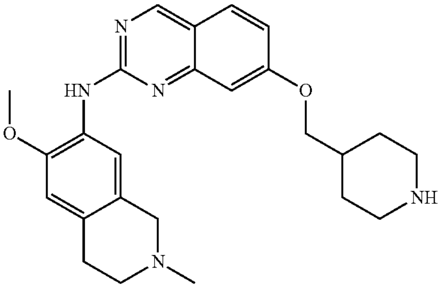 [SMILES: COc1cc2c(cc1Nc1ncc3ccc(OCC4CCNCC4)cc3n1)CN(C)CC2] | N-(6-methoxy-2-methyl-1,2,3,4-tetrahydroisoquinolin-7-yl)-7-[(piperidin-4-yl)methoxy]quinazolin-2-amine | Calc'd 434, found 434; 4A |

TABLE 4-continued

| Example Number | Structure | Name | Exact Mass $[M + H]^+$; Method |
|---|---|---|---|
| 4-4 | 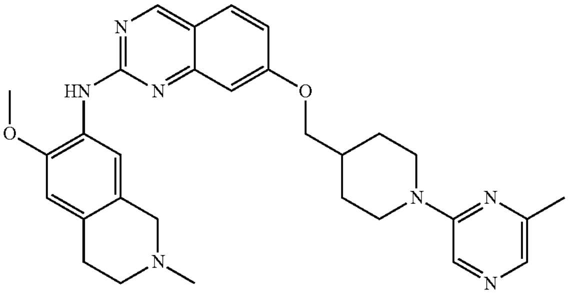 [SMILES: COc1cc2c(cc1Nc1ncc3ccc(OCC4CCN(c5cncc(C)n5)CC4)cc3n1)CN(C)CC2] | N-(6-methoxy-2-methyl-1,2,3,4-tetrahydroisoquinolin-7-yl)-7-{[1-(6-methylpyrazin-2-yl)piperidin-4-yl]methoxy}quinazolin-2-amine | Calc'd 526, found 526; 4A |
| 4-5 | 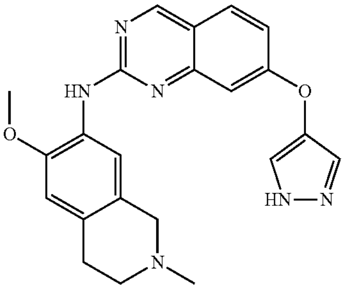 [SMILES: COc1cc2c(cc1Nc1ncc3ccc(Oc4cn[nH]c4)cc3n1)CN(C)CC2] | N-(6-methoxy-2-methyl-1,2,3,4-tetrahydroisoquinolin-7-yl)-7-[(1H-pyrazol-4-yl)oxy]quinazolin-2-amine | Calc'd 403, found 403; 4A |
| 4-6 | 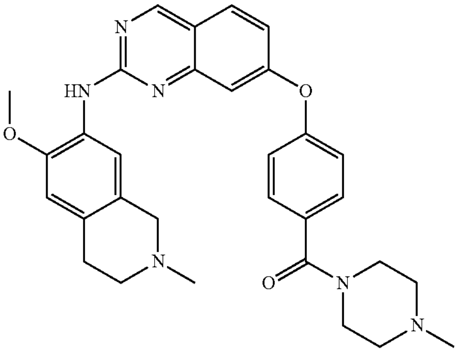 [SMILES: COc1cc2c(cc1Nc1ncc3ccc(Oc4ccc(C(=O)N5CCN(C)CC5)cc4)cc3n1)CN(C)CC2] | [4-({2-[(6-methoxy-2-methyl-1,2,3,4-tetrahydroisoquinolin-7-yl)amino]-quinazolin-7-yl}oxy)phenyl](4-methylpiperazin-1-yl)methanone | Calc'd 539, found 539; 4A |
| 4-7 | 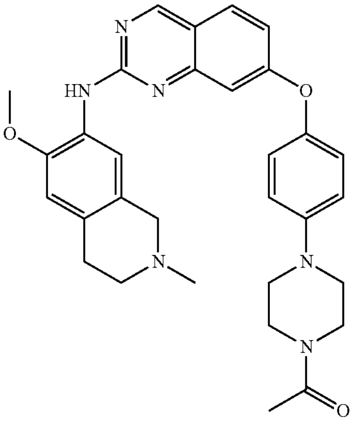 [SMILES: COc1cc2c(cc1Nc1ncc3ccc(Oc4ccc(N5CCN(C(C)=O)CC5)cc4)cc3n1)CN(C)CC2] | 1-{4-[4-({2-[(6-methoxy-2-methyl-1,2,3,4-tetrahydroisoquinolin-7-yl)amino]-quinazolin-7-yl}oxy)phenyl]piperazin-1-yl}ethan-1-one | Calc'd 539, found 539; 4A |

TABLE 4-continued

| Example Number | Structure | Name | Exact Mass [M + H]$^+$; Method |
| --- | --- | --- | --- |
| 4-8 | 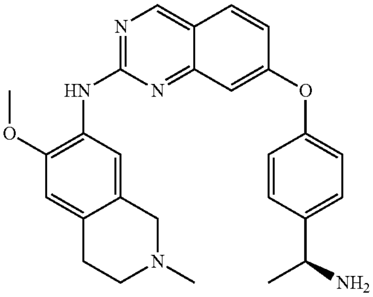 [SMILES: COc1cc2c(cc1Nc1ncc3ccc(Oc4ccc([C@H](C)N)cc4)cc3n1)CN(C)CC2] | 7-{4-[(1S)-1-aminoethyl]-phenoxy}-N-(6-methoxy-2-methyl-1,2,3,4-tetrahydro-isoquinolin-7-yl)quinazolin-2-amine | Calc'd 456, found 456; 4A |
| 4-9 | 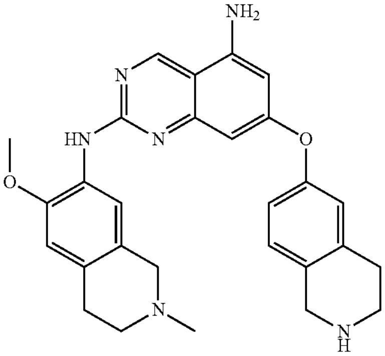 [SMILES: COc1cc2c(cc1Nc1ncc3c(N)cc(Oc4ccc5c(c4)CCNC5)cc3n1)CN(C)CC2] | N~2~-(6-methoxy-2-methyl-1,2,3,4-tetrahydroisoquinolin-7-yl)-7-[(1,2,3,4-tetrahydroisoquinolin-6-yl)-oxy]quinazoline-2,5-diamine | Calc'd 483, found 483; 4B |

Compound Examples of Table 5

Example 5A. Preparation of 5-1

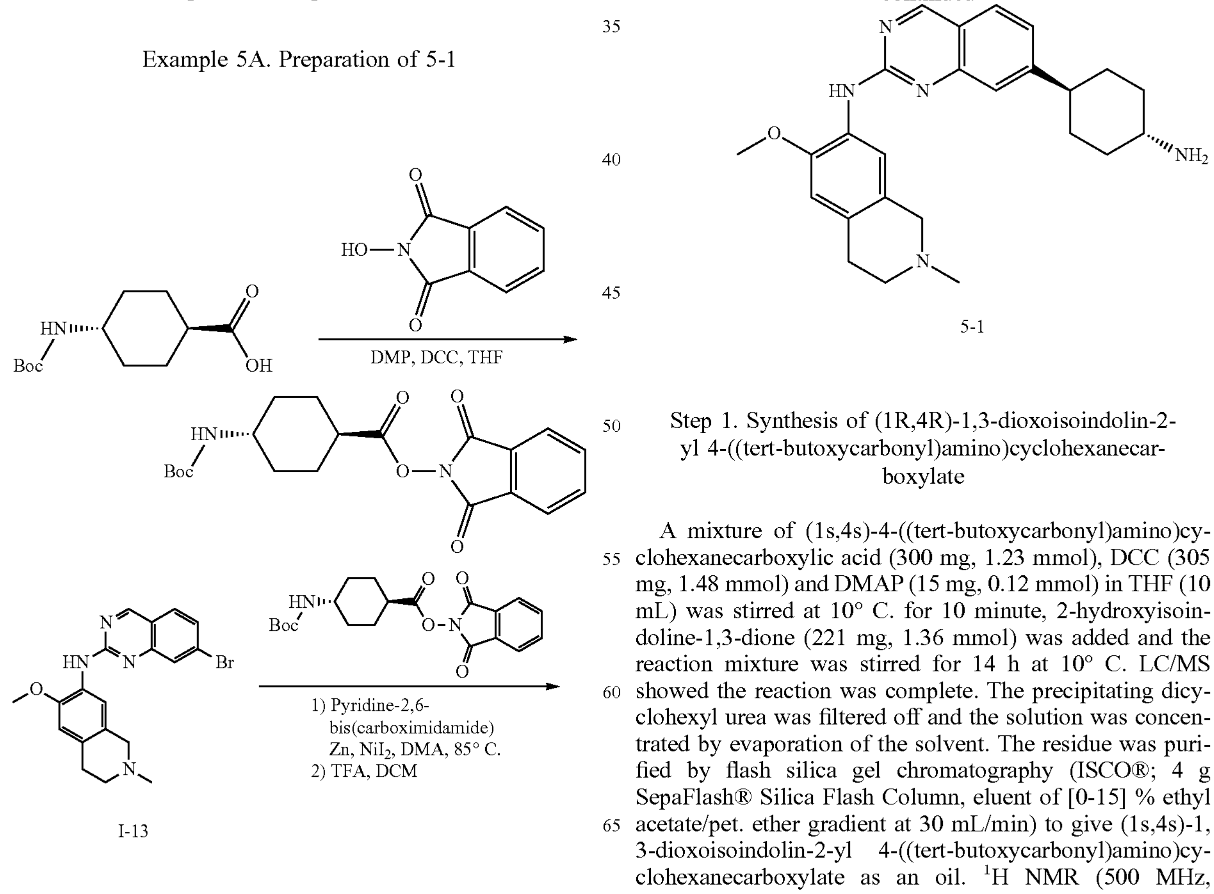

I-13

-continued 5-1

Step 1. Synthesis of (1R,4R)-1,3-dioxoisoindolin-2-yl 4-((tert-butoxycarbonyl)amino)cyclohexanecarboxylate A mixture of (1s,4s)-4-((tert-butoxycarbonyl)amino)cyclohexanecarboxylic acid (300 mg, 1.23 mmol), DCC (305 mg, 1.48 mmol) and DMAP (15 mg, 0.12 mmol) in THF (10 mL) was stirred at 10° C. for 10 minute, 2-hydroxyisoindoline-1,3-dione (221 mg, 1.36 mmol) was added and the reaction mixture was stirred for 14 h at 10° C. LC/MS showed the reaction was complete. The precipitating dicyclohexyl urea was filtered off and the solution was concentrated by evaporation of the solvent. The residue was purified by flash silica gel chromatography (ISCO®; 4 g SepaFlash® Silica Flash Column, eluent of [0-15] % ethyl acetate/pet. ether gradient at 30 mL/min) to give (1s,4s)-1,3-dioxoisoindolin-2-yl 4-((tert-butoxycarbonyl)amino)cyclohexanecarboxylate as an oil. $^1H$ NMR (500 MHz, DMSO-$d_6$) δ 7.90 (dd, J=3.0, 5.0 Hz, 2H), 7.81 (dd, J=3.0, 5.0 Hz, 2H), 4.56 (br d, J=3.5 Hz, 1H), 3.65 (br d, J=3.6 Hz, 1H), 2.95 (br s, 1H), 2.14 (br d, J=5.0 Hz, 2H), 1.85 (br d, J=11.0 Hz, 4H), 1.60-1.69 (m, 2H), 1.45 (s, 9H). MS (EI) calc'd for $C_{20}H_{25}N_2O_6$ $[M+H]^+$, 389; found, 389.

Steps 2-3. Synthesis of 7-((1r,4r)-4-aminocyclohexyl)-N-(6-methoxy-2-methyl-1,2,3,4-tetrahydroisoquinolin-7-yl)quinazolin-2-amine A mixture of zinc (66 mg, 1.0 mmol) and isophthalimidamide (16 mg, 0.10 mmol) in DMA (1 mL) was degassed and backfilled with nitrogen (three times) and the mixture was stirred at room temperature for 10 min. Then a mixture of zinc iodide (16 mg, 0.050 mmol), (1r,4r)-1,3-dioxoisoindolin-2-yl 4-((tert-butoxycarbonyl)amino)cyclohexanecarboxylate (97 mg, 0.25 mmol) and intermediate I-13 (100 mg, 0.250 mmol) in DMA (1.5 mL) was added to the mixture under nitrogen. The mixture was heated to 85° C. for 14 h to give black mixture. After cooling to RT. LC/MS showed that the target was formed. The mixture was filtered and the filtrate was purified by Pre-HPLC (Column YMC-Actus Triart C18 150*30 mm*5 um Condition water (0.1% TFA)-ACN Begin B 30 End B 60 Gradient Time (min) 11 100% B Hold Time (min) 1.1 FlowRate (mL/min) 40) to give tert-butyl ((1r,4r)-4-(2-((6-methoxy-2-methyl-1,2,3,4-tetrahydroisoquinolin-7-yl)amino)quinazolin-7-yl)cyclohexyl) carbamate as a solid. The solid was dissolved in DCM (2 mL) and TFA (2 mL) was stirred at 12° C. for 2 h. LC/MS showed that the starting material was used up and the mixture was concentrated under reduced pressure. The residue was purified by Pre-HPLC (Column YMC-Actus Triart C18 150*30 mm*5 um Condition water (0.1% TFA)-ACN Begin B 0 End B 30 Gradient Time (min) 11 100% B Hold Time (min) 1.1 FlowRate (mL/min) 40) to give 7-((1r,4r)-4-aminocyclohexyl)-N-(6-methoxy-2-methyl-1,2,3,4-tetrahydroisoquinolin-7-yl)quinazolin-2-amine as solid. $^1$H NMR (500 MHz, $CD_3OD$) δ 9.17 (s, 1H), 8.56 (s, 1H), 7.85 (d, J=8.4 Hz, 1H), 7.58 (s, 1H), 7.38 (dd, J=1.6, 8.4 Hz, 1H), 6.95 (s, 1H), 4.52-4.66 (m, 1H), 4.28-4.42 (m, 1H), 3.97 (s, 3H), 3.78 (br d, J=4.4 Hz, 1H), 3.43 (br s, 1H), 3.20-3.28 (m, 2H), 3.09 (s, 3H), 2.74-2.85 (m, 1H), 2.21 (br d, J=9.6 Hz, 2H), 2.11 (br d, J=12.4 Hz, 2H), 1.91-2.05 (m, 1H), 1.70-1.84 (m, 2H), 1.56-1.69 (m, 2H). MS (EI) calc'd for $C_{25}H_{32}NO_5O$ $[M+H]^+$, 418; found, 418.

Compounds listed in the table below were prepared using the synthetic methods described in the aforementioned examples. The table provides the compound structure, the name, the calculated and observed masses, and the example method used for preparation.

TABLE 5

| Example Number | Structure | Name | Exact Mass $[M + H]^+$; Method |
|---|---|---|---|
| 5-1 | 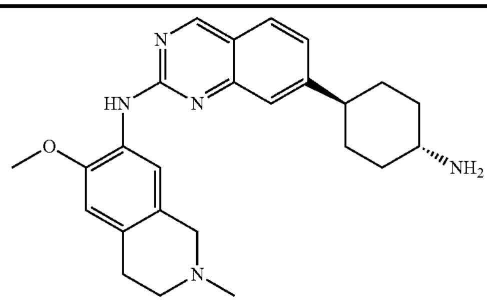 | 7-((1r,4r)-4-aminocyclohexyl)-N-(6-methoxy-2-methyl-1,2,3,4-tetrahydroisoquinolin-7-yl)quinazolin-2-amine | Calc'd 418, found 418; 7A |
| 5-2 | 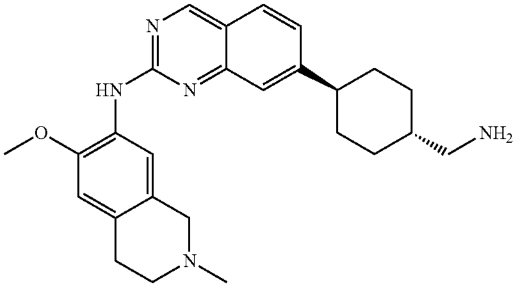 [SMILES: COc1cc2c(cc1Nc1ncc3ccc([C@H]4CC[C@H](CN)CC4)cc3n1)CN(C)CC2] | 7-((1r,4r)-4-(aminomethyl)-cyclohexyl)-N-(6-methoxy-2-methyl-1,2,3,4-tetrahydroisoquinolin-7-yl)quinazolin-2-amine | Calc'd 432, found 432; 7A |

HPK1-SLP76 TR-FRET Assay

Assay Principle:

HPK1-Catalytic domain enzyme is preincubated for 30 minutes with varying concentrations of investigational test compounds, or DMSO reference. HPK1 activity is initiated by the addition of ATP and results in phosphorylation of a His-tagged SLP-76 protein substrate. Following a 60-minute reaction time, the reaction is quenched and FRET partners Eu-anti-His Ab and phospho-SLP-76 (Ser376) (D7S1K) XP Rabbit mAb (AF 647 Conjugate) are added to detect the phosphorylated His-tagged SLP-76 product.

Instrumentation:

Labcyte Echo
Beckman Coulter BioRaptr
Perkin Elmer Envision

Final Assay Conditions:

HPK1-Kinase Domain: 0.075 nM
Full length SLP-76: 10 nM
ATP: 10 μM
Eu-anti-His Tag: 0.75 nM
pSLP76(Ser376)-AF647: 0.75 nM Preincubation Time: 30 minutes Kinase Reaction Time: 60 minutes Temperature: Ambient Room Temperature Reaction Volume: 7.5 μL Total Volume: 10.0 μL Materials:

Assay Plate: Black Corning NBS 384-well microplate #3820

Kinase: Human HPK1, catalytic domain [1-346 amino acids of accession number NP_009112.1]

Substrate: Full Length SLP76, C-Terminal 8× His-tag

ATP: 100 mM

BSA: 10%

Reaction Buffer: 50 mM HEPES (pH 7.5), 10 mM $MgCl_2$, 1 mM EGTA, 0.01% Brij-35, 0.05% BSA and 0.5 mM TCEP.

Detection Solution: Reaction Buffer with LANCE Eu-W1024 Anti-6×His Ab, Phospho-SLP-76 (Ser376) (D7S1K) XP Rabbit mAb (AF 647 Conjugate) (Cell Signaling Technologies) and 10 mM EDTA.

General Assay Procedure:

To each well of black Corning #3820 384-well plate, an ECHO was used to dispense 7.5 nL of DMSO or Test compound in DMSO. A 1.5× kinase solution, 5 μL/well, was added and preincubated for 30 minutes before 2.5 μL/well of 3× substrate solution was added. The reaction solution incubated for 60 minutes and quenched with 2.5 μL of 4× detection solution. The solutions were incubated for an additional 60 minutes prior to reading on a Perkin Elmer Envision. The TR-FRET signal was measured at both 615 and 665 nm. The calculated emission ratio of 665/615 was used to determine the percent effect for each compound concentration.

Detailed HPK1 Assay Protocol:

Compounds are serially diluted (3-fold in 100% DMSO) across a 384-well polypropylene source plated from column 3 to column 12 and column 13 to column 22, to yield 10 concentration dose responses for each test compound. Columns 1, 2, 23 and 24 contain either only DMSO or a pharmacological known control inhibitor. Once titrations are made, 7.5 nL of the compounds on 384 well plates are transferred by acoustic dispersion into a 384-well assay plate (Corning 3820) to assay the HPK1 enzyme.

The HPK1 kinase biochemical assay was developed using commercially available HTRF reagents. The assay contains the following reagents: 1) Assay Buffer: 50 mM HEPES (pH 7.5), 10 mM $MgCl_2$, 1 mM EGTA, 0.01% Brij-35, 0.05% BSA and 0.5 mM TCEP; 2) Enzyme Solution: HPK1 (Carna); 3) Substrate Solution: ATP and Full Length SLP76 with His-Tag; 4) Stop and Detection Solution: EDTA, LANCE Eu-W1024 Anti-6×His Ab (Perkin Elmer) and Phospho-SLP-76 (Ser376) (D7S1K) XP Rabbit mAb (AF 647 Conjugate) (Cell Signaling Technologies).

Enzyme, Substrate and Stop/Detection solutions are prepared in assay buffer. Enzyme solution (75 pM HPK1 Final), 5 μL/well, is added to 384-well assay plate and incubated with 7.5 nL of compound or DMSO for 30 minutes. Kinase reaction is initiated with addition of 2.5 μL of substrate solution (ATP 10 uM and SLP76 10 nM Final) and allowed to proceed for 60 minutes.

Enzyme addition and compound pre-incubation are initiated by the addition of 5 μL of HPK1 enzyme solution (at one and a half times its final concentration of 75 pM) to all wells using a BioRaptr. Plates are incubated at room temperature for 30 minutes. Reactions are initiated by addition of 2.5 μL of 3× substrate solution (10 nM SLP76 and 10 uM ATP FInal) using BioRaptr. Plates are incubated at room temperature for one hour. Reactions are quenched, and activity detected by addition of 2.5 μL of 4× stop and detection solution (10 mM EDTA, 0.75 nM LANCE Eu-W1024 Anti-6×His Ab and 0.75 nM Phospho-SLP-76 (Ser376) (D7S1K) XP Rabbit mAb (AF 647 Conjugate) Final) to all wells using the BioRaptr. Following a one-hour incubation, the HTRF signal is measured on the Envision plate reader set for 320 nm excitation and dual emission detection at 615 nM (Eu) and 665 nM (AF647).

Data Analysis:

The loss of the HTRF signal is due to the inhibition of HPK1 activity and decreased phosphorylation of SLP76 substrate. All data were calculated using the ratio of acceptor (AF647) to donor (Europium) fluorescence in each well of the assay plate. The percent effect for each compound concentration was calculated as follows: % Effect=100×(Emission ratio−Minimum Effect Control)/(Maximum Effect Control−Minimum Effect Control) where Minimum Effect Control=HPK1+DMSO and Maximum Effect Control=HPK1 Kinase reaction+known reference inhibitor. An $EC_{50}$ was then calculated fitting the % effect data. Dose response data were analyzed using the 4 parameter logistic nonlinear regression model: Y=Bottom+(Top−Bottom)/(1+10^((Log($EC_{50}$)−X)*Hill Slope)). Where: Y=% E (percent effect) described above: X=base 10 logarithm of molar drug concentration: Bottom=lower limit of dose response (minimum % E); Top=upper limit of dose response (maximum % E); $EC_{50}$=concentration at which 50%, effect is achieved: Hill Slope=Hill slope coefficient; slope of curve at $EC_{50}$.

HPK1-SLP76 TR-FRET Assay Data

The following table tabulates the biological data disclosed for the current invention. The biological data was collected using the methodology described above. For each compound. HPK1 $IC_{50}$ values are listed in nanomolar (nM) concentration units.

| Example | $IC_{50}$ (nM) |
|---|---|
| 1-1 | 140.2 |
| 1-2 | 26.24 |
| 1-3 | 1.525 |
| 1-4 | 1.513 |
| 1-5 | 230.3 |
| 1-6 | 92.24 |
| 1-7 | 244.8 |
| 1-8 | 402.7 |
| 1-9 | 42.94 |
| 1-10 | 27.03 |
| 1-11 | 179 |
| 1-12 | 340.7 |
| 1-13 | 7.701 |
| 1-14 | 55.32 |
| 1-15 | 42.66 |
| 1-16 | 153.7 |
| 1-17 | 19.1 |
| 1-18 | 82.19 |
| 1-19 | 2.573 |
| 1-20 | 4.611 |
| 1-21 | 294.2 |
| 1-22 | 735.3 |
| 1-23 | 693.3 |
| 1-24 | 10.46 |
| 1-25 | 19.98 |
| 1-26 | 10.8 |
| 1-27 | 9.91 |
| 1-28 | 197.6 |
| 1-29 | 85.82 |
| 1-30 | 45.53 |
| 1-31 | 204.2 |

-continued

| Example | $IC_{50}$ (nM) |
|---|---|
| 1-32 | 107.7 |
| 1-33 | 136.4 |
| 1-34 | 1.488 |
| 1-35 | 0.6891 |
| 1-36 | 182.5 |
| 1-37 | 27.92 |
| 1-38 | 17.89 |
| 1-39 | 34.79 |
| 1-40 | 8.936 |
| 1-41 | 9.67 |
| 1-42 | 38.55 |
| 1-43 | 82.81 |
| 1-44 | 9.452 |
| 1-45 | 0.8848 |
| 1-46 | 59.37 |
| 1-47 | 272.8 |
| 1-48 | 387.2 |
| 1-49 | 3.25 |
| 1-50 | 5.896 |
| 1-51 | 48 |
| 1-52 | 11.02 |
| 1-53 | 5.601 |
| 1-54 | 18.95 |
| 1-55 | 52.8 |
| 1-56 | 203.6 |
| 1-57 | 79.17 |
| 1-58 | 76.17 |
| 1-59 | 36.21 |
| 1-60 | 20.46 |
| 1-61 | 13.9 |
| 1-62 | 113.7 |
| 1-63 | 45.71 |
| 1-64 | 81.98 |
| 1-65 | 120.4 |
| 1-66 | 130.5 |
| 1-67 | 33.85 |
| 1-68 | 161.1 |
| 1-69 | 215.2 |
| 1-70 | 140.5 |
| 1-71 | 138 |
| 1-72 | 53.44 |
| 1-73 | 88.48 |
| 1-74 | 142.9 |
| 1-75 | 91.63 |
| 1-76 | 218.1 |
| 1-77 | 24.67 |
| 1-78 | 353.1 |
| 1-79 | 147.7 |
| 1-80 | 23.94 |
| 1-81 | 191.7 |
| 1-82 | 15.23 |
| 1-83 | 222.5 |
| 1-84 | 53.69 |
| 1-85 | 461.8 |
| 1-86 | 44.07 |
| 1-87 | 49.21 |
| 1-88 | 96.87 |
| 1-89 | 155.8 |
| 1-90 | 392.6 |
| 1-91 | 209.8 |
| 1-92 | 92.42 |
| 1-93 | 480.6 |
| 1-94 | 81.3 |
| 1-95 | 2.322 |
| 1-96 | 1.854 |
| 1-97 | 53.77 |
| 1-98 | 203 |
| 1-99 | 119.5 |
| 1-100 | 280.8 |
| 1-101 | 130.3 |
| 1-102 | 22.24 |
| 1-103 | 327.6 |
| 1-104 | 211.6 |
| 1-105 | 195.9 |
| 1-106 | 44.08 |
| 1-107 | 488.1 |
| 1-108 | 56.01 |

-continued

| Example | $IC_{50}$ (nM) |
|---|---|
| 1-109 | 0.8117 |
| 1-110 | 301.7 |
| 1-111 | 0.7656 |
| 1-112 | 5.199 |
| 1-113 | 0.0625 |
| 1-114 | 0.0883 |
| 1-115 | 0.0508 |
| 1-116 | 0.2213 |
| 1-117 | 0.07048 |
| 1-118 | 0.0363 |
| 1-119 | 1.173 |
| 1-120 | 0.5954 |
| 1-121 | 0.2558 |
| 1-122 | 0.5321 |
| 1-123 | 0.02326 |
| 1-124 | 0.04107 |
| 1-125 | 0.06062 |
| 1-126 | 0.6799 |
| 1-127 | 0.9489 |
| 1-128 | 0.08277 |
| 1-129 | 0.09175 |
| 1-130 | 0.07262 |
| 1-131 | 0.1649 |
| 1-132 | 0.1319 |
| 1-133 | 0.0835 |
| 1-134 | 0.0425 |
| 1-135 | 0.4816 |
| 2-1 | 0.2486 |
| 2-2 | 0.09155 |
| 2-3 | 322.6 |
| 2-4 | 0.9793 |
| 2-5 | 270.5 |
| 2-6 | 48.06 |
| 2-7 | 0.1119 |
| 2-8 | 115.5 |
| 2-9 | 0.1291 |
| 2-10 | 0.1247 |
| 2-11 | 0.08208 |
| 2-12 | 685.3 |
| 2-13 | 0.04961 |
| 2-14 | 0.082 |
| 2-15 | 0.07314 |
| 2-16 | 0.09318 |
| 2-17 | 0.08505 |
| 2-18 | 0.3816 |
| 2-19 | 1.339 |
| 2-20 | 76.08 |
| 2-21 | 486.7 |
| 2-22 | 0.6868 |
| 2-23 | 0.0508 |
| 2-24 | 0.0508 |
| 2-25 | 0.2748 |
| 2-26 | 11.49 |
| 2-27 | 0.1174 |
| 2-28 | 0.1492 |
| 2-29 | 0.2726 |
| 2-30 | 0.0811 |
| 2-31 | 4.619 |
| 2-32 | 0.6691 |
| 2-33 | 0.1861 |
| 2-34 | 0.1179 |
| 2-35 | 0.1525 |
| 2-36 | 0.1007 |
| 2-37 | 0.372 |
| 2-38 | 35.14 |
| 2-39 | 0.9424 |
| 2-40 | 0.6334 |
| 2-41 | 0.0761 |
| 2-42 | 0.1529 |
| 2-43 | 0.0849 |
| 2-44 | 0.1939 |
| 2-45 | 0.1631 |
| 2-46 | 3.086 |
| 2-47 | 24.65 |
| 2-48 | 0.6964 |
| 2-49 | 10.46 |
| 2-50 | 0.0594 |

-continued

| Example | $IC_{50}$ (nM) |
|---|---|
| 2-51 | 473.5 |
| 2-52 | 424.4 |
| 2-53 | 130.9 |
| 2-54 | 0.0784 |
| 2-55 | 1.622 |
| 2-56 | 0.1015 |
| 2-57 | 0.9054 |
| 2-58 | 0.07906 |
| 2-59 | 0.0508 |
| 2-60 | 468.7 |
| 2-61 | 1.269 |
| 2-62 | 0.06122 |
| 2-63 | 0.0861 |
| 2-64 | 0.7817 |
| 2-65 | 16.62 |
| 2-66 | 0.7224 |
| 2-67 | 0.0508 |
| 2-68 | 14.28 |
| 2-69 | 0.5098 |
| 2-70 | 0.0508 |
| 2-71 | 0.2536 |
| 2-72 | 0.117 |
| 2-73 | 0.0508 |
| 2-74 | 0.2662 |
| 2-75 | 0.325 |
| 2-76 | 0.03215 |
| 2-77 | 0.7821 |
| 2-78 | 0.0198 |
| 2-79 | 0.0305 |
| 2-80 | 0.0728 |
| 2-81 | 0.0441 |
| 2-82 | 0.0309 |
| 2-83 | 0.0417 |
| 2-84 | 0.0222 |
| 2-85 | 0.0328 |
| 2-86 | 0.0382 |
| 2-87 | 100 |
| 2-88 | 0.3767 |
| 2-89 | 0.0117 |
| 2-90 | 0.0355 |
| 2-91 | 1.317 |
| 2-92 | 0.03992 |
| 2-93 | 0.02125 |
| 2-94 | 5.769 |
| 2-95 | 0.0589 |
| 2-96 | 0.08245 |
| 2-97 | 0.6793 |
| 2-98 | 6.732 |
| 2-99 | 12.66 |
| 2-100 | 1.194 |
| 2-101 | 0.1214 |
| 2-102 | 0.2037 |
| 2-103 | 0.0946 |
| 2-104 | 0.7955 |
| 2-105 | 0.0714 |
| 2-106 | 5.756 |
| 2-107 | 0.0862 |
| 2-108 | 0.0134 |
| 2-109 | 0.0528 |
| 2-110 | 0.0706 |
| 2-111 | 0.0199 |
| 2-112 | 0.8159 |
| 2-113 | 0.0389 |
| 2-114 | 0.0654 |
| 2-115 | 0.1205 |
| 2-116 | 0.1416 |
| 2-117 | 0.04055 |
| 2-118 | 0.06067 |
| 2-119 | 0.038 |
| 2-120 | 0.0066 |
| 2-121 | 0.02484 |
| 2-122 | 0.22 |
| 2-123 | 0.03699 |
| 2-124 | 0.04736 |
| 2-125 | 0.1046 |
| 2-126 | 0.08977 |
| 2-127 | 100 |

-continued

| Example | $IC_{50}$ (nM) |
|---|---|
| 2-128 | 0.03369 |
| 2-129 | 0.4535 |
| 2-130 | 0.103 |
| 2-131 | 0.1259 |
| 2-132 | 2.778 |
| 2-133 | 0.4049 |
| 2-134 | 57.68 |
| 2-135 | 72.5 |
| 2-136 | 0.1012 |
| 2-137 | 100 |
| 2-138 | 0.06803 |
| 2-139 | 0.04216 |
| 2-140 | 0.1206 |
| 2-141 | 0.0505 |
| 2-142 | 1.226 |
| 2-143 | 0.0888 |
| 2-144 | 0.2319 |
| 2-145 | 0.051 |
| 2-146 | 0.0505 |
| 2-147 | 0.0753 |
| 2-148 | 0.0831 |
| 2-149 | 0.1942 |
| 2-150 | 0.0614 |
| 2-151 | 0.2673 |
| 2-152 | 0.0714 |
| 2-153 | 0.0471 |
| 2-154 | 0.5147 |
| 2-155 | 0.0647 |
| 2-156 | 0.2351 |
| 2-157 | 0.0689 |
| 2-158 | 0.02512 |
| 2-159 | 47.05 |
| 2-160 | 0.03263 |
| 2-161 | 0.2524 |
| 2-162 | 0.1256 |
| 2-163 | 0.0588 |
| 2-164 | 0.4872 |
| 2-165 | 0.1028 |
| 2-166 | 0.05891 |
| 2-167 | 70.45 |
| 2-168 | 0.104 |
| 2-169 | 4.97 |
| 2-170 | 0.0392 |
| 2-171 | 0.05066 |
| 2-172 | 24.63 |
| 2-173 | 0.1283 |
| 2-174 | 11.44 |
| 2-175 | 0.0298 |
| 2-176 | 17.25 |
| 2-177 | 4.075 |
| 2-178 | 0.09328 |
| 2-179 | 2.93 |
| 2-180 | 0.02479 |
| 2-181 | 100 |
| 2-182 | 32.68 |
| 2-183 | 0.03795 |
| 2-184 | 3.666 |
| 2-185 | 0.0303 |
| 2-186 | 0.1359 |
| 2-187 | 0.08121 |
| 2-188 | 0.08056 |
| 3-1 | 240.6 |
| 3-2 | 1.794 |
| 3-3 | 391.2 |
| 3-4 | 9.357 |
| 3-5 | 205.1 |
| 3-6 | 45.23 |
| 3-7 | 45.47 |
| 3-8 | 92.56 |
| 3-9 | 63 |
| 3-10 | 107.1 |
| 3-11 | 82.36 |
| 3-12 | 94.16 |
| 3-13 | 1.046 |
| 3-14 | 24.65 |
| 3-15 | 3.238 |
| 3-16 | 0.169 |

-continued

| Example | $IC_{50}$ (nM) |
|---|---|
| 3-17 | 0.07567 |
| 3-18 | 204.3 |
| 3-19 | 638 |
| 3-20 | 770.5 |
| 3-21 | 30.39 |
| 3-22 | 534.6 |
| 3-23 | 46.29 |
| 3-24 | 2.599 |
| 3-25 | 46.83 |
| 3-26 | 148.7 |
| 3-27 | 22.51 |
| 3-28 | 51.83 |
| 3-29 | 20.52 |
| 3-30 | 147.7 |
| 3-31 | 29.42 |
| 3-32 | 57.11 |
| 3-33 | 18.38 |
| 3-34 | 81.5 |
| 3-35 | 1.667 |
| 3-36 | 4.175 |
| 3-37 | 73.06 |
| 3-38 | 369.1 |
| 3-39 | 227.9 |
| 3-40 | 0.8886 |
| 3-41 | 10.01 |
| 3-42 | 3.167 |
| 3-43 | 68.48 |
| 3-44 | 12.99 |
| 3-45 | 291.6 |
| 3-46 | 118.3 |
| 3-47 | 169.8 |
| 3-48 | 530.8 |
| 3-49 | 96.75 |
| 3-50 | 771.4 |
| 3-51 | 233.6 |
| 3-52 | 97.9 |
| 3-53 | 668.8 |
| 3-54 | 188.9 |
| 3-55 | 240.3 |
| 3-56 | 97.61 |
| 3-57 | 799 |
| 3-58 | 180 |
| 3-59 | 365 |
| 3-60 | 806.6 |
| 3-61 | 823.9 |
| 3-62 | 110.7 |
| 3-63 | 38.26 |
| 3-64 | 115.1 |
| 3-65 | 136.3 |
| 3-66 | 293.7 |
| 3-67 | 107.6 |
| 3-68 | 520.3 |
| 3-69 | 470 |
| 3-70 | 392.5 |
| 3-71 | 91.66 |
| 3-72 | 289.5 |
| 3-73 | 718.6 |
| 3-74 | 138.4 |
| 3-75 | 90.07 |
| 3-76 | 0.1008 |
| 3-77 | 24.32 |
| 3-78 | 0.1686 |
| 3-79 | 0.2547 |
| 3-80 | 2.813 |
| 4-1 | 15.18 |
| 4-2 | 4.667 |
| 4-3 | 377.2 |
| 4-4 | 157.6 |
| 4-5 | 258.3 |
| 4-6 | 582.7 |
| 4-7 | 224.1 |
| 4-8 | 2.37 |
| 4-9 | 2.192 |
| 5-1 | 661.7 |
| 5-2 | 164.8 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is selected from the group consisting of:

7-(5-amino-4-methylpyridin-3-yl)-6-fluoro-N~2~-(6-methoxy-2-methyl-1,2,3,4-tetrahydroisoquinolin-7-yl)quinazoline-2,5-diamine;

6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

methyl (3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetate;

6-fluoro-N~2~-(6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(3-{[5-amino-6-fluoro-7-(8-methyl-2,3-dihydro-1H-pyrido[2,3-b][1,4]oxazin-7-yl)quinazolin-2-yl]amino}-4-methoxyphenyl)acetonitrile;

4-{[5-amino-6-fluoro-7-(8-methyl-2,3-dihydro-1H-pyrido[2,3-b][1,4]oxazin-7-yl)quinazolin-2-yl]amino}-3-methoxybenzene-1-sulfonamide;

1-[6-{[5-amino-6-fluoro-7-(8-methyl-2,3-dihydro-1H-pyrido[2,3-b][1,4]oxazin-7-yl)quinazolin-2-yl]amino}-3,4-dihydroquinolin-1 (2H)-yl]ethan-1-one;

6-fluoro-7-(8-methyl-2,3-dihydro-1H-pyrido[2,3-b][1,4]oxazin-7-yl)-N~2~-[2-(trifluoromethoxy)phenyl]quinazoline-2,5-diamine;

6-fluoro-7-(8-methyl-2,3-dihydro-1H-pyrido[2,3-b][1,4]oxazin-7-yl)-N~2~-(pyridin-3-yl)quinazoline-2,5-diamine;

(R or S)—N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide;

(R or S)—N-(5-{[5-amino-6-fluoro-7-(8-methyl-2,3-dihydro-1H-pyrido[2,3-b][1,4]oxazin-7-yl)quinazolin-2-yl]amino}-2,3-dihydro-1H-inden-1-yl)acetamide;

1-[7-{[5-amino-6-fluoro-7-(8-methyl-2,3-dihydro-1H-pyrido[2,3-b][1,4]oxazin-7-yl)quinazolin-2-yl]amino}-6-methoxy-3,4-dihydroisoquinolin-2 (1H)-yl]ethan-1-one;

2-(4-{[5-amino-6-fluoro-7-(8-methyl-2,3-dihydro-1H-pyrido[2,3-b][1,4]oxazin-7-yl)quinazolin-2-yl]amino}phenyl)-N-methylacetamide;

6-fluoro-7-(8-methyl-2,3-dihydro-1H-pyrido[2,3-b][1,4]oxazin-7-yl)-N~2~-[3-(methylsulfonyl)phenyl]quinazoline-2,5-diamine;

N-(4-{[5-amino-6-fluoro-7-(8-methyl-2,3-dihydro-1H-pyrido[2,3-b][1,4]oxazin-7-yl)quinazolin-2-yl]amino}phenyl)acetamide;

N-(4-{[5-amino-6-fluoro-7-(8-methyl-2,3-dihydro-1H-pyrido[2,3-b][1,4]oxazin-7-yl)quinazolin-2-yl]amino}phenyl)methanesulfonamide;

6-fluoro-7-(8-methyl-2,3-dihydro-1H-pyrido[2,3-b][1,4]oxazin-7-yl)-N~2~-[4-(methylsulfonyl)phenyl]quinazoline-2,5-diamine;

1-(4-{[5-amino-6-fluoro-7-(8-methyl-2,3-dihydro-1H-pyrido[2,3-b][1,4]oxazin-7-yl)quinazolin-2-yl]amino}phenyl)cyclopropane-1-carbonitrile;

6-fluoro-7-(8-methyl-2,3-dihydro-1H-pyrido[2,3-b][1,4]oxazin-7-yl)-N~2~-(pyrimidin-5-yl)quinazoline-2,5-diamine;

6-fluoro-N~2~-(4-methoxypyridin-3-yl)-7-(8-methyl-2,3-dihydro-1H-pyrido[2,3-b][1,4]oxazin-7-yl)quinazoline-2,5-diamine;

7-{[5-amino-6-fluoro-7-(8-methyl-2,3-dihydro-1H-pyrido[2,3-b][1,4]oxazin-7-yl)quinazolin-2-yl]amino}-6-methoxy-1,3,4,5-tetrahydro-2H-3-benzazepin-2-one;

6-fluoro-N~2~-(2-fluorophenyl)-7-(8-methyl-2,3-dihydro-1H-pyrido[2,3-b][1,4]oxazin-7-yl)quinazoline-2,5-diamine;

4-{[5-amino-6-fluoro-7-(8-methyl-2,3-dihydro-1H-pyrido[2,3-b][1,4]oxazin-7-yl)quinazolin-2-yl]amino}-N-methylbenzamide;

6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

6-fluoro-7-(8-methyl-2,3-dihydro-1H-pyrido[2,3-b][1,4]oxazin-7-yl)-N~2~-phenylquinazoline-2,5-diamine;

N~2~-(2-cyclopropylphenyl)-6-fluoro-7-(8-methyl-2,3-dihydro-1H-pyrido[2,3-b][1,4]oxazin-7-yl)quinazoline-2,5-diamine;

6-fluoro-N~2~-(2-methoxypyridin-3-yl)-7-(8-methyl-2,3-dihydro-1H-pyrido[2,3-b][1,4]oxazin-7-yl)quinazoline-2,5-diamine;

(R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one;

(R or S)-1-[2-(4-{[5-amino-6-fluoro-7-(8-methyl-2,3-dihydro-1H-pyrido[2,3-b][1,4]oxazin-7-yl)quinazolin-2-yl]amino}phenyl)pyrrolidin-1-yl]ethan-1-one;

N-[(4-{[5-amino-6-fluoro-7-(8-methyl-2,3-dihydro-1H-pyrido[2,3-b][1,4]oxazin-7-yl)quinazolin-2-yl]amino}phenyl)methyl]acetamide;

N~2~-(2-chlorophenyl)-6-fluoro-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2-methylpyridin-3-yl)quinazoline-2,5-diamine;

3-{[5-amino-6-fluoro-7-(8-methyl-2,3-dihydro-1H-pyrido[2,3-b][1,4]oxazin-7-yl)quinazolin-2-yl]amino}-N-tert-butylbenzene-1-sulfonamide;

3-{[5-amino-6-fluoro-7-(8-methyl-2,3-dihydro-1H-pyrido[2,3-b][1,4]oxazin-7-yl)quinazolin-2-yl]amino}-N-methylbenzene-1-sulfonamide;

(R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(R or S)-6-fluoro-N~2~-(6-methoxy-1,2-dimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

N~2~-(6-methoxy-1,2,3,4-tetrahydroisoquinolin-7-yl)-7-(4-methylpyridin-3-yl)quinazoline-2,5-diamine;

7-(2-fluoro-6-methylphenyl)-N~2~-(6-methoxy-2-methyl-1,2,3,4-tetrahydroisoquinolin-7-yl)quinazoline-2,5-diamine;

7-(5-amino-4-methylpyridin-3-yl)-N~2~-(6-methoxy-2-methyl-1,2,3,4-tetrahydroisoquinolin-7-yl)quinazoline-2,5-diamine;

N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

5-{[5-amino-6-fluoro-7-(8-methyl-2,3-dihydro-1H-pyrido[2,3-b][1,4]oxazin-7-yl)quinazolin-2-yl]amino}-3,3-dimethyl-2-benzofuran-1 (3H)-one;

5-{[5-amino-6-fluoro-7-(8-methyl-2,3-dihydro-1H-pyrido[2,3-b][1,4]oxazin-7-yl)quinazolin-2-yl]amino}-2-(2-hydroxy-2-methylpropyl)-2,3-dihydro-1H-isoindol-1-one;

5-{[5-amino-6-fluoro-7-(8-methyl-2,3-dihydro-1H-pyrido[2,3-b][1,4]oxazin-7-yl)quinazolin-2-yl]amino}-2,3-dihydro-1H-1-benzothiophene-1,1-dione;

6-fluoro-7-(4-methylpyridin-3-yl)-N~2~-{4-[(methylsulfonyl)methyl]phenyl}-quinazoline-2,5-diamine;

6-fluoro-N~2~-(6'-methoxy-2'-methyl-2',3'-dihydro-l'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(R and S)-(7-{[5-amino-6-fluoro-7-(8-methyl-2,3-dihydro-1H-pyrido[2,3-b][1,4]oxazin-7-yl)quinazolin-2-yl]amino}-6-methoxy-2-methyl-1,2,3,4-tetrahydroisoquinolin-1-yl)methanol;

6-fluoro-N~2~-(6-methoxy-2-methyl-1,2,3,4-tetrahydroisoquinolin-7-yl)-7-([1,3]thiazolo[4,5-b]pyridin-6-yl)quinazoline-2,5-diamine;

(R,R and S,S)-6-fluoro-N~2~-(6-methoxy-1,2,3-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-(5-amino-6-fluoro-2-((6-methoxy-2-methyl-1,2,3,4-tetrahydroisoquinolin-7-yl)amino)quinazolin-7-yl)-5-methylbenzo[d]oxazol-2 (3H)-one;

6-fluoro-N2-(2-methoxy-4-((methylsulfonyl)methyl)phenyl)-7-(8-methyl-2,3-dihydro-1H-pyrido[2,3-b][1,4]oxazin-7-yl)quinazoline-2,5-diamine;

3-(5-amino-6-fluoro-2-((6-methoxy-2-methyl-1,2,3,4-tetrahydroisoquinolin-7-yl)amino)quinazolin-7-yl)-4-methylbenzonitrile;

3-(5-amino-6-fluoro-2-{[4-(methylsulfonyl)phenyl]amino}quinazolin-7-yl)-4-methylbenzonitrile;

3-[5-amino-6-fluoro-2-({4-[(methylsulfonyl)methyl]phenyl}amino)quinazolin-7-yl]-4-methylbenzonitrile;

(R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one;

(R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine;

(R or S)-6-fluoro-N~2~-{2-methoxy-4-[1-(methylsulfonyl)ethyl]phenyl}-7-(8-methyl-2,3-dihydro-1H-pyrido[2,3-b][1,4]oxazin-7-yl)quinazoline-2,5-diamine;

(R or S)-3-(4-{[5-amino-6-fluoro-7-(8-methyl-2,3-dihydro-1H-pyrido[2,3-b][1,4]oxazin-7-yl)quinazolin-2-yl]amino}-3-methoxyphenyl)-1-methylpyrrolidin-2-one;

4-{[5-amino-6-fluoro-7-(8-methyl-2,3-dihydro-1H-pyrido[2,3-b][1,4]oxazin-7-yl)quinazolin-2-yl]amino}-N-(3-methoxycyclobutyl)benzamide;

6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-fluoro-N~2~-(6-methoxy-2-methyl-1,2,3,4-tetrahydroisoquinolin-7-yl)-7-[2-methyl-4-(1,3-oxazol-2-yl)phenyl]quinazoline-2,5-diamine;

6-fluoro-N~2~-(6-methoxy-2-methyl-1,2,3,4-tetrahydroisoquinolin-7-yl)-7-[4-methyl-6-(1,3-oxazol-2-yl)pyridin-3-yl]quinazoline-2,5-diamine;

(R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine;

(R or S)-6-fluoro-7-(8-methyl-2,3-dihydro-1H-pyrido[2,3-b][1,4]oxazin-7-yl)-N~2~-{4-[1-(methylsulfonyl)ethyl]phenyl}quinazoline-2,5-diamine;

N~2~-(6-chloro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

6-fluoro-N~2~-(6-methoxy-2-methyl-1,2,3,4-tetrahydroisoquinolin-7-yl)-7-[2-(1-methyl-1H-pyrazol-5-yl)phenyl]quinazoline-2,5-diamine;

6-fluoro-N~2~-(2-methoxy-6-methylpyridin-3-yl)-7-(8-methyl-2,3-dihydro-1H-pyrido[2,3-b][1,4]oxazin-7-yl)quinazoline-2,5-diamine;

3-(4-{[5-amino-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

1-(5-{[5-amino-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

6-fluoro-N~2~-(4-fluoro-2-methoxyphenyl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

6-fluoro-N~2~-(2-methoxyphenyl)-7-(8-methyl-2,3-dihydro-1H-pyrido[2,3-b][1,4]oxazin-7-yl)quinazoline-2,5-diamine;

6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(2'-methyl-2',3'-dihydro-l'H-spiro[cyclopropane-1,4'-isoquinolin]-7'-yl)quinazoline-2,5-diamine;

4-{[5-amino-6-fluoro-7-(8-methyl-2,3-dihydro-1H-pyrido[2,3-b][1,4]oxazin-7-yl)quinazolin-2-yl]amino}-3-methoxy-N-methylbenzamide;

6-fluoro-N~2~-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

6-fluoro-N~2~-(6-methoxy-2-methylpyridin-3-yl)-7-(8-methyl-2,3-dihydro-1H-pyrido[2,3-b][1,4]oxazin-7-yl)quinazoline-2,5-diamine;

5-{[5-amino-6-fluoro-7-(8-methyl-2,3-dihydro-1H-pyrido[2,3-b][1,4]oxazin-7-yl)quinazolin-2-yl]amino}-2-methyl-2,3-dihydro-1H-isoindol-1-one;

(R,S and S,R)-6-fluoro-N2-(2-methyl-1,2,3,4-tetrahydro-1,4-methanoisoquinolin-7-yl)-7-(8-methyl-2,3-dihydro-1H-pyrido[2,3-b][1,4]oxazin-7-yl)quinazoline-2,5-diamine;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclohexane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopropane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclobutane-1-carboxamide;

1-(4-((5-amino-6-fluoro-7-(8-methyl-2,3-dihydro-1H-pyrido[2,3-b][1,4]oxazin-7-yl)quinazolin-2-yl)amino)phenyl)-N-methylcyclopentane-1-carboxamide;

6-fluoro-7-(8-methyl-2,3-dihydro-1H-pyrido[2,3-b][1,4]oxazin-7-yl)-N2-(6-((methylsulfonyl)methyl)pyridin-3-yl)quinazoline-2,5-diamine;

(R or S)—N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

(R or S)—N2-(2,3-dimethyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

7-((5-amino-6-fluoro-7-(8-methyl-2,3-dihydro-1H-pyrido[2,3-b][1,4]oxazin-7-yl)quinazolin-2-yl)amino)-2-methyl-1,2,3,4-tetrahydroisoquinoline-6-carboxamide;

6-fluoro-N2-(7-methoxy-2-methyl-1,2,3,4-tetrahydroisoquinolin-6-yl)-7-(8-methyl-2,3-dihydro-1H-pyrido[2,3-b][1,4]oxazin-7-yl)quinazoline-2,5-diamine;

N2-(4-((ethylsulfonyl)methyl)phenyl)-6-fluoro-7-(8-methyl-2,3-dihydro-1H-pyrido[2,3-b][1,4]oxazin-7-yl)quinazoline-2,5-diamine;

(+ and −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

(+ or −)-8-chloro-6-fluoro-7-(8-methyl-2,3-dihydro-1H-pyrido[2,3-b][1,4]oxazin-7-yl)-N~2~-{4-[(methylsulfonyl)methyl]phenyl}quinazoline-2,5-diamine;

(+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N~2~-(6-methoxy-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

(+ and −)-4-{[5-amino-8-chloro-6-fluoro-7-(8-methyl-2,3-dihydro-1H-pyrido[2,3-b][1,4]oxazin-7-yl)quinazolin-2-yl]amino}-3-methoxy-N-methylbenzamide;

(+ and −)-4-{[5-amino-8-chloro-7-(6-chloro-8-methyl-2,3-dihydro-1H-pyrido[2,3-b][1,4]oxazin-7-yl)-6-fluoroquinazolin-2-yl]amino}-3-methoxy-N-methylbenzamide;

(+ or −)-8-chloro-6-fluoro-N~2~-{2-methoxy-4-[(methylsulfonyl)methyl]phenyl}-7-(8-methyl-2,3-dihydro-1H-pyrido[2,3-b][1,4]oxazin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-(2'-methyl-2',3'-dihydro-l'H-spiro[cyclopropane-1,4'-isoquinolin]-7'-yl)quinazoline-2,5-diamine;

(+ or −)-8-chloro-6-fluoro-N~2~-{2-methoxy-4-[(methylsulfonyl)methyl]phenyl}-7-(8-methyl-2,3-dihydro-1H-pyrido[2,3-b][1,4]oxazin-7-yl)quinazoline-2,5-diamine;

(+ and −)-8-chloro-6-fluoro-N~2~-[6-methoxy-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-[4-(methylsulfonyl)phenyl]quinazoline-2,5-diamine;

8-chloro-6-fluoro-N2-(6-methoxy-2,4,4-trimethyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2-isopropyl-6-methoxy-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-N2-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ or −)-8-chloro-6-fluoro-N2-(2'-methyl-2',3'-dihydro-l'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(+ and −)-5-amino-6-fluoro-2-((2'-methyl-2',3'-dihydro-1'H-spiro[cyclopropane-1,4'-isoquinolin]-7'-yl)amino)-7-(8-methyl-2,3-dihydro-1H-pyrido[2,3-b][1,4]oxazin-7-yl)quinazoline-8-carbonitrile;

(+ and −)-6-fluoro-8-methyl-N2-(2'-methyl-2',3'-dihydro-1'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

(+ and −)-8-bromo-6-fluoro-7-(8-methyl-2,3-dihydro-1H-pyrido[2,3-b][1,4]oxazin-7-yl)-N~2~-(2'-methyl-2',3'-dihydro-1'H-spiro[cyclopropane-1,4'-isoquinolin]-7'-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

(+ or −)-8-chloro-6-fluoro-7-(8-methyl-2,3-dihydro-1H-pyrido[2,3-b][1,4]oxazin-7-yl)-N~2~-[2-(propan-2-yl)-1,2,3,4-tetrahydroisoquinolin-7-yl]quinazoline-2,5-diamine;

6-fluoro-N~2~-{3-fluoro-4-[(methanesulfonyl)methyl]phenyl}-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-{4-[(pyrrolidine-1-sulfonyl)methyl]phenyl}quinazoline-2,5-diamine;

3-(4-{[5-amino-6-fluoro-7-(8-methyl-2,3-dihydro-1H-pyrido[2,3-b][1,4]oxazin-7-yl)quinazolin-2-yl]amino}phenyl)propanenitrile;

6-fluoro-7-(8-methyl-2,3-dihydro-1H-pyrido[2,3-b][1,4]oxazin-7-yl)-N~2~-(2-methyl-2,3,4,5-tetrahydro-1H-2-benzazepin-8-yl)quinazoline-2,5-diamine;

N~2~-(3,4-dihydro-1H-2-benzopyran-7-yl)-6-fluoro-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-(3-methyl-2,3,4,5-tetrahydro-1H-3-benzazepin-7-yl)quinazoline-2,5-diamine;

6-fluoro-7-(8-methyl-2,3-dihydro-1H-pyrido[2,3-b][1,4]oxazin-7-yl)-N~2~-(2,3,4,5-tetrahydro-1H-2-benzazepin-8-yl)quinazoline-2,5-diamine;

6-fluoro-7-(8-methyl-2,3-dihydro-1H-pyrido[2,3-b][1,4]oxazin-7-yl)-N~2~-(9-methyl-1,2,3,4-tetrahydro-1,4-epiminonaphthalen-6-yl)quinazoline-2,5-diamine;

6-fluoro-7-(4-methylpyridin-3-yl)-N~2~-(2-methyl-1,2,3,4-tetrahydroisoquinolin-7-yl)quinazoline-2,5-diamine;

7-(8-chloro-2,3-dihydro-1H-pyrido[2,3-b][1,4]oxazin-7-yl)-6-fluoro-N~2~-{4-[(methylsulfonyl)methyl]phenyl}quinazoline-2,5-diamine;

7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine;

(R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-6-yl)quinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-5-yl)quinazoline-2,5-diamine;

6-fluoro-7-(8-methyl-2,3-dihydro-1H-pyrido[2,3-b][1,4]oxazin-7-yl)-N2-(2,3,3-trimethyl-1,2,3,4-tetrahydroisoquinolin-7-yl)quinazoline-2,5-diamine;

(R or S)-7-(3,8-dimethyl-2,3-dihydro-1H-pyrido[2,3-b][1,4]oxazin-7-yl)-N2-(4-((ethylsulfonyl)methyl)-2-fluorophenyl)-6-fluoroquinazoline-2,5-diamine;

6-fluoro-7-(7-methyl-1H-pyrrolo[3,2-b]pyridin-6-yl)-N~2~-(2-methyl-1,2,3,4-tetrahydroisoquinolin-7-yl)quinazoline-2,5-diamine;

(+ or −)-8-chloro-6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

(+ or −)-8-chloro-N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

(+ and −)-8-chloro-6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine;

8-chloro-N~2~-{4-[(ethylsulfonyl)methyl]phenyl}-6-fluoro-7-(8-methyl-2,3-dihydro-1H-pyrido[2,3-b][1,4]oxazin-7-yl)quinazoline-2,5-diamine;

8-chloro-6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

(+ or −)-8-chloro-N~2~-{4-[(cyclopropylsulfonyl)methyl]phenyl}-6-fluoro-7-(8-methyl-2,3-dihydro-1H-pyrido[2,3-b][1,4]oxazin-7-yl)quinazoline-2,5-diamine;

6-{[5-amino-6-fluoro-7-(8-methyl-2,3-dihydro-1H-pyrido[2,3-b][1,4]oxazin-7-yl)quinazolin-2-yl]amino}-3,4-dihydro-2-benzothiopyran-2,2 (1H)-dione;

6-fluoro-N~2~-(2-methyl-1,2,3,4-tetrahydroisoquinolin-7-yl)-7-(1H-pyrrolo[2,3-c]pyridin-4-yl)quinazoline-2,5-diamine;

8-chloro-N~2~-{4-[(ethylsulfonyl)methyl]phenyl}-6-fluoro-7-(8-methyl-2,3-dihydro-1H-pyrido[2,3-b][1,4]oxazin-7-yl)quinazoline-2,5-diamine;

(R or S)-7-(3,8-dimethyl-2,3-dihydro-1H-pyrido[2,3-b][1,4]oxazin-7-yl)-6-fluoro-N2-(2-methyl-1,2,3,4-tetrahydroisoquinolin-7-yl)quinazoline-2,5-diamine;

6-fluoro-7-(8-methyl-2,3-dihydro-1H-pyrido[2,3-b][1,4]oxazin-7-yl)-N~2~-(6-methyl-5,6,7,8-tetrahydro-2,6-naphthyridin-3-yl)quinazoline-2,5-diamine;

N~2~-{4-[(ethylsulfonyl)methyl]-2-fluorophenyl}-6-fluoro-7-(8-methyl-2,3-dihydro-1H-pyrido[2,3-b][1,4]oxazin-7-yl)quinazoline-2,5-diamine;

N~2~-{4-[(ethylsulfonyl)methyl]-2-fluorophenyl}-6-fluoro-7-(3,3,8-trimethyl-2,3-dihydro-1H-pyrido[2,3-b][1,4]oxazin-7-yl)quinazoline-2,5-diamine;

7-(3,8-dimethyl-2,3-dihydro-1H-pyrido[2,3-b][1,4]oxazin-7-yl)-6-fluoro-N2-(2-isopropyl-1,2,3,4-tetrahydroisoquinolin-7-yl)quinazoline-2,5-diamine;

(R or S)-3-(4-{[5-amino-6-fluoro-7-(8-methyl-2,3-dihydro-1H-pyrido[2,3-b][1,4]oxazin-7-yl)quinazolin-2-yl]amino}phenyl)-1-methylpyrrolidin-2-one;

(R or S)-3-(4-{[5-amino-6-fluoro-7-(8-methyl-2,3-dihydro-1H-pyrido[2,3-b][1,4]oxazin-7-yl)quinazolin-2-yl]amino}phenyl)-1-methylpyrrolidin-2-one;

6-fluoro-N~2~-{4-[1-(methanesulfonyl)cyclopropyl]phenyl}-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-{4-[(2,2,2-trifluoroethanesulfonyl)methyl]phenyl}quinazoline-2,5-diamine;

6-fluoro-7-(8-methyl-2,3-dihydro-1H-pyrido[2,3-b][1,4]oxazin-7-yl)-N~2~-(2,4,4-trimethyl-1,2,3,4-tetrahydroisoquinolin-7-yl)quinazoline-2,5-diamine;

7-(2,3-dihydro-1H-pyrido[2,3-b][1,4]oxazin-7-yl)-6-fluoro-N~2~-(2'-methyl-2',3'-dihydro-1'H-spiro[cyclopropane-1,4'-isoquinolin]-7'-yl)quinazoline-2,5-diamine;

7-(8-chloro-2,3-dihydro-1H-pyrido[2,3-b][1,4]oxazin-7-yl)-6-fluoro-N~2~-(2'-methyl-2',3'-dihydro-l'H-spiro[cyclopropane-1,4'-isoquinolin]-7'-yl)quinazoline-2,5-diamine;

7-(5-amino-4-methylpyridin-3-yl)-6-fluoro-N~2~-(2'-methyl-2',3'-dihydro-1'H-spiro[cyclopropane-1,4'-isoquinolin]-7'-yl)quinazoline-2,5-diamine;

N~2~-(4,4-difluoro-2-methyl-1,2,3,4-tetrahydroisoquinolin-7-yl)-6-fluoro-7-(8-methyl-2,3-dihydro-1H-pyrido[2,3-b][1,4]oxazin-7-yl)quinazoline-2,5-diamine;

6-fluoro-N~2~-{2-fluoro-4-[(methylsulfonyl)methyl]phenyl}-7-(8-methyl-2,3-dihydro-1H-pyrido[2,3-b][1,4]oxazin-7-yl)quinazoline-2,5-diamine;

3-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

6-fluoro-7-(8-methyl-2,3-dihydro-1H-pyrido[2,3-b][1,4]oxazin-7-yl)-N~2~-(4-{[(propan-2-yl)sulfonyl]methyl}phenyl)quinazoline-2,5-diamine;

6-fluoro-7-(8-methyl-2,3-dihydro-1H-pyrido[2,3-b][1,4]oxazin-7-yl)-N~2~-(2-methyl-1,2,3,4-tetrahydroisoquinolin-6-yl)quinazoline-2,5-diamine;

3-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-1,3-oxazolidin-2-one;

7-(8-chloro-2,3-dihydro-1H-pyrido[2,3-b][1,4]oxazin-7-yl)-6-fluoro-N~2~-(2-methyl-1,2,3,4-tetrahydroisoquinolin-7-yl)quinazoline-2,5-diamine;

(+ and −)-8-chloro-6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine;

6-fluoro-7-(7-methyl-1H-imidazo[4,5-b]pyridin-6-yl)-N~2~-(2-methyl-1,2,3,4-tetrahydroisoquinolin-7-yl)quinazoline-2,5-diamine;

8-chloro-6-fluoro-N~2~-(6'-methoxy-2'-methyl-2',3'-dihydro-l'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol;

6-fluoro-N~2~-{4-[(methylsulfonyl)methyl]phenyl}-7-(3,3,8-trimethyl-2,3-dihydro-1H-pyrido[2,3-b][1,4]oxazin-7-yl)quinazoline-2,5-diamine;

6-fluoro-N~2~-(2-methyl-1,2,3,4-tetrahydroisoquinolin-7-yl)-7-(3,3,8-trimethyl-2,3-dihydro-1H-pyrido[2,3-b][1,4]oxazin-7-yl)quinazoline-2,5-diamine;

1-(4-{[5-amino-8-chloro-6-fluoro-7-(8-methyl-2,3-dihydro-1H-pyrido[2,3-b][1,4]oxazin-7-yl)quinazolin-2-yl]amino}phenyl)-2-methylpropan-2-ol;

6-fluoro-N~2~-(2-methoxy-4-{[(propan-2-yl)sulfonyl]methyl}phenyl)-7-(8-methyl-2,3-dihydro-1H-pyrido[2,3-b][1,4]oxazin-7-yl)quinazoline-2,5-diamine;

8-chloro-6-fluoro-N~2~-(6'-methoxy-2'-methyl-2',3'-dihydro-l'H-spiro[cyclopropane-1,4'-isoquinolin]-7'-yl)-7-(8-methyl-2,3-dihydro-1H-pyrido[2,3-b][1,4]oxazin-7-yl)quinazoline-2,5-diamine;

6-fluoro-7-(8-methyl-2,3-dihydro-1H-pyrido[2,3-b][1,4]oxazin-7-yl)-N~2~-[4-(methylsulfinyl)phenyl]quinazoline-2,5-diamine;

6-fluoro-N~2~-[6-fluoro-2-(propan-2-yl)-1,2,3,4-tetrahydroisoquinolin-7-yl]-7-(8-methyl-2,3-dihydro-1H-pyrido[2,3-b][1,4]oxazin-7-yl)quinazoline-2,5-diamine;

6-fluoro-7-(5-fluoro-2-methylphenyl)-N~2~-{4-[(methylsulfonyl)methyl]phenyl}quinazoline-2,5-diamine;

N~2~-(6-ethylpyridin-3-yl)-6-fluoro-7-(8-methyl-2,3-dihydro-1H-pyrido[2,3-b][1,4]oxazin-7-yl)quinazoline-2,5-diamine;

6-fluoro-7-(5-fluoro-2-methylphenyl)-N~2~-(2-methyl-1,2,3,4-tetrahydroisoquinolin-7-yl)quinazoline-2,5-diamine;

6-fluoro-7-(8-methyl-2,3-dihydro-1H-pyrido[2,3-b][1,4]oxazin-7-yl)-N~2~-[6-(propan-2-yl)-5,6,7,8-tetrahydro-1,6-naphthyridin-3-yl]quinazoline-2,5-diamine;

N~2~-(4-cyclopropyl-2-methoxyphenyl)-6-fluoro-7-(8-methyl-2,3-dihydro-1H-pyrido[2,3-b][1,4]oxazin-7-yl)quinazoline-2,5-diamine;

6-fluoro-N~2~-(2-methoxy-4-methylphenyl)-7-(8-methyl-2,3-dihydro-1H-pyrido[2,3-b][1,4]oxazin-7-yl)quinazoline-2,5-diamine;

1-(4-{[5-amino-6-fluoro-7-(8-methyl-2,3-dihydro-1H-pyrido[2,3-b][1,4]oxazin-7-yl)quinazolin-2-yl]amino}phenyl)-2-methylpropan-2-ol;

(+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ or −)-8-chloro-6-fluoro-7-(8-methyl-2,3-dihydro-1H-pyrido[2,3-b][1,4]oxazin-7-yl)-N~2~-(2-methyl-1,2,3,4-tetrahydroisoquinolin-7-yl)quinazoline-2,5-diamine;

(+ or −)-1-(5-{[5-amino-8-chloro-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

(+ or −)-1-(5-{[5-amino-8-chloro-6-fluoro-7-(8-methyl-2,3-dihydro-1H-pyrido[2,3-b][1,4]oxazin-7-yl)quinazolin-2-yl]amino}-6-methoxypyridin-2-yl)cyclopropane-1-carbonitrile;

6-fluoro-7-(8-methyl-2,3-dihydro-1H-pyrido[2,3-b][1,4]oxazin-7-yl)-N~2~-(6-methyl-5,6,7,8-tetrahydro-1,6-naphthyridin-3-yl)quinazoline-2,5-diamine;

(+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

(+ and −)-8-chloro-6-fluoro-N~2~-(6-fluoro-2-methyl-1,2,3,4-tetrahydroisoquinolin-7-yl)-7-(8-methyl-2,3-dihydro-1H-pyrido[2,3-b][1,4]oxazin-7-yl)quinazoline-2,5-diamine;

2-(4-{[5-amino-6-fluoro-7-(8-methyl-2,3-dihydro-1H-pyrido[2,3-b][1,4]oxazin-7-yl)quinazolin-2-yl]amino}phenyl)-2,2-difluoro-N-methylacetamide;

2-(4-{[5-amino-6-fluoro-7-(8-methyl-2,3-dihydro-1H-pyrido[2,3-b][1,4]oxazin-7-yl)quinazolin-2-yl]amino}phenyl)-N,2-dimethylpropanamide;

5-{[5-amino-6-fluoro-7-(8-methyl-2,3-dihydro-1H-pyrido[2,3-b][1,4]oxazin-7-yl)quinazolin-2-yl]amino}-N-methyl-2,3-dihydro-1H-indene-1-carboxamide;

or a pharmaceutically acceptable salt thereof.

2. A pharmaceutical composition which comprises an inert carrier and a compound of claim 1, or a pharmaceutically acceptable salt thereof.

* * * * *